United States Patent
Asberom et al.

(10) Patent No.: US 8,569,521 B2
(45) Date of Patent: Oct. 29, 2013

(54) BENZENESULFONYL-CHROMANE, THIOCHROMANE, TETRAHYDRONAPHTHALENE AND RELATED GAMMA SECRETASE INHIBITORS

(75) Inventors: Theodros Asberom, West Orange, NJ (US); Thomas A. Bara, Linden, NJ (US); Chad E. Bennett, Metuchen, NJ (US); Duane A. Burnett, Bernardsville, NJ (US); Mary Anne Caplen, Sayreville, NJ (US); John W. Clader, Millton, VT (US); David J. Cole, Springfield, NJ (US); Martin S. Domalski, Verona, NJ (US); Hubert B. Josien, Jersey City, NJ (US); Chad E. Knutson, Garwood, NJ (US); Hongmei Li, Warren, NJ (US); Mark D. McBriar, Clinton, NJ (US); Dmitri A. Pissarnitski, Scotch Plains, NJ (US); Li Qiang, Edison, NJ (US); Murali Rajagopalan, Edison, NJ (US); Thavalakulamgara K. Sasikumar, Edison, NJ (US); Jing Su, Scotch Plains, NJ (US); Haiqun Tang, Belle Mead, NJ (US); Wen-Lian Wu, Edison, NJ (US); Ruo Xu, Watchung, NJ (US); Zhiqiang Zhao, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/267,324

(22) Filed: Oct. 6, 2011

(65) Prior Publication Data
US 2012/0264736 A1    Oct. 18, 2012

Related U.S. Application Data

(62) Division of application No. 11/654,821, filed on Jan. 18, 2007, now Pat. No. 8,067,621.

(60) Provisional application No. 60/760,842, filed on Jan. 20, 2006, provisional application No. 60/814,871, filed on Jun. 19, 2006.

(51) Int. Cl.
    *C07D 493/00*    (2006.01)
(52) U.S. Cl.
    USPC ............................................. 549/387

(58) Field of Classification Search
    USPC ............................................. 549/387
    See application file for complete search history.

(56) References Cited

FOREIGN PATENT DOCUMENTS

| EP | 1586561 | 10/2005 |
|---|---|---|
| WO | WO0050391 | 8/2000 |
| WO | WO03014075 A2 | 2/2003 |
| WO | WO2004031137 A1 | 4/2004 |
| WO | WO2004101539 A1 | 11/2004 |
| WO | WO2006004880 A2 | 1/2006 |
| WO | WO2007084595 A | 7/2007 |
| WO | WO2007/143523 A | 12/2007 |
| WO | WO2009008980 | 1/2009 |

OTHER PUBLICATIONS

PCT International Search Report for related International Application No. PCT/US2008/008192 mailed on Jan. 28, 2009; 5 pages.
Written Opinion of the PCT International Search Report dated Jan. 28, 2009 for related International Application No. PCT/US2008/008192; 8 pages.
PCT International Search Report dated Jul. 13, 2007 for corresponding International Application No. PCT/US2007/001302; 2 pages.
McCombie, S.W., et. al, "A Cyclization-trapping Route to Carbocyclic and Heterocyclic Benzylic Sulfones", Tetrahedron Letters, vol. 34, No. 50, pp. 8033-8036 (1993).

*Primary Examiner* — John Mabry
(74) *Attorney, Agent, or Firm* — Susan L. Hess; Henry Jeanette; Gerard M. Devlin

(57) ABSTRACT

This invention discloses novel gamma secretase inhibitors of the formula:

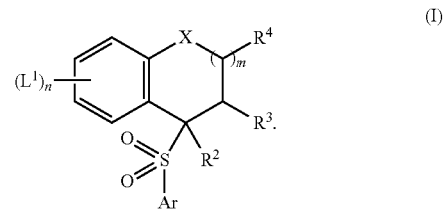

$R^2$ and $R^3$, or $R^2$ and $R^4$, or $R^3$ and $R^4$, together with the atoms to which they are bound, can form a fused cycloalkyl or fused heterocycloalkyl ring. The cycloalkyl ring or the heterocycloalkyl ring can be optionally substituted with one or more substituents. One or more compounds of formula (I), or formulations comprising such compounds, may be useful, e.g. in treating Alzheimer's Disease.

64 Claims, No Drawings

BENZENESULFONYL-CHROMANE, THIOCHROMANE, TETRAHYDRONAPHTHALENE AND RELATED GAMMA SECRETASE INHIBITORS

CROSS REFERENCE TO RELATED APPLICATIONS

This application is a divisional application of U.S. application Ser. No. 11/654,821, filed Jan. 18, 2007, which claims the benefit of U.S. provisional application 60/814,871, filed Jun. 19, 2006 and U.S. provisional application 60/760,842, filed Jan. 20, 2006. Each of the aforementioned applications is incorporated by reference in its entirety as if fully set forth herein.

BACKGROUND

WO 00/50391, published Aug. 13, 2000, discloses compounds having a sulfonamide moiety that are useful for the treatment and prevention of Alzheimer's Disease and other diseases relating to the deposition of amyloid protein.

McCombie et al., Tetrahedron Letters, Vol. 34, No. 50, pp. 8033-8036 (1993) describe methods of preparing chromans and thiochromans. However, the chromans and thiochromans described therein are quite different from the compounds of the present invention.

In view of the present interest in the treatment or prevention of neurodegenerative diseases, such as Alzheimer's Disease, a welcome contribution to the art would be compounds for use in such treatment or prevention. This invention provides such a contribution.

SUMMARY OF THE INVENTION

This invention provides compounds that are inhibitors (e.g., antagonists) of gamma-secretase (also termed "γ-secretase") and have the Formula (I):

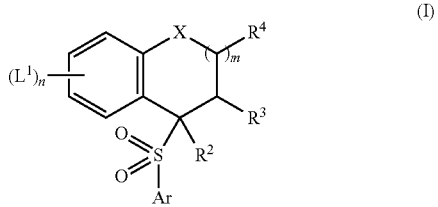

or a pharmaceutically acceptable salt, solvate, or ester thereof, wherein $L^1$, m, n, Ar, X, $R^2$, $R^3$, and $R^3$ are defined below.

This invention also provides the compounds of formula (I) in pure and isolated form.

This invention also provides the compounds of formula (I) in pure form.

This invention also provides the compounds of formula (I) in isolated form.

This invention also provides the final compounds of Examples 1, 1A-1V, 2, 3, 3A-3H, 4, 5, 5A-5C, 6, 6A, 7, 7A-7E, 8, 8A-8Z, 9, 9A-9D, 10, 10A-10E, 11, 11A-11E, 12, 13, 13A, 14, 14A, 15, 15A, 16, 17, 18, 19, 20, 20D-20K, 21, 22, 23, 24, 24C, 25, 26, 27A, 27B, 28 to 400, and 403 to 447.

This invention also provides the final compounds of Examples 13A, 14A, 15A, 16, 17, 18, 19, 20, 20D-20K, 21, 22, 23, 24, 24C, 25, 26, 27A, 27B, and 28.

This invention also provides the compounds in Table 93.

This invention also provides the compounds in Table 94.

This invention also provides a pharmaceutical composition comprising an effective amount of one or more compounds of Formula (I) and at least one pharmaceutically acceptable carrier.

This invention also provides a pharmaceutical composition comprising an effective amount a compound of Formula (I) and at least one pharmaceutically acceptable carrier.

This invention also provides a method for inhibiting gamma-secretase comprising administering an effective (i.e., therapeutically effective) amount of one or more compounds of formula (I) to a patient in need of treatment.

This invention also provides a method for inhibiting gamma-secretase comprising administering an effective (i.e., therapeutically effective) amount of a compound of formula (I) to a patient in need of treatment.

This invention also provides a method of treating one or more neurodegenerative diseases comprising administering an effective (i.e., therapeutically effective) amount of one or more compounds of formula (I) to a patient in need of treatment.

This invention also provides a method of treating one or more neurodegenerative diseases comprising administering an effective (i.e., therapeutically effective) amount of a compound of formula (I) to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of one or more compounds of formula (I) to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of a compound of formula (I) to a patient in need of treatment.

This invention also provides a method of treating Alzheimer's disease comprising administering an effective (i.e., therapeutically effective) amount of one or more compounds of formula (I) to a patient in need of treatment.

This invention also provides a method of treating Alzheimer's disease comprising administering an effective (i.e., therapeutically effective) amount of a compound of formula (I) to a patient in need of treatment.

This invention also provides a method of treating Alzheimer's disease comprising administering an effective (i.e., therapeutically effective) amount of one or more compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept brand of donepezil hydrochloride), to a patient in need of treatment.

This invention also provides a method of treating Alzheimer's disease comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept brand of donepezil hydrochloride), to a patient in need of treatment.

This invention also provides any one of the above mentioned methods of treatment wherein the compound of formula I is selected from the group consisting of the compounds in Table 93.

This invention also provides any one of the above mentioned methods of treatment wherein the compound of formula I is selected from the group consisting of the compounds in Table 94.

This invention also provides any one of the above mentioned methods of treatment wherein the compound of formula I is selected from the group consisting of the final compounds of Examples 1, 1A-1V, 2, 3, 3A-3H, 4, 5, 5A-5C, 6, 6A, 7, 7A-7E, 8, 8A-8Z, 9, 9A-9D, 10, 10A-10E, 11, 11A-11E, 12, 13, 13A, 14, 14A, 15, 15A, 16, 17, 18, 19, 20, 20D-20K, 21, 22, 23, 24, 24C, 25, 26, 27A, 27B, 28 to 400, and 403 to 447.

This invention also provides any one of the above mentioned methods of treatment wherein the compound of formula I is selected from the group consisting of the final compounds of Examples 13A, 14A, 15A, 16, 17, 18, 19, 20, 20D-20K, 21, 22, 23, 24, 24C, 25, 26, 27A, 27B, and 28.

DETAILED DESCRIPTION OF THE INVENTION

This invention provides compounds that are inhibitors (e.g., antagonists) of gamma-secretase (also termed "γ-secretase") and have the Formula (I):

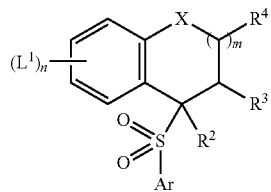

or a pharmaceutically acceptable salt, solvate, or ester thereof, wherein:

X is selected from the group consisting of —C($R^1$)$_2$—, —O—, —S—, —S(O$_2$)—, —N$R^1$—, and —N(C(O)$R^1$)—;

each $R^1$ is independently selected from the group consisting of H and alkyl;

$R^2$, $R^3$, and $R^4$ are each independently selected from the group consisting of: (1) H, (2) alkyl, (3) —O$R^5$, (4) alkylene-O$R^5$, (5) -alkylene-$R^6$, (6) —C(O)-alkyl, (7) -alkylene-C(O)-alkyl, (8) —C(O)—$R^6$, (9) -alkylene-C(O)—$R^6$, (10) —C(O)O-alkyl, (11) -alkylene-C(O)O-alkyl, (12) —C(O)NH-alkyl, (13) -alkylene-C(O)NH-alkyl, (14) —C(O)N(alkyl)$_2$, (15) -alkylene-C(O)N(alkyl)$_2$, (16) —$R^8$, (17) -alkylene-$R^8$, (18) —NH$R^5$, (19) —N($R^5$)$_2$, (20) -alkylene-NH$R^5$, (21) -alkylene-N($R^5$)$_2$, (22) alkenyl, (23) —NH—$R^8$ (e.g., —NH-(dihydro-furan-2-one), (24) —NH—CH(C(O)O($C_1$-$C_6$)alkyl)-alkylene-O-alkylene-$R^6$ (e.g., —NHCH(C(O)OCH$_3$)CH$_2$CH$_2$OCH$_2$-phenyl), (25) —NHCH(C(O)O($C_1$-$C_6$) alkyl)-alkylene-OH (e.g., —NHCH(C(O)OCH$_3$)CH$_2$CH$_2$OH), (26) —NH—C(O)-alkenyl (e.g., —NHC(O)CH=CH$_2$), and (27) —N($C_1$-$C_6$ alkyl)C(O)-alkenyl (e.g., —N(CH$_3$)C(O)CH=CH$_2$) (wherein examples of said alkyl groups (including the alkyl portion of said $R^2$, $R^3$, and $R^4$ substituents) include $C_1$-$C_6$ alkyl groups, and wherein examples of said alkylene portion of said $R^2$, $R^3$, and $R^4$ substituents include $C_1$-$C_6$ alkylene groups, and wherein examples of said alkenyl groups of said $R^2$, $R^3$, and $R^4$ substituents include $C_2$-$C_6$ alkylene groups); or $R^2$ and $R^3$, or $R^2$ and an $R^4$, or $R^3$ and an $R^4$, together with the atoms to which they are shown attached form a fused cycloalkyl or heterocycloalkyl ring, wherein said fused cycloalkyl or heterocycloalkyl ring is unsubstituted or substituted with one or more $L^3$ groups (wherein examples of said fused ring cycloalkyl groups include $C_3$-$C_{10}$ rings (including the carbon atoms common to both rings), and examples of said fused heterocycloalkyl rings include 4 to 8 membered rings (including the carbon atoms common to both rings) comprising 1 to 3 heteroatoms independently selected from the group consisting of: O, N, S, SO$_2$, SO, Si and P, and in other examples said heteroatoms of said heterocycloalkyl rings are independently selected from the group consisting of: O, N, S, SO$_2$, SO, and P, and in other examples said heteroatoms of said heterocycloalkyl rings are independently selected from the group consisting of: O, N and S); and wherein those skilled in the art will appreciate that the substituted fused rings can be substituted with the $L^3$ groups on the substitutable atoms selected from the group consisting of: the ring carbons (including the carbon atoms common to the two fused rings) and the heteroatoms (e.g., N or S); and with the proviso that when X is —O— and m is 1, then at least one of $R^2$, $R^3$ or $R^4$ is not H;

Each $R^5$ is independently selected from the group consisting of: (1) H, (2) ($C_1$-$C_6$)alkyl, (3) hydroxyl substituted alkyl (such as, for example, alkyl substituted with at least one —OH group, such as, for example, ($C_1$ to $C_6$) alkyl substituted with 1 to 3 —OH groups, and in one example ($C_1$ to $C_6$) alkyl substituted with 1 or 2 —OH groups, and in another example ($C_1$ to $C_6$) alkyl substituted with 2 —OH groups, and in another example —CH$_2$CH(OH)CH$_2$CH$_3$ and in another example —CH$_2$CH$_2$CH(OH)CH$_2$OH), (4) $R^6$ (in one example $R^6$ is heteroaryl, such as, for example, pyridyl), (5) $R^7$, (6) —C(O)—($C_1$-$C_6$)alkyl, (7) —C(O)—($C_1$-$C_6$)haloalkyl, (8) —C(O)—$R^6$, (9) —C(O)—$R^7$, (10) —C(O)NH—($C_1$-$C_6$)alkyl, (11) —C(O)N(($C_1$-$C_6$)alkyl)$_2$ wherein each alkyl group is independently selected, (12) —S(O)$_2$—($C_1$-$C_6$)alkyl, (13) —S(O)$_2$—($C_1$-$C_6$)haloalkyl, (14) —S(O)$_2$—$R^6$, (15) —S(O)$_2$—$R^7$, (16) —S(O)$_2$—$R^8$, (17) -alkylene-C(O)—($C_1$-$C_6$)alkyl, (18) -alkylene-C(O)—($C_1$-$C_6$)haloalkyl, (19) -alkylene-C(O)—$R^6$, (20) -alkylene-C(O)—$R^7$, (21) -alkylene-S(O)$_2$—($C_1$-$C_6$)alkyl, (22) -alkylene-S(O)$_2$—($C_1$-$C_6$)haloalkyl, (23) -alkylene-S(O)$_2$—$R^6$, (24) -alkylene-S(O)$_2$—$R^7$, (25) -alkylene-S(O)$_2$—$R^8$, (26) -alkylene-NHC(O)—($C_1$-$C_6$)alkyl, (27) -alkylene-NHC(O)—($C_1$-$C_6$)haloalkyl, (28) -alkylene-NHC(O)—$R^6$, (29) -alkylene-NHC(O)—$R^7$, (30) -alkylene-NHS(O)$_2$—($C_1$-$C_6$)alkyl, (31) -alkylene-NHS(O)$_2$—($C_1$-$C_6$)haloalkyl, (32) -alkylene-NHS(O)$_2$—$R^6$, (33) -alkylene-NHS(O)$_2$—$R^7$, (34) -alkylene-N(alkyl)C(O)—($C_1$-$C_6$)alkyl (e.g., -alkylene-N(($C_1$-$C_6$)alkyl)-C(O)—($C_1$-$C_6$)alkyl, such as, for example, —CH$_2$N(C$_2$H$_5$)C(O)CH$_3$), (35) -alkylene-N(alkyl)C(O)—($C_1$-$C_6$)haloalkyl, (36) -alkylene-N(alkyl)C(O)—$R^6$, (37) -alkylene-N(alkyl)C(O)—$R^7$, (38) -alkylene-N(alkyl)S(O)$_2$—($C_1$-$C_6$)alkyl, (39) -alkylene-N(alkyl)S(O)$_2$—($C_1$-$C_6$)haloalkyl, (40) -alkylene-N(alkyl)S(O)$_2$—$R^6$, (41) -alkylene-N(alkyl)S(O)$_2$—$R^7$, (42) -alkylene-C(O)—NH—($C_1$-$C_6$) alkyl, (43) -alkylene-C(O)—NH$R^6$, (44) -alkylene-C(O)—NH$R^7$, (45) -alkylene-S(O)$_2$NH—($C_1$-$C_6$)alkyl, (46) -alkylene-S(O)$_2$NH—$R^6$, (47) -alkylene-S(O)$_2$NH—$R^7$, (48) -alkylene-C(O)—N(($C_1$-$C_6$)alkyl)$_2$ wherein each alkyl group is independently selected, (49) -alkylene-C(O)—N(alkyl)$R^6$, (50) -alkylene-C(O)—N(alkyl)$R^7$, (51) -alkylene-S(O)$_2$N(($C_1$-$C_6$)alkyl)$_2$ wherein each alkyl group is independently selected, (52) -alkylene-S(O)$_2$N(alkyl)-$R^6$, (53) -alkylene-S(O)$_2$N(alkyl)-$R^7$, (54) -alkylene-OH (e.g., —(CH$_2$)$_2$OH and —CH$_2$OH), (55) -alkylene-OC(O)—NHalkyl (e.g., -alkylene-OC(O)—NH—(C$_1$-C$_6$)alkyl), (56) -alkylene-OC(O)NH—R$^8$, (57) -alkylene-CN (e.g., —(CH$_2$)$_2$ CN), (58) —R$^8$ (e.g., cyclopropyl), (59) -alkylene-SH, (60) -alkylene-S(O)$_2$—NH—R$^8$ (wherein examples of said R$^8$ group in this moiety include cyclopropyl, cyclobutyl and cyclohexyl), (61) -alkylene-S(O)$_2$-alkylene-R$^6$ (e.g., -alkylene-S(O)$_2$-alkylene-heteroaryl, such as, for example, —CH$_2$—S(O)$_2$—CH$_2$-furanyl), (62) halo substituted alkylene (e.g., -alkylene-halo, such as, for example, —CH$_2$I), (63) —C(O)OR$^8$ (e.g., —C(O)O-cyclopentyl), (64) —C(O)O(C$_1$-C$_6$)alkyl (e.g., —C(O)OCH$_3$), (65) —C(O)R$^8$ (e.g., —C(O)-cyclopropyl), (66) —C(O)-alkylene-O—(C$_1$-C$_6$)alkyl (e.g., —C(O)—CH$_2$—O—CH$_3$), (67) —C(O)NH$_2$, (68) -alkylene-O—(C$_1$-C$_6$)alkyl (e.g. —CH$_2$OCH$_3$), (69) -alkylene-R$^8$ (e.g., —CH$_2$-cyclopropyl), (70) —S(O)$_2$-halo(C$_1$-C$_6$)alkyl (e.g., —S(O)$_2$CF$_3$), (71) hydroxy substituted halo(C$_1$-C$_6$) alkyl (e.g. —CH$_2$CH$_2$CH(OH)CF$_3$), (72) -alkylene-NH$_2$ (e.g., —CH$_2$NH$_2$), (73) -alkylene-NH—S(O)$_2$—R$^8$ (e.g., —CH$_2$—NH—S(O)$_2$-cyclopropyl), (74) -alkylene-NH—C(O)—R$^8$, (75) -alkylene-NH—C(O)O—(C$_1$-C$_6$)alkyl (e.g., —CH$_2$NHC(O)CH$_2$CH(CH$_3$)$_2$), (76) -alkylene-O—C(O)—(C$_1$-C$_6$)alkyl (e.g., —CH$_2$CH$_2$OC(O)CH$_3$), (77) -alkylene-O—S(O)$_2$—(C$_1$-C$_6$)alkyl (e.g., —CH$_2$CH$_2$OSO$_2$CH$_3$), (78) -alkylene-R$^6$ (e.g., —CH$_2$-isoxazolyl, —CH$_2$-benzothiazolyl, —CH$_2$-benzoimidazolyl, and —CH$_2$-phenyl), (79) -alkylene-R$^7$ (e.g., —CH$_2$-thiazolidinyl), (80) -alkylene-NH—C(O)—NH—(C$_1$-C$_6$)alkyl (e.g., —CH$_2$NHC(O)NHC$_2$H$_5$), (81) -alkylene-N(S(O)$_2$halo(C$_1$-C$_6$)alkyl)$_2$ wherein each —S(O)$_2$halo(C$_1$-C$_6$)alkyl moiety is independently selected, (82) -alkylene-N((C$_1$-C$_6$)alkyl)S(O)$_2$R$^8$ (e.g., —CH$_2$N(C$_2$H$_5$)S(O)$_2$-cyclopropyl), (83) -alkylene-OC(O)—N(alkyl)$_2$ (e.g., -alkylene-OC(O)—N(C$_1$-C$_6$)alkyl)$_2$) wherein each alkyl is independently selected, (84) -alkylene-NH—(C$_1$-C$_6$)alkyl (e.g., —CH$_2$NHCH$_3$), (85) —C(O)-alkylene-C(O)O—(C$_1$-C$_6$)alkyl (e.g., —C(O)CH$_2$C(O)OC$_2$H$_5$), (86) —C(O)—C(O)—O—(C$_1$-C$_6$)alkyl (e.g., —C(O)C(O)OCH$_3$), (87) —C(O)-alkylene-R$^6$ (e.g., —C(O)—CH$_2$-thienyl), (88) —C(O)—NH—R$^8$ (e.g., —C(O)—NH-cyclopentyl), (89) —C(O)—NH—R$^6$ (e.g., —C(O)—NH-thienyl), (90) —C(O)—NH-alkylene-R$^6$ (e.g., —C(O)—NH—(CH$_2$)$_2$-thienyl), (91) —C(O)-alkylene-NH—S(O)$_2$-halo(C$_1$-C$_6$)alkyl (e.g., —C(O)CH$_2$NHSO$_2$CF$_3$), (92) —C(O)-alkylene-NH—C(O)—O—(C$_1$-C$_6$)alkyl (e.g., —C(O)—CH$_2$—NH—C(O)—O-t-butyl), (93) —C(O)-alkylene-NH$_2$ (e.g., —C(O)CH$_2$NH$_2$), (94) —C(O)-alkylene-NH—S(O)$_2$—R$^8$ (e.g., —C(O)—CH$_2$—NH—S(O)$_2$-cyclopropyl), (95) —C(O)-alkylene-NH—S(O)$_2$—(C$_1$-C$_6$)alkyl (e.g., —C(O)CH$_2$NHS(O)$_2$CH$_3$), (96) —C(O)-alkylene-NH—C(O)—(C$_1$-C$_6$)alkyl (e.g., —C(O)CH$_2$NHC(O)CH$_3$), (97) —C(O)-alkylene-N(S(O)$_2$(C$_1$-C$_6$)alkyl)$_2$ wherein each —S(O)$_2$(C$_1$-C$_6$)alkyl moiety is independently selected (e.g. —C(O)CH$_2$N(S(O)$_2$C$_2$H$_5$)$_2$), (98) —C(O)-alkylene-NH—C(O)—NH—(C$_1$-C$_6$)alkyl (e.g., —C(O)CH$_2$NHC(O)NH-isopropyl), (99) -alkylene-O—R$^6$ (e.g., —(CH$_2$)$_3$OCH$_2$-phenyl), (100) -alkylene-R$^7$ (e.g., —CH$_2$-[1,3]dioxolanyl), (101) —C(O)OH, (102) -alkylene-N(S(O)$_2$(C$_1$-C$_6$)alkyl)$_2$ (e.g., —(CH$_2$)$_2$N(S(O)$_2$CH$_3$)$_2$), (103) -alkylene-C(O)—O—(C$_1$-C$_6$)alkyl (e.g., —CH$_2$C(O)OC$_2$H$_5$), (104) haloalkyl (i.e., halo substituted alkyl, such as, for example, —CF$_3$), (105) halo (e.g., F), (106) -alkylene —C(O)—NH$_2$ (e.g., —CH$_2$C(O)NH$_2$), (107) =N—O—(C$_1$-C$_6$)alkyl (e.g., =N—O—CH$_3$), (108) =N—O-alkylene-R$^6$ (e.g., =N—O—CH$_2$-phenyl), (109) =N—O-alkenyl (e.g., =N—O—CH$_2$=CH$_2$), (110) =N—O—R$^6$ (e.g., =N—O-phenyl), (111) =N—NH—S(O)$_2$—R$^6$ (e.g., =N—NH—S(O)$_2$-p-methylphenyl), (112) alkenyl (e.g., =CH$_2$, i.e., CH$_2$ double bonded to the rest of the molecule), (113)=R$^8$ (e.g., =cyclopropyl, i.e., cyclopropyl double bonded to the rest of the molecule), (114) -alkylene-O-alkylene-SK(C$_1$-C$_6$)alkyl)$_3$ wherein each alkyl is independently selected (e.g., —CH$_2$—O—(CH$_2$)$_2$Si(CH$_3$)$_3$), (115) -alkylene-S(O)$_2$—N(alkylene-R$^6$)$_2$ wherein each alkylene-R$^6$ moiety is independently selected (e.g., —(CH$_2$)$_2$—S(O)$_2$—N(CH$_2$-p-methoxyphenyl)$_2$), (116) -alkylene-S(O)$_2$—NH$_2$, (117) —O—C(O)—R$^9$, (118) —O—C(O)—(C$_1$-C$_6$) alkyl (e.g., —O—C(O)—CH$_3$), (119) —S(O)$_2$NH((C$_1$-C$_6$) alkyl), (120) —S(O)$_2$N((C$_1$-C$_6$)alkyl)$_2$ wherein each alkyl is independently selected, (121) —S(O)$_2$NHR$^8$ (e.g., —S(O)$_2$N-cyclopropyl), (122) -alkylene-C(O)OH (e.g., —CH$_2$C(O)OH), (123) -alkylene-C(O)NH(halo(C$_1$-C$_6$)alkyl) (e.g., —CH$_2$—C(O)NHCH$_2$CF$_3$), (124) -alkylene-C(O)—NH-alkylene-R$^8$ (e.g., —CH$_2$—C(O)—NH—CH$_2$-cyclopropyl), (125) -alkylene-C(O)—NH-alkylene-OH (e.g., —CH$_2$—C(O)—NH—CH$_2$CH$_2$—OH), (126) —C(O)O(haloC$_1$-C$_6$alkyl), (127) —C(O)OR$^6$, (128) —C(O)OR$^7$, (129) -alkylene-NHSO$_2$N(alkyl)$_2$ wherein each alkyl is independently selected, (130) -alkylene-NHSO$_2$NHalkyl, (131) -alkylene-N(alkyl)-SO$_2$N(alkyl)$_2$ wherein each alkyl is independently selected, (132) -alkylene-N(alkyl)-SO$_2$NHalkyl wherein each alkyl is independently selected, (133) -alkylene-O—SO$_2$-alkyl, (134) -alkylene-NH—C(O)—N(alkyl)$_2$ wherein each alkyl is independently selected, (135) -alkylene-NH—C(O)—NHalkyl, (136) -alkylene-N(alkyl)-C(O)—N(alkyl)$_2$ wherein each alkyl is independently selected, (137) -alkylene-N(alkyl)-C(O)—NHalkyl, (138) —CN, (139) -alkylene-P(O)(Oalkyl)$_2$ (e.g., -alkylene-P(O)(O(C$_1$-C$_6$) alkyl)$_2$) wherein each alkyl is independently selected, (140) -alkylene-CH(OH)—P(O)(Oalkyl)$_2$ (e.g., -alkylene-CH(OH)—P(O)(O(C$_1$-C$_6$)alkyl)$_2$ wherein each alkyl is independently selected, (141) -alkylene-OC(O)N(C$_1$-C$_6$ alkyl)-R$^8$, (142) -alkylene-S(O)$_2$—N(C$_1$-C$_6$ alkyl)-R$^8$, (143) -alkylene-N(C$_1$-C$_6$ alkyl)-S(O)$_2$—R$^8$, (144) -alkylene-N(C$_1$-C$_6$ alkyl)-C(O)—R$^8$, (145) -alkylene-N(C$_1$-C$_6$ alkyl)-C(O)O—(C$_1$-C$_6$)alkyl wherein each alkyl is independently selected, (146) -alkylene-N(C$_1$-C$_6$ alkyl)-C(O)—NH—(C$_1$-C$_6$)alkyl wherein each alkyl is independently selected, (147) -alkylene-NH—C(O)—N(C$_1$-C$_6$ alkyl)$_2$ wherein each alkyl is independently selected, (148) -alkylene-N(C$_1$-C$_6$ alkyl)-C(O)—N(C$_1$-C$_6$ alkyl)$_2$ wherein each alkyl is independently selected, (149) —C(O)—N(C$_1$-C$_6$ alkyl)-R$^8$, (150) —C(O)—N(C$_1$-C$_6$ alkyl)-R$^6$, (151) —C(O)—N(C$_1$-C$_6$ alkyl)-alkylene-R$^6$, (152) —C(O)-alkylene-N(C$_1$-C$_6$ alkyl)-S(O)$_2$-halo(C$_1$-C$_6$)alkyl wherein each alkyl is independently selected, (153) —C(O)-alkylene-N(C$_1$-C$_6$ alkyl)-C(O)—O—(C$_1$-C$_6$)alkyl wherein each alkyl is independently selected, (154) —C(O)-alkylene-NH(C$_1$-C$_6$ alkyl), (155) —C(O)-alkylene-N(C$_1$-C$_6$ alkyl)$_2$ wherein each alkyl is independently selected, (156) —C(O)-alkylene-N(C$_1$-C$_6$ alkyl)-S(O)$_2$—R$^8$, (157) —C(O)-alkylene-N(C$_1$-C$_6$ alkyl)-S(O)$_2$—(C$_1$-C$_6$)alkyl, (158) —C(O)-alkylene-N(C$_1$-C$_6$ alkyl)-C(O)—(C$_1$-C$_6$)alkyl, (159) —C(O)-alkylene-N(C$_1$-C$_6$ alkyl)-C(O)—NH—(C$_1$-C$_6$)alkyl wherein each alkyl is independently selected, (160) —C(O)-alkylene-NH—C(O)—N((C$_1$-C$_6$)alkyl)$_2$ wherein each alkyl is independently selected, (161) —C(O)-alkylene-N(C$_1$-C$_6$ alkyl)-C(O)—N((C$_1$-C$_6$)alkyl)$_2$ wherein each alkyl is independently selected, (162) -alkylene-C(O)—NH(C$_1$-C$_6$ alkyl), (163) -alkylene-C(O)—N(C$_1$-C$_6$ alkyl)$_2$ wherein each alkyl is independently selected, (164) =N—N(C$_1$-C$_6$ alkyl)-S(O)$_2$—R$^6$, (165) —S(O)$_2$N(C$_1$-C$_6$ alkyl)R$^8$, (166) -alkylene-C(O)N(C$_1$-C$_6$ alkyl)(halo(C$_1$-C$_6$)alkyl) wherein each alkyl group is independently selected, (167) -alkylene-C(O)N(halo(C$_1$-C$_6$) alkyl)$_2$ wherein each alkyl group is independently selected, (168) -alkylene-C(O)—N(C$_1$-C$_6$ alkyl)-alkylene-R$^8$, (169) -alkylene-C(O)—N(C$_1$-C$_6$ alkyl)-alkylene-OH, (170)

—O—C(O)—R$^7$ (e.g., —O—C(O)-(3-OH-pyrrolidinyl)); and wherein examples of the alkylene groups of the R$^5$ substituents include $C_1$-$C_6$ alkylene groups, for example, $C_1$ to $C_4$ alkylene groups, and in another example, $C_1$-$C_3$ alkylene groups, and in another example $C_1$ to $C_2$ alkylene groups; and wherein examples of the alkyl groups of the R$^5$ substituents include $C_1$-$C_6$ alkyl groups;

R$^6$ is selected from the group consisting of: unsubstituted ($C_6$-$C_{14}$)aryl, ($C_6$-$C_{14}$)aryl substituted with one or more L$^1$ groups, unsubstituted ($C_6$-$C_{14}$)heteroaryl, and ($C_5$-$C_{14}$)heteroaryl substituted with one or more L$^1$ groups;

R$^7$ is selected from the group consisting of unsubstituted heterocycloalkyl and heterocycloalkyl substituted with one or more L$^2$ groups (wherein examples of said heterocycloalkyl rings (unsubstituted or substituted) include 4 to 8 membered rings comprising 1 to 3 heteroatoms independently selected from the group consisting of: O, N, S, —S(O)$_2$, —S(O)—, Si and P, and in other examples said heteroatoms of said heterocycloalkyl rings are independently selected from the group consisting of: O, N, S, —S(O)$_2$, —S(O)—, and P, and in other examples said heteroatoms of said heterocycloalkyl rings are independently selected from the group consisting of: O, N and S);

R$^8$ is selected from the group consisting of unsubstituted cycloalkyl and cycloalkyl substituted with one or more L$^3$ groups (wherein examples of said cycloalkyl groups (unsubstituted or substituted) include C3-C10 cycloalkyl rings);

Ar is selected from the group consisting of: (a) unsubstituted aryl, (b) aryl substituted with one or more L$^1$ groups, (c) unsubstituted heteroaryl (e.g., pyridyl), and (d) substituted heteroaryl (e.g., substituted pyridyl) substituted with one or more L$^1$ groups;

R$^9$ is a bridged multicyclic heterocycloalkyl ring (e.g., a bridged bicyclic heterocycloalkyl ring) wherein said R$^9$ moiety is unsubstituted or said R$^9$ moiety is substituted with one or more L$^2$ groups, and wherein said heterocycloalkyl rings include 4 to 8 membered rings comprising 1 to 3 heteroatoms independently selected from the group consisting of: O, N, S, Si and P (and in one example said heteroatoms are N), examples of said R$^9$ moiety include but are not limited to:

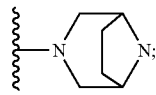

each L$^1$ is independently selected from the group consisting of: halogen, alkyl (e.g., $C_1$-$C_6$ alkyl), —CN, —CF$_3$, —O—($C_1$-$C_6$)alkyl (e.g., —OCH$_3$), —O-(halo($C_1$-$C_6$)alkyl) (e.g., —OCF$_3$), —C(O)—O—($C_1$-$C_6$)alkyl (e.g., —C(O)OCH$_3$), -alkylene-OH(—CH$_2$OH), halo($C_1$-$C_6$)alkyl (e.g., —CF$_3$), hydroxyalkoxy—(e.g., HOCH$_2$CH$_2$O—), and alkoxyalkoxy—(e.g., CH$_3$OCH$_2$CH$_2$O—);

each L$^2$ is independently selected from the group consisting of: (a) —OH, (b) alkyl (e.g., $C_1$-$C_6$ alkyl), (c) alkyl (e.g., $C_1$-$C_6$ alkyl), substituted with one or more —OH groups, (d) halo, (e) haloalkyl (e.g., halo($C_1$-$C_6$)alkyl), and (f) heterocycloalkyl (e.g., said heterocycloalkyl rings include unsubstituted or substituted heterocycloalkyl rings comprising 4 to 8 membered rings comprising 1 to 3 heteroatoms independently selected from the group consisting of: O, N, S, and in other examples said heteroatoms of said heterocycloalkyl rings are independently selected from the group consisting of: O, N, S and P, and in other examples said heteroatoms of said heterocycloalkyl rings are independently selected from the group consisting of: O, N and S and P);

each L$^3$ is independently selected from the group consisting of: —CN, =O, R$^5$, —OR$^5$; =N—R$^5$ and —N(R$^5$)$_2$ (e.g., —NHR$^5$); (in one example L$^3$ is selected from the group consisting of: —CH$_2$OH, —CH$_2$NH$_2$, —CH$_2$NHalkyl (such as, for example, —CH$_2$NH($C_1$-$C_6$)alkyl), and —C(O)OH, and in another example L$^3$ is selected from the group consisting of: -alkylene-C(O)NH($C_1$ to $C_6$)alkyl, -alkylene-C(O)N(($C_1$ to $C_6$)alkyl)$_2$ wherein each alkyl is independently selected, -alkylene-C(O)NH($C_1$ to $C_6$)haloalkyl, and -alkylene-C(O)N(($C_1$ to $C_6$)haloalkyl)$_2$ wherein each alkyl is independently selected);

n is 0, 1, 2 or 3; and m is 0, 1, 2, or 3; and provided that for the substituent —OR$^5$, the R$^5$ moiety and the oxygen atom to which it is bound to does not form a —O—O— group (i.e., for the substituent —OR$^5$, the R$^5$ moiety is not bound through an oxygen atom of the R$^5$ moiety to the oxygen atom of the —OR$^5$ substituent); and provided that for the substituents —OR$^5$, =N—R$^5$ and —NHR$^5$, R$^5$ is not —CH$_2$OH, —CH$_2$NH$_2$, —CH$_2$NHalkyl, —CH$_2$NHaryl or —C(O)OH.

In a first embodiment, the present invention is directed to compounds of Formula (I), or pharmaceutically acceptable salts, solvates or esters thereof, as described herein above.

Another embodiment of this invention is directed to compounds of formula (I).

Another embodiment of this invention is directed to pharmaceutically acceptable salts of the compounds of formula (I).

Another embodiment of this invention is directed to solvates of the compounds of formula (I).

Another embodiment of this invention is directed to pharmaceutically acceptable esters of the compounds of formula (I).

In one embodiment of the compounds of formula (I), Ar is unsubstituted aryl (e.g., unsubstituted phenyl).

In another embodiment of the compounds of formula (I), Ar is substituted aryl (e.g., substituted phenyl).

In another embodiment of the compounds of formula (I), Ar is unsubstituted heteroaryl (e.g., unsubstituted pyridyl).

In another embodiment of the compounds of formula (I), Ar is substituted heteroaryl (e.g., substituted pyridyl).

In one embodiment of the compounds of formula (I), Ar is unsubstituted aryl (e.g., unsubstituted phenyl) and said compound of formula (I) is a compound of formula (IA).

In another embodiment of the compounds of formula (I), Ar is substituted aryl (e.g., substituted phenyl) and said compound of formula (I) is a compound of formula (IA).

In another embodiment of the compounds of formula (I), Ar is unsubstituted heteroaryl (e.g., unsubstituted pyridyl) and said compound of formula (I) is a compound of formula (IA).

In another embodiment of the compounds of formula (I), Ar is substituted heteroaryl (e.g., substituted pyridyl) and said compound of formula (I) is a compound of formula (IA).

In one embodiment of the compounds of formula (I), Ar is unsubstituted aryl (e.g., unsubstituted phenyl) and said compound of formula (I) is a compound of formula (IB).

In another embodiment of the compounds of formula (I), Ar is substituted aryl (e.g., substituted phenyl) and said compound of formula (I) is a compound of formula (IB).

In another embodiment of the compounds of formula (I), Ar is unsubstituted heteroaryl (e.g., unsubstituted pyridyl) and said compound of formula (I) is a compound of formula (IB).

In another embodiment of the compounds of formula (I), Ar is substituted heteroaryl (e.g., substituted pyridyl) and said compound of formula (I) is a compound of formula (IB).

In one embodiment of the compounds of formula (I), Ar is unsubstituted aryl (e.g., unsubstituted phenyl) and said compound of formula (I) is a compound of formula (IC).

In another embodiment of the compounds of formula (I), Ar is substituted aryl (e.g., substituted phenyl) and said compound of formula (I) is a compound of formula (IC).

In another embodiment of the compounds of formula (I), Ar is unsubstituted heteroaryl (e.g., unsubstituted pyridyl) and said compound of formula (I) is a compound of formula (IC).

In another embodiment of the compounds of formula (I), Ar is substituted heteroaryl (e.g., substituted pyridyl) and said compound of formula (I) is a compound of formula (IC).

In one embodiment of the compounds of formula (I), Ar is unsubstituted aryl (e.g., unsubstituted phenyl) and said compound of formula (I) is a compound of formula (ID).

In another embodiment of the compounds of formula (I), Ar is substituted aryl (e.g., substituted phenyl) and said compound of formula (I) is a compound of formula (ID).

In another embodiment of the compounds of formula (I), Ar is unsubstituted heteroaryl (e.g., unsubstituted pyridyl) and said compound of formula (I) is a compound of formula (ID).

In another embodiment of the compounds of formula (I), Ar is substituted heteroaryl (e.g., substituted pyridyl) and said compound of formula (I) is a compound of formula (ID).

In one embodiment of the compounds of formula (I), Ar is unsubstituted aryl (e.g., unsubstituted phenyl) and said compound of formula (I) is a compound of formula (IE).

In another embodiment of the compounds of formula (I), Ar is substituted aryl (e.g., substituted phenyl) and said compound of formula (I) is a compound of formula (IE).

In another embodiment of the compounds of formula (I), Ar is unsubstituted heteroaryl (e.g., unsubstituted pyridyl) and said compound of formula (I) is a compound of formula (IE).

In another embodiment of the compounds of formula (I), Ar is substituted heteroaryl (e.g., substituted pyridyl) and said compound of formula (I) is a compound of formula (IE).

In one embodiment of the compounds of formula (I), Ar is unsubstituted aryl (e.g., unsubstituted phenyl) and said compound of formula (I) is a compound of formula (IF).

In another embodiment of the compounds of formula (I), Ar is substituted aryl (e.g., substituted phenyl) and said compound of formula (I) is a compound of formula (IF).

In another embodiment of the compounds of formula (I), Ar is unsubstituted heteroaryl (e.g., unsubstituted pyridyl) and said compound of formula (I) is a compound of formula (IF).

In another embodiment of the compounds of formula (I), Ar is substituted heteroaryl (e.g., substituted pyridyl) and said compound of formula (I) is a compound of formula (IF).

In one embodiment of the compounds of formula (I), Ar is unsubstituted aryl (e.g., unsubstituted phenyl) and said compound of formula (I) is a compound of formula (IF.1A).

In another embodiment of the compounds of formula (I), Ar is substituted aryl (e.g., substituted phenyl) and said compound of formula (I) is a compound of formula (IF.1A).

In another embodiment of the compounds of formula (I), Ar is unsubstituted heteroaryl (e.g., unsubstituted pyridyl) and said compound of formula (I) is a compound of formula (IF.1A).

In another embodiment of the compounds of formula (I), Ar is substituted heteroaryl (e.g., substituted pyridyl) and said compound of formula (I) is a compound of formula (IF.1A).

In one embodiment of the compounds of formula (I), Ar is unsubstituted aryl (e.g., unsubstituted phenyl) and said compound of formula (I) is a compound of formula (IG).

In another embodiment of the compounds of formula (I), Ar is substituted aryl (e.g., substituted phenyl) and said compound of formula (I) is a compound of formula (IG).

In another embodiment of the compounds of formula (I), Ar is unsubstituted heteroaryl (e.g., unsubstituted pyridyl) and said compound of formula (I) is a compound of formula (IG).

In another embodiment of the compounds of formula (I), Ar is substituted heteroaryl (e.g., substituted pyridyl) and said compound of formula (I) is a compound of formula (IG).

In one embodiment of the compounds of formula (I), Ar is unsubstituted aryl (e.g., unsubstituted phenyl) and said compound of formula (I) is a compound of formula (IH).

In another embodiment of the compounds of formula (I), Ar is substituted aryl (e.g., substituted phenyl) and said compound of formula (I) is a compound of formula (IH).

In another embodiment of the compounds of formula (I), Ar is unsubstituted heteroaryl (e.g., unsubstituted pyridyl) and said compound of formula (I) is a compound of formula (IH).

In another embodiment of the compounds of formula (I), Ar is substituted heteroaryl (e.g., substituted pyridyl) and said compound of formula (I) is a compound of formula (IH).

In one embodiment of the compounds of formula (I) one or more $L^3$ groups are —$N(R^5)_2$ substituents wherein one of the $R^5$ groups is H, i.e., one or more of the $L^3$ groups is —$NHR^5$. Thus, in one embodiment of the compounds of formula (I), each $L^3$ is independently selected from: =O, $R^5$, —$OR^5$— $NHR^5$, and —$N(R^5)_2$ In one preferred embodiment of the compounds of formula (I) each $L^3$ is the same or different —$NHR^5$ group, and each $R^5$ is independently selected from the group consisting of: —$S(O)_2$—$(C_1$-$C_6)$alkyl, —$S(O)_2$—$(C_1$-$C_6)$haloalkyl, —$S(O)_2R^6$, —$S(O)_2R^7$, and —$S(O)_2R^8$.

In another preferred embodiment of the compounds of formula (I) each $L^3$ is the same or different $OR^5$ group, and each $R^5$ is independently selected from the group consisting of: H, $(C_1$-$C_6)$alkyl, $R^6$, $R^7$, —C(O)—$(C_1$-$C_6)$alkyl, —C(O)—$C_1$-$C_6)$haloalkyl, —C(O)—$R^6$, and —C(O)—$R^7$.

In another preferred embodiment of the compounds of formula (I) each $L^3$ is the same or different $R^5$ group, and each $R^5$ is independently selected from the group consisting of: H, $(C_1$-$C_6)$alkyl, $R^6$, $R^7$, —$S(O)_2$—$(C_1$-$C_6)$alkyl, —$S(O)_2$— $(C_1$-$C_6)$haloalkyl, —$S(O)_2R^6$, —$S(O)_2R^7$, —$S(O)_2R^8$, —C(O)—$(C_1$-$C_6)$alkyl, —C(O)—$(C_1$-$C_6)$haloalkyl, —C(O)—$R^6$, and —C(O)—$R^7$.

Thus, another embodiment of this invention is directed to compounds of Formula (I), or pharmaceutically acceptable salts, solvates or esters thereof, wherein each $L^3$ is the same or different —$NHR^5$ group, and each $R^5$ is independently selected from the group consisting of: —$S(O)_2$—$(C_1$-$C_6)$ alkyl, —$S(O)_2$—$(C_1$-$C_6)$haloalkyl, —$S(O)_2R^6$, —$S(O)_2R^7$, and —$S(O)_2R^8$.

Another embodiment of this invention is directed to compounds of Formula (I) wherein each $L^3$ is the same or different —$NHR^5$ group, and each $R^5$ is independently selected from the group consisting of: —$S(O)_2$—$(C_1$-$C_6)$alkyl, —$S(O)_2$— $(C_1$-$C_6)$haloalkyl, —$S(O)_2R^6$, —$S(O)_2R^7$, and —$S(O)_2R^8$.

Another embodiment of this invention is directed to the pharmaceutically acceptable salts of the compounds of Formula (I) wherein each $L^3$ is the same or different —$NHR^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2$R$^6$, and —S(O)$_2$R$^7$, and —S(O)$_2$R$^8$.

Another embodiment of this invention is directed to solvates of the compounds of Formula (I) wherein each $L^3$ is the same or different —NHR$^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2$R$^6$, and —S(O)$_2$R$^7$, and —S(O)$_2$R$^8$.

Another embodiment of this invention is directed to the pharmaceutically acceptable esters of the compounds of Formula (I) wherein each $L^3$ is the same or different —NHR$^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2$R$^6$, and —S(O)$_2$R$^7$, and —S(O)$_2$R$^8$.

Another embodiment of this invention is directed to compounds of Formula (I), or pharmaceutically acceptable salts, solvates or esters thereof, wherein each $L^3$ is the same or different OR$^5$ group, and each $R^5$ is independently selected from the group consisting of: H, (C$_1$-C$_6$)alkyl, R$^6$, R$^7$, —C(O)—(C$_1$-C$_6$)alkyl, —C(O)—C$_1$-C$_6$)haloalkyl, —C(O)—R$^6$, and —C(O)—R$^7$.

Another embodiment of this invention is directed to compounds of Formula (I) wherein each $L^3$ is the same or different OR$^5$ group, and each $R^5$ is independently selected from the group consisting of: H, (C$_1$-C$_6$)alkyl, R$^6$, R$^7$, —C(O)—(C$_1$-C$_6$)alkyl, —C(O)—C$_1$-C$_6$)haloalkyl, —C(O)—R$^6$, and —C(O)—R$^7$.

Another embodiment of this invention is directed to the pharmaceutically acceptable salts of the compounds of Formula (I) wherein each $L^3$ is the same or different OR$^5$ group, and each $R^5$ is independently selected from the group consisting of: H, (C$_1$-C$_6$)alkyl, R$^6$, R$^7$, —C(O)—(C$_1$-C$_6$)alkyl, —C(O)—C$_1$-C$_6$)haloalkyl, —C(O)—R$^6$, and —C(O)—R$^7$.

Another embodiment of this invention is directed to solvates of the compounds of Formula (I) wherein each $L^3$ is the same or different OR$^5$ group, and each $R^5$ is independently selected from the group consisting of: H, (C$_1$-C$_6$)alkyl, R$^6$, R$^7$, —C(O)—(C$_1$-C$_6$)alkyl, —C(O)—C$_1$-C$_6$)haloalkyl, —C(O)—R$^6$, and —C(O)—R$^7$.

Another embodiment of this invention is directed to the pharmaceutically acceptable esters of the compounds of Formula (I) wherein each $L^3$ is the same or different OR$^5$ group, and each $R^5$ is independently selected from the group consisting of: H, (C$_1$-C$_6$)alkyl, R$^6$, R$^7$, —C(O)—(C$_1$-C$_6$)alkyl, —C(O)—C$_1$-C$_6$)haloalkyl, —C(O)—R$^6$, and —C(O)—R$^7$.

Another embodiment of this invention is directed to compounds of Formula (I), or pharmaceutically acceptable salts, solvates or esters thereof, wherein each $L^3$ is the same or different R$^5$ group, and each $R^5$ is independently selected from the group consisting of: H, (C$_1$-C$_6$)alkyl, R$^6$, R$^7$, —S(O)$_2$—(C$_1$-C$_6$)alkyl, —S(O)$_2$—(C$_1$-C$_6$)haloalkyl, —S(O)$_2$R$^6$, S(O)$_2$R$^7$, —S(O)$_2$R$^8$, —C(O)—(C$_1$-C$_6$)alkyl, —C(O)—(C$_1$-C$_6$)haloalkyl, —C(O)—R$^6$, and —C(O)—R$^7$.

Another embodiment of this invention is directed to compounds of Formula (I) wherein each $L^3$ is the same or different R$^5$ group, and each $R^5$ is independently selected from the group consisting of: H, (C$_1$-C$_6$)alkyl, R$^6$, R$^7$, —S(O)$_2$—(C$_1$-C$_6$)alkyl, —S(O)$_2$—(C$_1$-C$_6$)haloalkyl, —S(O)$_2$R$^6$, —S(O)$_2$R$^7$, —S(O)$_2$R$^8$, —C(O)—(C$_1$-C$_6$)alkyl, —C(O)—(C$_1$-C$_6$)haloalkyl, —C(O)—R$^6$, and —C(O)—R$^7$.

Another embodiment of this invention is directed to the pharmaceutically acceptable salts of the compounds of Formula (I) wherein each $L^3$ is the same or different R$^5$ group, and each $R^5$ is independently selected from the group consisting of: H, (C$_1$-C$_6$)alkyl, R$^6$, R$^7$, —S(O)$_2$—(C$_1$-C$_6$)alkyl, —S(O)$_2$—(C$_1$-C$_6$)haloalkyl, —S(O)$_2$R$^6$, —S(O)$_2$R$^7$, —S(O)$_2$R$^8$, —C(O)—(C$_1$-C$_6$)alkyl, —C(O)—(C$_1$-C$_6$)haloalkyl, —C(O)—R$^6$, and —C(O)—R$^7$.

Another embodiment of this invention is directed to solvates of the compounds of Formula (I) wherein each $L^3$ is the same or different R$^5$ group, and each $R^5$ is independently selected from the group consisting of: H, (C$_1$-C$_6$)alkyl, R$^6$, R$^7$, —S(O)$_2$—(C$_1$-C$_6$)alkyl, —S(O)$_2$—(C$_1$-C$_6$)haloalkyl, —S(O)$_2$R$^6$, S(O)$_2$R$^7$, —S(O)$_2$R$^8$, —C(O)—(C$_1$-C$_6$)alkyl, —C(O)—(C$_1$-C$_6$)haloalkyl, —C(O)—R$^6$, and —C(O)—R$^7$.

Another embodiment of this invention is directed to the pharmaceutically acceptable esters of the compounds of Formula (I) wherein each $L^3$ is the same or different R$^5$ group, and each $R^5$ is independently selected from the group consisting of: H, (C$_1$-C$_6$)alkyl, R$^6$, R$^7$, —S(O)$_2$—(C$_1$-C$_6$)alkyl, —S(O)$_2$—(C$_1$-C$_6$)haloalkyl, —S(O)$_2$R$^6$, —S(O)$_2$R$^7$, —S(O)$_2$R$^8$, —C(O)—(C$_1$-C$_6$)alkyl, —C(O)—(C$_1$-C$_6$)haloalkyl, —C(O)—R$^6$, and —C(O)—R$^7$.

In another embodiment of the compounds of Formula (I), or pharmaceutically acceptable salts, solvates and/or esters thereof:

$R^1$ is selected from the group consisting of H and (C$_1$-C$_6$) alkyl;

$R^2$ is selected from the group consisting of H, —(C$_1$-C$_6$) alkyl, —(C$_1$-C$_6$)alkylene-OR$^5$, —(C$_1$-C$_6$)alkylene-R$^6$, —(C$_1$-C$_6$)alkylene-C(O)O—(C$_1$-C$_6$)alkyl, —(C$_1$-C$_6$)alkylene-R$^8$, —C(O)O—(C$_1$-C$_6$)alkyl, and —(C$_2$-C$_6$)alkenyl;

$R^3$ is selected from the group consisting of H, —(C$_1$-C$_6$) alkyl, —(C$_1$-C$_6$)alkylene-OR$^5$, —(C$_2$-C$_6$)alkenyl, —C(O)O—(C$_1$-C$_6$)alkyl, and —(C$_1$-C$_6$)alkylene-C(O)O—(C$_1$-C$_6$) alkyl; or $R^2$ and $R^3$, or $R^2$ and an $R^4$, or $R^3$ and an $R^4$, together with the atoms to which they are shown attached form a fused (C$_3$-C$_{10}$)cycloalkyl ring, wherein said fused (C$_3$-C$_{10}$)cycloalkyl ring is unsubstituted or substituted with one or more $L^3$ groups;

each $R^4$ is independently selected from the group consisting of H, —(C$_1$-C$_6$)alkyl, and —(C$_1$-C$_6$)alkylene-R$^6$; and with the proviso that when X is —O— and m is 1, at least one of $R^2$, $R^3$ or $R^4$ is not H;

each $R^5$ is independently selected from the group consisting of H, (C$_1$-C$_6$)alkyl, R$^6$, —C(O)—(C$_1$-C$_6$)alkyl, —C(O)—R$^6$, and —C(O)—R$^7$;

$R^6$ is selected from the group consisting of unsubstituted (C$_6$-C$_{14}$)aryl and (C$_6$-C$_{14}$)aryl substituted with one or more $L^1$ groups;

$R^7$ is selected from the group consisting of unsubstituted (C$_3$-C$_{10}$)heterocycloalkyl and (C$_3$-C$_{10}$)heterocycloalkyl substituted with one or more $L^2$ groups;

$R^8$ is selected from the group consisting of unsubstituted (C$_3$-C$_{10}$)cycloalkyl and (C$_3$-C$_{10}$)cycloalkyl substituted with one or more $L^3$ groups;

Ar is unsubstituted aryl or aryl substituted with one or more $L^1$ groups;

each $L^1$ is independently selected from the group consisting of halogen, (C$_1$-C$_6$)alkyl, —CN, and —CF$_3$; and each $L^2$ is independently selected from the group consisting of —OH, (C$_1$-C$_6$)alkyl, (C$_1$-C$_6$)alkyl substituted with one or more —OH groups, and (C$_3$-C$_{10}$)heterocycloalkyl.

In another embodiment, the compounds of Formula (I), or pharmaceutically acceptable salts, solvates and/or esters thereof, have the following Formula (IA):

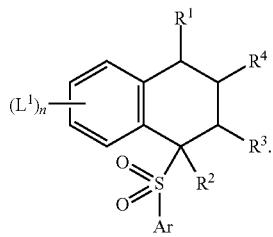

In another embodiment, the compounds of Formula (I), or pharmaceutically acceptable salts, solvates and/or esters thereof, have the following Formula (IB):

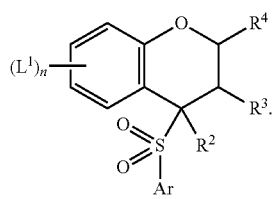

In another embodiment, the compounds of Formula (I), or pharmaceutically acceptable salts, solvates and/or esters thereof, have the following Formula (IC):

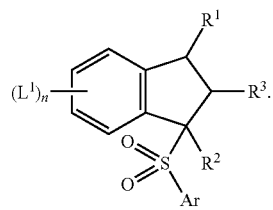

In another embodiment, the compounds of Formula (I), or pharmaceutically acceptable salts, solvates and/or esters thereof, have the following Formula (ID):

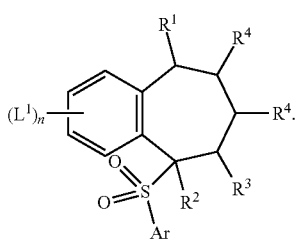

In another embodiment, the compounds of Formula (I), or pharmaceutically acceptable salts, solvates and/or esters thereof, have the following Formula (IE):

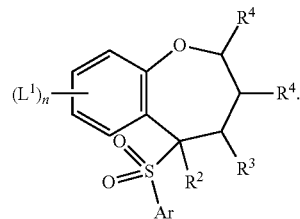

In another embodiment, the compounds of Formula (I), or pharmaceutically acceptable salts, solvates and/or esters thereof, have the following Formula (IA):

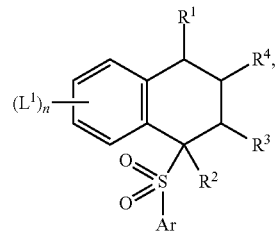

wherein:
$R^1$ is H or alkyl;
$R^2$ is selected from the group consisting of H, alkyl, alkylene-$OR^5$, -alkylene-$R^6$, -alkylene-C(O)O-alkyl, —C(O)O-alkyl, and alkenyl;
$R^3$ is selected from the group consisting of H, alkyl, alkylene-$OR^5$, and -alkylene-C(O)O-alkyl;
$R^4$ is independently H or alkyl;
each $R^5$ is independently H or —C(O)—$R^7$;
$R^6$ is selected from the group consisting of unsubstituted aryl and aryl substituted with one or more $L^1$ groups;
$R^7$ is selected from the group consisting of unsubstituted heterocycloalkyl and heterocycloalkyl substituted with one or more $L^2$ groups;
Ar is unsubstituted aryl or aryl substituted with one or more $L^1$ groups;
each $L^1$ is independently halogen or alkyl;
each $L^2$ is independently —OH or heterocycloalkyl; and
n is 0, 1, or 2.

In another embodiment, the compounds of Formula (I), or pharmaceutically acceptable salts, solvates and/or esters thereof, have the following Formula (IA):

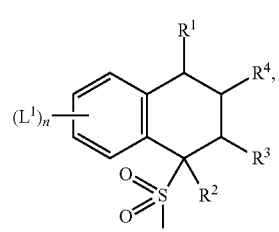

wherein:
$R^1$ is H or —$CH_3$;
$R^2$ is selected from the group consisting of H, —CH($CH_3$)$_2$, —$CH_3$, —$CH_2CH_3$, —($CH_2$)$_3CH_3$, —$CH_2$—$R^6$, —CH₂CH₂—OH, —CH₂—C(O)O—CH₂CH₃, —C(O)O—CH₂CH₃, —CH₂CH₂—O—C(O)-pyrrolidinyl substituted with one or more L² group, —CH₂CH₂—O—C(O)-piperidyl substituted with one or more L² group, —CH₂CH=CH₂,
R³ is selected from the group consisting of H, —CH₃, —CH₂CH₃, —CH₂—OH, —CH₂—O—C(O)-piperidyl substituted with one or more L² group, —CH₂—O—C(O)-pyrrolidinyl substituted with one or more L² group, —CH₂—C(O)O—CH₃, —CH₂—C(O)O—CH₂CH₃, ;
R⁴ is H or —CH₃;
R⁶ is selected from the group consisting of unsubstituted phenyl and phenyl substituted with one or more L¹ groups;
Ar is unsubstituted phenyl or phenyl substituted with one or more L¹ groups;
each L¹ is independently F, CL or —CH₃;
each L² is independently —OH or piperidyl; and
n is 0, 1 or 2.

In another embodiment, the compounds of Formula (I), or pharmaceutically acceptable salts, solvates and/or esters thereof, have the following Formula (IB):

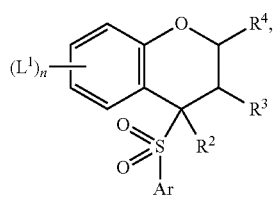

wherein:
R² is selected from the group consisting of H, alkyl, alkylene-OR⁵, -alkylene-R⁶, -alkylene-C(O)O-alkyl, -alkylene-R⁸, and alkenyl;
R³ is selected from the group consisting of H, alkyl, and alkylene-OR⁵; or
R² and R³, or R² and an R⁴, or R³ and an R⁴, together with the atoms to which they are shown attached form a fused cycloalkyl or heterocycloalkyl ring, wherein said fused cycloalkyl or heterocycloalkyl ring is unsubstituted or substituted with one or more L³ groups;
R⁴ is selected from the group consisting of H, alkyl, and -alkylene-R⁶;
each R⁵ is independently selected from the group consisting of H, alkyl, and —C(O)—R⁷;
R⁶ is selected from the group consisting of unsubstituted aryl and aryl substituted with one or more L¹ groups;
R⁷ is selected from the group consisting of unsubstituted heterocycloalkyl and heterocycloalkyl substituted with one or more L² groups;
R⁸ is selected from the group consisting of unsubstituted cycloalkyl and cycloalkyl substituted with one or more L³ groups;
Ar is unsubstituted aryl or aryl substituted with one or more L¹ groups;
each L¹ is independently halogen or alkyl;
each L² is independently selected from the group consisting of —OH, alkyl, alkyl substituted with one or more —OH groups, and heterocycloalkyl;
each L³ is —OR⁵; and
n is an integer of from 0 to 3.

In another embodiment, the compounds of Formula (I), or pharmaceutically acceptable salts, solvates and/or esters thereof, have the following Formula (IB):

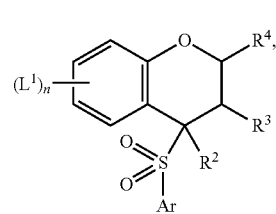

wherein:
R² is selected from the group consisting of H, —CH₂—C(O)O—CH₃, —CH₃, —CH₂CH₃, —CH(CH₃)₂, —CH₂—R⁶, —CH₂—R⁸, —CH₂CH₂—OR⁵, —CH₂CH=CH₂, and —CH(CH₃)CH₂CH₂—OH;
R³ is selected from the group consisting of H, —CH₃, —CH₂—OH, and —CH₂—O—CH₃; or
R² and R³, or R² and an R⁴, or R³ and an R⁴, together with the atoms to which they are shown attached form a fused cycloalkyl or heterocycloalkyl ring, wherein said fused cycloalkyl or heterocycloalkyl ring is unsubstituted or substituted with one or more L³ groups;
R⁴ is selected from the group consisting of H, —CH₃, —CH₂CH₃, and —CH₂—R⁶;
each R⁵ is independently selected from H or —C(O)—R⁷;
R⁶ is selected from the group consisting of unsubstituted phenyl and phenyl substituted with one or more L¹ groups;
R⁷ is selected from the group consisting of unsubstituted piperidyl, piperidyl substituted with one or more L² groups, unsubstituted piperazinyl, piperazinyl substituted with one or more L² groups, unsubstituted pyrrolidinyl, pyrrolidinyl substituted with one or more L² groups;
R⁸ is selected from the group consisting of unsubstituted cyclopropyl and cyclopropyl substituted with one or more L³ groups;
Ar is unsubstituted phenyl or phenyl substituted with one or more L¹ groups;
each L¹ is independently F, Cl, or —CH₃;
each L² is independently selected from the group consisting of —OH, —CH₂CH₂—OH, piperidyl, and —C(CH₃)₃;
each L³ is independently —OH or —C(O)—R⁷; and
n is 0, 1, 2, or 3.

In another embodiment, the compounds of Formula (I), or pharmaceutically acceptable salts, solvates and/or esters thereof, have the following Formula (IC):

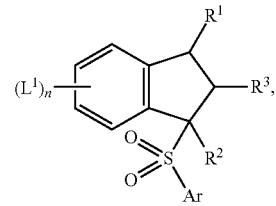

wherein:
R¹ is selected from the group consisting of H and alkyl;
R² is H;
R³ is H;
Ar is unsubstituted aryl or aryl substituted with one or more L¹ groups;
each L¹ is independently selected from the group consisting of halogen, alkyl, —CN, and —CF₃; and
n is 0, 1, or 2.

In another embodiment, the compounds of Formula (I), or pharmaceutically acceptable salts, solvates and/or esters thereof, have the following Formula (IC):

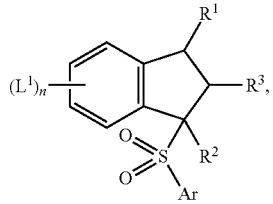
(IC)

wherein:
$R^1$ is selected from the group consisting of H and —$CH_3$;
$R^2$ is H;
$R^3$ is H;
Ar is unsubstituted phenyl or phenyl substituted with one or more $L^1$ groups;
each $L^1$ is independently F or CL; and
n is 0, 1, or 2.

In another embodiment, the compounds of Formula (I), or pharmaceutically acceptable salts, solvates and/or esters thereof, have the following Formula (ID):

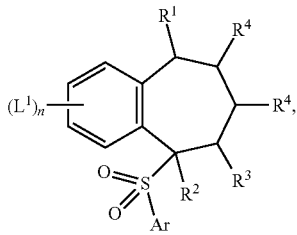
(ID)

wherein:
$R^1$ is H;
$R^2$ is selected from the group consisting of H, alkyl, and alkenyl;
$R^3$ is selected from the group consisting of H, alkyl, and alkenyl;
each $R^4$ is H;
Ar is unsubstituted aryl or aryl substituted with one or more $L^1$ groups;
each $L^1$ is independently selected from the group consisting of halogen, alkyl, —CN, and —$CF_3$; and
n is 0, 1, 2 or 3.

In another embodiment, the compounds of Formula (I), or pharmaceutically acceptable salts, solvates and/or esters thereof, have the following Formula (ID):

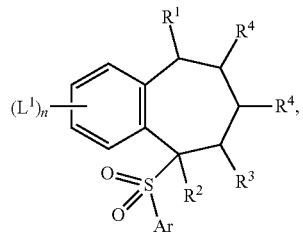
(ID)

wherein:
$R^1$ is H;
$R^2$ is selected from the group consisting of H, —$CH_3$, —CH($CH_3$)$_2$, and —$CH_2CH{=}CH_2$;
$R^3$ is selected from the group consisting of H, —$CH_3$, and —$CH_2CH{=}CH_2$;
each $R^4$ is H;
Ar is unsubstituted phenyl or phenyl substituted with one or more $L^1$ groups;
each $L^1$ is independently F or CL; and
n is 0, 1, or 2.

In another embodiment, the compounds of Formula (I), or pharmaceutically acceptable salts, solvates and/or esters thereof, have the following Formula (IE):

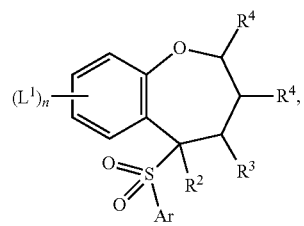
(IE)

wherein:
$R^2$ is H or alkyl;
$R^3$ is H or alkyl;
each $R^4$ is H;
Ar is unsubstituted aryl or aryl substituted with one or more $L^1$ groups;
each $L^1$ is independently selected from the group consisting of halogen, alkyl, —CN, and —$CF_3$; and
n is 0, 1, 2 or 3.

In another embodiment, the compounds of Formula (I), or pharmaceutically acceptable salts, solvates and/or esters thereof, have the following Formula (IE):

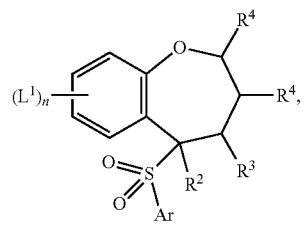
(IE)

wherein:
$R^2$ is H or —$CH_3$;
$R^3$ is H or —$CH_3$;
each $R^4$ is H;

Ar is unsubstituted phenyl or phenyl substituted with one or more $L^1$ groups;

each $L^1$ is independently F or CL; and n is 0, 1, or 2.

In another embodiment of the compounds of Formula (I), or pharmaceutically acceptable salts, solvates and/or esters thereof, $R^2$ and $R^3$, or $R^2$ and an $R^4$, or $R^3$ and an $R^4$, together with the atoms to which they are shown attached form a fused cycloalkyl or heterocycloalkyl ring, wherein said fused cycloalkyl or heterocycloalkyl ring is unsubstituted or substituted with one or more $L^3$ groups.

For example, compounds of formula (I) include compounds wherein $R^2$ and $R^3$ together with the carbon atoms to which they are shown attached form a fused ring (Q), such compounds have the formula (IF) or (IF.1A):

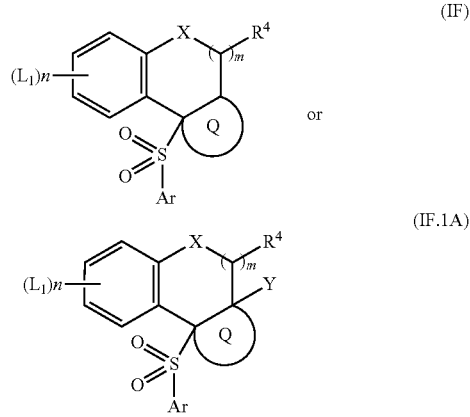

wherein Q is a fused ring selected from the group consisting of: unsubstituted cycloalkyl, cycloalkyl substituted with one or more independently selected $L^3$ groups, unsubstituted heterocycloalkyl, and heterocycloalkyl substituted with one or more independently selected $L^3$ groups, and wherein Y is bound to the carbon atom common to the two fused rings and Y is selected from the group consisting of: —$NHR^5$, —OH, and —$OR^5$. In one embodiment $R^5$ of the Y substituent is selected from the group consisting of: —O-alkylene-S(O)$_2$NHC(O)—(C$_1$-C$_6$)alkyl, —O-alkylene-S(O)$_2$NHC(O)-haloalkylalkyl, —O-alkylene-S(O)$_2$NHC(O)—$R^6$, —O-alkylene-S(O)$_2$NHC(O)—$R^7$, —O-alkylene-C(O)NH—S(O)$_2$—(C$_1$-C$_6$)alkyl, —O—alkylene-C(O)NH—S(O)$_2$-haloalkyl, —O-alkylene-C(O)NH—S(O)$_2$—(C$_1$-C$_6$)alkyl, —O-alkylene-C(O)NH—S(O)$_2$—$R^6$, and —O-alkylene-C(O)NH—S(O)$_2$—$R^7$.

In one embodiment of the invention the compound of formula I is a compound of formula (IF).

In another embodiment of the invention the compound of formula I is a compound of formula (IF.1A).

Other embodiments of this invention are directed to compounds of formula (IF.1A) wherein Y is as defined above, and the remaining substituents are as defined in any one of the embodiments described below for the compounds of formula (IF).

In one preferred embodiment of the compounds of formula (IF), each $L^3$ is the same or different —$NHR^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2R^6$, —S(O)$_2R^7$, and —S(O)$_2R^8$.

In another preferred embodiment of the compounds of formula (IF) each $L^3$ is the same or different $OR^5$ group, and each $R^5$ is independently selected from the group consisting of: H, (C$_1$-C$_6$)alkyl, $R^6$, $R^7$, —C(O)—(C$_1$-C$_6$)alkyl, —C(O)—C$_1$-C$_6$)haloalkyl, —C(O)—$R^6$, and —C(O)—$R^7$.

In another preferred embodiment of the compounds of formula (IF) each $L^3$ is the same or different $R^5$ group, and each $R^5$ is independently selected from the group consisting of: H, (C$_1$-C$_6$)alkyl, $R^6$, $R^7$, —S(O)$_2$—(C$_1$-C$_6$)alkyl, —S(O)$_2$—(C$_1$-C$_6$)haloalkyl, —S(O)$_2R^6$, S(O)$_2R^7$, —S(O)$_2R^8$.—C(O)—(C$_1$-C$_6$)alkyl, —C(O)—(C$_j$—C$_6$)haloalkyl, —C(O)—$R^6$, and —C(O)—$R^7$.

Preferred are compounds of formula (I) are compounds of formula (IF) wherein each $L^3$ is the same or different —$NHR^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2R^6$, —S(O)$_2R^7$, and —S(O)$_2R^8$.

Preferred compounds of formula (I) also include compounds of formula (IF) wherein each $L^3$ is the same or different $OR^5$ group, and each $R^5$ is independently selected from the group consisting of: H, (C$_1$-C$_6$)alkyl, $R^6$, $R^7$, —C(O)—(C$_1$-C$_6$)alkyl, —C(O)—C$_1$-C$_6$)haloalkyl, —C(O)—$R^6$, and —C(O)—$R^7$.

Preferred compounds of formula (I) also include compounds of formula (IF) wherein each $L^3$ is the same or different $R^5$ group, and each $R^5$ is independently selected from the group consisting of: H, (C$_1$-C$_6$)alkyl, $R^6$, $R^7$, S(O)$_2$—(C$_1$-C$_6$)alkyl, —S(O)$_2$—(C$_1$-C$_6$)haloalkyl, —S(O)$_2R^6$, —S(O)$_2R^7$, —S(O)$_2R^8$, —C(O)—(C$_1$-C$_6$)alkyl, —C(O)—(C$_1$-C$_6$)haloalkyl, —C(O)—$R^6$, and —C(O)—$R^7$.

In another embodiment of the compounds of formula (IF), "Q" is a fused cycloalkyl ring.

In one embodiment of the compounds of formula (IF) m is 1.

In another embodiment of the compounds of formula (IF) $R^4$ is H.

In another embodiment of the compounds of formula (IF) X is O.

In another embodiment of the compounds of formula (IF) $L^1$ is halogen.

In another embodiment of the compounds of formula (IF) $L^1$ is halogen wherein each halogen is individually selected from the group consisting of: Cl and F.

In another embodiment of the compounds of formula (IF) substituent Ar is an aryl moiety substituted with one or more $L^1$ groups.

In another embodiment of the compounds of formula (IF) substituent Ar is phenyl substituted with one or more $L^1$ groups.

In another embodiment of the compounds of formula (IF) substituent Ar is phenyl substituted with an $L^1$ group wherein said $L^1$ group is halogen.

In another embodiment of the compounds of formula (IF) substituent Ar is phenyl substituted with an $L^1$ group wherein said $L^1$ group is Cl (e.g., Ar is p-Cl-phenyl).

In another embodiment of the compounds of formula (IF) n is 1 or 2.

In another embodiment of the compounds of formula (IF) n is 1.

In another embodiment of the compounds of formula (IF) n is 2.

In another embodiment of the compounds of formula (IF) $L^1$ is halogen wherein each halogen is independently selected from the group consisting of Cl and Br, and n is 2.

In another embodiment of the compounds of formula (IF) $L^1$ is F and n is 2.

In another embodiment of the compounds of formula (IF) m is 1, and X is O.

In another embodiment of the compounds of formula (IF) m is 1, X is O and $R^4$ is H.

In another embodiment of the compounds of formula (IF) m is 1, X is O and $R^4$ is H, n is 2, and $L^1$ is selected from the group consisting of Cl and F.

In another embodiment of the compounds of formula (IF) m is 1, X is O and $R^4$ is H, n is 2, $L^1$ is selected from the group consisting of Cl and F, and Ar is phenyl substituted with Cl.

In another embodiment of the compounds of formula (IF) m is 1, X is O and $R^4$ is H, n is 2, and $L^1$ is F.

In another embodiment of the compounds of formula (IF) m is 1, X is O and $R^4$ is H, n is 2, $L^1$ is F, and Ar is phenyl substituted with Cl.

Another embodiment of the compounds of formula (IF) is directed to compounds of formula (IF.1):

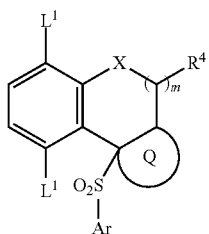

(IF.1)

Other embodiments of the compounds of formula (IF) are directed to any one of the embodiments described above for formula (IF), just as if each embodiment where individual described, wherein the compound of formula (IF) is a compound of formula (IF.1).

Other embodiments of the compounds of formula (IF), as described in any one of the above embodiments, are directed to compounds wherein Q is as described in any one of the embodiments below.

In another embodiment of the compounds of formula (IF) Q is an unsubstituted cyclohexyl ring:

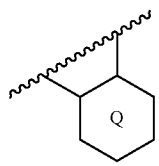

such as, for example,

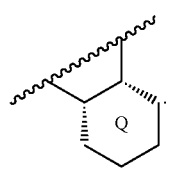

In another embodiment of the compounds of formula (IF) Q is a substituted cyclohexyl ring:

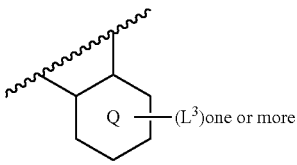

such as, for example,

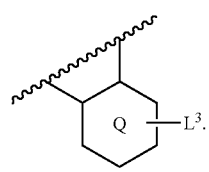

In another embodiment of the compounds of formula (IF) Q is a substituted cyclohexyl ring:

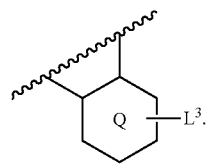

In one embodiment the cyclohexyl ring Q:

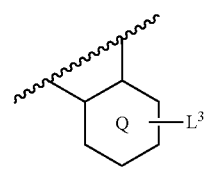

is a cyclohexyl ring of the formula:

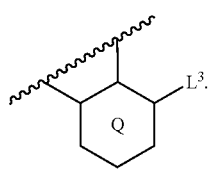

In another embodiment the cyclohexyl ring Q:

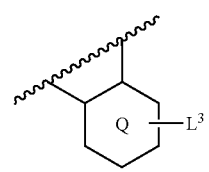

is a cyclohexyl ring of the formula:

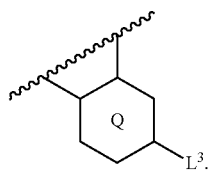

In another embodiment of the compounds of formula (IF) Q is a substituted cyclohexyl ring:

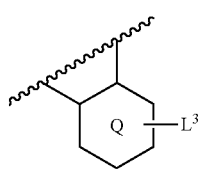

wherein $L^3$ is selected from the group consisting of: =O, —OR$^5$, —NHR$^5$, —SO$_2$R$^6$, —SO$_2$R$^7$, and —SO$_2$R$^8$, wherein R$^5$ is selected from the group consisting of: —SO$_2$—(C$_1$-C$_6$)haloalkyl (e.g., —SO$_2$CF$_3$), —C(O)—(C$_1$-C$_6$)alkyl (e.g., —C(O)CH$_3$), —C(O)NH(C$_1$-C$_6$)alkyl (e.g., C(O)NHC$_2$H$_5$), —SO$_2$—(C$_1$-C$_6$)alkyl (e.g., —SO$_2$CH$_3$, —SO$_2$C$_2$H$_5$, and —SO$_2$C$_3$H$_7$), and —(C$_1$-C$_6$)alkyl (e.g., methyl), and wherein R$^6$ is unsubstituted heteroaryl (e.g., thienyl and pyridyl), and wherein R$^7$ is an unsubstituted heterocycloalkyl ring (e.g., azetidinyl), and wherein R$^8$ is an unsubstituted cycloalkyl ring (e.g., cyclopropyl).

In another embodiment of the compounds of formula (IF) Q is a substituted cyclohexyl ring:

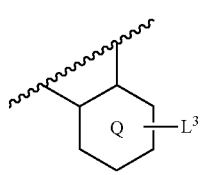

wherein $L^3$ is selected from the group consisting of: =O, —OH, —NH$_2$, —NHSO$_2$CF$_3$, —NHC(O)CH$_3$, —NHC(O)NHCH$_2$CH$_3$, —NHSO$_2$CH$_3$, —NHSO$_2$CH$_2$CH$_3$, —NHSO$_2$CH$_2$CH$_2$CH$_3$, —OCH$_3$,

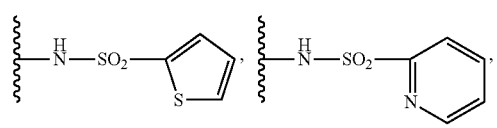

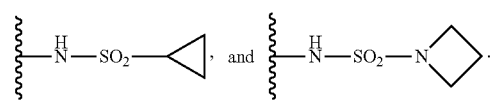

In another embodiment of the compounds of formula (IF) Q is a substituted cyclohexyl ring:

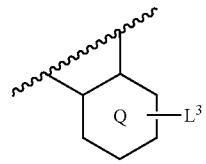

wherein $L^3$ is selected from the group consisting of: -alkylene-C(O)NH(C$_1$ to C$_6$)alkyl (e.g., —CH$_2$C(O)NHC$_2$H$_5$ and —CH$_2$C(O)NHCH$_3$), -alkylene-C(O)N((C$_1$ to C$_6$)alkyl)$_2$ wherein each alkyl is independently selected, -alkylene-C(O)NH(C$_1$ to C$_6$)haloalkyl (e.g., —CH$_2$C(O)NHCH$_2$CF$_3$), and -alkylene-C(O)N((C$_1$ to C$_6$)haloalkyl)$_2$ wherein each alkyl is independently selected.

In another embodiment of the compounds of formula (IF) Q is a substituted cyclohexyl ring:

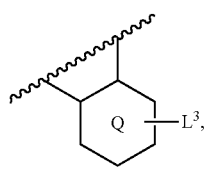

such as, for example,

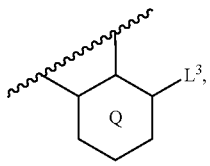

wherein $L^3$ is selected from the group consisting of: —CH$_2$C(O)NHC$_2$H$_5$, —CH$_2$C(O)NHCH$_3$, and —CH$_2$C(O)NHCH$_2$CF$_3$.

In another embodiment of the compounds of formula (IF) Q is a substituted cyclohexyl ring:

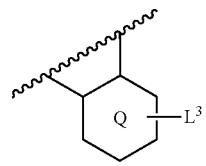

wherein $L^3$ is selected from the group consisting of: -alkylene-NHS(O)$_2$—(C$_1$-C$_6$)alkyl (e.g., —CH$_2$NHS(O)$_2$CH$_2$CH$_3$), and -alkylene-NHS(O)$_2$—(C$_1$-C$_6$)haloalkyl (e.g., —CH$_2$NHS(O)$_2$CF$_3$).

In another embodiment of the compounds of formula (IF) Q is a substituted cyclohexyl ring:

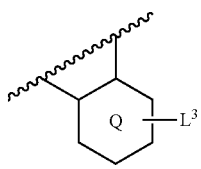

wherein L³ is selected from the group consisting of: hydroxyl substituted alkyls (such as, for example, alkyl substituted with at least one —OH group, such as, for example, ($C_1$ to $C_6$) alkyl substituted with 1 to 3 —OH groups, and in one example ($C_1$ to $C_6$) alkyl substituted with 1 or 2 —OH groups, and in another example ($C_1$ to $C_6$) alkyl substituted with 2 —OH groups, and in another example —CH₂CH(OH)CH₂CH₃ and in another example —CH₂CH₂CH(OH)CH₂OH).

In another embodiment of the compounds of formula (IF) Q is a substituted cyclohexyl ring:

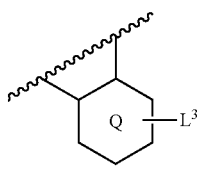

wherein L³ is selected from the group consisting of: wherein L³ is selected from the group consisting of: -alkylene-S(O)₂—($C_1$-$C_6$)alkyl (e.g., is —CH₂CH₂SO₂CH₂CH₃ or —CH₂CH₂SO₂CH₃).

In another embodiment of the compounds of formula (IF) Q is a substituted cyclohexyl ring:

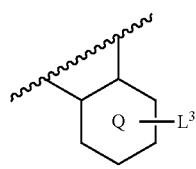

wherein L³ is selected from the group consisting of: -alkylene-C(O)—($C_1$-$C_6$)alkyl (e.g., —CH₂CH₂—C(O)—CH₃).

In another embodiment of the compounds of formula (IF) Q is an unsubstituted cycloheptyl ring:

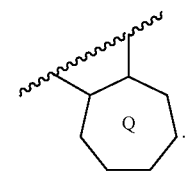

In another embodiment of the compounds of formula (IF) Q is a substituted cycloheptyl ring:

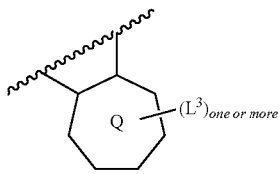

such as, for example,

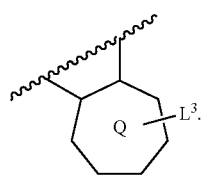

In another embodiment of the compounds of formula (IF) Q is a substituted cycloheptyl ring:

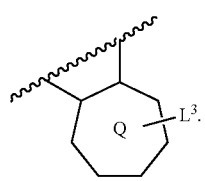

In another embodiment of the compounds of formula (IF) Q is a substituted cycloheptyl ring:

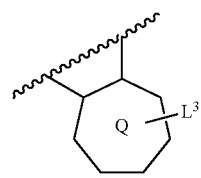

wherein L³ is selected from the group consisting of: —OR⁵ (wherein, for example, R⁵ is H), and —NHR⁵ (wherein, for example, R⁵ is —SO₂—($C_1$-$C_6$)haloalkyl (such as, for example, —SO₂CF₃)).

In another embodiment of the compounds of formula (IF) Q is a substituted cycloheptyl ring:

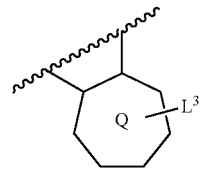

wherein L³ is selected from the group consisting of: —OH and —NHSO₂CF₃.

In another embodiment of the compounds of formula (IF) Q is an unsubstituted heterocycloalkyl ring comprising one heteroatom selected from the group consisting of —O— and —NH—.

In another embodiment of the compounds of formula (IF) Q is a heterocycloalkyl ring substituted with one or more $L^3$ groups (e.g., one $L^3$ group), said heterocycloalkyl ring comprising at least one heteroatom selected from the group consisting of —O— —NH— and —N($L^3$)— (e.g., wherein $L^3$ on said N is, for example, the $R^5$ group —C(O)—($C_1$-$C_6$)alkyl, such as, for example, —C(O)$CH_3$). Examples of said $L^3$ group when, for example, said heterocycloalkyl ring comprises —O— as the heteroatom include methyl and butyl.

In another embodiment of the compounds of formula (IF) Q is the unsubstituted heterocycloalkyl ring:

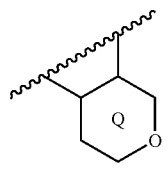

such as, for example,

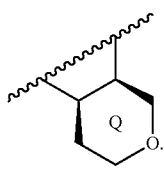

In another embodiment of the compounds of formula (IF) Q is the substituted heterocycloalkyl ring:

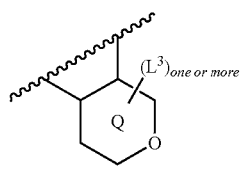

such as, for example,

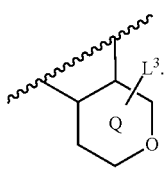

In another embodiment of the compounds of formula (IF) Q is the substituted heterocycloalkyl ring:

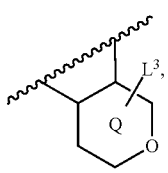

such as, for example,

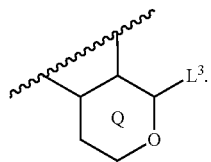

Examples of $L^3$ include alkyl, such as, for example, methyl and butyl. Thus, examples of these Q groups include:

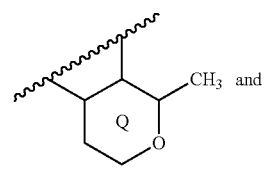

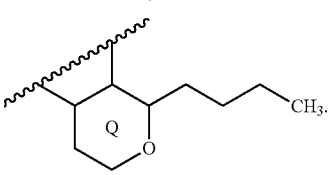

In another embodiment of the compounds of formula (IF) Q is the substituted heterocycloalkyl ring:

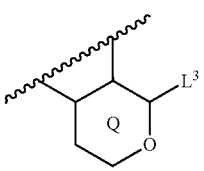

wherein $L^3$ is selected from the group consisting of: -alkylene-C(O)NH($C_1$ to $C_6$)alkyl (e.g., —$CH_2$C(O)NH$C_2H_5$ and —$CH_2$C(O)NH$CH_3$), -alkylene-C(O)N(($C_1$ to $C_6$)alkyl)$_2$ wherein each alkyl is independently selected, -alkylene-C(O)NH($C_1$ to $C_6$)haloalkyl (e.g., —$CH_2$C(O)NH$CH_2CF_3$), and -alkylene-C(O)N(($C_1$ to $C_6$)haloalkyl)$_2$ wherein each alkyl is independently selected.

In another embodiment of the compounds of formula (IF) Q is the substituted heterocycloalkyl ring:

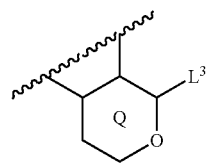

wherein $L^3$ is selected from the group consisting of: -alkylene-NHS(O)$_2$—($C_1$-$C_6$)alkyl (e.g., —$CH_2$NHS(O)$_2$$CH_2CH_3$), and -alkylene-NHS(O)$_2$—($C_1$-$C_6$)haloalkyl (e.g., —$CH_2$NHS(O)$_2$$CF_3$).

In another embodiment of the compounds of formula (IF) Q is the substituted heterocycloalkyl ring:

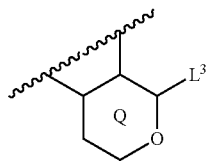

wherein $L^3$ is selected from the group consisting of: hydroxyl substituted alkyls (such as, for example, alkyl substituted with at least one —OH group, such as, for example, ($C_1$ to $C_6$) alkyl substituted with 1 to 3 —OH groups, and in one example ($C_1$ to $C_6$) alkyl substituted with 1 or 2 —OH groups, and in another example ($C_1$ to $C_6$) alkyl substituted with 2 —OH groups, and in another example —$CH_2CH(OH)CH_2CH_3$ and in another example —$CH_2CH_2CH(OH)CH_2OH$).

In another embodiment of the compounds of formula (IF) Q is the substituted heterocycloalkyl ring:

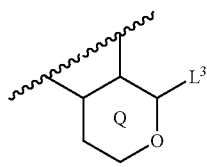

wherein $L^3$ is selected from the group consisting of: 3-hydroxybutyl (—$CH_2CH(OH)CH_2CH_3$) and 2,3-dihydroxybutyl (—$CH_2CH_2CH(OH)CH_2OH$).

In another embodiment of the compounds of formula (IF) Q is the substituted heterocycloalkyl ring:

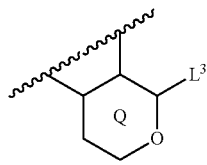

wherein $L^3$ is selected from the group consisting of: -alkylene-$S(O)_2$—($C_1$-$C_6$)alkyl.

In another embodiment of the compounds of formula (IF) Q is the substituted heterocycloalkyl ring:

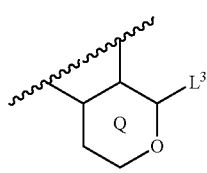

wherein $L^3$ is —$CH_2CH_2SO_2CH_2CH_3$ or —$CH_2CH_2SO_2CH_3$.

In another embodiment of the compounds of formula (IF) Q is the substituted heterocycloalkyl ring:

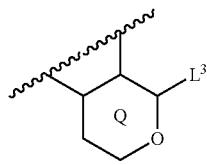

wherein $L^3$ is selected from the group consisting of: -alkylene-C(O)—($C_1$-$C_6$)alkyl.

In another embodiment of the compounds of formula (IF) Q is the substituted heterocycloalkyl ring:

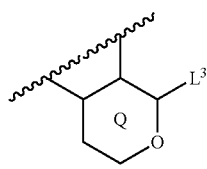

wherein $L^3$ is —$CH_2CH_2$—C(O)—$CH_3$.

In another embodiment of the compounds of formula (IF) Q is the unsubstituted heterocycloalkyl ring:

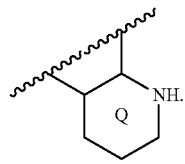

In another embodiment of the compounds of formula (IF) Q is the substituted heterocycloalkyl ring:

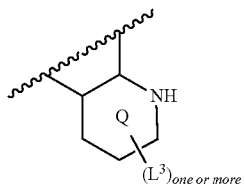

such as, for example,

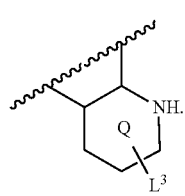

In another embodiment of the compounds of formula (IF) Q is the substituted heterocycloalkyl ring:

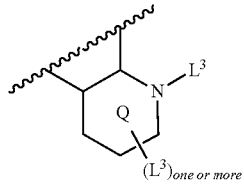

such as, for example,

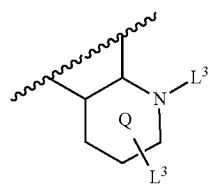

wherein the $L^3$ group bound to the N is the same or different as an $L^3$ group bound to a ring carbon.

In another embodiment of the compounds of formula (IF) Q is the substituted heterocycloalkyl ring:

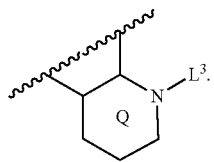

In one example $L^3$ is a —C(O)-alkyl group, such as, for example, —C(O)CH$_3$.

Also, for example, compounds of formula (I) include compounds wherein m is 1, and $R^2$ and $R^4$ together with the carbon atoms to which they are shown attached form a fused ring (Q), such compounds have the formula (IG):

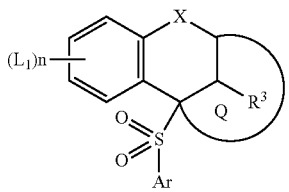

(IG)

wherein Q is a fused ring selected from the group consisting of: unsubstituted cycloalkyl, cycloalkyl substituted with one or more independently selected $L^3$ groups, unsubstituted heterocycloalkyl, and heterocycloalkyl substituted with one or more independently selected $L^3$ groups.

In one preferred embodiment of the compounds of formula (IG), each $L^3$ is the same or different —NHR$^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2$R$^6$, —S(O)$_2$R$^7$ and —S(O)$_2$R$^8$.

In another preferred embodiment of the compounds of formula (IG) each $L^3$ is the same or different OR$^5$ group, and each $R^5$ is independently selected from the group consisting of: H, (C$_1$-C$_6$)alkyl, R$^6$, R$^7$, —C(O)—(C$_1$-C$_6$)alkyl, —C(O)—C$_1$-C$_6$)haloalkyl, —C(O)—R$^6$, and —C(O)—R$^7$.

In another preferred embodiment of the compounds of formula (IG) each $L^3$ is the same or different R$^5$ group, and each $R^5$ is independently selected from the group consisting of: H, (C$_1$-C$_6$)alkyl, R$^6$, R$^7$, S(O)$_2$—(C$_1$-C$_6$)alkyl, —S(O)$_2$—(C$_1$-C$_6$)haloalkyl, S(O)$_2$R$^6$, S(O)$_2$R$^7$, —S(O)$_2$R$^7$, —C(O)—(C$_1$-C$_6$)alkyl, —C(O)—(C$_1$-C$_6$)haloalkyl, —C(O)—R$^6$, and —C(O)—R$^7$.

In another embodiment of the compounds of formula (IG) ring "Q" is a fused cycloalkyl ring.

Also, for example, compounds of formula (I) include compounds wherein m is 1, and $R^3$ and $R^4$ together with the carbon atoms to which they are shown attached form a fused ring (Q), such compounds have the formula (IH):

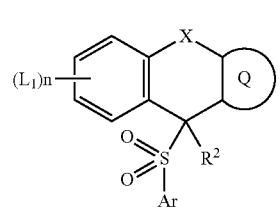

(IH)

wherein Q is a fused ring selected from the group consisting of: unsubstituted cycloalkyl, cycloalkyl substituted with one or more independently selected $L^3$ groups, unsubstituted heterocycloalkyl, and heterocycloalkyl substituted with one or more independently selected $L^3$ groups.

In one preferred embodiment of the compounds of formula (IH), each $L^3$ is the same or different —NHR$^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2$R$^6$, —S(O)$_2$R$^7$ and —S(O)$_2$R$^8$.

In another preferred embodiment of the compounds of formula (IH) each $L^3$ is the same or different OR$^5$ group, and each $R^5$ is independently selected from the group consisting of: H, (C$_1$-C$_6$)alkyl, R$^6$, R$^7$, —C(O)—(C$_1$-C$_6$)alkyl, —C(O)—C$_1$-C$_6$)haloalkyl, —C(O)—R$^6$, and —C(O)—R$^7$.

In another preferred embodiment of the compounds of formula (IH) each $L^3$ is the same or different R$^5$ group, and each $R^5$ is independently selected from the group consisting of: H, (C$_1$-C$_6$)alkyl, R$^6$, R$^7$, S(O)$_2$—(C$_1$-C$_6$)alkyl, —S(O)$_2$—(C$_1$-C$_6$)haloalkyl, S(O)$_2$R$^6$, S(O)$_2$R$^7$, —S(O)$_2$R$^8$, —C(O)—(C$_1$-C$_6$)alkyl, —C(O)—(C$_1$-C$_6$)haloalkyl, —C(O)—R$^6$, and —C(O)—R$^7$.

In another embodiment of the compounds of formula (IH) ring "Q" is a fused cycloalkyl ring.

In another embodiment of the compounds of Formula (I), or pharmaceutically acceptable salts, solvates, and/or esters thereof, said compounds can have the Formula (IF):

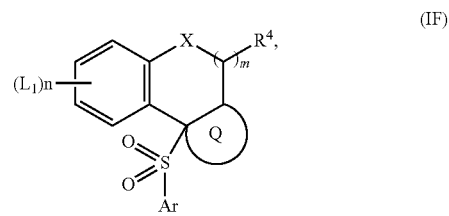

(IF)

wherein:

X is —O—;

R$^3$ is selected from the group consisting of H, alkyl, alkylene-OR$^5$, alkenyl, —C(O)O-alkyl, and -alkylene-C(O)O-alkyl; or R$^2$ and R$^3$, or R$^2$ and an R$^4$, together with the atoms to which they are shown attached form a fused cycloalkyl ring, wherein said fused cycloalkyl ring is unsubstituted or substituted with one or more L$^3$ groups;

each R$^4$ is independently selected from the group consisting of H, alkyl, and -alkylene-R$^6$; and each R$^5$ is independently selected from the group consisting of H, alkyl, R$^6$, —C(O)-alkyl, —C(O)—R$^6$, and —C(O)—R$^7$;

R$^6$ is selected from the group consisting of unsubstituted aryl and aryl substituted with one or more L$^1$ groups;

R$^7$ is selected from the group consisting of unsubstituted heterocycloalkyl and heterocycloalkyl substituted with one or more L$^2$ groups;

Ar is unsubstituted aryl or aryl substituted with one or more L$^1$ groups;

each L$^1$ is independently selected from the group consisting of halogen, alkyl, —CN, and —CF$_3$;

each L$^2$ is independently selected from the group consisting of —OH, alkyl, alkyl substituted with one or more —OH groups, and heterocycloalkyl;

L$^3$ is —OR$^5$;

n is 0, 1, 2 or 3; and m is 1.

In another embodiment of the compounds of Formula (I), or pharmaceutically acceptable salts, solvates, and/or esters thereof, said compounds can have the Formula (1G):

wherein

X is —O—;

R$^3$ is selected from the group consisting of H, alkyl, alkylene-OR$^5$, alkenyl, —C(O)O-alkyl, and -alkylene-C(O)O-alkyl; or R$^2$ and R$^3$, or R$^2$ and an R$^4$, together with the atoms to which they are shown attached form a fused cycloalkyl ring, wherein said fused cycloalkyl ring is unsubstituted or substituted with one or more L$^3$ groups;

each R$^4$ is independently selected from the group consisting of H, alkyl, and -alkylene-R$^6$; and each R$^5$ is independently selected from the group consisting of H, alkyl, R$^6$, —C(O)-alkyl, —C(O)—R$^6$, and —C(O)—R$^7$;

R$^6$ is selected from the group consisting of unsubstituted aryl and aryl substituted with one or more L$^1$ groups;

R$^7$ is selected from the group consisting of unsubstituted heterocycloalkyl and heterocycloalkyl substituted with one or more L$^2$ groups;

Ar is unsubstituted aryl or aryl substituted with one or more L$^1$ groups;

each L$^1$ is independently selected from the group consisting of halogen, alkyl, —CN, and —CF$_3$;

each L$^2$ is independently selected from the group consisting of —OH, alkyl, alkyl substituted with one or more —OH groups, and heterocycloalkyl;

L$^3$ is —OR$^5$;

n is 0, 1, 2 or 3; and m is 1.

In another embodiment of the compounds of Formula (I), or pharmaceutically acceptable salts, solvates, and/or esters thereof, said compounds can have the Formula (1H):

wherein

X is —O—;

R$^3$ is selected from the group consisting of H, alkyl, alkylene-OR$^5$, alkenyl, —C(O)O-alkyl, and -alkylene-C(O)O-alkyl; or R$^2$ and R$^3$, or R$^2$ and R$^4$, together with the carbon atoms to which they are shown attached form a fused cycloalkyl ring, wherein said fused cycloalkyl ring is unsubstituted or substituted with one or more L$^3$ groups;

each R$^4$ is independently selected from the group consisting of H, alkyl, and -alkylene-R$^6$; and each R$^5$ is independently selected from the group consisting of H, alkyl, R$^6$, —C(O)-alkyl, —C(O)—R$^6$, and —C(O)—R$^7$;

R$^6$ is selected from the group consisting of unsubstituted aryl and aryl substituted with one or more L$^1$ groups;

R$^7$ is selected from the group consisting of unsubstituted heterocycloalkyl and heterocycloalkyl substituted with one or more L$^2$ groups;

Ar is unsubstituted aryl or aryl substituted with one or more L$^1$ groups;

each L$^1$ is independently selected from the group consisting of halogen, alkyl, —CN, and —CF$_3$;

each L$^2$ is independently selected from the group consisting of —OH, alkyl, alkyl substituted with one or more —OH groups, and heterocycloalkyl;

L$^3$ is —OR$^5$;

n is 0, 1, 2 or 3; and m is 1.

Other embodiments of this invention are directed to any one of the embodiments described above for the compounds of formula (IF) wherein said compound is the free acid or free base.

Other embodiments of this invention are directed to any one of the embodiments described above for the compounds of formula (IF) wherein said compound is a pharmaceutically acceptable salt.

Other embodiments of this invention are directed to any one of the embodiments described above for the compounds of formula (IF) wherein said compound is a pharmaceutically acceptable ester.

Other embodiments of this invention are directed to any one of the embodiments described above for the compounds of formula (IF) wherein said compound is a solvate.

Other embodiments of this invention are directed to any one of the embodiments described above for the compounds of formula (IG) wherein said compound is the free acid or free base.

Other embodiments of this invention are directed to any one of the embodiments described above for the compounds of formula (IG) wherein said compound is a pharmaceutically acceptable salt.

Other embodiments of this invention are directed to any one of the embodiments described above for the compounds of formula (IG) wherein said compound is a pharmaceutically acceptable ester.

Other embodiments of this invention are directed to any one of the embodiments described above for the compounds of formula (IG) wherein said compound is a solvate.

Other embodiments of this invention are directed to any one of the embodiments described above for the compounds of formula (IH) wherein said compound is the free acid or free base.

Other embodiments of this invention are directed to any one of the embodiments described above for the compounds of formula (IH) wherein said compound is a pharmaceutically acceptable salt.

Other embodiments of this invention are directed to any one of the embodiments described above for the compounds of formula (IH) wherein said compound is a pharmaceutically acceptable ester.

Other embodiments of this invention are directed to any one of the embodiments described above for the compounds of formula (IH) wherein said compound is a solvate.

X, for compounds of formula (I), is selected from the group consisting of —C(R$^1$)$_2$—, —O—, —NR$^1$—, and —N(C(O)R$^1$), with the proviso that when X is —O— and m is 1, at least one of R$^2$, R$^3$ or R$^4$ is a group other than H. Non-limiting examples of —C(R$^1$)$_2$—, —NR$^1$—, and —N(C(O)R$^1$) include those groups wherein R$^1$ is as defined herein.

Each R$^1$, for compounds of formula (I), is independently H and alkyl wherein the term "alkyl" includes, for example, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —C(CH$_3$)CH$_2$CH$_3$, —CH$_2$CH(CH$_3$)$_2$, etc.

R$^2$, in one embodiment of the compounds of formula (I), is selected from the group consisting of H, alkyl, alkylene-OR$^5$, -alkylene-R$^6$, -alkylene-C(O)O-alkyl, -alkylene-R$^8$, —C(O)O-alkyl, and alkenyl. When R$^2$ is "alkyl", non-limiting examples of said "alkyls" include, for example, those defined above and elsewhere herein. Likewise, when R$^2$ is —C(O)O-alkyl or -alkylene-C(O)O-alkyl, the alkyl portion of these groups can include for example the "alkyl" groups defined above or elsewhere herein. When R$^2$ is -alkylene-OR$^5$, non-limiting examples of alkylene-OR$^5$ include those groups wherein the R$^5$ portion is as defined herein, and the "alkylene" portion of includes, e.g., —CH$_2$—, —CH$_2$CH$_2$—, —CH$_2$CH$_2$CH$_2$—, wherein each of the preceding alkylene groups may be optionally substituted with a lower alkyl group, thereby forming a branched alkylene. Such branched alkylenes include, for example —CH(CH$_3$) —, —C(CH$_3$)$_2$-, —CH(CH$_3$)CH$_2$—, —CH$_2$CH(CH$_3$) —, etc., Likewise, when R$^2$ is -alkylene-R$^6$, -alkylene-C(O)O-alkyl, and -alkylene-R$^8$ the "alkylene" portions of these groups can include the unbranched or branched alkylene groups defined above or elsewhere herein. When R$^2$ is "alkenyl", non-limiting examples of "alkenyl" include those described herein, including —CH═CH$_2$, —C(CH$_3$)═CH$_2$, —CH═CH(CH$_3$), —CH$_2$CH═CH$_2$, —CH$_2$CH$_2$CH═CH$_2$, etc.

R$^3$, in one embodiment of the compounds of formula (I), is selected from the group consisting of H, alkyl, alkylene-OR$^5$, alkenyl, —C(O)O-alkyl, and -alkylene-C(O)O-alkyl. When R$^3$ is alkyl, non-limiting examples of alkyl include those described above and elsewhere herein. When R$^3$ is —C(O)O-alkyl or -alkylene-C(O)O-alkyl, non-limiting examples include groups wherein the alkyl portion thereof can include, for example, alkyl groups described above or elsewhere herein. Likewise, when R$^3$ is alkylene-OR$^5$ or -alkylene-C(O)O-alkyl, non-limiting examples thereof include groups wherein the alkylene portion includes those described above or elsewhere herein.

R$^4$, in one embodiment of the compounds of formula (I), is independently selected from the group consisting of H, alkyl, and -alkylene-R$^6$. When an R$^4$ is alkyl, non-limiting examples of such groups include the alkyl groups described above or elsewhere herein. Likewise, when an R$^4$ is -alkylene-R$^6$, non-limiting examples of such groups include those wherein the R$^6$ portion is as defined herein, and the alkylene portion includes those alkylenes described above or elsewhere herein.

Groups R$^2$ and R$^3$, or R$^2$ and an R$^4$, or R$^3$ and an R$^4$, together with the atoms to which they are shown attached can form a fused cycloalkyl ring, wherein said fused cycloalkyl ring is unsubstituted or substituted with one or more L$^3$ groups. One of skill in the art will understand that when R$^2$ and an R$^4$, or R$^3$ and an R$^4$ form a fused cycloalkyl ring, only one fused cycloalkyl ring is formed. Thus, when m is 2 or more, only one R$^4$ forms part of the fused cycloalkyl ring, and the other R$^4$ groups are independently one of the groups defined herein for R$^4$.

Each R$^5$, in one embodiment of the compounds of formula (I), is independently selected from the group consisting of H, alkyl, R$^6$, —C(O)-alkyl, —C(O)—R$^6$, and —C(O)—R$^7$. Non-limiting examples of such groups include those wherein alkyl, or the R$^6$, R$^7$ and alkyl portion thereof, are as defined above and herein.

When the compounds of Formula (I) include a group R$^6$, or one of the substituents of said compound includes an R$^6$ portion, said R$^6$, in one embodiment of the compounds of formula (I), includes any chemically stable, optionally substituted aryl group. Non-limiting examples of such aryl groups include phenyl, naphthyl, biphenyl, anthacenyl, etc.

When the compounds of Formula (I) include a group R$^7$, or one of the substituents of said compound includes an R$^7$ portion, said R$^7$ includes any chemically stable, optionally substituted heterocycloalkyl group. Non-limiting examples of such heterocycloalkyl groups include piperidyl, pyrrolidinyl, piperidinyl, piperazinyl, morpholinyl, thiomorpholinyl, thiazolidinyl, 1,4-dioxanyl, tetrahydrofuranyl, tetrahydrothiophenyl, thiazolinyl, 2,3-dihydrofuranyl, 2,3-dihydrothiophenyl, etc.

When the compounds of Formula (I) include a group R$^8$, or one of the substituents of said compound includes an R$^8$ portion, said R$^8$ includes any chemically stable, optionally substituted cycloalkyl group. Non-limiting examples thereof include, for example, cyclopropyl, cyclobutyl, cyclopentyl, cyclohexyl, cycloheptyl, cyclooctyl, cyclononyl, etc.

Ar includes any chemically stable, optionally substituted aryl group. Non-limiting examples of such aryl groups include phenyl, naphthyl, biphenyl, anthacenyl, etc.

Each L$^1$ is independently selected from the group consisting of halogen, alkyl, —CN, and —CF$_3$. When an L$^1$ is halogen, each halogen in independently F, Cl, Cr, or I. When an L$^1$ is alkyl, non-limiting example of said alkyl include those described above and elsewhere herein.

Each L$^2$, in one embodiment of the compounds of formula (I), is independently selected from the group consisting of —OH, alkyl, alkyl substituted with one or more —OH groups, and heterocycloalkyl. When an L$^2$ is alkyl or heterocycloalkyl, non-limiting examples of said alkyl or heterocycloalkyl include those described above and elsewhere herein. When an L$^2$ is alkyl substituted with one or more —OH groups, non-limiting examples of such groups include —CH$_2$-OH, —CH$_2$CH$_2$—OH, —CH(OH)CH$_3$, —CH$_2$CH$_2$CH$_2$—OH, —CH$_2$CH(OH)CH$_3$, etc.

L$^3$, in one embodiment of the compounds of formula (I), is —OR$^5$. Non-limiting examples thereof include —OH, —O-alkyl (wherein said alkyl portion includes the alkyl groups described above and elsewhere herein), —O-aryl (wherein said aryl portion includes the aryl groups described above and elsewhere herein), —O-acyl, —O-aroyl, —O—C(O)—R$^7$, wherein the acyl, aroyl, and R$^7$ portions thereof are defined above and elsewhere herein.

As used above, and throughout this disclosure, the following terms, unless otherwise indicated, shall be understood to have the following meanings:

"Patient" includes both human and animals.

"Mammal" means humans and other mammalian animals.

"One or more" means at least one, for example, 1, 2 or 3, or 1 or 2, or 1, thus, for example, "one or more L$^3$ groups" means at least one L$^3$ group, and examples include 1-3 L$^3$ groups, 1 or 2 L$^3$ groups, and one L$^3$ group.

"At least one" means there is at least one, and examples include 1, 2 or 3, or 1 or 2, or 1.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O)O-alkyl (unless expressly defined otherwise). Non-limiting examples of suitable alkyl groups include methyl, ethyl, n-propyl, isopropyl and t-butyl.

"Alkylene" means a divalent aliphatic hydrocarbon radical derived from an alkyl group, as defined above. Both "open" valences may be on the same carbon atom, or on different carbon atoms. Examples of alkylene groups include $C_1$-$C_6$ alkylene groups, for example, $C_1$ to $C_4$ alkylene groups, and in another example, $C_1$-$C_3$ alkylene groups, and in another example $C_1$ to $C_2$ alkylene groups. Non-limiting examples of alkylene groups include —CH$_2$—, —CH$_2$—CH$_2$—, —CH(CH$_3$)—, etc.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain, which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable saturated monocyclic cycloalkyls include cyclopropyl, cyclopentyl, cyclohexyl, cycloheptyl and the like, and non-limiting examples of non-aromatic, unsaturated monocyclic cycloalkyls include cyclopentenyl, cyclohexenyl, etc. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Fluorine, chlorine and bromine are preferred.

"Ring system substituent" means a substituent attached to an aromatic or non-aromatic ring system, which, for example, replaces an available hydrogen on the ring system. Ring system substituents may be the same or different, each being independently selected from the group consisting of alkyl, alkenyl, alkynyl, aryl (substituted or unsubstituted, heteroaryl (substituted or unsubstituted, alkylene-aryl, heteroarylalkenyl, heteroarylalkynyl, hydroxy, hydroxyalkyl, alkoxy, aryloxy, aryl substituted alkoxy, acyl, aroyl, halo, nitro, cyano, carboxy, alkoxycarbonyl, aryloxycarbonyl, arylalkoxycarbonyl, alkylsulfonyl, arylsulfonyl, heteroarylsulfonyl, alkylthio, arylthio, heteroarylthio, arylalkylthio, heteroarylalkylthio, cycloalkyl, heterocycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and -alkylene-aryl (unless expressly defined otherwise). The term "ring system substituent" may also mean a single moiety in which two available hydrogens on two adjacent carbon atoms are simultaneously replaced (e.g., one H on each carbon) on a ring system. Examples of such moiety are methylenedioxy, ethylenedioxy, —C(CH$_3$)$_2$— and the like which form moieties such as, for example:

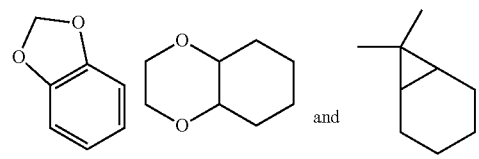

"Heterocycloalkyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist in protected form, for example, as an —N(Boc), —N(CBz), —N(Tos) group and the like; such protected forms are also considered part of this invention. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of non-aromatic, unsaturated monocyclic heterocycloalkyl rings include thiazolinyl, 2,3-dihydrofuranyl, 2,3-dihydrothiophenyl, etc.

It should be noted that in the hetero-atom containing ring systems of this invention, there are no hydroxyl groups on carbon atoms adjacent to a N, O or S, as well as there are no N or S groups on carbon atoms adjacent to another heteroatom. Thus, for example, in the ring:

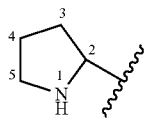

there is no —OH attached directly to carbons marked 2 and 5.

It should also be noted that tautomeric forms such as, for example, the moieties:

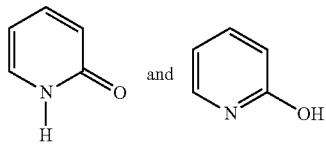 [SMILES: O=c1cccc[nH]1 ; Oc1ccccn1]

are considered equivalent in this invention.

"Hydroxyalkyl" means an alkyl group substituted with a hydroxyl (—OH) group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an —O-alky; group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an —O-aryl group in which the aryl group is as previously described. Non-limiting examples of suitable aryloxy groups include phenoxy and naphthoxy. The bond to the parent moiety is through the ether oxygen.

"Alkylthio" means an —S-alkyl group in which the alkyl group is as previously described. Non-limiting examples of suitable alkylthio groups include methylthio and ethylthio. The bond to the parent moiety is through the sulfur.

"Arylthio" means an —S-aryl group in which the aryl group is as previously described. Non-limiting examples of suitable arylthio groups include phenylthio and naphthylthio. The bond to the parent moiety is through the sulfur.

"Arylalkylthio" means an —S-alkylene-aryl group in which the alkylene and aryl groups are as previously described. A non-limiting example of a suitable arylalkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylalkoxycarbonyl" means an —C(O)—O-alkylene-aryl group. A non-limiting example of a suitable arylalkoxycarbonyl group is benzyloxycarbonyl. The bond to the parent moiety is through the carbonyl.

"Alkylsulfonyl" means an alkyl-S($O_2$)— group. Preferred groups are those in which the alkyl group is a lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When a group is substituted with "one or more" substituents, the indicated group may be substituted with one substituent, two substituents, etc., provided that the resulting substituted group forms a stable structure, as described above.

The term "optionally substituted" means optional substitution with the specified groups, radicals or moieties. For example, an aryl optionally substituted with an indicated group of substituents includes unsubstituted aryl as well as aryl substituted with any of the indicated substituents.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon atom as well as any heteroatom with unsatisfied valences in the text, schemes, examples, Tables, etc. herein is assumed to have the sufficient number of hydrogen atom(s) to satisfy the valences.

When a functional group in a compound is termed "protected", this means that the group is present in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York, herein incorporated by reference in its entirety.

When any variable (e.g., aryl, heterocycloalkyl, $R^2$, etc.) occurs more than one time in any constituent or in Formula (I), its definition on each occurrence is independent of its definition at every other occurrence (unless otherwise expressly indicated).

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are $H_2O$.

"Effective amount" or "therapeutically effective amount" is meant to describe an amount of compound or a composition of the present invention effective in preventing the formation and/or deposition of amyloid protein, and thus producing the desired therapeutic, ameliorative, inhibitory or preventative effect.

The compounds of Formula (I) can form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula (I), and of the salts, solvates and prodrugs of the compounds of Formula (I), are intended to be included in the present invention.

The compounds according to the invention have pharmacological properties; in particular, the compounds of Formula (I) can inhibit gamma-secretase, and are therefore useful in the treatment or prevention of neurodegenerative diseases, e.g., Alzheimer's Disease.

Representative compounds of the invention include but are not limited to the compounds and Examples described herein.

Pharmaceutical compositions can comprise one or more of the compounds of Formula (I). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

EXAMPLES

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents, reagents, and conditions may be referred to by their abbreviations in parenthesis:

Acetyl (Ac), i.e., CH$_3$C(O)—
Butyl (Bu)
Cyclopropyl (Pr-c)
Dichloroethane (DCE)
Dichloromethane (DCM)
Diethyl ether (Et$_2$O)
Diisobutylaluminum hydride (DIBAL-H)
Dimethyl formamide (DMF)
Ethanol (EtOH)
Ethyl (Et)
Ethyl acetate (EtOAc)
High resolution mass spectrometry (HRMS)
Lithium diisopropyl amide (LDA)
Liquid chromatography/mass spectrometry (LCMS)
m-Chloroperoxybenzoic acid (mCPBA)
Mesyl (Ms), i.e., —S(O)$_2$CH$_3$
Methanol (MeOH)
Methyl (Me)
Nuclear magnetic resonance spectroscopy (NMR)
Preparative thin-layer chromatography (PTLC)
Pyridine (Pyr)

Room temperature (RT)
Tert-butyldimethylsilyl (TBS)
Tetrabutyl ammonium fluoride (TBAF)
Tetrahydrofuran (THF)
Trifluoroacetic acid (TFA)
Trimethylsilyl (TMS)
Trimethylsilyl chloride (TMSCl)
Triethylamine ($NEt_3$ or $Et_3N$)

Compounds of Formula (I) can be prepared by various methods well known to those skilled in the art, and by the methods described below. The following methods are typical.

Compounds of Formula (I) can be prepared according to the procedure outlined in General Procedure 1.

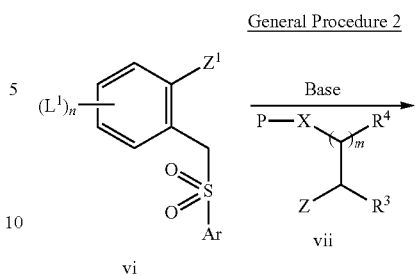

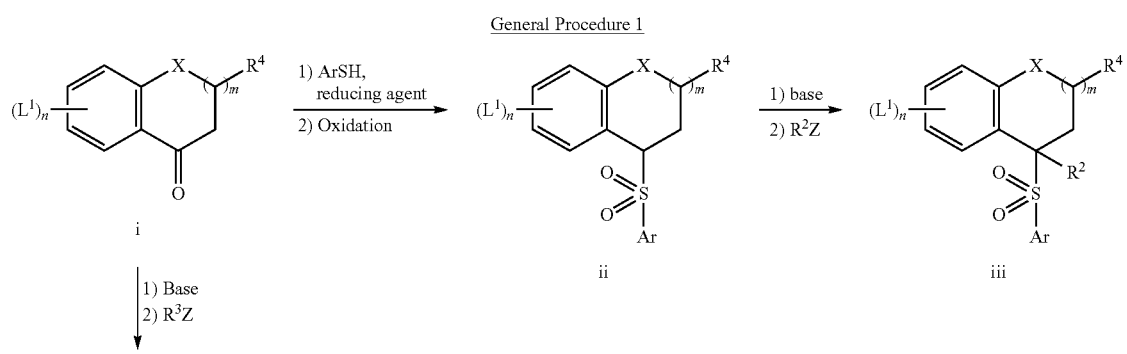

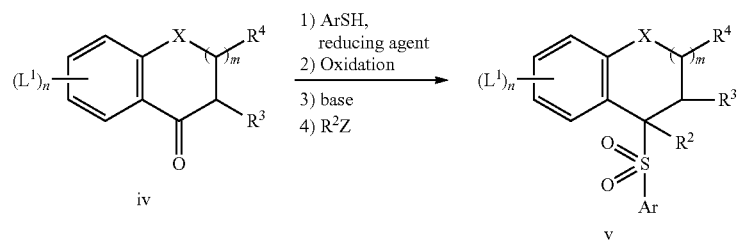

A cyclic ketone such as (i) is treated with a thiol in the presence of a suitable reducing agent such as borane optionally in the presence of an acid such as trifluoroacetic acid. The resulting sulfide is oxidized according to known procedures, for instance using a peracid or oxone, to give sulfone (ii). Compounds of Formula (I), wherein $R^3$ is H and $R^2$ is not H, can be prepared by treating sulfone (ii) with a suitable base such as LDA or n-butyllithium followed by alkylation with a group $R^2Z$, wherein Z is a leaving group such as halo or sulfonate or other functional group that causes $R^3$ to be electrophilic. Compounds of Formula (I) wherein $R^3$ is not H can be prepared by treating compound (i) with a suitable base such as LDA followed by alkylation with a group $R^3Z$, wherein Z is a leaving group such as halo or sulfonate or other functional group that causes $R^3$ to be electrophilic. The resulting ketone (iv) is converted to sulfone (v) as described for the conversion of (i) to (iii).

Compounds of Formula (I), especially when X is —O—, S, —$NR^1$—, and —$N(C(O)R^1)$, can be prepared according to General Procedure 2.

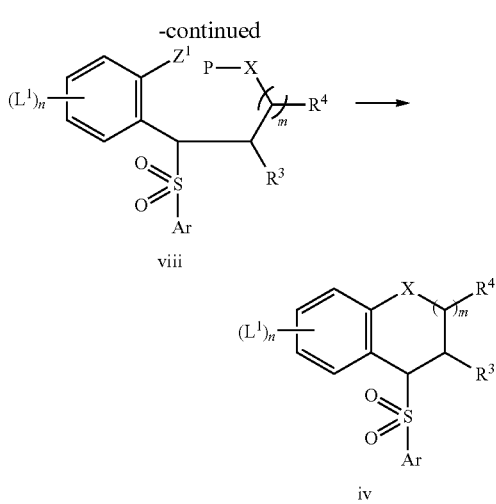

Sulfone (vi), wherein $Z^1$ is defined as Z above, is treated with a suitable base such as sodium hydride or LDA. The resulting anion is treated with an alkylating agent (vii), wherein Z is as defined above, and P is an optional protecting group such as trimethylsilyl, t-butyldimethylsilyl, t-butoxycarbonyl, or benzyloxycarbonyl. After removing the optional protecting group, cyclization optionally in the presence of base such as sodium hydride, potassium carbonate, or LDA, yields compound (iv). Compound (iv) can be transformed into other compounds of formula (I) as describe elsewhere.

Compounds of formula (I), especially when $R^3$ is not H, can be also be prepared by General Procedure 3.

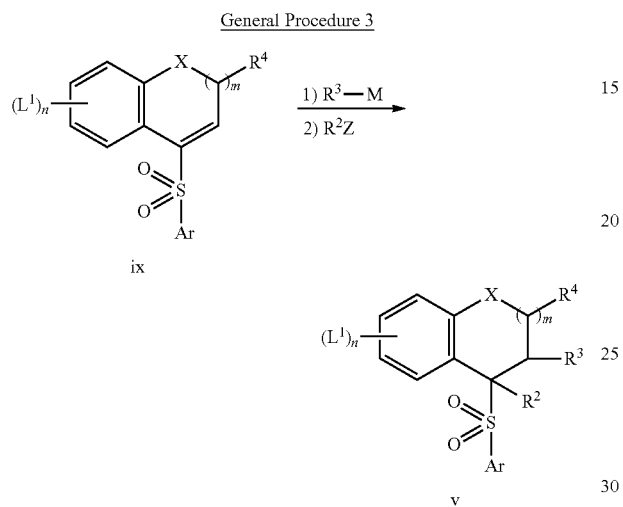

Vinylsulfone (ix) is treated with a nucleophile $R^3$-M, wherein M is a metal such as sodium, lithium, potassium, magnesium, copper, or zinc, optionally followed by treatment with an electrophile $R^2Z$, wherein Z is as defined above.

Compounds of formula (IF) can be prepared by general procedures 1, 2, or 3 by joining together two $R^2$ and $R^3$ groups. Alternatively, compounds of formula (IF) where Q is a substituted or unsubstituted cyclohexyl ring can be prepared according to General Procedure 4.

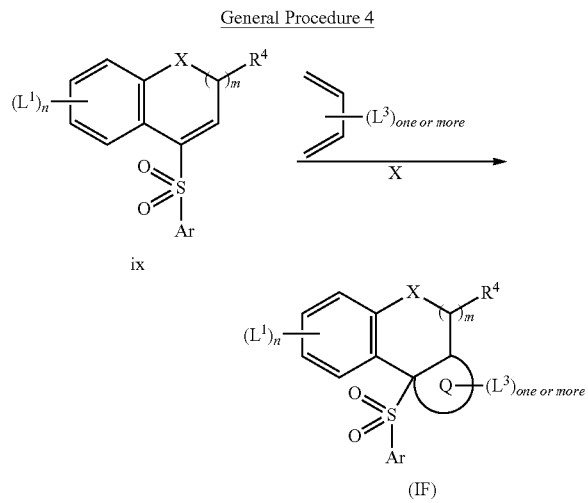

Vinylsulfone (ix) is treated with a diene (x) optionally in the presence of an acid catalyst such as zinc chloride or boron trifluoride in a solvent such as toluene or trifluorotoluene to give compounds of formula (IF).

In addition, compounds of formula (IF) where Q is a substituted or unsubstituted heterocyclic ring, and in particular where said substituted or unsubstituted heterocyclic ring is a pyran ring as in XI, can be prepared according to general procedure 5.

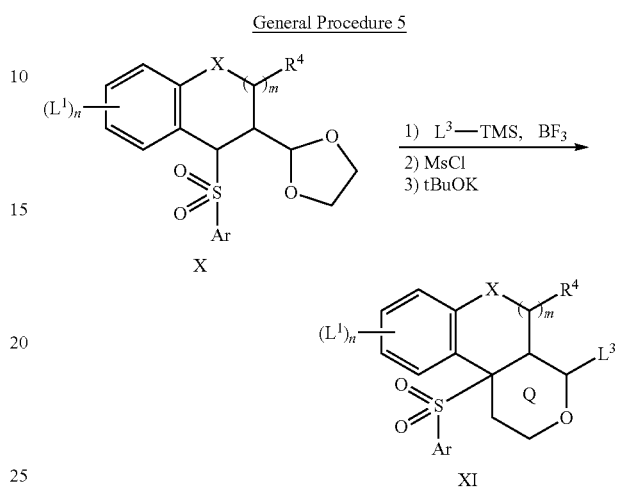

Procedures 1-5 illustrate general procedures for preparing compounds of this invention. Certain compounds of this invention can be transformed into other compounds of this invention by functional group manipulations as described below.

Examples 1 and 2

1-(4-Chloro-benzenesulfonyl-5,8-difluoro-1,2,3,4-tetrahydro-naphthalene and 1-(4-Chloro-benzenesulfonyl-5,8-difluoro-1-methyl-1,2,3,4-tetrahydro-naphthalene

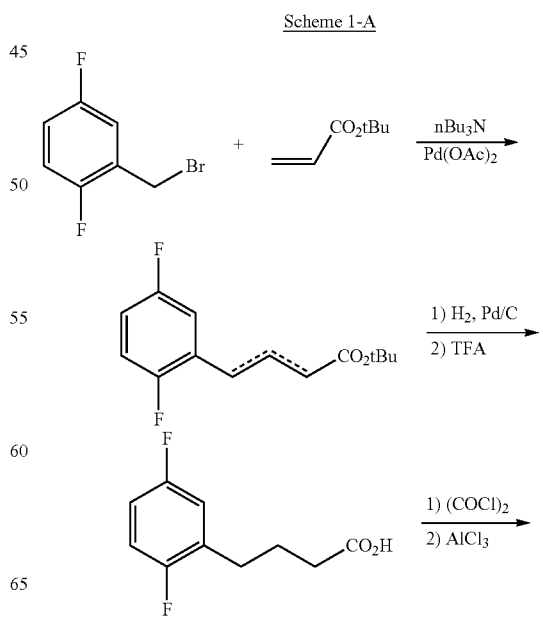

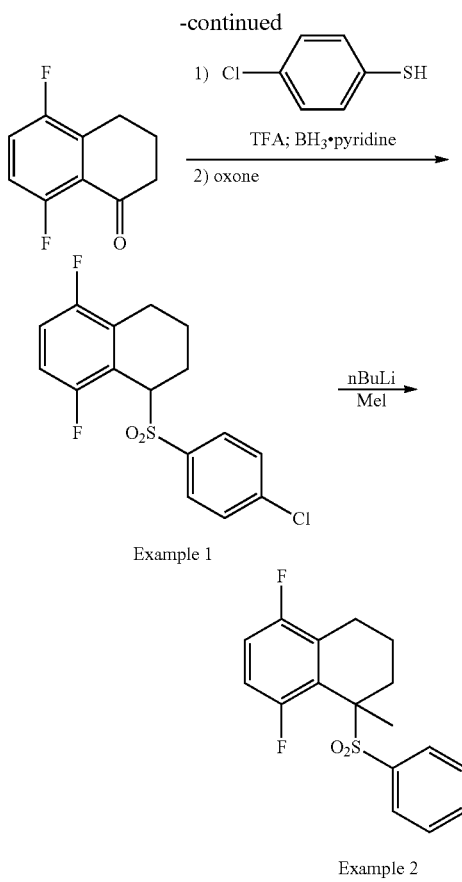

Example 1

Example 2

Step 1

To a solution of LiCl (3.39 g, 80 mmol) and palladium (II) acetate (450 mg, 2.0 mmol) in DMF (75 mL) in a sealed tube was added 2,5-difluorobenzylbromide (9.65 mL, 75 mmol), tert-butylacrylate (11.9 mL, 82 mmol) and tributylamine (19.5 mL, 82 mmol). The reaction was then stirred 2 h at 45° C. and overnight at 120° C. The cooled solution was taken up in Et$_2$O, washed with water and brine, dried and concentrated. The residue was purified by flash-chromatography over silica gel (eluted with hexanes/DCM 75:25 to DCM) to give 9.26 g (49%) of alkene.

Step 2

A mixture of the alkene product of Step 1 (6.36 g, 25 mmol) and 10% Pd/C (650 mg) in EtOH (20 mL) and EtOAc (20 mL) was hydrogenated at 25 psi for 90 min then filtered over CELITE and concentrated to provide 6.34 g (99%) of tert-butyl ester.

Step 3

A solution of the tert-butyl ester product from Step 2: (5.00 g, 19.5 mmol) in DCM (10 mL) and TFA (10 mL) was stirred at RT for 1 hr then concentrated. The crude product (3.95 g) was dissolved in DCM (20 mL) and treated with oxalyl chloride (3.35 mL, 39 mmol) and a drop of DMF. The reaction was stirred at RT for 30 min then concentrated. To a solution of this crude in DCM (15 mL) was added AlCl3 (5.20 g, 39 mmol) and the reaction was stirred at RT for 2 days. The final mixture was poured into ice-cooled 0.1 N HCl, extracted with DCM, dried and concentrated. The residue was purified by flash-chromatography over silica gel (eluted with hexanes/DCM 7:3 to DCM) to afford 3.17 g (89%) of ketone.

Step 4

To a solution of the ketone product from Step 3 (67 mg, 0.37 mmol) and 4-chlorothiophenol (56 mg, 0.39 mmol) in DCM (0.4 mL) at 0° C. was added TFA (0.5 mL) followed, 10 min later, by pyridine borane complex (40 µL). The solution was then allowed to stir 40 min at 0° C. then concentrated. The residue was taken up in Et$_2$O and 1N NaOH, extracted with Et$_2$O, dried over sodium sulfate and concentrated. The residue was taken up in DCM (1 mL) and treated with mCPBA 57 (172 mg, 1.0 mmol). After reaction overnight, the crude product was washed with sodium carbonate solution, dried and concentrated and the residue was purified by preparative-chromatography over silica gel (eluted with hexanes/DCM 1:1) to give 45.5 mg of Example 1: $^1$H NMR (CDCl$_3$ 400 MHz) δ 7.67 (d, J=8.7 Hz, 2H), 7.47 (d, J=8.7 Hz, 2H), 6.97 (m, 1H), 6.72 (m, 1H), 4.61 (d, 1H), 3.92 (m, 1H), 2.65-2.75 (m, 2H), 2.43 (m, 1H), 1.90 (m, 1H), 1.78 (m, 1H); LCMS (MH$^+$)=343.2; retention time=4.71 min.

Step 5

To a solution of the Example 1 product from Step 4 (21.9 mg, 0.064 mmol) in THF (0.3 mL) at −78° C. was added BuLi 2.5 N in hexanes (30 µL, 0.07 mmol) followed, 2 min later by iodomethane (30 µL) and the reaction mixture was allowed to warm to RT. After 10 min, the reaction mixture was poured into saturated NH$_4$Cl, extracted with DCM, dried over sodium sulfate and concentrated. The residue was purified by preparative-chromatography over silica gel (eluted with hexanes/EtOAc 9:1) to give 12.6 mg of Example 2: $^1$H NMR (CDCl$_3$ 400 MHz) δ 7.62 (d, J=8.7 Hz, 2H), 7.45 (d, J=8.7 Hz, 2H), 6.98 (m, 1H), 6.76 (m, 1H), 2.90 (m, 1H), 2.55-2.70 (m, 2H), 2.44 (m, 1H), 1.75-1.85 (m, 2H), 1.80 (s, 3H); LCMS (2 MH$^+$)=713.4; retention time=4.90 min.

Following procedures similar to those used in Scheme 1-A to prepare Examples 1 and 2, substituting appropriate electrophiles and also substituting readily available ketones for the ketone product of Step 4, the compounds in Table 1-A were prepared.

TABLE 1-A

| Example No. | STRUCTURE | Mass Spec (M$^+$ except as otherwise noted); retention time (min) |
|---|---|---|
| 1-A | ![structure] | 585.3 (2MH+); 3.44 |

TABLE 1-A-continued
| Example No. | STRUCTURE | Mass Spec (M+ except as otherwise noted); retention time (min) |
|---|---|---|
| 1-B | 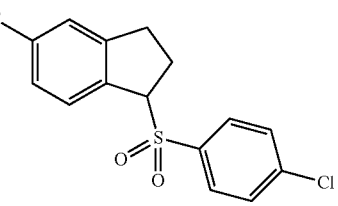 | 621.3 (2MH+); 7.52 |
| 1-C | 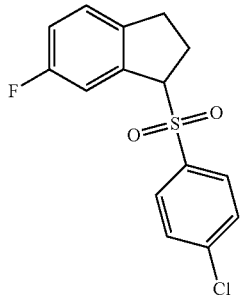 [SMILES: O=S(=O)(c1ccc(Cl)cc1)C1CCc2ccc(F)cc21] | 311.2; 4.56 |
| 1-D | 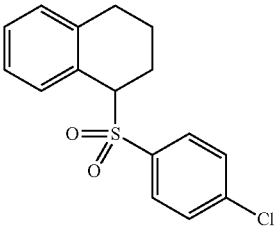 [SMILES: O=S(=O)(c1ccc(Cl)cc1)C1CCCc2ccccc21] | 613.3 (2MH+); 7.86 |
| 1-E | 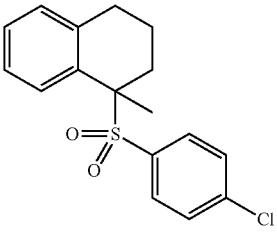 | 641.4 (2MH+); 5.05 |
| 1-F | 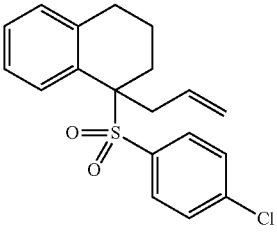 | 695.4 (2MH+); 5.36 |
| 1-G | 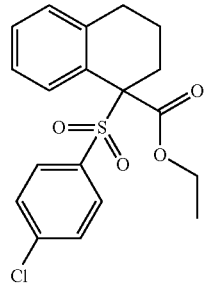 [SMILES: CCOC(=O)C1(S(=O)(=O)c2ccc(Cl)cc2)CCCc2ccccc21] | 379.2; 4.99 |
| 1-H | 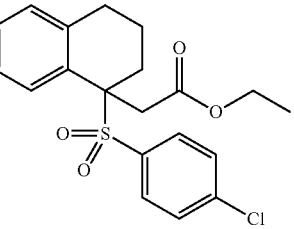 | 393.2; 4.96 |
| 1-I | 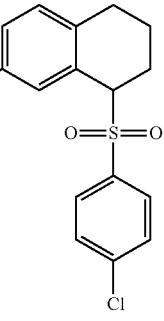 | 651.4 (2MH+); 3.57 |
| 1-J | 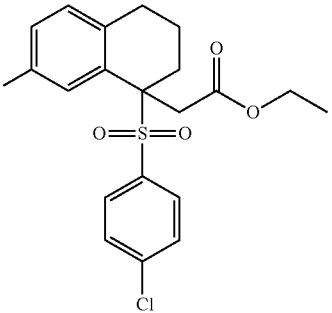 | 411.2; 3.75 |
| 1-K | 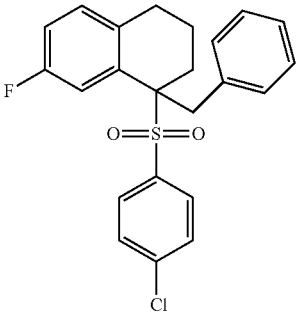 [SMILES: O=S(=O)(c1ccc(Cl)cc1)C1(Cc2ccccc2)CCCc2ccc(F)cc21] | 411.2; 4.10 |

TABLE 1-A-continued

| Example No. | STRUCTURE | Mass Spec (M+ except as otherwise noted); retention time (min) |
|---|---|---|
| 1-L | (7-fluoro-1,2,3,4-tetrahydronaphthalen-1-yl with ethyl ester and 4-chlorophenylsulfonyl) | 397.2; 4.96 |
| 1-M | (5,7-difluoro-1,2,3,4-tetrahydronaphthalen-1-yl with 4-chlorophenylsulfonyl) | 687.4 (2MH+); 4.80 |
| 1-N | (5,7-difluoro-1-methyl-1,2,3,4-tetrahydronaphthalen-1-yl with 4-chlorophenylsulfonyl) | 713.4 (2MH+); 5.25 |
| 1-O | (5,7-difluoro-1-ethyl-1,2,3,4-tetrahydronaphthalen-1-yl with 4-chlorophenylsulfonyl) | 763.4 (2MNa); 5.41 |
| 1-P | (8-fluoro-1,2,3,4-tetrahydronaphthalen-1-yl with 4-chlorophenylsulfonyl) | 325.2; 4.66 |
| 1-Q | (8-fluoro-1-butyl-1,2,3,4-tetrahydronaphthalen-1-yl with 4-chlorophenylsulfonyl) | 381.2; 5.17 |
| 1-R | (5,8-difluoro-1-ethyl-1,2,3,4-tetrahydronaphthalen-1-yl with 4-chlorophenylsulfonyl) | (2MH+) 741.4; 5.08 |
| 1-S | (5,8-difluoro-1-isopropyl-1,2,3,4-tetrahydronaphthalen-1-yl with 4-chlorophenylsulfonyl) | (2MNa) 791.4; 5.23 |

Example 1-T (3R)-3-Hydroxy-pyrrolidine-1-carboxylic acid 2-[1-(4-chloro-benzenesulfonyl)-7-fluoro-1,2,3,4-tetrahydro-naphthalen-1-yl]-ethyl ester

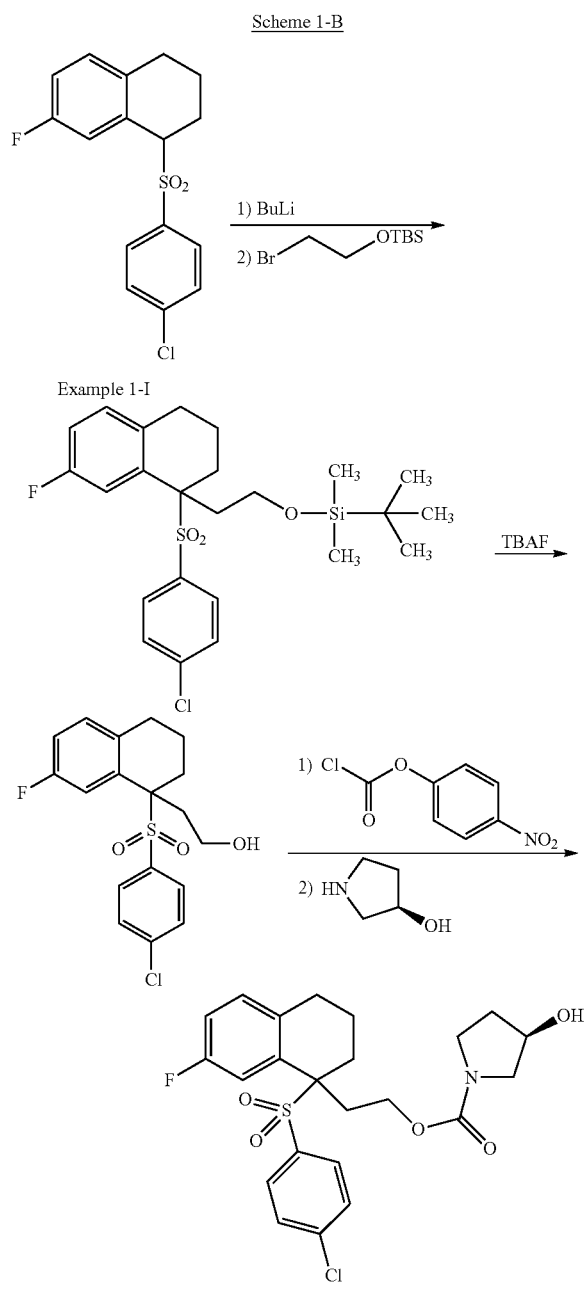

Scheme 1-B

Example 1-T

Step 1

To a solution of Example 1-I (100 mg, 0.30 mmol) in THF (2 mL) at −78° C. was added n-BuLi 2.5 N in hexanes (0.12 mL, 0.30 mmol) and the resulting solution was stirred 10 minutes, warmed to RT for 5 min then cooled again to −78° C. It was quenched with TBS protected bromoethanol (0.32 mL, 1.50 mmol). The reaction was allowed to warm to RT for 2 days. The final mixture was poured into water, extracted with DCM, dried and concentrated. The residue was purified by preparative-chromatography over silica gel (eluted with hexanes/EtOAc 90:10) to afford 90 mg of TBS-protected alcohol.

Step 2

A solution of TBS-protected alcohol product from Step 1 (90 mg; 0.186 mmol) in THF (5 mL) was treated with TBAF 1N in THF (0.20 mL, 0.20 mmol) and stirred for 2 h. The reaction was then concentrated and purified by preparative-chromatography over silica gel (eluted with hexanes/EtOAc 80:20) to give 54 mg of alcohol.

Step 3

To a solution of alcohol product from Step 2: (55 mg, 0.149 mmol) in THF (1 mL) and acetonitrile (0.5 mL) was added 4-nitrophenylchloroformate (60 mg, 0.298 mmol) and pyridine (0.08 mL) and the reaction was stirred at RT for 2 h. The final mixture was washed with 1N HCl, then extracted with DCM. After concentration, the crude was purified by preparative-chromatography over silica gel (eluted with hexanes/EtOAc 80:20) to provide 70 mg of nitrophenylcarbonate.

Step 4

A solution of nitrophenylcarbonate product from Step 3 (15 mg) and (S)-3-hydroxypyrrolidine (15 mg) in DCE (1 mL) was stirred overnight at RT. The reaction was washed with water, extracted with DCM and dried. After concentration, the crude was purified by preparative-chromatography over silica gel (eluted with hexanes/EtOAc 50:50) to give 6.0 mg of Example 1-T: $^1$H NMR (CDCl$_3$ 400 MHz) δ 7.48 (d, J=8.7 Hz, 1H), 7.35 (br s, 4H), 6.95 (d, J=7.2, 2H), 4.42 (br s, 1H), 4.10-4.25 (m, 1H), 3.90-4.05 (m, 1H), 3.10-3.50 (m, 3H), 2.90-3.00 (m, 1H), 2.40-2.60 (m, 2H), 2.15-2.35 (m, 2H), 2.00-2.15 (m, 1H), 1.75-1.95 (m, 2H), 1.40-1.70 (m, 3H), 1.25 (br s, 1H); LCMS (MH$^+$)=482.3; retention time=3.98 min.

Following procedures similar to those used in Scheme 1-B to prepare Example 1-T, the compounds in Table 1-B were prepared.

TABLE 1-B

| Example No. | STRUCTURE | Mass Spec (M$^+$ except as otherwise noted); retention time (min) |
|---|---|---|
| 1-U | 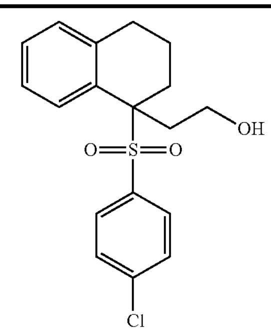 | 351.2; 3.14 |

TABLE 1-B-continued

| Example No. | STRUCTURE | Mass Spec (M+ except as otherwise noted); retention time (min) |
|---|---|---|
| 1-V | 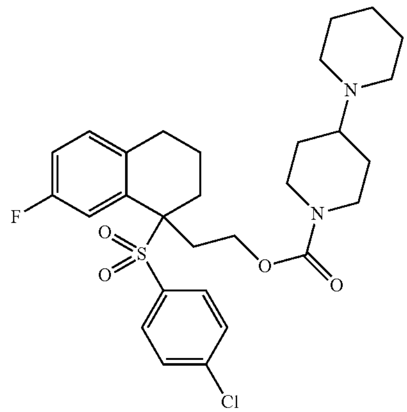 [SMILES: O=C(OCCC1(S(=O)(=O)c2ccc(Cl)cc2)CCCc2ccc(F)cc21)N1CCC(N2CCCCC2)CC1] | 563.3; 3.08 |

Examples 3 and 4

Cis-1-(4-chloro-benzenesulfonyl-2-ethyl-5,8-difluoro-1,2,3,4-tetrahydro-naphthalene and Trans-1-(4-chloro-benzenesulfonyl)-2-ethyl-5,8-difluoro-1,2,3,4-tetrahydro-naphthalene

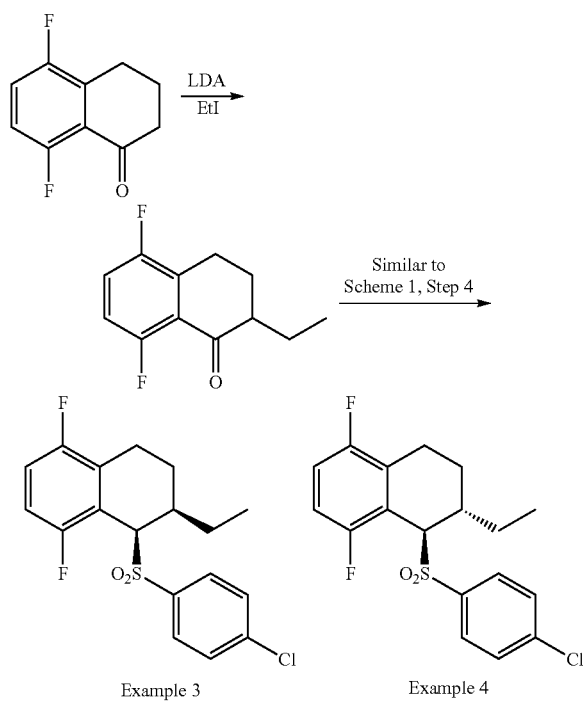

Scheme 2-A

Example 3     Example 4

Step 1

To a solution of the ketone product from Scheme 1-A, Step 3 (398 mg, 2.18 mmol) in THF (2 mL) at −78° C. was added LDA 1.8 N in hexanes (1.20 mL, 2.19 mmol). The reaction was warmed to −30° C., cooled to −78° C. again and EtI (175 uL, 2.18 mmol) was slowly added. The reaction was allowed to warm to RT overnight then poured into saturated $NH_4Cl$ and extracted with DCM. After concentration, the crude was purified by flash-chromatography over silica gel (eluted with hexanes/EtOAc 95:5 to 7:3) to allow, in order of elution, 32.7 mg of ethylketone followed by 314 mg of the starting ketone.

Step 2

The ethylketone product from Step 1 was reacted with 4-chlorothiophenol following conditions similar to those described in Step 4 of Scheme 1-A, to provide, after separation over silica gel, the cis compound i.e., Example 3, and the trans compound Example 4. Example 3: $^1$H-NMR ($CDCl_3$ 400 MHz) δ 7.55 (d, J=8.7 Hz, 2H), 7.39 (d, J=8.7 Hz, 2H), 6.91 (m, 1H), 6.58 (m, 1H), 4.65 (br s, 1H), 3.10 (m, 1H), 2.88 (m, 1H), 2.57 (m, 1H), 1.80-2.15 (m, 4H), 1.07 (t, J=7.2 Hz, 3H); LCMS (MH+)=371.2; retention time=5.27 min. Example 4: $^1$H-NMR ($CDCl_3$ 400 Mhz) δ 7.61 (d, J=8.7 Hz, 2H), 7.43 (d, J=8.7 Hz, 2H), 6.95 (m, 1H), 6.67 (m, 1H), 4.39 (br s, 1H), 2.70-2.80 (m, 3H), 2.46 (m, 1H), 1.46 (m, 1H), 1.30-1.40 (m, 2H), 0.93 (t, J=7.2 Hz, 3H); LCMS (MH+)= 371.2; retention time=5.21 min.

Following procedures similar to those described in Schemes 1-A, 1-B and 2-A, the compounds in Table 2-A were prepared.

TABLE 2-A

| Example No. | STRUCTURE | Mass Spec (M+ except otherwise noted); retention time (min) |
|---|---|---|
| 3-A | 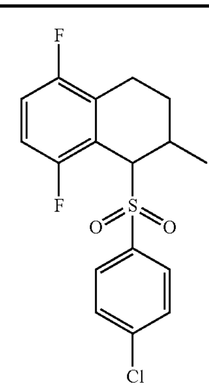 | 357.2; 5.53 |

TABLE 2-A-continued

| Example No. | STRUCTURE | Mass Spec (M+ except otherwise noted); retention time (min) |
|---|---|---|
| 3-B | 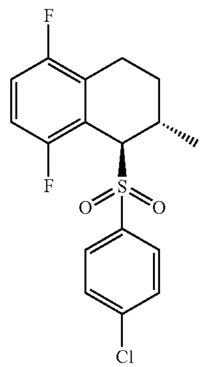 [SMILES: C[C@H]1CCc2c(F)ccc(F)c2[C@@H]1S(=O)(=O)c1ccc(Cl)cc1] | 357.2; 5.23 |
| 3-C | 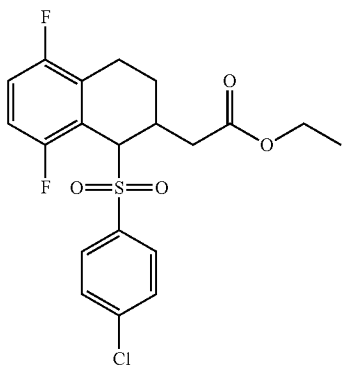 [SMILES: CCOC(=O)CC1CCc2c(F)ccc(F)c2C1S(=O)(=O)c1ccc(Cl)cc1] | 429.2; 5.19 |
| 3-D | 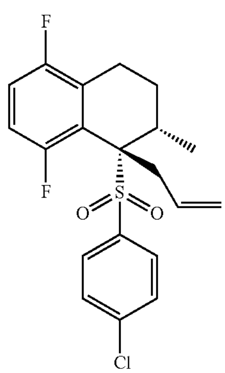 [SMILES: C=CC[C@@]1(S(=O)(=O)c2ccc(Cl)cc2)c2c(F)ccc(F)c2CC[C@@H]1C] | (2MNa) 815.4; 5.77 |
| 3-E | 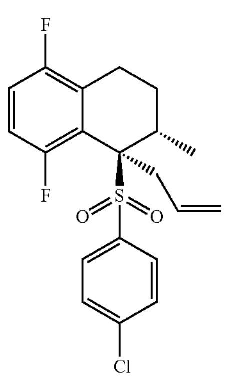 [SMILES: C=CC[C@]1(S(=O)(=O)c2ccc(Cl)cc2)c2c(F)ccc(F)c2CC[C@@H]1C] | (2MNa) 815.4; 5.67 |
| 3-F | | (2MNa) 763.4; 5.42 |

Example 3-G (3R)-3-Hydroxy-pyrrolidine-1-carboxylic acid 1-(4-chloro-benzenesulfonyl)-1,2,3,4-tetrahydro-naphthalen-2-yl-methyl ester Scheme 2-B

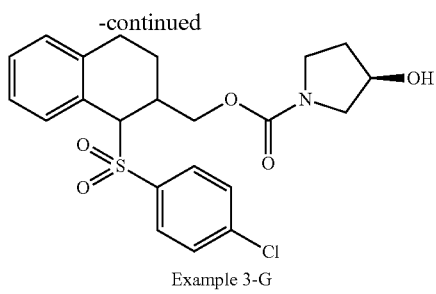

Example 3-G

Step 1

To a mixture of NaH 60% (700 mg, 17.5 mmol) in THF (35 mL) was added alpha-tetralone (0.665 mL, 5.0 mmol) followed by dimethylcarbonate (1.20 mL, 14.3 mmol) and the reaction was refluxed overnight. It was then concentrated, taken up in Et2O and half-brine, washed twice with half-brine, dried and concentrated. The residue was purified by flash-chromatography over silica gel (eluted with Hexanes/DCM 80:20 to DCM) to give 936 mg of ester ketone.

Step 2

The ester ketone product from Step 1 (408 mg, 2.00 mmol) was reacted with 4-chlorothiophenol following conditions similar to those described in Step 4 of Scheme 1-A, to provide, after separation over silica gel, 85 mg of the ester sulfone.

Step 3

To a solution of ester sulfone product from Step 2: (100 mg, 0.27 mmol) in THF (2.5 mL) was added lithium borohydride (120 mg, 5.84 mmol) and the reaction was refluxed for 3 h. The final mixture was quenched with saturated sodium bicarbonate, extracted with EtOAc, dried and concentrated. The residue was purified by preparative-chromatography over silica gel (eluted with hexanes/EtOAc 60:40) to give 65 mg of alcohol: $^1$H-NMR (CDCl$_3$ 400 MHz) δ 7.35-7.45 (m, 3H), 7.10-7.25 (m, 3H), 6.87 (m, 1H), 6.37 (d, 1H), 4.60 and 4.51 (d, 1H), 4.22 (m, 1H), 3.92 and 3.80 (m, 1H), 2.00-2.10 (m, 1H), 2.80-2.90 (m, 1H), 2.53 (m, 1H), 2.15-2.25 (m, 1H), 1.74 (m, 1H), 1.25 (br s, 1H); LCMS (MH$^+$)=337.2; retention time=3.10 min.

Step 4

The alcohol product from Step 3 was subjected to conditions similar to those described in Steps 3 and 4 of Scheme 1-B, to provide, after separation over silica gel, Example 3-G: $^1$H-NMR (CDCl$_3$ 400 MHz) δ 7.35-7.45 (m, 3H), 7.00-7.30 (m, 3H), 6.94 (m, 1H), 6.58 (m, 1H), 4.65-4.75 (m, 1H), 4.35-4.55 (m, 2H), 3.30-3.60 (m, 3H), 2.80-3.05 (m, 2H), 2.50-2.60 (m, 1H), 2.20-2.35 (m, 1H), 1.55-2.10 (m, 5H), 1.25 (br s, 1H); LCMS (MH$^+$)=450.2; retention time=3.87 min.

Following procedures similar to those described in Scheme 2-B, the compound in Table 2-B was prepared.

TABLE 2-B

| Example No. | STRUCTURE | Mass Spec (M$^+$ except otherwise noted); retention time (min) |
|---|---|---|
| 3-H | ![structure] | 531.3; 3.11 |

Example 5

1-(4-Chloro-benzenesulfonyl)-5,8-difluoro-4-methyl-1,2,3,4-tetrahydro-naphthalene Scheme 3

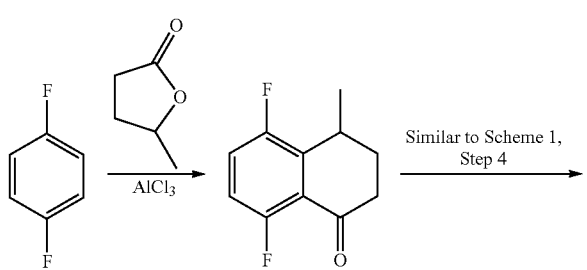

Similar to Scheme 1, Step 4

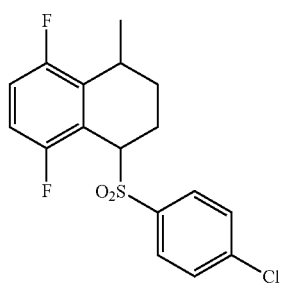

Example 5

Step 1

To a solution of 1,4-difluorobenzene (9.75 mL, 100 mmol) and gamma-valerolactone (1.90 mL, 20 mmol) in an acetone bath was added slowly AlCl$_3$ (13.4 g, 100 mmol) then the reaction was stirred under reflux overnight. The mixture was then slowly poured into ice-cooled 1N HCl, extracted with DCM, washed with water and saturated sodium bicarbonate, dried over sodium sulfate and concentrated to give 3.92 g (100%) of ketone.

Step 2

The ketone product from Step 1 was reacted with 4-chlorothiophenol following conditions similar to the ones described in Step 4 of Scheme 1-A, to provide Example 5, as an approximately 65:35 trans:cis mixture of diastereoisomers: $^1$H-NMR (CDCl$_3$ 400 MHz) δ 7.71 (d, J=8.7 Hz, 2H cis), 7.70 (d, J=8.7 Hz, 2H trans), 7.51 (d, J=8.7 Hz, 2H cis+trans), 6.97 (m, 1H cis+trans), 6.72 (m, 1H cis+trans), 4.60 (br s, 1H cis), 4.56 (d, 1H trans), 3.37 (m, 1H trans), 3.17 (1H cis), 2.55-2.75 (m, 2H cis+trans), 2.00-2.20 (m, 1H cis+trans), 1.83 (m, 1H cis), 1.60 (br d, 1H trans), 1.44 (d, J=6.8 Hz, 3H cis), 1.18 (d, J=7.2 Hz, 3H trans); LCMS (MH$^+$)= 357.2; retention time=3.79 min.

Following procedures similar to those described in Schemes 1-A and 3, the compounds in Table 3 were prepared using the appropriate electrophile and lactone reactants.

TABLE 3

| Example No. | STRUCTURE | Mass Spec (M$^+$ except otherwise noted); retention time (min) |
|---|---|---|
| 5-A | ![structure] | 343.2; 3.71 |
| 5-B | ![structure] | 443.2; 3.89 |
| 5-C | ![structure] | 429.2; 3.88 |

Example 6

1-(4-Chloro-benzenesulfonyl-5,8-difluoro-3-methyl-1,2,3,4-tetrahydro-naphthalene Scheme 4

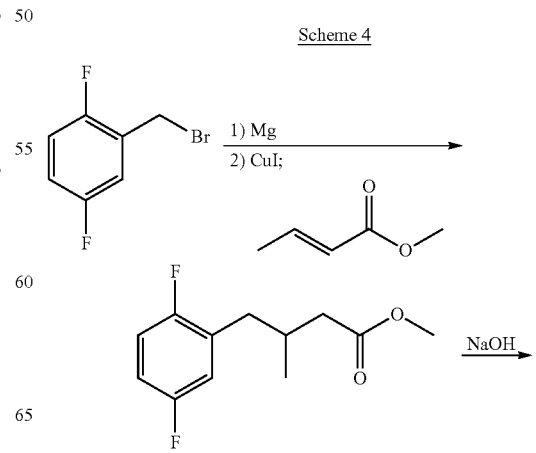

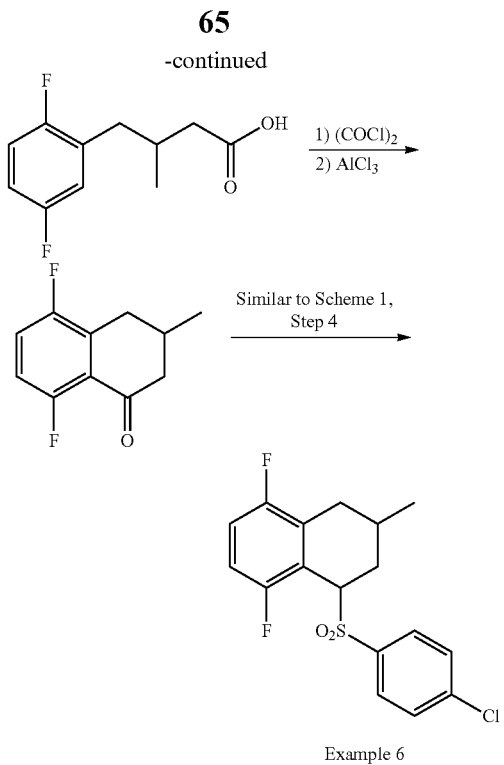

Example 6

Step 1

To a solution of magnesium turnings (7.0 g; 290 mmol) in Et₂O (40 mL) were added a hexane solution containing a catalytic amount of iodine and dibromoethane (1 mL). The reaction was heated to 40° C. and a solution of 2,5-difluorobenzyl bromide (15.0 g, 72.4 mmol) in Et₂O (40 mL) was added over 1 h. The reaction mixture was then stirred another hour at 40° C. then cooled and diluted with Et₂O to 100 mL to provide a benzyl Grignard reagent solution (16.7 g).

To a solution of Cu (I) iodide (4.6 g, 24.1 mmol) in THF (80 mL) was added N,N,N',N'-tetramethylethylenediamine (4.0 mL, 26.6 mmol) and the reaction mixture was stirred for 15 minutes at RT. The mixture was then cooled to −78° C. and the benzyl Grignard solution prepared above (5 g, 21.6 mmol) in Et₂O (30 mL) was added to the mixture, followed by 15 minutes of stirring. A solution of TMSCl (6.0 mL, 60.4 mmol) and trans-methyl crotonate (2.0 mL, 21.7 mmol) in THF (30 mL) was then added and the reaction mixture was allowed to warm to −50° C. and stirred at −50° C. overnight. The crude product was poured into a saturated solution of NH₄OH and NH₄Cl, extracted with Et₂O, washed with water and dried over sodium sulfate. The crude product obtained after concentration was purified by chromatography over silica gel (eluted with hexanes/EtOAc 95:5) to give 2.5 g (45%) of ester.

Step 2

To a solution of the ester from Step 1 (200 mg, 0.88 mmol) in MeOH (4 mL) was added 1N NaOH (4 mL) and the reaction was stirred at RT overnight. The reaction was diluted with water, washed with EtOAc then acidified with 1N HCl, extracted with EtOAc, dried over sodium sulfate and concentrated to give 173 mg (92%) of acid.

Step 3

To a solution of the acid from Step 2: (170 mg, 0.79 mmol) in DCM (2 mL) was added oxalyl chloride (0.14 mL, 1.60 mmol) and a drop of DMF and the reaction mixture was stirred 30 min at RT then concentrated. The resulting residue was taken up in DCM (3 mL), treated with AlCl₃ (213 mg, 1.60 mmol) and then stirred at RT overnight. The crude product was poured into 0.1 N HCl, extracted with DCM and EtOAc, dried over sodium sulfate and concentrated. The residue was purified by chromatography over silica gel (hexanes/DCM 1:1) to afford 112 mg (70) of ketone.

Step 4

The ketone product from Step 3 was reacted with 4-chlorothiophenol following conditions similar to the ones described in Step 4 of Scheme 1-A, to provide Example 6, as a 55:45 mixture of diastereoisomers 1 and 2: ¹H-NMR (CDCl₃ 400 MHz) δ 7.76 (d, J=8.7 Hz, 2H diast 1), 7.45-7.55 (m, 2H diast 1 and 2), 7.42 (d, J=8.7 Hz, diast 2), 6.90-7.00 (m, 1H diast 1 and 2), 6.60-6.75 (m, 1H diast 1 and 2), 4.81 (dd, 1H diast 2), 4.60 (br s, 1H diast 1), 3.45-3.50 (m, 1H diast 2), 3.15 (dd, 1H diast 1), 2.87 (br d, 1H diast 2), 2.60-2.80 (m), 2.38 (m, 1H diast 2), 2.10-2.30 (m), 1.50-1.60 (m), 1.18 (d, J=6.4 Hz, 3H diast 2), 1.11 (d, J=6.4 Hz, 3H diast 1); LCMS (2 MH⁺) 713.4; retention time=5.00.

Following procedures similar to those described in Scheme 1, the compound in Table 4 was prepared.

TABLE 4

| Example No. | Structure | Mass Spec (M⁺ except otherwise noted); retention time (min) |
|---|---|---|
| 6-A | 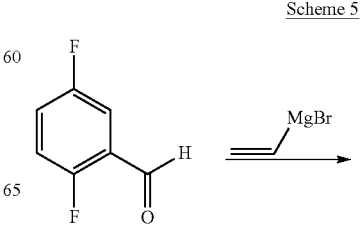 | (2MNa) 763.4; 5.17 |

Example 7

5-(4-Chloro-benzenesulfonyl-1,4-difluoro-6,7,8,9-tetrahydro-5H-benzocycloheptene Scheme 5

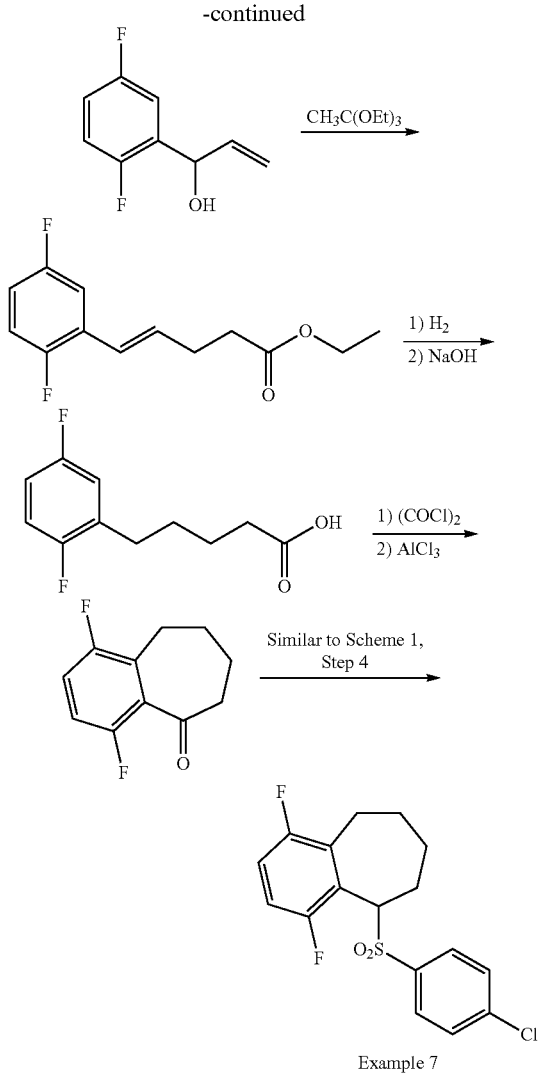

Example 7

Step 1

To a solution of 2,5-difluorobenzaldehyde (8.65 g, 60.9 mmol) in THF (150 mL) was slowly added vinylmagnesium bromide 1 N in THF (85 mL, 85 mmol) at −40° C. and the reaction mixture was allowed to warm to 0° C. over 45 min. It was then quenched into saturated NH$_4$Cl, extracted with DCM and EtOAc, dried over sodium sulfate and concentrated. The residue was purified by flash-chromatography over silica gel (eluted with hexanes/EtOAc 95:5 to 70:30) to provide 5.37 g (37%) of alcohol.

Step 2

A solution of the alcohol product from Step 1 (5.35 g, 31.4 mmol), triethyl orthoacetate (41.3 mL, 220 mmol) and propionic acid (155 mg) was stirred at 180° C. under reflux overnight. The reaction mixture was concentrated and purified by flash-chromatography over silica gel (eluted with hexanes/EtOAc 95:5 to 70:30) to give 6.42 g (85%) of alkene.

Step 3

A solution of the alkene product from Step 2: (6.42 g, 26.7 mmol) and 10% Pd/C (720 mg) in EtOH (20 mL) and EtOAc (20 mL) was hydrogenated at 30 psi for 60 min then filtered over CELITE and concentrated to afford 6.19 g (96%) of ester.

Step 4

A solution of ester product from Step 3 (5.35 g, 31.4 mmol) in EtOH (50 mL) was treated with 1N NaOH (50 mL) and stirred at 50° C. then the organic solvent was concentrated. After washing with Et$_2$O, the aqueous layers is acidified with 1N HCl, extracted with EtOAc and DCM, dried over sodium sulfate and concentrated to provide 4.76 g (87%) of acid.

Step 5

To a solution of the acid product from Step 4 (3.05 g, 14.2 mmol) in DCM (30 mL) at 0° C. was added oxalyl chloride (2.45 mL, 28.4 mmol) followed by a drop of DMF. The reaction mixture was allowed to warm to RT and stirred 30 min then concentrated. The residue was immediately dissolved in DCE (8 mL), treated with AlCl$_3$ (3.79 g, 28.4 mmol) and stirred overnight at 60° C. It was then poured into diluted HCl, extracted with DCM, dried over sodium sulfate and concentrated. The residue was purified by flash-chromatography over silica gel (eluted with hexanes/EtOAc 95:5 to EtOAc) to provide 1.20 g (43%) of ketone.

Step 6

The ketone product from Step 5 was reacted with 4-chlorothiophenol following conditions similar to the ones described in Step 4 of Scheme 1-A, to provide Example 7: $^1$H-NMR (CDCl$_3$ 400 MHz) δ 7.58 (d, J=8.7 Hz, 2H), 7.40 (d, J=8.7 Hz, 2H), 6.96 (m, 1H), 6.63 (m, 1H), 4.84 (m, 1H), 3.20-3.35 (m, 2H), 2.72 (m, 1H), 2.23 (m, 1H), 1.90-2.10 (m, 2H), 1.70 (m, 1H), 1.40 (m, 1H); LCMS (MH$^+$)=357.2; retention time=5.04 min.

Following procedures similar to those described in Schemes 1-A, 1-B, 2-A, 2-B, and 5, the compounds in Table 5 were prepared.

TABLE 5

| Example No. | STRUCTURE | Mass Spec (M$^+$ except otherwise noted); retention time (min) |
|---|---|---|
| 7-A | 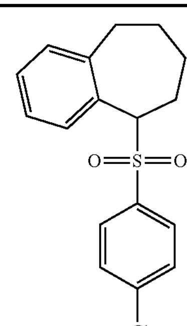 | 321.2; 4.99 |

TABLE 5-continued

| Example No. | STRUCTURE | Mass Spec (M+ except otherwise noted); retention time (min) |
|---|---|---|
| 7-B | 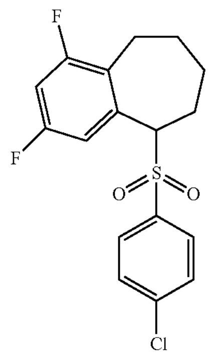 [SMILES: O=S(=O)(c1ccc(Cl)cc1)C1CCCCc2c(F)cc(F)cc21] | 715.2 (2MH+); 6.42 |
| 7-C | 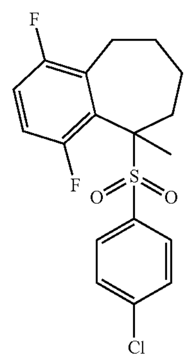 | 741.4 (2MH+); 5.13 |
| 7-D | 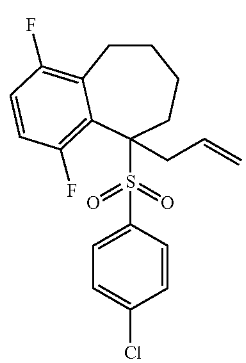 | 793.4 (2MH+); 5.47 |

TABLE 5-continued

| Example No. | STRUCTURE | Mass Spec (M+ except otherwise noted); retention time (min) |
|---|---|---|
| 7-E | | 371.2; 5.35 |
| 7-E | | 371.2; 5.29 |

Example 8

4-(4-Chloro-benzenesulfonyl)-4-ethyl-5,8-difluoro-chroman

Step 1

2-(4-Chloro-phenylsulfanylmethyl)-1,3,4-trifluoro-benzene

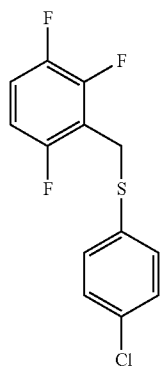

2,3,6-Trifluorobenzyl bromide (9.79 g, 43.3 mmol) and 4-chlorothiophenol (6.23 g, 43.3 mmol) were dissolved in 300 mL of THF. Triethylamine (4.59 g, 45.4 mmol) was added. The solution was stirred at room temperature overnight. 300 mL of EtOAc and 300 mL of water were added. The organic layers were washed with 200 mL 1N HCl solution, dried over $Na_2SO_4$ and concentrated. The residue was pure product (12.5 g, quant. yield). $^1$H NMR ($CDCl_3$ 400 MHz) δ 7.30 (d, J=8.8 Hz, 2H), 7.24 (d, J=8.8 Hz, 2H), 7.03 (m, 1H), 6.77 (m, 1H), 4.08 (s, 2H).

Step 2

2-(4-Chloro-benzenesulfonylmethyl)-1,3,4-trifluoro-benzene

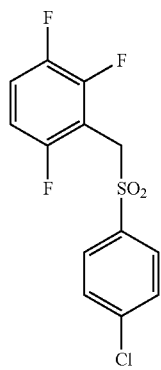 [SMILES: O=S(=O)(Cc1c(F)ccc(F)c1F)c1ccc(Cl)cc1]

2-(4-Chloro-phenylsulfanylmethyl)-1,3,4-trifluoro-benzene (12.5 g, 43.3 mmol) was dissolved in 600 mL of DCM, mCPBA (77%, 19.3 g, 86.4 mmol) was added slowly and the reaction mixture was stirred at room temperature overnight. The excess mCPBA was quenched with 10.2 g of $Na_2SO_3$ in 300 mL of water. The organic layer was separated and washed with 1N NaOH (2×200 mL), brine (200 mL), dried over $Na_2SO_4$, filtered and concentrated. The residue was used in the next step without further purification (14.8 g, quant. yield). $^1$H NMR ($CDCl_3$ 400 MHz) δ 7.70 (d, J=8.8 Hz, 2H), 7.50 (d, J=8.8 Hz, 2H), 7.17 (m, 1H), 6.87 (m, 1H), 4.49 (s, 2H).

Step 3

Tert-Butyl-[3-(4-chloro-benzenesulfonyl)-3-(2,3,6-trifluoro-phenyl)-propoxy]-dimethyl-silane

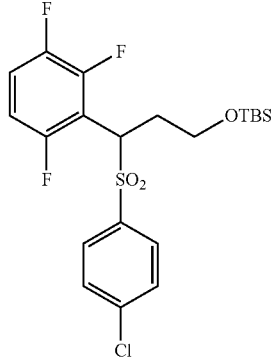 [SMILES: CC(C)(C)[Si](C)(C)OCCC(c1c(F)ccc(F)c1F)S(=O)(=O)c1ccc(Cl)cc1]

2-(4-Chloro-benzenesulfonylmethyl)-1,3,4-trifluoro-benzene (4.0 g, 12.5 mmol) was dissolved in 40 mL dry DMF. (2-Bromo-ethoxy)-tert-butyl-dimethylsilane (4.1 g, 17.1 mmol) and NaH (2.28 g, 95.0 mmol) were added respectively. The solution was stirred at room temperature overnight. 200 mL of water and 200 mL of EtOAc were added. The aqueous layer was washed with 100 mL of EtOAc. The combined organic layers were washed with brine (100 mL), dried over $Na_2SO_4$ and concentrated. The product was purified using column chromatography (hex./EtOAc 100/0 to 90/10 in 45 min, 1.7 g, 28%). $^1$H NMR ($CDCl_3$ 400 MHz) δ 7.65 (m, 2H), 7.46 (m, 2H), 7.14 (m, 1H), 6.84 (m, 0.5), 6.73 (m, 0.5H), 4.87 (m, 1H), 4.79 (m, 1H), 4.37 (m, 1H), 2.55 (m, 2H), 2.04 (s, 9H), −0.13 (d, J=22.7 Hz, 6H).

Step 4

3-(4-Chloro-benzenesulfonyl)-3-(2,3,6-trifluoro-phenyl)-propan-1-ol

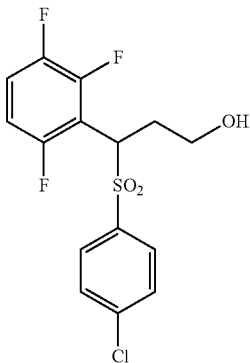 [SMILES: O=S(=O)(c1ccc(Cl)cc1)C(CCO)c1c(F)ccc(F)c1F]

Tert-butyl-[3-(4-chloro-benzenesulfonyl)-3-(2,3,6-trifluoro-phenyl)-propoxy]-dimethyl-silane (2.62 g, 5.47 mmol) was dissolved in 80 mL of THF and tetrabutylammonium fluoride (1.96 g, 7.51 mmol) was added at room temperature.

The solution was stirred at room temperature overnight. 200 mL of EtOAc and 200 mL of water were added and the organic layer was separated. The organic layer was dried over Na$_2$SO$_4$ and concentrated. The product was purified by column chromatography using hex./EtOAc as the eluent (gradient from 0/100 to 75/25 in 45 min, 1.38 g, 69%). $^1$H NMR (CDCl$_3$ 400 MHz) δ 7.63 (d, J=8.8 Hz, 2H), 7.45 (d, J=8.8 Hz, 2H), 7.12 (m, 1H), 6.82 (m, 0.5H), 6.71 (m, 0.5H), 4.91 (m, 1H), 3.89 (m, 1H), 4.44 (m, 1H), 2.60 (m, 2H).

Step 5

4-[(4-Chlorophenyl)sulfonyl]-5,8-difluoro-3,4-dihydro-2H-1-benzopyran

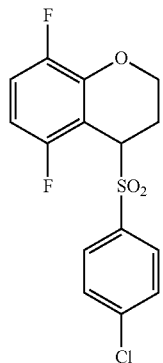

SCH 791199

3-(4-Chloro-benzenesulfonyl)-3-(2,3,6-trifluoro-phenyl)-propan-1-ol (1.28 g, 3.51 mmol) was dissolved in 40 mL THF and NaH (60% in oil, 0.5 g, excess) was added. The solution was stirred at room temperature overnight. The reaction mixture was diluted with water (40 mL) and extracted with ethyl acetate (3×50 mL), the organic layer was combined, dried over Na$_2$SO$_4$ and concentrated. The product was purified using column chromatography (hex./EtOAc 100/0 to 85/15 in 40 minutes, then up to 70/30 in 60 min, 0.81 g, 67%). $^1$H NMR (CDCl$_3$ 400 MHz) δ 7.73 (d, J=8.8 Hz, 2H), 7.51 (d, J=8.8 Hz, 2H), 7.01 (m, 1H), 6.39 (m, 1H), 4.85 (m, 1H), 4.51 (m, 2H), 2.80 (m, 1H), 2.17 (m, 1H).

Step 6

4-[(4-Chlorophenyl)sulfonyl]-4-ethyl-5,8-difluoro-3,4-dihydro-2H-1-benzopyran

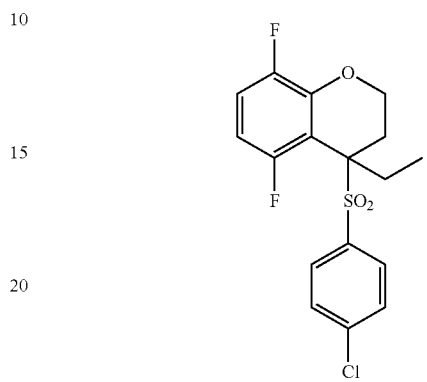

SCH 796492

4-[(4-Chlorophenyl)sulfonyl]-5,8-difluoro-3,4-dihydro-2H-1-benzopyran (101.1 mg, 0.294 mmol) was dissolved in 10 mL of THF. Ethyl bromide (600 mg, 4.88 mmol) was added, followed by potassium tert-butoxide (1 M in THF, 3.05 mL, 3.05 mmol). The solution was stirred at room temperature overnight. The reaction mixture was diluted with water and extracted with ethyl acetate (3×50 mL). The organic layer was separated, washed with brine (50 mL), dried over Na$_2$SO$_4$ and concentrated. The product was purified using column chromatography (Hex./EtOAc 100/0 to 70/30 in 60 min, 55 mg, 50%). $^1$H NMR (CDCl$_3$ 400 MHz) δ 7.63 (d, J=8.8 Hz, 2H), 7.47 (d, J=8.8 Hz, 2H), 7.03 (m, 1H), 6.38 (m, 1H), 4.91 (m, 1H), 4.39 (m, 1H), 2.55 (m, 2H), 2.30 (m, 1H), 1.89 (m, 1H), 0.74 (t, J=7.3 Hz, 3H).

Following procedures similar to those described for preparing Example 8, the compounds in Table 6 were prepared.

TABLE 6

| Ex. No | STRUCTURE | LCMS (Min. MS) | HRMS | Comments |
|---|---|---|---|---|
| 8-A | (+)Chiral | 3.34 Min. 367 (M + Na) | | Separated by Chiral AS Column, with IPA/Hexane(40/60) as mobile phase |

TABLE 6-continued
| Ex. No | STRUCTURE | LCMS (Min. MS) | HRMS | Comments |
|---|---|---|---|---|
| 8-B | 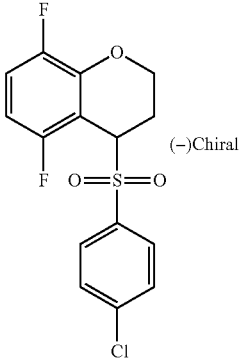 [SMILES: O=S(=O)(c1ccc(Cl)cc1)C1CCOc2c(F)ccc(F)c21] (−)Chiral | 3.35 Min. 345.2 (M + 1) | | Separated by Chiral AS Column, with IPA/Hexane(40/60) as mobile phase |
| 8-C | 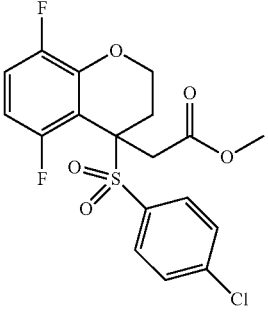 [SMILES: COC(=O)CC1(S(=O)(=O)c2ccc(Cl)cc2)CCOc2c(F)ccc(F)c21] | 3.46 Min. 417.2 (M + 1) | 417.0382 | |
| 8-D | 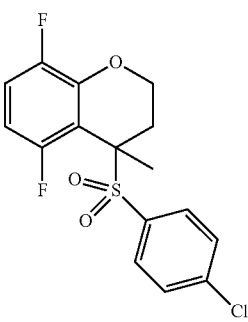 [SMILES: CC1(S(=O)(=O)c2ccc(Cl)cc2)CCOc2c(F)ccc(F)c21] | 3.48 Min. | | $^1$H NMR (CDCl$_3$ 400 MHz δ 7.66 (d, J = 8.8 Hz, 2H), 7.49 (d, J = 8.8 Hz, 2H), 7.02 (m, 1H), 6.39 (m, 1H), 4.92 (m, 1H), 4.40 (m, 1H), 2.81 (tt, J = 15.4 and 2.9 Hz, 1H), 2.11 (m, 1H), 1.77 (d, J = 2.9 Hz, 3H). |
| 8-E | 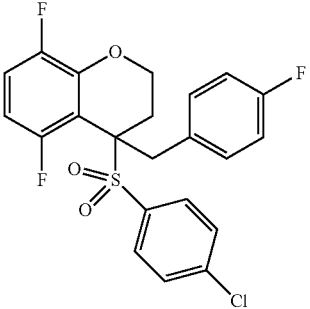 [SMILES: O=S(=O)(c1ccc(Cl)cc1)C1(Cc2ccc(F)cc2)CCOc2c(F)ccc(F)c21] | 3.92 Min. 453.2 (M + 1) | | |

TABLE 6-continued

| Ex. No | STRUCTURE | LCMS (Min. MS) | HRMS | Comments |
|---|---|---|---|---|
| 8-F | 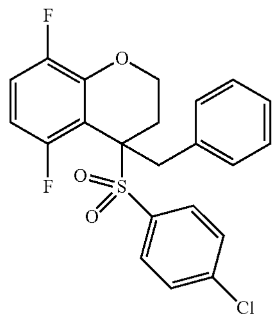 [SMILES: O=S(=O)(c1ccc(Cl)cc1)C1(Cc2ccccc2)CCOc2c(F)ccc(F)c21] | 3.89 Min. 435.2 (M + 1) | | |
| 8-G | 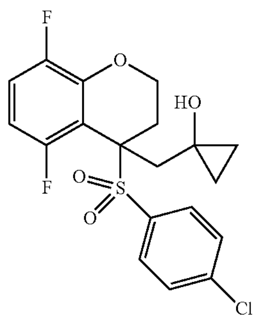 [SMILES: O=S(=O)(c1ccc(Cl)cc1)C1(CC2(O)CC2)CCOc2c(F)ccc(F)c21] | 4.25 Min. 415.2 (M + 1) | | |
| 8-H | 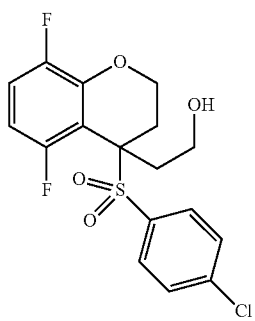 [SMILES: O=S(=O)(c1ccc(Cl)cc1)C1(CCO)CCOc2c(F)ccc(F)c21] | 3.90 Min. 389.2 (M + 1) | | |
| 8-I | 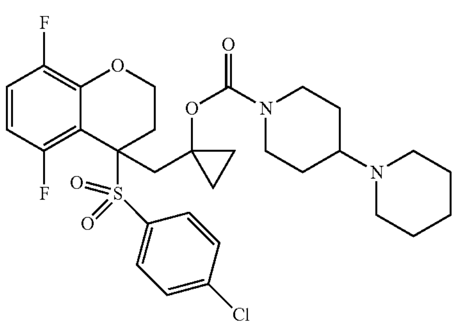 [SMILES: O=C(OC1(CC2(S(=O)(=O)c3ccc(Cl)cc3)CCOc3c(F)ccc(F)c32)CC1)N1CCC(N2CCCCC2)CC1] | 3.50 Min. 609.3 (M + 1) | 609.2002 | |
| 8-J | 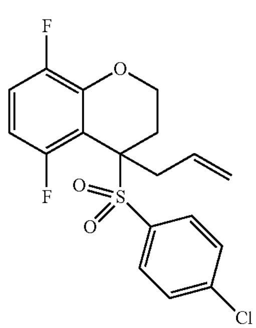 [SMILES: C=CCC1(S(=O)(=O)c2ccc(Cl)cc2)CCOc2c(F)ccc(F)c21] | 4.84 Min. 407.2 (M + Na) | | |

TABLE 6-continued

| Ex. No | STRUCTURE | LCMS (Min. MS) | HRMS | Comments |
|---|---|---|---|---|
| 8-K | 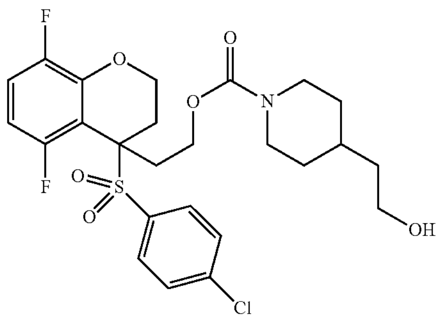 [SMILES: O=C(OCCC1(S(=O)(=O)c2ccc(Cl)cc2)CCOc2c(F)ccc(F)c21)N1CCC(CCO)CC1] | 4.13 Min. 544.3 (M + 1) | 544.1375 | |
| 8-L | 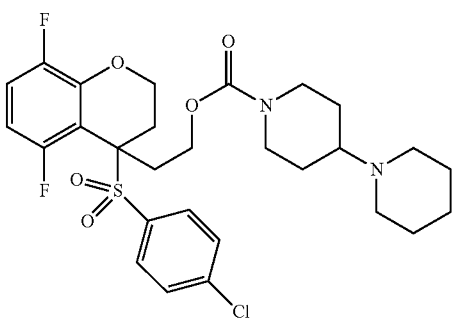 [SMILES: O=C(OCCC1(S(=O)(=O)c2ccc(Cl)cc2)CCOc2c(F)ccc(F)c21)N1CCC(N2CCCCC2)CC1] | 3.42 Min. 583.3 (M + 1) | 583.1855 | |
| 8-M | 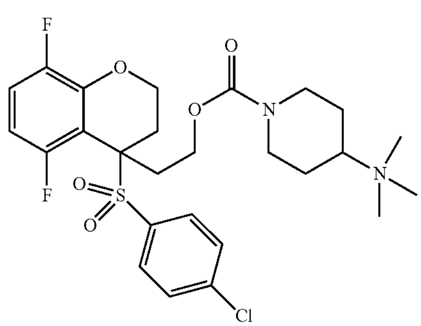 | 3.33 Min. 557.3 (M + 1) | 557.168 | |
| 8-N | 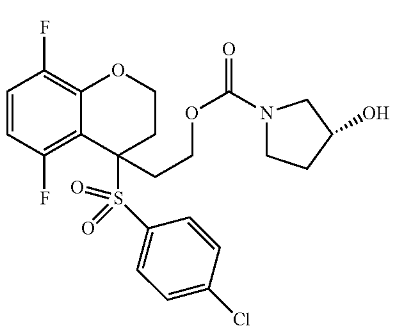 [SMILES: O=C(OCCC1(S(=O)(=O)c2ccc(Cl)cc2)CCOc2c(F)ccc(F)c21)N1CC[C@@H](O)C1] | 3.70 Min. 502.3 (M + 1) | | |

TABLE 6-continued

| Ex. No | STRUCTURE | LCMS (Min. MS) | HRMS | Comments |
|---|---|---|---|---|
| 8-O | 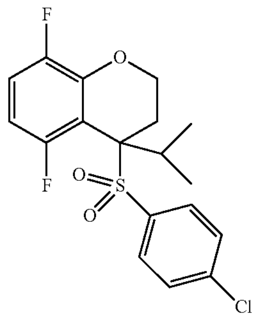 [SMILES: CC(C)C1(S(=O)(=O)c2ccc(Cl)cc2)CCOc2c(F)ccc(F)c21] | 4.98 Min. | | ¹H NMR (CDCl₃ 400 MHz δ 7.64 (d, J = 8.8 Hz, 2H), 7.43 (d, J = 8.8 Hz, 2H), 6.97 (m, 1H), 6.40 (m, 1H), 4.65 (m, 1H), 4.42 (m, 1H), 2.99 (m, 1H), 2.90 (tt, J = 15.4 and 2.9 Hz, 1H), 2.20 (m, 1H), 1.31 (d, J = 6.6 Hz, 3H), 0.71 (d, J = 6.6 Hz, 3H). |
| 8-P | 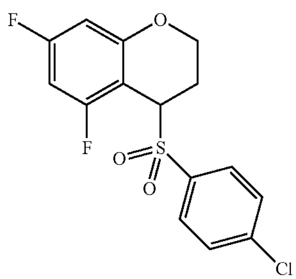 [SMILES: O=S(=O)(c1ccc(Cl)cc1)C1CCOc2cc(F)cc(F)c21] | 460 Min. 689.4 (2M + 1) | 436.0543 (M + Na + ACN) | |
| 8-Q | 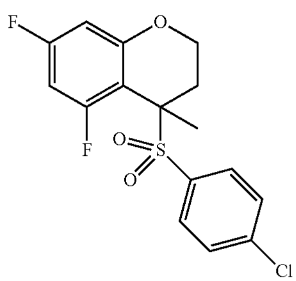 [SMILES: CC1(S(=O)(=O)c2ccc(Cl)cc2)CCOc2cc(F)cc(F)c21] | 4.70 Min. | | |
| 8-R | 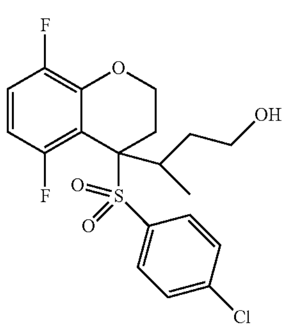 [SMILES: CC(CCO)C1(S(=O)(=O)c2ccc(Cl)cc2)CCOc2c(F)ccc(F)c21] | 4.05 Min. 417.2 (M + 1) | 417.0725 | |
| 8-S | 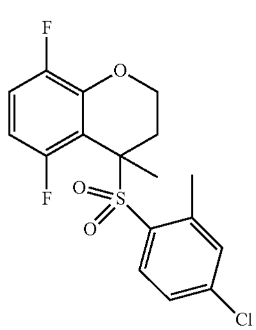 [SMILES: Cc1cc(Cl)ccc1S(=O)(=O)C1(C)CCOc2c(F)ccc(F)c21] | 4.89 Min. | | |

TABLE 6-continued

| Ex. No | STRUCTURE | LCMS (Min. MS) | HRMS | Comments |
|---|---|---|---|---|
| 8-T | 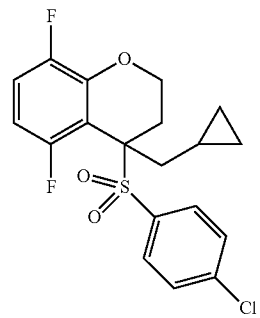 [SMILES: O=S(=O)(c1ccc(Cl)cc1)C1(CC2CC2)CCOc2c(F)ccc(F)c21] | 5.02 Min. | | |
| 8-U | 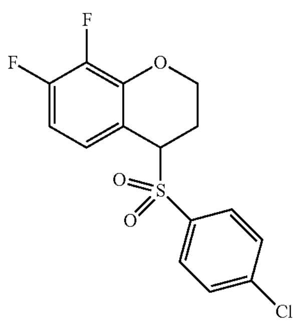 [SMILES: O=S(=O)(c1ccc(Cl)cc1)C1CCOc2c1ccc(F)c2F] | 3.91 Min. | | |
| 8-V | 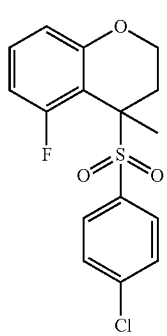 [SMILES: CC1(S(=O)(=O)c2ccc(Cl)cc2)CCOc2cccc(F)c21] | 4.68 Min. | 341.0403 | $^1$H NMR (CDCl$_3$ 400 MHz δ 7.64 (d, J = 8.8 Hz, 2H), 7.43 (d, J = 8.8 Hz, 2H), 6.97 (m, 1H), 6.40 (m, 1H), 4.65 (m, 1H), 4.42 (m, 1H), 2.99 (m, 1H), 2.90 (tt, J = 15.4 and 2.9 Hz, 1H), 2.20 (m, 1H), 1.31 (d, J = 6.6 Hz, 3H), 0.71 (d, J = 6.6 Hz, 3H). |
| 8-W | 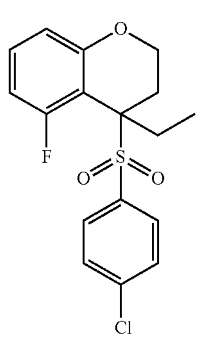 [SMILES: CCC1(S(=O)(=O)c2ccc(Cl)cc2)CCOc2cccc(F)c21] | 4.85 Min. 731.4 (2M + Na) | 353.0414 | |

TABLE 6-continued
| Ex. No | STRUCTURE | LCMS (Min. MS) | HRMS | Comments |
|---|---|---|---|---|
| 8-X | 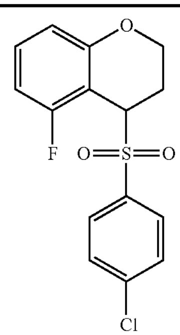 | 4.45 Min. 327.2 (M + 1) | | |
| 8-Y | 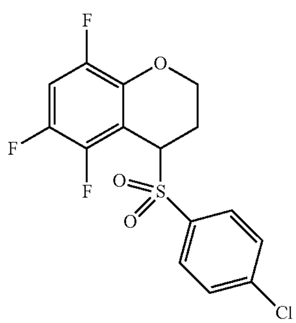 [SMILES: O=S(=O)(c1ccc(Cl)cc1)C1CCOc2c(F)cc(F)c(F)c21] | 4.61 Min. | | |
| 8-Z | 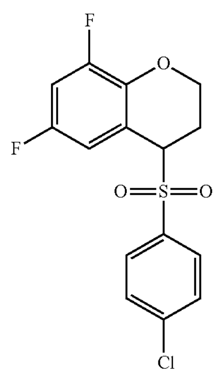 [SMILES: O=S(=O)(c1ccc(Cl)cc1)C1CCOc2c(F)cc(F)cc21] | 5.51 Min. | | |
Example 9
4-(4-Chloro-benzenesulfonyl)-6-fluoro-chroman
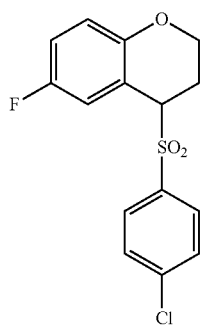 [SMILES: O=S(=O)(c1ccc(Cl)cc1)C1CCOc2ccc(F)cc21]
Step 1
4-[(4-Chlorophenyl)sulfonyl]-6-fluoro-3,4-dihydro-2H-1-benzopyran
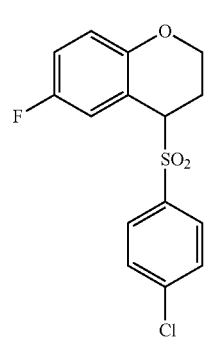 [SMILES: O=S(=O)(c1ccc(Cl)cc1)C1CCOc2ccc(F)cc21]

6-Fluorochroman-4-one (352 mg, 2.12 mmol) and 4-chlorothiophenol (320 mg, 2.2 mmol) were dissolved in 5 mL DCM. The reaction mixture was cooled to 0° C. and 2.4 mL of trifluoroacetic acid was added. After 5 min at 0° C., pyridine-borane complex (0.20 mL) was slowly added. The reaction mixture was stirred for 1 h at 0° C. Et$_2$O (100 mL) and sat. NaHCO$_3$ solution (100 mL) were added. The ether layer was dried over Na$_2$SO$_4$ and concentrated. The residue was dissolved in 10 mL DCM, mCPBA (77%, 1.01 g, 4.50 mmol) was added and the reaction mixture was stirred at room temperature overnight. 2 g of Na$_2$SO$_3$ in 20 mL of water was added and the reaction was stirred for 1 h then filtered. The layers were separated, then the organic layer was washed with 1N NaOH solution (100 mL), dried over Na$_2$SO$_4$ and concentrated. The product was purified by column chromatography using hex./EtOAc as the eluent (gradient from 100/0 to 30/70 in 60 min, 0.37 g, 53%). $^1$H NMR (CDCl$_3$ 400 MHz) δ 7.67 (d, J=8.8 Hz, 2H), 7.49 (d, J=8.8 Hz, 2H), 6.92 (m, 2H), 6.77 (m, 1H), 4.24 (m, 2H), 4.10 (m, 1H), 2.36 (m, 1H), 2.18 (m, 1H).

Following procedures similar to those described in the preparation of Example 9, the compounds in Table 7 were prepared.

TABLE 7

| Example No | STRUCTURE | LCMS (Min. MS) | HRMS |
|---|---|---|---|
| 9-A | 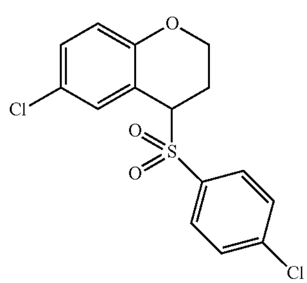 [SMILES: O=S(=O)(c1ccc(Cl)cc1)C1CCOc2ccc(Cl)cc21] | 4.73 Min. | 341.9885 |
| 9-B | 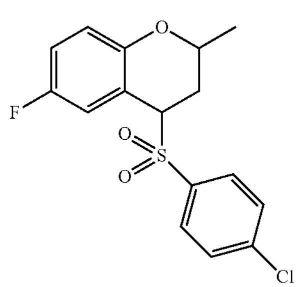 [SMILES: CC1CC(S(=O)(=O)c2ccc(Cl)cc2)c2cc(F)ccc2O1] | 4.72 Min. 341.2 (M + 1) | |
| 9-C | 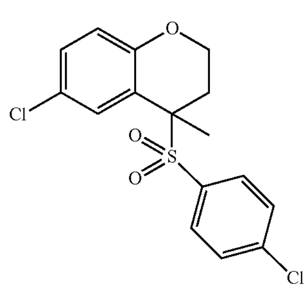 [SMILES: CC1(S(=O)(=O)c2ccc(Cl)cc2)CCOc2ccc(Cl)cc21] | 4.88 Min. | |
| 9-D | | 4.63 Min. | |

Example 10

4-(4-Chloro-benzenesulfonyl)-5,8-difluoro-3-methyl-chroman

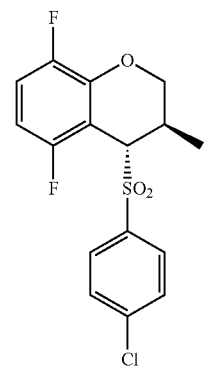 [SMILES: C[C@@H]1COc2c(F)ccc(F)c2[C@H]1S(=O)(=O)c1ccc(Cl)cc1]

Step 1

2-[Hydroxy-(2,3,6-trifluoro-phenyl)-methyl]-malonic Acid Dimethyl Ester

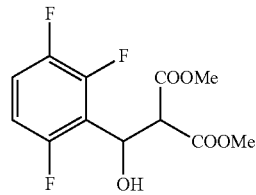 [SMILES: COC(=O)C(C(=O)OC)C(O)c1c(F)ccc(F)c1F]

2,3,6-trifluorobenzoaldehyde (10.2 g, 63.8 mmol) and dimethyl malonate (8.41 g, 63.8 mmol) were dissolved in 50 mL of DMF. 3 g of K$_2$CO$_3$ was added and the reaction mixture was heated to 80° C. for three hours. 500 mL of EtOAc and 500 mL of water were added. The organic layer was washed with saturated NH$_4$Cl solution (200 mL), dried over Na$_2$SO$_4$ and concentrated. The product was purified by column chromatography using EtOAc/hex as the eluent (gradient from 0/100 to 40/60 in 40 min, 13 g, 70%). $^1$H NMR (CDCl$_3$ 400

MHz) δ 7.12 (m, 1H), 6.85 (m, 1H), 5.72 (d, J=9.5 Hz, 1H), 4.17 (d, J=9.5 Hz, 1H), 3.84 (s, 3H), 3.61 (s, 3H).

Step 2

2-(2,3,6-Trifluoro-benzylidene)-malonic Acid Dimethyl Ester

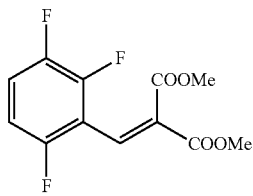 [SMILES: COC(=O)C(=Cc1c(F)ccc(F)c1F)C(=O)OC]

2-[Hydroxy-(2,3,6-trifluoro-phenyl)-methyl]-malonic acid dimethyl ester (13 g, 44.5 mmol) and NEt₃ (9 g, 89 mmol) were dissolved in 300 mL CH₂Cl₂. MsCl (10.3 g, 89 mmol) was then added. The reaction mixture was stirred at room temperature for 1 hour. The reaction mixture was washed with 1N HCl solution (200 mL×2), brine (100 mL), dried over Na₂SO₄ and concentrated. The product was purified by column chromatography using EtOAc/Hexane as eluent (gradient from 0/100 to 25/75 in 40 min, 6.5 g, 53%). ¹H NMR (CDCl₃ 400 MHz) δ 7.71 (s, 1H), 7.20 (m, 1H), 6.89 (m, 1H), 3.87 (s, 3H), 3.80 (s, 3H).

Step 3

2-[(4-Chloro-phenylsulfanyl)-(2,3,6-trifluoro-phenyl)-methyl]-malonic Acid Dimethyl Ester

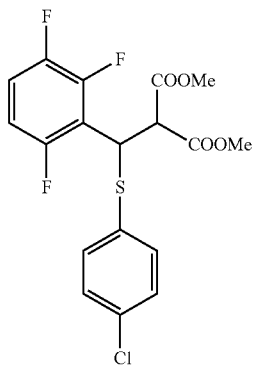 [SMILES: COC(=O)C(C(=O)OC)C(Sc1ccc(Cl)cc1)c1c(F)ccc(F)c1F]

2-(2,3,6-Trifluoro-benzylidene)-malonic acid dimethyl ester (6.5 g, 23.7 mmol) and 4-chlorothiophenol (5.1 g, 35.5 mmol) were dissolved in 100 mL THF. K₂CO₃ (5 g, excess) was added, the reaction mixture was stirred at 60° C. for three hours. 300 mL of EtOAc and 300 mL of water were added. The organic layer was separated, washed with water, dried over Na₂SO₄ and concentrated. The product was purified by column chromatography using EtOAc/hexane as the eluent. (Gradient from 0/100 to 25/75 in 45 min, 7.1 g, 72%). ¹H NMR (CDCl₃ 400 MHz) δ 7.26 (m, 4H), 7.03 (m, 1H), 6.75 (m, 1H), 5.08 (d, J=11.7 Hz, 1H), 4.34 (d, J=12.4 Hz, 1H), 3.84 (s, 3H), 3.56 (s, 3H).

Step 4

2-[(4-Chloro-benzenesulfonyl)-(2,3,6-trifluoro-phenyl)-methyl]-propane-1,3-diol

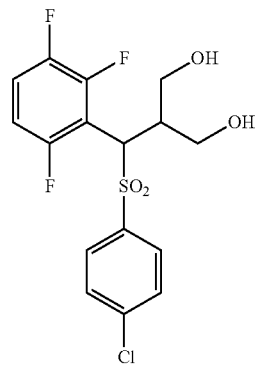

2-[(4-Chloro-phenylsulfanyl)-(2,3,6-trifluoro-phenyl)-methyl]-malonic acid dimethyl ester (7.1 g, 17 mmol) was dissolved in 50 mL THF and DIBAL-H (1M in hexane, 68 mL) was added. The reaction was stirred at room temperature overnight. 100 mL of water was added to quench the reaction and 100 mL EtOAc was added to extract the product. The organic layer was washed with 1N HCl solution (2×50 mL), brine (50 mL), dried over Na₂SO₄ and concentrated. The residue was dissolved in 200 mL DCM and mCPBA (77%, 7.6 g, 34 mmol) was added. The reaction was stirred at room temperature for three hours. 8 g Na₂SO₃ in 50 mL of water was added to quench excess mCPBA. The organic layer was separated, washed with 1N NaOH solution, brine, dried over Na₂SO₄ and concentrated. The product was purified by column using EtOAc/hex as the eluent (gradient from 0/100 to 75/25 in 40 min, 2.7 g, 40%). ¹H NMR (CDCl₃ 400 MHz) δ 7.59 (m, 2H), 7.36 (m, 2H), 7.06 (m, 1H), 6.81 (m, 0.5H), 6.57 (m, 0.5H), 5.26 (d, J=11.0 Hz, 1H), 4.65 (m, 1H), 4.20 (dt, J=11.7 and 2.2 Hz, 1H), 3.93 (m, 1H), 3.42 (m, 1H), 3.02 (m, 1H).

Step 5

Trans-4-[(4-chlorophenyl)sulfonyl)]-5,8-difluoro-3,4-dihydro-2H-1-benzopyran-3-methanol

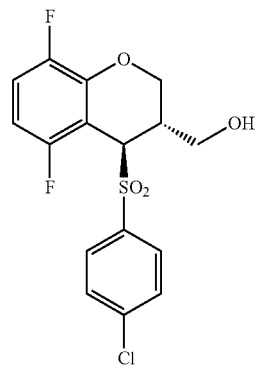 [SMILES: O=S(=O)(c1ccc(Cl)cc1)[C@H]1c2c(F)ccc(F)c2OC[C@@H]1CO]

SCH 795753
2-[(4-Chloro-benzenesulfonyl)-(2,3,6-trifluoro-phenyl)-methyl]-propane-1,3-diol (2.7 g, 6.9 mmol) was dissolved in 70 mL THF and NaH (2 g, excess) was added. The reaction mixture was stirred at room temperature overnight. 50 mL of water and 50 mL of EtOAc were added. The organic layer was washed with brine (50 mL), dried over Na$_2$SO$_4$ and concentrated. The product was purified by column chromatography using EtOAc/hex as the eluent (gradient from 0/100 to 50/50 in 40 min, 2.3 g, 90%). Only the trans isomer was isolated from the reaction. $^1$H NMR (CDCl$_3$ 400 MHz) δ 7.72 (d, J=8.8 Hz, 2H), 7.50 (d, J=8.8 Hz, 2H), 7.03 (m, 1H), 6.41 (m, 1H), 4.93 (dd, J=11.7 and 3.7 Hz, 1H), 4.63 (s, 1H), 4.41 (d, J=11.7 Hz, 1H), 3.69 (dd, J=11.0 and 6.6 Hz, 1H), 3.43 (t, J=11.0 Hz, 1H), 3.02 (m, 1H).

Step 6

Methanesulfonic acid O-[4-(4-chloro-benzenesulfonyl-5,8-difluoro-3,4-dihydro-2H-1-benzopyran-3-yl-methyl]ester

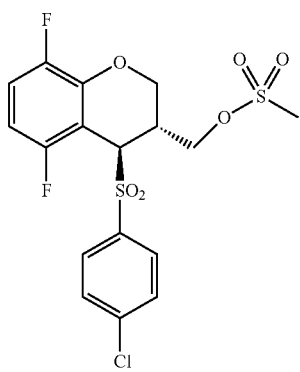 [SMILES: CS(=O)(=O)OC[C@H]1COc2c(F)ccc(F)c2[C@@H]1S(=O)(=O)c1ccc(Cl)cc1]

Trans-4-[(4-chlorophenyl)sulfonyl]-5,8-difluoro-3,4-dihydro-2H-1-benzopyran-3-methanol (1.0 g, 2.54 mmole), mesyl chloride (0.87 g, 7.6 mmole) and triethylamine (0.77 g, 7.6 mmole) were stirred in 50 ml CH$_2$Cl$_2$ at room temperature for two hours. 50 ml water was added. The organic layer was washed with 1N HCl solution (50 ml×2), brine (50 mL), dried over Na$_2$SO$_4$ and concentrated. The product was purified by column chromatography using EtOAc/Hexane as eluent (gradient from 0/100 to 50/50 in 40 minutes, 1.1 g, 96%). $^1$H NMR (400 MHz, CDCl$_3$) δ 7.75 (d, J=8.8 Hz, 2H), 7.54 (d, J=8.8 Hz, 2H), 7.43 (s, 1H), 7.07 (m, 1H), 7.47 (s, 1H), 4.98 (dd, J=12.4 and 2.9 Hz, 1H), 4.52 (s, 1H), 4.44 (d, J=12.4 Hz, 1H), 4.20 (dd, J=10.3 and 6.6 Hz, 1H), 4.00 (dd, J=10.3 and 8.7 Hz, 1H), 3.31 (m, 1H), 2.98 (s, 3H).

Step 7

Trans-4-[(4-chlorophenyl)sulfonyl]-5,8-difluoro-3,4-dihydro-3-methyl-2H-1-benzopyran

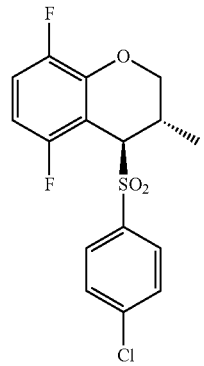 [SMILES: C[C@H]1COc2c(F)ccc(F)c2[C@@H]1S(=O)(=O)c1ccc(Cl)cc1]

Methanesulfonic acid O-[4-(4-chloro-benzenesulfonyl)-5,8-difluoro-3,4-dihydro-2H-1-benzopyran-3-yl-methyl]ester (0.5 g, 1.1 mmole), NaI (0.83 g, 5.5 mmole) Zinc dust (0.71 g, 11 mole) and 0.1 mL acetic acid were refluxed in 15 mL ethylene glycol dimethyl ether for 6 hours. The solid was filtered and the filtrate was partitioned between 100 mL 0.1N Na$_2$SO$_3$ solution and 100 mL EtOAc. The organic layer was washed with 0.5N NaOH solution (2×50 ml), brine, dried over Na$_2$SO$_4$ and concentrated. The residue was recrystallized from EtOAc/Hexane to pure product (0.33 g, 83%) $^1$H NMR (400 MHz, CDCl$_3$) δ7.71 (d, J=8.8 Hz, 2H), 7.50 (d, J=8.8 Hz, 2H), 7.03 (m, 1H), 6.40 (m, 1H), 4.92 (dd, J=11.7 and 2.9 Hz, 1H), 4.21 (m, 2H), 3.02 (m, 1H), 1.07 (d, J=7.3 Hz, 3H).

Following procedures similar to those described for the preparation of Example 10, the compounds in Table 8 were prepared.

TABLE 8

| Ex. No | STRUCTURE | LCMS (Min. MS) | HRMS | Comments |
|---|---|---|---|---|
| 10-A | 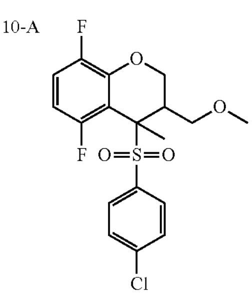 | 4.77 Min. 403.2 (M + 1) | | |

TABLE 8-continued

| Ex. No | STRUCTURE | LCMS (Min. MS) | HRMS | Comments |
|---|---|---|---|---|
| 10-B | 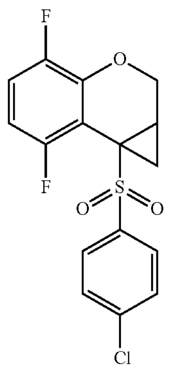 [SMILES: O=S(=O)(c1ccc(Cl)cc1)C12CC1COc1c(F)ccc(F)c12] | 4.37 Min. 357.2 (M + 1) | 420.0247 (M + Na + ACN) | |
| 10-C | 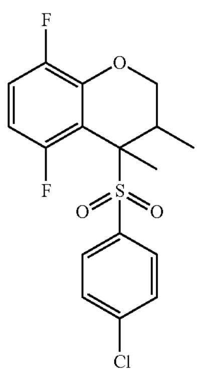 [SMILES: CC1COc2c(F)ccc(F)c2C1(C)S(=O)(=O)c1ccc(Cl)cc1] | 4.82 Min. | | ¹H NMR (CDCl₃ 400 MHz δ 7.63 (d, J = 8.1 Hz, 2H), 7.49 (d, J = 8.1 Hz, 2H), 7.04 (m, 1H), 6.40 (m, 1H), 5.23 (dd, J = 11.0 and 2.9 Hz, 1H), 4.48 (dd, J = 11.7 and 1.5 Hz, 1H), 2.78 (m, 1H), 1.72 (d, J = 4.4 Hz, 3H), 1.12 (d, J = 7.3 Hz, 3H). |
| 10-D | 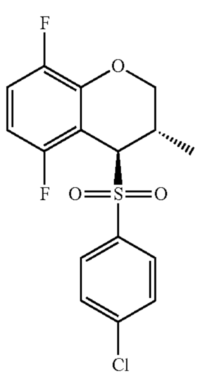 [SMILES: C[C@H]1COc2c(F)ccc(F)c2[C@@H]1S(=O)(=O)c1ccc(Cl)cc1] | 4.60 Min. 359.2 (M + 1) | | Separated by Chiral OD Column, with IPA/Hexane (10/90) as mobile phase |
| 10-E | 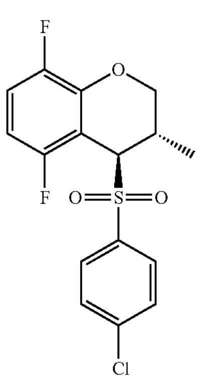 [SMILES: C[C@H]1COc2c(F)ccc(F)c2[C@@H]1S(=O)(=O)c1ccc(Cl)cc1] | | | Separated by Chiral OD Column, with IPA/Hexane (10/90) as mobile phase |

Example 11

4-(4-Chloro-benzenesulfonyl)-5,8-difluoro-2,4-dimethyl-chroman

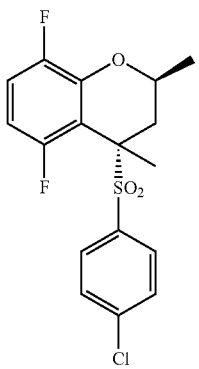 [SMILES: C[C@H]1C[C@](C)(S(=O)(=O)c2ccc(Cl)cc2)c2c(F)ccc(F)c2O1]

Step 1

4-(4-Chloro-benzenesulfonyl)-4-(2,3,6-trifluoro-phenyl)-butan-2-ol

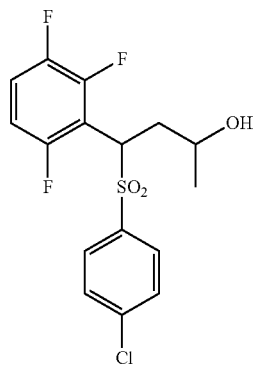 [SMILES: CC(O)CC(c1c(F)ccc(F)c1F)S(=O)(=O)c1ccc(Cl)cc1]

2-(4-Chloro-benzenesulfonylmethyl)-1,3,4-trifluoro-benzene (Example 8, step 2, 305 mg, 0.95 mmol) was dissolved in 4 mL THF. The solution was cooled to −78° C. and butyl-lithium (2.5M in hexane, 0.4 mL) was added slowly. The solution was stirred at −78° C. for 2 h then warmed to 0° C. and stirred for 0.5 h. The solution was then cooled to −78° C. again and propylene oxide (178.0 mg, 3.1 mmol) in 3.25 mL of THF was added slowly and the reaction mixture was allowed to stir and warm to room temperature overnight. The reaction mixture was quenched with a saturated NH₄Cl solution (50 mL). The reaction mixture was extracted three times with EtOAc (50 mL each) and the combined organics were washed with water (100 mL) and brine (100 mL). The organic layer was then dried over Na₂SO₄ and concentrated. The product was purified using column chromatography (hex./EtOAc 100/0 to 70/30 in 60 min. 0.19 g, 52%). ¹H NMR (CDCl₃ 400 MHz) δ 7.59 (m, 2H), 7.42 (m, 2H), 7.10 (m, 1H), 6.81 (m, 0.5H), 6.66 (m, 0.5H), 4.83-4.99 (m, 1H), 4.06 (m, 0.5H), 3.51 (m, 0.5H), 2.50-2.74 (m, 1H), 2.26 (m, 1H), 1.03-2.24 (m, 3H). The product is a mixture of diastereomers.

Step 2

Trans-4-[(4-chlorophenyl)sulfonyl]-5,8-difluoro-3,4-dihydro-2-methyl-2H-1-benzopyran

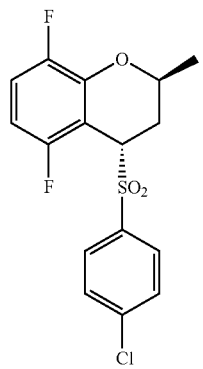 [SMILES: C[C@H]1C[C@H](S(=O)(=O)c2ccc(Cl)cc2)c2c(F)ccc(F)c2O1]

The above intermediate was prepared using the procedure of Example 8, step 5. Only the trans isomer was obtained from the reaction. $^1$H NMR (CDCl$_3$ 400 MHz) δ 7.72 (d, J=8.8 Hz, 2H), 7.50 (d, J=8.8 Hz, 2H), 6.99 (m, 1H), 6.36 (m, 1H), 5.00 (m, 1H), 4.50 (m, 1H), 2.79 (dt, J=15.4 and 2.2 Hz, 1H), 1.85 (m, 1H), 1.50 (d, J=6.6 Hz, 3H).

Step 3

Trans-4-[(4-chlorophenyl)sulfonyl]-5,8-difluoro-3,4-dihydro-2,4-dimethyl-2H-1-benzopyran

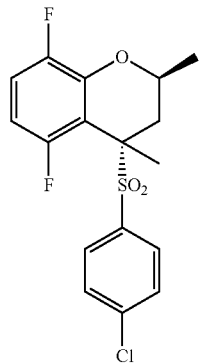 [SMILES: C[C@H]1C[C@](C)(S(=O)(=O)c2ccc(Cl)cc2)c2c(F)ccc(F)c2O1]

Trans-4-[(4-chlorophenyl)sulfonyl]-5,8-difluoro-3,4-dihydro-2-methyl-2H-1-benzopyran (57 mg, 0.16 mmol) was dissolved in 10 mL of THF. Iodomethane (720 mg, 5.11 mmol) was added, followed by potassium tert-butoxide (1M in THF, 0.5 mL, 0.5 mmol). The solution was stirred at room temperature overnight. 50 mL of water was added and the product was extracted with ethyl acetate (3×50 mL). The organic layer was separated, washed with brine (50 mL), dried over Na$_2$SO$_4$ and concentrated. The product was purified using column chromatography (hex./EtOAc 100/0 to 70/30 in 60 min, 39 mg, 65%). Only the trans isomer was isolated from the reaction mixture. $^1$H NMR (CDCl$_3$ 400 MHz) δ 7.66 (d, J=8.8 Hz, 2H), 7.49 (d, J=8.8 Hz, 2H), 7.01 (m, 1H), 6.35 (m, 1H), 5.08 (m, 1H), 2.79 (dt, J=15.4 and 2.2 Hz, 1H), 1.72-1.81 (m, 4H), 1.47 (d, J=6.6 Hz, 3H).

Following procedures similar to those described for the preparation of Example 11, the compounds in Table 9 were prepared.

TABLE 9

| Example No | STRUCTURE | LCMS (Min. MS) | HRMS |
|---|---|---|---|
| 11-A | ![structure] | 5.18 Min. 457.3 (M + 23) | |
| 11-B | ![structure] | 4.86 Min. 373.2 (M + 1) | 373.0475 |
| 11-C | ![structure] | 4.77 Min. 355.2 (M + 1) | |
| 11-D | ![structure] | 5.37 Min. | |

TABLE 9-continued

| Example No | STRUCTURE | LCMS (Min. MS) | HRMS |
|---|---|---|---|
| 11-E | 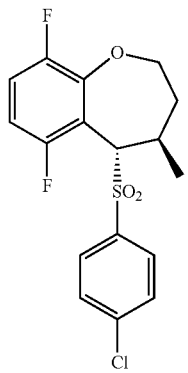 [SMILES: C[C@@H]1CCOc2c(F)ccc(F)c2[C@H]1S(=O)(=O)c1ccc(Cl)cc1] | 4.93 Min. | |

Example 12

5-(4-Chloro-benzenesulfonyl)-6,9-difluoro-4-methyl-2,3,4,5-tetrahydro-benzo[b]oxepine

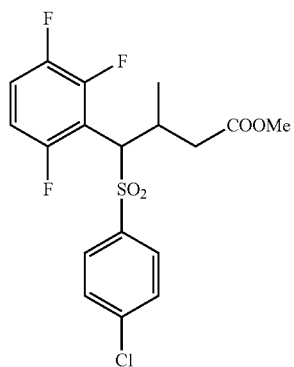 [SMILES: COC(=O)CC(C)C(c1c(F)ccc(F)c1F)S(=O)(=O)c1ccc(Cl)cc1]

Step 1

4-(4-Chloro-benzenesulfonyl)-3-methyl-4-(2,3,6-trifluoro-phenyl)-butyric acid methyl ester

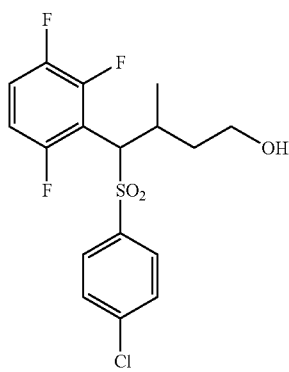 [SMILES: CC(CCO)C(c1c(F)ccc(F)c1F)S(=O)(=O)c1ccc(Cl)cc1]

2-(4-Chloro-phenylsulfanylmethyl)-1,3,4-trifluoro-benzene (Example 8, step 2, 1.0 g, 3.1 mmol) and methyl crotonate (1.55 g, 15.5 mmol) were dissolved in 50 mL of THF and potassium t-butoxide (1M in THF, 6.2 mL) was added. The reaction mixture was stirred at room temperature for five hours. 100 mL of water and 100 mL of EtOAc were added. The organic layer was washed with brine (100 mL), dried over $Na_2SO_4$ and concentrated. The product was purified by column chromatography using EtOAc/hexane as the eluent (gradient from 0/100 to 50/50 in 40 min, 0.79 g, 60%). The product is a mixture of diastereomers. $^1$H NMR (CDCl$_3$ 400 MHz) δ 7.60 (m, 2H), 7.37 (m, 2H), 7.07 (m, 1H), 6.83 (m, 0.5H), 6.63 (m, 0.5H), 5.03 (t, J=10.2 Hz, 0.5H), 4.80 (d, J=10.2 Hz, 0.5H), 3.71 (s, 1.5H), 3.60 (s, 1.5H), 3.33 (m, 1H), 3.10 (m, 0.5H), 2.89 (m, 0.5H), 2.42 (m, 0.5H), 2.15 (m, 0.5H), 1.49 (t, J=6.6 Hz, 1.5H), 0.95 (dd, J=8.8 and 7.3 Hz, 1.5H).

Step 2

4-(4-Chloro-benzenesulfonyl)-3-methyl-4-(2,3,6-trifluoro-phenyl)-butan-1-ol

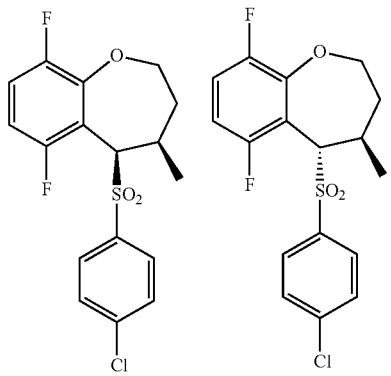

4-(4-Chloro-benzenesulfonyl)-3-methyl-4-(2,3,6-trifluoro-phenyl)-butyric acid methyl ester (0.79 g, 1.88 mmol) was dissolved in 10 mL of THF and lithium borohydride (0.5 g, excess) was added. The reaction mixture was stirred at room temperature overnight. 50 mL of water and 50 mL of EtOAc were added. The organic layer was washed with brine (50 mL), dried over $Na_2SO_4$ and concentrated. The residue was used in next step without further purification (0.71 g, 96%). $^1$H NMR (CDCl$_3$ 400 MHz) δ 7.61 (m, 2H), 7.36 (m, 2H), 7.06 (m, 1H), 6.82 (m, 0.5H), 6.60 (m, 0.5H), 4.79 (m, 0.5H), 4.56 (m, 0.5H), 3.85 (m, 1H), 3.68 (m, 1H), 3.12 (m, 1H), 2.39 (m, 0.5H), 1.95 (m, 0.5H), 1.57 (m, 0.5H), 1.46 (dd, J=4.4 and 5.9 Hz, 1.5H), 1.32 (m, 0.5H), 0.92 (dd, J=7.3 and 9.5 Hz, 1.5H).

Step 3

Trans-5-[(4-chlorophenyl)sulfonyl]-6,9-difluoro-2,3,4,5-tetrahydro-4-methyl-1-benzoxepin and Cis-5-[(4-chlorophenyl)sulfonyl]-6,9-difluoro-2,3,4,5-tetrahydro-4-methyl-1-benzoxepin 4-(4-Chloro-benzenesulfonyl)-3-methyl-4-(2,3,6-trifluoro-phenyl)-butan-1-ol (0.71 g, 1.8 mmol) was dissolved in 50 mL of THF and sodium hydride (60% in oil, 0.5 g, excess) was added. The reaction was stirred at room temperature for two hours. 50 mL of water and 50 mL of EtOAc were added. The organic layer was washed with saturated NaCl solution (50 mL), dried over $Na_2SO_4$ and concentrated. The product was purified by column chromatography using EtOAc/hex as the eluent (gradient from 0/100 to 25/75 in 40 min). Two products were isolated. Cis isomer (31 mg, 4.6%). $^1$H NMR ($CDCl_3$ 400 MHz) δ 7.57 (d, J=8.8 Hz, 2H), 7.34 (d, J=8.8 Hz, 2H), 6.95 (m, 1H), 6.44 (m, 1H), 4.74 (bs, 1H), 4.66 (dt, J=12.4 and 3.7 Hz, 1H), 3.81 (m, 1H), 3.07 (m, 1H), 2.39 (m, 1H), 1.85 (m, 1H), 1.65 (d, J=7.3 Hz, 3H). Trans isomer (0.46 g, 68%). $^1$H NMR ($CDCl_3$ 400 MHz) δ 7.52 (d, J=8.8 Hz, 2H), 7.37 (d, J=8.8 Hz, 2H), 7.03 (m, 1H), 6.54 (m, 1H), 4.52 (d, J=3.7 Hz, 1H), 4.40 (m, 1H), 3.93 (m, 1H), 3.21 (m, 1H), 2.79 (m, 1H), 2.72 (m, 1H), 1.11 (d, J=7.3 Hz, 3H).

Two enantiomers were isolated from the trans isomer by Chiral-AS® column using hexane/isopropanol (75/25) as the mobile phase.

Examples 13-15

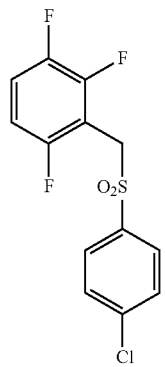
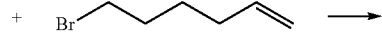
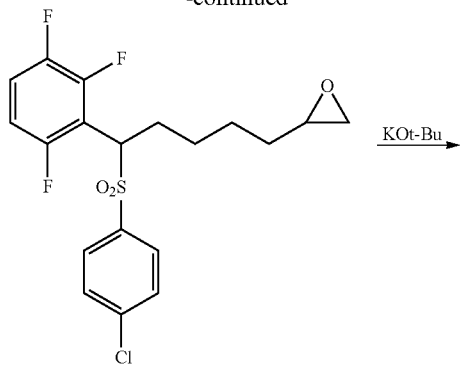
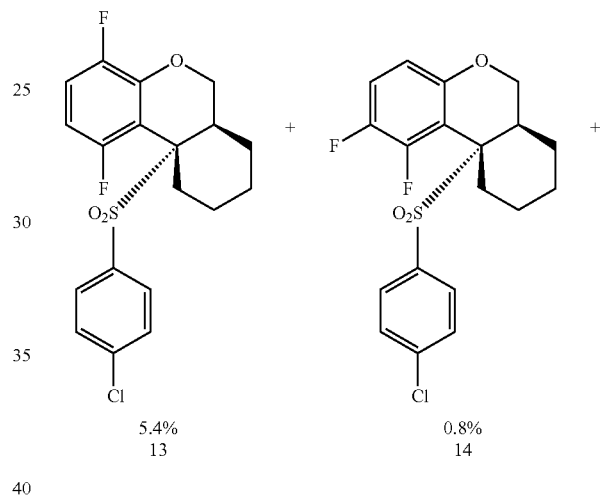

5.4%
13

0.8%
14

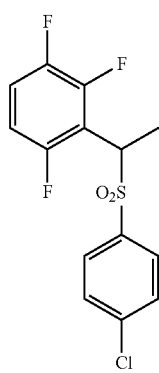
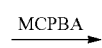
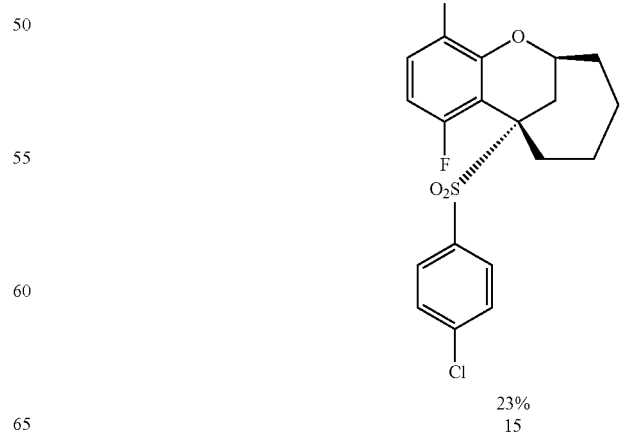

23%
15

Step 1

[7-(4-chloro-benzenesulfonyl)-7-(2,3,6-trifluoro-phenyl)-1-heptene

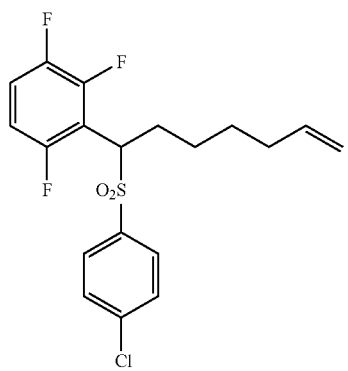 [SMILES: C=CCCCCC(c1c(F)ccc(F)c1F)S(=O)(=O)c1ccc(Cl)cc1]

2-(4-Chloro-benzenesulfonylmethyl)-1,3,4-trifluoro-benzene (1.0 g, 3.1 mmol, from example 8, step 2) and 6-bromo-1-hexene (1.5 g, 6.3 mmole) were dissolved in 20 mL THF and potassium t-butoxide (1 M in THF, 6.2 mL) was added. The reaction mixture was stirred at room temperature for three hours. 50 mL water and 50 mL EtOAc were added. The organic layer was washed with brine (50 mL), dried over $Na_2SO_4$ and concentrated. The product was purified by column chromatography using EtOAc/Hexane as eluent (gradient from 0/100 to 25/75 in 40 minutes, 0.65 g, 52%). $^1$H NMR (CDCl$_3$, 400 MHz) δ 7.63 (d, j=8.05 Hz, 2H), 7.45 (d, j=8.05 Hz, 2H), 7.14 (m, 1H), 6.83 (m, 0.5), 6.74 (m, 0.5H), 5.70 (m, 1H), 4.93 (m, 2H), 4.58 (d, j=5.1 and 6.5 Hz, 1H), 2.43 (m, 1H), 2.31 (m, 1H), 1.99 (m, 2H), 1.39 (m, 2H), 1.25 (m, 2H).

Step 2

2-[5-(4-Chloro-benzenesulfonyl)-5-(2,3,6-trifluorophenyl)-pentyl]-oxirane

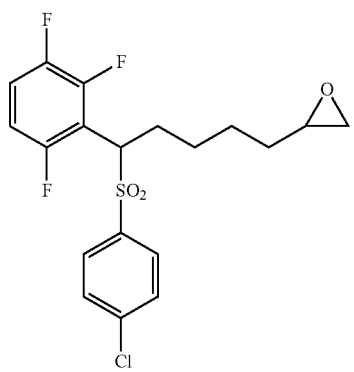 [SMILES: O=S(=O)(c1ccc(Cl)cc1)C(CCCCC1CO1)c1c(F)ccc(F)c1F]

[7-(4-chloro-benzenesulfonyl)-7-(2,3,6-trifluoro-phenyl)-1-heptene (0.65 g, 1.6 mmole) and mCPBA (77%, 0.71 g, 3.2 mmole) were stirred in 50 mL DCM for 5 hours. 2 g $Na_2S_2O_3$ in 100 mL water were added to quench excess mCPBA. The organic layer was separated, washed with 1N NaOH solution (50 mL), brine (50 mL), dried over $Na_2SO_4$ and concentrated. The product was purified by column chromatography using EtOAc/Hexane as eluent (Gradient from 0/100 to 40/60 in 40 minute, 0.52 g, 77%). $^1$H NMR (CDCl$_3$, 400 MHz) δ 7.63 (d, j=8.05 Hz, 2H), 7.45 (d, j=8.05 Hz, 2H), 7.15 (m, 1H), 6.83 (m, 0.5), 6.74 (m, 0.5H), 4.58 (dd, j=5.1 and 6.5 Hz, 1H), 2.84 (m, 1H), 2.71 (t, j=4.4 Hz, 1H), 2.41 (dd, j=2.9 and 5.1 Hz), 2.45 (m, 1H), 2.34 (m, 1H), 1.25-1.55 (m, 6H).

Step 3

(6aR)-10aS-[(4-Chloro-benzenesulfonyl)-1,4-difluoro-6a,7,8,9,10,10a-hexahydro-6H-dibenzo[b,d]pyran(racemic) and 7(S)-[(4-Chloro-benzenesulfonyl)-8,11-difluoro-2,3,4,5,6,7-hexahydro-2(S),7-methano-1-benzoxonin (racemic)

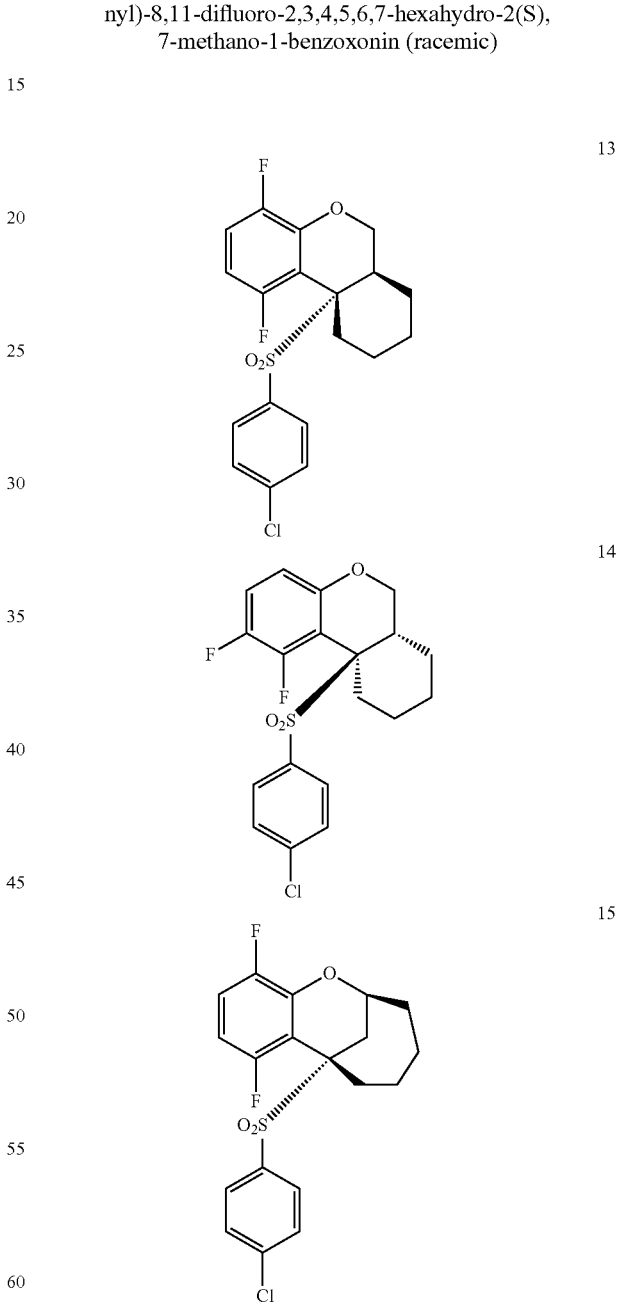

2-[5-(4-Chloro-benzenesulfonyl)-5-(2,3,6-trifluoro-phenyl)-pentyl]-oxirane (0.52 g, 1.24 mmole) was dissolved in 25 mL THF and potassium t-butoxide (1 M in THF, 3.72 mL) was added. The reaction mixture was stirred at room temperature for 2 hours, then heated to 50° C. for four hours, 50 mL of water and 50 mL of EtOAc were added. The organic layer was washed with brine (50 mL), dried over Na$_2$SO$_4$ and concentrated. The product was purified by column chromatography using EtOAc/Hexane as eluent (gradient from 0/100 to 25/75 in 40 minutes). Two major products were isolated. Example 13: (6aR)-10aS-[(4-chloro-benzenesulfonyl)-1,4-difluoro-6a,7,8,9,10,10a-hexahydro-6H-dibenzo[b,d]pyran (racemic, containing about 13% of 14, 31 mg, 5.4%). $^1$H NMR (CDCl$_3$, 400 MHz) δ 7.59 (d, j=8.05 Hz, 2H), 7.47 (d, j=8.05 Hz, 2H), 7.06 (m, 1H), 6.40 (m, 1H), 5.23 (dd, j=11.7 and 2.9 Hz, 1H), 4.14 (d, j=11.7 Hz, 1H), 2.61 (m, 2H), 1.90 (tt, j=13.9 and 2.9 Hz, 1H), 1.65-1.81 (m, 3H), 1.42 (m, 2H), 1.02 (m, 1H). Compound 15: 7(S)-[(4-chloro-benzenesulfonyl)-8,11-difluoro-2,3,4,5,6,7-hexahydro-2(S), 7-methano-1-benzoxonin (racemic, 112 mg, 23%). $^1$H NMR (CDCl$_3$, 400 MHz) δ 7.53 (d, j=8.05 Hz, 2H), 7.39 (d, j=8.05 Hz, 2H), 7.02 (m, 1H), 6.60 (m, 1H), 4.85 (m, 1H), 3.12 (d, j=13.9 Hz, 1H), 2.81 (m, 1H), 2.36 (m, 1H), 2.29 (dd, j=14.6 and 1.5 Hz, 1H), 2.10 (m, 1H), 1.97 (m, 1H), 1.65 (m, 1H), 1.09-1.37 (m, 3H).

Examples 13A, 14A and 15A

Following procedures similar to those described for the preparation of Examples 13 to 15, the compounds in Table 10 were prepared.

TABLE 10

| Example No. | STRUCTURE | Mass Spec (M$^+$ except otherwise noted); retention time (min) |
|---|---|---|
| 13-A 14-A | (structure: two isomers, 60% + 40%) | (2MNA) 853.1; 5.31 and 5.44 |
| 15-A | (structure) | (2MH) 831.5; 5.01 |

Example 16

105
-continued

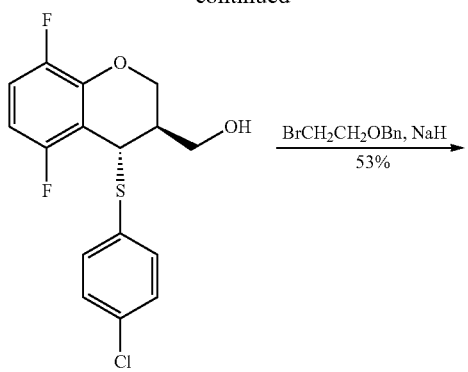

BrCH₂CH₂OBn, NaH
53%

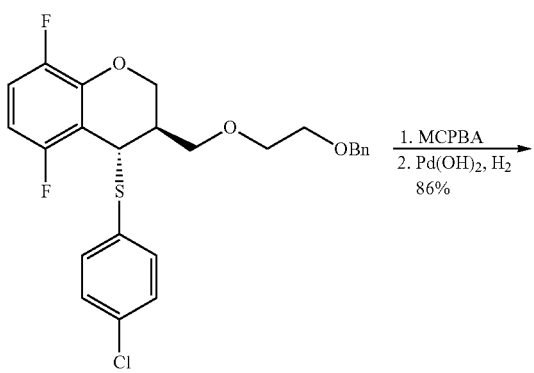

1. MCPBA
2. Pd(OH)₂, H₂
86%

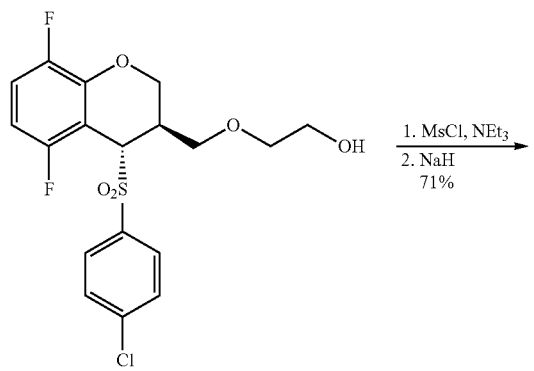

1. MsCl, NEt₃
2. NaH
71%

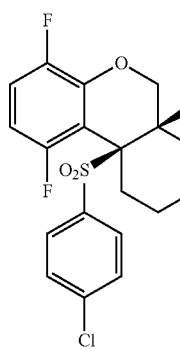

106
Step 1

2-[(4-Chloro-phenylsulfanyl)-(2,3,6-trifluoro-phenyl)-methyl]-propane-1,3-diol

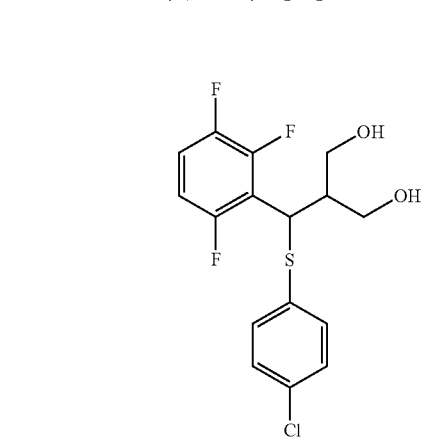

2-[(4-Chloro-phenylsulfanyl)-(2,3,6-trifluoro-phenyl)-methyl]-malonic acid dimethyl ester (Example 10, step 3, 11 g, 26.3 mmole) was dissolved in 200 mL THF and DIBAL-H (1M in hexane, 105 mL) was added. The reaction was stirred at room temperature for five hours. Additional DIBAL-H (1M in hexane, 100 mL) was added and the reaction was stirred at 60° C. for three hours. 300 mL water and 300 mL EtOAc were added. The organic layer was washed with 1N HCl solution (2×100 mL), brine (100 mL), dried over Na₂SO₄ and concentrated. The product was purified by column chromatography (EtOAc/hexane from 0/100 to 50/50 in 45 minutes). Yield: 6.2 g, 65%. ¹H NMR (CDCl₃ 400 MHz) δ 7.28 (d, J=8.1 Hz, 2H), 7.20 (d, J=8.1 Hz, 2H), 7.00 (m, 1H), 6.75 (m, 1H), 4.85 (d, J=11.0 Hz, 1H), 4.36 (dd, J=7.3 and 3.7 Hz, 1H), 4.21 (dd, J=8.1 and 2.9 Hz, 1H), 3.85 (dd, J=8.8 and 2.9 Hz, 1H), 3.49 (m, 1H), 2.46 (m, 1H), 2.22 (br, 1H), 2.10 (br, 1H).

Step 2

Trans-[4-(4-chloro-phenylsulfanyl-5,8-difluoro-chroman-3-yl]-methanol

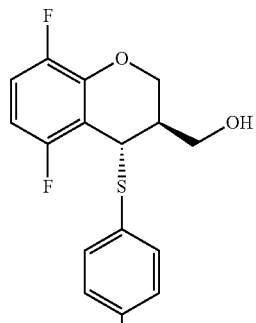

2-[(4-Chloro-phenylsulfanyl)-(2,3,6-trifluoro-phenyl)-methyl]-propane-1,3-diol (6.2 g, 14.8 mmole) was dissolved in 150 mL THF and NaH (60% in oil, 2 g) was added. The reaction was stirred at 60° C. for four hours. 300 mL of water and 400 mL of EtOAc were added. The organic layer was washed with brine (100 mL), dried over Na₂SO₄ and concentrated. The product was purified by column chromatography (EtOAc/hexane from 0/100 to 50/50 in 45 minutes). Yield: 5.0 g, 85%. $^1$H NMR (CDCl$_3$ 400 MHz) δ 7.45 (d, J=8.1 Hz, 2H), 7.32 (d, J=8.1 Hz, 2H), 6.97 (m, 1H), 6.58 (m, 1H), 4.62 (dd, J=11.7 and 2.2 Hz, 1H), 4.50 (br, 1H), 4.43 (td, J=11.7 and 2.2 Hz, 1H), 3.67 (m, 1H), 3.48 (m, 1H), 2.25 (m, 1H), 1.50 (t, J=5.1 Hz, 1H).

Step 3

3-(2-Benzyloxy-ethoxymethyl)-4-(4-chloro-phenyl-sulfanyl-5,8-difluoro-chroman

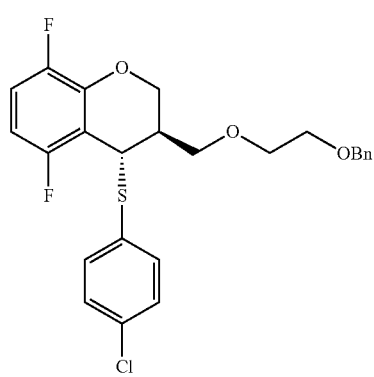 [SMILES: Fc1ccc(F)c2c1OC[C@@H](COCCOCc1ccccc1)[C@@H]2Sc1ccc(Cl)cc1]

Trans-[4-(4-chloro-phenylsulfanyl)-5,8-difluoro-chroman-3-yl]-methanol (0.6 g, 1.65 mmole) and (2-bromo-ethoxymethyl)-benzene (0.71 g, 3.3 mmole) were dissolved in 30 ml THF and NaH (0.5 g) was added. The reaction was stirred at room temperature overnight. (2-Bromo-ethoxymethyl)-benzene (0.71 g, 3.3 mmole) and NaH (0.5 g) were added and the reaction was refluxed overnight. 50 ml water and 50 ml EtOAc were added. The organic layer was washed with Sat. NaCl solution (50 ml), dried over Na$_2$SO$_4$ and concentrated. The product was purified by column chromatography (EtOAc/Hex. from 0/100 to 25/75 in 40 minute). Yield: 0.42 g, 53%. $^1$H NMR (CDCl$_3$ 400 MHz δ 7.42 (d, J=8.8 Hz, 2H), 7.25-7.37 (m, 7H), 6.96 (m, 1H), 6.57 (m, 1H), 4.60 (dd, J=11.7 and 2.2 Hz, 1H), 4.52 (bs, 3H), 4.40 (t, J=11.0, 1H), 3.3-3.56 (m, 6H), 2.38 (m, 1H).

Step 4

3-(2-Benzyloxy-ethoxymethyl-4-(4-chloro-benzene-sulfonyl-5,8-difluoro-chroman

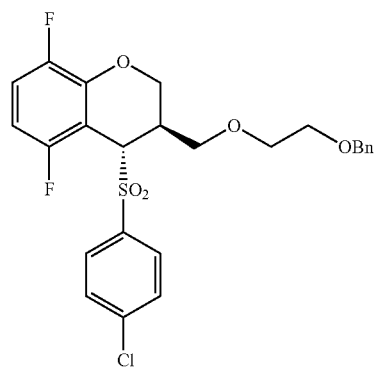 [SMILES: O=S(=O)(c1ccc(Cl)cc1)[C@@H]1c2c(F)ccc(F)c2OC[C@H]1COCCOCc1ccccc1]

3-(2-Benzyloxy-ethoxymethyl)-4-(4-chloro-phenylsulfanyl)-5,8-difluoro-chroman (0.42 g, 0.88 mmole) was dissolved in 15 ml DCM and MCPBA (77%, 0.6 g, 2.6 mmole) was added. The reaction was stirred at room temperature for 30 minutes. 0.5 g sodium thiosulfate in 50 ml water and 50 ml EtOAc were added. The organic layer was washed with 1N NaOH solution (50 ml), brine (50 ml), dried over sodium sulfate and concentrated. The product was purified by column (EtOAc/hexane from 0/100 to 50/50 in 45 minutes). Yield: 0.40 g, 89%. $^1$H NMR (CDCl$_3$ 400 MHz δ 7.73 (d, J=8.8 Hz, 2H), 7.4 (d, J=8.1 Hz, 2H), 7.25-7.37 (m, 5H), 7.02 (m, 1H), 6.42 (m, 1H), 4.90 (dd, J=11.7 and 2.9 Hz, 1H), 4.63 (s, 1H), 4.50 (s, 2H), 4.38 (t, J=11.0, 1H), 3.45-3.62 (m, 5H), 3.30 (t, J=9.5 Hz, 1H), 3.13 (m, 1H).

Step 5

2-[trans-4-(4-Chloro-benzenesulfonyl)-5,8-difluoro-chroman-3-ylmethoxy]-ethanol

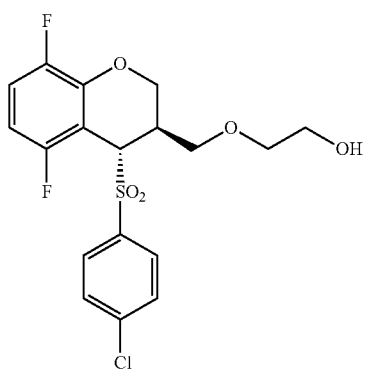 [SMILES: O=S(=O)(c1ccc(Cl)cc1)[C@@H]1c2c(F)ccc(F)c2OC[C@H]1COCCO]

3-(2-Benzyloxy-ethoxymethyl)-4-(4-chloro-benzene-sulfonyl)-5,8-difluoro-chroman (0.4 g, 0.79 mmole) was dissolved in 10 ml EtOAc and Pd(OH)$_2$ was added. Hydrogen was introduced via a balloon. The reaction was stirred at room temperature for 30 minutes. The catalyst was filtered and residue was used in next step without purification. Yield: 0.32 g, 97%. $^1$H NMR (CDCl$_3$ 400 MHz δ 7.73 (d, J=8.1 Hz, 2H), 7.51 (d, J=8.1 Hz, 2H), 7.03 (m, 1H), 6.41 (m, 1H), 4.90 (dd, J=8.8 and 2.9 Hz, 1H), 4.57 (s, 1H), 4.39 (td, J=11.7 and 1.5 Hz, 1H), 3.68 (br, 2H), 3.41-3.54 (m, 3H), 2.30 (t, J=9.5 Hz, 1H), 3.15 (m, 1H).

Step 6

Trans-10b-(4-Chloro-benzenesulfonyl)-7,10-difluoro-1,4-a,5,10b-tetrahydro-2H,4H-pyrano[3,4-c]chromene

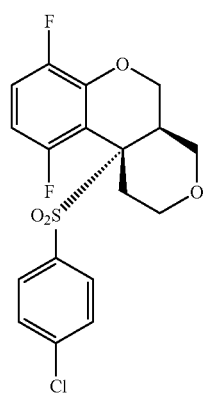 [SMILES: O=S(=O)(c1ccc(Cl)cc1)[C@@]12CCOC[C@@H]1COc1c(F)ccc(F)c12]

The compound was synthesized as previously disclosed method.

The racemic mixture can be separated into two pure enantiomers using Chiral OJ column with ethanol as solvent.

First fraction: [α]=−138.4 deg. (c=1.00 in DCM)

Second fraction: [α]=137.2 deg. (c=1.02 in DCM)

Example 17

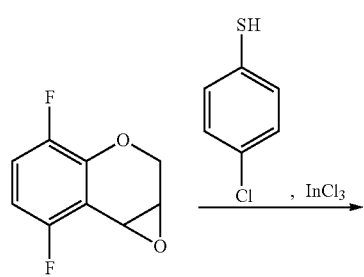

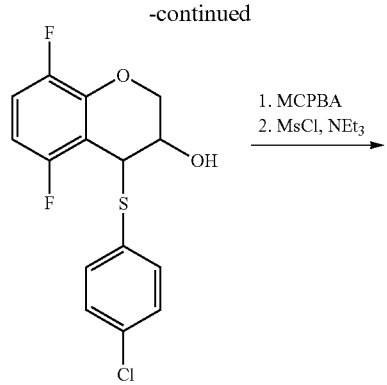

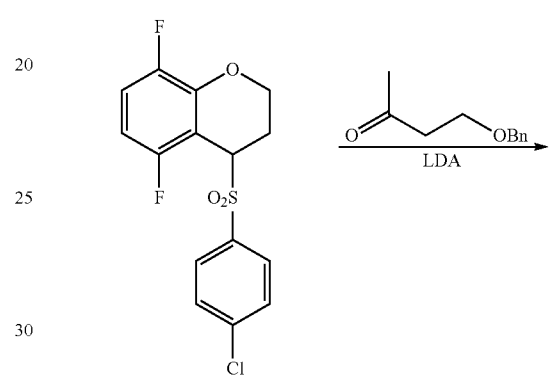

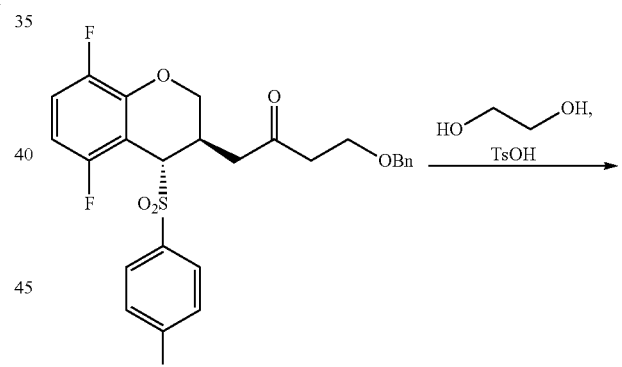

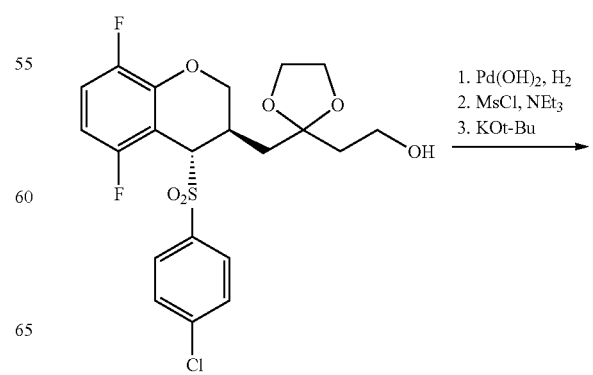

-continued

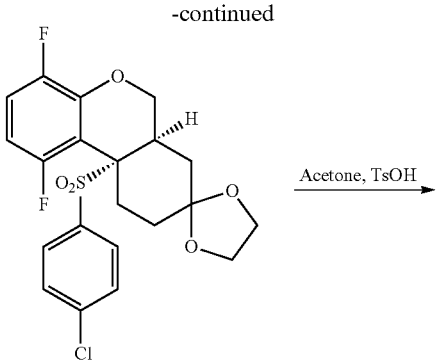

→ Acetone, TsOH

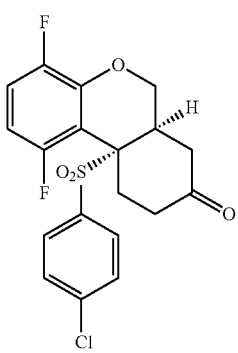

17

Step 1

5,8-Difluoro-2H-chromene oxide

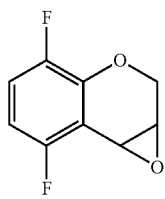 [SMILES: Fc1ccc(F)c2c1OCC1OC21]

5,8-Difluoro-2H-chromene (35 g, 0.21 mole) was dissolved in 500 ml DCM and MCPBA (77%, 93 g, 0.42 mole) was added. The reaction was stirred at room temperature for 30 minutes. 50 g Na$_2$S$_2$O$_3$ in 500 ml water was added to quench the reaction. The organic layer was washed with 2N NaOH solution (2×500 ml), brine (200 ml), dried over Na$_2$SO$_4$ and concentrated. The residue was recrystallized from EtOAc/Hexane solution to give rise to 21.6 g pure product. The residue from mother liquor was purified by column chromatography (EtOAc/hexane from 0/100 to 25/75 in 55 minute, additional 1.4 g obtained). Total Yield: 23 g, 60%. $^1$H NMR (CDCl$_3$ 400 MHz δ 7.00 (m, 1H), 6.63 (m, 1H), 4.67 (d, J=12.4 Hz, 1H), 4.27 (m, 2H), 3.84 (d, J=4.4 Hz, 1H).

Step 2

4-(4-Chloro-phenylsulfanyl)-5,8-difluoro-chroman-3-ol

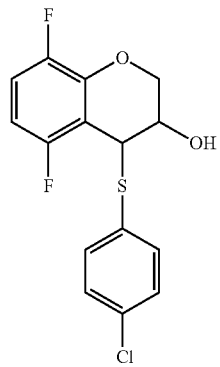 [SMILES: OC1COc2c(F)ccc(F)c2C1Sc1ccc(Cl)cc1]

5,8-Difluoro-2H-chromene oxide (23 g, 0.125 mole) and 4-Chloro-benzenethiol (18.1 g, 0.125 mmole) were dissolved in 500 ml DCM and InCl$_3$ (2.9 g, 0.013 mole) was added. The reaction was stirred at room temperature overnight. 200 ml DCM and 200 ml water were added. The organic layer was washed with brine, dried over Na$_2$SO$_4$ and concentrated. The product was purified by column chromatography (EtOAc/hexane from 0/100 to 50/50 in 55 minute). Yield: 23.2 g, 57%.
$^1$H NMR (CDCl$_3$ 400 MHz δ 7.48 (d, J=8.8 Hz, 2H), 7.34 (d, J=8.8 Hz, 2H), 7.01 (m, 1H), 6.64 (m, 1H), 4.63 (d, J=11.7 Hz, 1H), 4.32-4.41 (m, 2H), 4.12 (m, 1H).

Step 3

4-(4-Chloro-benzenesulfonyl)-5,8-difluoro-2H-chromene

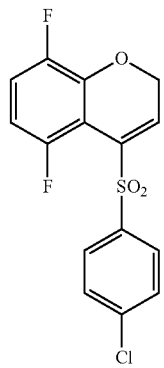 [SMILES: O=S(=O)(C1=CCOc2c(F)ccc(F)c21)c1ccc(Cl)cc1]

4-(4-Chloro-phenylsulfanyl)-5,8-difluoro-chroman-3-ol (23.2, 71 mmole) was dissolved in 200 ml DCM and MCPBA (77%, 31.7 g, 142 mmole) was added. The reaction was stirred at room temperature for 3 hours. 10 g Na$_2$S$_2$O$_3$ in 50 ml water was added to quench the reaction. The organic layer was washed with 1N NaOH solution (2×100 ml), brine (100 ml), dried over Na$_2$SO$_4$ and concentrated. The residue was dissolved in 200 ml DCM, mesyl chloride (16.1 g, 142 mmole) and triethylamine (14.3 g, 142 mmole) were added. The reaction was stirred at room temperature for one hour. The reaction solution was washed with brine (100 ml), dried over $Na_2SO_4$ and concentrated. The residue was recrystallized from EtOAc/Hexane solution to give rise to 8.4 g pure product. The residue from mother liquor was purified by column chromatography (EtOAc/hexane from 0/100 to 25/75 in 55 minute, 7.1 g). Total yield: 15.5 g, 64%. $^1$H NMR (CDCl$_3$ 400 MHz δ 7.84 (dd, J=8.8 and 2.2 Hz, 2H), 7.51 (d, J=8.1 Hz, 2H), 7.30 (t, J=4.4 Hz, 1H), 7.00 (m, 1H), 6.54 (m, 1H), 4.99 (d, J=4.4 Hz, 2H).

Step 4

4-Benzyloxy-1-[4-(4-chloro-benzenesulfonyl)-5,8-difluoro-chroman-3-yl]-butan-2-one

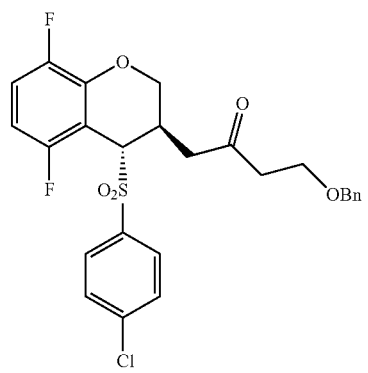 [SMILES: O=C(CCOCc1ccccc1)C[C@@H]1COc2c(F)ccc(F)c2[C@H]1S(=O)(=O)c1ccc(Cl)cc1]

Diisopropylamine (1.23 g, 12.2 mmole) was dissolved in 150 ml dry THF and the reaction was cooled to 0° C. n-Butyllithium (2.5 ml in Hexane, 4.5 ml, 11.2 mmole) was added and the reaction was stirred at 0° C. for 10 minutes. The reaction was cooled to −100° C. and 4-benzyloxy-2-butanone (1.83 g, 10.3 mmole) in 50 ml dry THF (pre-cooled to −78° C.) was added. The reaction was stirred for 30 minutes at −78° C. 4-(4-Chloro-benzenesulfonyl)-5,8-difluoro-2H-chromene (3.2 g, 9.36 mmole) in 20 ml THF (pre-cooled to −78° C.) was added. The reaction was stirred at −78° C. for 1 hour. 20 ml water was added at −78° C. to quench the reaction. After the reaction was warmed up to room temperature, 200 ml EtOAc was added. The organic layer was washed with brine (2×100 ml), dried over $Na_2SO_4$ and concentrated. The product was purified by column chromatography (EtOAc/hexane from 0/100 to 40/60 in 45 minute). Yield, 2.6 g, 53%. $^1$H NMR (CDCl$_3$ 400 MHz δ 7.82 (d, J=8.8 Hz, 2H), 7.54 (d, J=8.1 Hz, 2H), 7.20-7.35 (m, 5H), 7.05 (m, 1H), 6.47 (m, 1H), 4.89 (dd, J=11.7 and 2.9 Hz, 1H), 4.42 (s, 3H), 4.24 (dt, J=12.4 and 2.2 Hz, 1H), 3.65 (t, J=5.9 Hz, 2H), 3.31 (m, 1H), 2.33-2.67 (m, 4H).

Step 5

3-[2-(2-Benzyloxy-ethyl)-[1,3-dioxolan-2-ylmethyl]-4-(4-chloro-benzene-sulfonyl)-5,8-difluoro-chroman

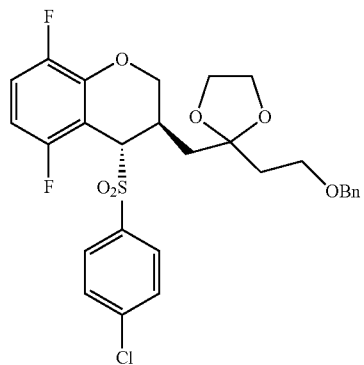 [SMILES: O=S(=O)(c1ccc(Cl)cc1)[C@@H]1c2c(F)ccc(F)c2OC[C@H]1CC1(CCOCc2ccccc2)OCCO1]

4-Benzyloxy-1-[4-(4-chloro-benzenesulfonyl)-5,8-difluoro-chroman-3-yl]-butan-2-one (10 g, 19.2 mmole), ethylene glycol (20 ml) and toluene sulfonic acid (1 g) were dissolved in 300 ml toluene. The reaction was refluxed for four hours with a Dean-Stark trap. The reaction was cooled to room temperature and 200 ml water and 200 ml EtOAc were added. The organic layer was washed with brine (2×50 ml), dried over $Na_2SO_4$ and concentrated. The residue was purified by column chromatography (EtOAc/hexane from 0/100 to 50/50 in 55 minute). Yield: 6.3 g, 58%. $^1$H NMR (CDCl$_3$ 400 MHz δ 7.74 (d, J=8.1 Hz, 2H), 7.51 (d, J=8.8 Hz, 2H), 7.20-7.39 (m, 5H), 7.02 (m, 1H), 6.42 (m, 1H), 4.89 (dd, J=11.0 and 2.9 Hz, 1H), 4.84 (s, 1H), 4.40 (d, J=2.0 Hz, 2H), 4.21 (d, J=11.7 Hz, 1H), 3.85 (m, 4H), 3.46 (t, J=5.9 Hz, 2H), 3.03 (d, J=8.1 Hz, 1H), 1.75-1.90 (m, 3H), 1.54-1.61 (m, 1H).

Step 6

Trans-10a-[(4-chlorophenyl)sulfonyl]-1,4-difluoro-6a,9,10,10a-tetrahydrospiro[6H-dibenzo[b,d]pyran-8(7H), 2'-[1,3]dioxolane]

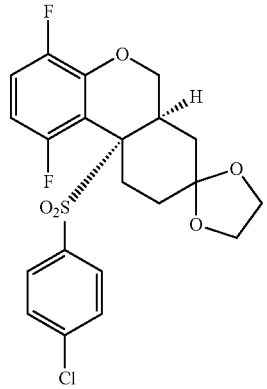 [SMILES: O=S(=O)(c1ccc(Cl)cc1)[C@@]12CCC3(C[C@@H]1COc1c(F)ccc(F)c12)OCCO3]

3-[2-(2-Benzyloxy-ethyl)-[1,3]dioxolan-2-ylmethyl]-4-(4-chloro-benzenesulfonyl)-5,8-difluoro-chroman (6.3 g, 11.2 mmole) was dissolved in 200 ml EtOAc and Pd(OH)$_2$ (0.5 g) was added. Hydrogen was introduced via a balloon. The reaction was stirred at room temperature for 45 minutes. The catalyst was filtered and the filtrate was concentrated. The residue was dissolved in 200 ml DCM and MSCl (1.4 g, 12 mmole) and NEt$_3$ (1.7 g, 17 mmole) were added. The mixture was stirred at room temperature for ten minutes. 200 ml water and 100 ml DCM were added. The organic layer was washed with 1N HCl (100 ml), water (100 ml), brine (100 ml), dried over Na$_2$SO$_4$ and concentrated. The residue was dissolved in 200 ml THF and KOt-Bu (1 M in THF, 14 ml) was added. The mixture was stirred at room temperature for twenty minutes. 200 ml water and 200 ml EtOAc were added. The organic layer was washed with brine (200 ml), dried over Na$_2$SO$_4$ and concentrated. The product was purified by column (EtOAc/hexane from 0/100 to 25/75 in 45 minutes). Yield: 3.1 g, 61%. $^1$H NMR (CDCl$_3$ 400 MHz δ 7.61 (d, J=8.8 Hz, 2H), 7.49 (d, J=8.8 Hz, 2H), 7.07 (m, 1H), 6.42 (m, 1H), 5.23 (dd, J=11.7 and 2.9 Hz, 1H), 4.12 (d, J=11.0 Hz, 1H), 3.88-4.01 (m, 4H), 2.97 (dt, J=13.2 and 2.9 Hz, 1H), 2.53 (dt, J=13.1 and 2.9 Hz, 1H), 2.33 (tt, J=13.2 and 2.9 Hz, 1H), 1.62-1.81 (m, 3H), 1.23-1.35 (m, 1H).

Step 7

Trans-10a-(4-chloro-benzenesulfonyl)-1,4-difluoro-6a,9,10,10a-tetrahydro-6H,7H-benzo[c]chromen-8-one

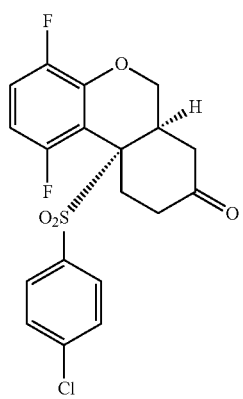 [SMILES: O=C1CC[C@@]2(S(=O)(=O)c3ccc(Cl)cc3)c3c(F)ccc(F)c3OC[C@H]2C1]

Trans-10a-[(4-chlorophenyl)sulfonyl]-1,4-difluoro-6a,9,10,10a-tetrahydrospiro[6H-dibenzo[b,d]pyran-8(7H), 2'-1,3]dioxolane] (3.1 g, 6.8 mmole) was dissolved in 200 ml acetone and 10 ml water. Toluenesulfonyl chloride (1 g) was added and the mixture was refluxed overnight. Acetone was removed. 100 water and 100 ml EtOAc were added. The organic layer was washed with water (50 ml), dried over Na$_2$SO$_4$ and concentrated. The residue was pure enough for next step. Yield: 2.8 g, 100%. $^1$H NMR (CDCl$_3$ 400 MHz δ 7.63 (d, J=8.1 Hz, 2H), 7.52 (d, J=8.8 Hz, 2H), 7.14 (m, 1H), 6.64 (m, 1H), 5.27 (dd, J=11.7 and 2.9 Hz, 1H), 4.13 (d, J=11.7 Hz, 1H), 3.18 (d, J=12.4 Hz, 1H), 2.79 (dt, J=12.4 and 3.7 Hz, 1H), 2.4-2.57 (m, 4H), 2.04-2.17 (m, 1H).

Example 18

10a-(4-chloro-benzenesulfonyl)-1,4-difluoro-6a,7,8,9,10,10a-hexahydro-6H-benzo[c]chromen-8-ol

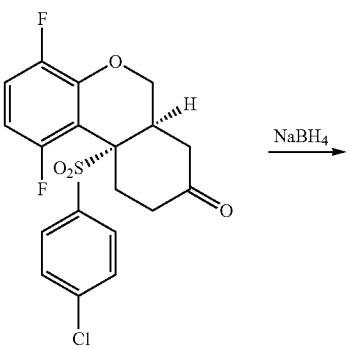

NaBH$_4$ →

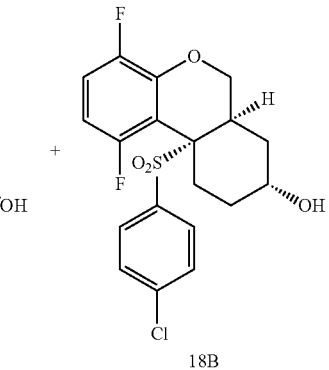

18A      18B

Trans-10a-(4-chloro-benzenesulfonyl)-1,4-difluoro-6a,7,8,9,10,10a-hexahydro-6H-benzo[c]chromen-8-ol (1.0 g, 2.4 mmole) was dissolved in 50 ml THF and sodium hydride (0.3 g) was added. The reaction was stirred at room temperature for 10 minutes. 100 ml water and 100 ml EtOAc were added. The organic layer was washed with water (50 ml), brine (50 ml), dried over Na$_2$SO$_4$ and concentrated. The residue was purified by column (EtOAc/hexane from 0/100 to 50/50 in 35 minutes). Yield: 0.81 g of 18A and 60 mg of 18B.

18A: $^1$H NMR (CDCl$_3$ 400 MHz) δ 7.58 (d, J=8.8 Hz, 2H), 7.48 (d, J=8.8 Hz, 2H), 7.05 (m, 1H), 6.61 (m, 1H), 5.22 (dd, J=8.8 and 2.9 Hz, 1H), 4.15 (d, J=11.0 Hz, 1H), 3.78 (m, 1H), 2.78 (dt, J=13.2 and 2.9 Hz, 1H), 2.60 (dt, J=13.2 and 2.9 Hz, 1H), 1.90-2.06 (m, 3H), 1.42 (m, 1H), 0.96-1.08 (m, 1H).

18B: $^1$H NMR (CDCl$_3$ 400 MHz) δ 7.63 (d, 2H, J=8.8 Hz), 7.50 (d, 2H, J=9.0 Hz), 7.10-7.04 (m, 1H), 6.45-6.39 (m, 1H), 5.28 (dd, 1H, J=2.8 Hz), 4.10 (d, 1H, J=11.6 Hz), 4.04 (dd,

1H, J=2.8 Hz), 3.10-3.06 (m, 1H), 2.54-2.46 (m, 1H), 2.37-2.33 (m, 1H), 1.85-1.59 (m, 3H), 1.49 (br s, 1H), 1.33-1.26 (m, 1H).

Example 19

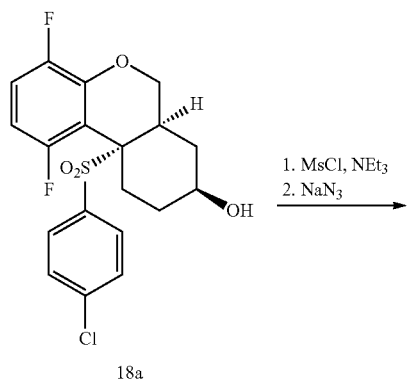

18a

1. MsCl, NEt₃
2. NaN₃

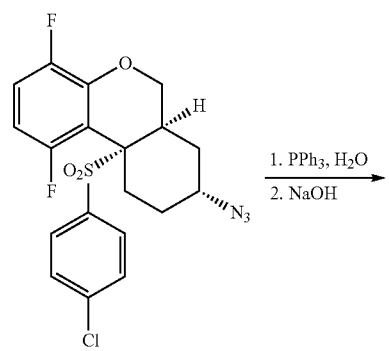

1. PPh₃, H₂O
2. NaOH

Step 1

Cis-8-Azido-10a-(4-chloro-benzenesulfonyl)-1,4-difluoro-6a,7,8,9,10,10a-hexahydro-6H-benzo[c]chromene

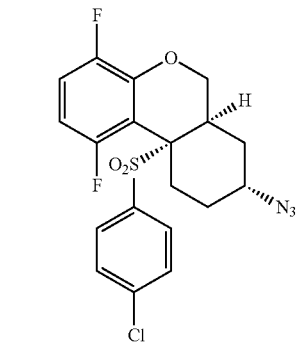 [SMILES: [N-]=[N+]=N[C@@H]1CC[C@@]2(S(=O)(=O)c3ccc(Cl)cc3)c3c(F)ccc(F)c3OC[C@H]2C1]

Trans-10a-(4-chloro-benzenesulfonyl)-1,4-difluoro-6a,7,8,9,10,10a-hexahydro-6H-benzo[c]chromen-8-ol (0.81 g, 2.0 mmole) was dissolved in 10 ml DCM. Mesyl chloride (0.23 g, 2.0 mmole) and triethylamine (0.5 ml) were added. The reaction was stirred at room temperature for 10 minutes. 50 ml brine and 50 ml DCM were added. The organic layer was washed with 1N HCl solution (50 ml), water (50 ml), brine (50 ml), dried over Na₂SO₄ and concentrated. The residue was dissolved in 20 ml DMF. Sodium azide (0.5 g, 7.4 mmole) and 50 mg 18-crown-6 were added. The reaction was heated to 80° C. over the weekend. 50 ml EtOAc and 50 ml hexane were added. The organic layer was washed with water (2×50 ml), dried over Na₂SO₄ and concentrated. The residue was pure product and it was used in next step without further purification. Yield: 0.68 g, 79%. $^1$H NMR (CDCl₃ 400 MHz δ 7.61 (d, J=8.8 Hz, 2H), 7.50 (d, J=8.8 Hz, 2H), 7.08 (m, 1H), 6.42 (m, 1H), 5.25 (dd, J=11.7 and 2.9 Hz, 1H), 4.12 (d, J=11.0 Hz, 1H), 3.87 (m, 1H), 2.96 (dt, J=11.7 and 2.9 Hz, 1H), 2.27-2.42 (m, 2H), 1.79-1.92 (m, 2H), 1.61-1.70 (m, 1H), 1.23-1.31 (m, 1H).

Step 2

(6aR)-10aS-(4-Chloro-benzenesulfonyl)-1,4-difluoro-6a,7,8,9,10,10a-hexahydro-6H-benzo[b,d]pyran-8(R)-amine (racemic)

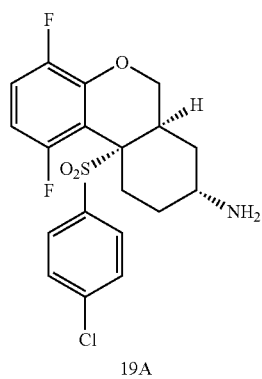

19A

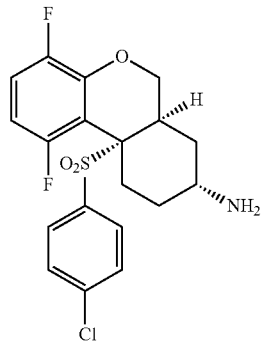 [SMILES: N[C@@H]1CC[C@@]2(S(=O)(=O)c3ccc(Cl)cc3)c3c(F)ccc(F)c3OC[C@H]2C1]

Cis-8-Azido-10a-(4-chloro-benzenesulfonyl)-1,4-difluoro-6a,7,8,9,10,10a-hexahydro-6H-benzo[c]chromene (0.63 g, 1.43 mmole) was dissolved in 25 ml THF and triphenylphosphine (0.45 g, 1.72 mmole) was added. 2 ml water was added and the reaction was refluxed for 4 hours. The reaction was cooled to room temperature. 10 ml 1N NaOH solution was added and the reaction was stirred at room temperature overnight. 50 ml water and 50 ml EtOAc were added. The organic layer was washed with water (2×50 ml), dried over $Na_2SO_4$ and concentrated. The residue was purified by column (EtOAc/2.5N NH3 in MeOH from 100/0 to 80/20 in 45 minutes). Yield: 0.46 g, 78%. $^1$H NMR (CDCl$_3$ 400 MHz δ 7.61 (d, J=8.8 Hz, 2H), 7.48 (d, J=8.8 Hz, 2H), 7.05 (m, 1H), 6.40 (m, 1H), 5.24 (dd, J=11.7 and 2.9 Hz, 1H), 4.07 (d, J=11.0 Hz, 1H), 3.24 (bs, 1H), 3.09 (m, 1H), 2.52 (tt, J=13.9 and 2.9 Hz, 1H), 2.27 (d, J=13.9 Hz, 1H), 1.49-1.31 (m, 3H), 1.30 (m, 1H).

Example 20

N-[(6aR)-10aS-(4-Chloro-benzenesulfonyl)-1,4-difluoro-6a,7,8,9,10,10a-hexahydro-6H-benzo[b,d]pyran-8(R)-yl]-1,1,1-trifluoro-methanesulfonamide

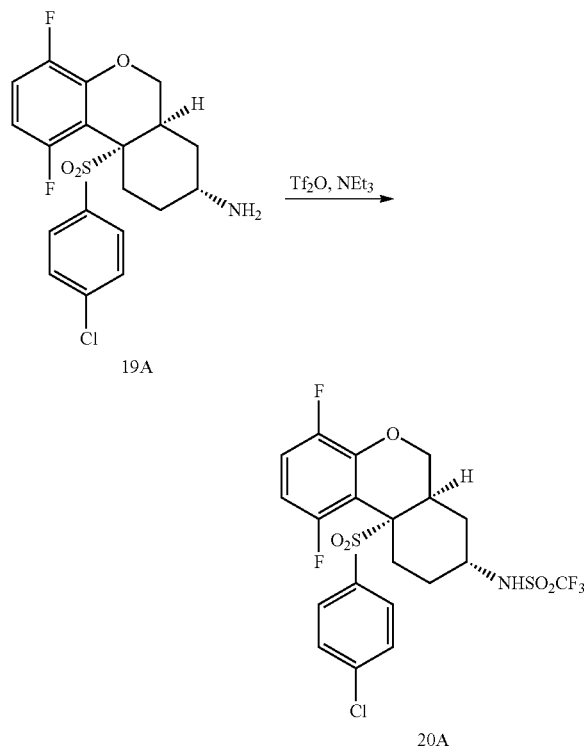

(6aR)-10aS-(4-Chloro-benzenesulfonyl)-1,4-difluoro-6a,7,8,9,10,10a-hexahydro-6H-benzo[b,d]pyran-8(R)-amine (150 mg, 0.36 mmole) was dissolved in 25 ml DCM and trifluoromethanesulfonyl chloride (0.15 g, 0.54 mmole) in 5 ml DCM was added, followed by triethylamine (0.2 ml). The reaction was stirred at room temperature for 10 minutes. 50 ml water and 50 ml DCM were added. The organic layer was separated, dried over $Na_2SO_4$ and concentrated. The residue was purified by column (EtOAc/hexane from 0/100 to 25/75 in 35 minutes). Yield: 0.18 g, 91% of racemic compound 20A. $^1$H NMR (CDCl$_3$ 400 MHz δ7.57 (d, J=8.1 Hz, 2H), 7.50 (d, J=8.8 Hz, 2H), 7.10 (m, 1H), 6.42 (m, 1H), 6.07 (d, J=8.1 Hz, 1H), 5.25 (dd, J=11.7 and 2.9 Hz, 1H), 4.13 (d, J=12.4 Hz, 1H), 3.90 (bs, 1H), 2.96 (dt, J=13.2 and 2.9 Hz, 1H), 2.52 (dt, J=13.9 and 2.9 Hz, 1H), 2.25 (tt, J=13.9 and 2.2 Hz, 1H), 1.81-2.01 (m, 3H), 1.41 (tt, J=14.6 and 2.9 Hz, 1H).

The racemic mixture can be separated into two pure enantiomers 20B and 20C using Chiral OJ column with hexane/isopropanol (65/35) as solvent.

First fraction: [α]=−72.2 deg. (c=0.90 in DCM)-Compounds 20B.

Second fraction: [α]=67.2 deg. (c=0.95 in DCM)-Compounds 20C

Using methods similar to those in Example 20 (i.e., methods similar to those used for the preparation of compound 20A) and substituting an appropriate acyl or sulfonyl halide, the compounds in Table 11 were prepared.

TABLE 11

| Ex. No. | Structure | LCMS (M + 1, retention time) |
|---|---|---|
| 20D | 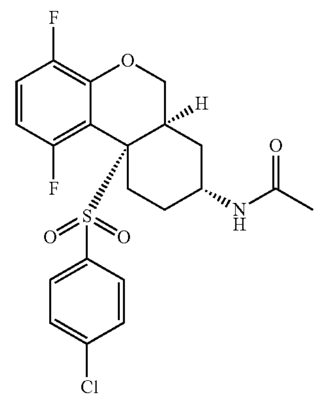 [SMILES: CC(=O)N[C@@H]1CC[C@@]2(S(=O)(=O)c3ccc(Cl)cc3)c3c(F)ccc(F)c3OC[C@H]2C1] | 456.3, 4.19 Min. |
| 20E | 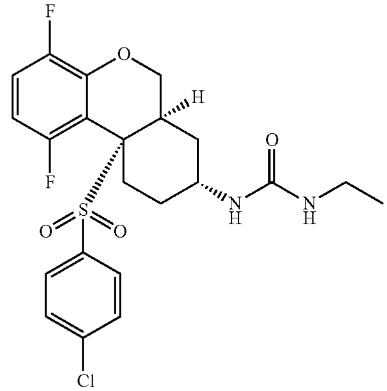 [SMILES: CCNC(=O)N[C@@H]1CC[C@@]2(S(=O)(=O)c3ccc(Cl)cc3)c3c(F)ccc(F)c3OC[C@H]2C1] | 485.3, 4.35 Min. |

TABLE 11-continued

| Ex. No. | Structure | LCMS (M + 1, retention time) |
|---|---|---|
| 20F | 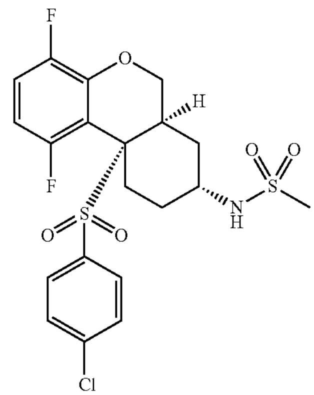 [SMILES: CS(=O)(=O)N[C@@H]1CC[C@@]2(S(=O)(=O)c3ccc(Cl)cc3)c3c(F)ccc(F)c3OC[C@H]2C1] | 492.3, 4.06 Min. |
| 20G | 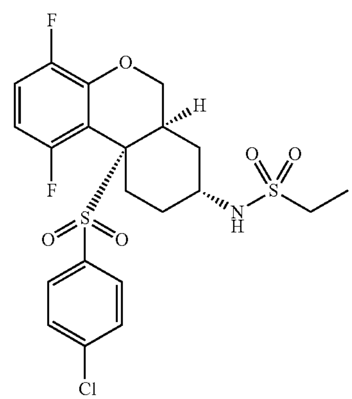 [SMILES: CCS(=O)(=O)N[C@@H]1CC[C@@]2(S(=O)(=O)c3ccc(Cl)cc3)c3c(F)ccc(F)c3OC[C@H]2C1] | 506.3, 4.18 Min. |
| 20H | 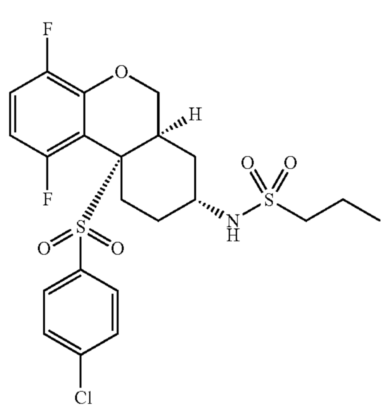 [SMILES: CCCS(=O)(=O)N[C@@H]1CC[C@@]2(S(=O)(=O)c3ccc(Cl)cc3)c3c(F)ccc(F)c3OC[C@H]2C1] | 520.3, 4.36 Min. |
| 20I | | 560.3, 4.77 Min. |
| 20J | | (No M + 1), 4.52 Min. |
| 20K | | 520.3, 4.50 Min. |

TABLE 11-continued

| Ex. No. | Structure | LCMS (M + 1, retention time) |
|---|---|---|
| 20L | 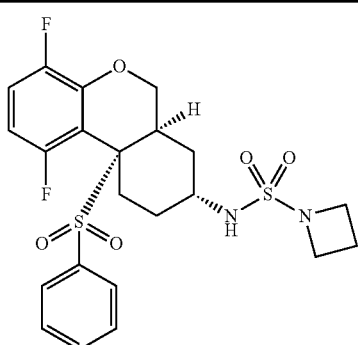 | 533.3, 4.70 Min. |

Example 21

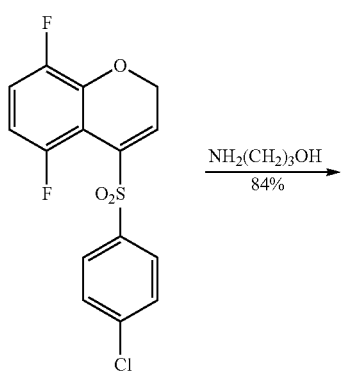

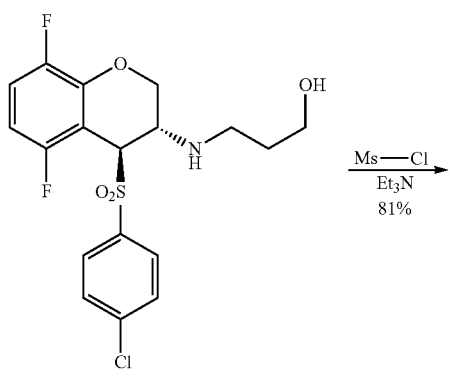

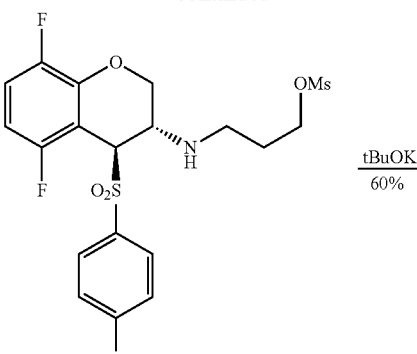

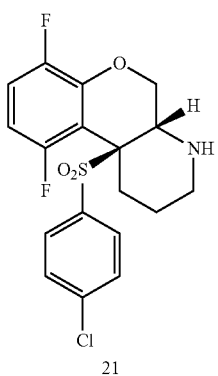

Step 1

3-[4-(4-Chloro-benzenesulfonyl)-5,8-difluoro-chroman-3-ylamino]-propan-1-ol

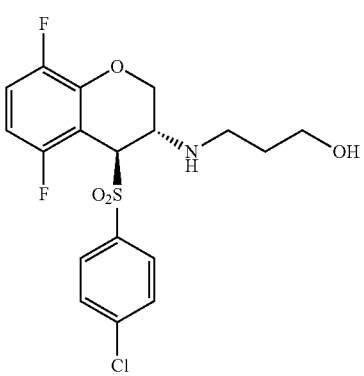 [SMILES: O=S(=O)(c1ccc(Cl)cc1)[C@H]1c2c(F)ccc(F)c2OC[C@@H]1NCCCO]

4-(4-Chloro-benzenesulfonyl)-5,8-difluoro-2H-chromene (0.3 g, 0.88 mmole) was dissolved in 15 ml THF and 3-aminopropanol (1 ml) was added. The mixture was stirred at room temperature for 30 minutes. 50 saturated $Na_2CO_3$ solution and 50 ml EtOAc were added. The organic layer was washed with water (50 ml), brine (50 ml), dried over $Na_2SO_4$ and concentrated. The product was purified by column (EtOAc/hexane from 50/50 to 100/0 in 45 minutes). Yield: 0.31 g, 84%. $^1$H NMR (CDCl$_3$ 400 MHz) δ 7.69 (d, J=8.8 Hz, 2H), 7.48 (d, J=8.1 Hz), 6.99 (td, J=9.5, 5.1 Hz, 1H), 6.38 (td, J=9.5, 3.7 HZ, 1H), 4.80 (dd, J=12.5, 2.9 Hz, 1H), 4.53 (s, 1H), 4.43 (d, J=11.8 Hz, 1H), 3.78 (s, 1H), 3.61 (t, J=5.9 Hz, 2H), 2.86-2.71 (m, 2H), 2.25 (bs, 1H), 1.57 (p, J=5.9 Hz, 2H).

Step 2

Methanesulfonic acid 3-[4-(4-chloro-benzenesulfonyl)-5,8-difluoro-chroman-3-ylamino]-propyl ester

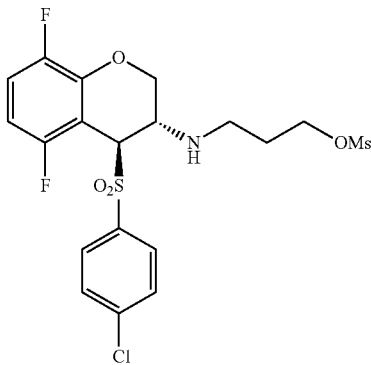 [SMILES: CS(=O)(=O)OCCCN[C@H]1COc2c(F)ccc(F)c2[C@@H]1S(=O)(=O)c1ccc(Cl)cc1]

Methanesulfonic acid 4-(4-chloro-benzenesulfonyl)-5,8-difluoro-chroman-3-yl ester (0.29 g, 0.69 mmol) was dissolved in 50 ml of dichloromethane. Methanesulfonyl chloride (64 µL, 0.83 mmol) and triethylamine (117 µL, 0.83 mmol) were added respectively and stirred at room temperature overnight. The solution was quenched with water (40 ml) and dichloromethane (40 ml). The layers were separated and the aqueous layer was washed with dichloromethane. The combined organics were dried over $Na_2SO_4$ and concentrated under vacuum. The product was used in next step without further purification. Crude yield: 280 mg, 81%. $^1$H NMR ($CDCl_3$ 400 MHz) δ 7.71 (d, J=8.8 Hz, 2H), 7.50 (d, J=8.8 Hz, 2H), 7.01 (td, J=10.3, 5.1 Hz), 6.41 (td, 8.8, 3.7 Hz, 1H), 4.80 (dd, J=11.8, 2.2 Hz, 1H), 4.53 (s, 1H), 4.48 (d, J=11.8 Hz, 1H), 4.22 (t, 5.9 Hz, 2H), 3.75 (s, 1H), 2.93 (s, 3H), 2.82-2.67 (m, 2H), 1.79 (p, J=5.9 Hz, 2H).

Step 3

4a-(4-Chloro-benzenesulfonyl-5,8-difluoro-2,3,4,4a,10,10a-hexahydro-1H-9-oxa-1-aza-phenanthrene

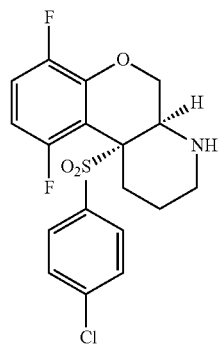 [SMILES: O=S(=O)(c1ccc(Cl)cc1)[C@@]12CCCN[C@@H]1COc1c(F)ccc(F)c12]

Methanesulfonic acid 3-[4-(4-chloro-benzenesulfonyl)-5,8-difluoro-chroman-3-ylamino]-propyl ester (0.28 g, 0.57 mmol) was dissolved in 25 ml of tetrahydrofuran then 1 M potassium tert-butoxide solution (2.40 ml, 2.40 mmol) was added. The reaction was stirred at room temperature for 3.5 h. The reaction was quenched with 50 ml of water and washed with 50 ml of ethyl acetate. The organic layer was dried over $Na_2SO_4$ and concentrated. The product was purified by prep TLC (EtOAc/Hex. 50/50). Yield: 140 mg, 60%. $^1$H NMR ($CDCl_3$ 400 MHz) δ 7.60 (d, J=8.1 Hz, 2H), 7.49 (d, J=8.8 Hz, 2H), 7.08 (td, J=9.5, 4.4 Hz, 1H), 6.47-6.40 (m, 1H), 5.21 (dd, J=11.8, 2.2 Hz, 1H), 4.33 (d, J=11.8 Hz, 1H), 3.70 (s, 1H), 3.00 (d, J=13.2 Hz, 1H), 2.76 (td, J=12.4 Hz, 2.9 Hz, 1H), 2.68 (d, J=13.2 Hz, 1H), 2.17 (tt, J=13.2, 2.9 Hz 1H), 1.66-1.44 (m, 2H), 1.21-1.07 (m, 1H).

Examples 22 and 23

4a-(4-Chloro-benzenesulfonyl-1-ethyl-5,8-difluoro-2,3,4,4a,10,10a-hexahydro-1H-9-oxa-1-aza-phenanthrene and 1-[4a-(4-Chloro-benzenesulfonyl)-5,8-difluoro-2,3,4,4a, 10,10a-hexahydro-9-oxa-1-aza-phenanthren-1-yl]-ethanone

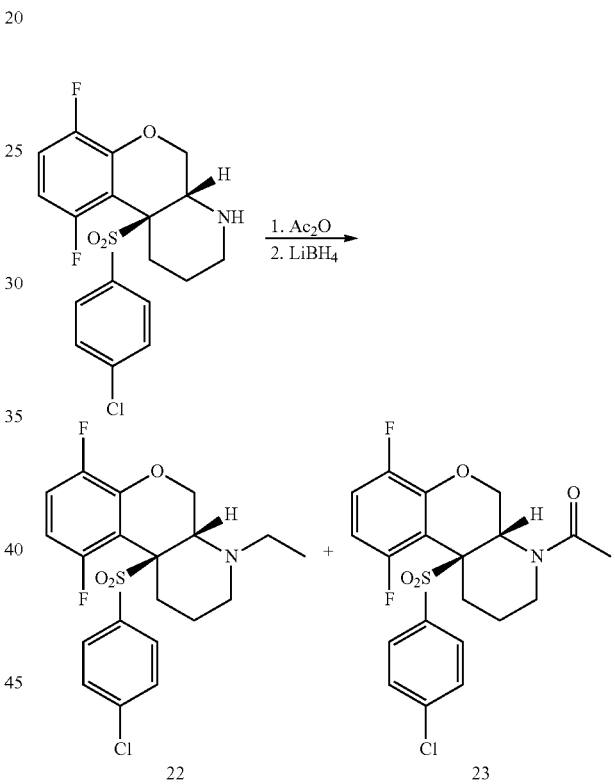

22          23

4a-(4-Chloro-benzenesulfonyl)-5,8-difluoro-2,3,4,4a,10,10a-hexahydro-1H-9-oxa-1-aza-phenanthrene (73 mg, 0.18 mmol) was dissolved in 5 ml of tetrahydrofuran then acetic anhydride (182 mg, 1.78 mmol) was added. The reaction was stirred at room temperature overnight. Lithium borohydride (64 mg, 2.91 mmol) was added and the reaction was stirred at room temperature for 3 h. The reaction was quenched with 25 ml of water then 25 ml of ethyl acetate was added. The organic layer was dried over $Na_2SO_4$ and concentrated. The product was purified by column using EtOAc/Hex. as the eluent (gradient from 0/100 to 50/50 in 40 minutes). Two compounds were isolated.

4a-(4-Chloro-benzenesulfonyl)-1-ethyl-5,8-difluoro-2,3,4,4a,10,10a-hexahydro-1H-9-oxa-1-aza-phenanthrene (22): Yield: 20.8 mg, 26%. $^1$H NMR ($CDCl_3$ 400 MHz) δ 7.60 (d, J=8.1 Hz, 2H), 7.48 (d, J=8.8 Hz, 2H), 7.07-6.99 (m, 1H), 6.43-6.35 (m, 1H), 5.16 (dd, J=13.2, 1.5 Hz, 1H), 4.67 (dd, J=13.2, 1.5 Hz, 1H), 3.34 (s, 1H), 3.15-3.04 (m, 1H), 2.84-2.67 (m, 2H), 2.61-2.51 (m, 2H), 2.04-1.94 (m, 1H), 1.66-1.58 (m, 1H), 1.39-1.27 (m, 1H), 1.00 (t, J=7.3 Hz, 3H).

1-[4a-(4-Chloro-benzenesulfonyl)-5,8-difluoro-2,3,4,4a,10,10a-hexahydro-9-oxa-1-aza-phenanthren-1-yl]-ethanone (23): Yield: 36.6 mg, 46%. $^1$H NMR (CDCl$_3$ 400 MHz) δ 7.61 (d, J=8.8 Hz, 2H), 7.43 (d, J=8.8 Hz, 2H), 7.05 (td, J=9.5, 4.4 Hz, 1H), 6.60-6.51 (m, 1H), 5.40 (bs, 1H), 4.50 (dd, J=11.8, 3.7 Hz, 1H), 4.20 (dd, J=11.8, 5.9 Hz, 1H), 3.62 (bs, 1H), 2.90 (bs, 1H), 2.70-2.60 (m, 1H), 2.50-2.40 (m, 1H), 2.22-2.03 (m, 4H), 1.52-1.41 (m, 1H).

Example 24

Example 24A and 24B

Trans-10b-(4-chloro-benzenesulfonyl)-7,10-difluoro-cis-4-methyl-1,4a,5,10b-tetrahydro-2H,4H-pyrano[3,4-c]chromene and trans-10b-(4-chloro-benzenesulfonyl)-O-difluoro-trans-4-methyl-1,4a,5,10b-tetrahydro-2H,4H-pyrano[3,4-c]chromene

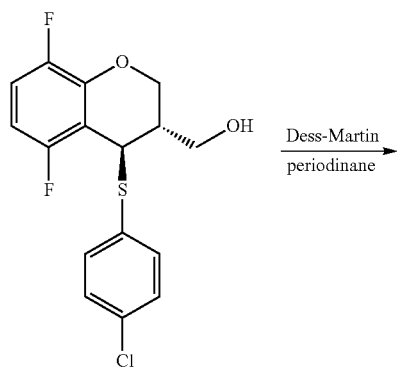

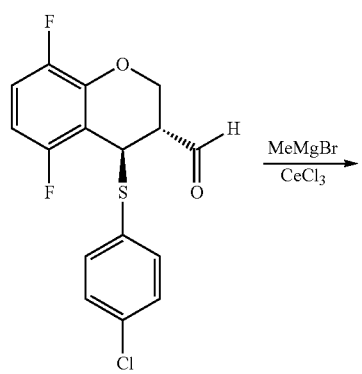

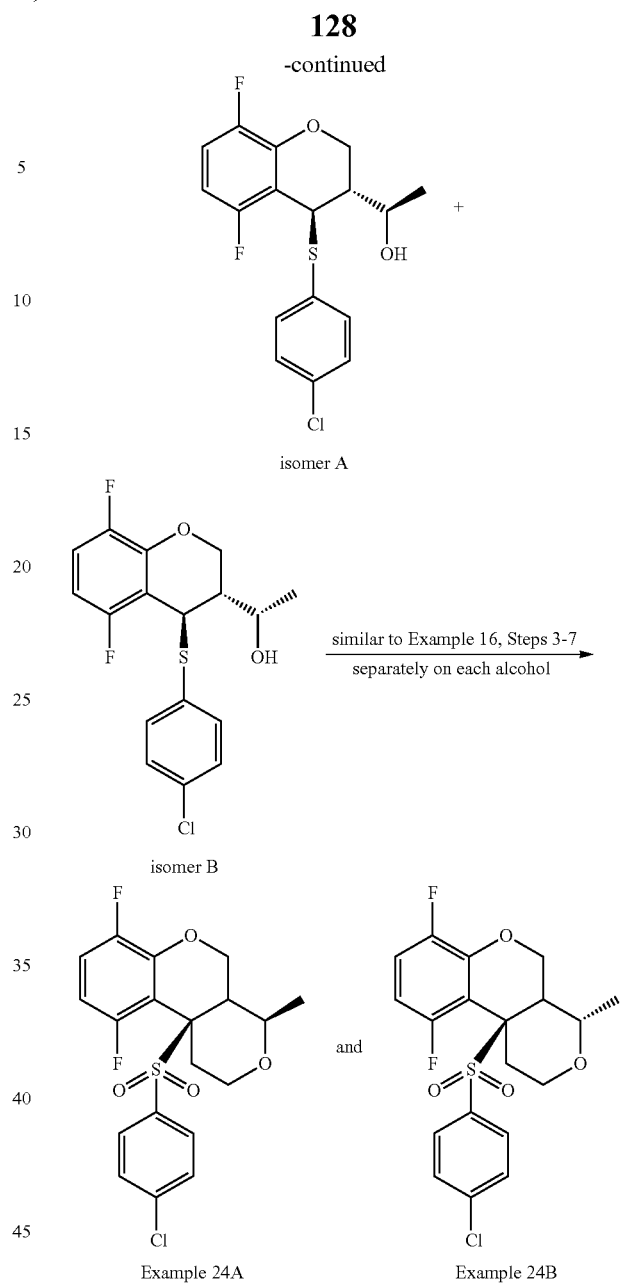

Step 1

A solution of the product from Example 16 Step 2: (500 mg, 1.46 mmol) in DCM (3 mL) was treated with Dess-Martin periodinane (732 mg, 1.72 mmol) and stirred at RT for 1 h before excess sodium thiosulfate was added. The slurry was diluted with EtOAc and half-saturated NaHCO3, washed with half-saturated NaHCO3, dried over Na$_2$SO4 and concentrated. The resulting aldehyde (500 mg) could be used as such in the next step.

Step 2

A solution of anhydrous cerium chloride (1.23 g, 5.00 mmol) in THF (6 mL) was stirred 90 min at RT then methyl-magnesium bromide 3N in Et$_2$O (1.66 mmol, 5.00 mmol) was added at 0 C. The slurry was stirred at 0 C for another hour then treated with a solution of aldehyde from Step 1 (500 mg)

in THF (3 mL), and stirred 1 h at 0 C. The final mixture was poured in saturated NH4Cl, extracted with EtOAc, dried and concentrated. The residue was purified by flash-chromatography over silica gel (eluted with Hexanes/AcOEt 99:1 to AcOEt) to afford, in order of elution, 217 mg (42%) of isomer A followed by 140 mg (27%) of isomer B.

Step 3

The isomer A product from Step 2: (217 mg, 0.61 mmol) was subjected to conditions similar to the ones described in Step 3 of Example 16 to give 153 mg (51%) of an intermediate. This intermediate (153 mg, 0.31 mmol) was oxidized with MCPBA according to conditions similar to the ones described in Step 4 of Example 16 then hydrogenated with 20% Pd(OH)$_2$ over charcoal in AcOEt at 1 atm for 1 h to provide 116 mg of alcohol intermediate. This alcohol intermediate (116 mg, 0.27 mmol) was subjected to conditions similar to the ones described in Steps 6 and 7 of Example 16 to provide 64 mg of Example 24A: $^1$H-NMR (CDCl$_3$ 400 MHz) δ 7.64 (d, J=8.8 Hz, 2H), 7.50 (d, J=8.8 Hz, 2H), 7.08 (m, 1H), 6.45 (m, 1H), 5.17 (dd, 1H), 4.43 (d, 1H), 3.87 (m, 1H), 3.40 (m, 1H), 3.18 (t, 1H), 2.45-2.55 (m, 2H), 2.33 (m, 1H), 1.38 (d, J=6 Hz, 3H); LCMS (MH$^+$)=415.2; retention time=4.86 min.

The isomer B product from Step 2: (140 mg, 0.40 mmol) was subjected to conditions similar to the ones described above to afford 26.5 mg of Example 24B: $^1$H-NMR (CDCl$_3$ 400 MHz) δ 7.50 (d, J=8.7 Hz, 2H), 7.42 (d, J=8.7 Hz, 2H), 7.01 (m, 1H), 6.42 (m, 1H), 4.88 (dd, 1H), 4.36 (m, 1H), 4.12 (dd, 1H), 3.88 (m, 1H), 3.63 (m, 1H), 2.97 (m, 1H), 2.76 (m, 1H), 2.53 (m, 1H), 1.17 (d, J=6.8 Hz, 3H); LCMS (MH$^+$)= 415.2; retention time=4.73 min.

Following procedures similar to those described for the preparation of Examples 24A and 24B, the compound in Table 12 was prepared.

TABLE 12

| Ex. No. | STRUCTURE | Mass Spec (M$^+$ except otherwise noted); retention time (min) |
|---|---|---|
| 24-C | 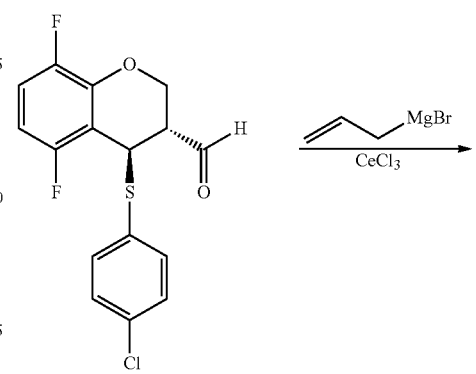 | 457.3; 5.62 |

Example 25

Example 25A and 25B

Trans-10a-(4-chloro-benzenesulfonyl)-1,4-difluoro-6a,7,8,9,10,10a-hexahydro-6H-benzo[c]chromen-trans-7-ol and trans-10a-(4-chloro-benzenesulfonyl)-1,4-difluoro-6a,7,8,9,10,10a-hexahydro-6H-benzo[c]chromen-cis-7-ol

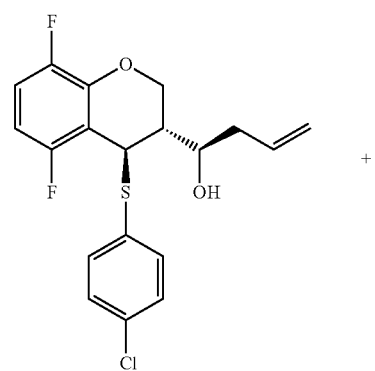

isomer A

+ isomer B

1) BnBr
2) BH$_3$ then H$_2$O$_2$
(separately on each isomer A or B)

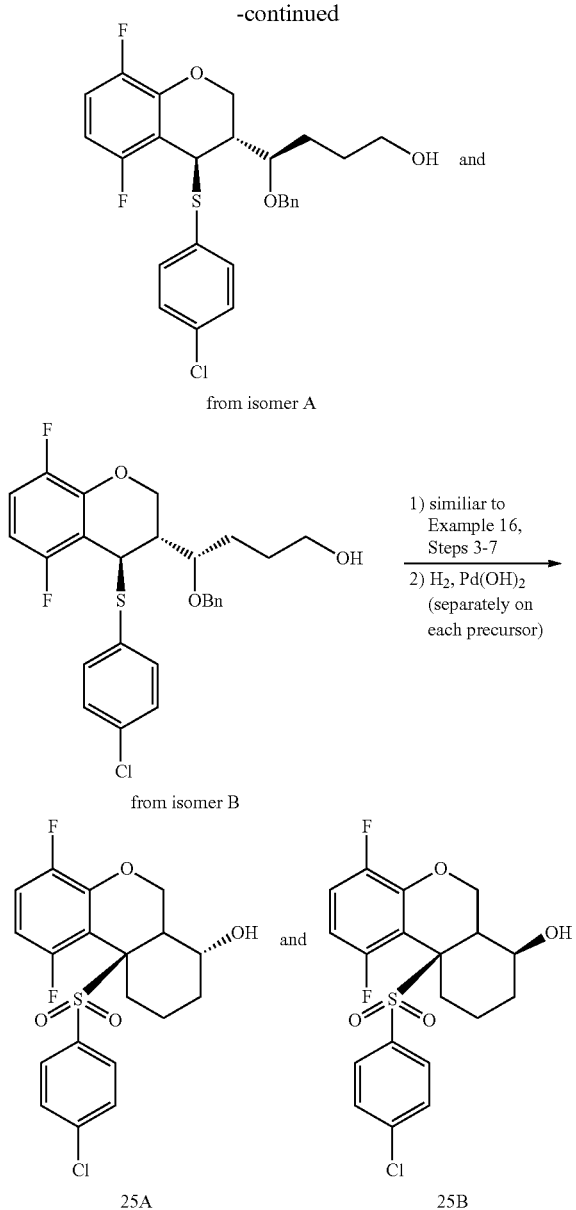

from isomer A from isomer B 25A            25B

Step 1

A solution of the product from Example 16 Step 2: (7.0, 20.0 mmol) was subjected to conditions similar to the ones describe in Steps 1 and 2 of Examples 24a and 24b, but using allylmagnesium bromide instead of methylmagnesium bromide to afford after similar flash-chromatography and in the same order of elution, 1.40 g (21%) of isomer A followed by 850 mg (11%) of isomer B.

Step 2

To a solution of isomer A product from Step 1 (1.62 g, 4.23 mmol) in THF (50 mL) was added NaH 60% (540 mg, 13.4 mmol) followed by benzylbromide (1.5 mL, 13.4 mmol) and the reaction was stirred at 55 C overnight. The cooled mixture was poured into water, extracted with EtOAc, dried over $Na_2SO_4$ and concentrated. The residue was purified by flash-chromatography over silica gel (eluted with Hexanes/AcOEt 99:1 to 50:50) to afford 1.07 g (53%) of allylbenzylether isomer A.

The isomer B product from Step 1 (950 mg, 2.48 mmol) was subjected to conditions similar to the one described above for the preparation of allylbenzylether isomer A to give 700 mg (59%) of allylbenzylether isomer B.

Step 3

To a solution of allylbenzylether isomer A product from Step 2: (900 mg, 1.90 mmol) in THF (2 mL) was added borane dimethylsulfide 2N in THF (4.7 mL, 9.4 mmol) and the reaction was stirred 90 min at RT and 30 min at 55 C. The reaction was then quenched with 3N NaOH (4 mL) followed by 30% $H_2O_2$ (4 mL) and stirred for 1 hr. The final mixture was diluted with water, extracted with EtOAc, dried over $Na_2SO_4$ and concentrated to provide 1.52 g of crude alcohol isomer A.

The allylbenzylether isomer B product from Step 2: (550 mg, 1.16 mmol) was subjected to conditions similar to the one described above for the preparation of alcohol isomer A to give 800 mg of crude alcohol isomer B.

Step 4

The crude alcohol isomer A product from Step 3 (1.52 g) was oxidized with MCPBA according to conditions similar to the ones described in Step 4 of Example 16 then the resulting intermediate was subjected to conditions similar to the ones described in Steps 6 and 7 of Example 16 to provide 320 mg of O-benzylated isomer A direct precursor of Example 25A: $^1$H-NMR (CDCl$_3$ 400 MHz) δ 7.40-7.60 (m, 4H), 7.15-7.30 (m, 3H), 7.03 (d, J=8.7 Hz, 2H), 6.95 (m, 1H), 6.24 (m, 1H), 5.18 (m, 1H), 4.39 (m, 2H), 4.27 (d, 1H), 3.94 (br s, 1H), 2.75 (m, 1H), 2.63 (m, 1H), 1.95-2.10 (m, 2H), 1.40-1.65 (m, 3H).

The crude alcohol isomer B product from Step 3 (800 mg) was oxidized with MCPBA according to conditions similar to the ones described in Step 4 of Example 16 then the resulting intermediate was subjected to conditions similar to the ones described in Steps 6 and 7 of Example 16 to provide 223 mg of O-benzylated isomer B direct precursor of Example 25B: $^1$H-NMR (CDCl$_3$ 400 MHz) δ 7.60 (d, J=8.8 Hz, 2H), 7.49 (d, J=8.8 Hz, 2H), 7.20-7.40 (m, 5H), 7.07 (m, 1H), 6.41 (m, 1H), 5.06 (m, 1H), 4.88 (d, 1H), 4.63 (d, 1H), 4.48 (d, 1H), 3.25 (m, 1H), 2.63 (br d, 1H), 2.55 (d, 1H), 2.16 (m, 1H), 1.70-1.95 (m, 2H), 1.00-1.45 (m, 2H); LCMS (MH$^+$)=505.3; retention time=5.31 min.

Step 5

The O-benzylated isomer A product from Step 4 (320 mg) in EtOAc was hydrogenated at 1 atm with over 20% Pd(OH)$_2$ over charcoal for 1 h then filtered over Celite and concentrated to provide 220 mg of Example 25A: $^1$H-NMR (CDCl$_3$ 400 MHz) δ 7.40-7.55 (m, 4H), 7.02 (m, 1H), 6.83 (m, 1H), 5.28 (dd, 1H), 4.49 (d, 1H), 4.27 (br s, 1H), 2.60-2.70 (m, 2H), 1.90-2.15 (m, 2H), 1.77 (m, 1H), 1.40-1.70 (m, 3H); LCMS (MH$^+$)=415.2; retention time=4.12 min.

The O-benzylated isomer A product from Step 4 (223 mg) in EtOAc (5 mL) was hydrogenated at 1 atm with over 20% Pd(OH)$_2$ over charcoal (30 mg) for 1 h then filtered over Celite and concentrated to provide 146 mg of Example 25B: $^1$H-NMR (CDCl$_3$ 400 MHz) δ 7.60 (d, J=8.8 Hz, 2H), 6.98 (d, J=8.8 Hz, 2H), 7.05 (m, 1H), 6.40 (m, 1H), 5.07 (m, 1H), 4.86 (d, 1H), 3.43 (m, 1H), 2.59 (br d, 1H), 2.40 (d, 1H), 2.28 (m,

Example 26

Trans-10a-(4-chloro-benzenesulfonyl)-1,4-difluoro-cis-7-methoxy-6a,7,8,9,10,10a-hexahydro-6H-benzo[c]chromene

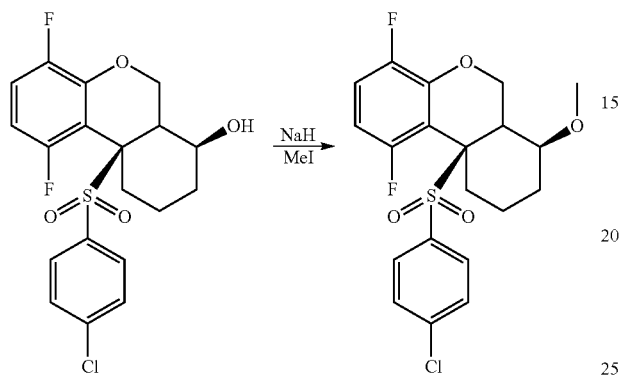

Example 26

Step 1

To a solution of Example 25A (15 mg, 0.036 mmol) in THF (1 mL) was added 60% NaH (3 mg, 0.072 mmol) followed by MeI (22 uL, 0.36 mmol) and the reaction was stirred at RT for 2 h then worked-up in water and EtOAc. The mixture was subjected to flash-chromatography over silica gel (eluted with Hexanes/EtOAc 99:1 to 50:50) to yield 13.5 mg of Example 26: $^1$H-NMR (CDCl$_3$ 400 MHz) δ 7.61 (d, J=8.8 Hz, 2H), 6.99 (d, J=8.8 Hz, 2H), 7.07 (m, 1H), 6.41 (m, 1H), 5.05 (m, 1H), 4.81 (d, 1H), 2.97 (m, 1H), 2.62 (br d, 1H), 2.45 (d, 1H), 2.16 (m, 1H), 1.89 (m, 1H), 1.78 (m, 1H), 1.25 (m, 1H), 1.06 (m, 1H); LCMS (MH$^+$)=429.2; retention time=5.15 min.

Example 27A and 27B

Trans-11a-(4-chloro-benzenesulfonyl-1,4-difluoro-6,6a,7,8,9,10,11,11a-octahydro-cyclohepta[c]chromen-cis-8-ol and trans-11a-(4-chloro-benzenesulfonyl)-1,4-difluoro-6,6a,7,8,9,10,11,11a-octahydro-cyclohepta[c]chromen-trans-8-ol

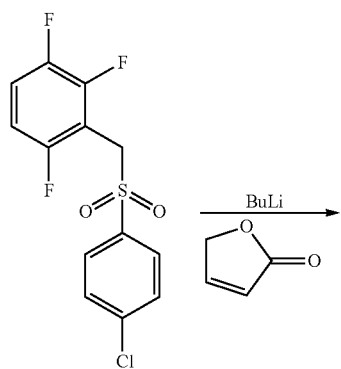

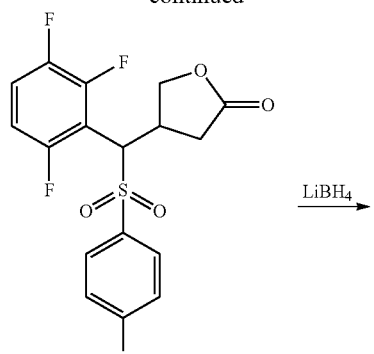

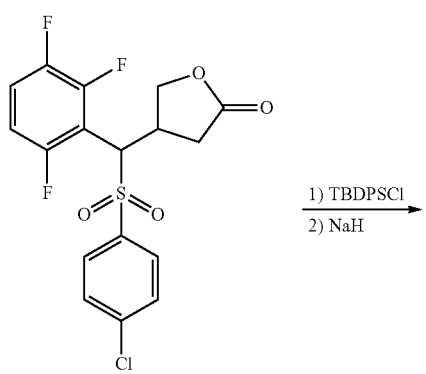

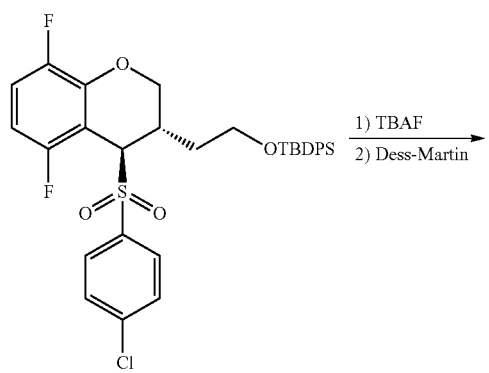

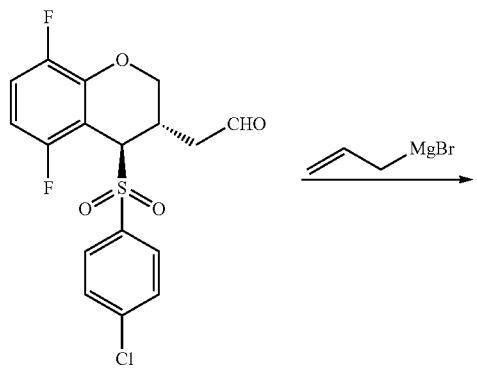

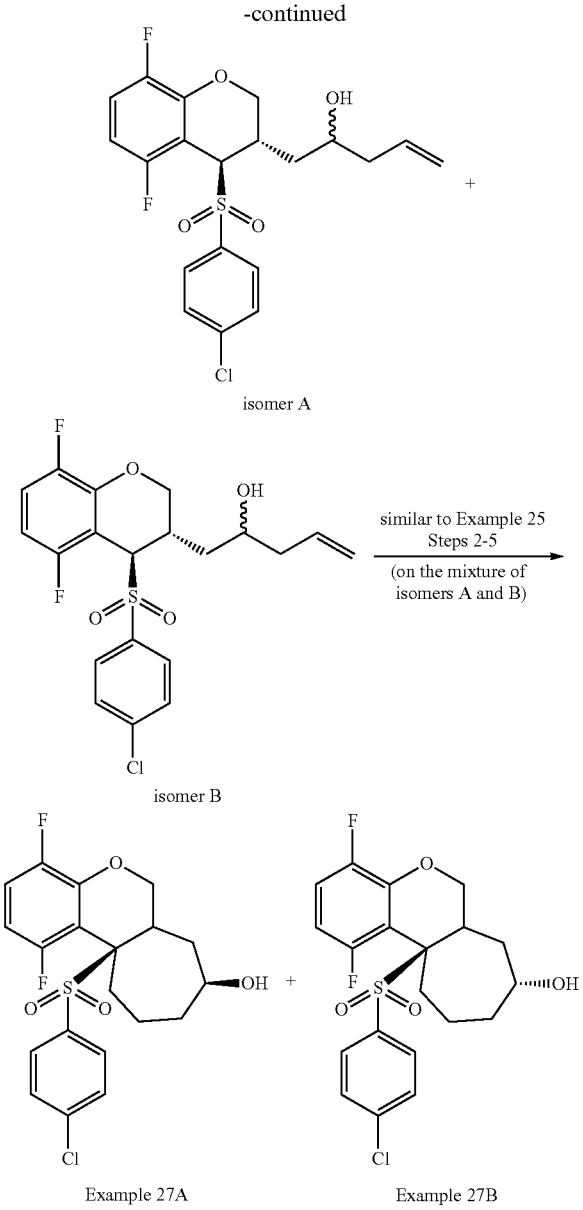

isomer A isomer B similar to Example 25
Steps 2-5
(on the mixture of isomers A and B)

Example 27A

Example 27B

Step 1

A solution of the product from Example 8 Step 2: (35.0 g, 109 mmol) in THF (500 mL) was cooled to −78 C and nBuLi 2.5N in hexanes (45.3 mL, 113.2 mmol) was added over 5 min. The reaction was stirred 10 min at −78 C and 2(5H) furanone (8.2 mL, 120 mmol) was added over 10 min. The mixture was slowly allowed to warm to −45 C over 2 h and kept at this temperature for another hour. The final mixture was quenched with saturated $NH_4Cl$, extracted with EtOAc and DCM, dried over $Na_2SO_4$ and concentrated. The residue was purified by flash-chromatography over silica gel (eluted with Hexanes/EtOAc 90:10 to EtOAc) to afford, in order of elution, 17.9 g of starting material and 10.4 g of lactone product.

Step 2

To a solution of lactone product from Step 1 (17.5 g, 43.2 mmol) in THF (500 mL) was added lithium borohydride (3.74 g, 172 mmol) and the reaction was stirred at RT overnight. The final mixture was slowly poured into 0.1 N HCl, extracted with EtOAc and DCM, dried over $Na_2SO_4$ and concentrated. The residue was purified by flash-chromatography over silica gel (eluted with DCM/EtOAc 99:1 to EtOAc) to provide 18.0 g (100%) of diol.

Step 3

A solution of diol product from Step 2: (18.0 g, 43.2 mmol) and imidazole (7.5 g, 110 mmol) in DMF (150 mL) was treated with TBDPSCl (11.4 mL, 44.0 mmol) and the reaction was heated overnight at 45 C. The mixture was diluted with water, extracted with $Et_2O$, dried over $Na_2SO4$ and concentrated. The residue was purified by flash-chromatography over silica gel (eluted with Hexanes/EtOAc 99:1 to 50:50) to provide 28.7 g (100%) of monoprotected diol, as a mixture of isomers.

Step 4

A solution of monoprotected diol product from Step 3 (5.5 g, 8.5 mmol) in THF (50 mL) was treated with NaH 60% in hexanes (375 mg, 9.4 mmol) and the reaction was heated at 60 C overnight. The final mixture was poured into 10% citric acid, extracted with DCM, dried over Na2SO4 and concentrated and the residue was purified by flash-chromatography over silica gel (eluted with Hexanes/EtOAc 99:1 to 50:50) to provide 4.8 g (90%) of O-protected chromene.

Step 5

A solution of O-protected chromene product from Step 4 (15.7 g, 25.0 mmol) in THF (100 mL) was treated with TBAF 1N in THF (30 mL, 30.0 mmol) and the reaction was stirred 3 h at 60 C. The final mixture was worked-up in water in EtOAc, dried over Na2SO4 and concentrated and the residue was purified by flash-chromatography over silica gel (eluted with Hexanes/EtOAc 99:1 to EtOAc) to provide 9.91 g (100%) of alcohol.

Step 6

To a solution of alcohol product from Step 5 (3.0 g, 7.7 mmol) in DCM (50 mL) was added Dess-Martin periodinane (6.5 g, 15.4 mmol) and the reaction was stirred 2 h at RT. The reaction was quenched with saturated sodium thiosulfate, diluted with saturated NaHCO3, extracted with EtOAc, dried over Na2SO4 and concentrated to yield 3.25 g (100%) of crude aldehyde.

Step 7

To a solution of crude aldehyde product from Step 6 (3.25 g, 8.4 mmol) in THF (60 mL) at −78 C was slowly added allylmagnesium bromide 1N in Et2O (12.6 mL, 12.6 mmol) and the reaction was stirred 2 h at −50 C then warmed to 0 C another 2 h. The final mixture was poured into saturated NH4Cl, extracted with EtOAc, dried over Na2SO4 and concentrated. The residue was purified by flash-chromatography over silica gel (eluted with Hexanes/EtOAc 99:1 to EtOAc) to provide 1.50 g (50%) of allylalcohol as a mixture of isomers A and B.

Step 8

The allylalcohol mixture of isomers product from Step 7 was subjected to conditions similar to the ones described in Steps 2 to 5 of Examples 25A and 25B to provide, after separation by flash-chromatography over silica gel (eluted with Hexanes/EtOAc 99:1 to EtOAc), Example 27A followed by Example 27B. Example 27A: ¹H-NMR (CDCl₃ 400 MHz) δ 7.66 (d, J=8.8 Hz, 2H), 7.49 (d, J=8.8 Hz, 2H), 7.03 (m, 1H), 6.91 (m, 1H), 5.18 (dd, 1H), 4.15-4.25 (m, 2H), 3.65 (br d, 1H), 2.96 (m, 1H), 2.15 (m, 1H), 1.98 (m, 1H), 1.70-1.90 (m, 3H), 1.35-1.65 (m, 3H); LCMS (MH⁺)=429.2; retention time=4.19 min. Example 27B: ¹H-NMR (CDCl₃ 400 MHz) δ 7.63 (d, J=8.7 Hz, 2H), 7.48 (d, J=8.7 Hz, 2H), 7.04 (m, 1H), 6.90 (m, 1H), 5.10 (dd, 1H), 4.26 (d, 1H), 3.94 (m, 1H), 2.99 (br d, 1H), 2.88 (m, 1H), 2.18 (m, 1H), 1.80-2.00 (m, 3H), 1.60-1.80 (m, 3H), 1.16 (m, 1H); LCMS (MH⁺)=429.2; retention time=4.03 min.

Example 28

Trans-11a-(4-chloro-benzenesulfonyl)-1,4-difluoro-6,6a,7,8,9,10,11,11a-octahydro-cyclohepta[c]chromen-cis-8-trifluoromethanesulfonamide

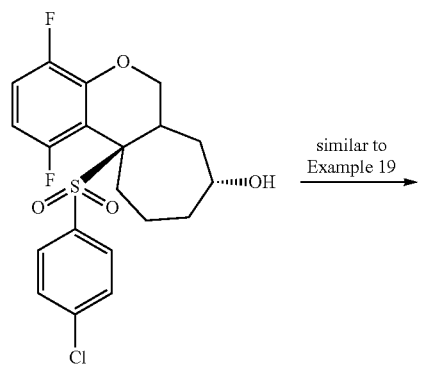

Example 27A

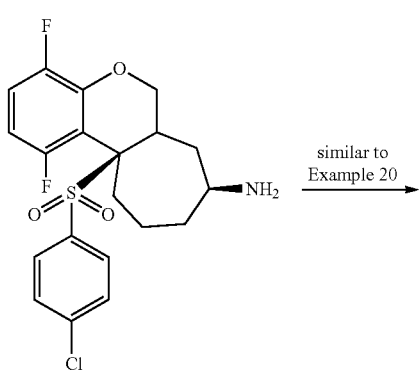

similar to Example 19 similar to Example 20

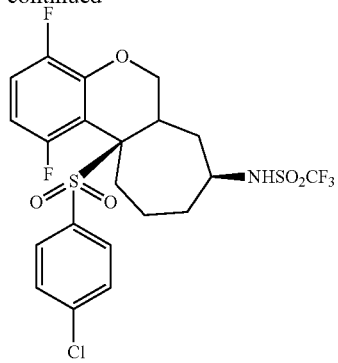

Example 28

Step 1

Example 27A was subjected to conditions similar to the ones described in Examples 19 and 20 SCH 1372731 to provide Example 28: ¹H-NMR (CDCl₃ 400 MHz) δ 7.61 (d, J=8.7 Hz, 2H), 7.48 (d, J=8.7 Hz, 2H), 7.05 (m, 1H), 6.92 (m, 1H), 5.64 (br s, 1H), 5.10 (dd, 1H), 4.19 (dd, 1H), 4.03 (br s, 1H), 3.49 (d, 1H), 3.27 (br d, 1H), 2.95 (m, 1H), 2.05-2.25 (m, 2H), 1.80-2.00 (m, 3H), 1.65-1.75 (m, 1H); LCMS (MH⁺)=560.3; retention time=4.78 min.

Example 29

4a-(4-Chloro-benzenesulfonyl-5,8-difluoro-4,4-a,10,10a-tetrahydro-1H,3H-9-oxa-2-thia-phenanthrene

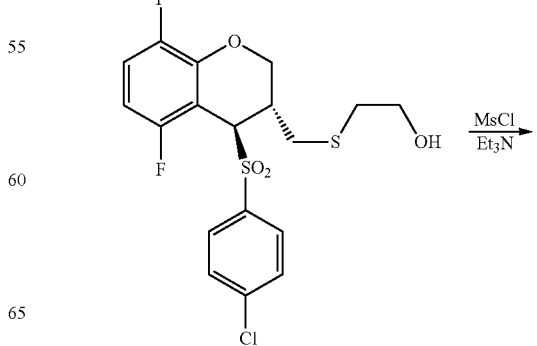

-continued

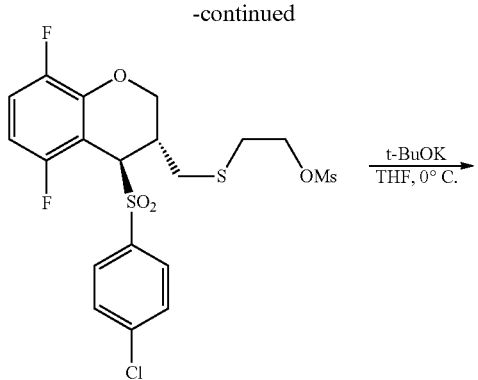

Step 1

2-[4-(4-Chloro-benzenesulfonyl)-5,8-difluoro-chroman-3-ylmethylsulfanyl]-ethanol

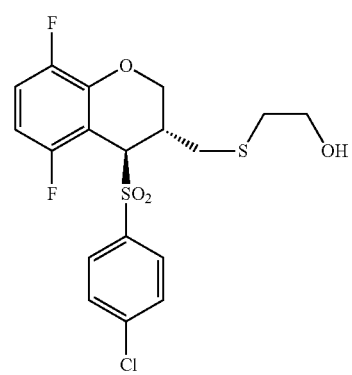 [SMILES: O=S(=O)(c1ccc(Cl)cc1)[C@H]1c2c(F)ccc(F)c2OC[C@@H]1CSCCO]

Methanesulfonic acid 4-(4-chloro-benzenesulfonyl)-5,8-difluoro-chroman-3-ylmethyl ester described in Example 10, Step 6 (230 mg, 0.51 mmol) was dissolved in 7.0 mL of methanol and treated with 992 mg (12.7 mmol) of 2-mercaptoethanol and 2.0 mL of 1 M aqueous NaOH. The mixture was heated with a reflux condenser at 77° C. overnight. The mixture was cooled and partitioned between water and DCM. Aqueous phase was extracted with DCM. Combined organic phase was dried over MgSO$_4$ and concentrated. The product was purified by column chromatography using 20% of EtOAc in hexanes as the eluent (140 mg, 63%)

Step 2

Methanesulfonic acid 2-[(4-(4-chloro-benzenesulfonyl)-5,8-difluoro-chroman-3-ylmethylsulfanyl]-ethyl ester

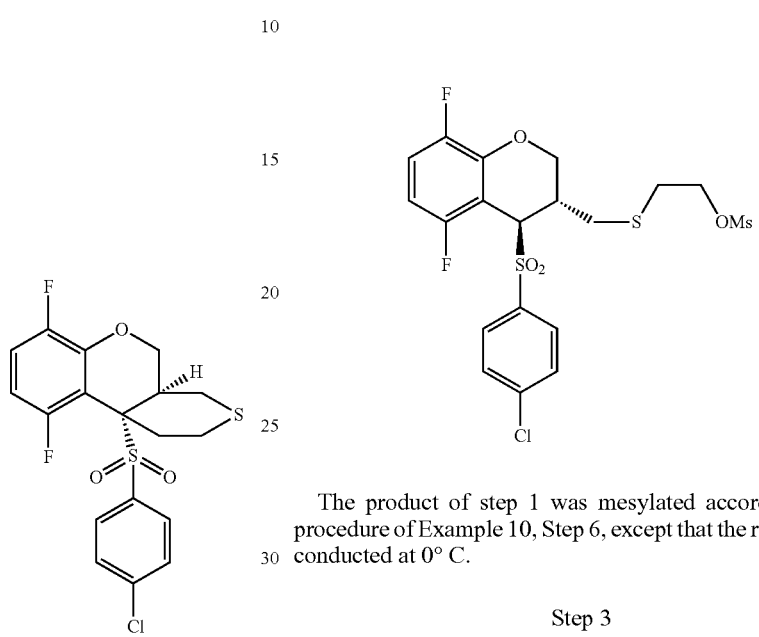

The product of step 1 was mesylated according to the procedure of Example 10, Step 6, except that the reaction was conducted at 0° C.

Step 3

(4aS)-10bS-[(4-Chlorophenyl)sulfonyl]-7,10-difluoro-1,4a,5,10b-tetrahydro-2H,4H-thiopyrano[3,4-c][1]benzopyran (racemic)

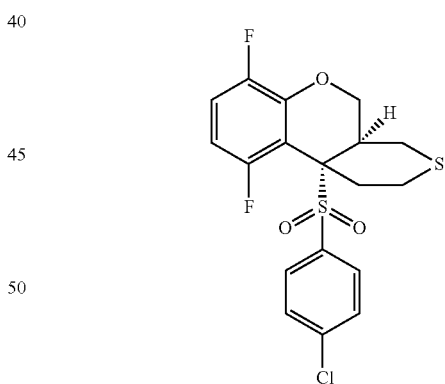

The product of Step 2: (140 mg, 0.273 mmol) was dissolved in 2.7 mL of THF, cooled to 0° C., and treated with 0.273 mL (0.273 mmol) of 1 M solution of potassium tert-butoxide in THF. The mixture was stirred at 0° C. for 10 min, quenched with water, extracted with DCM. Organic phase was dried over MgSO$_4$ and concentrated. The product was purified by column chromatography using 10% of EtOAc in hexanes as the eluent (50 mg, 44%). $^1$H NMR (CDCl$_3$ 400 MHz) δ 7.59 (d, J=8.5 Hz, 2H), 7.50 (d, J=8.5 Hz, 2H), 7.11 (m, 1H), 6.46 (m, 1H), 5.32 (dd, J=2.8 and 11.7 Hz, 1H), 4.21 (d, J=11.7 Hz, 1H), 2.94-2.86 (m, 2H), 2/7 (2, J=12.0 Hz, 1H), 2.6-2.28 (ser. m., 4H).

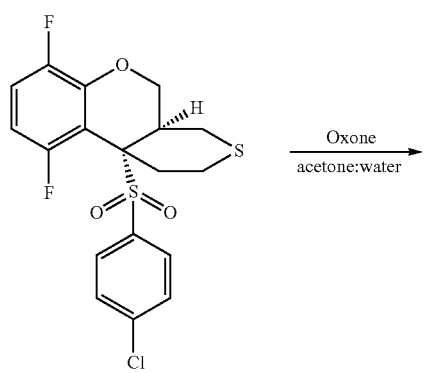

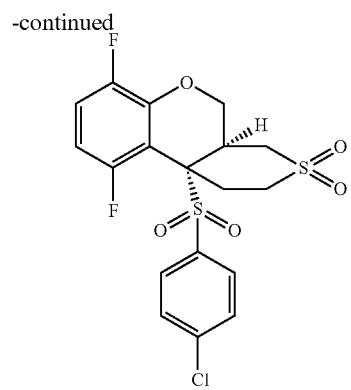

Example 32

Examples 30-31

A solution 30 mg (0.072 mmol) of Example 29 in 0.38 mL of acetone was treated with 0.095 mL of water and 48.7 mg (0.079 mmol) of Oxone™. After 4 hrs of stirring, the mixture was partitioned between water and DCM. Organic phase was dried over $MgSO_4$ and concentrated. The following three products were separated by prep. TLC using 30% of EtOAc in hexanes as the eluent.

Example 30

(4aS)-10bS-[(4-Chlorophenyl)sulfonyl]-7,10-difluoro-1,4-a,5,10b-tetrahydro-2H,4H-thiopyrano[3,4-c][1]benzopyran, 3-oxide (racemic) (sulfoxide diastereomer A)

LCMS m/z=433.2 (M+H)+, ret. time 3.65 min, $^1$H NMR (CDCl$_3$ 400 MHz) δ 7.68 (d, J=8.5 Hz, 2H), 7.54 (d, J=8.5 Hz, 2H), 7.14 (m, 1H), 6.53 (m, 1H), 5.44 (dd, J=2.7 and 12.0 Hz, 1H), 4.14 (d, J=12.0 Hz, 1H), 3.57 (d, J=12.2 Hz, 1H), 3.17 (tt, J=14.8 and 3.2 Hz, 1H), 3.02 (dt, J=14.0 and 2.9 Hz, 1H), 2.91 (dm, J=14.5 Hz, 1H), 2.60 (dm, J=14.3 Hz, 1H), 2.45 (dd, J=12.0 and 14.0 Hz, 1H), 2.24 (td, J=14.0 and 2.0 Hz, 1H).

Example 31

(4aS)-10bS-[(4-Chlorophenyl)sulfonyl]-7,10-difluoro-1,4-a,5,10b-tetrahydro-2H,4H-thiopyrano[3,4-c][1]benzopyran, 3-oxide (racemic) (sulfoxide diastereomer B)

LCMS m/z=433.2 (M+H)+, ret. time 3.57 min, $^1$H NMR (CDCl$_3$ 400 MHz) δ 7.58 (d, J=8.8 Hz, 2H), 7.52 (d, J=8.8 Hz, 2H), 7.17 (m, 1H), 6.52 (m, 1H), 5.31 (dd, J=3.1 and 9.0 Hz, 1H), 4.22 (dd, J=11.9 and 1.5 Hz, 1H), 3.49 (s, 1H), 3.39 (tt, J=13.0 and 3.0 Hz, 1H), 3.34-3.28 (ser. m, 1H), 3.13 (dm, J=12.2 Hz, 1H), 2.84 (dd, J=13.5 and 6.9 Hz, 1H), 2.69 (t, J=13.0 Hz, 1H), 2.37 (t, J=12.0 Hz, 1H).

Example 32

(4aS)-10bS-[(4-Chlorophenyl)sulfonyl]-7,10-difluoro-1,4-a,5,10b-tetrahydro-2H,4H-thiopyrano[3,4-c][1]benzopyran, 3,3-dioxide (racemic)

LCMS m/z=449.1 (M+H)+, ret. time 4.10 min, $^1$H NMR (CDCl$_3$ 400 MHz) δ 7.62 (d, J=8.8 Hz, 2H), 7.54 (d, J=8.8 Hz, 2H), 7.20 (m, 1H), 6.56 (m, 1H), 5.38 (dd, J=2.7 and 12.2 Hz, 1H), 4.18 (d, J=12.2 Hz, 1H), 3.46 (dm, J=12.6 Hz, 1H), 3.13-2.69 (ser. m., 6H).

Example 33

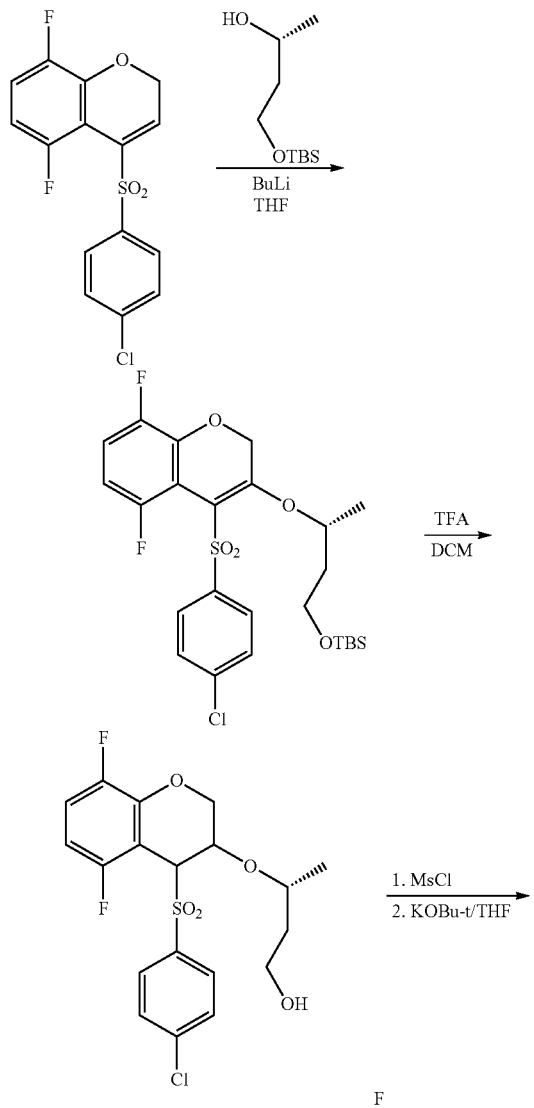

Example 33

Step 1

Tert-Butyl-{(R)-3-[4-(4-chloro-benzenesulfonyl)-5,8-difluoro-chroman-3-yloxy]butoxy}-dimethylsilane

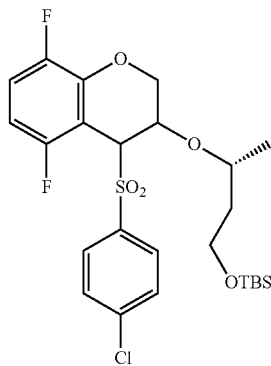 [SMILES: C[C@H](CCO[Si](C)(C)C(C)(C)C)OC1COc2c(F)ccc(F)c2C1S(=O)(=O)c1ccc(Cl)cc1]

To a solution of 1.80 g (8.77 mmol) of (R)-4-(tert-butyl-dimethyl-silanyloxy)-butan-2-ol in THF (10 mL) at 0° C. was added dropwise 0.28 mL (0.96 mmol) of 2.5 M n-BuLi in hexanes. The mixture was stirred for a few minutes and 300 mg of the product of Example 17, step 3 was added. Continued stirring at 0° C. for 30 minutes. The reaction was quenched with water, extracted with EtOAc, washed with water and brine, dried over MgSO₄ and concentrated. The product (550 mg) was isolated by flash chromatography using gradient from 0% to 40% of EtOAc in hexanes as the eluent.

Step 2

(R)-3-[4-(4-Chloro-benzenesulfonyl)-5,8-difluoro-chroman-3-yloxy]-butan-1-ol

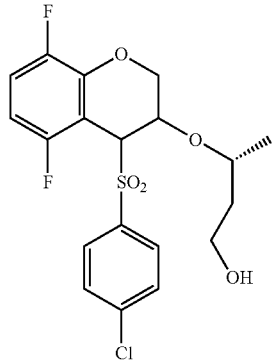 [SMILES: C[C@H](CCO)OC1COc2c(F)ccc(F)c2C1S(=O)(=O)c1ccc(Cl)cc1]

To the product of Step 1 (95 mg, 0.174 mmol) was dissolved in 2.0 mL of 3% TFA solution of DCM. The mixture was stirred for 40 minutes. The reaction was washed with water and brine, dried over MgSO₄ and concentrated. The product (60 mg) was isolated by prep. TLC using 40% EtOAc in hexanes as the eluent.

Step 3

(4aR)-10bR-[(4-Chlorophenyl)sulfonyl]-7,10-difluoro-1,2,3,4a,5,10b-hexahydro-3(R)-methylpyrano[2,3-c][1]benzopyran

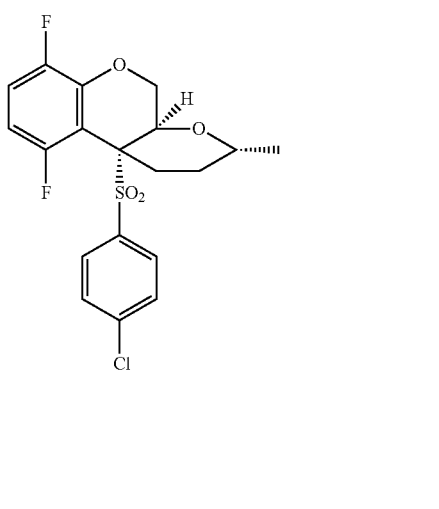 [SMILES: C[C@@H]1CC[C@@]2(S(=O)(=O)c3ccc(Cl)cc3)c3c(F)ccc(F)c3OC[C@H]2O1]

The product of Step 2 was mesylated according to the procedure of Example 10, Step 6 followed by cyclization according Example 29, Step 3. The desired compound was isolated from diastereomeric mixture by prep. TLC using 15% EtOAc in hexanes as the eluent.

¹H NMR (CDCl₃ 400 MHz) δ 7.60 (d, J=8.8 Hz, 2H), 7.49 (d, J=8.8 Hz, 2H), 7.05 (m, 1H), 6.38 (m, 1H), 5.05 (dd, J=12.2 and 2.0 Hz, 1H), 4.58 (m, 1H), 4.40 (dd, J=12.2 and 1.6 Hz, 1H), 4.12 (m, 1H), 2.58 (tt, J=13.0 and 3.1 Hz, 1H), 2.44 (tt, J=13.7 and 4.0 Hz, 1H), 1.71-1.62 (ser. m., 1H), 4.53-1.46 (ser. m., 1H), 1.37 (d, J=6.7 Hz, 3H).

Example 34

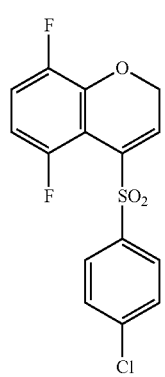 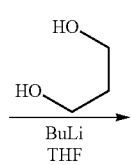

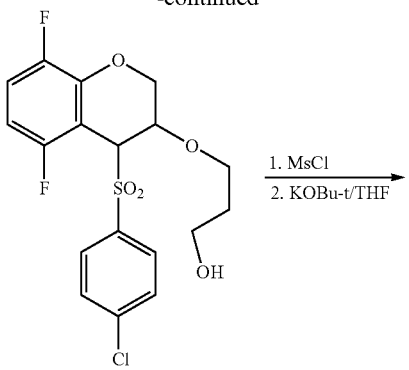

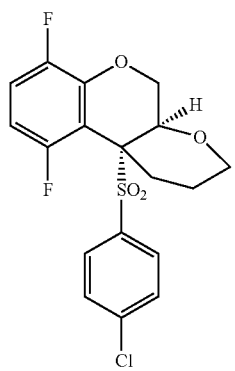

Example 34

Step 1

3-[4-(4-Chloro-benzenesulfonyl)-5,8-difluoro-chroman-3-yloxy]-propan-1-ol

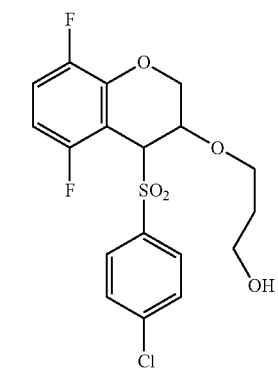 [SMILES: O=S(=O)(c1ccc(Cl)cc1)C1c2c(F)ccc(F)c2OCC1OCCCO]

This compound was prepared similarly to the procedure of Example 33 using 1,3-propanediol as the starting material.

Step 2

(4a S)-10bS-[(4-Chlorophenyl)sulfonyl]-7,10-difluoro-1,2,3,4a,5,10b-hexahydropyrano[2,3-c][1]benzopyran (racemic)

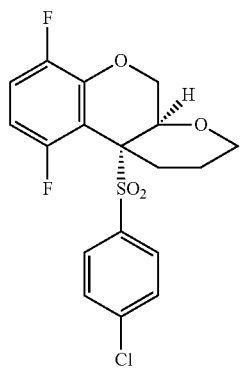 [SMILES: O=S(=O)(c1ccc(Cl)cc1)[C@@]12CCCO[C@@H]1COc1c(F)ccc(F)c12]

The product of Step 1, was mesylated according to Example 10, Step 6 and cyclized according to Example 29, Step 3. $^1$H NMR (CDCl$_3$ 400 MHz) δ 7.59 (d, J=8.7 Hz, 2H), 7.49 (d, J=8.7 Hz, 2H), 7.07 (m, 1H), 6.39 (m, 1H), 5.07 (dd, J=12.2 and 1.8 Hz, 1H), 4.48 (d, J=13.9 Hz, 1H), 4.30 (s, 1H), 3.94 (dd, J=11.2 and 4.7 Hz, 1H), 3.59 (td, J=11.9 and 2.5 Hz, 1H), 3.49 (d, J=5.5 Hz, 1H), 2.72 (dm, J=13.0 Hz, 1H), 2.30 (tt, J=13.0 and 3.3 Hz, 1H), 1.53-1.40 (ser. m., 1H).

Example 35

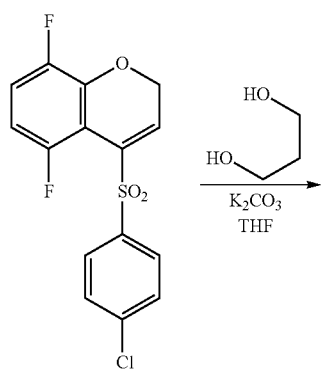

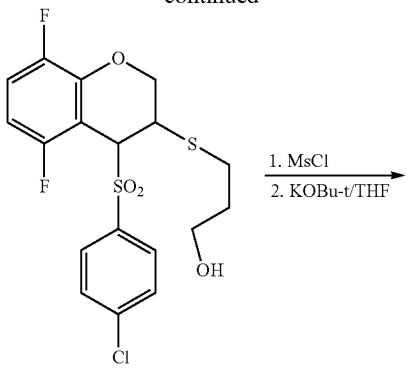

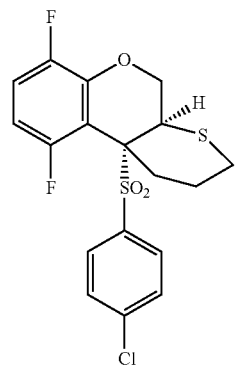

Example 35

Step 1

3-[4-(4-Chloro-benzenesulfonyl-5,8-difluoro-chroman-3-ylsulfanyl]-propan-1-ol

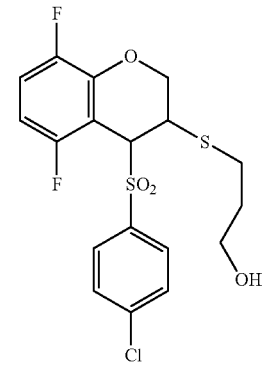 [SMILES: O=S(=O)(c1ccc(Cl)cc1)C1c2c(F)ccc(F)c2OCC1SCCCO]

149

This compound was prepared similarly to Example 33, Step 1, except that 3-mercapto-propan-1-ol was used as the reagent and potassium carbonate as the base.

Step 2

(4aS)-10bS-[(4-chlorophenyl)sulfonyl]-7,10-difluoro-1,2,3,4a,5,10b-hexahydrothiopyrano[2,3-c][1]benzopyran (racemic)

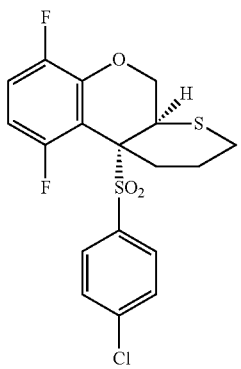 [SMILES: O=S(=O)(c1ccc(Cl)cc1)[C@@]12CCCS[C@@H]1COc1c(F)ccc(F)c12]

The product of Step 1, was mesylated according to Example 10, Step 6 and cyclized according to Example 29, Step 3. ¹H NMR (CDCl₃ 400 MHz) δ 7.57 (d, J=8.7 Hz, 2H), 7.49 (d, J=8.7 Hz, 2H), 7.10 (m, 1H), 6.44 (m, 1H), 5.44 (dd, J=12.2 and 1.8 Hz, 1H), 4.25 (d, J=12.5 Hz, 1H), 4.01 (s, 1H), 2.86 (td, J=12.5 and 2.7 Hz, 1H), 2.67 (d, J=11.2 Hz, 1H), 2.46 (d, J=13.5 Hz, 1H), 2.04-1.90 (ser. m., 2H), 1.53-1.40 (ser. m., 1H).

Examples 36 and 37

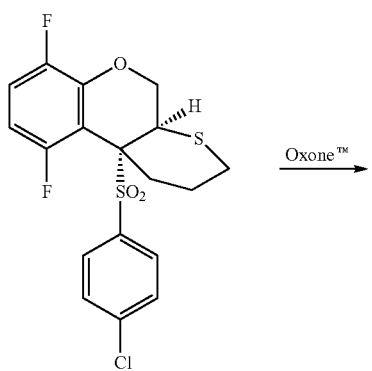

150

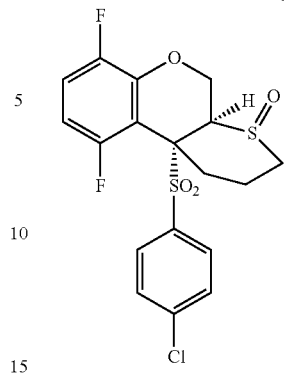 + 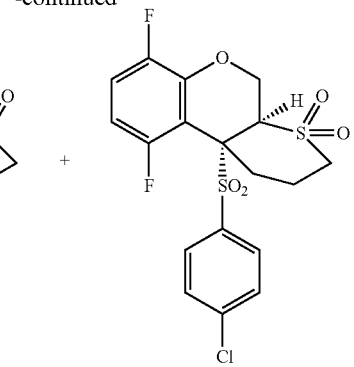

Example 36               Example 37

The product obtained in Example 35 was treated with oxone according to the procedure described in Examples 30-32. The two products, sulfoxide (Example 36) and sulfone (Example 37), were separated by prep. TLC using 30% EtOAc in hexanes as the eluent.

Example 36

(4aR)-10bR-[(4-chlorophenyl)sulfonyl]-7,10-difluoro-1,2,3,4a,5,10b-hexahydrothiopyrano[2,3-c][1]benzopyran, 4-oxide (racemic)

LCMS m/z=433.2 (M+H)⁺, ret. time 3.65 min. ¹H NMR (CDCl₃ 400 MHz) δ 7.59 (d, J=8.7 Hz, 2H), 7.52 (d, J=8.7 Hz, 2H), 7.13 (m, 1H), 6.46 (m, 1H), 5.43 (d, J=13.0 Hz, 1H), 5.16 (d, J=13.1 Hz, 1H), 3.51 (s, 1H), 3.45 (d, J=13.1 Hz, 1H), 2.83 (td, J=13.0 and 3.3 Hz, 1H), 2.70 (d, J=11.0 Hz, 1H), 2.23-2.08 (ser. m., 2H), 1.5-1.43 (ser. m., 1H).

Example 37

(4aR)-10R-[(4-chlorophenyl)sulfonyl]-7,10-difluoro-1,2,3,4a,5,10b-hexahydrothiopyrano[2,3-c][1]benzopyran, 4,4-dioxide (racemic)

LCMS m/z=449.2 (M+H)⁺, ret. time 4.19 min. ¹H NMR (CDCl₃ 400 MHz) 7.53-7.49 (m, 4H), 7.12 (m, 1H), 6.42 (m, 1H), 5.27 (s, 2H), 3.99 (t, J=2.9 Hz, 1H), 3.19-3.05 (ser. m., 2H), 2.85 (d, J=13.4 Hz, 1H), 2.32-2.16 (ser. m., 2H), 1.96 (m, 1H).

Example 38

1,4-Difluoro-10a-(4-trifluoromethyl-benzenesulfonyl)-6a,9,10,10a-tetrahydro-6H,7H-benzo[c]chromen-8-one O-methyl-oxime

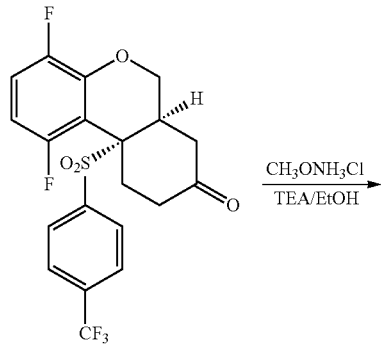

To a solution of trans-10a-(4-trifluoromethyl-benzenesulfonyl)-1,4-difluoro-6a,9,10,10a-tetrahydro-6H,7H-benzo[c]chromen-8-one (40 mg, 0.10 mmol) in EtOH (2 mL) was added O-methyl hydroxylamine hydrochloride (20 mg, 0.23 mmol), and NEt₃ (20 uL, 0.14 mmol). The reaction mixture was stirred overnight and then PS-dimethylaminoethyl resin was added, the stirring was continued for 2 h and then the resin removed by filtration. The solvent was removed under a stream of $N_2$ and the residue purified by preparative TLC eluting with 25% ethyl acetate in hexanes (22 mg, 47%).

TABLE 14

| Ex. No. | Structure | LCMS (M + 1, retention time) |
|---|---|---|
| 38 | 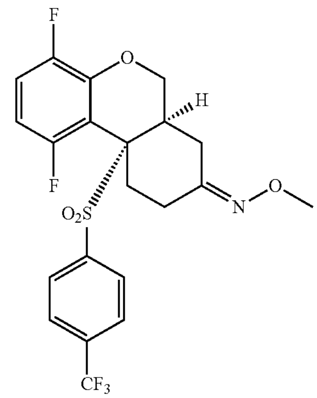 [SMILES: CO/N=C1/CC[C@@]2(S(=O)(=O)c3ccc(C(F)(F)F)cc3)c3c(F)ccc(F)c3OC[C@H]2C1] | 476, 4.66 Min. |

The compounds in the examples in Table 15 were prepared by a similar procedure as for Example 38.

TABLE 15

| Ex. No. | Structure | LCMS (M + 1, retention time) |
|---|---|---|
| 38B | 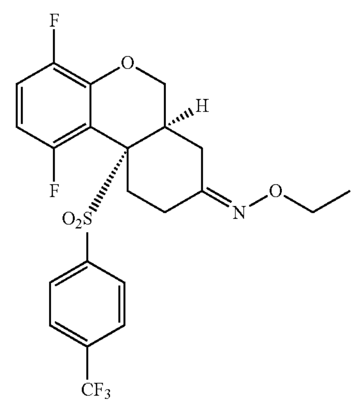 [SMILES: CCO/N=C1/CC[C@@]2(S(=O)(=O)c3ccc(C(F)(F)F)cc3)c3c(F)ccc(F)c3OC[C@H]2C1] | 490, 4.9 Min. |
| 38C | 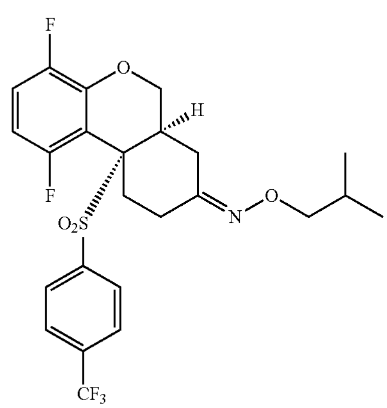 [SMILES: CC(C)CO/N=C1/CC[C@@]2(S(=O)(=O)c3ccc(C(F)(F)F)cc3)c3c(F)ccc(F)c3OC[C@H]2C1] | 518, 5.36 Min. |

TABLE 15-continued

| Ex. No. | Structure | LCMS (M + 1, retention time) |
|---|---|---|
| 38D | 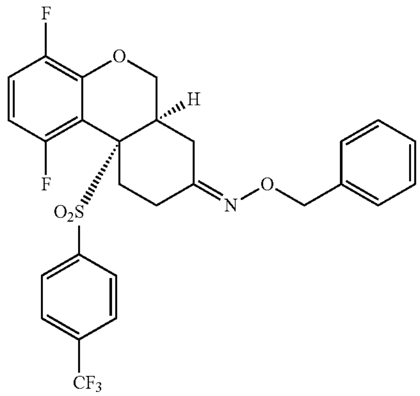 [SMILES: O=S(=O)(c1ccc(C(F)(F)F)cc1)[C@@]12CC/C(=N/OCc3ccccc3)C[C@@H]1COc1c(F)ccc(F)c12] | 552, 5.12 Min. |
| 38E | 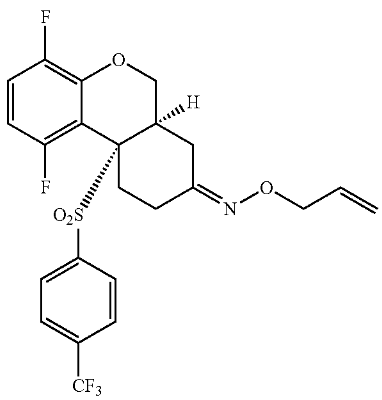 [SMILES: C=CCO/N=C1/CC[C@@]2(S(=O)(=O)c3ccc(C(F)(F)F)cc3)c3c(F)ccc(F)c3OC[C@H]2C1] | 502, 5.07 Min. |
| 38F | 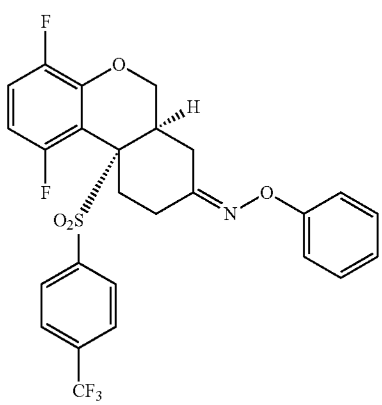 [SMILES: O=S(=O)(c1ccc(C(F)(F)F)cc1)[C@@]12CC/C(=N/Oc3ccccc3)C[C@@H]1COc1c(F)ccc(F)c12] | 538, 5.39 Min. |

Example 39

4-Methylbenzenesulfonic acid, [(E)(6aR)-10aS-[(4-chlorophenyl)sulfonyl]-1,4-difluoro-6a,9,10,10a-tetrahydro-6H-dibenzo[b,d]pyran-8(7H)-ylidine] hydrazide

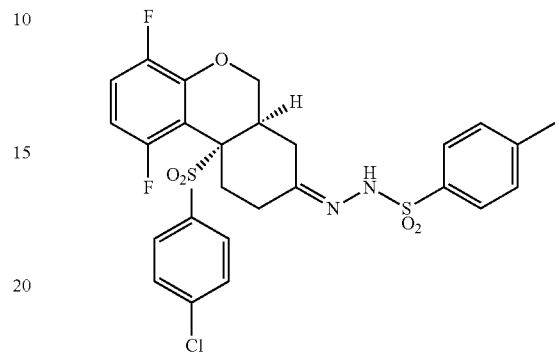

To a solution of trans-10a-(4-trifluoromethyl-benzene-sulfonyl)-1,4-difluoro-6a,9,10,10a-tetrahydro-6H,7H-benzo[c]chromen-8-one in (160 mg, 0.38 mmol) in THF (1.5 mL) was added pTolylsulfonyl hydrazine (80 mg, 0.43 mmol). The reaction mixture was stirred at rt for 2 h and then concentrated. The residue was purified on silica gel to give a white solid ~1:1 mixture of isomers (205 mg, 96%). $^1$H NMR (CDCl$_3$ 400 MHz) δ 7.77 (dd, 2H), 7.57 (d, 2H), 7.49 (d, 1H), 7.38 (s, 1H, isomer B) 7.34 (s, 1H, isomer A), 7.30 (dd, 2H), 7.10-7.04 (m, 1H), 6.46-6.4 (m, 2H), 5.23 (dd, 3H, isomer B), 5.15 (s, 3H, isomer A), 4.10 (dd, 1H), 2.91-2.77 (m, 1H), 2.71-2.44 (m, 2H), 2.28-2.16 (m, 5H); LCMS (MH$^+$) 581 au.

Example 40

10a-(4-Chloro-benzenesulfonyl)-1,4,7-trifluoro-6a,9,10,10a-tetrahydro-6H,7H-benzo[c]chromen-8-one

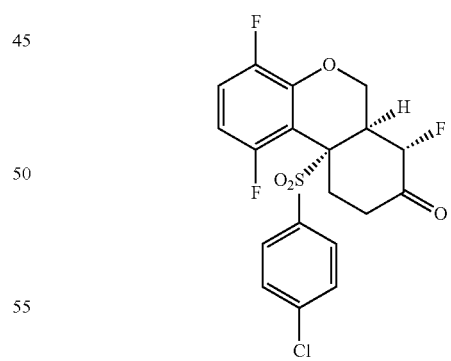

To a solution of trans-10a-(4-chloro-benzenesulfonyl)-1,4-difluoro-6a,9,10,10a-tetrahydro-6H,7H-benzo[c]chromen-8-one in DMF (4 mL) was added Selectfluor®. The reaction mixture was heated at 50° C. overnight, cooled to rt and water was added to precipitate the desired product. The product was isolated by filtration washing with water then dried under vacuum to provide a colorless solid. $^1$H NMR CDCl$_3$ 400 MHz) δ 7.61 (d, 2H), 7.53 (d, 2H), 7.19-7.14 (m, 1H), 6.55-6.49 (m, 1H), 5.20 (d, 1H), 4.74 (dd, $^2$J$_{H\text{-}F}$=46.7

Hz, $^3J_{H-F}$=11.8 Hz, 1H) 4.66 (d, 1H), 3.18 (t, 1H), 2.9 (m, 1H), 2.53 (m, 1H), 2.41 (m, 1H), 2.18 (m, 1H); LCMS (MH$^+$) 431.

Using a similar procedure, the compound of Example 40B was prepared:

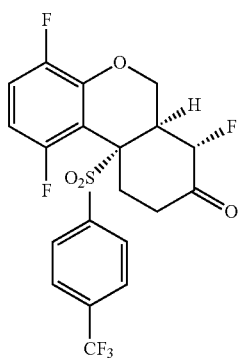 [SMILES: O=C1CC[C@@]2(S(=O)(=O)c3ccc(Cl)cc3)c3c(F)ccc(F)c3OC[C@H]2[C@@H]1F]

40B $^1$H NMR CDCl$_3$ 400 MHz) δ: 7.84 (s, 4H), 7.22-7.16 (m, 1H), 6.56-6.50 (dt 1H), 4.75 (dd, $^2J_{H-F}$=45.7 Hz, $^3J_{H-F}$=10.8 Hz, 1H), 4.67 (d, 1H), 3.23 (t, 1H), 2.88 (dt, 1H), 2.60-2.53 (m, 1H), 2.45 (tt, 1H), 2.18 (td, 1H).

Examples 41A and 41B

The compounds of Examples 41A and 41B (Table 16) were prepared according to the protocol described for the preparation of Example 18.

TABLE 16

| Ex. No. | Structure | LCMS (M + 1, retention time) |
|---|---|---|
| 41A | (structure) | 450 (M + H$_2$O), 4.08 Min. |

TABLE 16-continued

| Ex. No. | Structure | LCMS (M + 1, retention time) |
|---|---|---|
| 41B | (structure) | 450 (M + H$_2$O), 3.92 Min. |

Examples 42A, 42B and 42C

The compounds of Examples 42A, 42B and 42C were prepared according to the procedure of Example 20.

TABLE 17

| Ex. No. | Structure | LCMS (M + 1, retention time) |
|---|---|---|
| 42A | (structure) | 504, 3.98 Min. |
| 42B | (structure) | 505, 4.05 Min. |

TABLE 17-continued

| Ex. No. | Structure | LCMS (M + 1, retention time) |
|---|---|---|
| 42C | (structure: difluoro-chromene with 4-chloro-benzenesulfonyl, cyclohexyl with NHC(O)NHEt and 4-CF3-phenyl) | 533, 4.38 Min. |

Examples 43A, 43B, 43C and 43D

Examples 43A and 43B

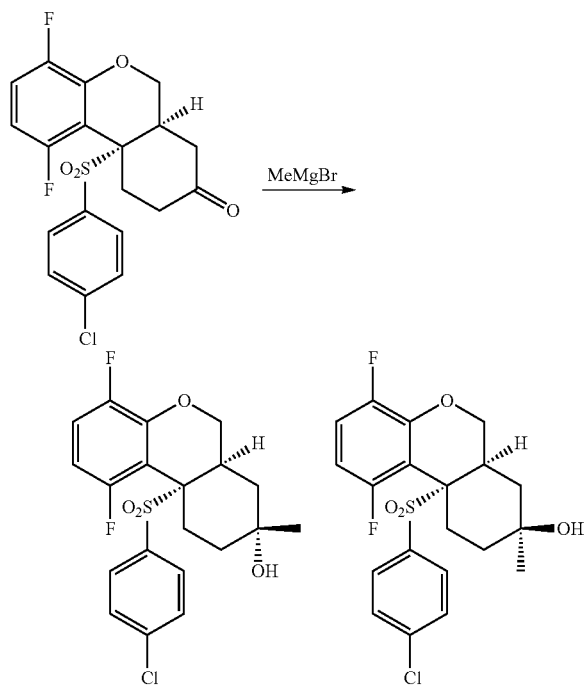

To a solution of the trans-10a-(4-chloro-benzenesulfonyl)-1,4-difluoro-6a,9,10,10a-tetrahydro-6H,7H-benzo[c]chromen-8-one (100 mg, 0.24 mmol) at 0° C. was added MeMgBr (500 µL, 1 M in THF), the bath was allowed to expire and reaction mixture was stirred overnight. The reaction mixture was diluted with ethyl acetate and treated with 1N HCl followed by NH₄Cl (sat. aq.). The aqueous was extracted with 2 additional portions of ethyl acetate. The dried organics were combined, dried over MgSO4 and concentrated. The products were purified and separated by chromatography on silica gel eluting with dichloromethane /methanol mixtures.

TABLE 18

| Ex. No. | Structure | NMR |
|---|---|---|
| 43A | (structure) | ¹H NMR (CDCl₃ 400 MHz) δ 7.62 (d, 2H), 7.49 (d, 2H), 7.10-7.04 (m, 1H), 6.45-6.39 (m, 1H), 5.24, (dd, 1H), 4.10 (d, 1H), 3.05 (dt, 1H), 2.50 (tt, 1H), 2.38 (br. dt, 1H), 1.6-1.56 (m, 1H), 1.4 (s, 3H), 0.9-0.82 (m, 1H). |
| 43B | (structure) | ¹H NMR (CDCl₃ 400 MHz) δ 7.58 (d, 2H), 7.48 (d, 2H), 7.09-7.00 (m, 1H), 6.43-6.37 (m, 1H), 5.20, (dd, 1H), 4.12 (d, 1H), 2.77 (br. d, 1H), 2.54 (br. dt, 1H), 2.09 (br. tt, 1H), 1.76-1.56 (m, 2H) 1.39 (s, 3H), 0.9-0.82 (m, 1H). |

Using a similar procedure to that for Examples 43A and 43B, the compounds of Examples 43C and 43D (Table 19) were prepared.

TABLE 19

| Ex. No. | Structure | LCMS (M + 1, retention time) |
|---|---|---|
| 43C | (structure with cyclopropyl and OH) | 472.3 (M + H2O): 4.67 |

TABLE 19-continued

| Ex. No. | Structure | LCMS (M + 1, retention time) |
|---|---|---|
| 43D | 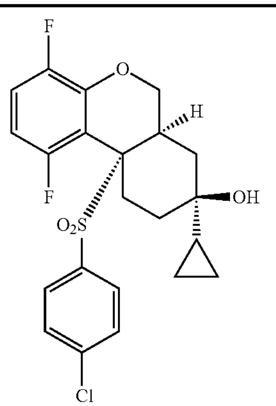 | 472.3 (M + H2O): 4.57 |

Example 44

10b-(4-Chloro-benzenesulfonyl-7,10-difluoro-1,4a,5,10b-tetrahydro-2H,4H-chromeno[3,4-c]pyridin-3-ylamine

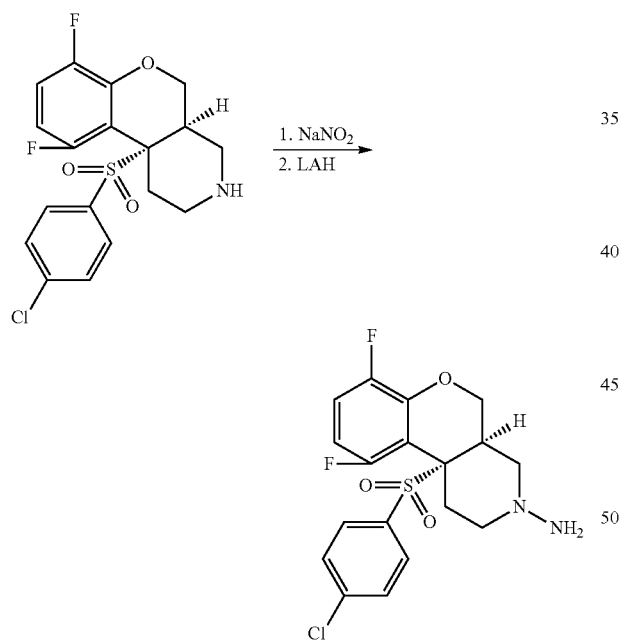

To a stirred solution of 0.09 g (0.22 mmol) of the amine and 0.035 g (0.5 mmol) of sodium nitrite in 3 mL of water and 5 mL of THF was added 0.024 g (0.4 mmol) of acetic acid slowly. The mixture was stirred at room temperature for 3 h. It was quenched with 15 mL of saturated sodium bicarbonate, and extracted with two 40 mL portions of methylene chloride. The combined organic extracts were concentrated, the residue was dissolved in 5 mL of THF and cooled to 0° C. To this solution was added 0.6 mL (0.6 mmol) of lithium aluminum hydride in THF. The mixture was stirred at room temperature for 1 h and quenched with 15 mL of water. It was extracted with two 40 mL portions of methylene chloride, and the combined organic extracts were concentrated to give 0.089 g of the title compound.

TABLE 20

| Example No. | STRUCTURE | Mass Spec (M+ except as otherwise noted); retention time (min) |
|---|---|---|
| 44 | 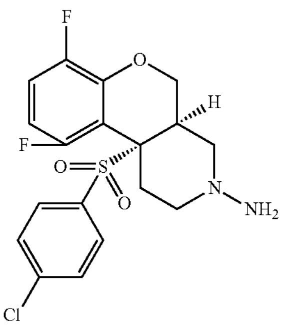 [SMILES: NN1CC[C@@]2(S(=O)(=O)c3ccc(Cl)cc3)c3c(F)ccc(F)c3OC[C@H]2C1] | 415.2 (MH+); 3.75 |

Examples 45 and 46

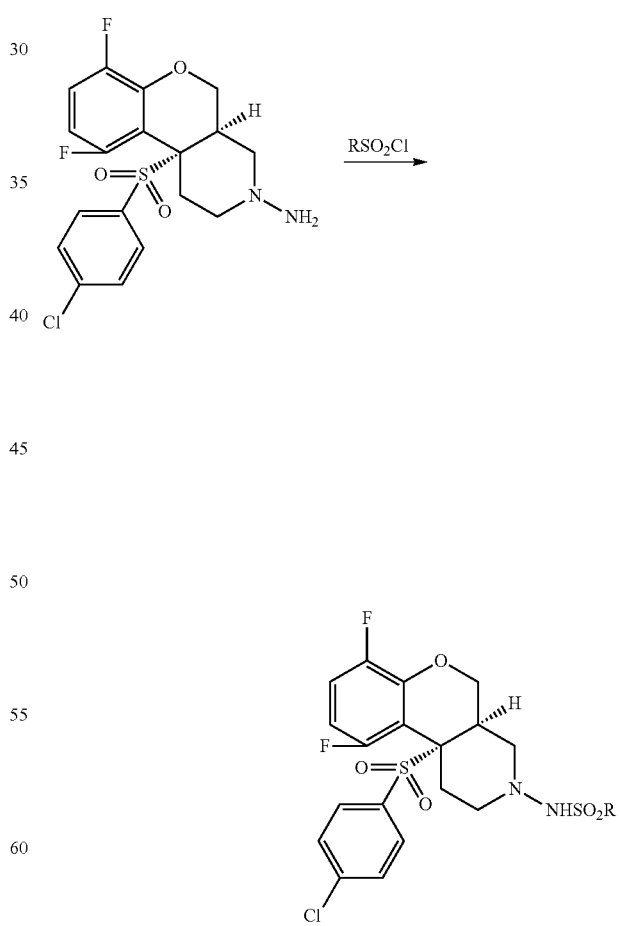

Using procedures described in Example 20, the compounds in Table 21 were prepared starting with the hydrazine of Example 44.

TABLE 21

| Example No. | STRUCTURE | Mass Spec (M+ except as otherwise noted); retention time (min) |
|---|---|---|
| 45 | 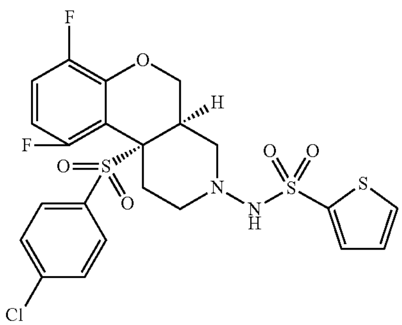 [SMILES: O=S(=O)(NN1CC[C@@]2(S(=O)(=O)c3ccc(Cl)cc3)c3c(F)ccc(F)c3OC[C@H]2C1)c1cccs1] | 561.3 (MH+); 4.42 |
| 46 | 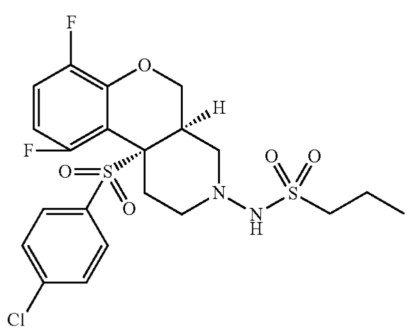 [SMILES: CCCS(=O)(=O)NN1CC[C@@]2(S(=O)(=O)c3ccc(Cl)cc3)c3c(F)ccc(F)c3OC[C@H]2C1] | 521.3; 4.47 |

Example 47

10a-(4-Chloro-benzenesulfonyl)-1,4-difluoro-8-trimethylsilanyl-6a,7,8,9,10,10a-hexahydro-6H-benzo[c]chromen-8-ol

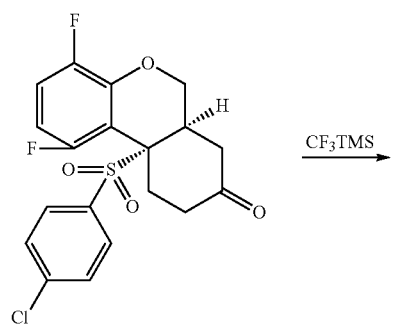

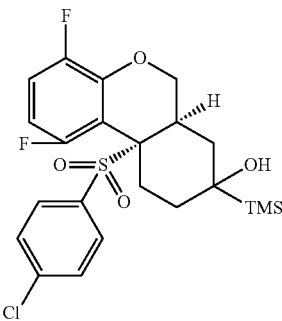

To a solution of 0.06 g (0.145 mmol) of the ketone and 1 mL (0.5 mmol) of trifluorotrimethylsilane in THF was added 0.005 g (cat.) of CsF. The mixture was stirred at room temperature for 2 h, and quenched with 3 mL of 3N HCl. The mixture was stirred overnight, and then diluted with 40 mL of methylene chloride. It was washed with 20 mL of brine. The aqueous layer was extracted with 20 mL of methylene chloride. The combined organic extracts were concentrated to give a crude product, which was dissolved in 5 mL of methanol. The unreacted ketone was reduced with 0.01 g (0.25 mmol) of sodium borohydride. The reaction mixture was concentrated, and the residue was purified by preparative TLC eluting with 40% ethyl acetate in hexanes to give the title compound, Example 47 in the Table 22.

TABLE 22

| Example No. | STRUCTURE | Mass Spec (M+ except as otherwise noted); retention time (min) |
|---|---|---|
| 47 | 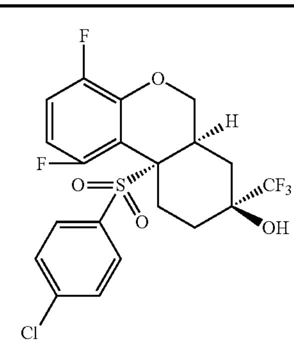 | 415.2 (MH+); 3.75 |

Example 48

10a-(4-Chloro-benzenesulfonyl)-1,4,8-trifluoro-6a,7,8,9,10,10a-hexahydro-6H-benzo[r]chromene

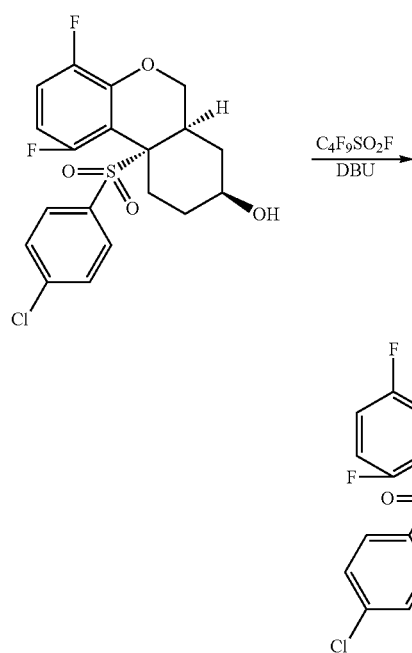

To a solution of 0.054 g (0.13 mmol) of the alcohol and 0.06 g (0.4 mmol) of DBU in 5 mL of toluene was added 0.06 g (0.2 mmol) of perfluorobutanesulfonyl fluoride in 1 mL of toluene at 0° C. The mixture was stirred at 0-5° C. for 1 h and left in refrigerator (4° C.) overnight. It was concentrated, the residue was purified by preparative TLC eluting with 20% ethyl acetate in hexanes to give 0.036 g of the product.

TABLE 23

| Example No. | STRUCTURE | Mass Spec (M+ except as otherwise noted); retention time (min) |
|---|---|---|
| 48 | 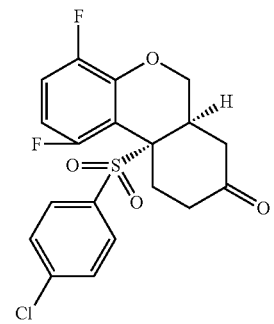 | 417.2 (MH+); 4.76 |

Example 49

Alternate Synthesis of the Product of Example 17

10a-(4-Chloro-benzenesulfonyl)-1,4-difluoro-6a,9,10,10a-tetrahydro-6H,7H-benzo[c]chromen-8-one

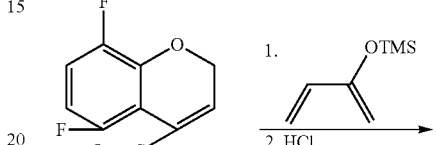

A mixture of 10.8 g (31.5 mmol) of the vinylsulphone product of step 3 of Example 17 and 24 g (165 mmol) of the 3-trimethylsiloxy-1,3-butadiene in 100 mL of trifluorotoluene in a sealed tube was heated at 150° C. for 15 h. It was concentrated, the residue was dissolved in 50 mL of THF. To this solution was added 3 mL of 1N HCl, the mixture was stirred at room temperature for 30 min. It was diluted with 300 mL of methylene chloride, washed with 50 mL of brine, and concentrated. The residue was recrystallized from ethyl

Example 50

2-[10a-(4-Chloro-benzenesulfonyl)-1,4-difluoro-8-oxo-6a,7,8,9,10,10a-hexahydro-6H-benzo[c]chromen-7-yl]-acetamide

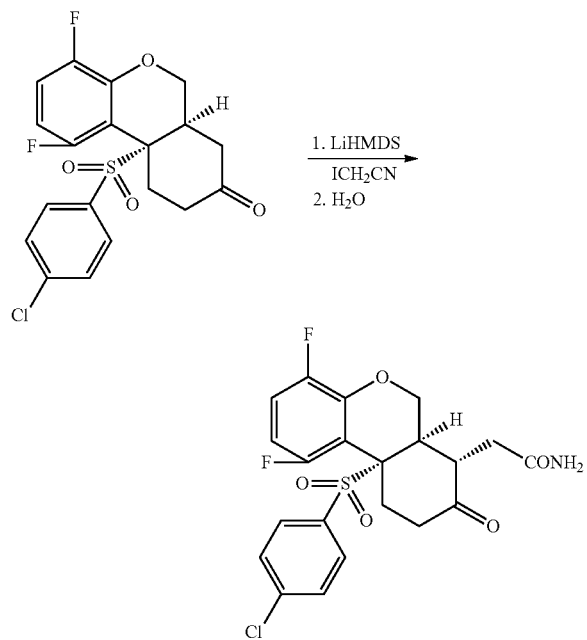

To a stirred solution of 3.0 g (7.27 mmol) of the ketone in 40 mL of THF was added 10 mL (10 mmol) of LiHMDS at −78° C. After 45 min., a solution of 1.83 g (11 mmol) of iodoacetonitrile was added. The mixture was stirred at −78° C. for 2 h, then warmed to room temperature over 5 h. It was quenched with 15 mL of water, and the mixture was stirred overnight. It was diluted with 100 mL of water, the precipitate was collected by filtration to give the title compound (Table 24).

TABLE 24

| Example No. | STRUCTURE | Mass Spec (M+ except as otherwise noted); retention time (min) |
|---|---|---|
| 50 | 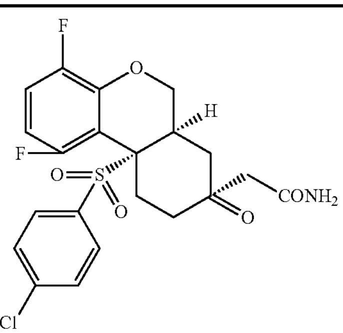 | 470.3 (MH+); 3.32 |

Example 51

3-[10a-(4-Chloro-benzenesulfonyl-1,4-difluoro-8-hydroxy-6a,7,8,9,10,10a-hexahydro-6H-benzo[c]chromen-7-yl]-propionitrile

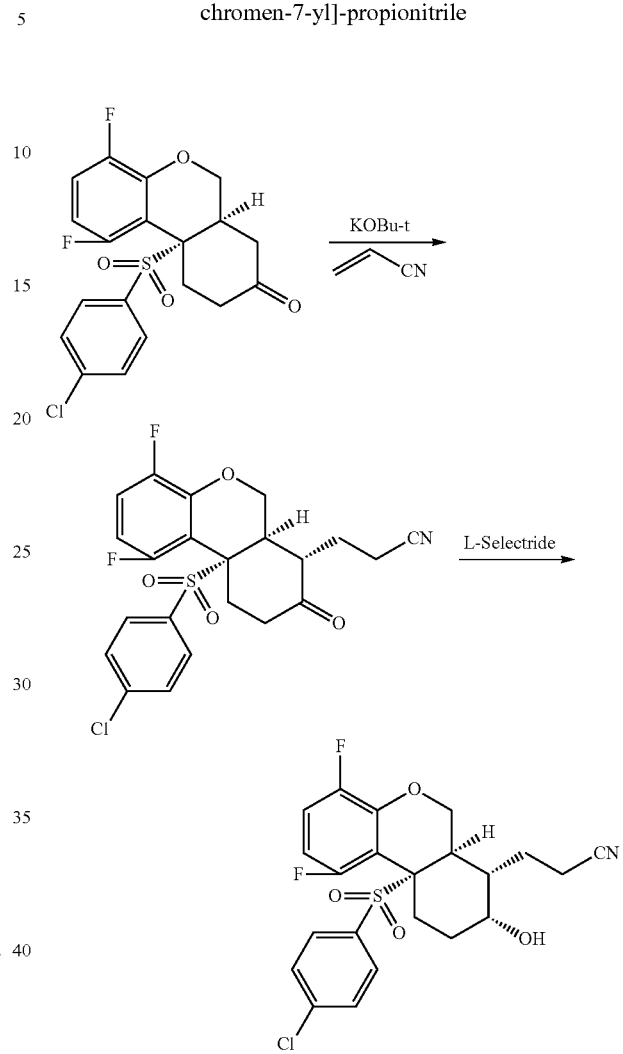

Step 1

To a suspension of the 0.41 g (1 mmol) of the ketone in 15 mL of t-BuOH were added 0.08 g (1.5 mmol) of acrylonitrile and 0.03 g (0.265 mmol) of potassium tert-butoxide. The mixture was stirred at room temperature for 4 days, additional 0.03 g of potassium tert-butoxide and 5 mL of THF was added. It was stirred for 2 h, quenched with 30 mL of brine, and extracted with three 40 mL portions of methylene chloride. It was concentrated to give a crude product, that we used directly in the next step.

Step 2

The product of step 1 was dissolved in 4 mL of THF. It was cooled to −78° C., and 3 mL (3 mmol) of L-Selectride in THF was added. After 2 h, it was quenched with 15 mL og brine, and extracted with three 40 mL portions of methylene chloride. The combined organic extracts were concentrated, the residue was purified by chromatography eluting with 15% to 50% ethyl acetate in hexanes to give the title compound (Example 51 Table 25).

Using a similar procedure as described in step 2, the compounds of Examples 52 and 53 (Table 25) are prepared.

TABLE 25

| Example No. | STRUCTURE | Mass Spec (M+ except as otherwise noted); retention time (min) |
|---|---|---|
| 51 | 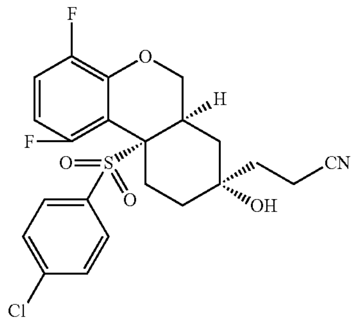 [SMILES: N#CCC[C@]1(O)CC[C@@]2(S(=O)(=O)c3ccc(Cl)cc3)c3c(F)ccc(F)c3OC[C@H]2C1] | 468.3 (MH+); 4.21 |
| 52 | 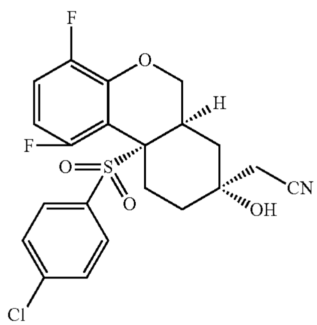 [SMILES: N#CC[C@]1(O)CC[C@@]2(S(=O)(=O)c3ccc(Cl)cc3)c3c(F)ccc(F)c3OC[C@H]2C1] | 454.2 (MH+); 4.19 |
| 53 | 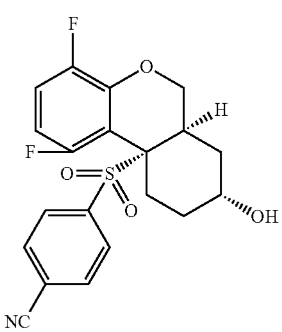 [SMILES: N#Cc1ccc(S(=O)(=O)[C@@]23CC[C@@H](O)C[C@@H]2COc2c(F)ccc(F)c23)cc1] | 406.2 (MH+); 3.62 |

TABLE 26

| Example No. | STRUCTURE | Mass Spec (M+ except as otherwise noted); retention time (min) |
|---|---|---|
| 54 | 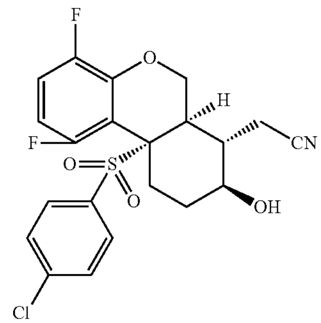 [SMILES: N#CC[C@@H]1[C@@H](O)CC[C@@]2(S(=O)(=O)c3ccc(Cl)cc3)c3c(F)ccc(F)c3OC[C@@H]12] | 454.2 (MH+); 3.97 |
| 55 | 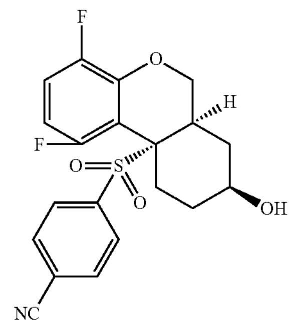 [SMILES: N#Cc1ccc(S(=O)(=O)[C@@]23CC[C@H](O)C[C@@H]2COc2c(F)ccc(F)c23)cc1] | 406.2 (MH+); 3.52 |

Example 56

4-(1,4-Difluoro-8-oxo-6,6a,7,8,9,10-hexahydro-benzo[c]chromene-10a-sulfonyl)-benzonitrile Examples 54 and 55

The compounds of Examples 54 and 55 (Table 26) are prepared using the method described for Example 18.

A mixture of 1.5 g (3.63 mmol) of the chloro ketone, 0.19 g (0.2 mmol) of $Pd_2(dba)_3$, 0.23 g (0.4 mmol) of dppf, 0.3 g (2.5 mmol) of zinc cyanide and 0.065 g (1 mmol) of zinc powder in 18 mL of DMA in a sealed tube was heated at 150° C. for 1 h in microwave (Biotage). It was diluted with 100 mL of water, and extracted with three 80 mL portions of ethyl acetate. The combined organic extracts were concentrated, the residue was purified by chromatography eluting with 10% to 40% ethyl acetate in hexanes to give 0.8 g of the title compound.

TABLE 27

| Example No. | STRUCTURE | Mass Spec (M+ except as otherwise noted); retention time (min) |
|---|---|---|
| 56 | 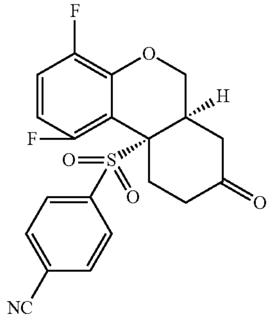 [SMILES: N#Cc1ccc(S(=O)(=O)[C@@]23CCC(=O)C[C@@H]2COc2c(F)ccc(F)c23)cc1] | 404.2 (MH+); 3.91 |

Example 57

The compound of Example 57 (Table 28) was prepared using the methods from Example 19.

TABLE 28

| Example No. | STRUCTURE | Mass Spec (M+ except as otherwise noted); retention time (min) |
|---|---|---|
| 57 | 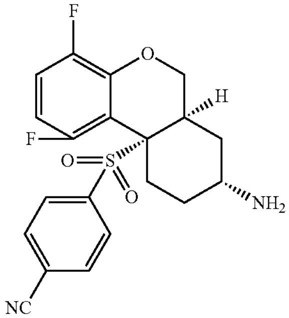 [SMILES: N#Cc1ccc(S(=O)(=O)[C@@]23CC[C@@H](N)C[C@@H]2COc2c(F)ccc(F)c23)cc1] | 405.2 (MH+); 2.60 |

Examples 58 and 59

The compounds of Examples 58 and 59 (Table 29) were prepared using the methods from Example 20.

TABLE 29

| Example No. | STRUCTURE | Mass Spec (M+ except as otherwise noted); retention time (min) |
|---|---|---|
| 58 | 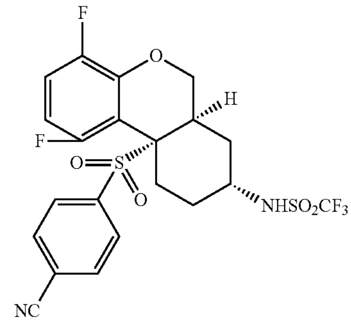 | 537.3 (MH+); 4.45 |
| 59 | 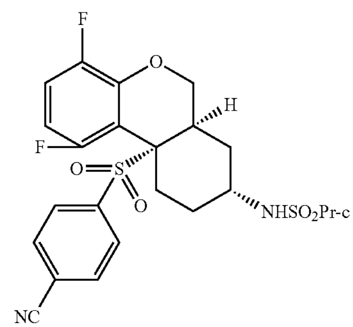 | 509.3 (MH+); 3.89 |

Example 60

1,4-Difluoro-7,7-dimethyl-10a-(4-trifluoromethyl-benzenesulfonyl-6a,9,10,10a-tetrahydro-6H,7H-benzo[c]chromen-8-one

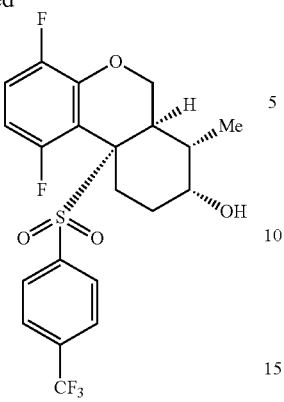

Example 60

1,4-Difluoro-7-methyl-10a-(4-trifluoromethyl-benzene-sulfonyl)-6a,9,10,10a-tetrahydro-6H,7H-benzo[c]chromen-8-one (48 mg, 0.104 mmol) was dissolved in tetrahydrofuran (2 mL). This solution was cooled in a dry ice/acetone bath, and then a 1.0 M solution of L-Selectride in tetrahydrofuran (0.16 mL) was added. The reaction was allowed to warm slowly as the cooling bath warmed. After 2 h, acetone was added to the reaction. The cooling bath was removed, and then aqueous 10% NH$_4$OH was added. After being stirred for 1 h, this mixture was extracted with dichloromethane (3×). The combined organic layers were dried over Na$_2$SO$_4$, filtered. and concentrated. The resulting crude residue was purified by silica gel chromatography with ethyl acetate/hexanes (0/100 to 40/60 over 20 min) to afford Example 60 (32 mg, 66%).

Example 60

$^1$H NMR (CDCl$_3$, 400 MHz) δ 7.86 (d, 2H), 7.78 (d, 2H), 7.10-7.04 (m, 1H), 6.47-6.41 (m, 1H), 5.18 (dd, 1H), 4.51 (d, 1H), 3.75 (br s, 1H), 2.78 (br d, 1H), 2.54 (dddd, 1H), 2.26 (br d, 1H), 1.79 (dq, 1H), 1.63-1.58 (m, 1H), 1.32 (br t, 1H), 1.18 (d, 3H). LCMS: (M+1)=463.3, retention time=4.46 min.

Example 61

2-[1,4-Difluoro-10a-(4-trifluoromethyl-benzene-sulfonyl)-6a,7,8,9,10,10a-hexahydro-6H-benzo[c]chromen-8-yl]-ethylamine

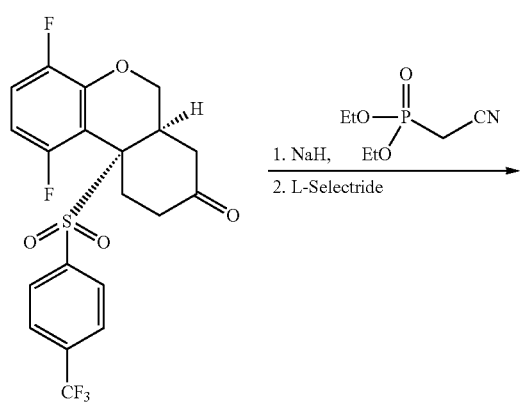

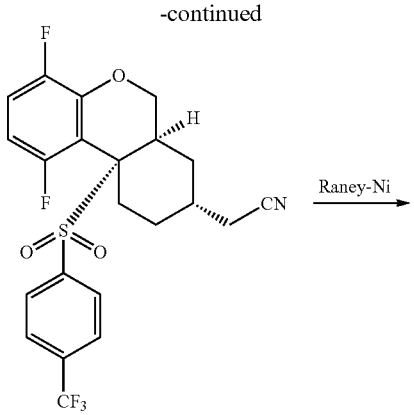

Example 61A

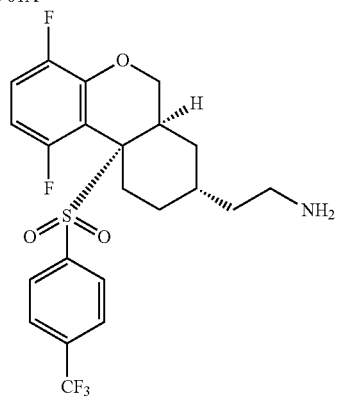

Example 61

Step 1

[1,4-Difluoro-10a-(4-trifluoromethyl-benzenesulfonyl)-6a,9,10,10a-tetrahydro-6H,7H-benzo[c]chromen-8-ylidene]-acetonitrile

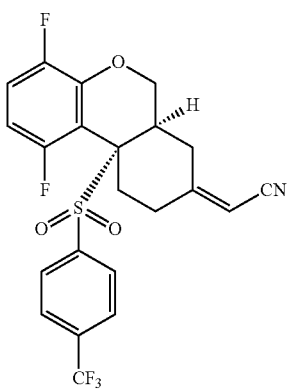

To a 0° C. mixture of 60% NaH oil dispersion (60 mg) in tetrahydrofuran (11 mL) was added diethyl cyanomethylphosphonate (0.235 mL). After being stirred for 10 min at 0° C., 1,4-difluoro-10a-(4-trifluoromethyl-benzenesulfonyl)-6a,9,10,10a-tetrahydro-6H,7H-benzo[c]chromen-8-one (0.50 g, 1.12 mmol) was added to the resulting clear and colorless solution. After 1 h, saturated aqueous NH$_4$Cl was added to the reaction solution. This mixture was then extracted with ethyl acetate (3×). The combined organic layers were dried over Na₂SO₄, filtered, and concentrated. The resulting crude residue (0.574 g) was used without further purification.

Step 2

[1,4-Difluoro-10a-(4-trifluoromethyl-benzenesulfonyl-6a,7,8,9,10,10a-hexahydro-6H-benzo[c]chromen-8-yl]-acetonitrile

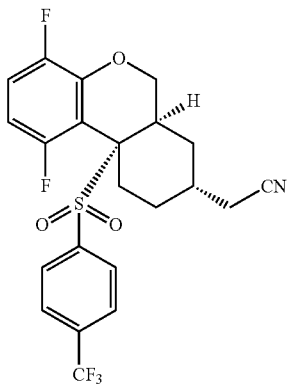 [SMILES: N#C/C=C1/CC[C@@]2(S(=O)(=O)c3ccc(C(F)(F)F)cc3)c3c(F)ccc(F)c3OC[C@H]2C1]

Example 61A

To a −78° C. solution of crude [1,4-difluoro-10a-(4-trifluoromethyl-benzenesulfonyl)-6a,9,10,10a-tetrahydro-6H,7H-benzo[c]chromen-8-ylidene]-acetonitrile (0.574 g) in tetrahydrofuran (22 mL) was added 1.0 M L-Selectride in tetrahydrofuran (1.8 mL). The reaction was allowed to warm slowly as the cooling bath warmed. After 1.5 h, brine (1.8 mL), aqueous 1 M NaOH (1.8 mL), and then aqueous 30% H₂O₂ (0.75 mL) were added to the reaction. After being stirred another 0.5 h, aqueous 25% Na₂SO₃ (5 mL) was added. This mixture was extracted with ethyl acetate (3×). The combined organic layers were dried over Na₂SO₄, filtered, and absorbed onto silica gel (5 g). This absorbed crude material was purified by silica gel chromatography with ethyl acetate/hexanes (0/100 to 50/50 over 25 min) to afford Example 61A (0.330 g, 62% over two steps).

Example 61A

¹H NMR (CDCl₃, 400 MHz) δ 7.79 (br s, 4H), 7.13-7.08 (m, 1H), 6.45-6.39 (m, 1H), 5.26 (dd, 1H), 4.14 (d, 1H), 2.81 (ddd, 1H), 2.58 (d, 2H), 2.40 (ddd, 1H), 2.24 (m, 1H), 2.12 (dddd, 1H), 1.82-1.73 (m, 3H), 1.42 (dddd, 1H). LCMS: (M+1)=472.3, retention time=4.53 min.

Step 3

2-[1,4-Difluoro-10a-(4-trifluoromethyl-benzenesulfonyl-6a,7,8,9,10,10a-hexahydro-6H-benzo[c]chromen-8-yl]-ethylamine

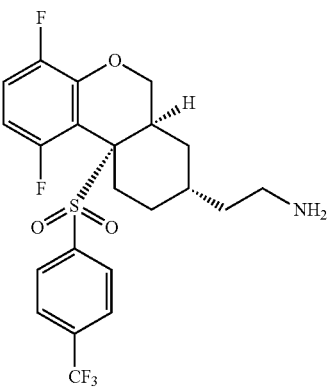

Example 61

To a room temperature mixture of [1,4-difluoro-10a-(4-trifluoromethyl-benzenesulfonyl)-6a,7,8,9,10,10a-hexahydro-6H-benzo[c]chromen-8-yl]-acetonitrile. (Example 61.1) (23 mg) in 7 M NH₃ in MeOH (1 mL) was added Raney 2800 Nickel. The reaction vessel was then fitted with a balloon of H₂. After being stirred overnight at room temperature, this reaction mixture was diluted with MeOH/CH₂Cl₂ (1:1) and filtered through Celite. The filtrate was concentrated. This resulting crude material was purified by silica gel chromatography with MeOH/NH₄OH/CH₂Cl₂ (0/0/100 to 10/1/89 over 15 min) and then by reverse phase HPLC using CH₃CN/H₂O with 0.1% formic acid (5/95 to 95/5 over 10 min) to afford the formate salt of Example 61 (13.6 mg).

Example 61

¹H NMR (CDCl₃, 400 MHz) δ 7.98 (br s, 2H), 7.77 (br s, 4H), 7.10-7.04 (m, 1H), 6.40-6.34 (m, 1H), 5.13 (d, 1H), 4.07 (d, 1H), 3.25-2.95 (m, 4H), 2.82 (br d, 1H), 2.30 (br d, 1H), 2.19 (br t, 1H), 1.93 (br s, 2H), 1.76 (br s, 1H), 1.70-1.61 (m, 2H), 1.51 (br d, 1H), 1.25 (br t, 1H). LCMS: (M+1)=476.3, retention time=3.12 min.

Examples 62 and 63

Following procedures similar to those described in Example 20, the compounds in Table 30 were prepared.

TABLE 30
| Ex. No. | Structure | LCMS (M + 1, retention time) |
|---|---|---|
| 62 | 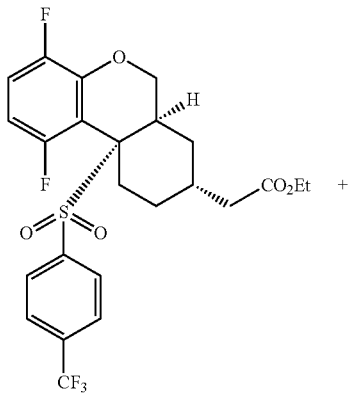 | 358.2 [M − HN(SO$_2$Me)$_2$], 4.74 min. |
| 63 | 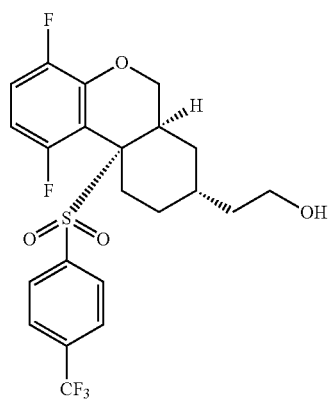 | 554.3, 4.53 min. |
Example 64
Following procedures similar to those described in Steps 1 and 2 of Example 61, the compounds of Example 64A and 64B (Table 31) were prepared.
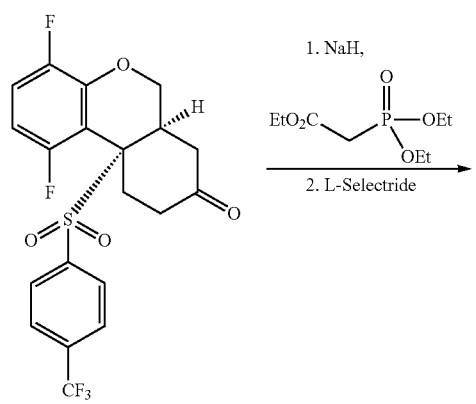
TABLE 31
| Ex. No. | Structure | LCMS (M + 1, retention time) |
|---|---|---|
| 64A | Example 64A | 519.3, 5.11 min. |
| 64B | Example 64B | |

TABLE 31-continued

| Ex. No. | Structure | LCMS (M + 1, retention time) |
|---|---|---|
| 64B | 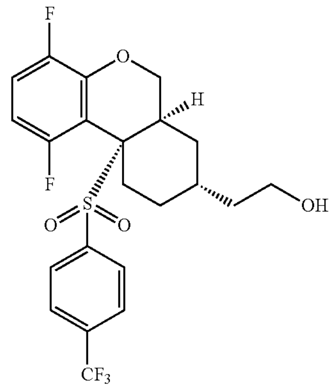 [SMILES: O=S(=O)(c1ccc(C(F)(F)F)cc1)[C@@]12CC[C@@H](CCO)C[C@@H]1COc1c(F)ccc(F)c12] | 477.3, 4.35 min. |

Examples 65-108

Following procedures of Example 23 the compounds in Table 32 are prepared.

TABLE 32

| Ex. No. | Structure | LCMS (M + 1, retention time) |
|---|---|---|
| 65 | 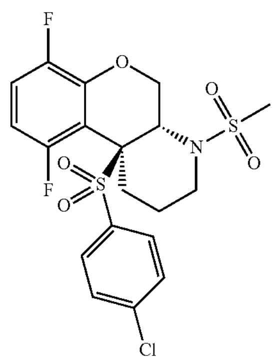 [SMILES: CS(=O)(=O)N1CCC[C@]2(S(=O)(=O)c3ccc(Cl)cc3)c3c(F)ccc(F)c3OC[C@H]12] | 478.3, 4.56 Min. |
| 66 | 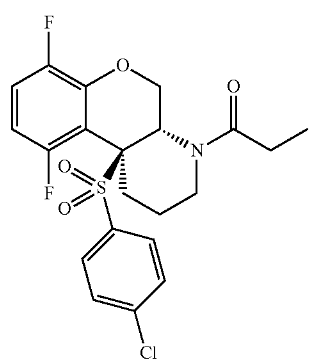 [SMILES: CCC(=O)N1CCC[C@]2(S(=O)(=O)c3ccc(Cl)cc3)c3c(F)ccc(F)c3OC[C@H]12] | 456.3, 4.18 Min. |

TABLE 32-continued

| Ex. No. | Structure | LCMS (M + 1, retention time) |
|---|---|---|
| 67 | 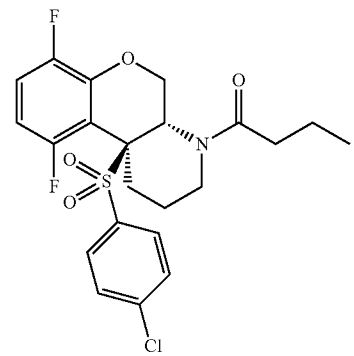 [SMILES: CCCC(=O)N1CCC[C@]2(S(=O)(=O)c3ccc(Cl)cc3)c3c(F)ccc(F)c3OC[C@H]12] | 470.3, 4.39 Min. |
| 68 | 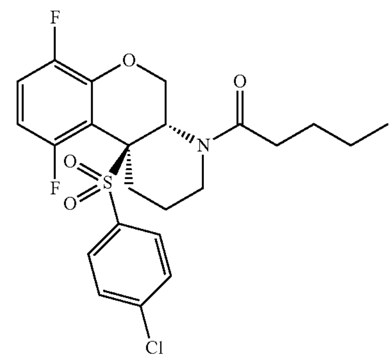 [SMILES: CCCCC(=O)N1CCC[C@]2(S(=O)(=O)c3ccc(Cl)cc3)c3c(F)ccc(F)c3OC[C@H]12] | 484.3, 4.62 Min. |
| 69 | 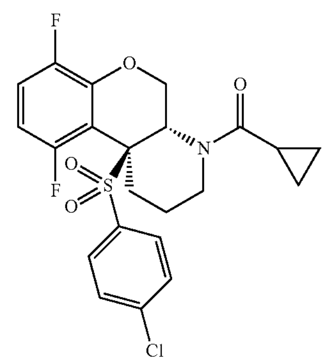 [SMILES: O=C(C1CC1)N1CCC[C@]2(S(=O)(=O)c3ccc(Cl)cc3)c3c(F)ccc(F)c3OC[C@H]12] | 468.3, 4.27 Min. |
| 70 | 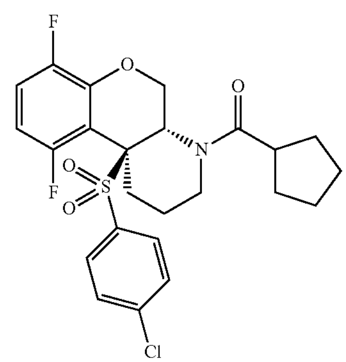 [SMILES: O=C(C1CCCC1)N1CCC[C@]2(S(=O)(=O)c3ccc(Cl)cc3)c3c(F)ccc(F)c3OC[C@H]12] | 496.3, 4.72 Min. |

TABLE 32-continued

| Ex. No. | Structure | LCMS (M + 1, retention time) |
|---|---|---|
| 71 | 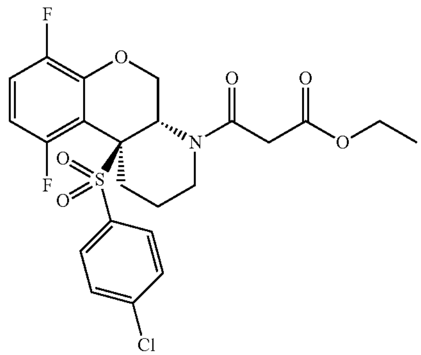 [SMILES: CCOC(=O)CC(=O)N1CCC[C@]2(S(=O)(=O)c3ccc(Cl)cc3)c3c(F)ccc(F)c3OC[C@H]12] | 514.3, 4.59 Min. |
| 72 | 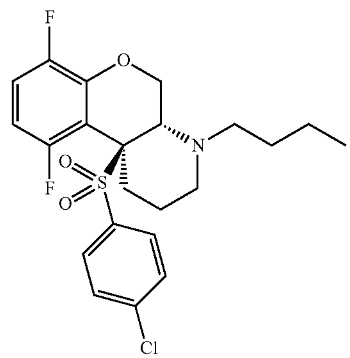 [SMILES: CCCCN1CCC[C@]2(S(=O)(=O)c3ccc(Cl)cc3)c3c(F)ccc(F)c3OC[C@H]12] | 442.2, 3.10 Min. |
| 73 | 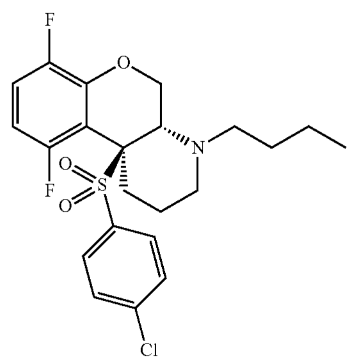 [SMILES: CCCCN1CCC[C@]2(S(=O)(=O)c3ccc(Cl)cc3)c3c(F)ccc(F)c3OC[C@H]12] | 456.3, 3.41 Min. |
| 74 | 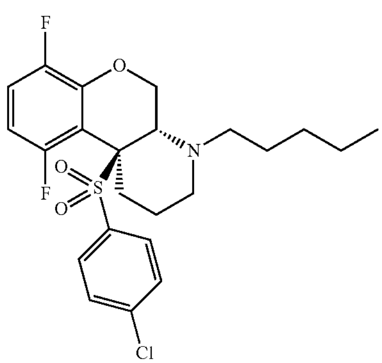 [SMILES: CCCCCN1CCC[C@]2(S(=O)(=O)c3ccc(Cl)cc3)c3c(F)ccc(F)c3OC[C@H]12] | 470.3, 3.60 Min. |
| 75 | | 482.3, 3.87 Min. |
| 76 | | 492.3, 4.66 Min. |
| 77 | | 471.3, 4.18 Min. |
| 78 | | 519.3, 4.80 Min. |

TABLE 32-continued

| Ex. No. | Structure | LCMS (M + 1, retention time) |
|---|---|---|
| 79 | 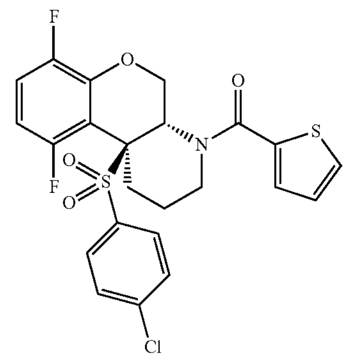 [SMILES: O=C(c1cccs1)N1CCC[C@]2(S(=O)(=O)c3ccc(Cl)cc3)c3c(F)ccc(F)c3OC[C@H]12] | 510.3, 4.44 Min. |
| 80 | 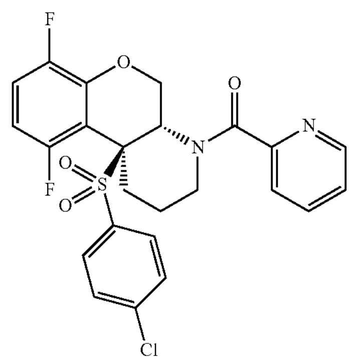 [SMILES: O=C(c1ccccn1)N1CCC[C@]2(S(=O)(=O)c3ccc(Cl)cc3)c3c(F)ccc(F)c3OC[C@H]12] | 505.3, 4.14 Min. |
| 81 | 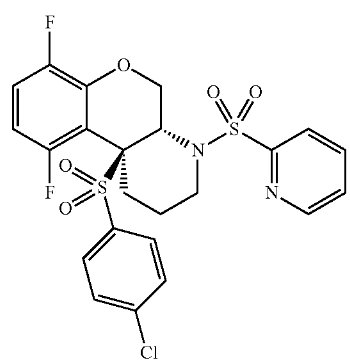 [SMILES: O=S(=O)(c1ccccn1)N1CCC[C@]2(S(=O)(=O)c3ccc(Cl)cc3)c3c(F)ccc(F)c3OC[C@H]12] | 541.3, 4.50 Min. |
| 82 | 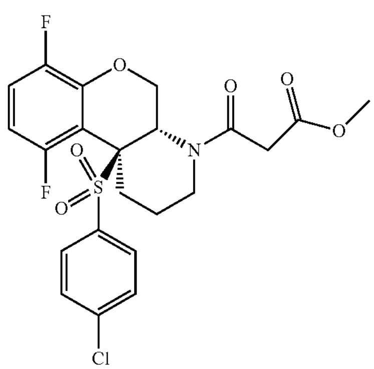 [SMILES: COC(=O)CC(=O)N1CCC[C@]2(S(=O)(=O)c3ccc(Cl)cc3)c3c(F)ccc(F)c3OC[C@H]12] | 500.3, 4.79 Min |
| 83 | | 524.3, 5.21 Min |
| 84 | | 486.3, 4.91 Min |
| 85 | | 494.3, 4.97 Min |
| 86 | | 496.3, 4.89 Min |

TABLE 32-continued

| Ex. No. | Structure | LCMS (M + 1, retention time) |
|---|---|---|
| 87 | 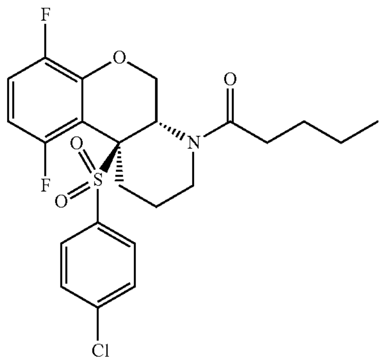 [SMILES: CCCCC(=O)N1CCC[C@]2(S(=O)(=O)c3ccc(Cl)cc3)c3c(F)ccc(F)c3OC[C@H]12] | 498.3, 5.39 Min |
| 88 | 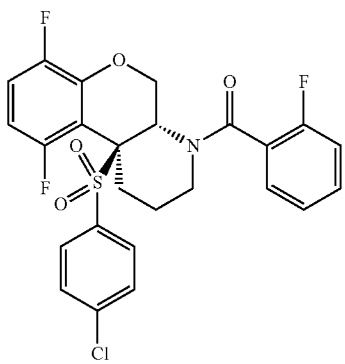 [SMILES: O=C(c1ccccc1F)N1CCC[C@]2(S(=O)(=O)c3ccc(Cl)cc3)c3c(F)ccc(F)c3OC[C@H]12] | 522.3, 4.76 Min. |
| 89 | 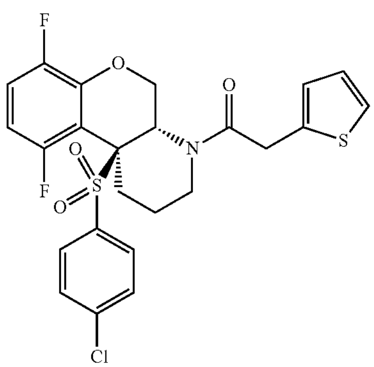 [SMILES: O=C(Cc1cccs1)N1CCC[C@]2(S(=O)(=O)c3ccc(Cl)cc3)c3c(F)ccc(F)c3OC[C@H]12] | 524.3, 5.13 Min |
| 90 | 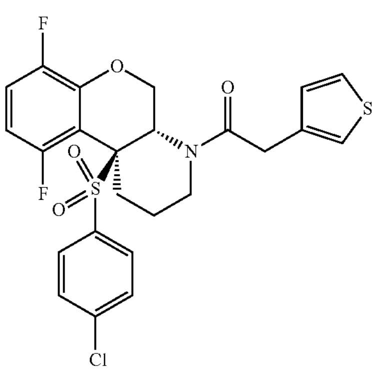 [SMILES: O=C(Cc1ccsc1)N1CCC[C@]2(S(=O)(=O)c3ccc(Cl)cc3)c3c(F)ccc(F)c3OC[C@H]12] | 524.3, 5.13 Min |
| 91 | | 536.3, 5.22 Min |
| 92 | | 540.3, 5.25 Min |
| 93 | | 544.3, 5.25 Min |
| 94 | | 562.3, 5.15 Min |

TABLE 32-continued

| Ex. No. | Structure | LCMS (M + 1, retention time) |
|---|---|---|
| 95 | 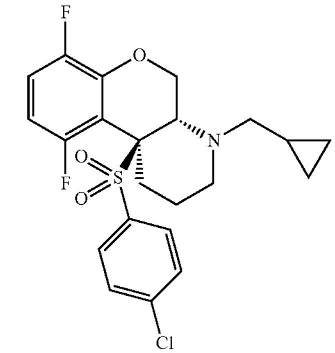 [SMILES: O=S(=O)(c1ccc(Cl)cc1)[C@]12CCCN(CC3CC3)[C@H]1COc1c(F)ccc(F)c12] | 454.2, 3.42 Min. |
| 96 | 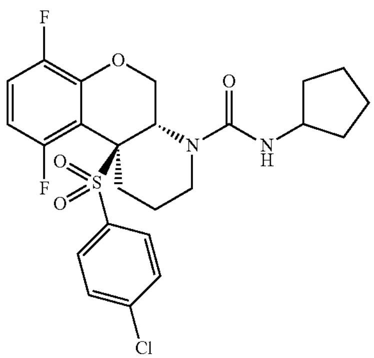 [SMILES: O=C(NC1CCCC1)N1CCC[C@]2(S(=O)(=O)c3ccc(Cl)cc3)c3c(F)ccc(F)c3OC[C@H]12] | 511.3, 4.37 Min. |
| 97 | 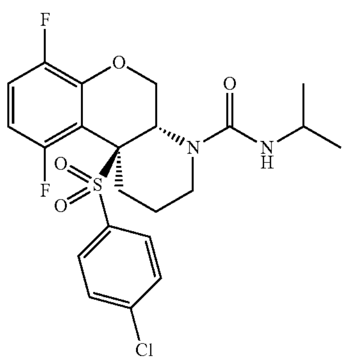 [SMILES: CC(C)NC(=O)N1CCC[C@]2(S(=O)(=O)c3ccc(Cl)cc3)c3c(F)ccc(F)c3OC[C@H]12] | 485.3, 4.10 Min. |
| 98 | 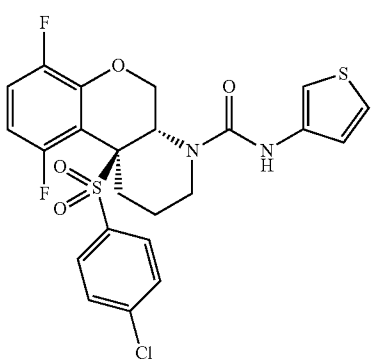 [SMILES: O=C(Nc1ccsc1)N1CCC[C@]2(S(=O)(=O)c3ccc(Cl)cc3)c3c(F)ccc(F)c3OC[C@H]12] | 525.3, 4.49 Min. |

TABLE 32-continued

| Ex. No. | Structure | LCMS (M + 1, retention time) |
|---|---|---|
| 99 | 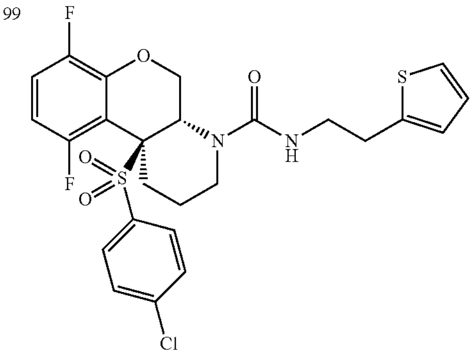 | 555.3, 4.40 Min. |
| 100 | 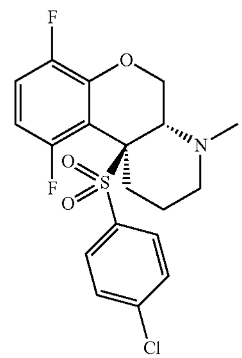 [SMILES: CN1CCC[C@]2(S(=O)(=O)c3ccc(Cl)cc3)c3c(F)ccc(F)c3OC[C@H]12] | 414.2, 2.91 Min |
| 101 | 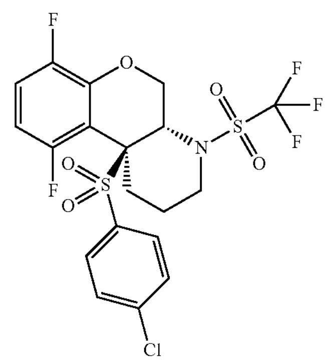 [SMILES: O=S(=O)(N1CCC[C@]2(S(=O)(=O)c3ccc(Cl)cc3)c3c(F)ccc(F)c3OC[C@H]12)C(F)(F)F] | No M + 1, 4.87 Min |
| 102 | 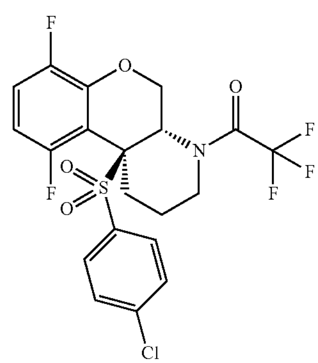 [SMILES: O=C(N1CCC[C@]2(S(=O)(=O)c3ccc(Cl)cc3)c3c(F)ccc(F)c3OC[C@H]12)C(F)(F)F] | 496.3, 4.89 Min |

TABLE 32-continued
| Ex. No. | Structure | LCMS (M + 1, retention time) |
|---|---|---|
| 103 | 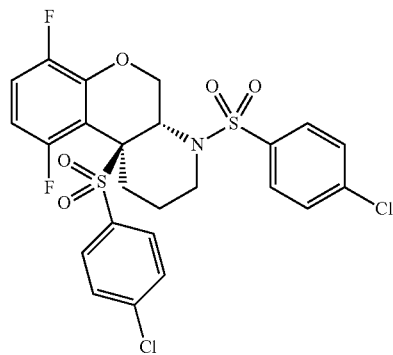 [SMILES: O=S(=O)(c1ccc(Cl)cc1)N1CCC[C@]2(S(=O)(=O)c3ccc(Cl)cc3)c3c(F)ccc(F)c3OC[C@H]12] | 574.3, 5.03 Min |
| 104 | 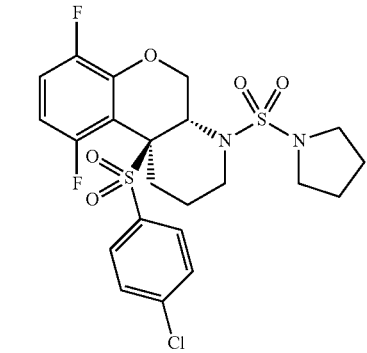 [SMILES: O=S(=O)(N1CCCC1)N1CCC[C@]2(S(=O)(=O)c3ccc(Cl)cc3)c3c(F)ccc(F)c3OC[C@H]12] | 533.3, 4.71 Min |
| 105 | 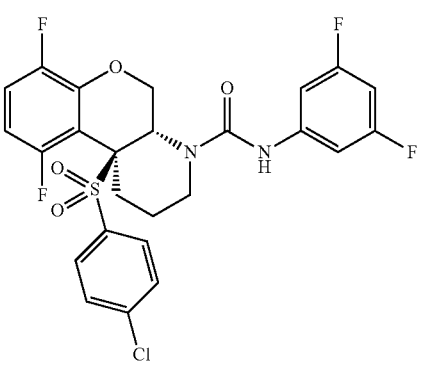 [SMILES: O=C(Nc1cc(F)cc(F)c1)N1CCC[C@]2(S(=O)(=O)c3ccc(Cl)cc3)c3c(F)ccc(F)c3OC[C@H]12] | 555.3, 4.74 Min |
TABLE 32-continued
| Ex. No. | Structure | LCMS (M + 1, retention time) |
|---|---|---|
| 106 | 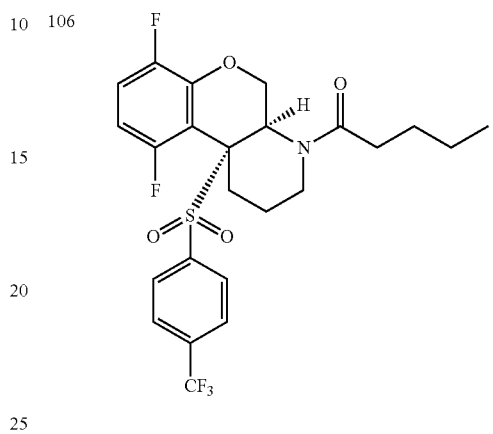 | 518.8, 4.90 min. |
| 107 | 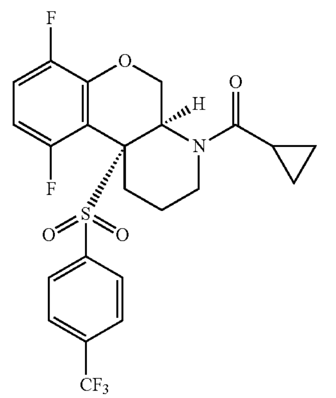 [SMILES: O=C(C1CC1)N1CCC[C@@]2(S(=O)(=O)c3ccc(C(F)(F)F)cc3)c3c(F)ccc(F)c3OC[C@@H]12] | 502.3, 4.46 min. |
| 108 | 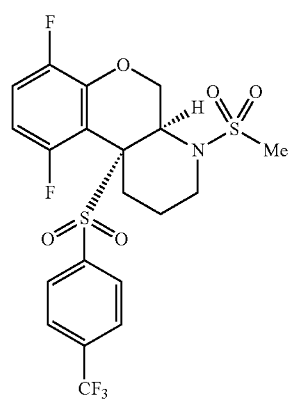 [SMILES: CS(=O)(=O)N1CCC[C@@]2(S(=O)(=O)c3ccc(C(F)(F)F)cc3)c3c(F)ccc(F)c3OC[C@@H]12] | 512.3, 4.42 min. |
Examples 109-116
Using the procedure described in Example 21 Step 1, the compounds in Table 33 were prepared.

TABLE 33

| Ex. No. | Structure | LCMS (M + 1, retention time) |
| --- | --- | --- |
| 109 | 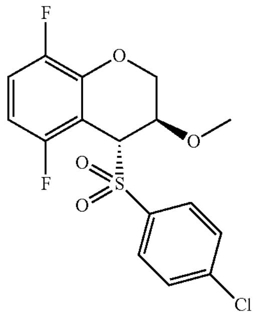 [SMILES: CO[C@@H]1COc2c(F)ccc(F)c2[C@H]1S(=O)(=O)c1ccc(Cl)cc1] | 375.2, 4.49 Min |
| 110 | 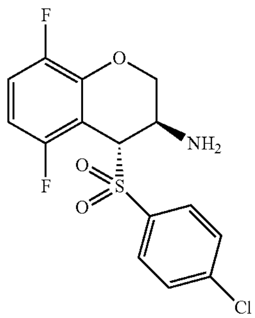 [SMILES: N[C@@H]1COc2c(F)ccc(F)c2[C@H]1S(=O)(=O)c1ccc(Cl)cc1] | 382.2 (M + Na), 2.52 Min |
| 111 | 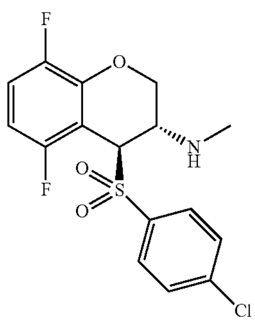 [SMILES: CN[C@H]1COc2c(F)ccc(F)c2[C@@H]1S(=O)(=O)c1ccc(Cl)cc1] | 374.2, 2.76 Min |
| 112 | 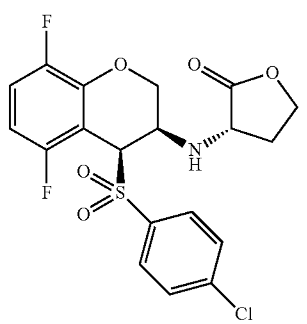 [SMILES: O=C1OCC[C@@H]1N[C@@H]1COc2c(F)ccc(F)c2[C@@H]1S(=O)(=O)c1ccc(Cl)cc1] | 444.2, 4.45 Min |
| 113 | 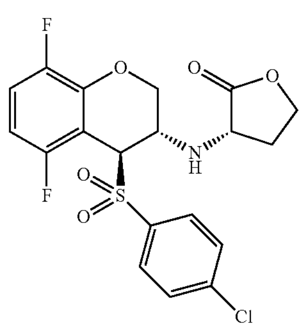 [SMILES: O=C1OCC[C@@H]1N[C@H]1COc2c(F)ccc(F)c2[C@@H]1S(=O)(=O)c1ccc(Cl)cc1] | 444.2, 4.40 Min |

TABLE 33-continued

| Ex. No. | Structure | LCMS (M + 1, retention time) |
|---|---|---|
| 114 | 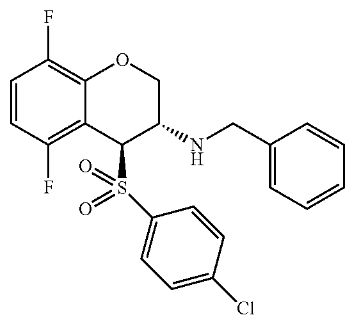 [SMILES: O=S(=O)(c1ccc(Cl)cc1)[C@H]1c2c(F)ccc(F)c2OC[C@@H]1NCc1ccccc1] | 450.2, 3.68 Min |
| 115 | 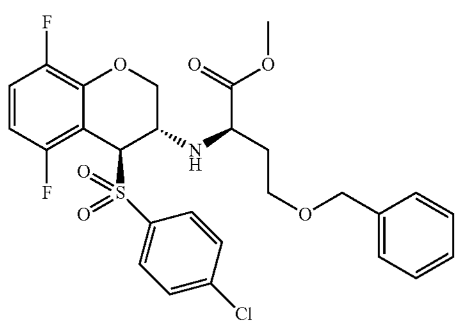 [SMILES: COC(=O)[C@@H](CCOCc1ccccc1)N[C@H]1COc2c(F)ccc(F)c2[C@@H]1S(=O)(=O)c1ccc(Cl)cc1] | 566.3, 5.25 Min |
| 116 | 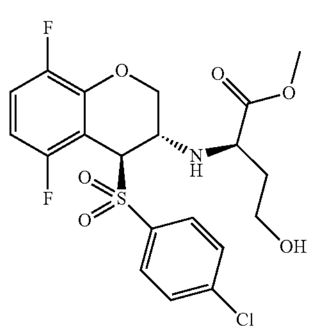 [SMILES: COC(=O)[C@@H](CCO)N[C@H]1COc2c(F)ccc(F)c2[C@@H]1S(=O)(=O)c1ccc(Cl)cc1] | 444.2, 4.08 Min |

Examples 117 and 118

Using the procedure described in Example 20, the compounds in Table 34 were prepared

TABLE 34

| Ex. No. | Structure | LCMS (M + 1, retention time) |
|---|---|---|
| 117 | 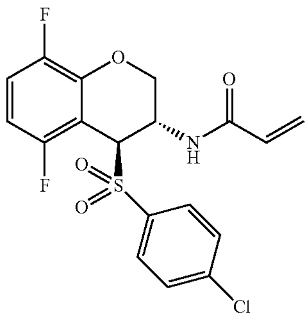 [SMILES: C=CC(=O)N[C@H]1COc2c(F)ccc(F)c2[C@@H]1S(=O)(=O)c1ccc(Cl)cc1] | 414.2, 4.35 Min |
| 118 | 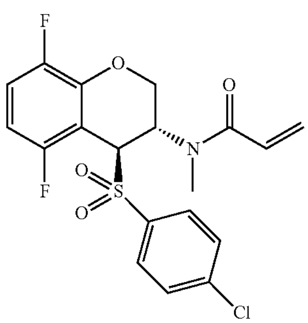 [SMILES: C=CC(=O)N(C)[C@H]1COc2c(F)ccc(F)c2[C@@H]1S(=O)(=O)c1ccc(Cl)cc1] | 428.2, 4.41 Min |

Example 119

(4aS)-10bS-[(4-chlorophenyl)sulfonyl]-7,10-difluoro-1,4a,5,10b-tetrahydro-2H-[1]benzopyrano[3,4-b]pyridin-3(4H)-one (racemic)

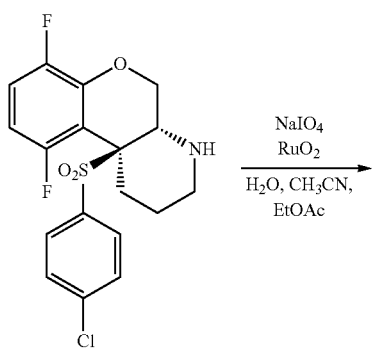

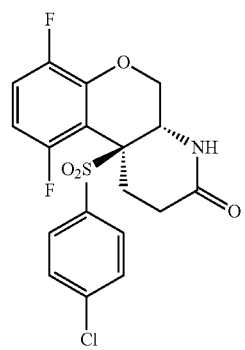

4a-(4-Chloro-benzenesulfonyl)-5,8-difluoro-2,3,4,4a,10,10a-hexahydro-1H-9-oxa-1-aza-phenanthrene (96.8 mg, 0.242 mmol) was dissolved in 2.35 ml of water, 11.5 mg of acetonitrile, and 11.5 ml of ethyl acetate. Then sodium periodate (399 mg, 1.86 mmol) and ruthenium dioxide (20.5 mg, 0.154 mmol) were added respectively and stirred overnight. The reaction was quenched with 50 ml of water and washed with 75 ml of ethyl acetate. The organic layer was treated with 50 ml of isopropanol and left for 2.5 h. The solution was filtered through celite, washed with brine, and dried over sodium sulfate. The product was purified by column using EtOAc/Hex. as the eluent (gradient from 50/50 to 100/0 in 60 minutes). Yield: 30.0 mg, 30%. $^1$H NMR (CDCl$_3$ 400 MHz) δ 7.65 (d, J=8.8 Hz, 2H), 7.52 (d, J=8.1 Hz, 2H), 7.10 (td, J=9.5, 5.1 Hz, 1H), 7.01 (bs, 1H), 6.50-6.41 (m, 1H), 5.10 (d, J=12.4 Hz, 1H), 4.50 (s, 1H), 4.32 (d, J=12.4 Hz, 1H), 2.80-2.70 (m, 1H), 2.60-2.41 (m, 1H), 2.06-1.93 (m, 1H), 1.68 (bs, 1H).

The compounds in Table 35 were made by a similar procedure to that of Example 119.

TABLE 35

| Ex. No. | Structure | LCMS (M + 1, retention time) |
|---|---|---|
| 120 | 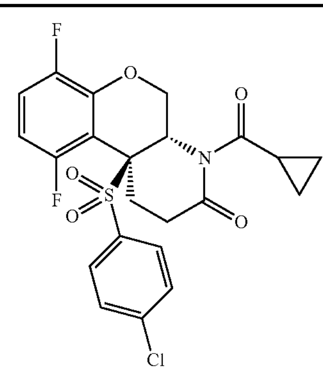 | 482.3, 4.41 Min |

TABLE 35-continued

| Ex. No. | Structure | LCMS (M + 1, retention time) |
|---|---|---|
| 121 | 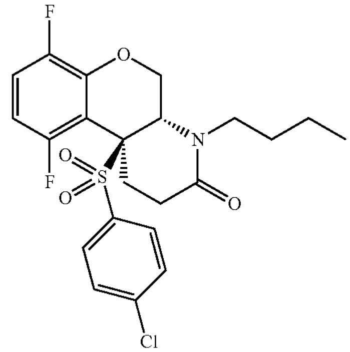 [SMILES: CCCCN1C(=O)CC[C@]2(S(=O)(=O)c3ccc(Cl)cc3)c3c(F)ccc(F)c3OC[C@H]12] | 470,3, 4.36 Min |

Example 122

Trans-9-chloro-10b-[(4-chlorophenyl)sulfonyl]-7,10-difluoro-1,3,4,4a,5,10b-hexahydro-2H-[1]benzopyrano[3,4-b]pyridine (racemic)

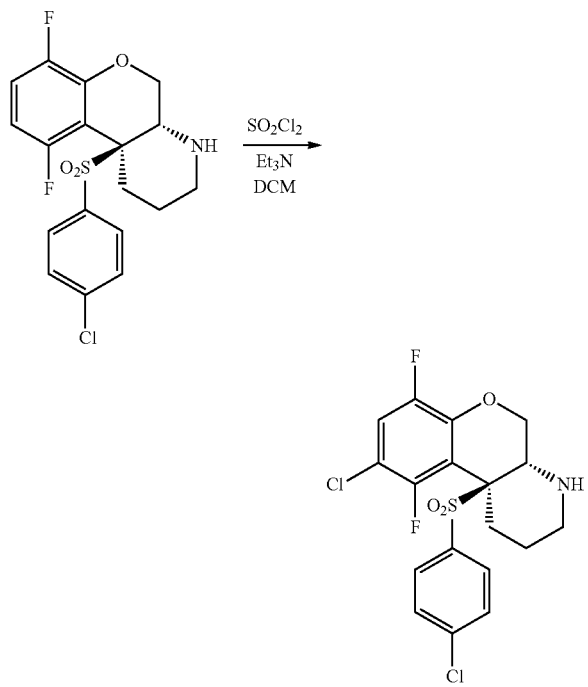

6-Chloro-4-a-(4-chloro-benzenesulfonyl)-5,8-difluoro-2,3,4,4a,10,10a-hexahydro-1H-9-oxa-1-aza-phenanthrene 4a-(4-Chloro-benzenesulfonyl)-5,8-difluoro-2,3,4,4a,10,10a-hexahydro-1H-9-oxa-1-aza-phenanthrene (1.0190 g, 2.5475 mmol) was dissolved in 75 ml dichloromethane and cooled to 0° C. then triethylamine (1.1 mL) was added. The solution was stirred at 0° C. for 10 minutes then II was added slowly and the solution was stirred at 0° C. for 3 h. Then the reaction was warmed to room temperature and stirred for 1 h. The reaction was quenched with 50 ml of ice water. The organic layer was washed with 50 ml of 1 N HCl solution and dried over sodium sulfate. The product was purified by column using EtOAc/Hex. as the eluent (gradient from 0/100 to 50/50 in 45 minutes). Yield: 124.0 mg, 11%. $^1$H NMR (CDCl$_3$ 400 MHz) δ 7.57 (d, J=8.8 Hz, 2H), 7.52 (d, J=8.8 Hz, 2H), 7.23 (dd, J=9.5, 6.6 Hz, 1H), 5.19 (dd, J=8.8, 6.6 Hz, 1H), 4.32 (d, J=11.7 Hz, 1H), 3.69 (s, 1H), 2.99 (d, J=13.1 Hz, 1H), 2.74 (td, J=13.1, 2.9 Hz, 1H), 2.64 (d, J=13.1 Hz, 1H), 2.20-2.11 (m, 1H), 1.62 (d, J=13.1 Hz, 2H), 1.19-1.06 (m, 1H).

TABLE 36

| Ex. No. | Structure | LCMS (M + 1, retention time) |
|---|---|---|
| 122 | 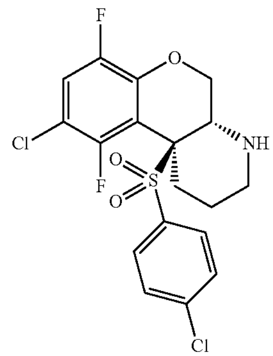 [SMILES: O=S(=O)(c1ccc(Cl)cc1)[C@]12CCCN[C@H]1COc1c(F)cc(Cl)c(F)c12] | 434.2, 3.92 Min |

Example 123

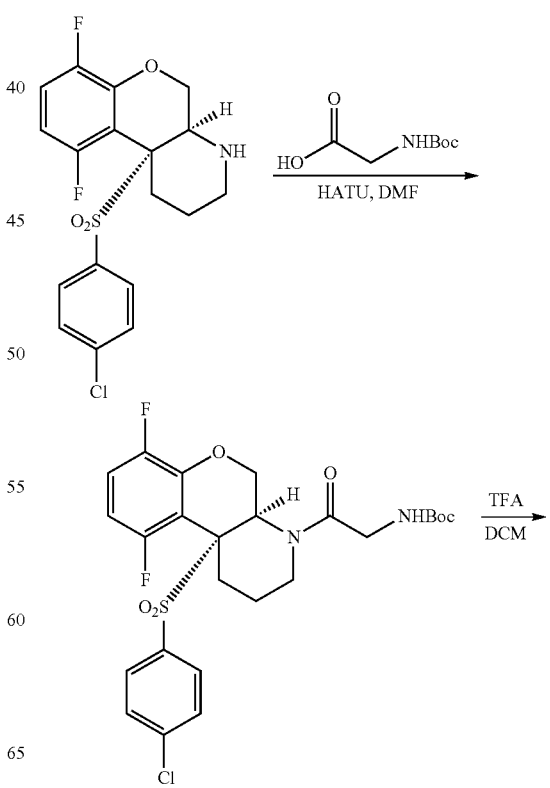

-continued

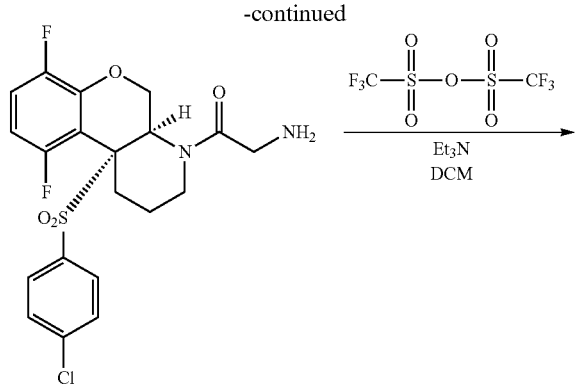

Step 1

{2-[4a-(4-Chloro-benzenesulfonyl-5,8-difluoro-2,3,4,4a,10,10a-hexahydro-9-oxa-1-aza-phenanthren-1-yl]-2-oxo-ethyl}-carbamic acid tert-butyl ester

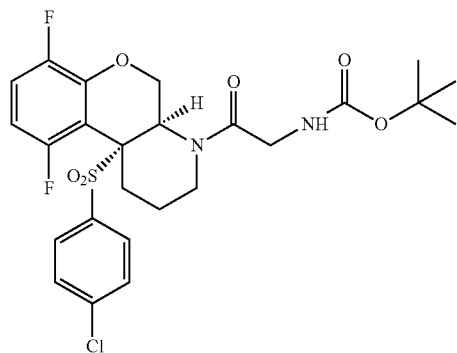 [SMILES: CC(C)(C)OC(=O)NCC(=O)N1CCC[C@@]2(S(=O)(=O)c3ccc(Cl)cc3)c3c(F)ccc(F)c3OC[C@@H]12]

BOC-Glycine was dissolved in 150 ml of DMF. 0.5 ml of diisopropylamine was added followed by HATU (2.54 g, 6.68 mmol). The solution was stirred at room temperature for 25 minutes then 4a-(4-Chloro-benzenesulfonyl)-5,8-difluoro-2,3,4,4a, 10,10a-hexahydro-1H-9-oxa-1-aza-phenanthrene (541 mg, 1.35 mmol) was added and the reaction was stirred overnight. The reaction was quenched with water and washed with 1:1 mixture of ethyl acetate and hexanes solution. The organic layer was dried over sodium sulfate and concentrated. The product was purified by column using EtOAc/Hex. as the eluent (0/100 to 25/75 in 35 minutes). Yield: 594.6 mg, 79%. $^1$H NMR (CDCl$_3$ 400 MHz) δ 7.57 (d, J=8.8 Hz, 2H), 7.41 (d, J=8.8 Hz, 2H), 7.03 (td, J=8.8, 4.4 Hz, 1H), 6.57-6.49 (m, 1H), 5.60-5.55 (m, 1H), 5.35 (bs, 1H), 4.49 (dd, J=11.7, 3.7 Hz, 1H), 4.18 (dd, J=11.7, 5.9 Hz, 1H), 4.00 (s, 1H), 3.90 (d, J=5.1 Hz, 1H), 3.54 (bs, 1H), 2.95-2.80 (m, 1H), 2.65-2.56 (m, 1H), 2.52-2.41 (m, 1H), 2.13-1.98 (m, 1H), 1.51-1.40 (m, 1H), 1.40 (s, 9H).

Step 2

2-Amino-1-[4a-(4-chloro-benzenesulfonyl)-5,8-difluoro-2,3,4,4a,10,10a-hexahydro-9-oxa-1-aza-phenanthren-1-yl]-ethanone

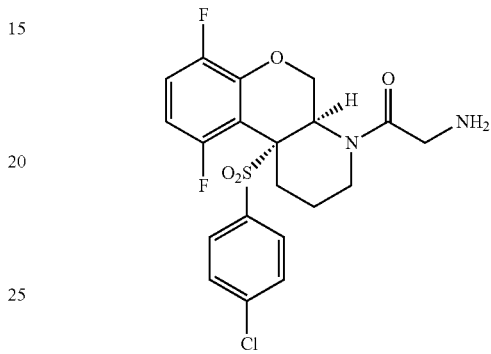

Trifluoroacetic acid (2 mL, 27.0 mmol) was dissolved in 16 ml of dichloromethane. The solution was added to {2-[4a-(4-Chloro-benzenesulfonyl)-5,8-difluoro-2,3,4,4a,10,10a-hexahydro-9-oxa-1-aza-phenanthren-1-yl]-2-oxo-ethyl}-carbamic acid tert-butyl ester (260 mg, 0.467 mmol). The solution was stirred at room temperature overnight. The reaction was quenched by washing with Sat. sodium carbonate solution. The organic layer was dried over sodium sulfate and concentrated. Yield: 20.0 mg, 9%. $^1$H NMR (CDCl$_3$ 400 MHz) δ 7.62 (d, J=8.1 Hz, 2H), 7.45 (d, J=8.8 Hz, 2H), 7.06 (td, J=8.8, 4.4 Hz, 1H), 6.61-6.52 (m, 1H), 5.41 (bs, 1H), 4.52 (dd, J=11.0, 3.7 Hz, 1H), 4.21 (dd, J=11.7, 5.1 Hz, 1H), 3.53 (bs, 2H), 2.86 (bs, 1H), 2.70-2.61 (m, 1H), 2.55-2.45 (m, 1H), 2.15-2.03 (m, 1H), 1.75-1.44 (m, 4H).

Step 3

N-{2-[4a-(4-Chloro-benzenesulfonyl)-5,8-difluoro-2,3,4,4a,10,10a-hexahydro-9-oxa-1-aza-phenanthren-1-yl]-2-oxo-ethyl}-C,C,C-trifluoro-methane-sulfonamide

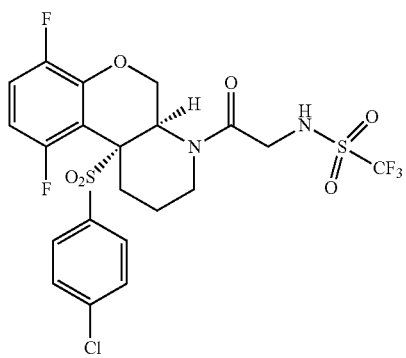 [SMILES: O=C(CNS(=O)(=O)C(F)(F)F)N1CCC[C@@]2(S(=O)(=O)c3ccc(Cl)cc3)c3c(F)ccc(F)c3OC[C@@H]12]

2-Amino-1-[4a-(4-chloro-benzenesulfonyl)-5,8-difluoro-2,3,4,4a,10,10a-hexahydro-9-oxa-1-aza-phenanthren-1-yl]-ethanone (40.0 mg, 0.0875 mmol) was dissolved in 1 ml of dichloromethane and triethylamine (1 ml) and trifluorosulfonic anhydride (343 mg, 1.54 mmol) were added respectively. The solution was stirred at room temperature overnight. 50 ml of 1 N HCl was added and then washed with 50 ml of dichloromethane. The aqueous layer was washed with an additional 50 ml of dichloromethane. The combined organics were dried over sodium sulfate and concentrated. The product was purified by column using EtOAc/Hex. as the eluent (0/100 to 100/0 in 35 minutes). Yield: 35.2 mg, 68%. $^1$H NMR (CDCl$_3$ 400 MHz) δ 7.60 (d, J=8.1 Hz, 2H), 7.47-7.41 (m, 1H), 7.07 (td, J=9.50, 4.4 Hz, 1H), 6.62-6.53 (m, 2H), 5.40 (bs, 1H), 4.52 (dd, J=11.7, 3.7 Hz, 1H), 4.26-4.12 (m, 2H), 3.44 (bs, 1H), 2.95 (bs, 1H), 2.71-2.59 (m, 1H), 2.61-2.50 (m, 1H), 2.20-2.06 (m, 1H), 1.70 (bs, 2H), 1.61-1.49 (m, 1H).

The compounds in Table 37 were made following similar procedures to those of Example 123.

TABLE 37

| No. Ex. | Structure | LCMS (M + 1, retention time) |
|---|---|---|
| 124 | | 557.3, 4.54 Min |
| 125 | | 457.3, 2.93 Min |
| 126 | 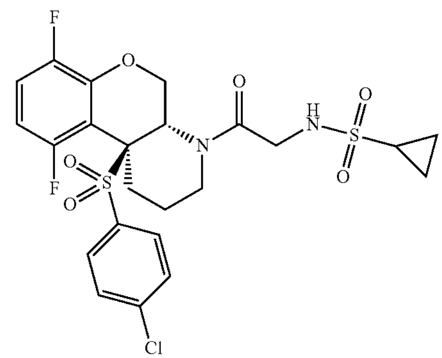 [SMILES: O=C(CNS(=O)(=O)C1CC1)N1CCC[C@]2(S(=O)(=O)c3ccc(Cl)cc3)c3c(F)ccc(F)c3OC[C@H]12] | 561.3, 3.99 Min. |
| 127 | 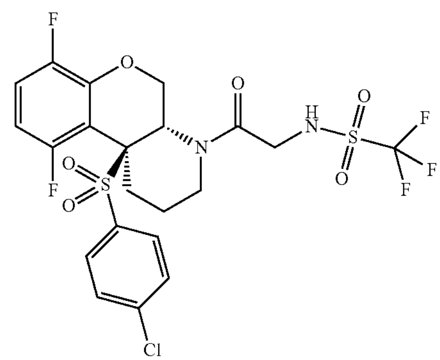 [SMILES: O=C(CNS(=O)(=O)C(F)(F)F)N1CCC[C@]2(S(=O)(=O)c3ccc(Cl)cc3)c3c(F)ccc(F)c3OC[C@H]12] | 589.3, 4.38 Min. |
| 128 | 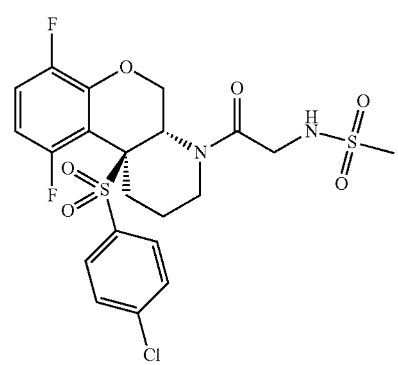 [SMILES: CS(=O)(=O)NCC(=O)N1CCC[C@]2(S(=O)(=O)c3ccc(Cl)cc3)c3c(F)ccc(F)c3OC[C@H]12] | 535.3, 4.00 Min. |
| 129 | 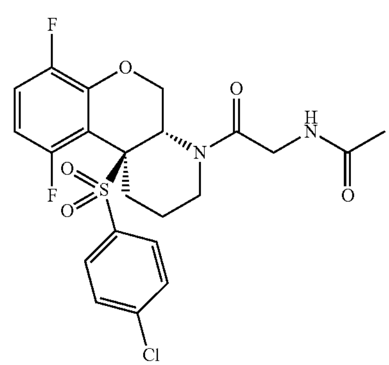 [SMILES: CC(=O)NCC(=O)N1CCC[C@]2(S(=O)(=O)c3ccc(Cl)cc3)c3c(F)ccc(F)c3OC[C@H]12] | 499.3, 3.65 Min. |

TABLE 37-continued
| No. Ex. | Structure | LCMS (M + 1, retention time) |
|---|---|---|
| 130 | 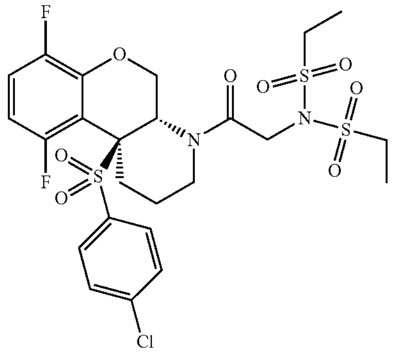 [SMILES: CCS(=O)(=O)N(CC(=O)N1CCC[C@]2(S(=O)(=O)c3ccc(Cl)cc3)c3c(F)ccc(F)c3OC[C@H]12)S(=O)(=O)CC] | 641.4, 4.46 Min. |
| 131 | 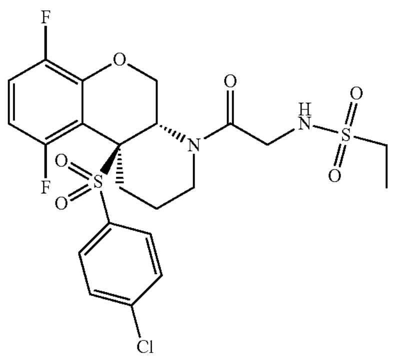 [SMILES: CCS(=O)(=O)NCC(=O)N1CCC[C@]2(S(=O)(=O)c3ccc(Cl)cc3)c3c(F)ccc(F)c3OC[C@H]12] | 549.3, 3.91 Min. |
| 132 | 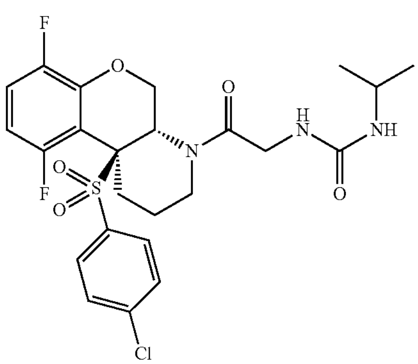 [SMILES: CC(C)NC(=O)NCC(=O)N1CCC[C@]2(S(=O)(=O)c3ccc(Cl)cc3)c3c(F)ccc(F)c3OC[C@H]12] | 542.3, 4.03 Min |
Example 133
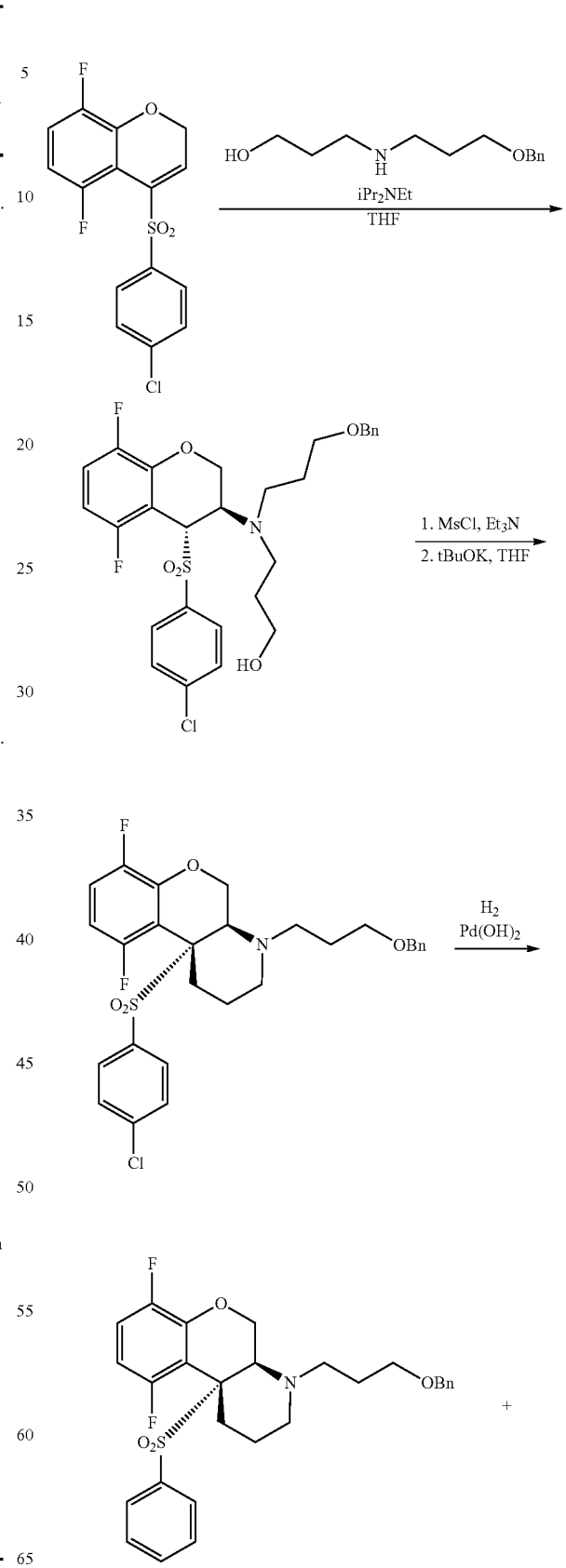
A -continued

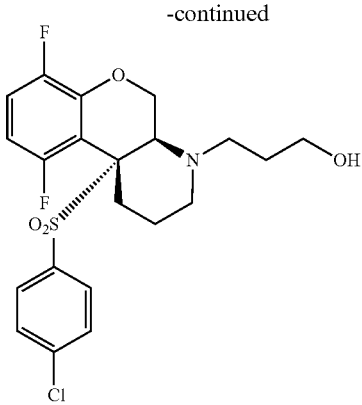

C

Step 1

3-{(3-Benzyloxy-propyl-[4-(4-chloro-benzenesulfonyl)-5,8-difluoro-chroman-3-yl]-amino}-propan-1-ol

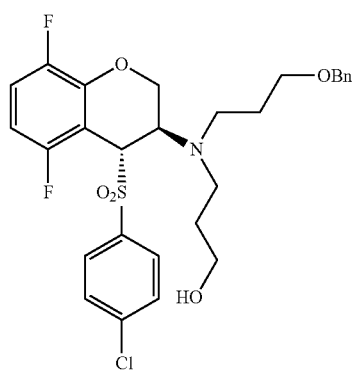 [SMILES: O=S(=O)(c1ccc(Cl)cc1)[C@@H]1c2c(F)ccc(F)c2OC[C@H]1N(CCCO)CCCOCc1ccccc1]

Benzyl 3-bromopropyl ether (7.8475 g, 34.27 mmol) was dissolved in 50 ml of THF then 3-aminopropanol (2.56 g, 34.13 mmol) was added the reaction was stirred at room temperature for three days. The reaction was quenched with 100 ml of Sat. potassium carbonate solution and the solution was washed with ethyl acetate. The organic layer washed with Sat. potassium carbonate solution (2×100 mL) then dried over sodium sulfate and concentrated. This amine solution was used without any further purification. The amine solution (3.91 g, 17.5 mmol) was dissolved in 100 ml of THF. 4-(4-Chloro-benzenesulfonyl)-5,8-difluoro-2H-chromene (2.0486 g, 5.97 mmol) was added and the reaction was stirred at room temperature overnight. Triethylamine (3 ml) was added and the reaction was stirred at room temperature for 2 h. Then additional amine solution (2.85 g, 12.8 mmol) was added and the reaction was stirred overnight at room temperature then warmed to reflux and stirred overnight. The reaction was quenched with water (100 ml) and washed with ethyl acetate (100 ml). The organic layer was dried over sodium sulfate and concentrated. The product was purified by column using EtOAc/Hex. as the eluent (gradient from 0/100 to 100/0 in 45 minutes). Yield: 570 mg, 17%. $^1$H NMR (CDCl$_3$ 400 MHz) δ7.64-7.59 (m, 2H), 7.45-7.40 (m, 2H), 7.36-7.25 (m, 5H), 7.00 (td, J=9.5, 5.1 Hz, 1H), 6.42 (td, J=8.8, 3.7 Hz, 1H), 4.74 (dd, J=12.4, 5.1 Hz, 1H), 4.65 (s, 1H), 4.42 (s, 2H), 4.32-4.26 (m, 1H), 4.06-4.01 (m, 1H), 3.59 (t, J=5.4 Hz, 2H), 3.41 (t, J=5.9 Hz, 2H), 2.87 (bs, 1H), 2.71-2.53 (m, 3H), 2.50-2.42 (m, 1H), 1.74-1.62 (m, 3H), 1.60-1.50 (m, 1H).

Step 2

1-(3-Benzyloxy-propyl)-4-a-(4-chloro-benzenesulfonyl)-5,8-difluoro-2,3,4,4a,10,10a-hexahydro-1H-9-oxa-1-aza-phenanthrene

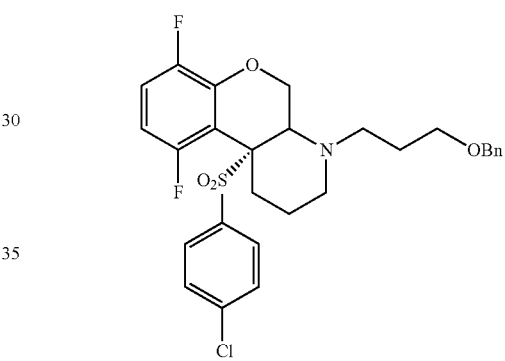

3-{(3-Benzyloxy-propyl)-[4-(4-chloro-benzenesulfonyl)-5,8-difluoro-chroman-3-yl]amino}-propan-1-ol (570 mg, 1.01 mmol) was dissolved in 50 ml of DCM methanesulfonyl chloride (439 μL, 5.68 mmol) and triethylamine (2 ml) were added respectively. The reaction was stirred at room temperature for 1 h. The reaction was quenched with 50 ml of water and washed with 50 ml of DCM. The organic layer was dried over sodium sulfate and concentrated. The Methanesulfonic acid 3-{(3-benzyloxy-propyl)-[4-(4-chloro-benzenesulfonyl)-5,8-difluoro-chroman-3-yl]-amino}-propyl ester was used without further purification.

The Methanesulfonic acid 3-{(3-benzyloxy-propyl)-[4-(4-chloro-benzenesulfonyl)-5,8-difluoro-chroman-3-yl]-amino}-propyl ester was dissolved in 60 mL of THF then potassium tertbutoxide (1 M solution in tertbutanol, 3.27 ml, 3.27 mmol) was added and the reaction was stirred at room temperature for 1 h. The reaction was quenched with 100 ml of brine and 100 ml of ethyl acetate. The layers were separated and the organic layer was dried over sodium sulfate then concentrated. The product was purified by column using EtOAc/Hex. as the eluent (gradient from 0/100 to 100/0 in 35 minutes). Yield: 438.8 mg, 80. $^1$H NMR (CDCl$_3$ 400 MHz) δ7.61 (d, J=8.1 Hz, 2H), 7.48 (d, J=8.8 Hz, 2H), 7.37-7.24 (m, 5H), 7.04 (td, 9.5, 5.1 Hz, 1H), 6.43-6.36 (m, 1H), 5.14 (d, J=12.4 Hz, 1H), 4.72 (d, J=13.9 Hz, 1H), 4.47 (dd, J=28.5, 11.7 Hz, 2H), 3.42 (t, J=6.2 Hz, 2H), 3.29 (s, 1H), 2.90-2.82 (m, 2H), 2.82-2.75 (m, 1H), 2.57 (d, 12.4 Hz, 1H), 2.45 (td, J=11.7, 2.2 Hz, 1H), 2.03-1.93 (m, 1H), 1.83-1.64 (m, 2H), 1.63-1.59 (m, 1H), 1.36-1.23 (m, 1H).

Step 3

3-[4a-(4-Chloro-benzenesulfonyl)-5,8-difluoro-2,3,4, 4a,10,10a-hexahydro-9-oxa-1-aza-phenanthren-1-yl]-propan-1-ol

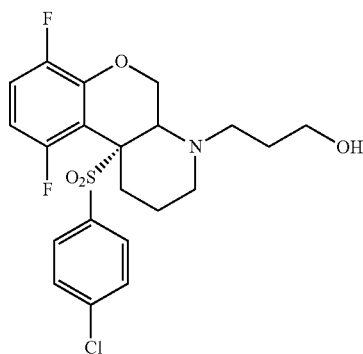 [SMILES: O=S(=O)(c1ccc(Cl)cc1)[C@@]12CCCN(CCCO)C1COc1c(F)ccc(F)c12]

1-(3-Benzyloxy-propyl)-4-a-(4-chloro-benzenesulfonyl)-5,8-difluoro-2,3,4,4a, 10,10a-hexahydro-1H-9-oxa-1-aza-phenanthrene (399.1 mg, 0.728 mmol) was dissolved in 20 ml of ethyl acetate. Palladium hydroxide (20% on carbon, 105 mg) was added and the system was purged with hydrogen gas. The reaction was stirred at room temperature for 1.5 h. More palladium hydroxide on carbon was added (203 mg) The reaction was stirred at room temperature for 3.5 h. Palladium hydroxide (307 mg) was added again and stirred for 1 h. The reaction was filter through a celite cake and concentrated. The product was purified by column using Hex./EtOAc as the eluent (gradient from 100/0 to 50/50 in 35 minutes, then to 0/100). This resulted in three products the desired product and two dechloronation products.

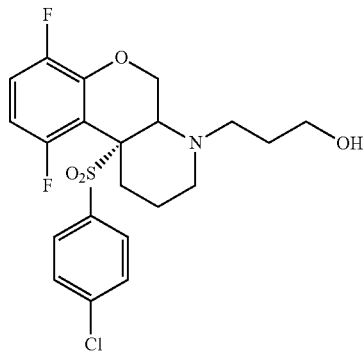 [SMILES: O=S(=O)(c1ccc(Cl)cc1)[C@@]12CCCN(CCCO)C1COc1c(F)ccc(F)c12]

3-[4a-(4-Chloro-benzenesulfonyl)-5,8-difluoro-2,3,4,4a, 10,10a-hexahydro-9-oxa-1-aza-phenanthren-1-yl]-propan-1-ol: Yield: 14.8 mg, 4.4%. $^1$H NMR (CDCl$_3$ 400 MHz) δ7.62 (d, J=8.1 Hz, 2H), 7.50 (d, J=8.1 Hz, 2H), 7.06 (td, 9.5, 4.4 Hz, 1H), 6.46-6.38 (m, 1H), 5.21 (d, J=13.2 Hz, 1H), 4.81 (d, J=13.2 Hz, 1H), 3.68-3.55 (m, 2H), 3.22 (s, 1H), 3.20-3.11 (m, 1H), 3.05 (d, J=11.0 Hz, 1H), 2.70 (s, 1H), 2.61-2.53 (m, 2H), 2.25 (td, J=11.7, 2.9 Hz, 1H), 2.02 (tt, J=13.2, 3.2 Hz, 1H), 1.85-1.74 (m, 1H), 1.69-1.56 (m, 2H), 1.35-1.22 (m, 1H).

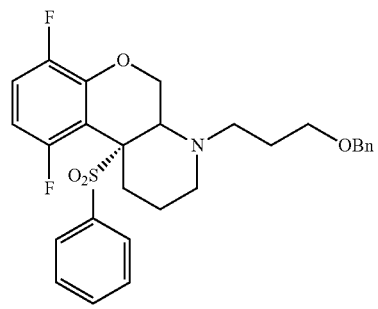 [SMILES: O=S(=O)(c1ccccc1)[C@@]12CCCN(CCCOCc3ccccc3)C1COc1c(F)ccc(F)c12]

4a-Benzenesulfonyl-1-(3-benzyloxy-propyl)-5,8-difluoro-2,3,4,4a,10,10a-hexahydro-1H-9-oxa-1-aza-phenanthrene: Yield: 7.1 mg, 1.9%. $^1$H NMR (CDCl$_3$ 400 MHz) δ7.68 (t, J=8.4 Hz, 3H), 7.69 (t, J=7.7 Hz, 2H), 7.37-7.25 (m, 5H), 7.02 (td, J=9.5, 5.1 Hz, 1H), 6.42-6.34 (m, 1H), 5.19 (d, J=13.2 Hz, 1H), 4.72 (d, J=13.2 Hz, 1H), 4.47 (dd, J=28.6, 11.7 Hz, 2H), 3.42 (t, J=6.2 Hz, 2H), 3.27 (s, 1H), 2.90-2.83 (m, 2H), 2.78 (d, J=5.9 Hz, 1H), 2.62 (d, J=5.9 Hz, 1H), 2.45 (td, J=11.7, 2.2 Hz, 1H), 1.99 (tt, J=13.1, 2.9 Hz, 1H), 1.82-1.64 (m, 2H), 1.62-1.56 (m, 1H), 1.36-1.23 (m, 1H).

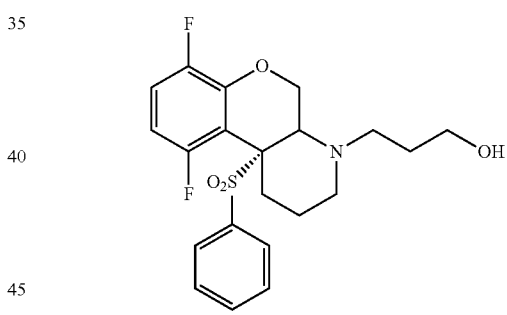

3-(4a-Benzenesulfonyl-5,8-difluoro-2,3,4,4a,10,10a-hexahydro-9-oxa-1-aza-phenanthren-1-yl)-propan-1-ol: Yield: 17.9 mg, 1.9%. $^1$H NMR (CDCl$_3$ 400 MHz) δ7.68 (t, J=8.8 Hz, 3H), 7.51 (t, J=7.7 Hz, 2H), 7.05 (td, J=9.5, 5.1 Hz, 1H), 6.44-6.34 (m, 1H), 5.24 (d, J=13.2 Hz, 1H), 4.81 (d, J=13.9 Hz, 1H), 3.68-3.54 (m, 2H), 3.22 (s, 1H), 3.20-3.10 (m, 1H), 3.04 (d, J=10.9 Hz, 1H), 2.83 (bs, 1H), 2.64-2.53 (m, 2H), 2.25 (td, J=11.7, 2.2 Hz, 1H), 2.02 (tt, J=13.1, 3.3 Hz, 1H), 1.85-1.73 (m, 1H), 1.67-1.55 (m, 2H), 1.37-1.22 (m, 1H).

The compounds in Table 38 were prepared via a similar procedure to that of Example 133.

TABLE 38
| Ex. No. | Structure | LCMS (M + 1, retention time) |
|---|---|---|
| 134 | 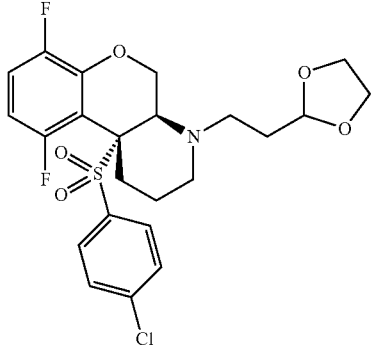 [SMILES: O=S(=O)(c1ccc(Cl)cc1)[C@@]12CCCN(CCC3OCCO3)[C@@H]1COc1c(F)ccc(F)c12] | 500,3, 3.27 Min |
| 135 | 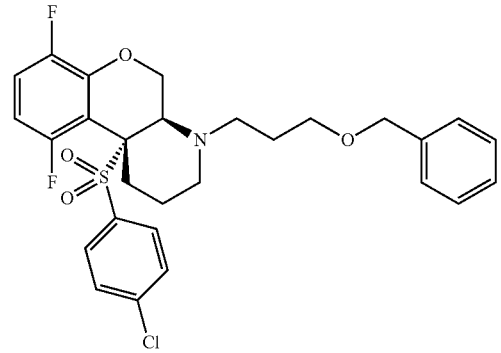 [SMILES: O=S(=O)(c1ccc(Cl)cc1)[C@@]12CCCN(CCCOCc3ccccc3)[C@@H]1COc1c(F)ccc(F)c12] | 548.3, 4.10 Min |
| 136 | 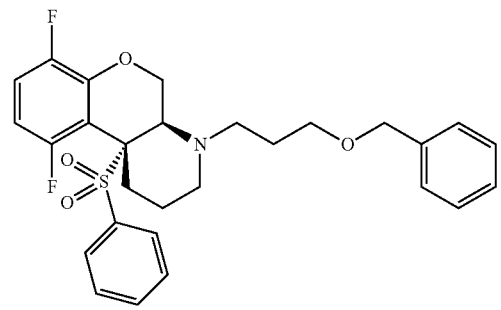 [SMILES: O=S(=O)(c1ccccc1)[C@@]12CCCN(CCCOCc3ccccc3)[C@@H]1COc1c(F)ccc(F)c12] | 514.3, 3.78 Min |
| 137 | 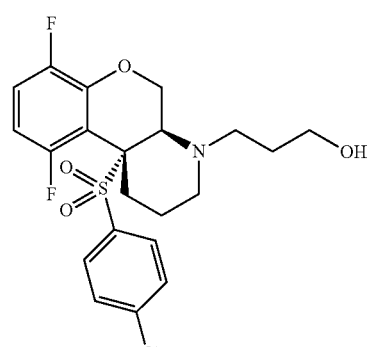 | 458.3, 3.01 Min |

TABLE 38-continued

| Ex. No. | Structure | LCMS (M + 1, retention time) |
|---|---|---|
| 138 | 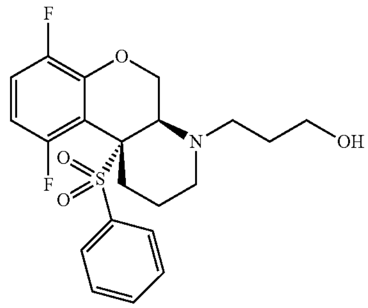 [SMILES: O=S(=O)(c1ccccc1)[C@@]12CCCN(CCCO)[C@@H]1COc1c(F)ccc(F)c12] | 424.2, 2.65 Min |

Example 139

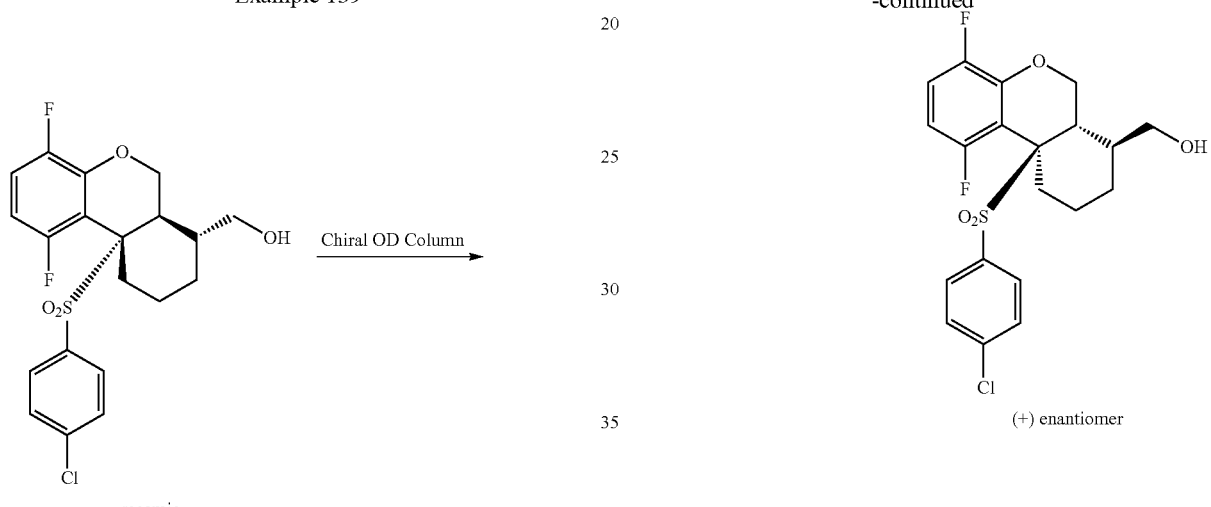

Step 1

[4a-(4-Chloro-benzenesulfonyl)-5,8-difluoro-1,2,3,4,4a,9,10,10a-octahydro-phenanthren-1-yl]-methanol (+) and (−) enantiomers

[4a-(4-Chloro-benzenesulfonyl)-5,8-difluoro-1,2,3,4,4a,9,10,10a-octahydro-phenanthren-1-yl]-methanol racemic mixture (1.11 g, 2.59 mmol) was dissolved in isopropanol separated on an OD column using Hexanes/isopropanol in an 80/20 ratio as the eluent.

[4a-(4-Chloro-benzenesulfonyl)-5,8-difluoro-1,2,3,4,4a, 9,10,10a-octahydro-phenanthren-1-yl]-methanol (−): Yield: 470 mg, 42%. [α]=−153.4 (c=1.035 in DCM). 98.3% enantiomerically pure by analytical OJ column.

[4a-(4-Chloro-benzenesulfonyl)-5,8-difluoro-1,2,3,4,4a, 9,10,10a-octahydro-phenanthren-1-yl]-methanol (+): Yield: 450 mg, 41%. [α]=+158.6 (c=0.955 in DCM). 97.9% enantiomerically pure by analytical OJ column.

TABLE 39

| Ex. No. | Structure | LCMS (M + 1, retention time) |
| --- | --- | --- |
| 139 (−)-enantiomer | (−) enantiomer | 429.2, 4.41 Min |
| 139 (+)-enantiomer | (+) enantiomer | 429.2, 4.41 Min |

TABLE 40

| Ex. No. | Structure | LCMS (M + 1, retention time) |
| --- | --- | --- |
| 140 | 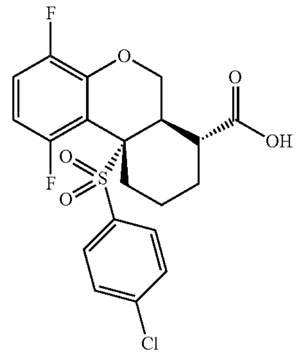 [SMILES: O=C(O)[C@@H]1CCC[C@@]2(S(=O)(=O)c3ccc(Cl)cc3)c3c(F)ccc(F)c3OC[C@@H]12] | 443.2, 4.35 Min |
| 141 | (−) | 560.3, 4.99 Min |
| 142 | (−) | 574.3, 4.59 Min |
| 143 | (−) | No M + 1, 4.43 Min |

Examples 140-148

The compounds in Table 40 were prepared using a similar procedure to that of Example 139.

TABLE 40-continued

| Ex. No. | Structure | LCMS (M + 1, retention time) |
|---|---|---|
| 144 | [Structure: 5,8-difluoro chroman with SO2-(4-chlorophenyl), CH2-NH-SO2-ethyl, (−)] | 520.3, 4.36 Min |
| 145 | [Structure: 5,8-difluoro chroman with SO2-(4-chlorophenyl), CH2-NH-SO2-CF3, (−)] | 524.3, 4.66 Min |
| 146 | [Structure: 5,8-difluoro chroman with SO2-(4-chlorophenyl), CH2-NH-C(O)-CH3, (−)] | 470.3, 3.98 Min |
| 147 | [Structure: 5,8-difluoro chroman with SO2-(4-chlorophenyl), CH2-NH-C(O)-NH-ethyl, (−)] | 499.3, 4.09 Min |
| 148 | [Structure: 5,8-difluoro chroman with SO2-(4-chlorophenyl), CH2-NH-SO2-CH3, (−)] | 506.3, 4.41 Min |

Example 149

4-(4-Chloro-benzenesulfonyl)-5,8-difluoro-thiochroman

[Scheme: 2,3,6-trifluorobenzaldehyde + Ph3P=CHCO2CH3, toluene, 50° C. →]

[Scheme: methyl (E)-3-(2,3,6-trifluorophenyl)acrylate, 1. 4-Chlorothiophenol K2CO3, THF; 2. m-cpba, DCM →]

[Scheme: methyl 3-(2,3,6-trifluorophenyl)-3-((4-chlorophenyl)sulfonyl)propanoate, LAH, THF →]

-continued

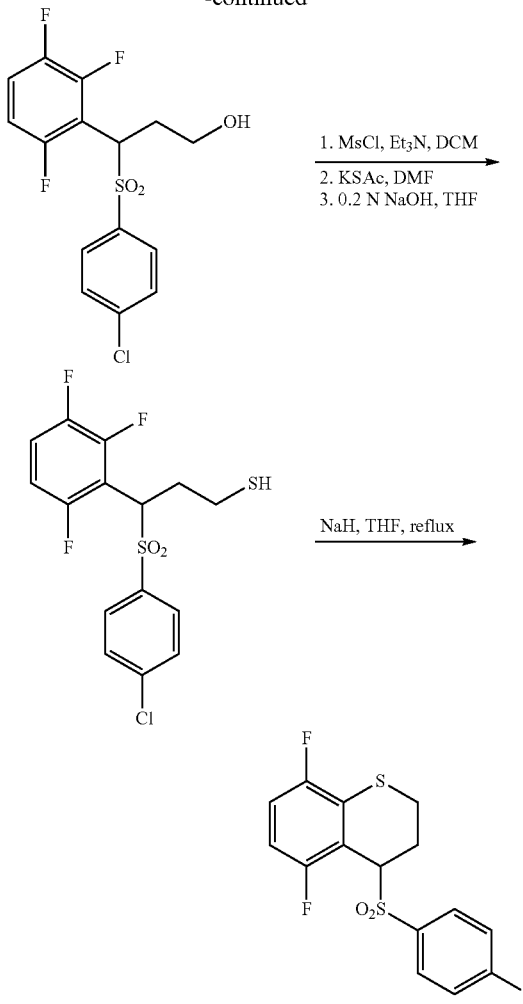

Step 1

To a stirred solution of 2,3,6-trifluorobenzylaldehyde (10 g, 60.6 mmol) in toluene (100 mL) was added 1-triphenyl-phosphoranylidene-2-propanone (24.3 g, 72.7 mmol, 1.2 equiv.), and the reaction mixture was stirred at 50° C. for 3 hrs. It was quenched with water, aqueous layer was extracted with EtOAc (3×100 mL), the combined organic layers were washed with brine, dried over MgSO$_4$, filtered, and evaporated. The crude reaction mixture was purified by the column chromatography (Eluent: EtOAc/Hexane: 10% then 20%) to afford Wittig reaction product (11.47 g, 85% yield). $^1$H-NMR (CDCl$_3$ 400 MHz) δ: 7.74 (d, J=16.84 Hz, 1H), 7.22-7.06 (m, 1H), 6.82-6.67 (m, 1H), 6.77 (d, J=16.84 Hz, 1H), 3.83 (s, 3H).

Step 2

To the α,β-unsaturated ketone (1.948 g, 9.01 mmol) from step 1 in THF (20 mL) was added 4-chlorothiophenol (1.303 g, 9.01 mmol, 1.0 equiv.) and K$_2$CO$_3$ (1.1 g, 7.96 mmol, 0.88 equiv.), the reaction mixture was stirred at room temperature overnight, and the starting material wasn't consumed completely. Followed by addition of excess 4-chlorothiophenol (0.65 g, 0.5 equiv.) and K$_2$CO$_3$ (0.6 g, 0.5 equiv.), the reaction mixture was then stirred at 40° C. for an hour. It was cooled to room temperature, diluted with EtOAc (200 mL), washed with water, 1N NaOH, and brine, dried over MgSO$_4$, filtered, and evaporated. The crude reaction mixture was purified with column chromatography (Eluent: EtOAc/Hexane: 5% to 50%), and the product was still contaminated with certain thiophenol. $^1$H-NMR (CDCl$_3$ 400 MHz) δ: 7.31 (d, J=8.4 Hz, 2H), 7.26-7.20 (2H), 7.03-6.98 (m, 1H), 6.75-6.73 (m, 1H), 4.95 (t, J=8.05 Hz, 1H), 3.65 (s, 3H), 3.13 (d, J=8.05 Hz, 2H).

To the Michael adduct product from the above step in DCM (150 mL) was added m-cpba, it was stirred at room temperature for 2 hrs, and quenched with saturated Na$_2$S$_2$O$_3$ to reduce the excess m-cpba. The reaction mixture was then washed with 1N NaOH and brine, dried over MgSO$_4$, filtered, and evaporated. The crude reaction mixture was purified by the column chromatography (Eluent: EtOAc/Hexane=10% to 100%), and sulfoxide was obtained (1.443 g, 3.67 mmol, 41% for two steps.) $^1$H-NMR (CDCl$_3$ 400 MHz) δ: 7.65 (d, J=7.6 Hz, 2H), 7.47 (d, J=8.0 Hz, 2H), 7.20-7.10 (m, 1H), 6.90-6.70 (broad s, 1H), 5.16 (t, J=7.4 Hz, 1H), 3.66 (s, 3H), 3.52 (dd, J=6.0, 17.6 Hz, 1H), 3.32 (dd, J=8.8, 17.6 Hz, 1H).

Step 3

To the sulfoxide from step 2: (1.35 g, 3.44 mmol) in THF (15 mL) was added LAH in Et$_2$O (1.0 M, 6.9 mL, 2.0 equiv.) dropwise at 0° C., it was stirred for an hr at this temperature. The reaction was quenched with saturated NaHCO$_3$, extracted with EtOAc (3×100 mL), the combined organic layers were washed with brine, dried over MgSO$_4$, filtered, and evaporated. The crude reaction mixture was obtained (1.289 g, quantitative.). $^1$H-NMR (CDCl$_3$ 400 MHz) δ: 7.63 (d, J=8.4 Hz, 2H), 7.44 (d, J=8.4 Hz, 2H), 7.16-7.10 (m, 1H), 6.90-6.68 (m, 1H), 6.92 (dd, J=5.6, 9.4 Hz, 1H), 3.87 (m, 1H), 3.47 (m, 1H), 2.70-2.50 (m, 2H).

Step 4

To the alcohol from step 3 (0.849 g, 2.33 mmol) in DCM (50 mL) at 0° C. was added Et$_3$N (0.65 mL, 0.471 g, 4.65 mmol, 2.0 equiv.) and MsCl (0.27 mL, 0.399 g, 3.49 mmol, 1.5 equiv.) respectively in the presence of molecule sieves, it was stirred at 0° C. for 50 mins, and quenched with 1.0 mL of CH$_3$OH. It was filtered through a pad of Celite, the filtrate was diluted with DCM (100 mL), washed with brine, dried over MgSO$_4$, filtered, and evaporated. The crude reaction mixture was obtained (1.215 g, quantitative.). $^1$H-NMR (CDCl$_3$ 400 MHz) δ: 7.63 (d, J=8.8 Hz, 2H), 7.46 (d, J=7.2 Hz, 2H), 7.22-7.15 (m, 1H), 6.96-6.67 (m, 1H), 4.81 (dd, J=5.6, 9.6 Hz, 1H), 4.48 (m, 1H), 4.13 (m, 1H), 3.14-3.05 (m, 1H), 2.95 (s, 3H), 2.84-2.70 (m, 1H). The Mesylate (2.33 mmol) from previous step and KSAc (1.064 g, 9.32 mmol, 4.0 equiv.) in DMF was stirred at 90° C. for 30 mins. It was cooled to room temperature, diluted with EtOAc (100 mL), and washed with water. The aqueous phase was extracted with EtOAc (3×50 mL), the combined organic phase was washed with water and brine, dried over MgSO$_4$, filtered, and evaporated. The crude reaction mixture was purified by the column chromatography. (Eluent: EtOAc/Hexane=5% to 50%), and the thioacetate was obtained (0.848 g, 2.00 mmol, 86% for two steps). $^1$H-NMR (CDCl$_3$ 400 MHz) δ: 7.62 (d, J=8.0 Hz, 2H), 7.45 (d, J=8.0 Hz, 2H), 7.21-7.10 (m, 1H), 6.90-6.70 (m, 1H), 4.74-4.68 (m, 1H), 3.04-2.94 (m, 1H), 2.85-2.50 (m, 3H), 2.29 (s, 3H).

To the thioacetate (0.542 g) in CH$_3$OH (10 mL) was added 1 N NaOH (10 mL) at 0° C., it was warmed to rt slowly and stirred overnight. The reaction mixture was diluted with EtOAc (100 mL), and acidified with 1 N HCl (12 mL). The aqueous phase was extracted with EtOAc (3×50 mL), the combined organic phase was washed with brine, dried over MgSO$_4$, filtered, and evaporated. The crude reaction residue was subjected to the next ring cyclization directly. $^1$H-NMR (CDCl$_3$ 400 MHz) δ: 7.62 (d, J=8.8 Hz, 2H), 7.45 (d, J=8.8 Hz, 2H), 7.25-7.10 (m, 1H), 6.90-6.70 (m, 1H), 4.85-4.76 (m, 1H), 2.86-2.64 (m, 3H), 2.55-2.40 (m, 1H).

Step 5

To the thiol (0.5 g) from step 4 in THF (30 mL) was added NaH (0.2 g, excess), and it was stirred at 60° C. overnight. The reaction was cooled to room temperature, quenched with saturated NH$_4$Cl, and extracted with EtOAc. The combined organic layers were washed with brine, dried over MgSO$_4$, filtered, and evaporated. The crude reaction mixture was purified by the column chromatography (Eluent: EtOAc/Hexane=2% to 50%), and 4-(4-Chloro-benzenesulfonyl)-5,8-difluoro-thiochroman was obtained (0.176 g, 0.49 mmol, 38% for two steps). $^1$H-NMR (CDCl$_3$ 400 MHz) δ: 7.67 (d, J=8.0 Hz, 2H), 7.48 (d, J=7.2 Hz, 2H), 7.00-6.92 (m, 1H), 6.60-6.50 (m, 1H), 4.68 (s, 1H), 3.87 (dt, J=3.6, 13.2 Hz, 1H), 3.17 (d, J=15.2 Hz, 1H), 3.04 (d, J=12.4 Hz, 1H), 2.04 (t, J=12.8 Hz, 1H).

Example 150

4-(4-Chloro-benzenesulfonyl)-4-ethyl-5,8-difluoro-thiochroman

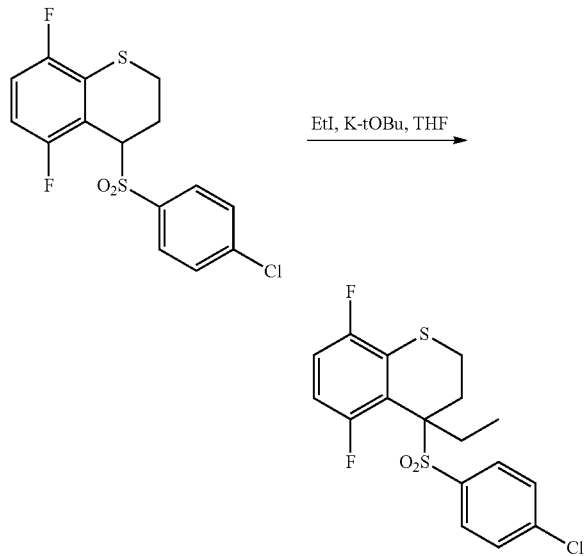

To 4-(4-Chloro-benzenesulfonyl)-5,8-difluoro-thiochroman (0.246 g, 0.68 mmol) in THF (20 mL) was added K-tOBu (1.0 M, 2 mL, 3.0 equiv.) and EtI (0.318 g, 0.16 mmol, 3.0 equiv.) separately. After 20 mins' stirring, TLC showed the completion of the reaction. It was quenched with saturated NH$_4$Cl, diluted with EtOAc, the aqueous layer was extracted with EtOAc (3×20 mL), the combined organic layer was washed with water and brine, dried over MgSO$_4$, filtered, and evaporated. The crude reaction mixture was purified by the column chromatography (Eluent: EtOAc/Hexane=2% to 50%), and ethylated thiochroman was obtained (0.143 g, 0.37 mmol, 54%). $^1$H-NMR (CDCl3 400 MHz) δ: 7.60 (d, J=8.8 Hz, 2H), 7.46 (d, J=8.8 Hz, 2H), 7.00-6.95 (m, 1H), 6.60-6.52 (m, 1H), 3.93 (t, J=13.2 Hz, 1H), 2.92 (dd, J=4.2, 12.6 Hz, 1H), 2.82 (d, J=15.2 Hz, 1H), 2.70-2.48 (m, 1H), 2.33 (dt, J=4.0, 14.4 Hz, 1H), 1.92-1.80 (m, 1H), 0.775 (t, J=7.4 Hz, 3H).

Example 151

4-(4-Chloro-benzenesulfonyl-4-ethyl-5,8-difluoro-thiochroman 1-oxide and 4-(4-Chloro-benzenesulfonyl)-4-ethyl-5,8-difluoro-thiochroman 1,1-dioxide

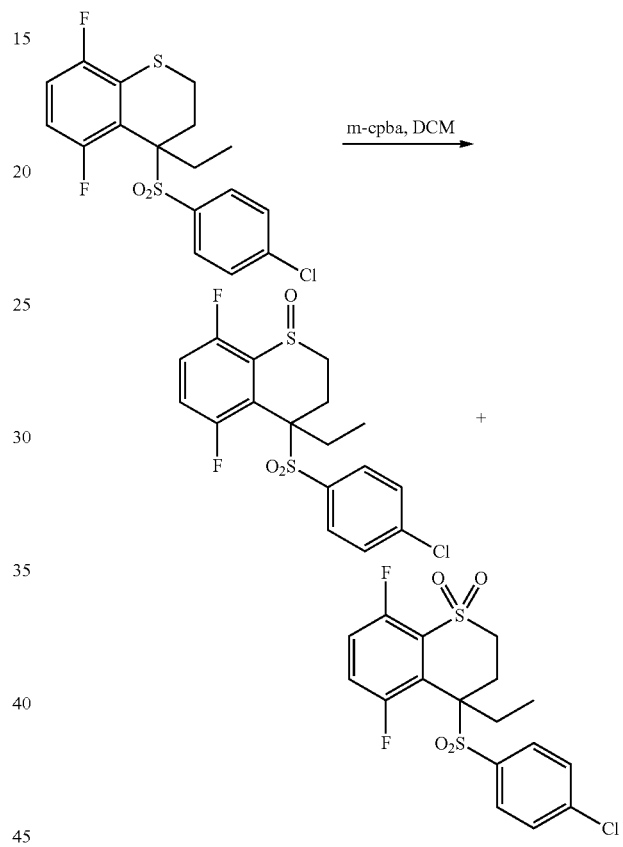

To 4-(4-Chloro-benzenesulfonyl)-4-ethyl-5,8-difluoro-thiochroman (0.119 g, 0.31 mmol) in DCM (20 mL) was added m-cpba (0.137 g, 0.61 mmol, 2.0 equiv.), and it was stirred at room temperature for 1 hr, and TLC showed the consumption of starting material. The reaction was quenched with saturated Na$_s$S$_2$O$_3$, diluted with DCM (100 mL), washed with 1N NaOH (20 mL) and brine, dried over MgSO$_4$, filtered, and evaporated. The crude reaction mixture was purified by the column chromatography (Eluent: EtOAc/hexane=25% to 75%), both sulfone (0.063 g, 0.15 mmol, 48%) and sulfoxide (0.028 g, 0.07 mmol, 22%) were obtained. $^1$H-NMR (CDCl3 400 MHz) for sulfone δ: 7.65 (d, J=8.8 Hz, 2H), 7.53 (d, J=8.8 Hz, 2H), 7.36-7.28 (m, 1H), 7.16-7.08 (m, 1H), 4.70 (td, J=2.9, 14.3 Hz, 1H), 3.40-3.32 (m, 1H), 3.10-3.00 (m, 1H), 2.87 (dt, J=4.1, 8.2 Hz, 1H), 2.70-2.58 (m, 1H), 1.90-1.76 (m, 1H), 0.83 (t, J=7.2 Hz, 3H). $^1$H-NMR (CDCl3 400 MHz) for sulfoxide δ: 7.65 (d, J=8.8 Hz, 2H), 7.53 (d, J=8.0 Hz, 2H), 7.35-7.25 (m, 1H), 7.20-7.10 (m, 1H), 4.05

(td, J=2.8, 14.8 Hz, 1H), 3.30-3.12 (m, 2H), 2.76-2.64 (m, 1H), 2.53 (d, J=16.4 Hz, 1H), 1.89-1.77 (m, 1H), 0.85 (t, J=7.00 Hz, 3H).

Example 152

11b-(4-Chloro-benzenesulfonyl-8,11-difluoro-1,4,4a,5,6,11b-hexahydro-2H-3,7-dioxa-dibenzo[a,c]cycloheptene

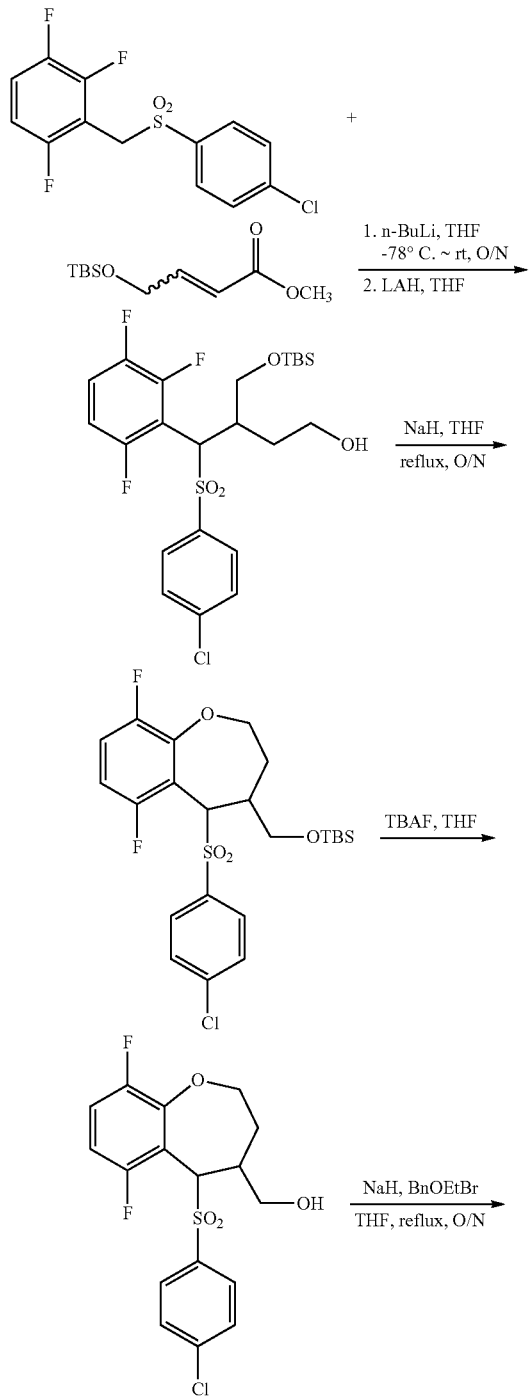

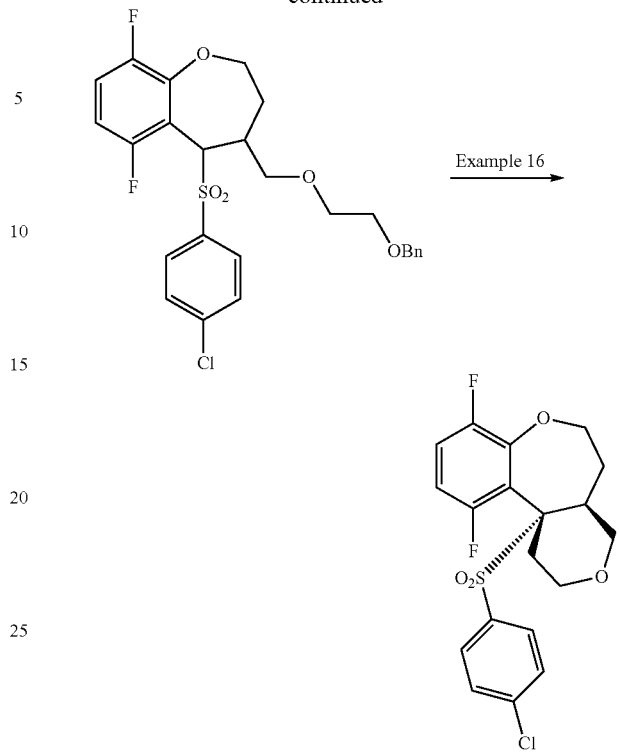

Step 1

At −78° C., to 2-(4-chloro-benzenesulfonylmethyl)-1,3,4-trifluoro-benzene (6.51 g, 20.3 mmol) in THF (100 mL) was added n-BuLi (2.0 M in pentanem 12.2 mL, 24.4 mmol, 1.2 equiv.) dropwise, it was stirred at this temperature for 30 mins, followed by addition of α,β-unsaturated methyl ester. The reaction was warmed to room temperature slowly over the night. It was quenched with water, extracted with EtOAc (3×150 mL), the combined organic layers were washed with brine, dried over MgSO$_4$, filtered, and evaporated. The crude reaction mixture was purified by column chromatography (Eluent: EtOAc/Hexane=5% to 75%), Michael adduct was obtained (2.637 g, 4.78 mmol, 24%) as mixture of diastereomers, and starting material (29%) was recovered. The ester (2.637 g, 4.78 mmol) in THF was treated with LAH (1.0 M in Et$_2$O, 9.6 mL, 2.0 equiv.) at 0° C., it was stirred for an hr., and quenched with saturated NaHCO$_3$. The aqueous phase was extracted with EtOAc (3×100 mL), the combined organic phase was washed with brine, dried over MgSO$_4$, filtered, and evaporated. The crude reaction mixture was separated with the column chromatography (Eluent: EtOAc/Hexane=10% to 50%), and three different fractions were obtained (1.457 g, 58%) and all had the right mass according to LCMS ([M+H]$^+$= 523). $^1$H-NMR (CDCl3 400 MHz) for the first fraction δ: 7.81 (d, J=8.8 Hz, 2H), 7.53 (d, J=7.6 Hz, 2H), 7.01-6.95 (m, 1H), 6.86-6.80 (m, 1H), 4.77 (s, 1H), 4.48 (s, 1H), 4.18-4.04 (m, 1H), 3.96 (t, J=9.6 Hz, 1H), 3.67 (dd, J=5.6, 10.0 Hz, 1H), 3.48 (dd, J=6.8, 10.8 Hz, 1H), 3.31-3.23 (m, 2H), 0.71 (s, 9H), 0.03 (s, 3H), 0.04 (s, 3H). $^1$H-NMR (CDCl3 400 MHz) for the second fraction δ: 7.59 (dd, J=2.8, 8.8 Hz, 2H), 7.37 (d, J=8.0 Hz, 2H), 7.12-6.98 (m, 1H), 6.90-6.48 (m, 1H), 4.87 (d, J=10.4 Hz, 1H), 3.96-3.77 (m, 2H), 3.73 (t, J=102 Hz, 1H), 3.31 (t, J=11.6 Hz, 1H), 3.17-3.02 (m, 1H), 2.60-2.41 (m, 1H), 2.31-2.11 (m, 1H), 0.75 (s, 9H), −0.16 (s, 3H), −0.32 (s, 3H). ¹H-NMR (CDCl3 400 MHz) for the third fraction δ: 7.75-7.45 (m, 2H), 7.44-7.29 (m, 2H), 7.11-6.98 (m, 1H), 6.92-6.52 (m, 1H), 5.09 (t, J=8.2 Hz, 1H), 4.28 (dt, J=3.6, 10.8 Hz, 1H), 3.92-3.80 (m, 1H), 3.72-3.48 (m, 2H), 3.19-3.06 (broad s, 1H), 1.60-1.48 (m, 2H), 0.90 (s, 9H), 0.13 (d, J=5.2 Hz, 3H), 0.10 (d, J=3.2 Hz, 3H).

Step 2

All three fractions from Step 1 in THF were treated with NaH, and the reaction mixture was stirred at 60° C. overnight. It was quenched with saturated NH4Cl, extracted with EtOAc, the combined organic phase was washed with brine, dried over MgSO4, filtered, and evaporated. The crude reaction mixture was purified by the column chromatography (Eluent: EtOAc/Hexane=5% to 50%), all three reactions afford the same ring cyclized product. ¹H-NMR (CDCl3 400 MHz) δ: 7.54 (d, J=8.8 Hz, 2H), 7.39 (d, J=8.4 Hz, 2H), 7.06-7.00 (m, 1H), 6.60-6.54 (m, 1H), 4.93 (d, J=4.4 Hz, 1H), 4.41-4.34 (m, 1H), 3.93-3.87 (m, 1H), 3.70-3.58 (m, 2H), 3.03 (broad s, 1H), 2.58-2.44 (m, 1H), 1.88-1.76 (m, 1H), 0.83 (s, 9H), 0.01 (s, 3H), −0.03 (s, 3H).

Step 3

At 0° C. to the bi-cyclic product (0.552 g, 1.10 mmol) from step 2: in THF (30 mL) was added TBAF (1.0 M in THF, 1.6 mL, 1.5 equiv.) slowly, it was stirred at this temperature for an hour, and quenched with saturated NH4Cl. The aqueous phase was extracted with EtOAc (3×50 mL), the combined organic phase was washed with brine, dried over MgSO4, filtered, and evaporated. The crude reaction mixture was purified by the column chromatography (Eluent: EtOAc/Hexane=5% to 100%), and the alcohol was obtained (0.394 g, 1.01 mmol, 92%). ¹H-NMR (CDCl3 400 MHz) δ: 7.54 (d, J=8.8 Hz, 2H), 7.39 (d, J=8.8 Hz, 2H), 7.05 (dt, J=5.2, 9.0 Hz, 1H), 6.59 (dt, J=3.6, 8.8 Hz, 1H), 4.89 (d, J=4.4 Hz, 1H), 4.40-4.30 (m, 1H), 3.95-3.85 (m, 1H), 3.75 (dd, J=6.2, 10.6 Hz, 1H), 3.66 (dd, J=7.6, 9.2 Hz, 1H), 3.09 (broad s, 1H), 2.48-2.36 (m, 1H), 2.00-1.86 (broad s, 1H, —OH), 1.86-1.74 (m, 1H).

Step 4

To alcohol from step 3 (0.469 g, 1.20 mmol) in THF (20 mL) was added NaH (0.096 g, 2.0 equiv.), it was stirred at room temperature for 30 mins, followed by addition of benzyl 2-bromoethyl ether (0.401 g, 0.30 mL, 1.5 equiv.), and the reaction mixture was stirred under reflux overnight. It was cooled to room temperature, quenched with saturated NH4Cl, and extracted with EtOAc. The combined organic phase was washed with brine, dried over MgSO4, filtered, and evaporated. The crude reaction mixture was purified by the column chromatography (Eluent: EtOAc/Hexane=10% to 75%), and alkylated product was obtained (0.459 g, 0.88 mmol, 73% yield). ¹H-NMR (CDCl3 400 MHz) δ: 7.53 (d, J=8.0 Hz, 2H), 7.35 (d, J=8.8 Hz, 2H), 7.33-7.20 (m, 5H), 7.02 (dt, J=5.2, 8.8 Hz, 1H), 6.55 (dt, J=4.0, 8.8 Hz, 1H), 4.88 (d, J=4.4 Hz, 1H), 4.50 (s, 2H), 4.40-4.30 (m, 1H), 3.91-3.80 (m, 1H), 3.62-3.44 (m, 6H), 3.23-3.12 (m, 1H), 2.65-2.50 (m, 1H), 1.88-1.74 (m, 1H).

Step 5

The product of step 4 was converted to the title compound following the procedures described in Example 16. ¹H-NMR (CDCl3 400 MHz) δ: 7.50 (d, J=8.0 Hz, 2H), 7.41 (d, J=8.4 Hz, 2H), 7.10 (dt, J=4.4, 8.8 Hz, 1H), 6.54 (ddd, J=4.4, 9.2, 13.2 Hz, 1H), 4.50-4.33 (broad s, 1H), 4.28-4.11 (broad s, 1H), 4.10-3.97 (m, 2H), 3.77 (dd, J=7.2, 12.0 Hz, 1H), 3.56-3.39 (broad s, 1H), 3.06-2.98 (m, 1H), 2.80-2.60 (broad s, 1H), 2.57-2.35 (m, 2H), 2.14-2.00 (m, 1H). LCMS (M+1, retention time)=415.2, 4.24 min Example 153

10a-(4-Chloro-benzenesulfonyl)-1,4-difluoro-7-hydroxymethyl-6a,7,8,9,10,10a-hexahydro-6H-benzo[c]chromen-8-ol

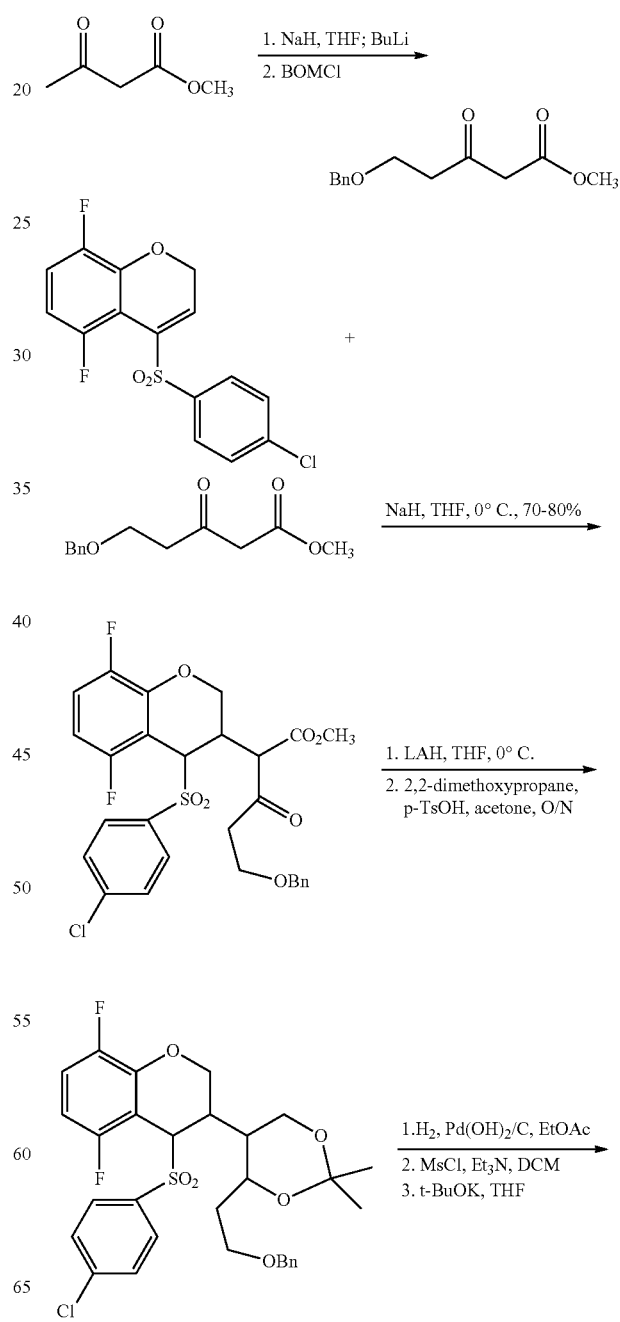

-continued

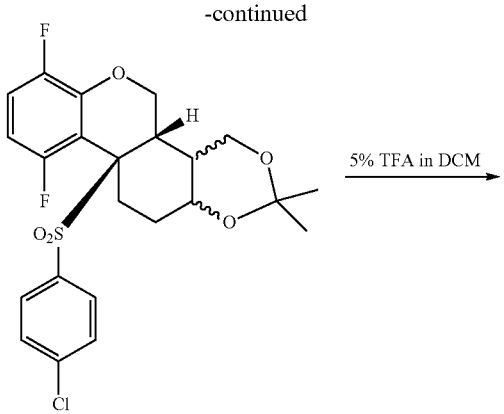

5% TFA in DCM →

-continued

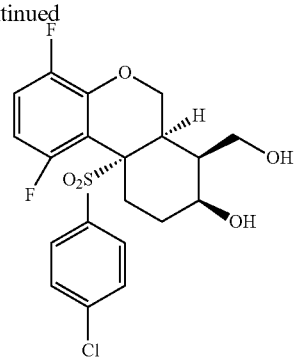

D

Step 1

At 0° C., to a suspension of NaH (3.93 g, 98.3 mmol, 1.06 Equiv.) in THF (100 mL) was added methyl acetoacetate dropwise within 30 mins by syringe pump, it was stirred at this temperature for another 30 mins. The reaction mixture was then cooled to −25° C., and 51 mL of n-BuLi (2.0 M in pentane, 102 mmol, 1.1 Equiv.) was added dropwise by dropping funnel over 15 mins, it was stirred at this temperature for another 30 mins after addition, followed by addition if BOMCl (14.2 mL, 15.98 g, 102.0 mmol, 1.1 Equiv.) slowly. It was stirred at −25° C. for 1 hr., and the reaction was quenched with 100 mL of ice cold 1N HCl. It was diluted with 100 mL of EtOAc, the aqueous phase was extracted with EtOAc (3×100 mL), and the combined organic phases were washed with brine, dried over MgSO$_4$, filtered, and evaporated. The crude reaction mixture was purified by the column chromatography (Eluent: EtOAc/Hexane=10% to 40%), and the pure product was obtained (9.14 g, 38.7 mmol, 41%). $^1$H-NMR (CDCl3 400 MHz) δ: 7.40-7.20 (m, 5H), 4.51 (s, 2H), 3.75 (t, J=6.0 Hz, 2H), 3.72 (s, 3H), 3.51 (s, 2H), 2.83 (t, J=6.0 Hz, 2H).

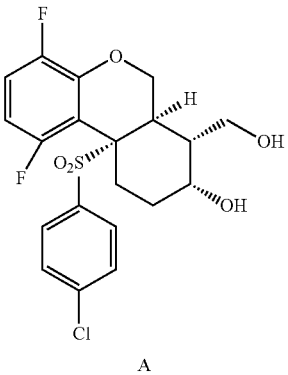

A

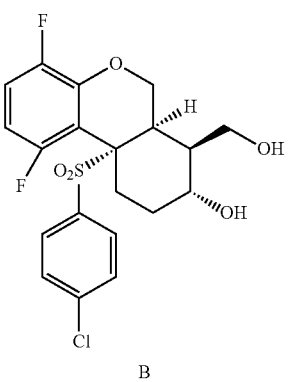

B

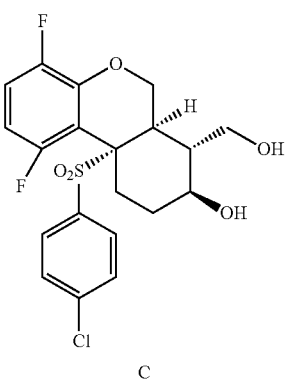

C

Step 2

At 0° C., to the β-keto methylester (3.825 g, 16.2 mmol, 1.05 Equiv.) in THF (100 mL) was added NaH (0.648 g, 16.2 mmol, 1.05 Equiv.), it was stirred at this temperature for 30 mins, followed by addition of vinyl sulfone (5.285 g, 15.4 mmol, 1.0 Equiv.). It was quenched with saturated NH$_4$Cl when starting material was consumed, the aqueous phase was extracted with EtOAc (3×150 mL), and the combined organic phase was washed with brine, dried over MgSO$_4$, filtered, and evaporated. The crude reaction mixture was purified by the column chromatography, and the Michael adduct was obtained (7.21 g, 12.4 mmol, 80%) as diastereomers (ratio: 1/1). $^1$H-NMR (CDCl3 400 MHz) δ: 7.85 (d, J=8.0 Hz, 2H), 7.80 (d, J=9.2 Hz, 2H), 7.56 (d, J=8.8 Hz, 2H), 7.49 (d, J=9.2 Hz, 2H), 7.38-7.22 (m, 8H), 7.18 (d, J=6.8 Hz, 2H), 7.12-6.97 (m, 2H), 6.55 (dt, J=3.66, 8.78 Hz, 1H), 6.48 (dt, J=3.66, 8.78 Hz, 1H), 4.91 (d, J=12.4 Hz, 1H), 4.81 (d, J=12.8 Hz, 1H), 4.51-4.28 (m, 7H), 4.25 (d, J=12.4 Hz, 1H), 3.74-3.65 (m, 5H), 3.61-3.53 (m, 5H), 3.53-3.47 (m, 4H), 2.89-2.75 (m, 2H), 2.72-2.55 (m, 2H).

Step 3

At 0° C., to the Michael adduct (10.59 g, 18.3 mmol, 1.0 equiv.) in THF (200 mL) was added LAH (2.92 g, 73.2 mmol, 4.0 equiv.), it was stirred at this temperature for 2 hrs, and quenched with 1N HCl (50 mL). It was extracted with EtOAc (3×100 mL) and DCM (3×100 mL), the combined organic phase was washed with brine, dried over MgSO$_4$, filtered, and evaporated. The crude reaction mixture was purified by the column chromatography (Eluent: EtOAc/Hexane=30% to 50%), and the diol was obtained (9.42 g, 17.0 mmol, 93%). To the diol (9.42 g, 17.1 mmol) in acetone (200 mL) was added p-TsOH (0.324 g, 1.7 mmol, 10% cat.) and 2,2-dimethoxypropane (1.774 g, 2.1 mL, 170 mmol, 10 equiv.) respectively, it was stirred at room temperature overnight. The reaction was diluted with EtOAc (500 mL), washed with saturated NaHCO$_3$, and extracted with EtOAc (2×100 mL). The combined organic phases were washed with brine, dried over MgSO$_4$, filtered, and evaporated. The crude reaction mixture was purified by the column chromatography (Eluent: EtOAc/Hexane=10% to 25%), and two fraction were obtained (5.66 g, 9.54 mmol, 56% for two steps).

Step 4

The two fractions from Step 3 were treated by the standard ring closure procedure from Example 16.

Step 5

The mixture of acetonide protected tricyclic diols in DCM was treated with TFA (5%) at room temperature for an hr., it was quenched with saturated NaHCO$_3$, extracted with DCM, and the combined organic layers were washed with brine, dried over MgSO$_4$, filtered, and evaporated. The crude reaction mixture was purified by the column chromatography (Eluent: EtOAc/Hexane=35% to 75%). to give four isomers of the title compound. $^1$H-NMR (CDCl3 400 MHz) for A δ: 7.65 (d, J=8.8 Hz, 2H), 7.50 (d, J=8.8 Hz, 2H), 7.12-7.00 (m, 1H), 6.50-6.40 (m, 1H), 5.22 (d, J=12.8 Hz, 1H), 4.55 (d, J=12.4 Hz, 1H), 4.17-4.07 (m, 2H), 3.93 (d, J=11.2 Hz, 1H), 3.28 (d, J=11.6 Hz, 1H), 2.98-2.89 (broad s, 1H), 2.83-2.74 (broad s, 1H), 2.55 (t, J=13.6 Hz, 1H), 2.32 (d, J=13.2 Hz, 1H), 1.74 (dd, J=3.0, 14.4 Hz, 1H), 1.52 (d, J=12.8 Hz, 1H), 1.30 (t, J=14.8 Hz, 1H). $^1$H-NMR (CDCl3 400 MHz) for δ δ: 7.51 (d, J=9.2 Hz, 2H), 7.43 (d, J=8.4 Hz, 2H), 7.08-7.00 (m, 1H), 6.48-6.37 (m, 1H), 5.04 (dd, J=4.0, 11.6 Hz, 1H), 4.17 (dd, J=3.6, 11.6 Hz, 1H), 4.10-4.03 (m, 1H), 3.84 (dd, J=4.0, 10.0 Hz, 1H), 3.29 (dd, J=5.2, 9.6 Hz, 1H), 3.22 (t, J=9.8 Hz, 1H), 2.80 (t, J=13.2 Hz, 1H), 2.45-2.29 (m, 2H), 1.86-1.78 m, 1H), 1.68-1.58 (m, 1H). $^1$H-NMR (CDCl3 400 MHz) for C δ: 7.61 (d, J=8.4 Hz, 2H), 7.50 (d, J=8.4 Hz, 2H), 7.13-7.03 (m, 1H), 6.49-6.39 (m, 1H), 5.17 (dd, J=3.2, 13.2 Hz, 1H), 4.53 (d, J=12.4 Hz, 1H), 4.22 (dd, J=2.92, 10.25 Hz, 1H), 3.89 (dd, J=6.0, 10.8 Hz, 1H), 3.78 (dt, J=4.4, 10.4 Hz, 1H), 2.74 (d, J=11.6 Hz, 1H), 2.60-2.50 (m, 1H), 2.01-1.92 (m, 2H), 1.58-1.42 (m, 1H), 1.20-1.07 (m, 1H). $^1$H-NMR (CDCl3 400 MHz) for D δ: 7.44 (d, J=8.8 Hz, 2H), 7.39 (d, J=9.6 Hz, 2H), 7.06-6.95 (m, 1H), 6.50-6.36 (m, 1H), 4.99 (dd, J=4.8, 11.6 Hz, 1H), 4.29 (dd, J=5.2, 11.6 Hz, 1H), 4.21-4.14 (m, 1H), 3.88 (dd, J=4.8, 11.2 Hz, 1H), 3.60 (dd, J=8.4, 9.8 Hz, 1H), 2.98 (dd, J=5.2, 10.0 Hz, 1H), 2.76-2.68 (m, 1H), 2.56 (t, J=5.8, 2H), 2.04-1.98 (m, 1H), 1.72-1.60 (m, 1H).

LCMS data for A, B, C and D are given in Table 41.

TABLE 41

| Ex. No. | Structure | LCMS (M + 1, retention time) |
|---|---|---|
| 153 Compound C | 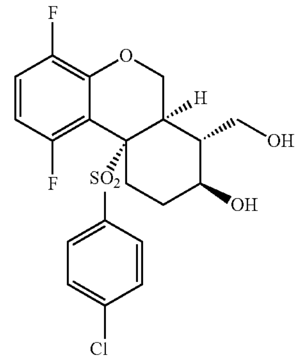 [SMILES: O=S(=O)(c1ccc(Cl)cc1)[C@@]12CC[C@H](O)[C@@H](CO)[C@@H]1COc1c(F)ccc(F)c12] | 445.2, 3.78 min. |
| 153 Compound B | 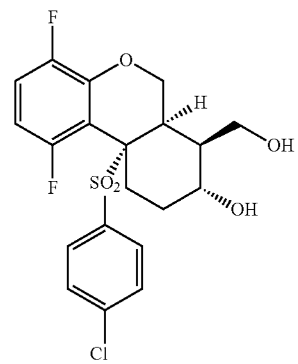 [SMILES: O=S(=O)(c1ccc(Cl)cc1)[C@@]12CC[C@@H](O)[C@H](CO)[C@@H]1COc1c(F)ccc(F)c12] | 445.2, 3.67 min |
| 153 Compound A | 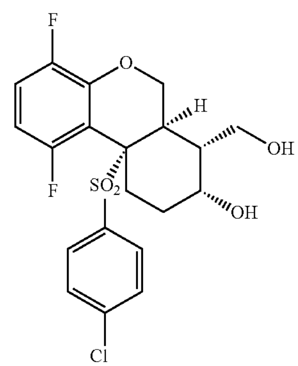 [SMILES: O=S(=O)(c1ccc(Cl)cc1)[C@@]12CC[C@@H](O)[C@@H](CO)[C@@H]1COc1c(F)ccc(F)c12] | 445.2, 3.79 min |
| 153 Compound D | 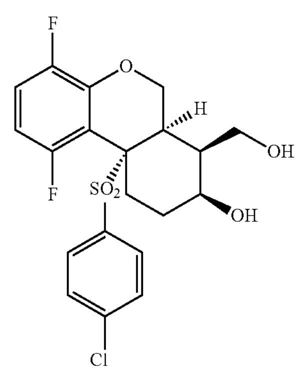 [SMILES: O=S(=O)(c1ccc(Cl)cc1)[C@@]12CC[C@H](O)[C@H](CO)[C@@H]1COc1c(F)ccc(F)c12] | 445.2, 3.62 min |

Examples 154 and 155

10a-(4-Chloro-benzenesulfonyl)-1,4-difluoro-7-methoxymethyl-6a,7,8,9,10,10a-hexahydro-6H-benzo[c]chromen-8-ol and 10a-(4-Chloro-benzenesulfonyl)-1,4-difluoro-8-methoxy-7-methoxymethyl-6a,7,8,9,10,10a-hexahydro-6H-benzo[c]chromene

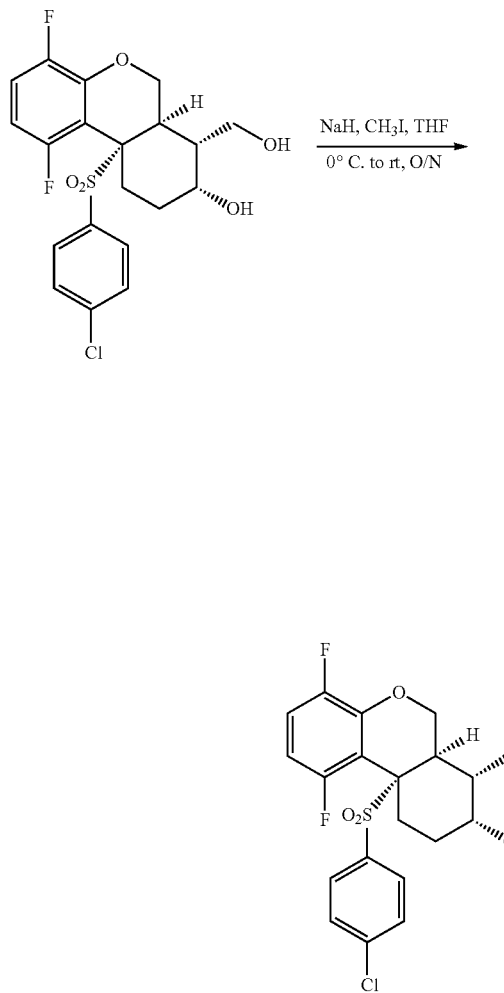

At 0° C., to diol (0.101 g, 0.22 mmol) in THF (5 mL) was added NaH (0.014 g, 0.34 mmol, 1.5 equiv.), it was stirred for 30 mins, followed by addition of CH₃I (16 uL, 0.25 mmol, 1.1 equiv.). The reaction mixture was warmed to room temperature slowly, and quenched with saturated NH₄Cl. The aqueous phase was extracted with EtOAc (3×50 mL), the combined organic phase was washed with brine, dried over MgSO₄, filtered, and evaporated. The crude reaction mixture was purified by the column chromatography, followed by preparative TLC to give the title compounds. ¹H-NMR for 10a-(4-Chloro-benzenesulfonyl)-1,4-difluoro-7-methoxymethyl-6a,7,8,9,10,10a-hexahydro-6H-benzo[c]chromen-8-ol: (CDCl3 400 MHz) δ: 7.65 (d, J=8.8 Hz, 2H), 7.49 (d, J=9.2 Hz, 2H), 7.12-7.00 (m, 1H), 6.51-6.39 (m, 1H), 5.21 (d, J=12.8 Hz, 1H), 4.45 (d, J=12.4 Hz, 1H), 4.03 (s, 1H), 3.94-3.87 (m, 1H), 3.65-3.59 (m, 1H), 3.40 (s, 3H), 3.25 (d, J=12.4 Hz, 1H), 2.58 (t, J=11.8 Hz, 1H), 2.23 (d, J=13.2 Hz, 1H), 1.86-1.75 (m, 1H), 1.56 (d, J=11.6 Hz, 1H), 1.21 (t, J=13.6 Hz, 1H).

TABLE 42

| Ex. No. | Structure | LCMS (M + 1. retention time) |
|---|---|---|
| 154 | (structure shown) | 459.3, 4.23 min |
| 155 | (structure shown) | 473.3, 4.80 min. |

Example 156

10a-(4-Chloro-benzenesulfonyl)-1,4-difluoro-7-methyl-6a,9,10,10a-tetrahydro-6H,7H-benzo[c]chromen-8-one, 10a-(4-Chloro-benzenesulfonyl)-1,4-difluoro-7,7-dimethyl-6a,9,10,10a-tetrahydro-6H,7H-benzo[c]chromen-8-one, and 10a-(4-Chloro-benzenesulfonyl)-1,4-difluoro-7,9-dimethyl-6a,9,10,10a-tetrahydro-6H,7H-benzo[c]chromen-8-one.

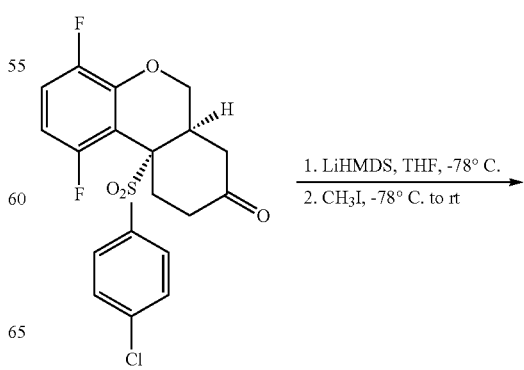

1. LiHMDS, THF, -78° C.
2. CH₃I, -78° C. to rt

-continued

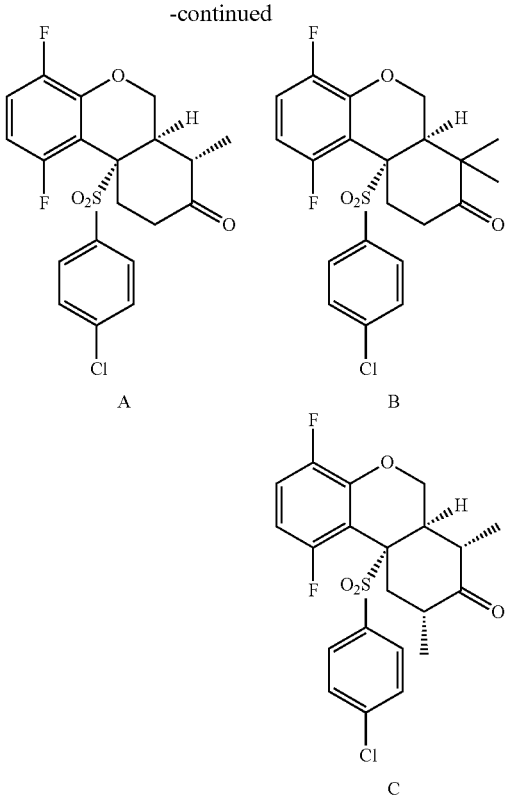

At −78° C., to tricyclic ketone (0.484 g, 1.17 mmol) in THF (20 mL) was added LiHMDS (1.0 M in THF, 1.3 mL, 1.3 mmol, 1.1 equiv.) dropwise, it was stirred at this temperature for 30 mins, followed by addition of CH₃I slowly. The reaction was warmed to room temperature slowly, and stirred at room temperature overnight. It was quenched with water, extracted with EtOAc (3×50 mL), the combined organic phase was washed with brine, dried over MgSO₄, filtered, and evaporated. The crude reaction mixture was purified by the column chromatography (Eluent: EtOAc/Hexane=5% to 50%), and three alkylated ketone were obtained (A, 41%; B, 4%; C, 3%). ¹H-NMR (CDCl3 400 MHz) for A δ: 7.64 (d, J=8.0 Hz, 2H), 7.52 (d, J=8.8 Hz, 2H), 7.19-7.08 (m, 1H), 6.56-6.44 (m, 1H), 5.26 (d, J=12.4 Hz, 1H), 4.50 (d, J=12.8 Hz, 1H), 2.83-2.70 (m, 2H), 2.52-2.28 (m, 3H), 2.21-2.09 (m, 1H), 1.26 (d, J=6.4 Hz, 3H). ¹H-NMR (CDCl3 400 MHz) for δ δ: 7.58 (d, J=8.0 Hz, 2H), 7.49 (d, J=8.8 Hz, 2H), 7.15-7.02 (m, 1H), 6.45-6.32 (m, 1H), 5.22 (dd, J=4.4, 13.4 Hz, 1H), 4.68 (d, J=12.4 Hz, 1H), 2.96 (d, J=4.4 Hz, 1H), 2.81-2.64 (m, 2H), 2.60-2.47 (m, 1H), 2.47-2.35 (m, 1H), 1.33 (s, 3H), 0.96 (s, 3H). ¹H-NMR (CDCl3 400 MHz) for C δ: 7.62 d, J=8.8 Hz, 2H), 7.52 (d, J=8.8 Hz, 2H), 7.19-7.07 (m, 1H), 6.57-6.44 (m, 1H), 5.27 (d, J=12.4 Hz, 1H), 4.49 (d, J=12.4 Hz, 1H), 2.77 (dd, J=4.0, 12.8 Hz, 1H), 2.72 (d, J=11.6 Hz, 1H), 2.44-2.32 (m, 1H), 2.26-2.14 (m, 1H), 2.09 (dd, J=2.8, 13.2 Hz, 1H), 1.24 (d, J=6.4 Hz, 3H), 0.98 (d, J=6.8 Hz, 3H).

Examples 157 to 161

Using similar procedures to that of Example 156 the compounds in Table 43 were prepared.

TABLE 43

| Ex. No. | Structure | LCMS (M + 1, retention time) |
|---|---|---|
| 157 | 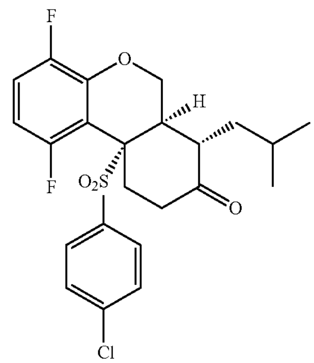 [SMILES: CC(C)C[C@@H]1C(=O)CC[C@@]2(S(=O)(=O)c3ccc(Cl)cc3)c3c(F)ccc(F)c3OC[C@@H]12] | 469.3, 5.01 min. |
| 158 | 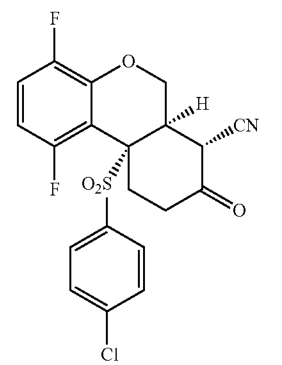 [SMILES: N#C[C@@H]1C(=O)CC[C@@]2(S(=O)(=O)c3ccc(Cl)cc3)c3c(F)ccc(F)c3OC[C@@H]12] | 438.2, 4.00 min |
| 159 | 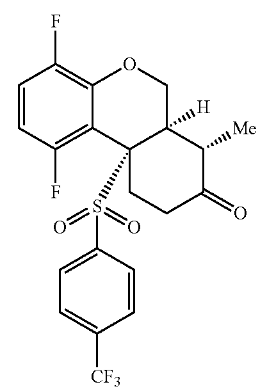 [SMILES: C[C@@H]1C(=O)CC[C@@]2(S(=O)(=O)c3ccc(C(F)(F)F)cc3)c3c(F)ccc(F)c3OC[C@@H]12] | 478.3 (M + H₂O), 4.48 min. |
| 160 | 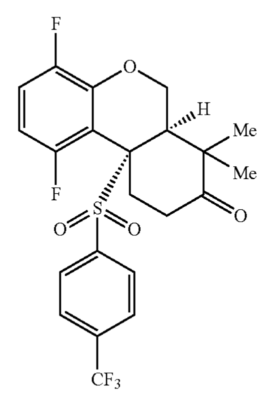 [SMILES: CC1(C)C(=O)CC[C@@]2(S(=O)(=O)c3ccc(C(F)(F)F)cc3)c3c(F)ccc(F)c3OC[C@@H]12] | 475.3, 4.84 min. |

TABLE 43-continued

| Ex. No. | Structure | LCMS (M + 1, retention time) |
|---|---|---|
| 161 | (structure) | 452.2; 4.18 |

Examples 162 to 165

The compounds in Table 44 were made following the procedure of Example 18.

TABLE 44

| Ex. No. | Structure | LCMS (M + 1, retention time |
|---|---|---|
| 162 | (structure) | 429.2, 4.24 min. |
| 163 | (structure) | 429.2, 4.06 min. |

TABLE 44-continued

| Ex. No. | Structure | LCMS (M + 1, retention time |
|---|---|---|
| 164 | (structure) | 440.2, 4.13 min. |
| 165 | (structure) | 440.2, 4.02 min. |

Example 166

Cyclopropanesulfonic acid [10a-(4-chloro-benzene-sulfonyl)-1,4-difluoro-8-hydroxy-6a,7,8,9,10,10a-hexahydro-6H-benzo[c]chromen-7-ylmethyl]-amide

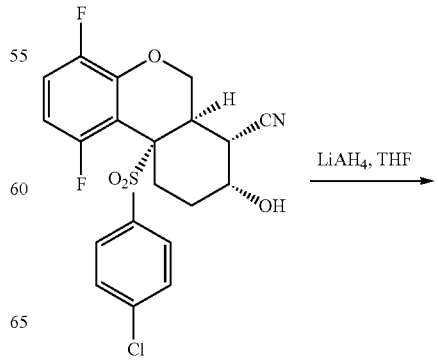

LiAH₄, THF

233
-continued

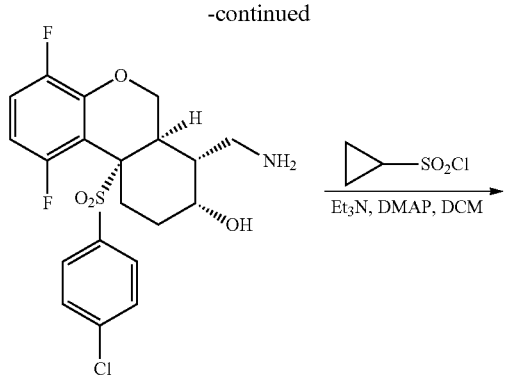
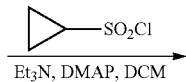

Step 1

At 0° C., to the nitrile alcohol (0.052 g, 0.12 mmol) in THF (10 mL) was added LAH (1.0 M in THF, 0.24 mL) dropwise, it was stirred for 1.5 hr, and diluted with DCM (20 mL). The reaction mixture was neutralized with 4 drops of saturated NaHCO₃, and stirred for 15 mins, followed by addition of Na₂SO₄ (solid). It was filtered, washed with CH₃OH/DCM (40%) several times, and evaporated. The crude reaction mixture was purified by the preparative TLC (Eluent: CH₃OH/DCM=30%), and hydroxyl amine was obtained (0.034 g, 0.08 mmol, 65%). $^1$H-NMR (CD3OD 400 MHz) δ: 7.69 (d, J=9.2 Hz, 2H), 7.63 (d, J=8.8 Hz, 2H), 7.23-7.14 (m, 1H), 6.61-6.51 (m, 1H), 5.15 (d, J=13.2 Hz, 1H), 4.51 (d, J=12.4 Hz, 1H), 3.98 (s, 1H), 3.57 (s, 1H), 3.34 (s, 1H), 3.16-2.96 (m, 1H), 2.91 (d, J=11.6 Hz, 1H), 2.53 (t, J=13.2 Hz, 1H), 2.36 (d, J=13.2 Hz, 1H), 1.77 (d, J=14.4 Hz, 1H), 1.63-1.47 (m, 2H), 1.36-1.20 (m, 1H).

Step 2

The product of Step 1 was converted to the title compound using the procedures described in Example 20.

234

TABLE 45

| Ex. No. | Structure | LCMS (M + 1, retention time) |
|---|---|---|
| 166 | 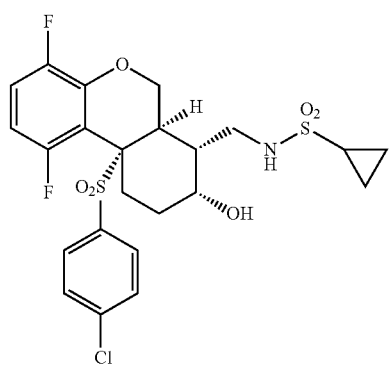 [SMILES: O=S(=O)(NC[C@@H]1[C@H](O)CC[C@@]2(S(=O)(=O)c3ccc(Cl)cc3)c3c(F)ccc(F)c3OC[C@@H]12)C1CC1] | 372.2 (M − phenylsulfone + 1), 4.03 min. |

Examples 167 and 168

Example 167

N-[10a-(4-Chloro-benzenesulfonyl)-1,4-difluoro-7-methyl-6a,7,8,9,10,10a-hexahydro-6H-benzo[c]chromen-8-yl]-C,C,C-trifluoro-methanesulfonamide

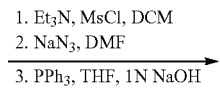
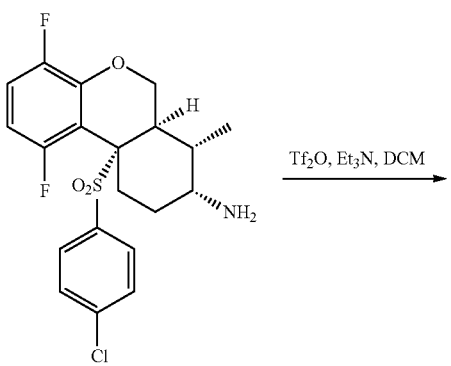

235
-continued

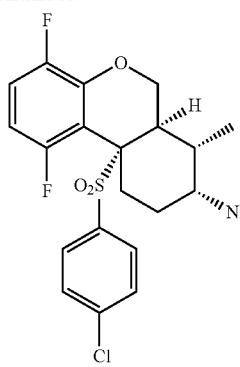

The title compound of Example 167 was prepared following the general procedures from Example 19 and 20. The compound of Example 168 (Table 46) was prepared following procedures similar to those of Example 167.

TABLE 46

| Ex. No. | Structure | LCMS (M + 1, retention time) |
|---|---|---|
| 167 | 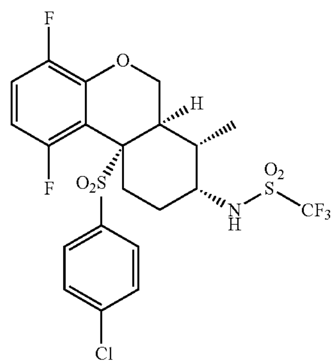 [SMILES: C[C@@H]1[C@H](NS(=O)(=O)C(F)(F)F)CC[C@@]2(S(=O)(=O)c3ccc(Cl)cc3)c3c(F)ccc(F)c3OC[C@@H]12] | 560.3, 5.06 min. |
| 168 | 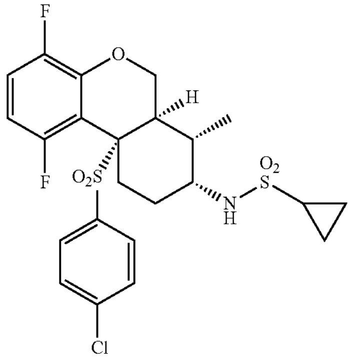 [SMILES: C[C@@H]1[C@H](NS(=O)(=O)C2CC2)CC[C@@]2(S(=O)(=O)c3ccc(Cl)cc3)c3c(F)ccc(F)c3OC[C@@H]12] | 374.2 (M − phenylsulfone + NH₄), 4.79 min. |

236

Example 169

N-[10a-(4-Chloro-benzenesulfonyl)-1,4-difluoro-6a,7,8,9,10,10a-hexahydro-6H-benzo[c]chromen-7-ylmethyl]-methanesulfonamide 1. LDA, THF
2. H₂, Pd(OH)₂, EtOAc
3. MsCl, Et₃N, DCM
4. K-tBuO, THF Example 169A LiBH₄, CH₃OH/THF 1. Et₃N, MsCl, DCM
2. NaN₃, DMF
3. PPh₃, THF, 1N NaOH Example 169B -continued

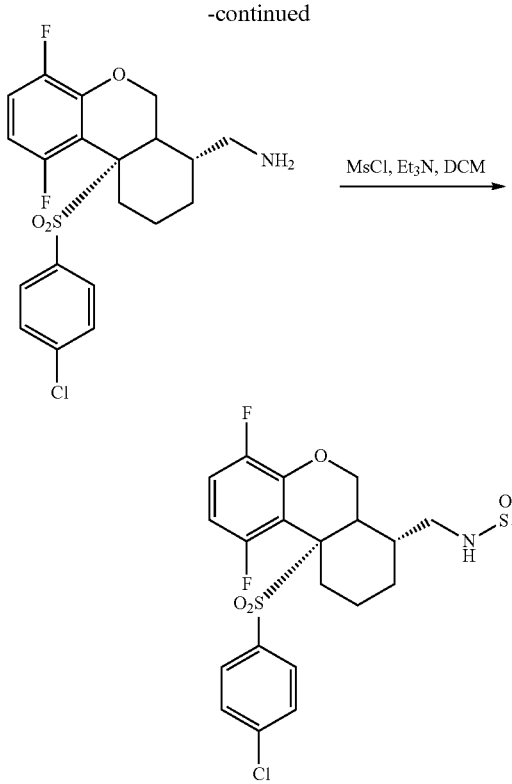

Step 1

At 0° C., to the ester in THF (40 mL) was added NH(i-Pr)$_2$ (4.0 mL, 2.86 g, 28.3 mmol, 3.0 Equiv.) first, followed by n-BuLi (11.3 mL, 28.3 mmol, 3.0 Equiv.) dropwise, it was stirred at this temperature for 10 mins before cooling to −78° C. The reaction mixture was then stirred at −78° C. for an hour followed by addition of vinyl sulfone (3.226 g, 9.43 mmol) in THF (20 mL) slowly, it was stirred at this temperature for another hr., quenched with water (40 mL), and warmed to room temperature slowly. It was extracted with EtOAc (3×100 mL), the combined organic layers were washed with water, brine, dried over MgSO$_4$, filtered, and evaporated. The crude reaction was obtained as a mixture of diastereomers (9.95 g), and was reduced directly. The Michael addition product was dissolved in EtOAc (100 mL), and stirred under H$_2$ (1 atm) on catalysis of Pd(OH)$_2$/C (10%, 3.0 g). When the reaction completed, it was filtered through a pad of Celite, rinsed with EtOAc, and evaporated under vacuum. The crude reaction mixture was purified by the column chromatography (Eluent: EtOAc/Hexane=10% to 75%), and the alcohol was obtained (3.039 g, 6.60 mmol, 70% for two steps).

The ring cyclization followed the general procedure from Example 16, and a pair of diastereomers was epimerized to the desired ester. $^1$H-NMR (CDCl3 400 MHz) for methyl ester δ: 7.61 (d, J=8.8 Hz, 2H), 7.49 (d, J=9.2 HZ, 2H), 7.14-7.00 (m, 1H), 6.50-6.35 (m, 1H), 5.19 (dd, J=3.2, 12.4 Hz, 1H), 4.20 (d, J=11.6 Hz, 1H), 3.72 (s, 3H), 2.98 (d, J=12.0 Hz, 1H), 2.64 (d, J=13.2 Hz, 1H), 2.45 (dt, J=4.4, 12.8 Hz, 1H), 1.98-1.87 (m, 2H), 1.82-1.73 (m, 1H), 1.54 (dd, J=4.0, 12.8 Hz, 1H), 1.18-1.02 (m, 1H). $^1$H-NMR (CDCl3 400 MHz) for t-Butyl ester δ: 7.60 (d, J=8.4 Hz, 2H), 7.48 (d, J=8.8 Hz, 2H), 7.14-7.01 (m, 1H), 6.48-6.35 (m, 1H), 5.18 (dd, J=2.8, 12.0 Hz, 1H), 4.23 (d, J=11.6 Hz, 1H), 2.90 (d, J=11.6 Hz, 1H), 2.65 (d, J=14.0 Hz, 1H), 2.31 (dt, J=4.0, 12.0 Hz, 1H), 1.96-1.84 (m, 2H), 1.80-1.70 (m, 1H), 1.46 (s, 9H), 1.54-1.40 (m, 1H), 1.16-1.06 (m, 1H).

Step 2

To the ester (0.454 g, 0.99 mmol) in THF/EtOH (10 mL/50 mL) was added LiBH$_4$ (0.433 g, 19.88 mmol, 20 Equiv.), and it was stirred overnight. Most solvent was removed under vacuum, the residue was dissolved in water, extracted with EtOAc, the combined organic phase was washed with brine, dried over MgSO$_4$, filtered, and evaporated. The crude reaction mixture was purified by the column chromatography (Eluent: EtOAc/Hexane=5% to 75%), and alcohol (0.285 g, 0.66 mmol, 67%) was obtained. $^1$H-NMR (CDCl3 400 MHz) δ: 7.61 (d, J=9.2 Hz, 2H), 7.48 (d, J=8.8 Hz, 2H), 7.09-7.04 (m, 1H), 6.46-6.39 (m, 1H), 5.16 (d, J=12.4 Hz, 1H), 4.63 (d, J=12.4 Hz, 1H), 3.88 (d, J=4.4, 10.8 Hz, 1H), 3.70 (dd, J=2.8, 11.2 Hz, 1H), 2.69 (d, J=11.2 Hz, 1H), 2.56 (d, J=13.2 Hz, 1H), 1.94-1.83 (m, 1H), 1.80-1.36 (m, 6H), 1.16-1.02 (m, 1H).

Step 3

The transformation from alcohol to amine followed the general procedure from Example 19.

Step 4

The synthesis of title compound followed the general procedure from Example 20.

TABLE 47

| Ex. No. | Structure | LCMS (M + 1, retention time) |
| --- | --- | --- |
| 169 | 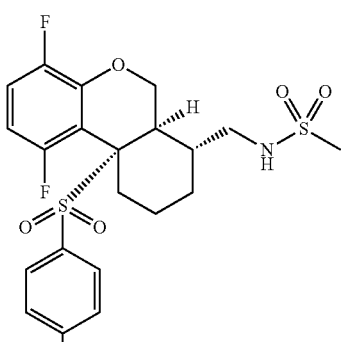 | 328.2 (M − phenylsulfone), 4.18 min. |

Examples 170 to 182

Using similar procedures to that of Example 169, the compounds in Table 48 were prepared.

TABLE 48

| Ex. No. | Structure | LCMS (M + 1, retention time) |
|---|---|---|
| 170 | 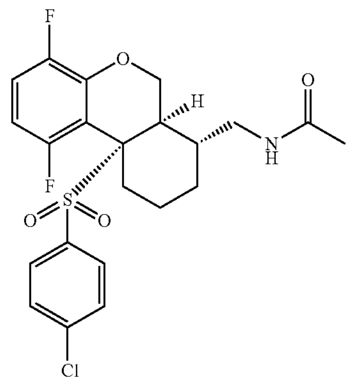 [SMILES: CC(=O)NC[C@@H]1CCC[C@@]2(S(=O)(=O)c3ccc(Cl)cc3)c3c(F)ccc(F)c3OC[C@@H]12] | 294.2 (M − phenyl-sulfone), 3.93 min. |
| 171 | 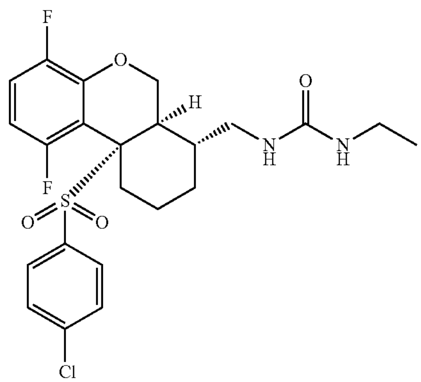 [SMILES: CCNC(=O)NC[C@@H]1CCC[C@@]2(S(=O)(=O)c3ccc(Cl)cc3)c3c(F)ccc(F)c3OC[C@@H]12] | 323.2 (M − phenyl-sulfone), 4.05 min. |
| 172 | 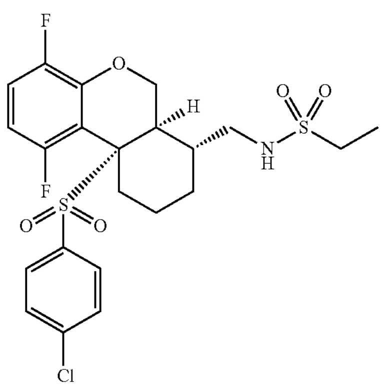 [SMILES: CCS(=O)(=O)NC[C@@H]1CCC[C@@]2(S(=O)(=O)c3ccc(Cl)cc3)c3c(F)ccc(F)c3OC[C@@H]12] | 344.2 (M − phenyl-sulfone), 4.33 min. |
| 173 | 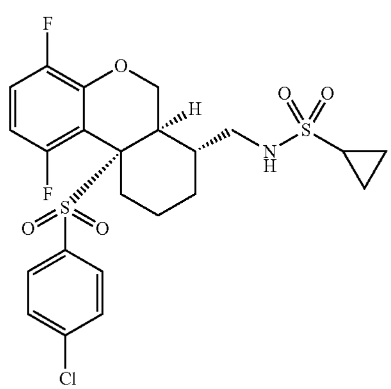 [SMILES: O=S(=O)(NC[C@@H]1CCC[C@@]2(S(=O)(=O)c3ccc(Cl)cc3)c3c(F)ccc(F)c3OC[C@@H]12)C1CC1] | 356.2 (M − phenyl-sulfone), 4.38 min. |
| 174 | | 384.2 (M − phenyl-sulfone), 4.81 min. |
| 175 | | 491.3, 4.99 Min |
| 176 | | 463.3, 4.50 Min |

TABLE 48-continued

| Ex. No. | Structure | LCMS (M + 1, retention time) |
|---|---|---|
| 177 | 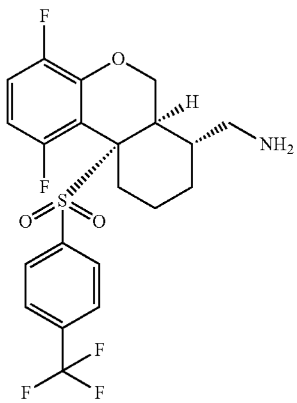 [SMILES: NC[C@@H]1CCC[C@@]2(S(=O)(=O)c3ccc(C(F)(F)F)cc3)c3c(F)ccc(F)c3OC[C@@H]12] | 462.3, 3.22 Min |
| 178 | 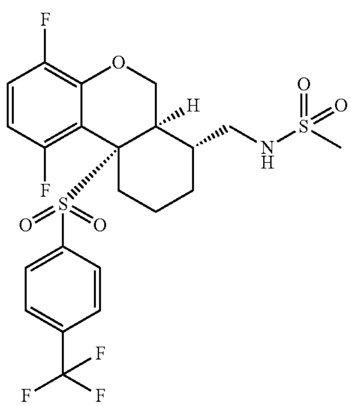 [SMILES: CS(=O)(=O)NC[C@@H]1CCC[C@@]2(S(=O)(=O)c3ccc(C(F)(F)F)cc3)c3c(F)ccc(F)c3OC[C@@H]12] | 540.3, 4.41 Min |
| 179 | 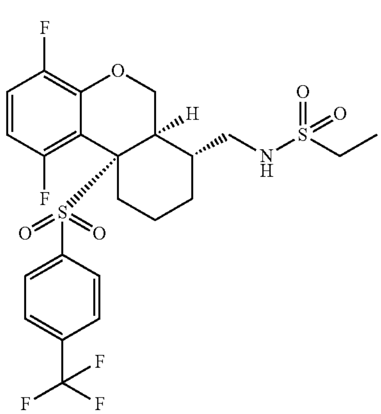 [SMILES: CCS(=O)(=O)NC[C@@H]1CCC[C@@]2(S(=O)(=O)c3ccc(C(F)(F)F)cc3)c3c(F)ccc(F)c3OC[C@@H]12] | 554.3, 4.68 Min |
| 180 | | 594.3, 5.05 Min |
| 181 | | 726.4, 5.52 Min |
| 182 | | 566.3, 4.61 Min |

Example 183

N-[10a-(4-Chloro-benzenesulfonyl-1,4-difluoro-6a,7,8,9,10,10a-hexahydro-6H-benzo[c]chromen-7-ylmethyl]-N-ethyl-methanesulfonamide

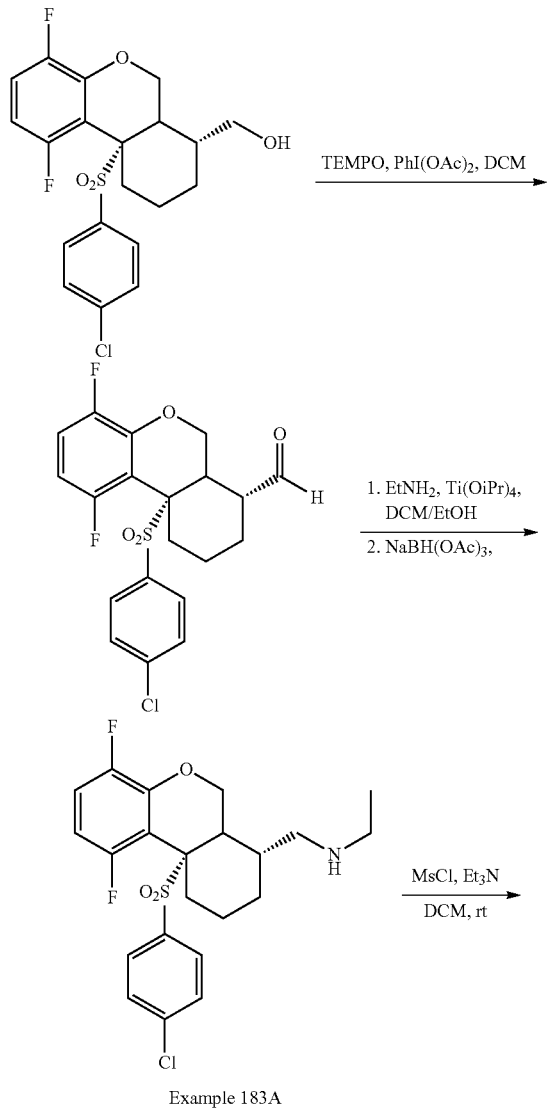

Example 183A

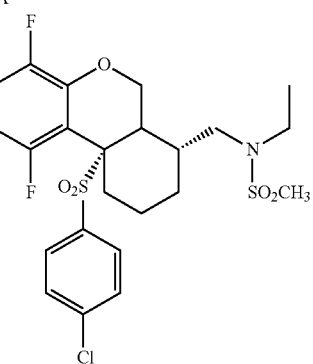

Example 183

Step 1

To the alcohol (0.431 g, 1.00 mmol) in DCM (10 mL) was added TEMPO (0.10 mmol, 10 mol %) and DIAB (0.363 g, 1.10 mmol, 1.1 Equiv.), it was stirred at room temperature until the completion of the reaction. It was diluted with DCM (100 mL), washed with saturated $Na_2S_2O_3$, and extracted with DCM (3×50 mL). The combined organic layers were washed with saturated $NaHCO_3$, brine, dried over $MgSO_4$, filtered, and evaporated. The crude reaction mixture was purified by the column chromatography (Eluent: EtOAc/Hexane=5% to 75%), and aldehyde (0.311 g, 0.73 mmol, 73%) was obtained. $^1$H-NMR (CDCl3 400 MHz) δ: 9.66 (s, 1H), 7.61 (d, J=8.8 Hz, 2H), 7.49 (d, J=8.8 Hz, 2H), 7.11-7.03 (m, 1H), 6.47-6.40 (m, 1H), 5.16 (dd, J=2.8, 12.6 Hz, 1H), 4.32 (d, J=12.8 Hz, 1H), 3.00 (d, J=11.2 Hz, 1H), 2.67 (d, J=12.4 Hz, 1H), 2.56-2.48 (m, 1H), 2.00-1.80 (m, 3H), 1.78-1.65 (m, 1H), 1.20-1.06 (m, 1H).

Step 2

To aldehyde (0.271 g, 0.63 mmol) in $CH_3OH/CH_3OH$ (10 mL/10 mL) was added ethylamine (2.0 M in $CH_3OH$, 0.48 mL, 0.95 mmol, 1.5 Equiv.) and $Ti(OiPr)_4$ (0.271 g, 0.28 mL, 0.95 mmol, 1.5 Equiv.), after being stirred overnight at room temperature, $NaBH(OAc)_3$ was added, and it was stirred for 4 hrs. The reaction mixture was quenched with 10 mL of $H_2O$, and stirred for 30 mins, it was filtered through a pad of Celite, rinsed with $CH_3OH$, filtered, and concentrated. The residue was diluted with saturated $NaHCO_3$, extracted with EtOAc (3×100 mL) and DCM (100 mL), the combined organic layers were washed with brine, dried over $MgSO_4$, filtered, and evaporated. The crude reaction mixture was purified by the column chromatography (Eluent: $DCM/CH_3OH$ (0.7 N $NH_3$) =5% to 50%), and amine Example 183A was obtained (0.169 g, 0.37 mmol, 59%). $^1$H-NMR (CDCl3 400 MHz) δ: 7.60 (d, J=8.4 Hz, 2H), 7.47 (d, J=8.8 Hz, 2H), 7.08-7.01 (m, 1H), 6.48-6.33 (m, 1H), 5.70-5.30 (broad s, 1H), 5.14 (d, J=12.4 Hz, 1H), 4.60 (d, J=12.8 Hz, 1H), 2.83 (d, J=12.8 Hz, 1H), 2.71-2.63 (m, 3H), 2.55 (d, J=10.4 Hz, 2H), 2.04-1.82 (m, 7H), 1.82-1.68 (m, 2H), 1.60-1.48 (m, 1H), 1.30-1.16 (m, 1H), 1.10 (t, J=7.0 Hz, 3H).

Step 3

The synthesis of sulfonamides and amide followed the general procedure from Example 20. $^1$H-NMR (CDCl3 400 MHz) δ: 7.62 (d, J=8.8 Hz, 2H), 7.49 (d, J=8.8 Hz, 2H), 7.11-7.04 (m, 1H), 6.49-6.42 (m, 1H), 5.18 (d, J=12.4 Hz, 1H), 4.56 (d, J=12.4 Hz, 1H), 3.40 (dd, J=4.0, 13.6 Hz, 1H), 3.32-3.11 (m, 3H), 2.84 (s, 3H), 2.56 (d, J=13.2 Hz, 1H), 2.45 (d, J=11.2 Hz, 1H), 1.95 (d, J=13.2 Hz, 1H), 1.86 (t, J=13.2 Hz, 1H), 1.66 (d, J=9.6 Hz, 1H), 1.68-1.60 (m, 1H), 1.16 (t, J=7.2 Hz, 3H), 1.05-0.98 (m, 1H).

Examples 184 to 188

Using similar procedures to that of Example 183, the compounds in Table 49 were prepared.

TABLE 49

| Ex. No. | Structure | LCMS (M + 1, retention time) |
|---|---|---|
| 184 | 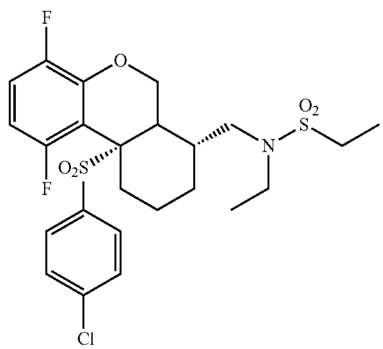 [SMILES: CCN(C[C@@H]1CCC[C@@]2(S(=O)(=O)c3ccc(Cl)cc3)c3c(F)ccc(F)c3OCC12)S(=O)(=O)CC] | 548.3, 4.88 min. |
| 185 | 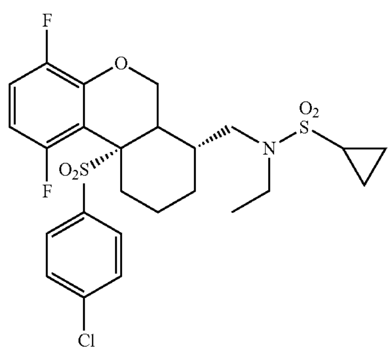 [SMILES: CCN(C[C@@H]1CCC[C@@]2(S(=O)(=O)c3ccc(Cl)cc3)c3c(F)ccc(F)c3OCC12)S(=O)(=O)C1CC1] | 560.3, 4.94 min. |
| 186 | 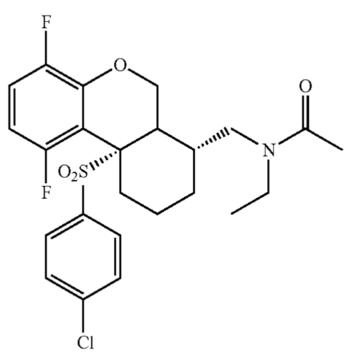 [SMILES: CCN(C[C@@H]1CCC[C@@]2(S(=O)(=O)c3ccc(Cl)cc3)c3c(F)ccc(F)c3OCC12)C(C)=O] | 498.3, 4.41 min |
| 187 | 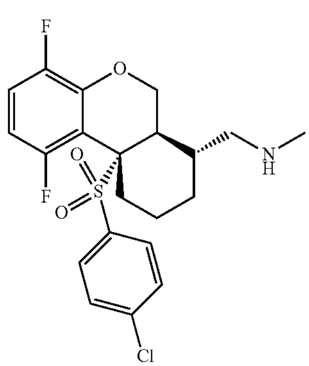 [SMILES: CNC[C@@H]1CCC[C@@]2(S(=O)(=O)c3ccc(Cl)cc3)c3c(F)ccc(F)c3OC[C@@H]12] | 442.2, 2.98 Min |

TABLE 49-continued

| Ex. No. | Structure | LCMS (M + 1, retention time) |
|---|---|---|
| 188 | 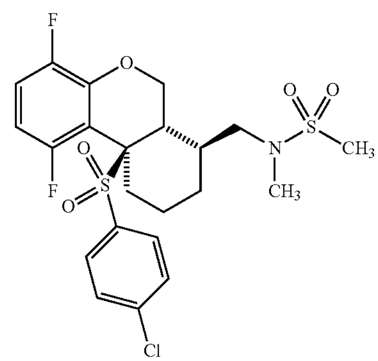 | 520.3, 4.57 Min |

Example 189

4-[10a-(4-Chloro-benzenesulfonyl)-1,4-difluoro-6a,7,8,9,10,10a-hexahydro-6H-benzo[c]chromen-7-yl]-butan-2-ol Example 189A

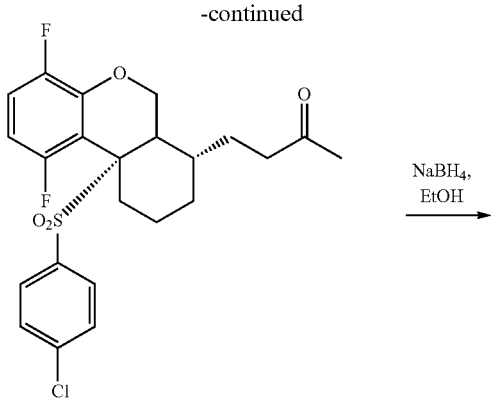

Example 189B

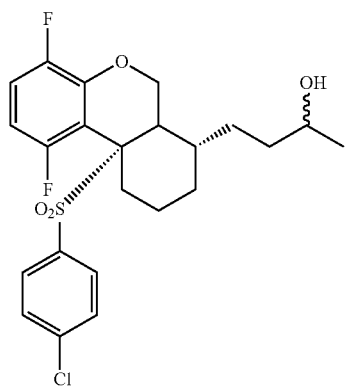

Example 189C

Step 1

To aldehyde (0.049 g, 0.11 mmol) in toluene (10 mL) was added the ylide (0.055 g, 0.17 mmol, 1.5 Equiv.), and it was stirred at 90° C. overnight. Solvent was removed, and the crude residue was purified by preparative TLC (Eluent: EtOAc/Hexane=20%), and Wittig reaction product was obtained (0.039 g, 0.08 mmol, 76%). $^1$H-NMR (CDCl3 400 MHz) δ: 7.60 (d, J=9.2 Hz, 2H), 7.49 (d, J=8.8 Hz, 2H), 7.08 (dd, J=9.4, 6.0 Hz, 1H), 6.47-6.40 (m, 1H), 6.20 (d, J=16.0 Hz, 1H), 5.09 (d, J=9.2 Hz, 1H), 4.30 (d, J=12.0 Hz, 1H), 2.62 (d, J=13.2 Hz, 1H), 2.51 (d, J=10.8 Hz, 1H), 2.27 (s, 3H), 2.26-2.18 (m, 1H), 1.94 (t, J=13.2 Hz, 1H), 1.80-1.74 (m, 1H), 1.71-1.57 (m, 1H), 1.39 (dq, J=4.0, 12.8, 16.0 Hz, 1H), 1.12 (q, J=13.2, 16.4 Hz, 1H).

Step 2

The α,β-unsaturated ketone was treated with hydrogenation on catalysis of Pd(OH)$_2$ in EtOAc, the catalyst was filtered off through a pad of Celite, and the filtrate was dried under vacuum. The crude reaction mixture was purified by preparative TLC (Eluent: EtOAc/Hexane=20%), and reduced product was obtained (0.0188 g, 0.04 mmol, 54%). $^1$H-NMR (CDCl3 400 MHz) δ: 7.60 (d, J=8.0 Hz, 2H), 7.48 (d, J=8.0 Hz, 2H), 7.08-7.02 (m, 1H), 6.44-6.32 (m, 1H), 5.15 (d, J=12.4 Hz, 1H), 4.58 (d, J=12.4 Hz, 1H), 2.55 (d, J=10.8 Hz, 1H), 2.52-2.44 (m, 1H), 2.44-2.38 (m, 1H), 2.34 (d, J=11.2 Hz, 1H), 2.14 (s, 3H), 2.08-1.96 (m, 1H), 1.86 (t, J=12.8 HZ, 1H), 1.70 (d, J=10.4 Hz, 2H), 1.60-1.48 (m, 1H), 1.44-1.28 (m, 1H), 1.14-0.96 (m, 2H).

Step 3

The ketone was reduced by use of the general procedure from Example 18, and a pair of diastereomer (1/1) was obtained. $^1$H-NMR (CDCl3 400 MHz) δ: 7.60 (d, J=8.8 Hz, 2H), 7.48 (d, J=8.8 Hz, 2H), 7.09-7.02 (m, 1H), 6.45-6.38 (m, 1H), 5.15 (d, J=11.6 Hz, 1H), 4.64-4.58 (m, 1H), 3.82-3.70 (m, 1H), 2.54 (d, J=11.6 Hz, 1H), 2.37 (d, J=10.8 Hz, 1H), 1.96-1.22 (m, 9H), 1.20 (d, J=6.4 Hz, 3H), 1.16-0.98 (m, 1H).

Example 190

1-[10a-(4-Chloro-benzenesulfonyl-1,4-difluoro-6a,7,8,9,10,10a-hexahydro-6H-benzo[c]chromen-7-yl]-ethanol

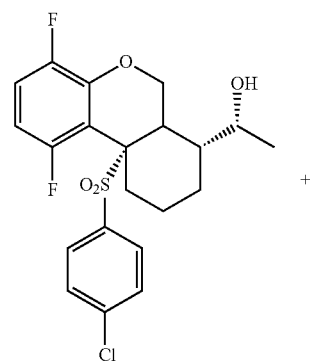

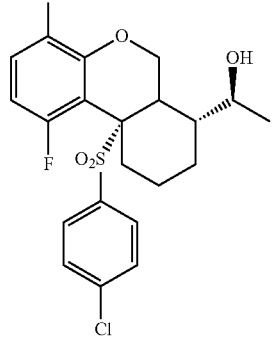

Example 190A

Example 190B

Following the general procedure from Example 24 Step two, two diastereomers (Example 190A and 190B) of the title compound were obtained. $^1$H-NMR (CDCl3 400 MHz) for 190A δ: 7.62 (d, J=8.8 Hz, 2H), 7.48 (d, J=8.8 Hz, 2H), 7.09-7.03 (m, 1H), 6.46-9.39 (m, 1H), 5.17 (d, J=12.4 Hz, 1H), 4.73 (d, J=12.0 Hz, 1H), 4.32-4.22 (m, 1H), 2.81 (d, J=10.4 Hz, 1H), 1.87 (t, J=12.8 Hz, 1H), 1.77 (d, J=13.6 Hz, 1H), 1.70-1.60 (m, 1H), 1.40-1.22 (m, 3H), 1.19 (d, J=6.8 Hz, 3H), 1.10-0.98 (m, 1H). $^1$H-NMR (CDCl3 400 MHz) for 190B δ: 7.60 (d, J=8.0 Hz, 2H), 7.49 (d, J=8.4 Hz, 2H), 7.10-7.03 (m, 1H), 6.48-6.39 (m, 1H), 5.16 (d, J=12.8 Hz, 1H), 4.51 (d, J=12.4 Hz, 1H), 4.36-4.24 (m, 1H), 2.56-2.42 (m, 2H), 1.92-1.84 (m, 2H), 1.84-1.72 (m, 1H), 1.72-1.52 (m, 2H), 1.20 (d, J=6.4 Hz, 3H), 1.12-0.96 (m, 1H).

Example 191

1-[10a-(4-Chloro-benzenesulfonyl)-1,4-difluoro-6a,7,8,9,10,10a-hexahydro-6H-benzo[c]chromen-7-yl]-ethanone

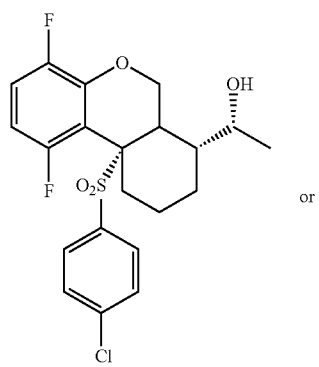

Example 190A or

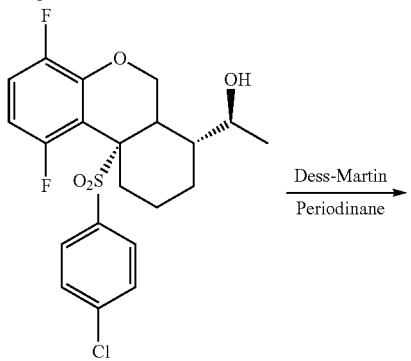

Example 190B

Dess-Martin Periodinane

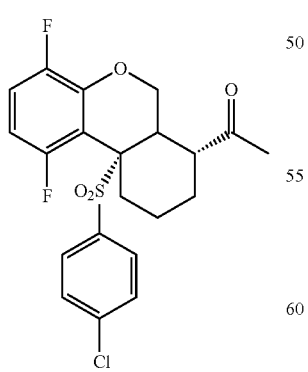

Example 191

The oxidation followed the general procedure from Example 24 step one. $^1$H-NMR (CDCl3 400 MHz) for δ: 7.61 (d, J=8.4 Hz, 2H), 7.49 (d, J=8.8 Hz, 2H), 7.12-7.05 (m, 1H), 6.48-6.42 (m, 1H), 5.13 (dd, J=2.8, 12.4 Hz, 1H), 4.10 (d, J=12.8 Hz, 1H), 3.02 (d, J=10.8 Hz, 1H), 2.70-2.58 (m, 2H), 2.20 (s, 3H), 1.96-1.74 (m, 3H), 1.32-1.20 (m, 1H), 1.20-1.08 (m, 1H).

Example 192

Methyl-carbamic acid 10a-(4-chloro-benzenesulfonyl)-1,4-difluoro-6a,7,8,9,10,10a-hexahydro-6H-benzo[c]chromen-7-ylmethyl ester

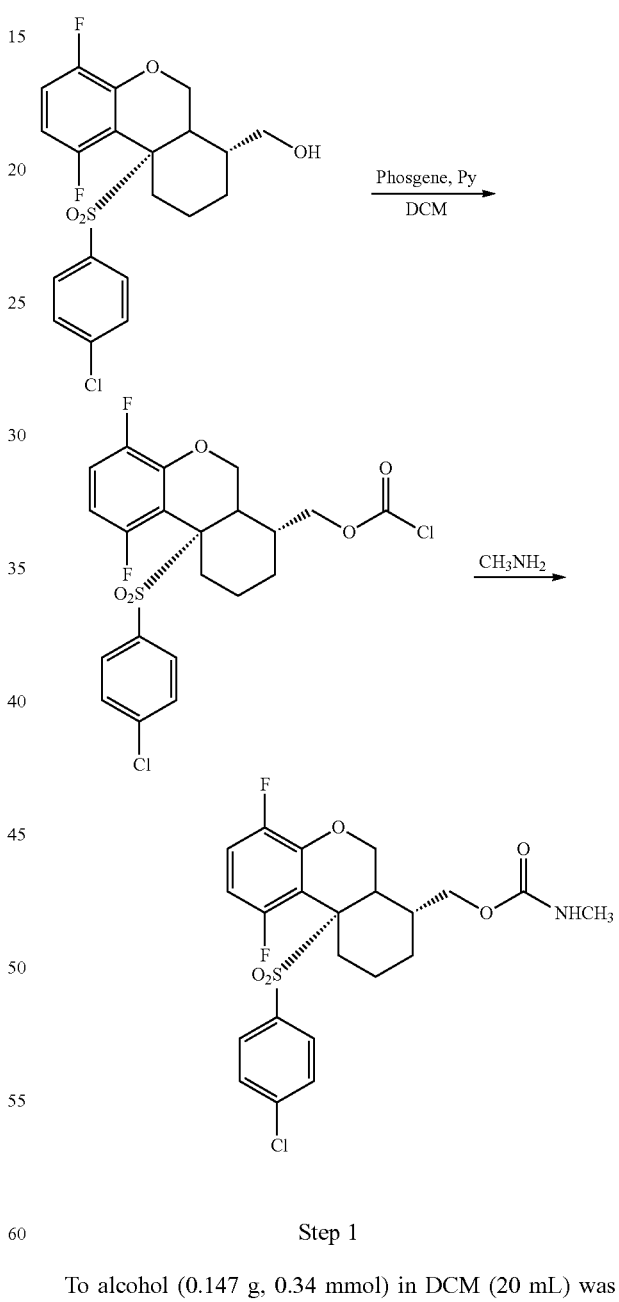

Step 1

To alcohol (0.147 g, 0.34 mmol) in DCM (20 mL) was added Py (0.28 mL, 0.271 g, 3.43 mmol, 10 Equiv.) and Phosgene (20% in toluene, 1.44 mL, 1.356 g, 2.74 mmol, 8.0 Equiv.), it was stirred at room temperature for 30 mins, and quenched with water (10 mL), The aqueous phase was extracted with DCM (50 mL), the combined organic phase was washed with brine, dried over MgSO₄, filtered, and evaporated. The crude reaction mixture was purified by the column chromatography (Eluent: EtOAc/Hexane=5% to 35%), and chloroformate (0.073 g, 0.15 mmol, 43%) was obtained. ¹H-NMR (CDCl3 400 MHz) for δ: 7.62 (d, J=8.4 Hz, 2H), 7.50 (d, J=8.0 Hz, 2H), 7.12-7.05 (m, 1H), 6.48-6.42 (m, 1H), 5.22 (d, J=12.8 Hz, 1H), 4.54 (dd, J=4.4, 11.6 Hz, 1H), 4.49 (d, J=12.4 Hz, 1H), 4.38 (dd, J=3.0, 11.8 Hz, 1H), 2.65 (d, J=11.6 Hz, 1H), 2.57 (d, J=12.8 Hz, 1H), 1.92 (t, J=13.2 Hz, 1H), 1.84-1.68 (m, 3H), 1.50-1.36 (m, 1H), 1.18-1.02 (m, 1H).

Step 2

To the chloroformate (0.036 g, 0.074 mmol) from step 1 in DCM (4 mL) was added $CH_3NH_2$ in THF (2.0 M, 74 uL, 0.15 mmol, 2.0 Equiv.), it was stirred at room temperature for 20 mins, and diluted with DCM, washed with brine, dried over MgSO₄, filtered, and evaporated. The crude reaction mixture was purified by the preparative TLC (Eluent: EtOAc/Hexane=35%), and the carbamate (0.014 g, 0.029 mmol, 39%) was obtained. ¹H-NMR (CDCl3 400 MHz) for δ: 7.60 (d, J=8.0 Hz, 2H), 7.48 (d, J=8.4 Hz, 2H), 7.10-6.98 (m, 1H), 6.50-6.38 (m, 1H), 5.15 (d, J=12.4 Hz, 1H), 4.71 (s, 1H), 4.60 (d, J=12.4 Hz, 1H), 4.35 (d, J=12.0 Hz, 1H), 4.07 (d, J=12.0 Hz, 1H), 2.82 (d, J=4.8 Hz, 3H), 2.62 (d, J=10.4 Hz, 1H), 2.54 (d, J=12.4 Hz, 1H), 1.88 (t, J=13.2 Hz, 1H), 1.80-1.50 (m, 4H), 1.48-1.32 (m, 1H), 1.16-1.00 (m, 1H).

Example 193

Using similar procedures to that in Example 192, the compound in Table 50 was prepared.

| Ex. No. | Structure | LCMS (M + 1, retention time) |
|---|---|---|
| 193 | [structure] | 500.3, 4.75 min. |

Examples 194 to 196

The compounds in Table 51 were prepared according to Example 20.

TABLE 51

| Ex. No. | STRUCTURE | Mass Spec (MH⁺ except otherwise noted); retention time (min) |
|---|---|---|
| 194 | [structure] | 443.2; 5.28 |
| 195 | [structure] | 429.2; 5.08 |
| 196 | [structure] | 445.2; 4.53 |

Examples 197 to 199

Following procedures similar to the ones described in Example 26, the compounds in Table 52 were prepared.

TABLE 52
| Ex. No. | STRUCTURE | Mass Spec (MH+ except otherwise noted); retention time (min) |
|---|---|---|
| 197 | 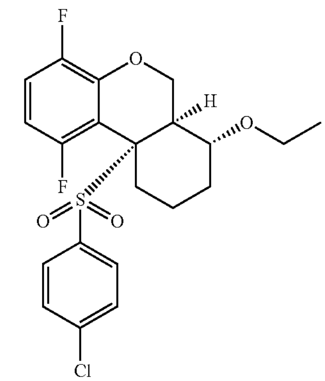 [SMILES: CCO[C@@H]1CCC[C@@]2(S(=O)(=O)c3ccc(Cl)cc3)c3c(F)ccc(F)c3OC[C@@H]12] | 457.3; 5.57 |
| 198 | 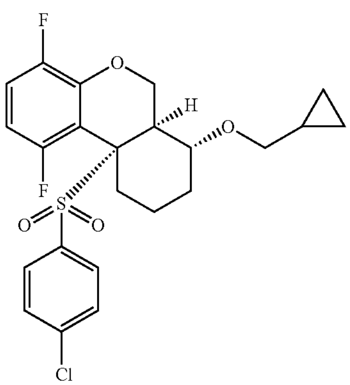 [SMILES: O=S(=O)(c1ccc(Cl)cc1)[C@@]12CCC[C@@H](OCC3CC3)[C@@H]1COc1c(F)ccc(F)c12] | 469.3; 5.40 |
| 199 | 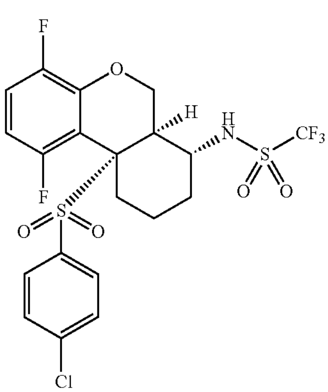 [SMILES: O=S(=O)(N[C@@H]1CCC[C@@]2(S(=O)(=O)c3ccc(Cl)cc3)c3c(F)ccc(F)c3OC[C@@H]12)C(F)(F)F] | 546.3; 4.86 |
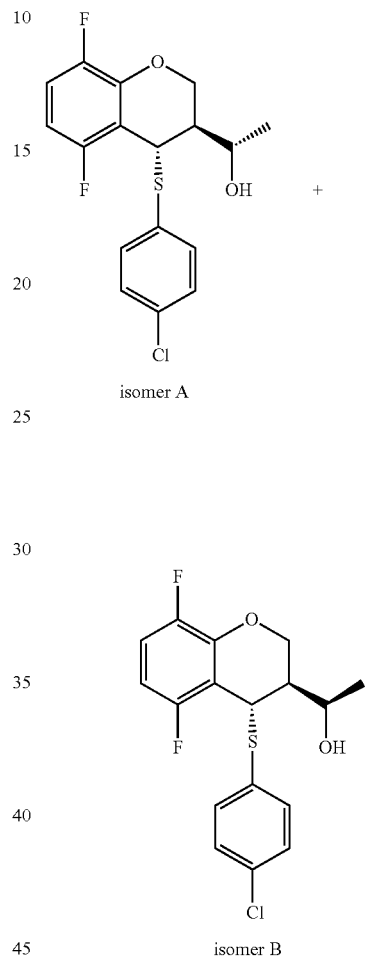
Example 200
10b-(4-Chloro-benzenesulfonyl)-7,10-difluoro-4,4-dimethyl-1,4a,5,10b-tetrahydro-2H,4H-pyrano[3,4-c]chromene
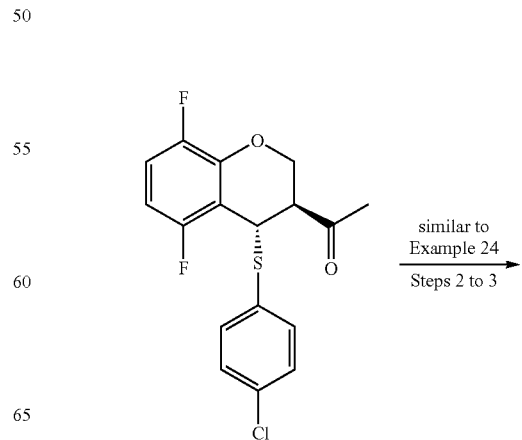

-continued

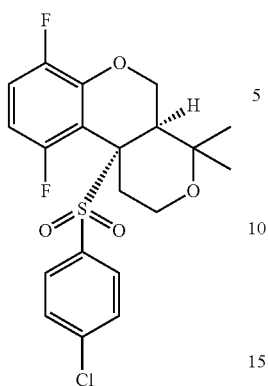

Example 200

Step 1

A solution of isomeric mixture A and B from Example 24 Step 2: (400 mg, 1.12 mmol) in DCM (5 mL) was treated with Dess-Martin periodinane (715 mg, 1.68 mmol) and stirred at RT for 1 h before excess sodium thiosulfate was added. The slurry was diluted with AcOEt and half-saturated NaHCO3, washed with sat NaHCO3, dried and concentrated. The crude ketone (~430 mg) was used as such in the next step.

Step 2

The crude ketone from Step 1 was subjected to conditions similar to the ones described in Steps 2 and 3 of Example 24 to provide Example HJ1: $^1$H NMR (CDCl$_3$ 400 MHz) δ 7.55 (d, J=8.6 Hz, 2H), 7.48 (d, J=8.6 Hz, 2H), 7.18 (m, 1H), 6.40 (m, 1H), 5.18 (dd, 1H), 4.46 (m, 1H), 3.72 (m, 1H), 3.41 (t, 1H), 2.71 (d, 1H), 2.53 (br d, 1H), 2.37 (m, 1H), 1.40 (s, 3H), 0.98 (s, 3H); LCMS (MH$^+$)=429.2; retention time=4.83 min.

Example 201

1-[10b-(4-Chloro-benzenesulfonyl)-7,10-difluoro-1,4-a,5,10b-tetrahydro-2H,4H-pyrano[3,4-c]chromen-4-yl]-butan-2-ol

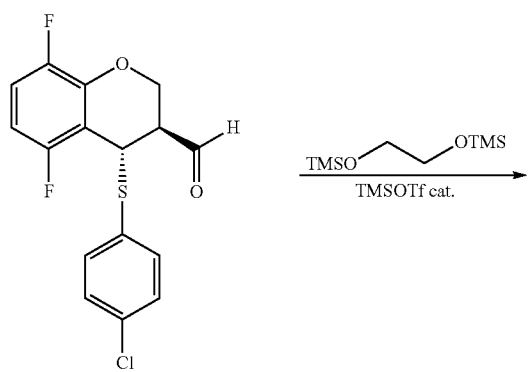

-continued

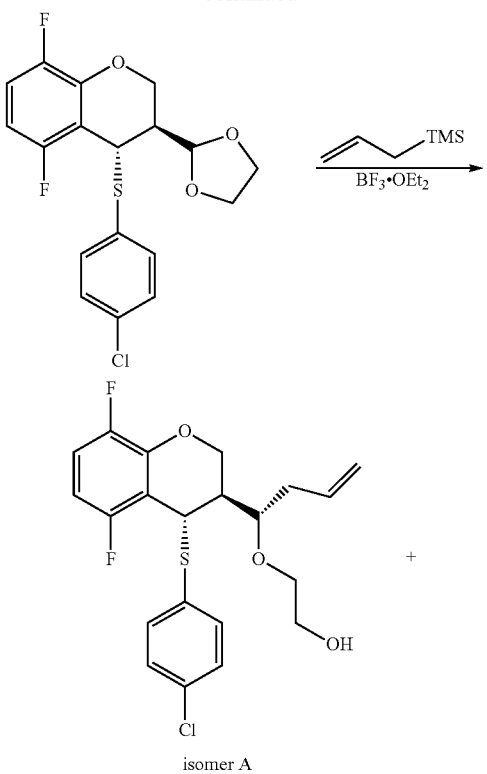

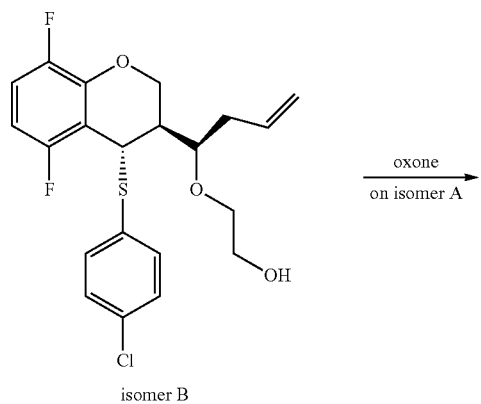

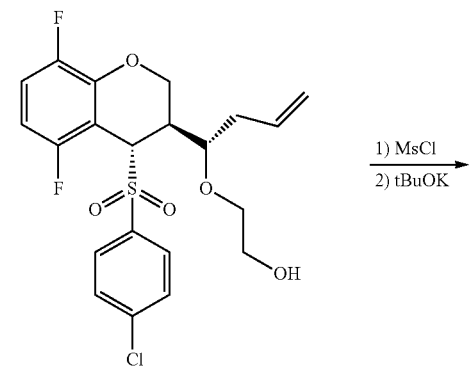

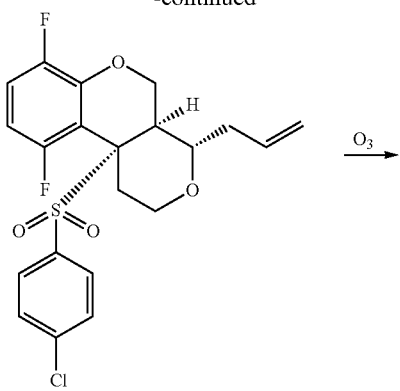

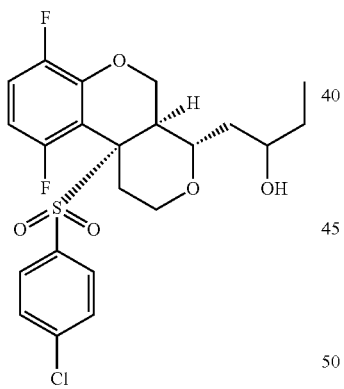

Example 201

Step 1

A solution of the product from Example 16 Step 2: (20.0 g, 58.6 mmol) in DCM (25 mL) at −78° C. was treated with 1,2-bistrimethylsilylglycol (18.7 mL, 76.2 mmol) and trimethylsilyltriflate (0.60 mL, 3.5 mmol) and the reaction was allowed to warm to RT overnight. The final mixture was diluted with sat. NaHCO3, extracted with DCM, dried and concentrated. The residue was purified by flash-chromatography over silica gel (eluted with Hexanes/AcOEt 99:1 to 50:50) to give 15.50 g (70%) of ketal.

Step 2

To a solution of ketal from Step 1 (13.72 g, 35.65 mmol) in DCM (200 mL) was added allyltrimethylsilane (28.7 mL, 180 mmol) followed by boron trifluoride etherate (22.6 mL, 180 mmol) and the reaction was stirred at 38° C. overnight then poured into water, extracted with DCM and AcOEt, dried and concentrated. The residue was purified by flash-chromatography over silica gel (eluted with Hexanes/AcOEt 95:5 to 70:30) to provide in order of elution 7.11 g (47%) of allyl alcohol isomer A followed by allyl alcohol isomer B.

Step 3

A solution of allyl alcohol isomer A from Step 2: (7.11 g, 16.65 mmol) and oxone (30.75 g, 50.0 mmol) in acetone (100 mL) and water (25 mL) was stirred at RT overnight then filtered, diluted with water and AcOEt, extracted with AcOEt, dried and concentrated. The residue is purified was purified by flash-chromatography over silica gel (eluted with Hexanes/AcOEt 99:1 to 60:40) to provide 5.50 g (72%) of allylsulfone.

Step 4

To a solution of allylsulfone from Step 3 (1.78 g, 3.87 mmol) in DCM (40 mL) was added methanesulfonyl chloride (480 uL, 6.20 mmol) followed by triethylamine (730 uL, 5.2 mmol) and the reaction was stirred overnight at RT. Workup with diluted HCl and DCM afforded 2.46 g of mesylate intermediate. This mesylate intermediate (2.46 g) in THF (40 mL) was treated slowly with tBuOK 1N in THF (10 mL, 10 mmol) and the reaction was stirred 35 min at RT then diluted with water, extracted with AcOEt and DCM, dried and concentrated. The residue was purified by flash-chromatography over silica gel (eluted with Hexanes/AcOEt 95:5 to 60:40) to give 1.50 g (88%) of allyl pyrane.

Step 5

To a solution of allyl pyrane from Step 4 (2.0 g, 4.35 mmol) in DCM (100 mL) at −78° C. was bubbled ozone until blue color persists. Nitrogen was then bubbled until the solution turns colorless and triphenylphosphine (1.87 g, 7.12 mmol) was added in one portion and the reactions was left to stir to RT for 1 h. The residue obtained after concentration was purified by flash-chromatography over silica gel (eluted with Hexanes/AcOEt 95:5 to 60:40) to provide 2.6 g (100%) of aldehyde.

Step 6

To a solution of aldehyde product from Step 5 (75 mg, 0.17 mmol) at −78° C. in THF (1 mL) was added EtMgBr 3N in Et2O (120 uL, 0.36 mmol) then the reaction was allowed to warm to 0° C. over 30 min, quenched into saturated NH4Cl, extracted with DCM and AcOEt, dried and concentrated. The residue was purified over silica gel (eluted with Hexanes/AcOEt 7:3) to provide 65.8 mg of Example 201 as a 1:1 diastereoisomeric mixture: $^1$H NMR (CDCl$_3$ 400 MHz) δ 7.63 (d, J=8.7 Hz, 2H), 7.52 (d, J=8.7 Hz, 2H), 7.11 (m, 1H), 6.46 (m, 1H), 5.14 (d, 1H), 4.41 (m, 1H), 3.92 (m, 1H), 3.65-3.85 (m, 1H), 3.45-3.60 (m, 1H), 3.18 (m, 1H), 2.62 (m, 1H), 2.53 (m, 1H), 2.33 (m, 1H), 1.85-2.05 (m, 1H), 1.60-1.80

(m, 1H), 1.45-1.55 (m, 1H), 0.95-1.00 (m, 3H); LCMS (MH⁺)= 473.3; retention time=4.51 min.

Example 202

1-[10b-(4-Chloro-benzenesulfonyl)-7,10-difluoro-1,4-a,5,10b-tetrahydro-2H,4H-pyrano[3,4-c]chromen-4-yl]-butan-2-ol

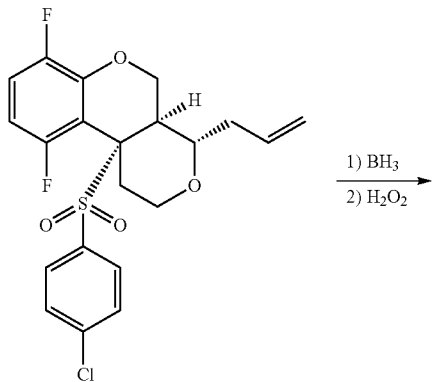

1) BH₃
2) H₂O₂

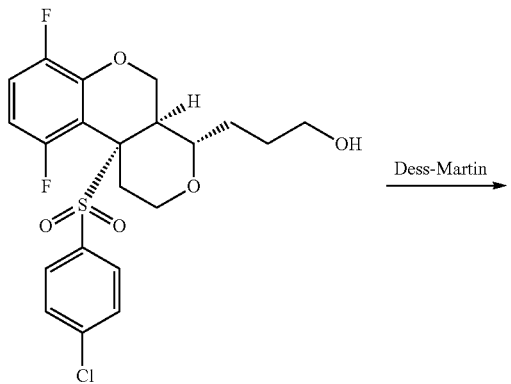

Dess-Martin

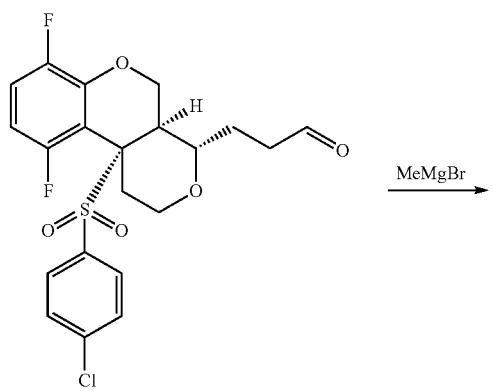

MeMgBr

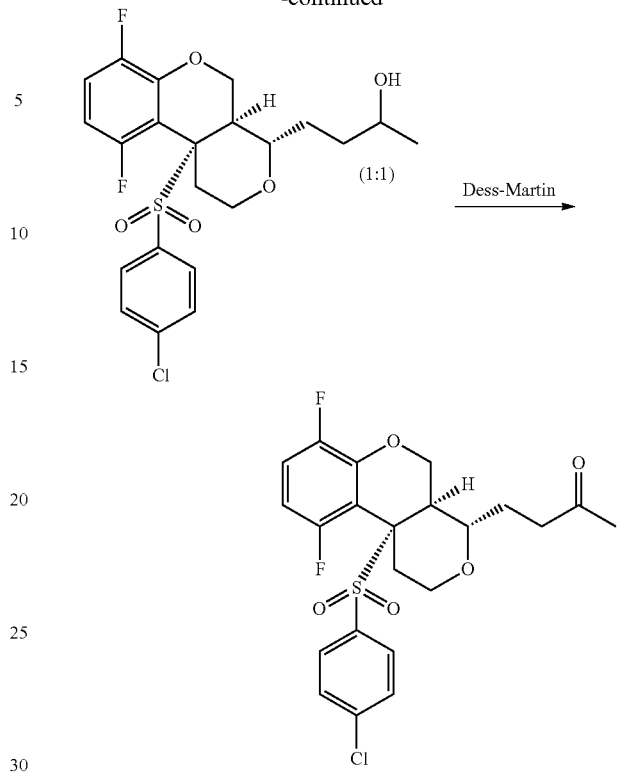

(1:1) Dess-Martin

Example 202

Step 1

A solution of the product from Example HJ2 Step 4 (433 mg, 0.98 mmol) in THF (3 mL) was treated with borane dimethylsulfide 2N in THF (1.5 mL, 1.50 mmol) and the reaction was stirred overnight at RT then treated at 10° C. slowly with 3N NaOH (9 mL) and 30% H2O2 (9 mL). After 1 h at RT the final mixture was diluted with water and extracted with DCM and AcOEt, dried and concentrated. The residue was purified by flash-chromatography over silica gel (eluted with Hexanes/AcOEt 95:5 to 60:40) to afford 281 mg (63%) of alcohol.

Step 2

A solution of alcohol from Step 1 (281 mg, 0.61 mmol) in DCM (5 mL) was treated with Dess-Martin periodinane (320 mg, 0.75 mmol) and the reaction was stirred 45 min at RT then diluted with AcOEt, washed with sat NaHCO3, dried and concentrated. The residue was diluted with DCM then filtered and concentrated to give 391 mg of crude ketone.

Step 3

A solution of crude ketone from Step 2: (178 mg) in THF (2 mL) was treated at −78° C. by MeMgBr 3N in Et2O (350 uL, 1.05 mmol) then the reaction was allowed to warm to 0 C over 45 min and poured into sat NH4Cl. After extraction with DCM and AcOEt followed by drying over Na2SO4 and concentration, the residue purified by flash-chromatography over silica gel (eluted with Hexanes/AcOEt 95:5 to 60:40) to afford 95 mg of alcohol.

Step 4

The alcohol from Step 3 (95 mg, 0.20 mmol) was subjected to the conditions described in Step 2: to afford, after purification over silica gel (eluted with Hexanes/AcOEt 8:2), 69 mg of Example 202: $^1$H NMR (CDCl$_3$ 400 MHz) δ 7.62 (d, J=8.6 Hz, 2H), 7.50 (d, J=8.6 Hz, 2H), 7.09 (m, 1H), 6.44 (m, 1H), 5.14 (m, 1H), 4.48 (m, 1H), 3.86 (m, 1H), 3.23 (m, 1H), 3.10 (m, 1H), 2.60-2.70 (m, 1H), 2.45-2.55 (m, 3H), 2.10-2.35 (m, 2H), 2.12 (s, 3H), 1.78 (m, 1H); LCMS (MH$^+$)= 471.3; retention time=4.55 min.

Example 203

4-[10b-(4-Chloro-benzenesulfonyl)-7,10-difluoro-1,4-a,5,10b-tetrahydro-2H,4H-pyrano[3,4-c]chromen-4-yl]-1,1,1-trifluoro-butan-2-ol

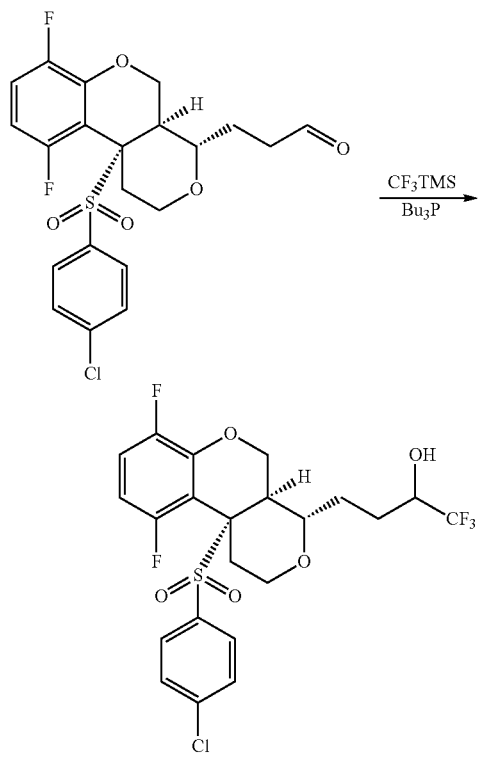

Example 203

Step 1

To a solution of product from Example 202 Step 2: (33.3 mg, 0.072 mmol) and tributylphosphine (20 uL) in DMF (0.6 mL) was added trifluoromethyltrimethylsilane (200 u) followed, slowly in a water bath, by TBAF 1N (65 uL). The reaction was stirred at RT for 60 hours then worked up with water and DCM then AcOEt. The residue was purified over silica gel (eluted with Hexanes/AcOEt 8:2) to give 11 mg of Example HJ4 as a 1:1 diastereoisomeric mixture: $^1$H NMR (CDCl$_3$ 400 MHz) δ 7.53 (d, J=8.6 Hz, 2H), 7.26 (d, J=8.6 Hz, 2H), 7.11 (m, 1H), 6.46 (m, 1H), 5.17 (m, 1H), 4.44 (m, 1H), 3.83 (m, 2H), 3.31 (m, 1H), 3.10-3.20 (m, 1H), 2.50-2.65 (m, 2H), 2.33 (m, 1H), 2.14 (m, 1H), 1.65-1.95 (m, 3H); LCMS (MH$^+$)=527.3; retention time=4.74 min.

Example 204

(4S)-[10b(S)-(4-Chloro-benzenesulfonyl)-7,10-difluoro-1,4-a,5,10b-tetrahydro-2H,4H-pyrano[3,4-c]chromen-4-yl]-butan-(2S)-ol

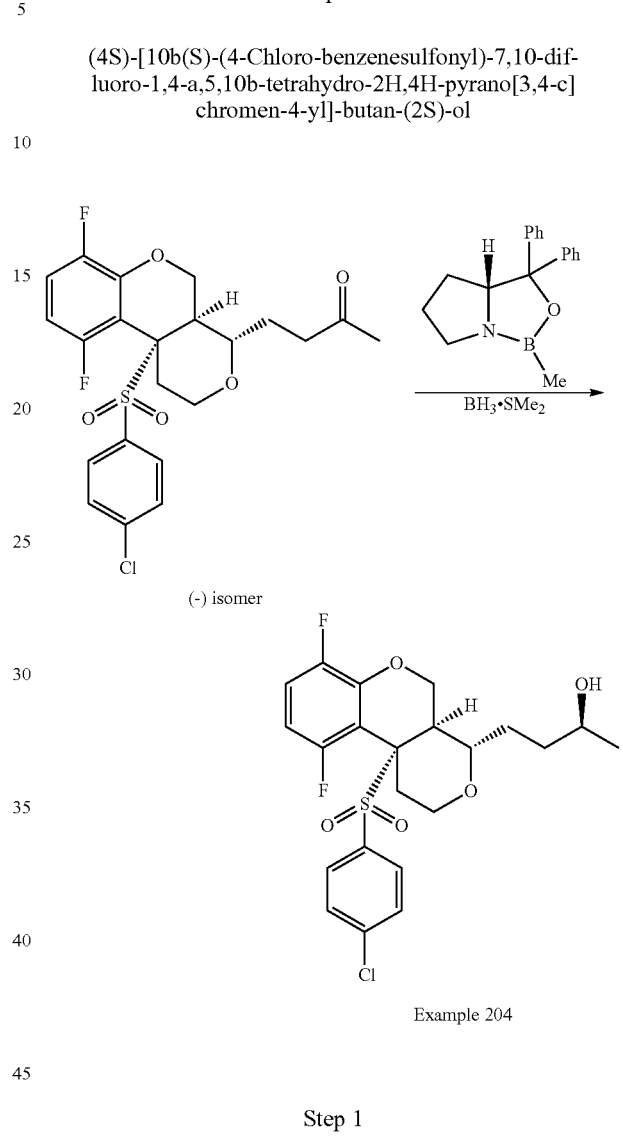

Example 204

Step 1

The ketone product of Example 202 was purified over Chiracel OD® column using Hexanes/isopropanol (30/70) as the mobile phase to afford, in order of elution, the (−) enantiomer ([α]$_D^{20}$=−1.17° (c=1, DCM)) followed by the (+) enantiomer ([α]$_D^{20}$=+0.98° (c=1, DCM)). To a solution of (−) enantiomer (10 mg, 0.021 mmol) in THF (200 uL) at 0° C. was added (R)-methyl-CBS-oxazaborolidine 1N in toluene (15 uL, 0.015 mmol) then, 5 min later, borane dimethylsulfide 2N in THF (30 uL, 0.06 mmol) over 5 min. The reaction was stirred 45 min at 0° C. then diluted with DCM, quenched with MeOH (~0.5 mL) and stirred for 5 min, diluted with sat NaHCO3, extracted with DCM and AcOEt. The residue was purified over silica gel (eluted with Hexanes/AcOEt 6:4) to give 8.4 mg of Example 204: $^1$H NMR (CDCl$_3$ 400 MHz) δ 7.63 (d, J=8.6 Hz, 2H), 7.50 (d, J=8.6 Hz, 2H), 7.08 (m, 1H), 6.45 (m, 1H), 517 (m, 1H), 4.46 (m, 1H), 3.89 (m, 1H), 3.77 (m, 1H), 3.26 (m, 1H), 3.14 (m, 1H), 2.50-2.60 (m, 2H), 2.30 (m, 1H), 2.00 (m, 1H), 1.45-1.70 (m, 3H), 1.19 (d, 3H); LCMS (MH$^+$)=473.3; retention time=4.37 min.

Examples 205-218

Following procedures similar to the ones described in Examples 200 to 204, the compounds in Table 53 were prepared.

TABLE 53

| Ex. No. | STRUCTURE | Mass Spec (MH+ except otherwise noted); retention time (min) |
|---|---|---|
| 205 | 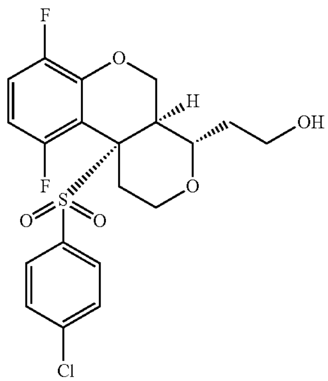 [SMILES: O=S(=O)(c1ccc(Cl)cc1)[C@@]12CCO[C@@H](CCO)[C@@H]1COc1c(F)ccc(F)c12] | 445.2; 3.92 |
| 206 | 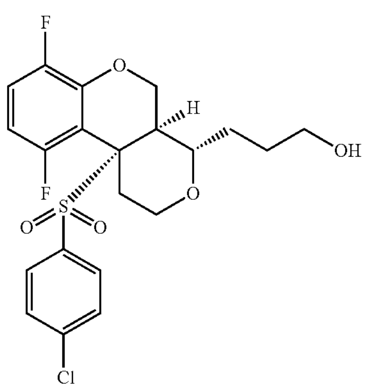 [SMILES: O=S(=O)(c1ccc(Cl)cc1)[C@@]12CCO[C@@H](CCCO)[C@@H]1COc1c(F)ccc(F)c12] | 459.3; 3.98 |
| 207 | 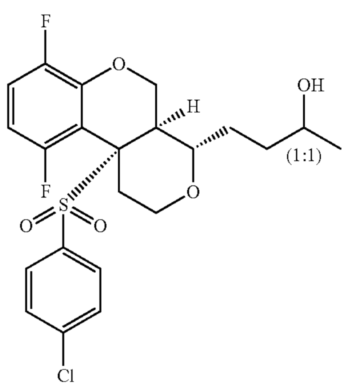 [SMILES: CC(O)CC[C@@H]1OCC[C@@]2(S(=O)(=O)c3ccc(Cl)cc3)c3c(F)ccc(F)c3OC[C@@H]12] | 473.3; 4.26 |

TABLE 53-continued

| Ex. No. | STRUCTURE | Mass Spec (MH+ except otherwise noted); retention time (min) |
|---|---|---|
| 208 | 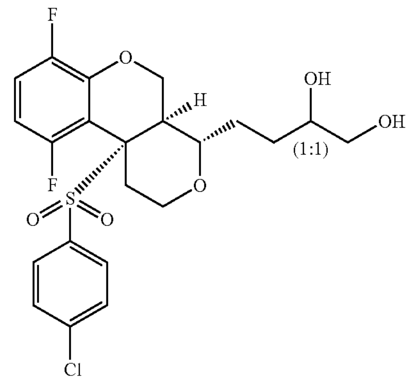 [SMILES: O=S(=O)(c1ccc(Cl)cc1)[C@@]12CCO[C@@H](CCC(O)CO)[C@@H]1COc1c(F)ccc(F)c12] | 489.3; 3.63 |
| 209 | 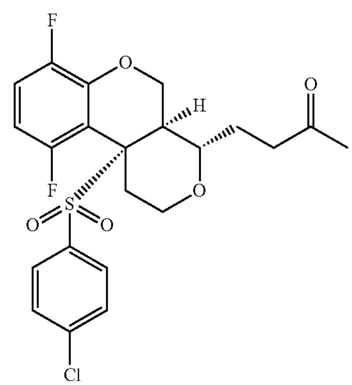 [SMILES: CC(=O)CC[C@@H]1OCC[C@@]2(S(=O)(=O)c3ccc(Cl)cc3)c3c(F)ccc(F)c3OC[C@@H]12] | 471.3; 4.55 |
| 210 | 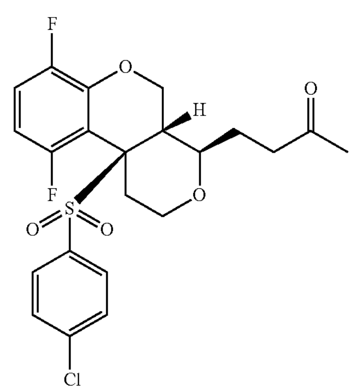 [SMILES: CC(=O)CC[C@H]1OCC[C@]2(S(=O)(=O)c3ccc(Cl)cc3)c3c(F)ccc(F)c3OC[C@H]12] | 471.3; 4.55 |

TABLE 53-continued
| Ex. No. | STRUCTURE | Mass Spec (MH+ except otherwise noted); retention time (min) |
|---|---|---|
| 211 | 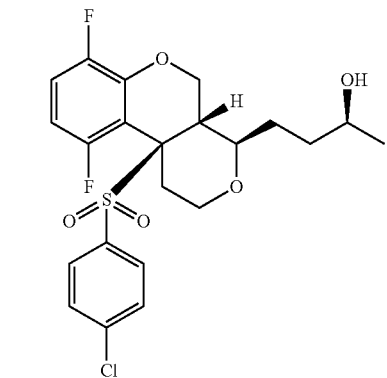 [SMILES: C[C@H](O)CC[C@H]1OCC[C@]2(S(=O)(=O)c3ccc(Cl)cc3)c3c(F)ccc(F)c3OC[C@H]12] | 473.3; 4.38 |
| 212 | 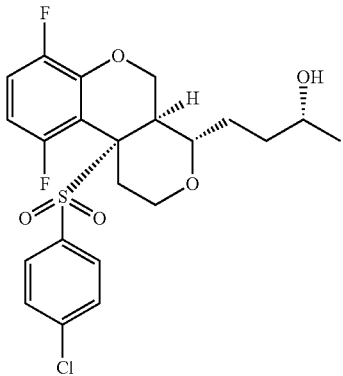 [SMILES: C[C@@H](O)CC[C@@H]1OCC[C@@]2(S(=O)(=O)c3ccc(Cl)cc3)c3c(F)ccc(F)c3OC[C@@H]12] | 473.3; 4.37 |
| 213 | 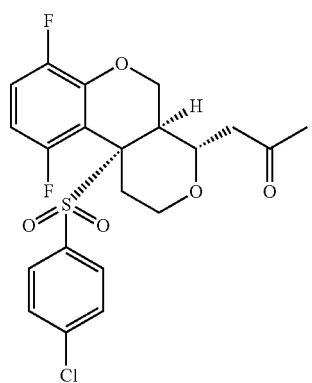 [SMILES: CC(=O)C[C@@H]1OCC[C@@]2(S(=O)(=O)c3ccc(Cl)cc3)c3c(F)ccc(F)c3OC[C@@H]12] | 457.3; 4.38 |
| 214 | 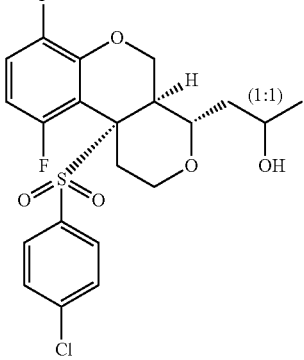 | 459.3; 4.18 |
| 215 | 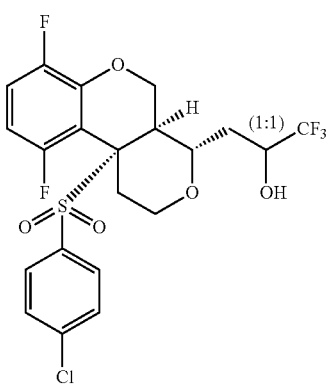 [SMILES: O=S(=O)(c1ccc(Cl)cc1)[C@@]12CCO[C@@H](CC(O)C(F)(F)F)[C@@H]1COc1c(F)ccc(F)c12] | 513.3; 4.68 |
| 216 | 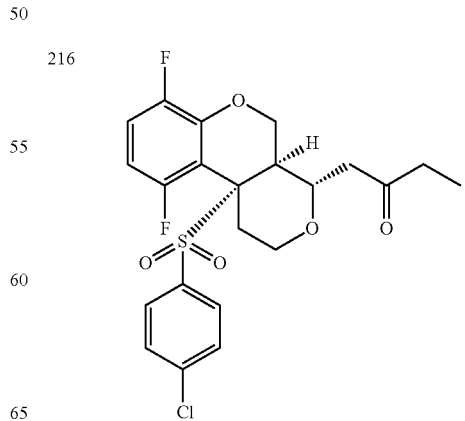 | 471.3; 4.79 |

TABLE 53-continued
| Ex. No. | STRUCTURE | Mass Spec (MH+ except otherwise noted); retention time (min) |
|---|---|---|
| 217 | 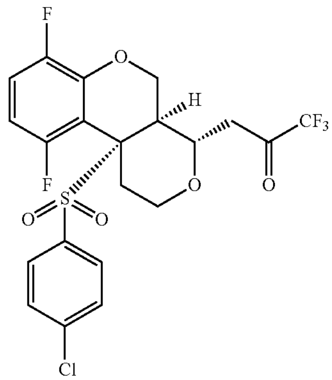 [SMILES: O=C(C[C@@H]1OCC[C@@]2(S(=O)(=O)c3ccc(Cl)cc3)c3c(F)ccc(F)c3OC[C@@H]12)C(F)(F)F] | 511.3; 4.52 |
| 218 | 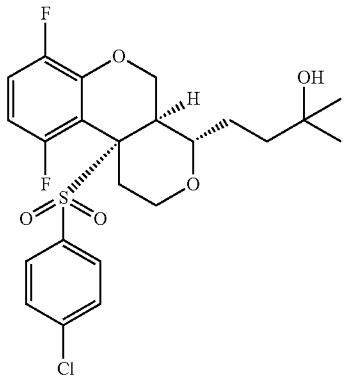 [SMILES: CC(C)(O)CC[C@@H]1OCC[C@@]2(S(=O)(=O)c3ccc(Cl)cc3)c3c(F)ccc(F)c3OC[C@@H]12] | 487.3; 4.41 |
Example 219
Ethanesulfonic acid [10b-(4-chloro-benzenesulfonyl-7,10-difluoro-1,4a,5,10b-tetrahydro-2H,4H-pyrano[3,4-c]chromen-4-ylmethyl]-amide
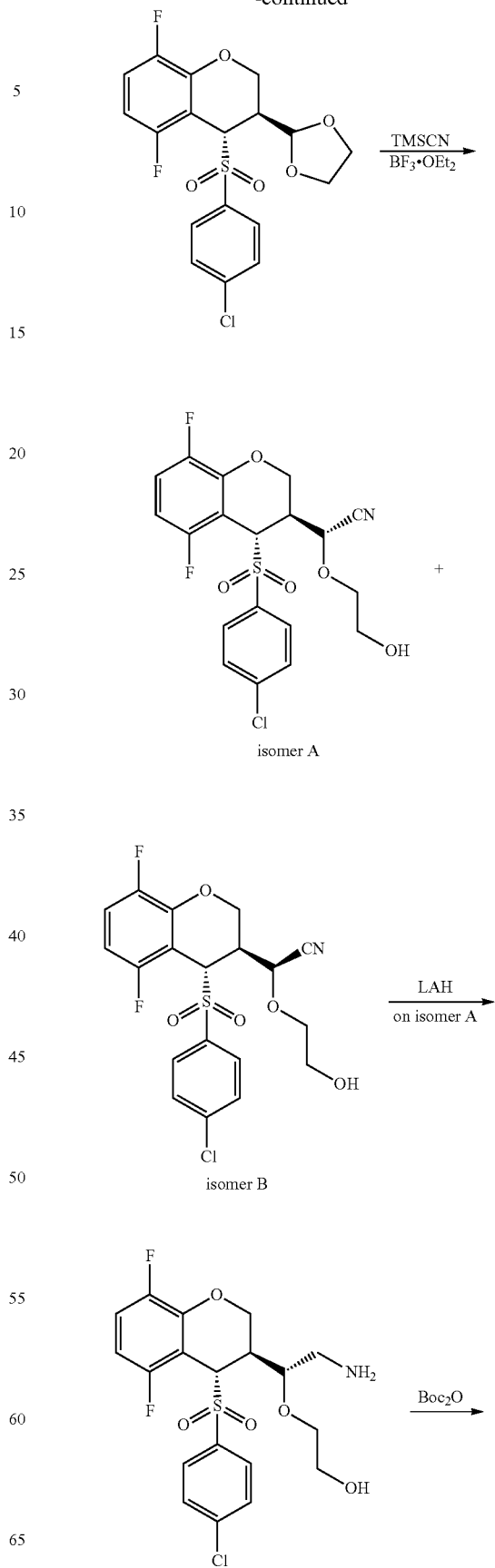

-continued

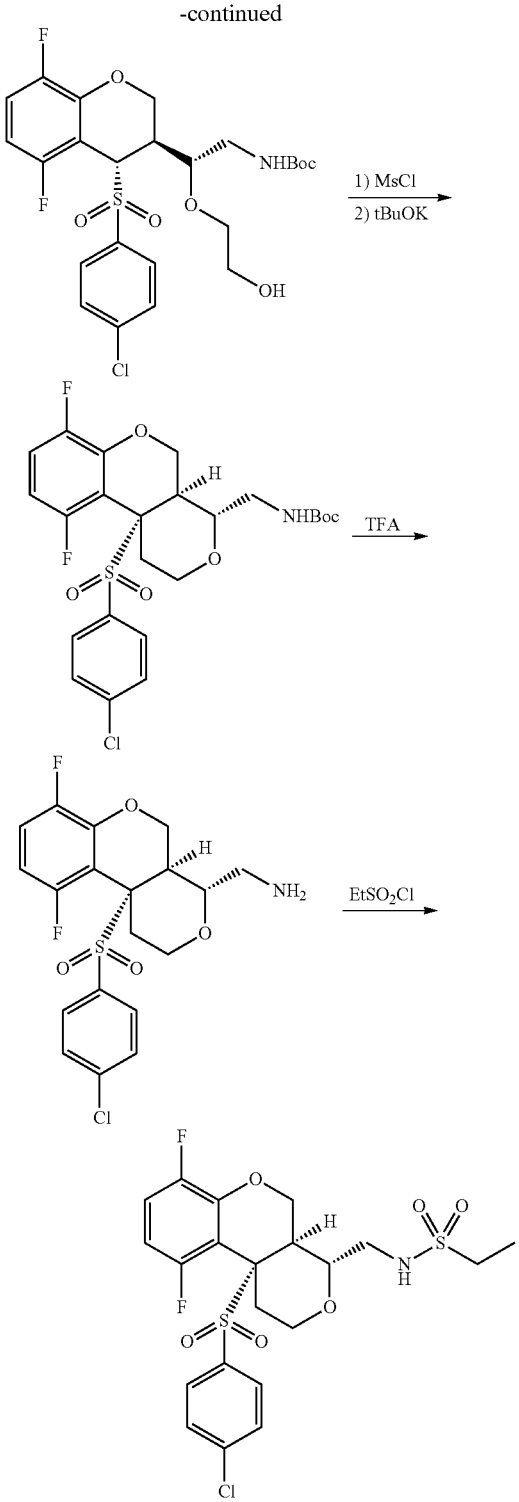

Example 219

Step 1

A solution of ketal product from Example 201 Step 1 (15.0 g, 39.0 mmol) in acetone (480 mL) and water (120 mL) was added oxone (51.0 g, 82.0 mmol) and the reaction was stirred at RT 48 h. The final mixture was filtered, rinsed with DCM, then diluted with water and extracted with DCM. After drying and concentrating, the residue was purified by flash-chromatography over silica gel (eluted with Hexanes/AcOEt 99:1 to 50:50) to give 13.5 g (70%) of sulfone ketal.

Step 2

To a solution of sulfone ketal from Step 1 (5.0 g, 12.0 mmol) in DCM (100 mL) at 0° C. was added trimethylsilylcyanide (2.40 mL, 18.0 mmol) followed by borontrifluoride etherate (1.50 mL, 12.0 mmol) and the reaction was warmed to RT over 1 h. Additional trimethylsilylcyanide (1.20 mL, 9.0 mmol) and borontrifluoride etherate (0.75 mL, 6.0 mmol) were added and the mixture was stirred 1 h. The final mixture was diluted with DCM and water, extracted with DCM, dried and concentrated. The residue was purified by flash-chromatography over silica gel (eluted with a slow gradient of DCM/AcOEt 99:1 to 60:40) to give 2.20 g (41%) of cyano alcohol isomer A (41%) followed by 2.8 g (52%) of cyano alcohol isomer B.

Step 3

To a solution of cyano alcohol isomer A from Step 2: (2.70 g, 6.08 mmol) in THF (200 mL) at 0° C. was added lithium aluminum hydride 1N in THF (12.0 mL, 12.0 mmol) and the reaction was stirred 1 h at RT. The final mixture was diluted with DCM, quenched slowly with 3 mL of sat. NaHCO3, stirred 15 min at RT then treated with Na2SO4 and filtered over Celite (eluted with DCM/MeOH 9:1). Upon concentration, 2.60 g (96%) of amino alcohol was obtained.

Step 4

To a solution of amino alcohol from Step 3 (2.60 g, 5.81 mmol) in DCM (60 mL) was added triethylamine (1.60 mL, 12.0 mmol) followed by tert-butyldicarbonate (1.50 g, 6.88 mmol) and the reaction was stirred overnight at RT. The final mixture was concentrated and purified by flash-chromatography over silica gel (eluted with Hexanes/AcOEt 80:20 to 20:80) to provide 2.80 g (88%) of Boc-amino alcohol.

Step 5

To a solution of Boc-amino alcohol from Step 4 (2.80 g, 5.11 mmol) in DCM (60 mL) was added methanesulfonyl chloride (0.60 mL, 7.60 mmol) followed by diisopropylethylamine (1.80 mL, 10.2 mmol) and the reaction was stirred overnight at RT. The final mixture was concentrated and purified by flash-chromatography over silica gel (eluted with Hexanes/AcOEt 80:20 to AcOEt) to provide 3.0 g (94%) of mesylate intermediate. This mesylate intermediate (3.0 g, 4.80 mmol) in THF (60 mL) was treated at −30° C. with tBuOK 1N in THF (10 mL, 10 mmol) and the reaction was stirred 30 min then diluted with water, extracted with AcOEt and DCM, dried and concentrated. The residue was purified by flash-chromatography over silica gel (eluted with Hexanes/AcOEt 80:20 to AcOEt) to provide 2.20 g (90%) of Boc-amino pyrane.

Step 6

To a solution of Boc-amino pyrane from Step 5 (900 mg, 1.70 mmol) in DCM (60 mL) was added TFA (1 mL) and the reaction was stirred 1 h at RT. Workup by adding 0.5 N NaOH followed by extraction with DCM, drying and concentration afforded 700 mg (95%) of aminopyrane.

Step 7

A solution of aminopyrane from Step 6 (25 mg, 0.058 mmol) in DCM (1 mL) was treated with ethanesulfonyl chloride (50 uL) followed by diisopropylethylamine (100 uL) and the reaction was stirred overnight at RT then purified over silica gel (eluted with Hexanes/AcOEt 50:50) to afford 19.0 mg of Example 219: $^1$H NMR (CDCl$_3$ 400 MHz) δ 7.64 (d, J=8.7 Hz, 2H), 7.54 (d, J=8.7 Hz, 2H), 7.11 (m, 1H), 6.49 (m, 1H), 5.17 (m, 1H), 4.56 (m, 1H), 4.43 (m, 1H), 3.90 (m, 1H), 3.35-3.50 (m, 3H), 3.20 (m, 1H), 3.00-3.10 (m, 2H), 2.88 (m, 1H), 2.61 (m, 1H), 2.15 (m, 1H), 1.37 (t, 3H); LCMS (MH$^+$) =522.3; retention time=4.23 min.

Following procedures similar to the ones described in Examples 20 and 219 including the use of the same sub sequential procedures of cyano alcohol isomer A from Step 2: on cyano alcohol isomer B from Step 2, the compounds in Table 54 were prepared

TABLE 54

| Ex. No. | STRUCTURE | Mass Spec (MH$^+$ except otherwise noted); retention time (min) |
|---|---|---|
| 220 | | 430.2; 3.03 |
| 221 | | 508.3; 3.99 |
| 222 | 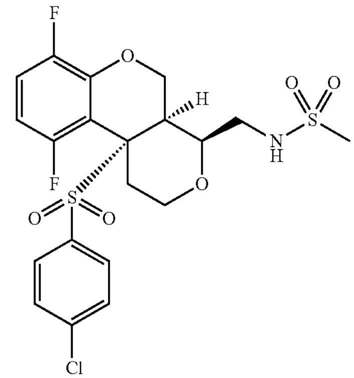 [SMILES: CS(=O)(=O)NC[C@H]1OCC[C@@]2(S(=O)(=O)c3ccc(Cl)cc3)c3c(F)ccc(F)c3OC[C@@H]12] | 508.3; 4.19 |
| 223 | 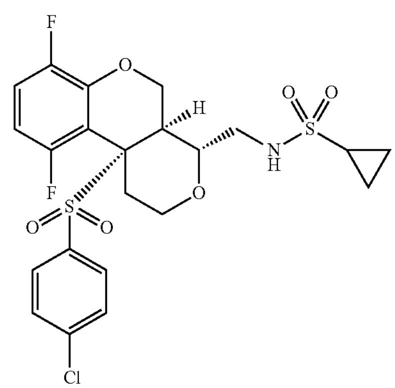 [SMILES: O=S(=O)(NC[C@@H]1OCC[C@@]2(S(=O)(=O)c3ccc(Cl)cc3)c3c(F)ccc(F)c3OC[C@@H]12)C1CC1] | 534.1; 4.78 |
| 224 | 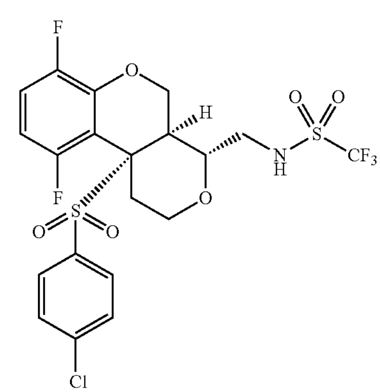 [SMILES: O=S(=O)(NC[C@@H]1OCC[C@@]2(S(=O)(=O)c3ccc(Cl)cc3)c3c(F)ccc(F)c3OC[C@@H]12)C(F)(F)F] | 562.3; 4.78 |

TABLE 54-continued

| Ex. No. | STRUCTURE | Mass Spec (MH+ except otherwise noted); retention time (min) |
|---|---|---|
| 225 | (structure) | 576.3; 4.61 |
| 226 | (structure) | 526.3; 4.46 |
| 227 | (structure) | 544.3; 4.54 |

TABLE 54-continued

| Ex. No. | STRUCTURE | Mass Spec (MH+ except otherwise noted); retention time (min) |
|---|---|---|
| 228 | (structure) | 536.3; 4.48 |
| 229 | (structure) | 563.3; 4.57 |
| 230 | (structure) | 526.3; 4.61 |

TABLE 54-continued

| Ex. No. | STRUCTURE | Mass Spec (MH+ except otherwise noted); retention time (min) |
|---|---|---|
| 231 | 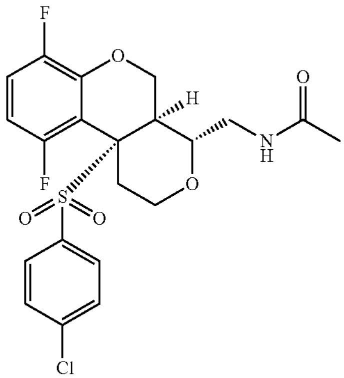 [SMILES: CC(=O)NC[C@@H]1OCC[C@@]2(S(=O)(=O)c3ccc(Cl)cc3)c3c(F)ccc(F)c3OC[C@@H]12] | 472.3; 3.74 |
| 232 | 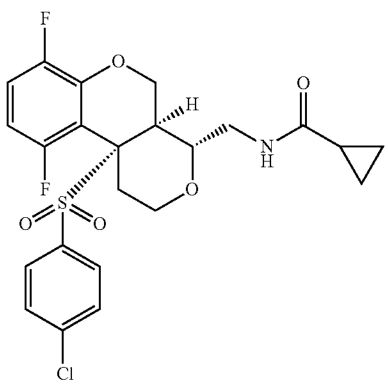 [SMILES: O=C(NC[C@@H]1OCC[C@@]2(S(=O)(=O)c3ccc(Cl)cc3)c3c(F)ccc(F)c3OC[C@@H]12)C1CC1] | 498.3; 4.02 |
| 233 | 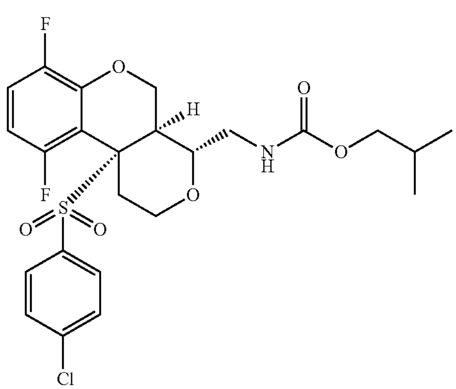 [SMILES: CC(C)COC(=O)NC[C@@H]1OCC[C@@]2(S(=O)(=O)c3ccc(Cl)cc3)c3c(F)ccc(F)c3OC[C@@H]12] | 530.3; 4.92 |

Example 234

10b-(4-Chloro-benzenesulfonyl-7,10-difluoro-1,4a,5,10b-tetrahydro-2H,4H-pyrano[3,4-c]chromene-4-carbonitrile

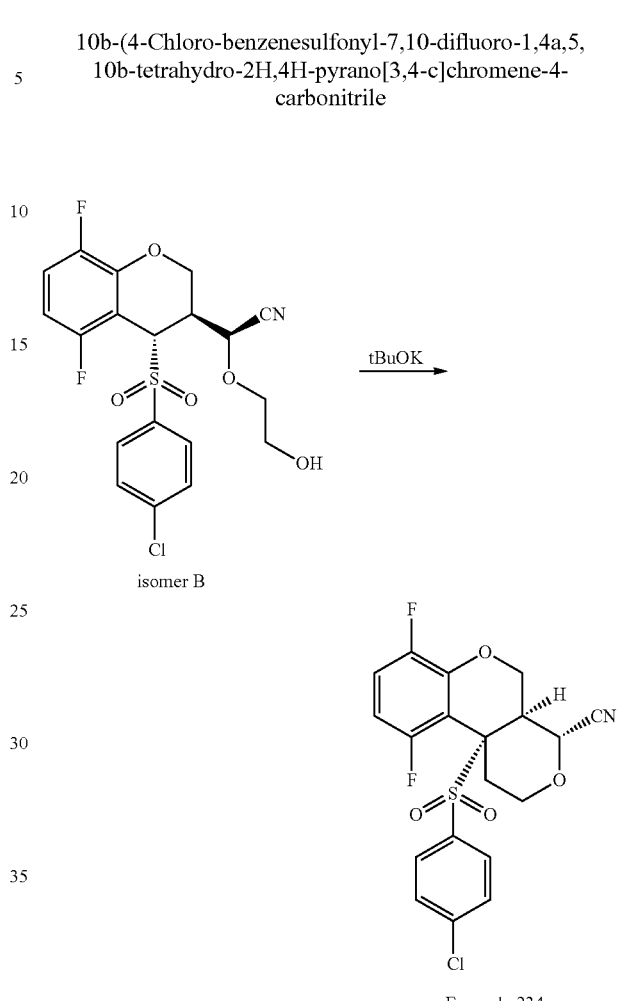

Step 1

To a solution of cyano alcohol isomer B product from Example 219 Step 2: (50 mg, 0.11 mmol) in THF (1 mL) at −40° C. was added tBuOK 1N in THF (0.17 ml, 0.17 mmol) and the reaction was stirred 30 min at this temperature then 2 h at 0° C. The final mixture was diluted with water, extracted with AcOEt, dried and concentrated. The residue was purified over silica gel (eluted with Hexanes/AcOEt 50:50) to give 5.7 mg of Example 234: $^1$H NMR (CDCl$_3$ 400 MHz) δ 7.63 (d, J=8.7 Hz, 2H), 7.53 (d, J=8.7 Hz, 2H), 7.15 (m, 1H), 6.52 (m, 1H), 5.25 (m, 1H), 4.60 (m, 1H), 4.15 (m, 1H), 4.00 (m, 1H), 3.19 (m, 1H), 3.03 (m, 1H), 2.58 (m, 1H), 2.38 (m, 1H); LCMS (MH$^+$+H2O)=443.3; retention time=4.61 min.

Examples 235 and 236

Following procedures similar to the ones described in Example 234 using tBuOK/KOH mixture instead of pure tBuOK, and also including the possible subsequential addition of a N-alkylating agent, the compounds in Table 55 were prepared

TABLE 55

| Ex. No. | STRUCTURE | Mass Spec (MH⁺ except otherwise noted); retention time (min) |
|---|---|---|
| 235 | 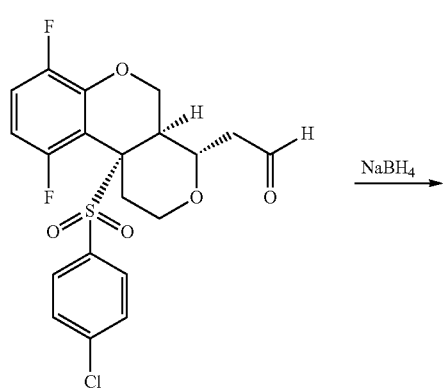 | 444.2; 3.66 |
| 236 | 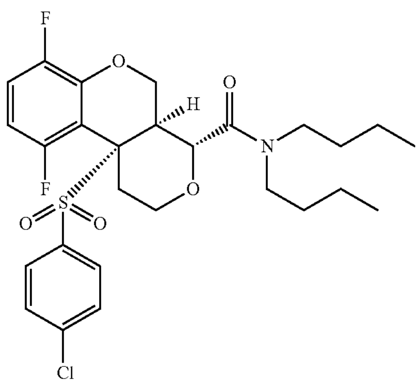 [SMILES: CCCCN(CCCC)C(=O)[C@@H]1OCC[C@@]2(S(=O)(=O)c3ccc(Cl)cc3)c3c(F)ccc(F)c3OC[C@@H]12] | 556.3; 5.35 |

Example 237

N-{2-[10b-(4-Chloro-benzenesulfonyl)-7,10-difluoro-1,4-a,5,10b-tetrahydro-2H,4H-pyrano[3,4-c]chromen-4-yl]ethyl}-methanesulfonamide

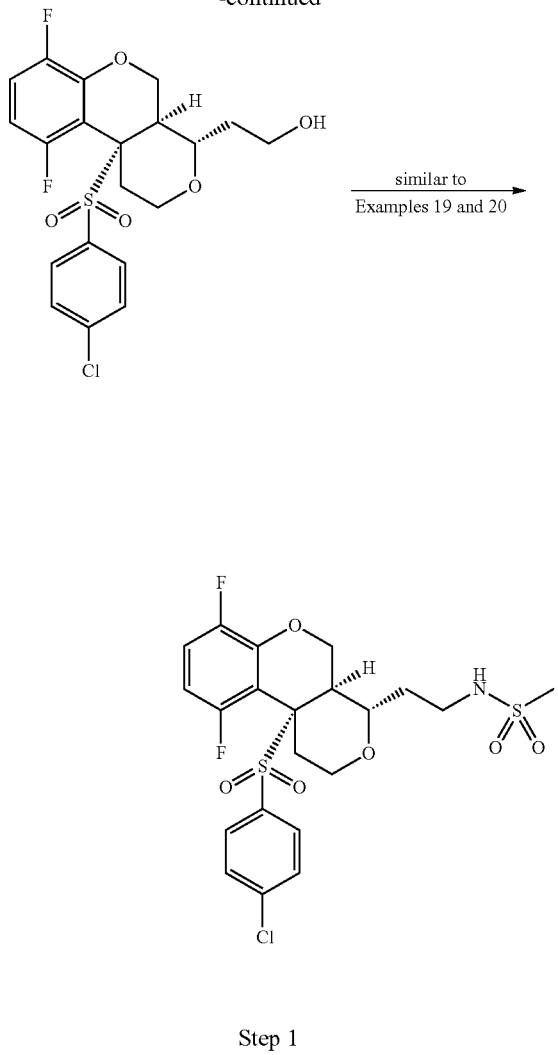

Step 1

To a solution of aldehyde product from Example 201 Step 5 (1.50 g, 3.39 mmol) in MeOH (50 mL) was slowly added sodium borohydride (160 mg, 4.23 mmmol) and the reaction was stirred 2 h at RT. The mixture was then diluted with brine and DCM, extracted with DCM, dried and concentrated to give 1.54 g (100%) of alcohol.

Step 2

The alcohol from Step 1 was subjected to conditions similar to the ones described in Examples 19 and 20 to provide Example 237: $^1$H NMR (CDCl$_3$ 400 MHz) δ 7.63 (d, J=8.7 Hz, 2H), 7.52 (d, J=8.7 Hz, 2H), 7.12 (m, 1H), 6.47 (m, 1H), 5.66 (m, 1H), 4.84 (m, 1H), 4.38 (m, 1H), 3.90 (m, 1H), 3.10-3.45 (m, 4H), 2.90 (s, 3H), 2.45-2.60 (m, 2H), 2.30 (m, 1H), 2.17 (m, 1H), 1.82 (m, 1H); LCMS (MH⁺)=522.3; retention time=4.02 min.

Examples 238 to 243

Following procedures similar to the ones described in Examples 20 and 237 including similar procedures on the alcohol product from Step 1, the compounds in Table 56 were prepared.

TABLE 56

| Ex. No. | STRUCTURE | Mass Spec (MH+ except otherwise noted); retention time (min) |
|---|---|---|
| 238 | 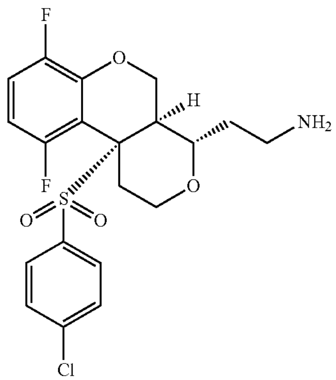 [SMILES: NCC[C@@H]1OCC[C@@]2(S(=O)(=O)c3ccc(Cl)cc3)c3c(F)ccc(F)c3OC[C@@H]12] | 444.2; 2.99 |
| 239 | 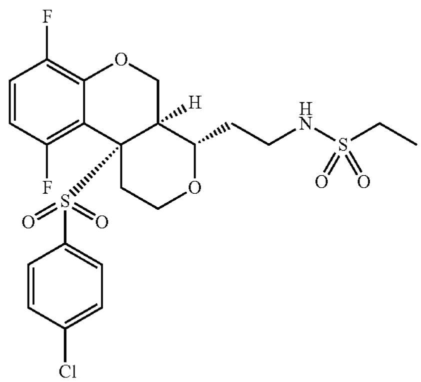 [SMILES: CCS(=O)(=O)NCC[C@@H]1OCC[C@@]2(S(=O)(=O)c3ccc(Cl)cc3)c3c(F)ccc(F)c3OC[C@@H]12] | 536.3; 4.16 |
| 240 | 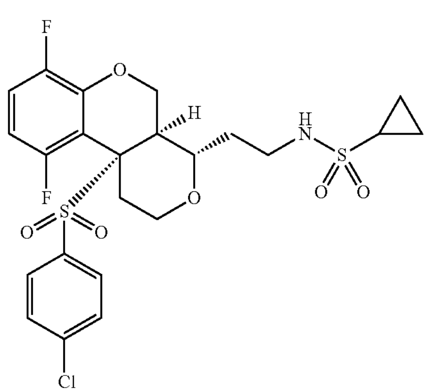 [SMILES: O=S(=O)(NCC[C@@H]1OCC[C@@]2(S(=O)(=O)c3ccc(Cl)cc3)c3c(F)ccc(F)c3OC[C@@H]12)C1CC1] | 548.3; 4.24 |

TABLE 56-continued

| Ex. No. | STRUCTURE | Mass Spec (MH+ except otherwise noted); retention time (min) |
|---|---|---|
| 241 | 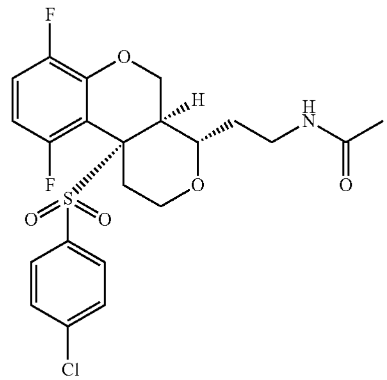 [SMILES: CC(=O)NCC[C@@H]1OCC[C@@]2(S(=O)(=O)c3ccc(Cl)cc3)c3c(F)ccc(F)c3OC[C@@H]12] | 486.3; 3.72 |
| 242 | 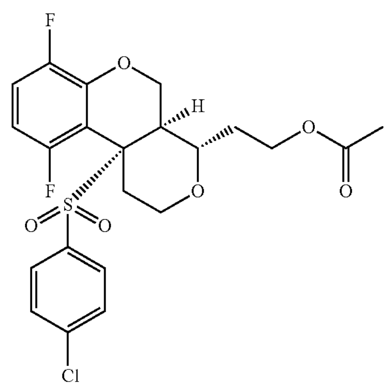 [SMILES: CC(=O)OCC[C@@H]1OCC[C@@]2(S(=O)(=O)c3ccc(Cl)cc3)c3c(F)ccc(F)c3OC[C@@H]12] | 487.3; 4.63 |
| 243 | 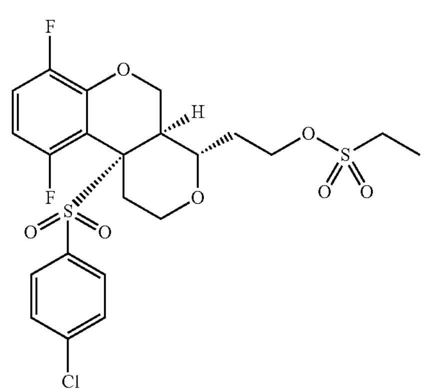 [SMILES: CCS(=O)(=O)OCC[C@@H]1OCC[C@@]2(S(=O)(=O)c3ccc(Cl)cc3)c3c(F)ccc(F)c3OC[C@@H]12] | 537.3; 4.56 |

Example 244

3-[10b-(4-Chloro-benzenesulfonyl-7,10-difluoro-1,4-a,5,10b-tetrahydro-2H,4H-pyrano[3,4-c]chromen-4-ylmethyl]-isoxazole

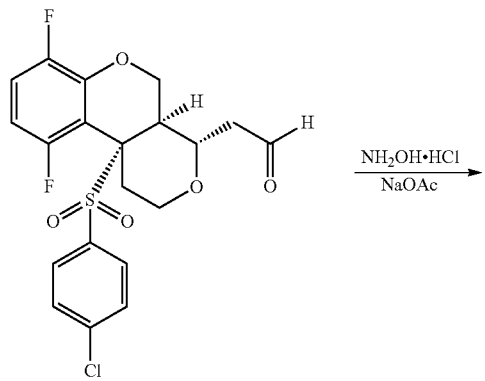

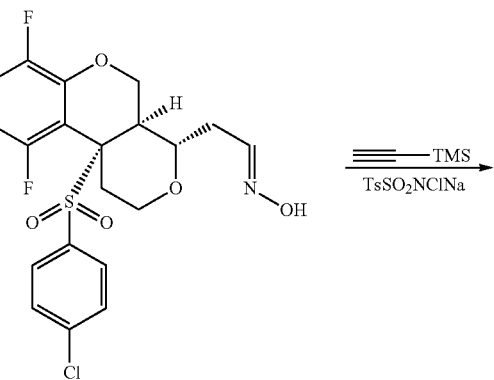

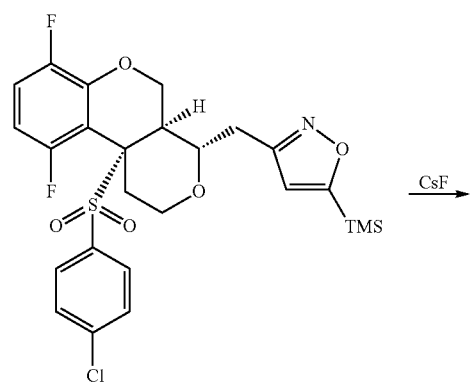

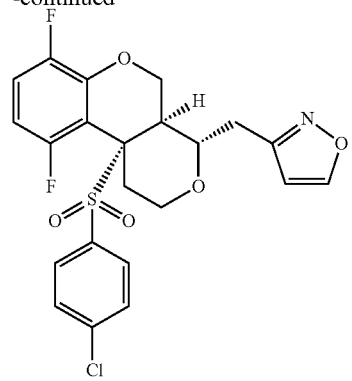

Example 244

Step 1

To a solution of aldehyde product from Example 201 Step 5 (250 mg, 0.56 mmol) in EtOH (5 mL) were added hydroxylamine hydrochloride (150 mg) and sodium acetate (300 mg). The reaction was stirred at RT overnight then filtered and concentrated and the residue was purified by flash-chromatography over silica gel (eluted with Hexanes/AcOEt 99:1 to AcOEt) to give 209 mg (82%) of hydroxime.

Step 2

To a solution of hydroxime from Step 1 (35 mg, 0.076 mmol) and trimethylsilylacetylene (25 uL) in EtOH (1 mL) and water (0.3 mL) was added chloramines-T trihydrate (28.1 mg, 0.10 mmol) and the reaction was stirred 1 h at RT. It was then diluted with water and extracted with DCM and AcOEt, dried and concentrated. The residue was purified over silica gel (eluted with Hexanes/AcOEt 6:4) to give 15 mg of TMS isoxazole.

Step 3

A solution of TMS isoxazole from Step 2: (15 mg) and CsF (40 mg) in acetonitrile (2 mL) and EtOH (0.4 mL) were refluxed for 10 min then concentrated and purified over silica gel (eluted with Hexanes/AcOEt 7:3) to give 8 mg of Example 244: $^1$H NMR (CDCl$_3$ 400 MHz) δ 8.32 (s, 1H), 7.62 (d, J=8.7 Hz, 2H), 7.49 (d, J=8.7 Hz, 2H), 7.11 (m, 1H), 6.48 (m, 1H), 6.30 (s, 1H), 5.14 (m, 1H), 4.56 (m, 1H), 3.91 (m, 1H), 3.52 (m, 1H), 3.10-3.20 (m, 2H), 2.70-2.85 (m, 1H), 2.56 (m, 1H), 2.46 (m, 1H), 2.21 (m, 1H); LCMS (MH$^+$)=482.3; retention time=4.62 min.

Example 245

Following procedures similar to the ones described in Example 244, the compound in Table 57 was prepared.

TABLE 57

| Ex. No. | STRUCTURE | Mass Spec (MH+ except otherwise noted); retention time (min) |
|---|---|---|
| 245 | 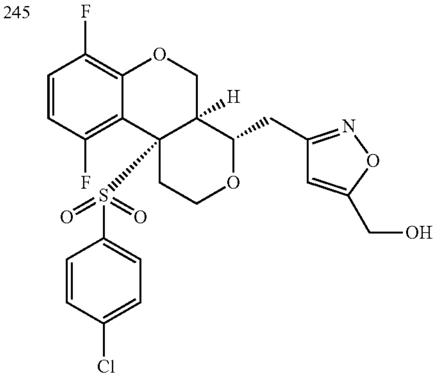 | 512.3; 4.17 |

Example 246

2-[10b-(4-Chloro-benzenesulfonyl)-7,10-difluoro-1,4-a,5,10b-tetrahydro-2H,4H-pyrano[3,4-c]chromen-4-ylmethyl]-benzothiazole

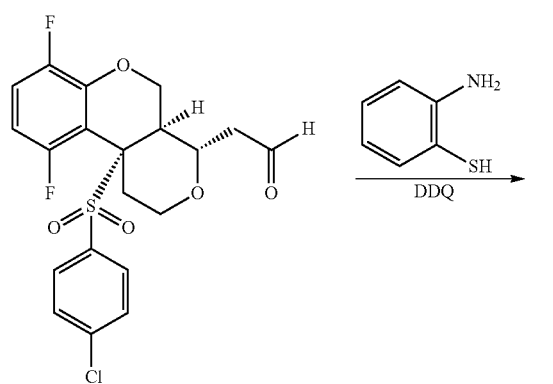

Example 246

Step 1

To a solution of aldehyde product from Example 201 Step 5 (35 mg, 0.08 mmol) and 2-aminothiophenol (8 uL, 0.10 mmol) in DCM (0.6 mL) was added DDQ (23 mg, 0.10 mmol) and the reaction was stirred overnight at RT then purified over silica gel (eluted with Hexanes/AcOEt 7:3) to provide 17.9 mg of Example 24612: $^1$H NMR (CDCl$_3$ 400 MHz) δ 7.98 (d, 1H), 7.83 (d, 1H), 7.62 (d, J=8.6 Hz, 2H), 7.48 (t, 1H), 7.35-7.45 (m, 3H), 7.12 (m, 1H), 6.49 (m, 1H), 5.20 (m, 1H), 4.65 (m, 1H), 3.96 (m, 1H), 3.77 (m, 1H), 3.45-3.65 (m, 2H), 3.21 (m, 1H), 2.55-2.65 (m, 2H), 2.23 (m, 1H); LCMS (MH+)=548.3; retention time=5.16 min.

Examples 247 and 248

Following procedures similar to the ones described in Example 246 including the use or not of oxidant such as air, the compounds in Table 58 were prepared.

TABLE 58

| Ex. No. | STRUCTURE | Mass Spec (MH+ except otherwise noted); retention time (min) |
|---|---|---|
| 247 | 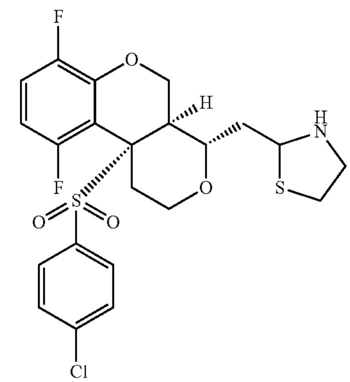 [SMILES: O=S(=O)(c1ccc(Cl)cc1)[C@@]12CCO[C@@H](CC3NCCS3)[C@@H]1COc1c(F)ccc(F)c12] | 502.3; 3.07 |
| 248 | 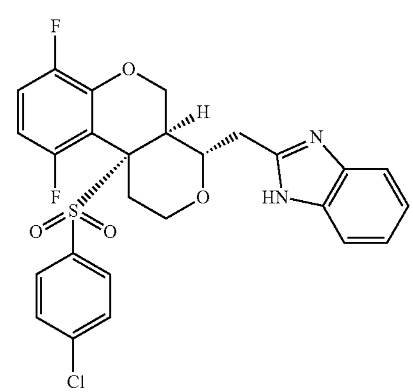 [SMILES: O=S(=O)(c1ccc(Cl)cc1)[C@@]12CCO[C@@H](Cc3nc4ccccc4[nH]3)[C@@H]1COc1c(F)ccc(F)c12] | 531.3; 3.38 |

Example 249

1-{2-[10b-(4-Chloro-benzenesulfonyl-7,10-difluoro-1,4a,5,10b-tetrahydro-2H,4H-pyrano[3,4-c]chromen-4-yl]-ethyl}-1H-imidazole

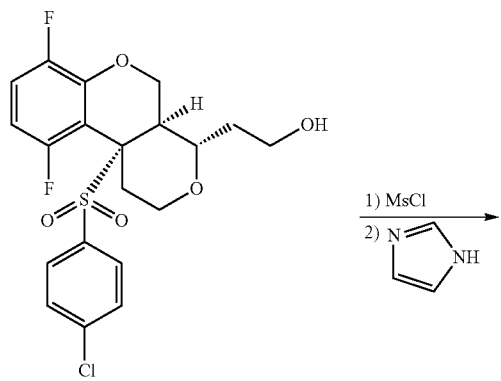

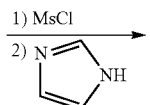

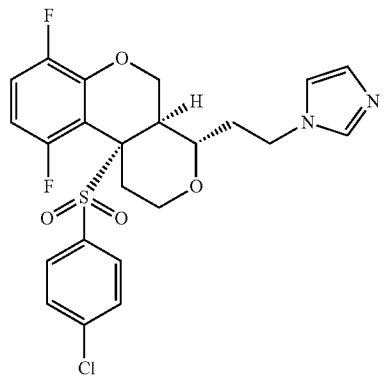

Example 249

Step 1

To a solution of alcohol product from Example 237 Step 1 (50 mg) in DCM (3 mL) was added methanesulfonyl chloride (10 uL) followed by triethylamine (30 uL) then the reaction was stirred 30 min at RT, filtered over a pad of silica gel and concentrated. The residue was taken up in DMF (0.5 mL), Na2CO3 (24 mg) followed by imidazole (12 mg) were added and the mixture was heated at 60 C for 48 h. The reaction was diluted with water, extracted with AcOEt, dried and concentrated then purified over silica gel (eluted with Hexanes/AcOEt 60:40) to give 6 mg of Example 249: $^1$H NMR (CDCl$_3$ 400 MHz) δ 7.64 (d, J=8.7 Hz, 2H), 7.52 (d, J=8.7 Hz, 2H), 7.40 (br s, 1H), 7.12 (m, 1H), 7.03 (br s, 1H), 6.89 (br s, 1H), 6.47 (m, 1H), 5.17 (m, 1H), 4.38 (br d, 1H), 4.00-4.15 (m, 2H), 3.93 (m, 1H), 3.05-3.15 (m, 2H), 2.50-2.60 (m, 2H), 2.25-2.40 (m, 2H), 1.97 (m, 1H); LCMS (MH$^+$)=495.3; retention time=3.04 min.

Example 250

Following procedures similar to the ones described in Example 249, the compound in Table 59 was prepared.

TABLE 59

| Ex. No. | STRUCTURE | Mass Spec (MH$^+$ except otherwise noted); retention time (min) |
|---|---|---|
| 250 | 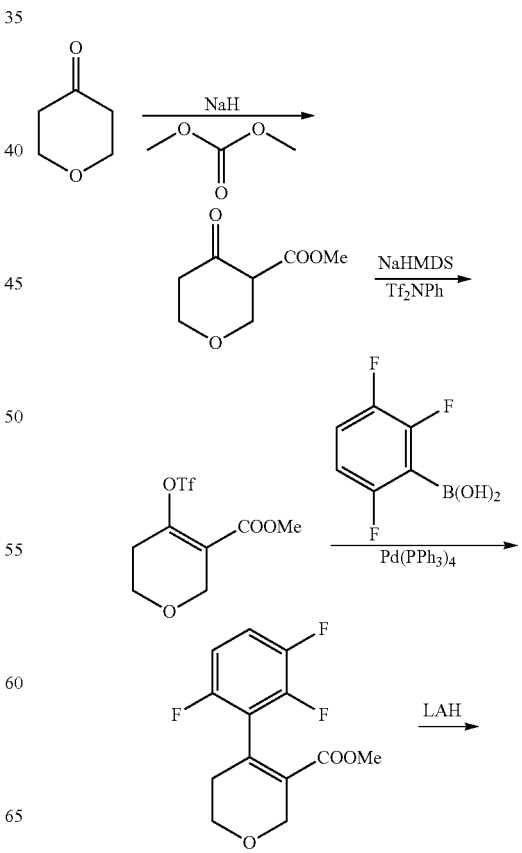 | 495.3; 4.54 |

Examples 251 and 252

Example 251

10b-(4-Chloro-benzenesulfonyl-7,10-difluoro-1,10b-dihydro-2H-pyrano[3,4-c]chromen-4a-ol

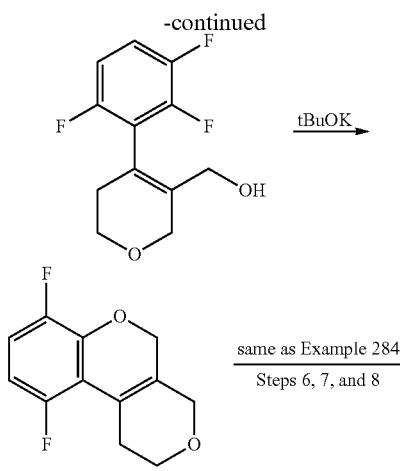

Example 251

Step 1

To a mixture of NaH 60% in hexanes (10.0 g, 250 mmol) in THF (300 mL) at RT was added tetrahydro-4H-pyran-4-one (10.0 g, 100 mmol) followed, 30 min later by dimethylcarbonate (21.0 mL, 250 mmol) then the mixture was heated at 45° C. overnight. The final mixture was poured into 0.01 N HCl and Et2O, filtered over Celite, diluted with AcOEt, washed with brine and concentrated. The lower liquid was purified over silica gel (eluted with Hexanes/AcOEt 99:1 to 60:40) to give 1.30 g of ketoester.

Step 2

To a solution of ketoester product from Step 1 (2.22 g, 14.0 mmol) in THF (60 mL) at −78° C. was added NaHMDS 1N in THF (15.4 mL, 15.4 mmol) followed, 10 min later by N-phenylbis(trifluoromethanesulfonimide) (5.50 g, 15.4 mmol) in THF (20 mL). The reaction was allowed to warm to RT overnight, poured into 1N HCl, extracted with DCM and AcOEt, dried and concentrated. The residue was purified over silica gel (eluted with Hexanes/AcOEt 99:1 to 60:40) to give 6.76 g of enol triflate.

Step 3

A mixture of enol triflate from Step 2: (5.65 g, 19.5 mmol), 2,3,6-trifluorophenylboronic acid (4.46 g, 25.4 mmol), sodium acetate (6.00 g, 73 mmol) and tetrakistriphenylphosphine palladium (0) (1.75 g, 1.50 mmol) in dioxane (75 mL) was stirred overnight at 50° C. then at 85° C. for 3 h then cooled down, diluted with AcOEt, washed with brine, dried and concentrated. The residue was purified over silica gel (eluted with Hexanes/DCM 80:20 to DCM) to give 4.80 g of aryl unsaturated ester.

Step 4

To a solution of aryl unsaturated ester from Step 3 (4.40 g, 16.2 mmol) in THF (40 mL) at −78° C. was slowly added LAH 1N in THF (16.2 mL, 16.2 mmol) and the reaction was allowed to warm to RT over 45 min. It was then quenched with sat. NaHCO3, diluted with AcOEt, Na2SO4 was added and the mixture was filtered over Celite and concentrated. The residue was purified over silica gel (eluted with Hexanes/AcOEt 99:1 to AcOEt) to afford 2.42 g of unsaturated alcohol.

Step 5

To a solution of unsaturated alcohol from Step 4 (2.42 g, 9.90 mmol) in THF (20 mL) at −20° C. was added t-BuOK 1N in THF (10.0 mL, 10.0 mmol) and the reaction was allowed to warm to RT over 30 min. It was then quenched with sat. NH4Cl, extracted with DCM, dried and concentrated then purified over silica gel (eluted with Hexanes/AcOEt 99:1 to 60:40) to give 1.03 g of unsaturated pyrane.

Step 6

The unsaturated pyrane from Step 5 was subjected to conditions described in Example 284 Steps 6 to 8 to afford Example 251: $^1$H NMR (CDCl$_3$ 400 MHz) δ 7.61 (d, J=8.7 Hz, 2H), 7.49 (d, J=8.7 Hz, 2H), 7.12 (m, 1H), 6.45 (m, 1H), 5.13 (d, 1H), 4.23 (br s, 1H), 4.04 (d, 1H), 3.98 (m, 1H), 3.62 (m, 1H), 3.50 (m, 1H), 3.25 (m, 1H), 2.84 (m, 1H), 2.57 (m, 1H); LCMS (MH$^+$)=417.2; retention time=3.94 min.

Following procedures similar to the ones described in Example 251, the compound of Example 252 in Table 60 was prepared.

TABLE 60

| Ex. No. | STRUCTURE | Mass Spec (MH+ except otherwise noted); retention time (min) |
|---|---|---|
| 252 | 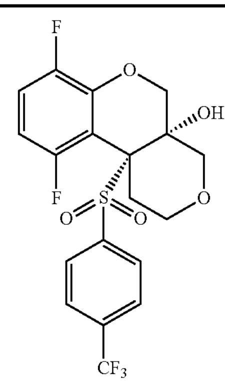 | 451.2; 4.13 |

Examples 253 to 255

Following procedures similar to those described in Schemes 1-A, 1-B and 2-A, the compounds in Table 61 were prepared.

TABLE 61

| Example No. | STRUCTURE | Mass Spec (M+ except otherwise noted); retention time (min) |
|---|---|---|
| 253 | 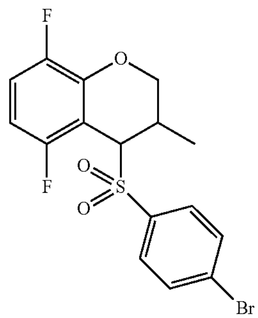 [SMILES: CC1COc2c(F)ccc(F)c2C1S(=O)(=O)c1ccc(Br)cc1] | 481, 483; 4.49 |
| 254 | 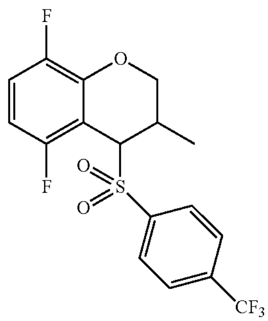 [SMILES: CC1COc2c(F)ccc(F)c2C1S(=O)(=O)c1ccc(C(F)(F)F)cc1] | 393.2; 4.57 |
| 255 | 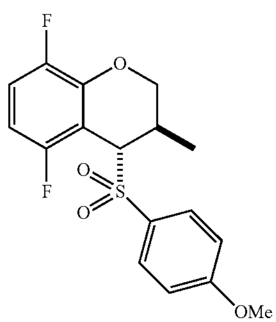 [SMILES: COc1ccc(S(=O)(=O)[C@@H]2c3c(F)ccc(F)c3OC[C@H]2C)cc1] | 355.2; 4.21 |

Examples 256 to 263

Following procedures similar to those described for preparing Example 8, the compounds in Table 62 were prepared.

TABLE 62

| Ex. No | STRUCTURE | LCMS (Min. MS) |
|---|---|---|
| 256 | | 4.57 Min. 745.4 (2M + 1) |
| 257 | 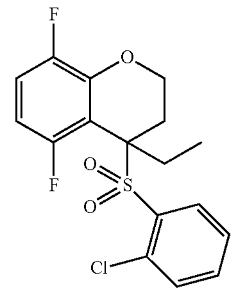 [SMILES: CCC1(S(=O)(=O)c2ccccc2Cl)CCOc2c(F)ccc(F)c21] | 4.45 Min. 373.2 (M + 1) |
| 258 | 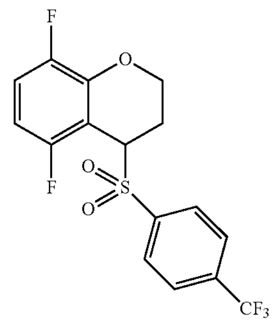 [SMILES: O=S(=O)(c1ccc(C(F)(F)F)cc1)C1CCOc2c(F)ccc(F)c21] | 3.39 Min. 379.2 (M + 1) |
| 259 | 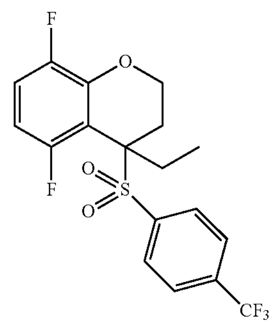 | 4.70 Min. 813.4 (2M + 1) |
| 260 | 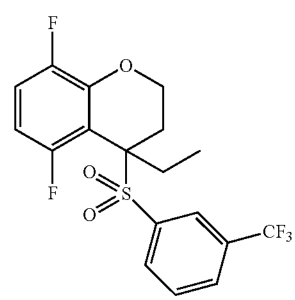 | 4.82 Min. 813.4 (2M + 1) |
| 261 | 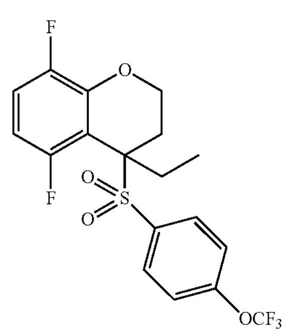 | 4.95 Min. 845.5 (2M + 1) |

TABLE 62-continued

| Ex. No | STRUCTURE | LCMS (Min. MS) |
|---|---|---|
| 262 | 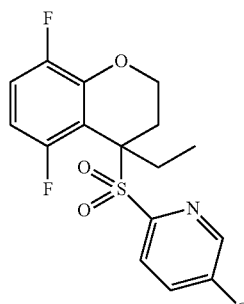 | 4.53 Min. 408.2 (M + 1) |
| 263 | 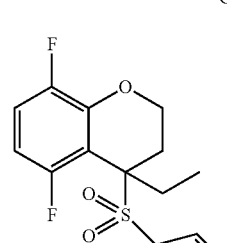 | 3.91 Min. 340.2 (M + 1) |

Example 264

Following procedures of Example 16 the following compound was prepared.

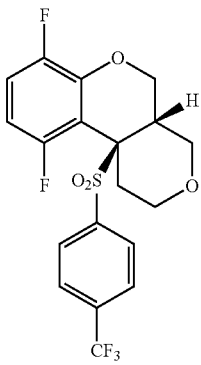 [SMILES: O=S(=O)(c1ccc(C(F)(F)F)cc1)[C@]12CCOC[C@H]1COc1c(F)ccc(F)c12]

(MS: 435.2 (M+1); 4.69 min).

Examples 265 to 282

Using methods similar to those in Example 20 (i.e., methods similar to those used for the preparation of compound 20A) and substituting an appropriate acyl or sulfonyl halide, the compounds in Table 63 were prepared.

TABLE 63

| Ex. No. | Structure | LCMS (M + 1, retention time) |
|---|---|---|
| 265* | 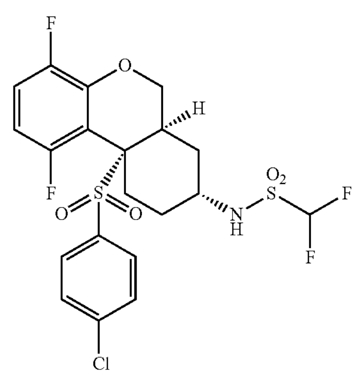 [SMILES: O=S(=O)(N[C@@H]1CC[C@@]2(S(=O)(=O)c3ccc(Cl)cc3)c3c(F)ccc(F)c3OC[C@H]2C1)C(F)F] | 528.3, 4.69 Min. |
| 266* | 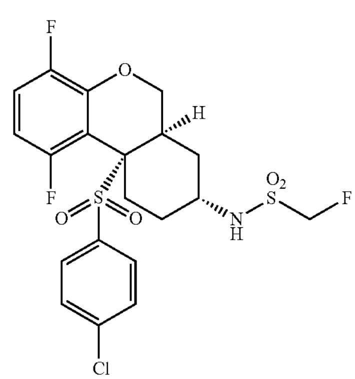 [SMILES: O=S(=O)(CF)N[C@@H]1CC[C@@]2(S(=O)(=O)c3ccc(Cl)cc3)c3c(F)ccc(F)c3OC[C@H]2C1] | 510.3, 4.38 Min. |

TABLE 63-continued

| Ex. No. | Structure | LCMS (M + 1, retention time) |
|---|---|---|
| 267 | 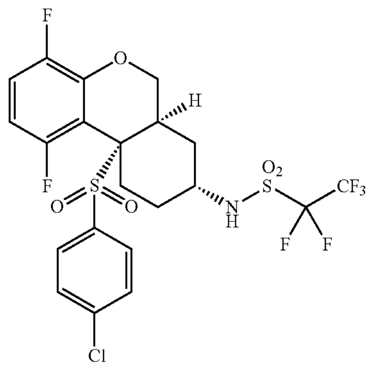 [SMILES: O=S(=O)(N[C@@H]1CC[C@@]2(S(=O)(=O)c3ccc(Cl)cc3)c3c(F)ccc(F)c3OC[C@H]2C1)C(F)(F)C(F)(F)F] | 596.3; 4.71 Min |
| 268 | 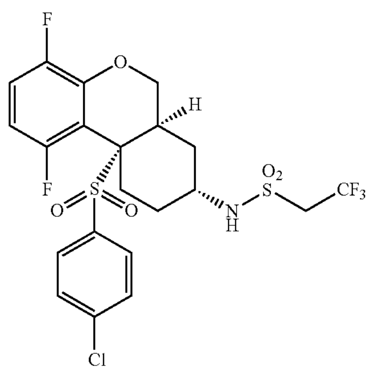 [SMILES: O=S(=O)(CC(F)(F)F)N[C@@H]1CC[C@@]2(S(=O)(=O)c3ccc(Cl)cc3)c3c(F)ccc(F)c3OC[C@H]2C1] | 560.3; 5.09 Min |
| 269* | 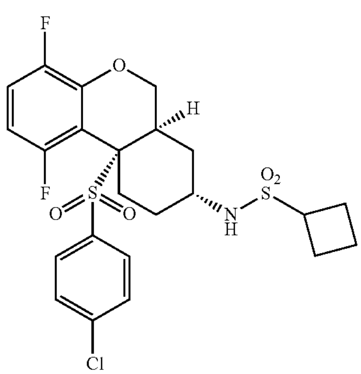 [SMILES: O=S(=O)(N[C@@H]1CC[C@@]2(S(=O)(=O)c3ccc(Cl)cc3)c3c(F)ccc(F)c3OC[C@H]2C1)C1CCC1] | 549.1 (M + NH$_3$), 3.67 Min. |
| 270 | 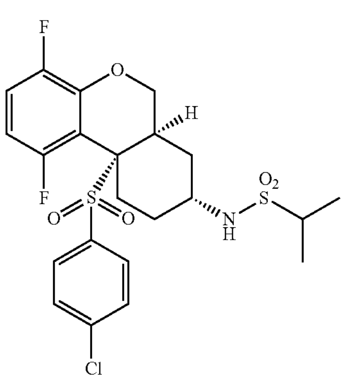 [SMILES: CC(C)S(=O)(=O)N[C@@H]1CC[C@@]2(S(=O)(=O)c3ccc(Cl)cc3)c3c(F)ccc(F)c3OC[C@H]2C1] | 520.3; 4.44 Min |

TABLE 63-continued

| Ex. No. | Structure | LCMS (M + 1, retention time) |
|---|---|---|
| 271 | 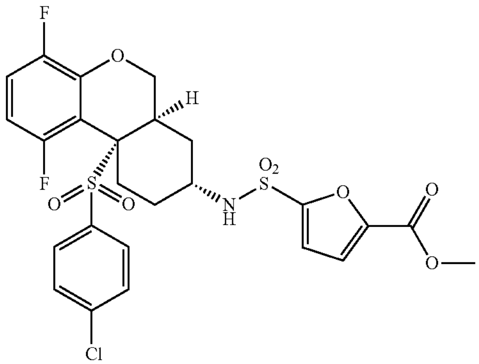 [SMILES: COC(=O)c1ccc(S(=O)(=O)N[C@@H]2CC[C@@]3(S(=O)(=O)c4ccc(Cl)cc4)c4c(F)ccc(F)c4OC[C@H]3C2)o1] | 602.3; 5.13 Min |
| 272 | 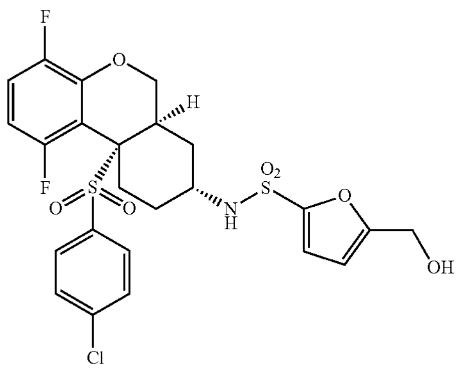 [SMILES: O=S(=O)(N[C@@H]1CC[C@@]2(S(=O)(=O)c3ccc(Cl)cc3)c3c(F)ccc(F)c3OC[C@H]2C1)c1ccc(CO)o1] | 574.3; 4.32 Min |
| 273 | 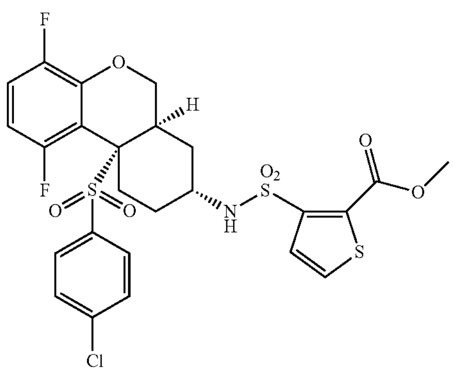 [SMILES: COC(=O)c1sccc1S(=O)(=O)N[C@@H]1CC[C@@]2(S(=O)(=O)c3ccc(Cl)cc3)c3c(F)ccc(F)c3OC[C@H]2C1] | 618.3; 5.30 Min |
| 274 | 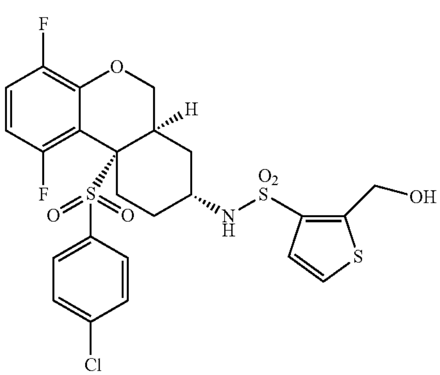 [SMILES: O=S(=O)(N[C@@H]1CC[C@@]2(S(=O)(=O)c3ccc(Cl)cc3)c3c(F)ccc(F)c3OC[C@H]2C1)c1ccsc1CO] | 590.3; 4.47 Min |

TABLE 63-continued

| Ex. No. | Structure | LCMS (M + 1, retention time) |
|---|---|---|
| 275 | 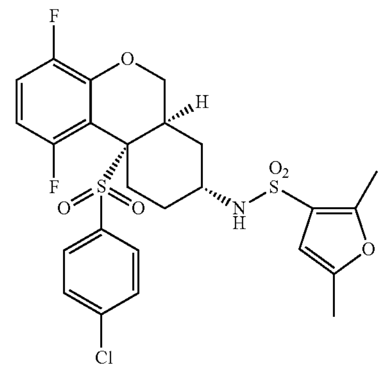 [SMILES: Cc1cc(S(=O)(=O)N[C@@H]2CC[C@@]3(S(=O)(=O)c4ccc(Cl)cc4)c4c(F)ccc(F)c4OC[C@H]3C2)c(C)o1] | 572.3; 5.32 Min |
| 276 | 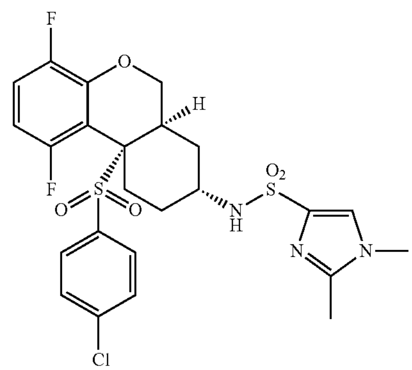 [SMILES: Cc1nc(S(=O)(=O)N[C@@H]2CC[C@@]3(S(=O)(=O)c4ccc(Cl)cc4)c4c(F)ccc(F)c4OC[C@H]3C2)cn1C] | 572.3; 4.59 Min |
| 277 | 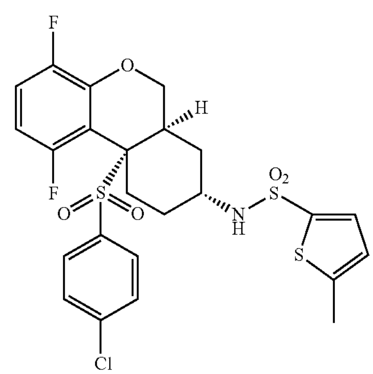 [SMILES: Cc1ccc(S(=O)(=O)N[C@@H]2CC[C@@]3(S(=O)(=O)c4ccc(Cl)cc4)c4c(F)ccc(F)c4OC[C@H]3C2)s1] | 574.3; 4.70 Min |
| 278 | 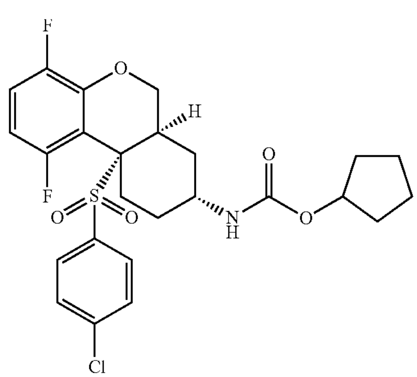 [SMILES: O=C(N[C@@H]1CC[C@@]2(S(=O)(=O)c3ccc(Cl)cc3)c3c(F)ccc(F)c3OC[C@H]2C1)OC1CCCC1] | 562.3; 5.31 Min |

TABLE 63-continued

| Ex. No. | Structure | LCMS (M + 1, retention time) |
|---|---|---|
| 279 | 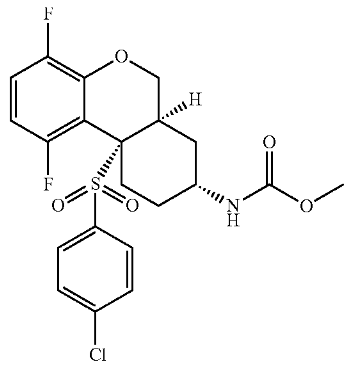 [SMILES: COC(=O)N[C@@H]1CC[C@@]2(S(=O)(=O)c3ccc(Cl)cc3)c3c(F)ccc(F)c3OC[C@H]2C1] | 472.3; 4.84 Min |
| 280 | 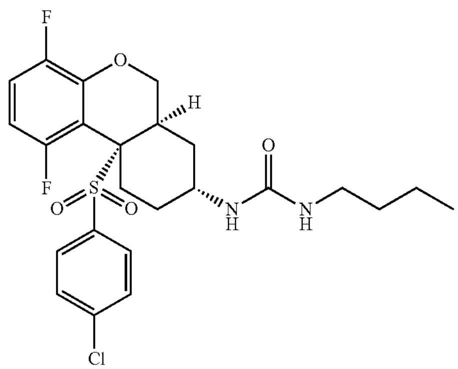 [SMILES: CCCCNC(=O)N[C@@H]1CC[C@@]2(S(=O)(=O)c3ccc(Cl)cc3)c3c(F)ccc(F)c3OC[C@H]2C1] | 513.3; 5.06 Min |
| 281 | 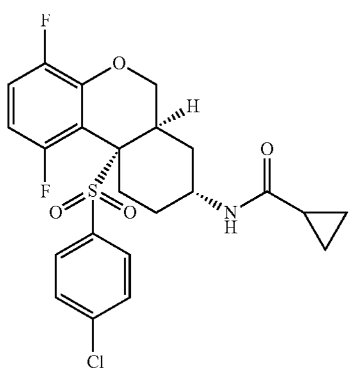 [SMILES: O=C(N[C@@H]1CC[C@@]2(S(=O)(=O)c3ccc(Cl)cc3)c3c(F)ccc(F)c3OC[C@H]2C1)C1CC1] | 482.3; 4.86 Min |
| 282 | 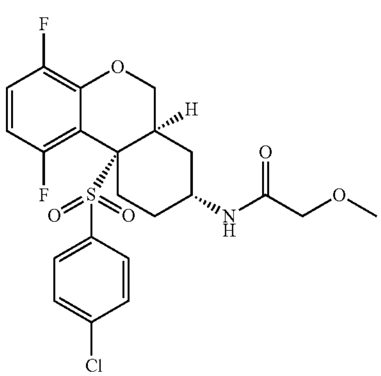 [SMILES: COCC(=O)N[C@@H]1CC[C@@]2(S(=O)(=O)c3ccc(Cl)cc3)c3c(F)ccc(F)c3OC[C@H]2C1] | 486.3; 4.75 Min |

* The corresponding sulfonyl chloride was synthesized according to: Moore, G. J. Org. Chem., 1979, 44, 1708

Example 283

[10a-(4-Chloro-benzenesulfonyl)-1,4-difluoro-6a,7,8,9,10,10a-hexahydro-6H-benzo[c]chromen-8-yl]-pyridin-2-yl-amine

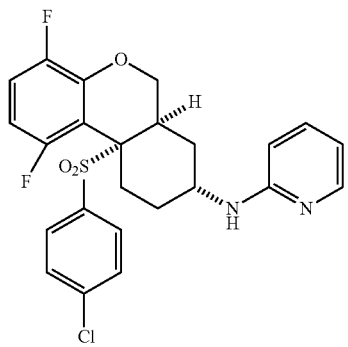 [SMILES: O=S(=O)(c1ccc(Cl)cc1)[C@@]12CC[C@@H](Nc3ccccn3)C[C@@H]1COc1c(F)ccc(F)c12]

To a vial containing 18 mg (0.043 mmol) of the amine from Example 19 were added 3.5 mg (0.018 mmol) of tris(dibenzylidineacetone)palladium(0), 5.4 mg (0.004 mmol) of 2-(di-t-butylphosphine)diphenyl, 0.5 mL of anhydrous THF, 2-bromopyridine (0.11 mmol), and lithium hexamethyldisilazide (0.11 mmol). The mixture was purged with nitrogen and heated to 65° C. for 14 h. The crude was directly purified by prep TLC plate using 3% MeOH in DCM with 1% NH$_3$. $^1$H NMR (CDCl$_3$ 400 MHz) δ 1.40 (m, 1H) 1.80 (m, 2H) 2.00 (m, 2H) 2.40 (m, 1H) 3.00 (m, 1H) 3.90 (m, 1H) 4.15 (d, J=11.9 Hz, 1H) 5.24 (d, J=11.9 Hz, 1H) 6.41 (m, 2H) 6.66 (m, 1H) 7.10 (m, 1H) 7.50-7.62 (m, 4H) 8.10 (m, 1H).

Example 284

10aR-[(4-chlorophenyl)sulfonyl]-1,4-difluoro-6a,9,10,10a-tetrahydro-6aR-hydroxy-6H-dibenzo[b,d]pyran-8(7H)-one

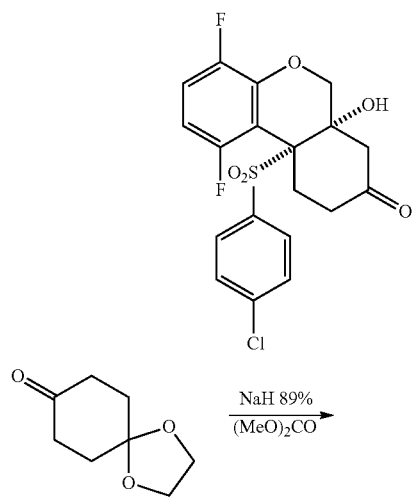

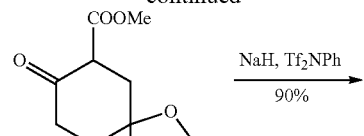

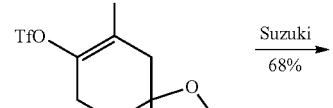

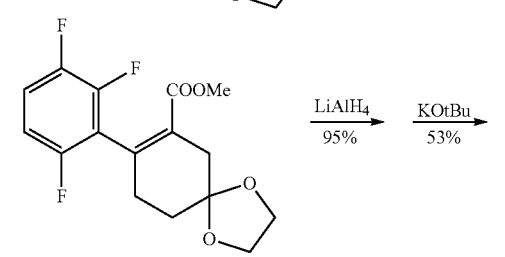

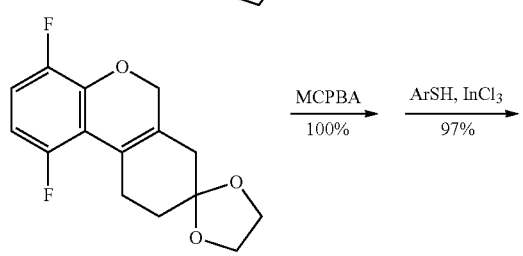

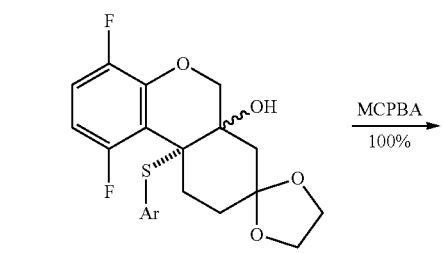

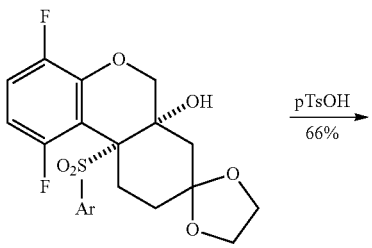

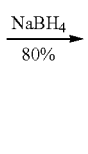

-continued

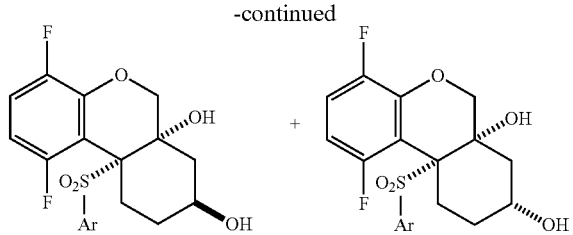

Step 1

NaH (60% oil dispersion, 24.36 g, 2 eq) was washed with hexane three times. A solution of ketone (47.51 g, 304.6 mmol) in THF (1.2 L) was added to NaH under nitrogen at it and the resulting solution was stirred for 30 minutes followed by addition of dimethyl carbonate (54.82 g, 2 eq). The mixture was stirred for 60 h at rt. The reaction was quenched by water. 0.6 L of EtOAc, 0.6 L of hexane was added. The crude was washed with 1.75 N HCl (350 mL, 2.01 eq). After drying over $Na_2SO_4$, evaporation of the solvent resulted in 60 g of the keto ester as white solid in 89% yield. $^1$H NMR ($CDCl_3$ 400 MHz) δ 1.80 (m, 2H) 2.50 (m, 4H) 3.70 (s, 3H) 4.00 (s, 4H) 12.15 (s, 1H).

Step 2

NaH (60% oil dispersion, 5 g, 1.1 eq) was added to the keto ester from Step 1 (24.28 g; 113.5 mmol) in THF (1 L) at 0° C. under nitrogen. 10 min later, N-phenyl-bis(trifluoromethanesulfonimide) (44.59 g, 1.1 eq) was added. The resulting red solution was stirred at rt for 24 h. At this point, another 0.5 g of NaH and 2.4 g of N-phenyl-bis(trifluoromethanesulfonimide) was added and the mixture was further stirred for 24 h. Saturated $NH_4Cl$ (100 mL) was added. After most of THF solvent was evaporated, 800 mL of EtOAc was added. The organic layer was washed with 1 N HCl, saturated $NaHCO_3$, water and brine and dried over $Na_2SO_4$. Flash chromatography (hexane/EtOAc 90:10) afforded the triflate (35.3 g) in 90% yield. $^1$H NMR ($CDCl_3$ 400 MHz) δ 1.90 (m, 2H) 2.60-2.70 (m, 4H) 3.80 (s, 3H) 4.00 (m, 4H).

Step 3

To a solution of the product from Step 2: (10.0 g, 28.9 mmol) in Toluene (160 mL) and EtOH (50 mL) was added 2,3,6-trifluorophenylboronic acid (6.1 g, 1.2 eq), tetrakistriphenylphosphinepalladium (1.2 g, 0.05 eq), 2 M $Na_2CO_3$ (28.9 mL, 2 eq). The mixture was purged with argon and heated to 48° C. for 14 h. The mixture was cooled to rt and filtered through celite. Upon removal of the solvent, EtOAc was added. After washing with water, brine, dried over $Na_2SO_4$ and concentration, the crude was purified by flash chromatography (hexane/EtOAc 70:30) to provide 6.4 g of the Suzuki coupling product in 68% yield. $^1$H NMR ($CDCl_3$ 400 MHz) δ 1.90 (m, 2H) 2.60 (m, 2H) 2.75 (br s, 2H) 2.60-2.70 (m, 4H) 3.58 (s, 3H) 4.00 (m, 4H) 6.80 (m, 1H) 7.00 (m, 1H).

Step 4

The product from Step 3 (10.0 g, 30.49 mmol)/300 mL THF was treated with $LiAlH_4$ (2.3 N in THF, 13.25 mL, 0.9 eq) at −78° C. under nitrogen. After warming up to 0° C. in 2 h, the reaction was quenched by water (1.2 mL), 15% NaOH (3.6 mL), water (1.2 mL) and the mixture was stirred for 10 min and filtered through celite. Upon removal of the solvent, EtOAc was added. After washing with water, brine, dried over $Na_2SO_4$ and concentration, the crude was obtained as the desired product (8.7 g, 95% yield) without further purification. $^1$H NMR ($CDCl_3$ 400 MHz) δ 1.90 (m, 2H) 2.42 (m, 2H) 2.60 (br s, 2H) 3.84 (d, J=5.9 Hz, 2H) 4.06 (m, 4H) 6.83 (m, 1H) 7.10 (m, 1H).

Step 5

The product from Step 4 (11.8 g, 39.33 mmol)/400 mL THF was treated with KOtBu (1 N in THF, 1 eq) at 0° C. After 1.5 h, EtOAc was added and the organic layer was washed with water, brine and dried over $Na_2SO_4$. Upon removal of solvent, the crude was washed with cold ethyl ether and white solid was collected as the desired cyclized product (5.8 g, 53% yield). $^1$H NMR ($CDCl_3$ 400 MHz) δ 1.90 (m, 2H) 2.30 (br s, 2H) 2.80 (m, 2H) 4.00 (br s, 4H) 4.55 (br s, 2H) 6.55 (m, 1H) 6.84 (m, 1H).

Step 6

The product from Step 5 (0.16 g, 0.57 mmol)/5 mL DCM was treated with MCPBA (70% pure, 0.28 g, 2 eq) at rt. After 40 min, 10 mL of 10% $Na_2S_2O_3$ was added. The organic layer was washed with 1 N NaOH, saturated $Na_2HCO_3$, water, brine and dried over $Na_2SO_4$. Upon removal of solvent, 0.18 g of the crude was obtained and was used for the next step. $^1$H NMR ($CDCl_3$ 400 MHz) δ 1.60 (m, 1H) 1.80 (m, 1H) 1.92 (d, J=14.1 Hz, 1H) 2.17 (d, J=15.2 Hz, 1H) 2.56 (m, 1H) 2.82 (m, 1H) 3.90 (m, 4H) 4.05 (d, J=12.1 Hz, 1H) 4.35 (d, J=12.1 Hz, 1H) 6.59 (m, 1H) 6.90 (m, 1H).

Step 7

To a solution of the epoxide product from Step 6 (1.0 g, 3.4 mmol)/15 mL DCM was added 4-chlorothiophenol (1.03 g, 2 eq), indium trichloride (80 mg, 0.1 eq) at 0° C. The mixture was stirred at rt for 14 h and quenched by saturated $Na_2CO_3$. After washing with water, brine, dried over $Na_2SO_4$ and concentration, the crude was purified by flash chromatography (hexane/EtOAc 5:1) to provide 0.32 g of the cis adduct (first eluent, 21% yield) and 1.14 g of the trans adduct (second eluent, 76% yield). Cis adduct: $^1$H NMR ($CDCl_3$ 400 MHz) δ 1.43 (dt, J=2.6, 13.8 Hz, 1H) 1.70 (m, 1H) 1.83 (dd, J=3.1, 14.2 Hz, 1H) 2.06 (d, J=14.4 Hz, 1H) 2.38 (m, 1H) 2.95 (br d, J=14.7 Hz, 1H) 3.90 (m, 5H) 4.40 (s, 1H) 4.80 (d, J=11.1 Hz, 1H) 6.21 (m, 1H) 6.82 (m, 1H) 7.13 (d, J=7.9 Hz, 2H) 7.24 (d, J=7.9 Hz, 2H).

Trans adduct: $^1$H NMR ($CDCl_3$ 400 MHz) δ 1.84 (m, 2H) 2.20-2.40 (m, 2H) 2.58 (m, 1H) 2.65 (m, 1H) 4.00 (s, 4H) 4.06 (d, J=10.9 Hz, 1H) 4.75 (d, J=11.0 Hz, 1H) 5.00 (s, 1H) 6.19 (m, 1H) 6.80 (m, 1H) 7.13 (d, J=7.9 Hz, 2H) 7.24 (d, J=7.9 Hz, 2H).

Step 8

To a solution of the cis adduct from Step 7 (0.32 g, 0.73 mmol)/6 mL DCM was added 0.36 g MCPBA (70% pure, 2 eq) at rt and the mixture was stirred for 1 h. 5 mL of 10% $Na_2S_2O_3$ was added. The organic layer was washed with 1 N NaOH, saturated $Na_2HCO_3$, water, brine and dried over $Na_2SO_4$. Upon removal of solvent, 0.35 g of the crude was obtained and was used for the next step. $^1$H NMR ($CDCl_3$ 400 MHz) δ 1.46 (dt, J=3.8, 14.0 Hz, 1H) 1.60 (dd, J=2.9, 14.6 Hz, 1H) 1.80 (m, 1H) 1.95 (d, J=14.6 Hz, 1H) 2.40 (m, 1H) 2.99

(br d, J=15.2 Hz, 1H) 3.90 (m, 5H) 4.38 (s, 1H) 5.28 (d, J=11.0 Hz, 1H) 6.41 (m, 1H) 7.05 (m, 1H) 7.42 (d, J=8.0 Hz, 2H) 7.70 (d, J=8.0 Hz, 2H).

Step 9

To a solution of the product from Step 8 (0.35 g, 0.73 mmol)/20 mL acetone, 5 mL of water was added 0.12 g p-toluenesulfonic acid at it and the mixture was stirred at 70° C. for 14 h. Additional p-toluenesulfonic acid (60 mg) was added and the mixture was stirred at 70° C. for 5 h. The solvent was removed and EtOAc added. The organic layer was washed with saturated NaHCO$_3$, water, brine and dried over Na$_2$SO$_4$. Upon removal of solvent, the crude was purified by flash chromatography (hexane/EtOAc 65:35) to provide the desired ketone product (0.21 g, 66% yield). $^1$H NMR (CDCl$_3$ 400 MHz) δ 2.10 (m, 1H) 2.40-2.60 (m, 4H) 3.01 (m, 1H) 4.10 (d, J=11.0 Hz) 4.60 (d, J=2.8 Hz, 1H) 5.15 (d, J=11.0 Hz, 1H) 6.45 (m, 1H) 7.10 (m, 1H) 7.50 (m, 4H).

Step 10

To a solution of the product from Step 9 (70 mg, 0.16 mmol)/0.6 mL THF/0.3 mL EtOH was added 7.3 mg of NaBH$_4$. After stirring at it for 3 h, the reaction was quenched by MeOH. Upon removal of the solvent, the crude was purified by Prep TLC (hexane/EtOAc 2:1) to provide the desired cis diol (16 mg, 23% yield) and trans diol (40 mg, 57% yield). Cis diol: $^1$H NMR (CDCl$_3$ 400 MHz) δ 1.43 (m, 1H) 1.80-1.99 (m, 3H) 2.50 (m, 1H) 2.82 (m, 1H) 3.40 (m, 1H) 4.00 (br s, 1H) 4.06 (d, J=11.1 Hz, 1H) 5.10 (m, 1H) 5.12 (d, J=11.1 Hz, 1H) 6.43 (m, 1H) 7.10 (m, 1H) 7.50 (d, J=8.6 Hz, 2H). 7.62 (d, J=8.6 Hz, 2H).

Trans diol: $^1$H NMR (CDCl$_3$ 400 MHz) δ 1.18 (m, 1H) 1.60 (m, 2H) 2.00 (m, 2H) 2.42 (m, 1H) 2.70 (m, 1H) 4.07 (d, J=11.0 Hz, 1H) 4.10 (m, 1H) 4.60 (s, 1H) 5.10 (d, J=11.0 Hz, 1H) 6.40 (m, 1H) 7.10 (m, 1H) 7.50 (m, 4H).

Examples 285 to 288

Following similar procedures to that of Example 284, the compounds in Table 64 were prepared.

TABLE 64

| Example No. | STRUCTURE | Mass Spec (M$^+$ except as otherwise noted); retention time (min) |
|---|---|---|
| 285 | 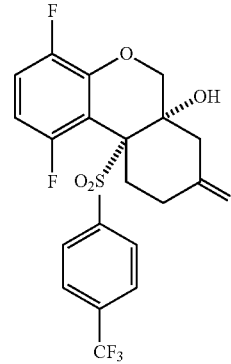 | 431.2 (M + 1); 3.58 |
| 286 | 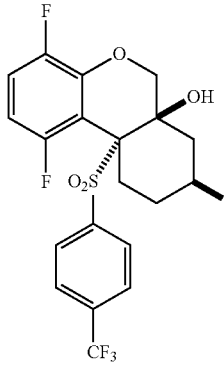 | 463.3 (M + 1); 4.10 |
| 287 | 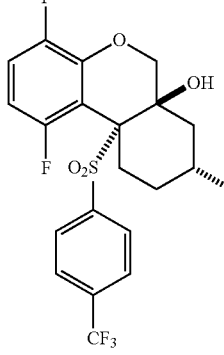 | 465.3 (M + 1); 4.16 |
| 288 | 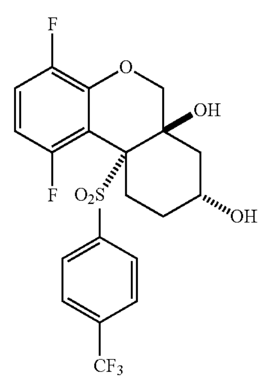 | 465.3 (M + 1); 3.78 |

Examples 289 to 296

Example 289

N-[10aR-[(4-chlorophenyl)sulfonyl]-1,4-difluoro-6a,7,8,9,10,10a-hexahydro-6aS-hydroxy-6H-dibenzo[b,d]pyran-8(R)-yl]-1,1,1-trifluoromethanesulfonamide (cis)

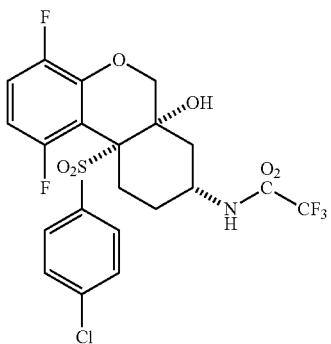

Example 289

The compound of Example 289, and the compounds of Examples 290 to 296 (Table 65), were prepared following similar procedures to that of Examples 19 and 20.

TABLE 65

| Example No. | STRUCTURE | Mass Spec (M+ except as otherwise noted); retention time (min) |
|---|---|---|
| 289 | 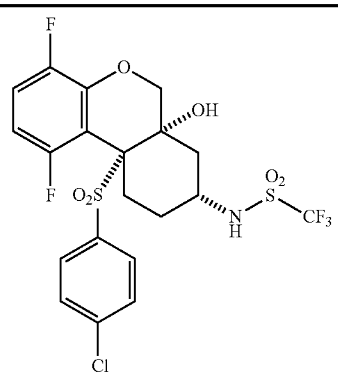 | 562.3 (M + 1); 4.81 |
| 290 | 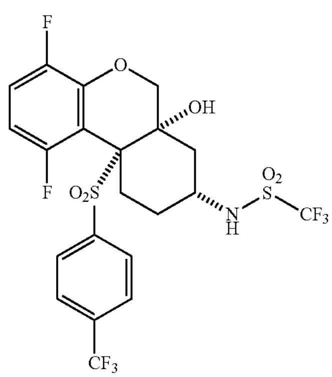 | 596.3 (M + 1); 4.67 |

TABLE 65-continued

| Example No. | STRUCTURE | Mass Spec (M+ except as otherwise noted); retention time (min) |
|---|---|---|
| 291 | 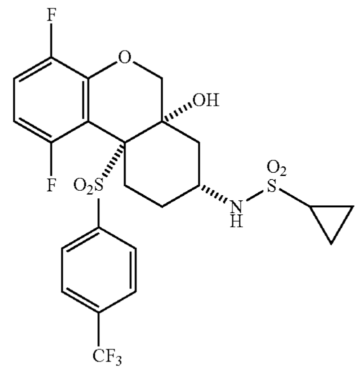 | 568.3 (M + 1); 4.45 |
| 292 | 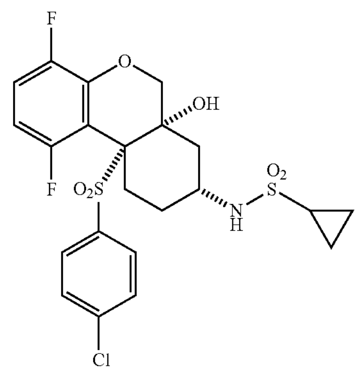 | 534.3 (M + 1); 4.41 |
| 293 | 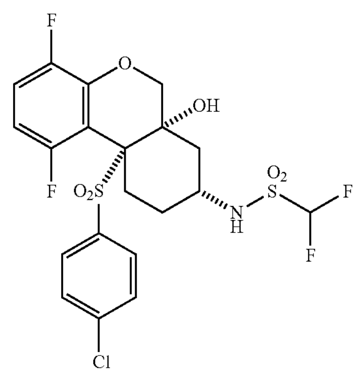 | 544.3 (M + 1); 4.61 |
| 294 | 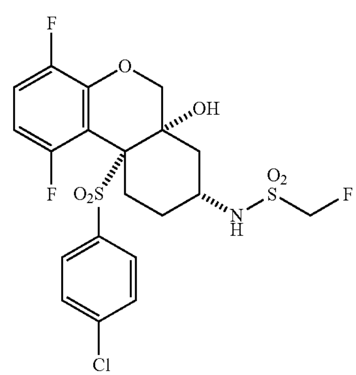 | 526.3 (M + 1); 4.11 |

TABLE 65-continued

| Example No. | STRUCTURE | Mass Spec (M+ except as otherwise noted); retention time (min) |
|---|---|---|
| 295 | 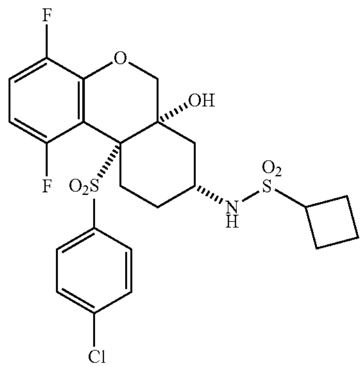 | 548.3 (M + 1); 4.27 |
| 296 | 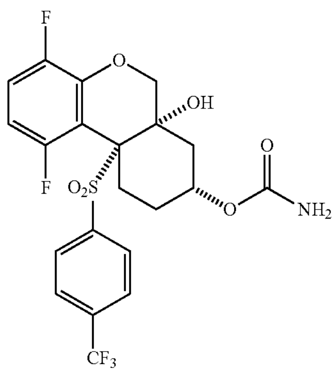 | 508.3 (M + 1); 3.85 |

Example 297

Using methods similar to those in Example 20 (i.e., methods similar to those used for the preparation of compound 20A) and substituting an appropriate acyl or sulfonyl halide, the compound in Table 66 was prepared.

TABLE 66

| Example No. | STRUCTURE | Mass Spec (M+ except as otherwise noted); retention time (min) |
|---|---|---|
| 297 | 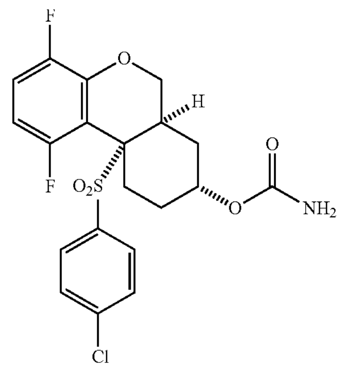 | 458.3; 4.20 Min |

Example 298

N-{2-[10a-(4-Chloro-benzenesulfonyl)-1,4-difluoro-8-oxo-8,9,10,10a-tetrahydro-7H-benzo[c]chromen-6a-yloxy]-ethyl}-C,C,C-trifluoro-methanesulfonamide

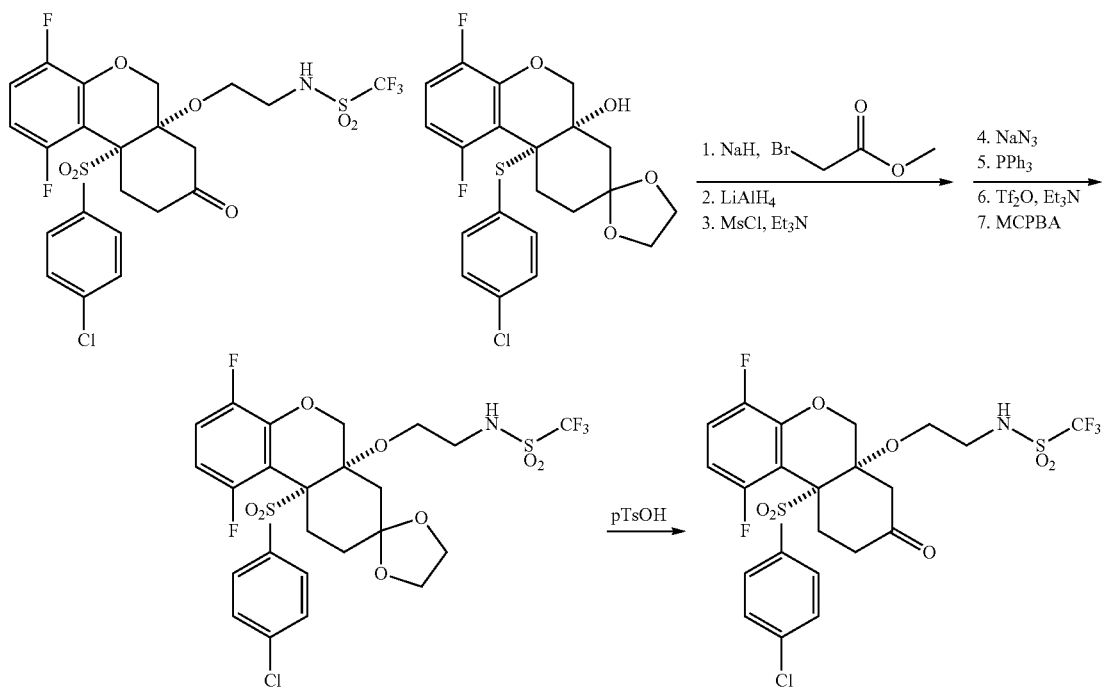

Step 1

The cis adduct from Example 284 step 7 (1.19 g, 2.70 mmol)/20 mL THF was treated with 0.13 g of NaH (60% oil dispersion, 1.2 eq) under nitrogen at rt. 30 min later, 0.83 g of methyl bromoacetate (0.83 g, 2 eq) was added and the mixture was heated to 80° C. for 16 h. Upon removal of the solvent, EtOAc was added and the organic layer was washed with water, brine and dried over $Na_2SO_4$. Flash chromatography (hexane/EtOAc 5:1) afforded the recovered starting alcohol (0.6 g) and the desired product (0.61 g) as white solid in 44% yield. $^1$H NMR (CDCl$_3$ 400 MHz) δ 1.40 (m, 1H) 1.70 (m, 1H) 1.94 (d, J=15.9 Hz, 1H) 2.13 (m, 1H) 2.56 (m, 1H) 2.67 (m, 1H) 3.79 (s, 3H) 3.83 (m, 2H) 3.93 (m, 2H) 4.01 (d, J=11.2 Hz, 1H) 4.13 (d, J=15.3 Hz, 1H) 4.36 (d, J=15.3 Hz, 1H) 4.85 (d, J=1011.2 Hz, 1H) 6.35 (m, 1H) 6.84 (m, 1H) 7.12 (d, J=9.0 Hz, 2H) 7.37 (d, J=9.0 Hz, 2H).

Step 2

The product from step 1 (0.45 g, 0.88 mmol)/30 mL THF was treated with LiAlH$_4$ (2.3 M in THF, 0.38 mL, 1 eq) under nitrogen at −78° C. The reaction was slowly warmed up to rt overnight. After quenching with 5 drops of brine, EtOAc was added and the crude was filtered through celite. Flash chromatography (hexane/EtOAc 1:1) afforded the desired product (0.23 g) as white solid in 54% yield. $^1$H NMR (CDCl$_3$ 400 MHz) δ 1.36 (dt, J=2.9, 13.9 Hz, 1H) 1.70 (m, 1H) 1.92 (d, J=15.3 Hz, 1H) 2.23 (dt, J=2.9, 15.4 Hz, 1H) 2.60 (m, 1H) 2.80 (m, 1H) 3.60-4.04 (m, 8H) 4.16 (d, J=10.1 Hz, 1H) 4.94 (d, J=10.9 Hz, 1H) 6.24 (m, 1H) 6.84 (m, 1H) 7.12 (d, J=8.7 Hz, 2H) 7.22 (d, J=8.7 Hz, 2H).

Steps 3-7

Following similar procedures in Examples 19 and 20, the desired product was obtained. $^1$H NMR (CDCl$_3$ 400 MHz) δ 1.31 (m, 1H) 1.75 (m, 2H) 2.10 (m, 1H) 2.60 (m, 1H) 2.80 (m, 2H) 3.18 (m, 1H) 3.35 (m, 1H) 3.58 (m, 1H) 3.70 (m, 1H) 3.80 (m, 2H) 3.90-4.03 (m, 2H) 4.15 (d, J=12.2 Hz, 1H) 5.36 (d, J=12.2 Hz, 1H) 6.35 (m, 1H) 7.08 (m, 1H) 7.36 (d, J=7.8 Hz, 2H) 7.54 (d, J=8.0 Hz, 2H).

Steps 8

Similar procedures to that of Step 9 of Example 284 were followed.

$^1$H NMR (CDCl$_3$ 400 MHz) δ 2.14 (m, 1H) 2.42-2.60 (m, 2H) 2.68 (m, 1H) 2.95 (m, 1H) 3.20 (m, 1H) 3.42-3.60 (m, 2H) 3.66 (m, 1H) 3.78 (m, 1H) 4.26 (d, J=10.3 Hz, 1H) 5.60 (d, J=11.0 Hz, 1H) 6.30 (m, 1H) 6.70 (m, 1H) 7.10 (m, 1H) 7.40 (m, 4H).

Example 299

Following similar procedures to that of Example 298 the following compound was synthesized.

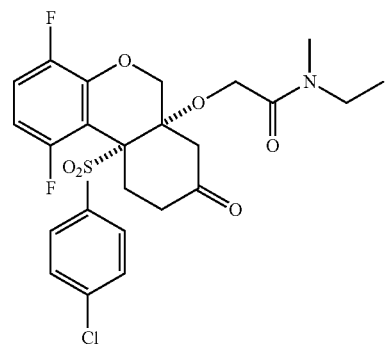

Example 299

$^1$H NMR (CDCl$_3$ 400 MHz, 1: rotamers) δ 0.97 (t, J=7.4 Hz, 1.5 H, rotamer 1) 1.02 (t, J=7.4 Hz, 1.5 H, rotamer 2) 2.30 (m, 1H) 2.40-2.60 (m, 2H) 2.65-2.90 (m, 5H) 2.90-3.10 (m, 1H) 3.20-3.39 (m, 2H) 3.95 (m, 1H) 4.13 (dt, J=3.6, 13.1 Hz, 1H) 4.26 (dd, J=5.8, 10.9 Hz, 1H) 5.50 (d, J=11.0 Hz, 1H) 6.60 (m, 1H) 7.18 (m, 1H) 7.40 (m, 2H) 7770 (m, 2H).

Example 300

(6As)-10Ar-[(4-chlorophenyl)sulfonyl]-1,4-difluoro-6A,7,8,9,10,10A-hexahydro-6h-dibenzo[B,D]pyran-8(s)-methanol, 4-methylbenzenesulfonate (racemic)

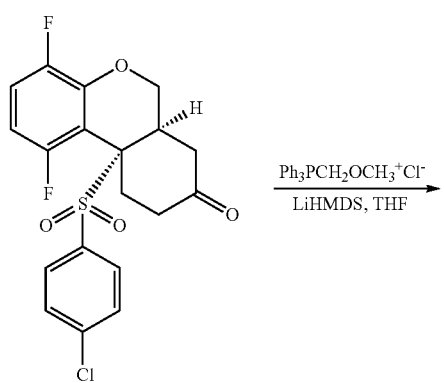

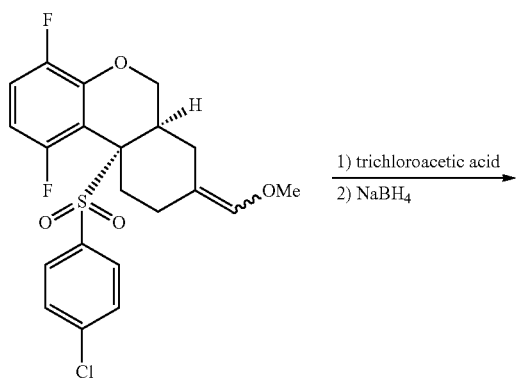

-continued

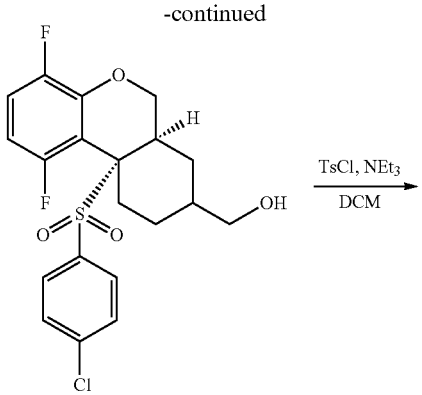

TsCl, NEt₃
DCM
→

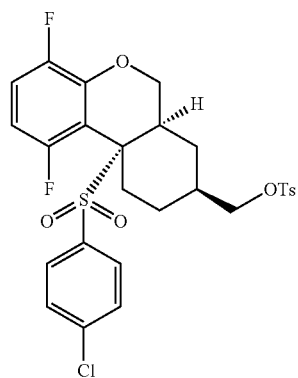 [SMILES: Cc1ccc(S(=O)(=O)OC[C@H]2CC[C@@]3(S(=O)(=O)c4ccc(Cl)cc4)c4c(F)ccc(F)c4OC[C@H]3C2)cc1]

Example 300

Step 1

To a solution of Ph₃PCH₂OCH₃⁺Cl⁻ (17.62 g, 0.051 mol) in THF (100 mL) at −78° C. was added LiHMDS (50.4 mL, 1.0M in THF) dropwise under nitrogen. After addition, the reaction was raised to room temperature and left for stir for 1 hour. The reaction solution turned orange. This mixture was cooled to −78° C. and treated with trans-10A-[(4-chlorophenyl)sulfonyl]-1,4-difluoro-6A,9,10,10A-tetrahydro-6h-dibenzo[B,D]pyran-8(7h)-one (racemic) (5.2 g, 0.0126 mol) in THF (100 mL) dropwise. The reaction mixture was left stir for 2 hours at −78° C., then raise to room temperature and quenched with saturated ammonia chloride solution. The mixture was then extracted with ethyl acetate (200 mL). The aqueous layer was extracted again with ethyl acetate (200 mL). The combined organic layer was washed with brine (200 mL), dried over sodium sulfate and concentrated. The product was purified by column (EtOAc/hexane from 0/100 to 30/70). Yield 4.74 g, 85%. ¹H NMR (CDCl₃ 400 MHz) δ 7.60 (d, 2H), 7.49 (d, 2H), 7.08 (m, 1H), 6.44 (m, 1H), 5.80 (s, 1H), 5.24 (d, 1H), 4.22 (m, 1H), 3.53 (s, 1H), 2.64-2.84 (m, 1H), 2.58-2.63 (m, 2H), 1.62-2.10 (m, 4H).

Step 2

To a solution of the vinyl ether product from Step 1 (2.0 g, 0.0045 mol) was added trichloroacetic acid and stirred at room temperature for 30 Min. The reaction was quenched with saturated sodium bicarbonate solution and extracted with dichloromethane (100 mL×2). The combined organic layer was washed with brine (100 mL), dried over sodium sulfate and concentrated. The residue was dissolved in THF and treated with NaBH₄ at 0° C. The reaction mixture was raised to room temperature and left for stir for 30 Min, then was quenched with water. It was then extracted with ethyl acetate (100 mL×2). The combined organic layer was washed with brine, dried over sodium sulfate and concentrated. The product was purified by column (EtOAc/hexane from 0/100 to 50/50). Yield 1.65 g, 84.8%. ¹H NMR (CDCl₃ 400 MHz) δ 7.58 (d, 2H), 7.49 (d, 2H), 7.07 (m, 1H), 6.39 (m, 1H), 5.22 (m, 1H), 4.17 (m, 1H), 3.75 (m, 1H), 3.38 (t, 1H), 2.63-2.72 (m, 2H), 1.74-1.89 (m, 3H), 1.35-1.47 (m, 1H), 0.65-1.17 (m, 1H).

Step 3

To a solution of the alcohol product from Step 2: (1.65 g, 0.0038 mol) in DCM (100 mL) was added triethylamine (1.1 ml, 0.0079 mol), p-toluenesulfonyl chloride (1.1 g, 0.0058 mol), left it for stir over night. The reaction mixture was washed with saturated sodium bicarbonate solution, then extracted with DCM (50 mL×2). The combined organic layer was washed with brine, dried over sodium sulfate and concentrated. The product was purified by column (EtOAc/hexane from 0/100 to 40/60). Yield: combination of cis and trans isomer is 1.82 g, 82.1%. The desired cis-isomer Example 30 0.82 g, yield 37%.

Example 300

¹H NMR (CDCl₃ 400 MHz) δ 7.82 (d, 2H), 7.42-7.52 (m, 6H), 7.09 (m, 1H), 6.39 (m, 1H), 5.09 (dd, 1H), 4.12 (d, 1H), 3.96 (d, 1H), 2.49 (m, 4H), 2.33 (d, 1H), 2.06 (m, 1H), 1.92 (t, 1H), 1.67 (m, 2H), 1.58 (m, 1H). LCMS (MH$^+$)=583.3; retention time=5.10 min.

Examples 301 to 320

Examples 301-303

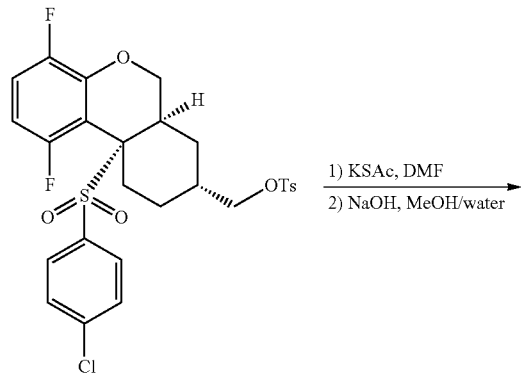

Example 300

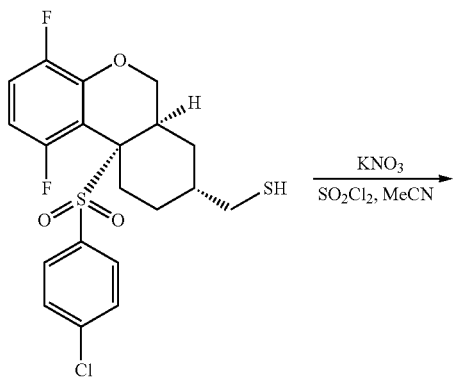

Example 301

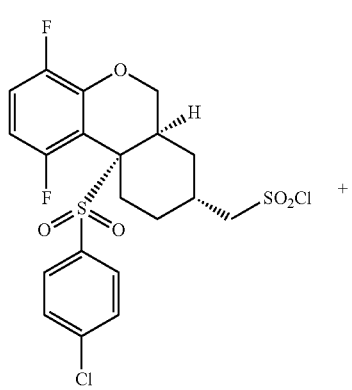

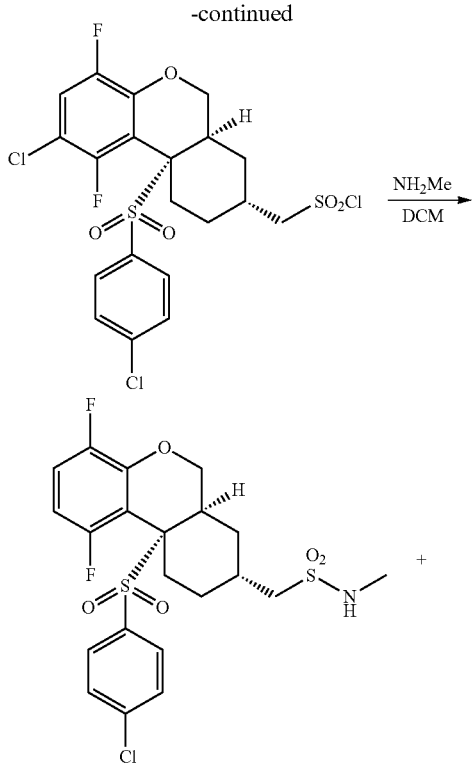

Example 302

Example 303

Step 1

To a solution of Example 300 (0.25 g, 0.43 mmol) in DMF (4 mL) was added potassium thioacetate and heated this suspension to 120° C. for 2 hours. The reaction mixture was added brine and extracted with ethyl acetate (50 mL×2). The combined organic layer was washed with brine, dried over sodium sulfate and evaporated. The residue was redissolved in methanol (20 mL), treated with aqueous 1N NaOH solution and left for stir at room temperature for 2 hours. The reaction mixture was added brine and extracted with ethyl acetate (50 mL ×3). The combined organic layer was washed with brine, dried over sodium sulfate and evaporated. The product Example 301 was purified by reverse-phase HPLC using water and acetonitrile as eluent. $^1$H NMR (CDCl$_3$ 400 MHz) δ 7.58 (dd, 2H), 7.49 (d, 2H), 7.08 (m, 1H), 6.43 (m, 1H), 5.24 (d, 1H), 4.13 (dd, 1H), 2.86 (d, 2H), 2.77 (d, 1H), 2.40 (d, 1H), 2.08 (m, 2H), 1.68-1.84 (m, 3H), 1.26-1.34 (m, 2H).

Step 2

To a solution of Example 301 (0.22 g, 0.49 mmol) in acetonitrile (20 mL) at 0° C. was added KNO₃ and SO₂Cl₂ and left for stir at 0° C. for 3 hours. The reaction mixture was quenched with saturated sodium bicarbonate solution and extracted with ethyl acetate. The organic layer was washed again with saturated sodium bicarbonate solution and brine, dried over sodium sulfate and evaporated to give an oil. This sulfonyl chloride was used as is in the next step.

Step 3

To a DCM solution of the crude sulfonyl chloride (0.02 g, 0.039 mmol) from Step 2: was added 2N methyl amine in THF (0.098 mL, 0.196 mmol), left it for stir over night. Solvent of the reaction mixture was evaporated and the products were purified by reverse-phase HPLC using water and acetonitrile as eluent. Two product were isolated from this reaction mixture. Example 302: ¹H NMR (CDCl₃ 400 MHz) δ 7.56 (d, 2H), 7.50 (d, 2H), 7.11 (m, 1H), 6.41 (m, 1H), 5.25 (dd, 1H), 4.16 (m, 2H), 3.19 (d, 2H), 2.86 (d, 3H), 2.79 (d, 1H), 2.47 (m, 2H), 2.10 (t, 1H), 1.70-1.94 (m, 3H), 1.36 (m, 1H). LCMS (MH⁺)=506.3; retention time=4.28 min. Example 303: ¹H NMR (CDCl₃ 400 MHz) δ 7.57 (m, 4H), 7.25 (m, 1H), 5.24 (dd, 1H), 4.17 (m, 2H), 3.19 (m, 2H), 2.86 (d, 3H), 2.68 (d, 1H), 2.40-2.46 (m, 2H), 1.62-2.06 (m, 4H), 1.38 (m, 1H). LCMS (MH⁺)=542.3; retention time=4.55 min.

Following procedures similar to those described for Examples 301 to 303, the compounds of Examples 304 to 320 in Table 67 were prepared.

TABLE 67

| Ex. No. | Structure | LCMS (M + 1, retention time) or NMR |
|---|---|---|
| 301 | 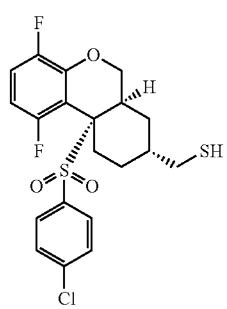 [SMILES: O=S(=O)(c1ccc(Cl)cc1)[C@@]12CC[C@@H](CS)C[C@@H]1COc1c(F)ccc(F)c12] | ¹H NMR (CDCl₃ 400 MHz) δ 7.58 (dd, 2H), 7.49 (d, 2H), 7.08 (m, 1H), 6.43 (m, 1H), 5.24 (d, 1H), 4.13(dd, 1H), 2.86 (d, 2H), 2.77 (d, 1H), 2.40 (d, 1H), 2.08 (m, 2H), 1.68-1.84 (m, 3H), 1.26-1.34 (m, 2H) |

TABLE 67-continued

| Ex. No. | Structure | LCMS (M + 1, retention time) or NMR |
|---|---|---|
| 302 | 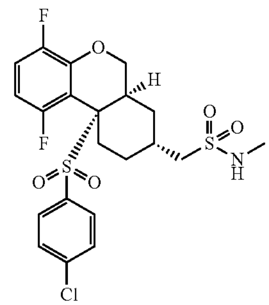 [SMILES: CNS(=O)(=O)C[C@@H]1CC[C@@]2(S(=O)(=O)c3ccc(Cl)cc3)c3c(F)ccc(F)c3OC[C@H]2C1] | 506.3, 4.28 Min. |
| 303 | 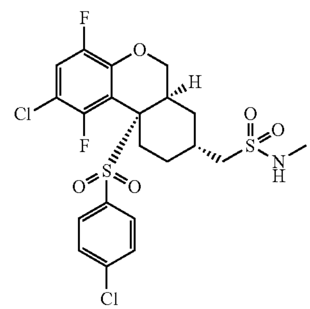 [SMILES: CNS(=O)(=O)C[C@@H]1CC[C@@]2(S(=O)(=O)c3ccc(Cl)cc3)c3c(F)c(Cl)cc(F)c3OC[C@H]2C1] | 542.3, 4.55 Min |
| 304 | 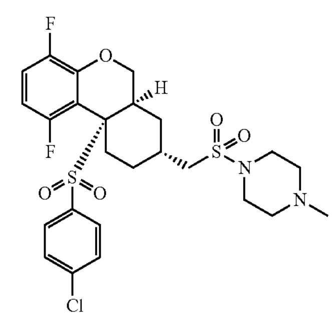 [SMILES: CN1CCN(S(=O)(=O)C[C@@H]2CC[C@@]3(S(=O)(=O)c4ccc(Cl)cc4)c4c(F)ccc(F)c4OC[C@H]3C2)CC1] | 575.3, 3.48 Min. |
| 305 | 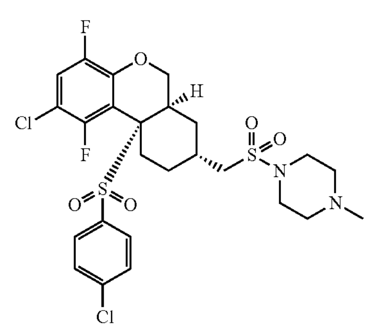 [SMILES: CN1CCN(S(=O)(=O)C[C@@H]2CC[C@@]3(S(=O)(=O)c4ccc(Cl)cc4)c4c(F)c(Cl)cc(F)c4OC[C@H]3C2)CC1] | 609.3, 3.74 Min. |

TABLE 67-continued

| Ex. No. | Structure | LCMS (M + 1, retention time) or NMR |
|---|---|---|
| 306 | 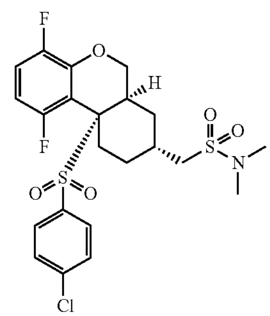 [SMILES: CN(C)S(=O)(=O)C[C@@H]1CC[C@@]2(S(=O)(=O)c3ccc(Cl)cc3)c3c(F)ccc(F)c3OC[C@H]2C1] | 520.3, 4.56 Min |
| 307 | 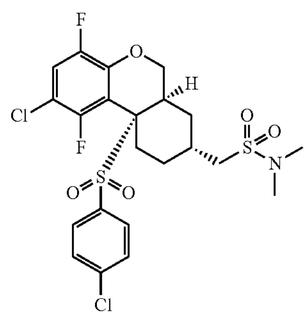 [SMILES: CN(C)S(=O)(=O)C[C@@H]1CC[C@@]2(S(=O)(=O)c3ccc(Cl)cc3)c3c(F)c(Cl)cc(F)c3OC[C@H]2C1] | 554.3, 4.83 Min |
| 308 | 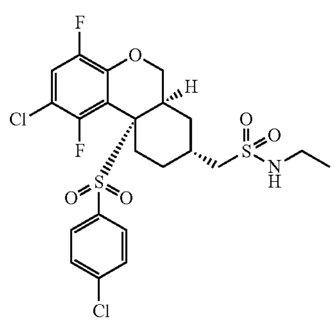 [SMILES: CCNS(=O)(=O)C[C@@H]1CC[C@@]2(S(=O)(=O)c3ccc(Cl)cc3)c3c(F)c(Cl)cc(F)c3OC[C@H]2C1] | 556.3, 4.69 Min |
| 309 | 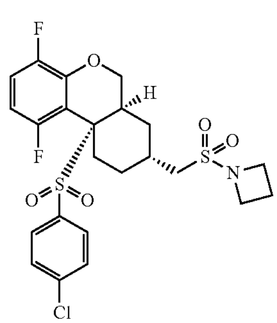 [SMILES: O=S(=O)(C[C@@H]1CC[C@@]2(S(=O)(=O)c3ccc(Cl)cc3)c3c(F)ccc(F)c3OC[C@H]2C1)N1CCC1] | 532.3, 4.61 Min |
| 310 | | 566.3, 4.94 Min |
| 311 | | 546.3, 4.68 Min |
| 312 | | 580.3, 4.93 Min |
| 313 | | 532.3, 4.46 Min |

TABLE 67-continued
| Ex. No. | Structure | LCMS (M + 1, retention time) or NMR |
|---|---|---|
| 314 | 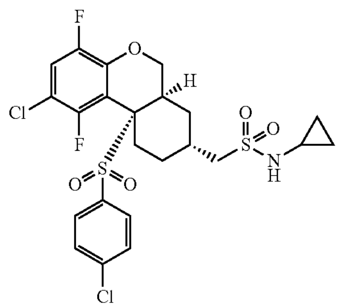 [SMILES: O=S(=O)(C[C@@H]1CC[C@@]2(S(=O)(=O)c3ccc(Cl)cc3)c3c(F)c(Cl)cc(F)c3OC[C@H]2C1)NC1CC1] | 568.3, 4.72 Min |
| 315 | 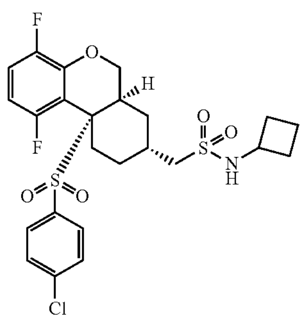 [SMILES: O=S(=O)(C[C@@H]1CC[C@@]2(S(=O)(=O)c3ccc(Cl)cc3)c3c(F)ccc(F)c3OC[C@H]2C1)NC1CCC1] | 546.3, 4.63 Min |
| 316 | 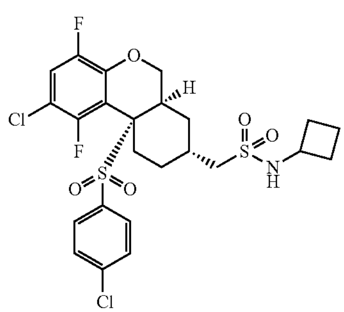 [SMILES: O=S(=O)(C[C@@H]1CC[C@@]2(S(=O)(=O)c3ccc(Cl)cc3)c3c(F)c(Cl)cc(F)c3OC[C@H]2C1)NC1CCC1] | 582.3, 4.88 Min |
| 317 | 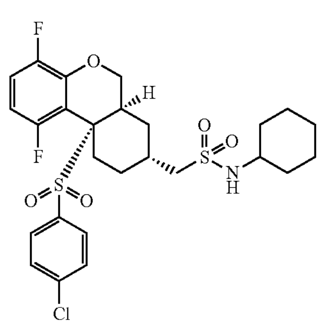 [SMILES: O=S(=O)(C[C@@H]1CC[C@@]2(S(=O)(=O)c3ccc(Cl)cc3)c3c(F)ccc(F)c3OC[C@H]2C1)NC1CCCCC1] | 574.3, 4.91 Min |
| 318 | 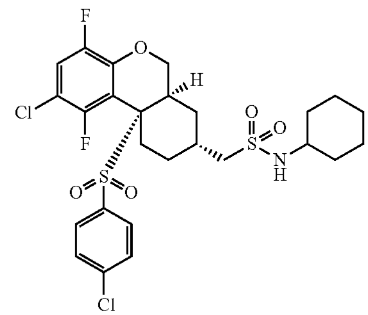 [SMILES: O=S(=O)(C[C@@H]1CC[C@@]2(S(=O)(=O)c3ccc(Cl)cc3)c3c(F)c(Cl)cc(F)c3OC[C@H]2C1)NC1CCCCC1] | 608.3, 5.15 Min |
| 319 | 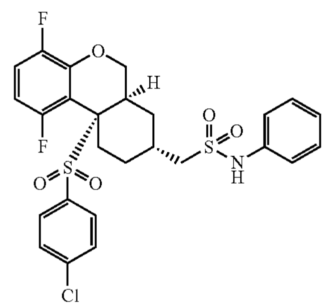 [SMILES: O=S(=O)(C[C@@H]1CC[C@@]2(S(=O)(=O)c3ccc(Cl)cc3)c3c(F)ccc(F)c3OC[C@H]2C1)Nc1ccccc1] | 568.3, 4.75 Min |
| 320 | 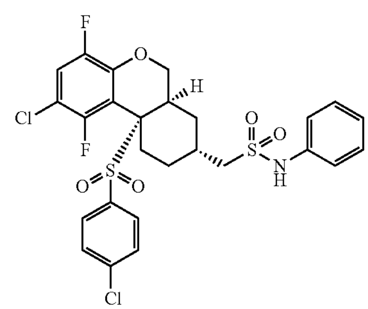 [SMILES: O=S(=O)(C[C@@H]1CC[C@@]2(S(=O)(=O)c3ccc(Cl)cc3)c3c(F)c(Cl)cc(F)c3OC[C@H]2C1)Nc1ccccc1] | 602.3, 4.98 Min |
Examples 321 to 326
Example 321
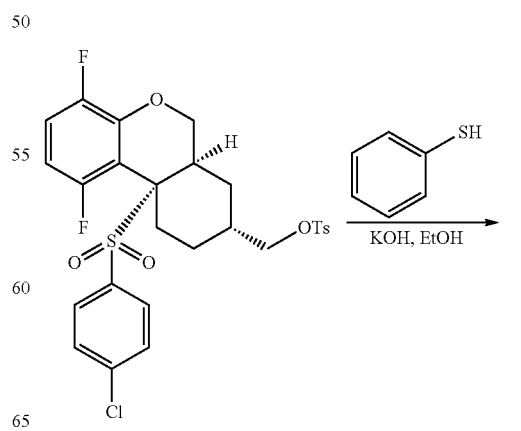
Example 300

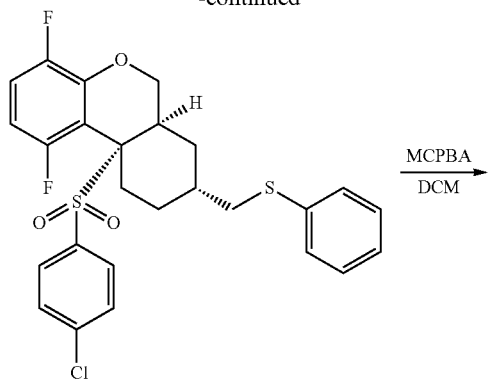
Following procedures similar to those described in Example 337, the compounds in Table 68 were prepared.
TABLE 68
| Ex. No. | Structure | LCMS (M + 1, retention time) |
|---|---|---|
| 321 | | 553.3, 4.71 Min |
| 322 | 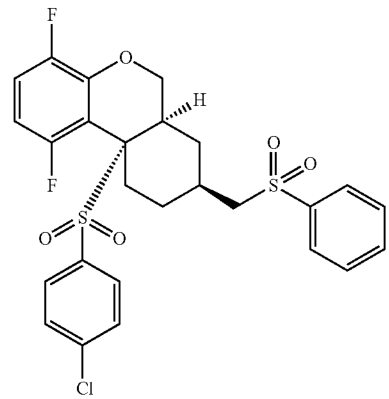 [SMILES: O=S(=O)(C[C@H]1CC[C@@]2(S(=O)(=O)c3ccc(Cl)cc3)c3c(F)ccc(F)c3OC[C@H]2C1)c1ccccc1] | 553.3, 4.64 Min. |
| 323 | 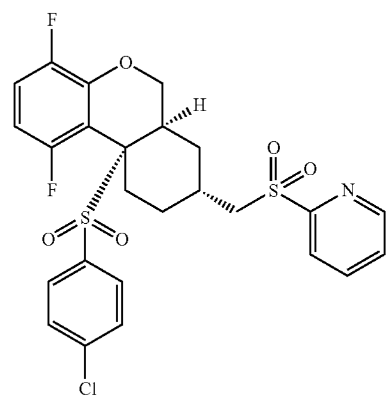 [SMILES: O=S(=O)(C[C@@H]1CC[C@@]2(S(=O)(=O)c3ccc(Cl)cc3)c3c(F)ccc(F)c3OC[C@H]2C1)c1ccccn1] | 554.3, 4.38 Min |
| 324 | 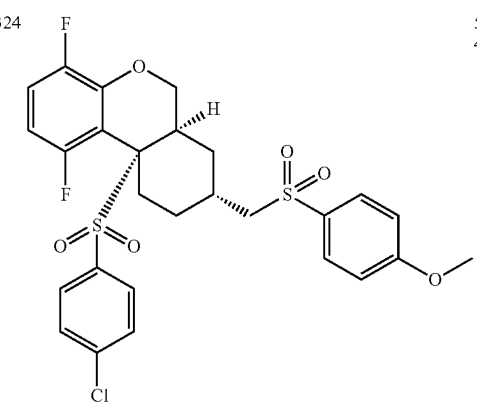 | 583.3, 4.67 Min |

TABLE 68-continued

| Ex. No. | Structure | LCMS (M + 1, retention time) |
|---|---|---|
| 325 | (structure) | 557.3, 4.47 Min |
| 326 | (structure) | 583.3, 4.76 Min |

Examples 327 and 328

(6As)-10Ar-[(4-chlorophenyl)sulfonyl]-1,4-difluoro-6A,7,8,9,10,10A-hexahydro-8(s)-(iodomethyl)6h-dibenzo[B,D]pyran (racemic)

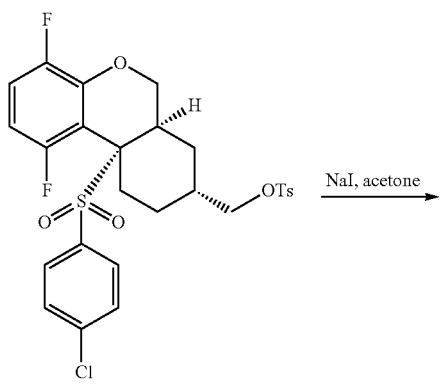

Example 300

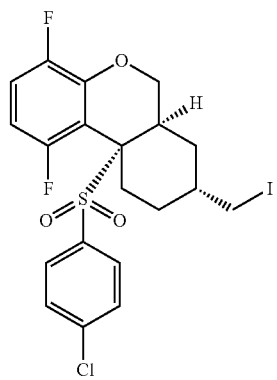

Example 327

To a solution of Example 300 (0.016 g, 0.027 mmol) in 2 mL acetone was added NaI (0.02 g, 0.13 mmol), heated to reflux for 12 hours. All solvent was removed in vacuo. The material was subjected to preparative TLC over silica gel (eluted with ethyl acetate/hexane 30/70) to give 0.013 g product Example 327. $^1$H NMR (CDCl$_3$ 400 MHz) δ 7.57 (d, 2H), 7.50 (d, 2H), 7.10 (m, 1H), 6.43 (m, 1H), 5.25 (dd, 1H), 4.12 (d, 1H), 3.40 (d, 2H), 2.79 (d, 1H), 2.35 (d, 1H), 2.12 (m, 2H), 1.93 (m, 2H), 1.77 (m, 1H), 1.35 (m, 1H).

Example 328 (Table 69) was prepared following similar procedures described in Example 327.

TABLE 69

| Ex. No. | Structure | LCMS (M + 1, retention time) |
|---|---|---|
| 327 | (structure) | 5.34 Min. |

TABLE 69-continued

| Ex. No. | Structure | LCMS (M + 1, retention time) |
|---|---|---|
| 328 | 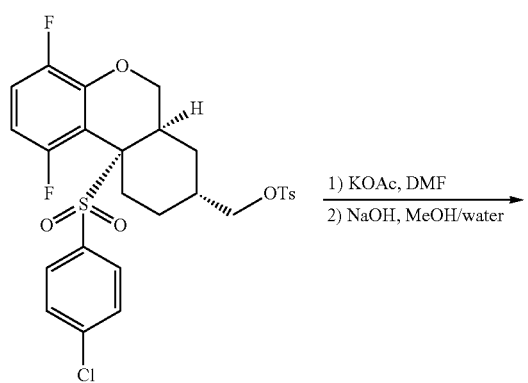 | 539.3, 5.39 Min. |

Following procedures similar to those described in Examples 301-303 Step-1 except using potassium acetate as the reagent the compound of Example 329 was prepared.

Example 329

(6As)-10Ar-[(4-chlorophenyl)sulfonyl]-1,4-difluoro-6A,7,8,9,10,10A-hexahydro-6h-dibenzo[B,D]pyran-8(s)-methanol (racemic)

Following procedures similar to those described in Examples 301-303 Step-1 except using potassium acetate as the reagent the compound of Example 329 was prepared.

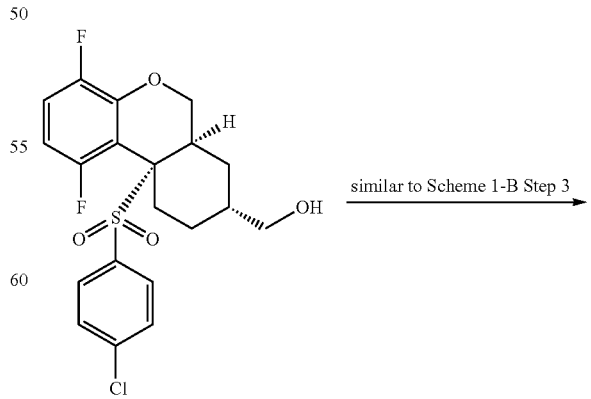

Example 300

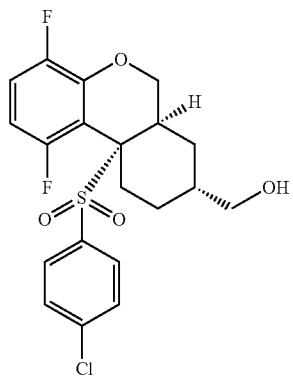

Example 329

Example 329

$^1$H NMR (CDCl$_3$ 400 MHz) δ 7.57 (d, 2H), 7.49 (d, 2H), 7.08 (m, 1H), 6.41 (m, 1H), 5.19 (d, 1H), 4.12 (d, 1H), 3.75 (d, 2H), 2.79 (d, 1H), 2.38 (d, 1H), 2.11 (m, 1H), 1.58-1.88 (m, 3H), 1.24-1.37 (m, 3H), LCMS (MH$^+$)=429.2; retention time=4.15 min.

Following procedures similar to those described in Scheme 1-B Step 3. Example LQ-31/LQ-Scheme-6 was prepared.

Example 330

(6As)-10Ar-[(4-chlorophenyl)sulfonyl]-1,4-difluoro-6A,7,8,9,10,10A-hexahydro-6h-dibenzo[B,D]pyran-8(s)-methanol, methylcarbamate (racemic)

Following procedures similar to those described in Scheme 1-B Step 3. Example 330 was prepared

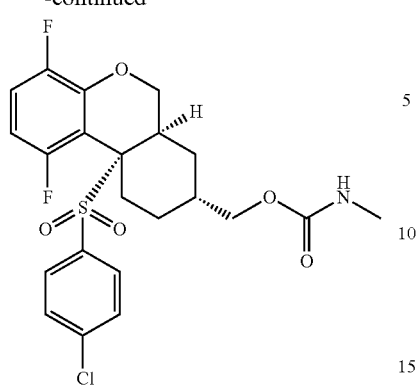

Example 330

Example 330 was made following procedures similar to those described in Scheme 1-B Step 3. $^1$H NMR (CDCl$_3$ 400 MHz) δ 7.57 (d, 2H), 7.49 (d, 2H), 7.10 (m, 1H), 6.43 (m, 1H), 5.20 (d, 1H), 4.70 (m, 1H), 4.19-4.21 (m, 2H), 4.12 (d, 1H), 2.83 (d, 3H), 2.38 (m, 1H), 2.19 (m, 1H), 1.99 (m, 1H), 1.66-1.73 (m, 2H), 1.25 (m, 2H), LCMS (MH$^+$)=486.3; retention time=4.44 min.

Example 331

2-[10b-(4-Chloro-benzenesulfonyl)-7,10-difluoro-1,4a,5,10b-tetrahydro-2H,4H-pyrano[3,4-c]chromen-4-yl]-ethanol

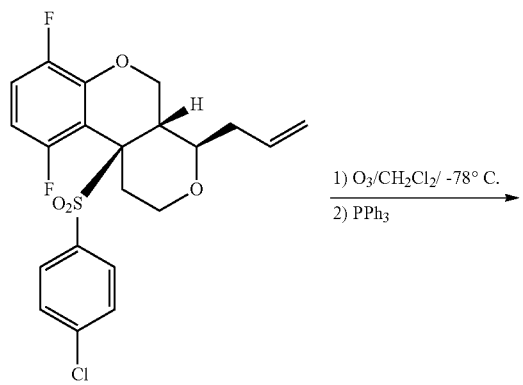

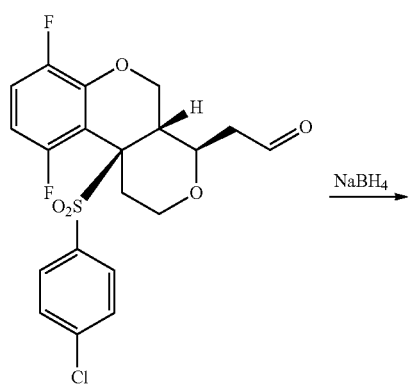

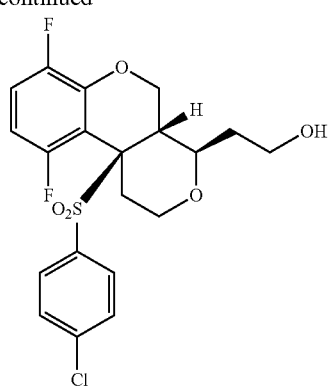

Step 1

A stream of O$_3$ was bubbled through a stirring solution of the alkene (1.57 g, 3.56 mmol) in DCM (120 mls) at −78° C. When the blue color persisted, the O$_3$ addition was stopped. Continued stirring at −78° C. for 10 min. A stream of N$_2$ was bubbled through the reaction until it became colorless. The PPh$_3$ (1.40 g, 5.34 mmol) was added in portions. The reaction was then stirred at room temperature for 2.5 hrs. This solution was dried over anhydrous Na$_2$SO$_4$. Filtration followed by evaporation to give an oil (~1.58 g of the aldehyde). This aldehyde was used as is in the next step.

Step 2

The crude aldehyde (~1.58 g, 3.56 mmol) was dissolved in EtOH (50 mls) and cooled to 0° C. The NaBH$_4$ (135 mg, 3.56 mmol) was added in portions. The reaction was continued to be stirred at 0° C. for 15 min and then at room temperature for 1 hr. The NaBH$_4$ was quenched with the dropwise addition of H$_2$O (2 mls). The EtOH was evaporated under vacuum. The residue was partitioned between DCM (150 mls) and H$_2$O (2×75 mls). The DCM was washed with brine (75 mls) and dried over anhydrous Na$_2$SO$_4$. The DCM was evaporated to give a solid residue. This material was purified by flash-chromatography on silica gel (eluted with hexane/EtOAc 95:5 to 50:50) to give the expected product as a solid (1.58 g, 100%).

Examples 332 to 335

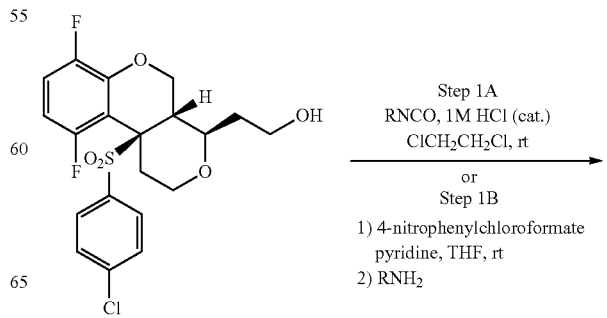

-continued (wherein R is identified in Table 70)

Step 1A

A solution of the alcohol (10 mg, 0.0224 mmol) and ethyl isocyanate (1.6 mg, 0.0224 mmol) in 1,2-dichloroethane (0.50 mls) containing 1 m HCl /ether (1 drop) was stirred at room temperature. After 2 hrs, the solvent was evaporated. The residue was purified by preparative tlc (50% EtOAc/hexane, 1000 micron silica gel GF) to give a solid (9.7 mg, 84%).

Step 1B

A solution of the alcohol (10 mg, 0.0224 mmol), 4-nitrophenylchloroformate (6.8 mg, 0.0337 mmol) and pyridine (2.7 mg, 0.0337 mmol) in THF (0.50 mls) was stirred at room temperature. The resulting mixture was stirred at room temperature for 1 hr. The 1M MeNH$_2$ in THF (1.4 mg, 0.0448 mmol) was added and the reaction was stirred overnight at room temperature. The solvent was removed under vacuum and the crude product was purified by preparative tlc (50% EtOAc/hexane, 1000 micron silica gel GF) to afford a solid (11 mg, 98%).

Using the general procedure of Steps 1A and 1B, the compounds in Table 70 were prepared

TABLE 70

| Example No. | STRUCTURE | Mass Spec (M$^+$ except as otherwise noted); retention time (min) |
|---|---|---|
| 332 | (structure: OCONHCH$_2$CH$_3$) | 516.3: 4.32 |
| 333 | (structure: OCONHCH$_3$) | 502.3: 4.27 |
| 334 | (structure: OCONHCH(CH$_3$)$_2$) | 530.3: 4.63 |
| 335 | (structure: OCONH-cyclopropyl) | 528.3: 4.48 |

Example 336

3-[10b-(4-Chloro-benzenesulfonyl)-7,10-difluoro-1,4-a,5,10b-tetrahydro-2H,4H-pyrano[3,4-c]chromen-4-yl]-propionitrile

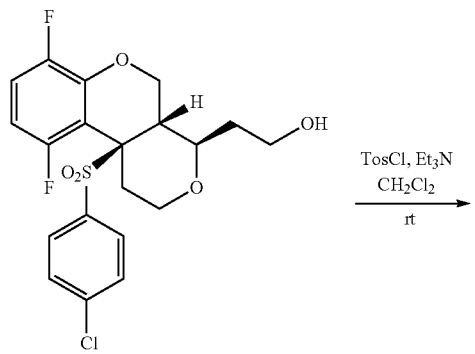

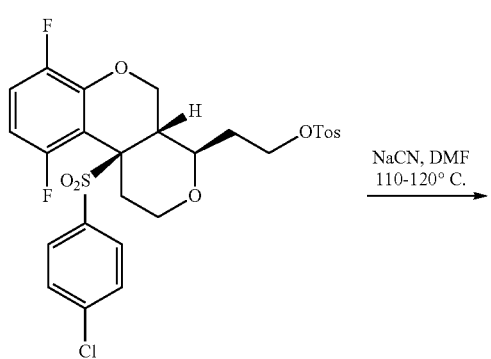

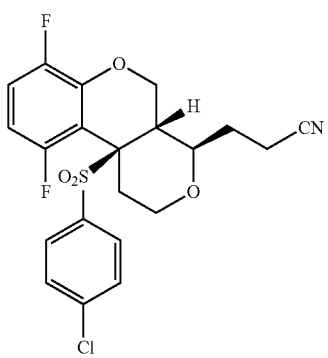

Step 1

The alcohol (1.06 g, 2.38 mmol) and TosCl (907 mg, 4.76 mmol) were dissolved in DCM (20 mls) at room temperature. The Et₃N (482 mg, 4.76 mmol) was added dropwise to the stirring solution. The reaction was stirred overnight. It was diluted with DCM (100 mls) and was extracted with saturated NaHCO₃ (50 mls) and H₂O (2×50 mls). The DCM solution was dried over anhydrous Na₂SO₄ and was evaporated to an oil. The crude product was purified by flash-chromatography on silica gel (eluted with EtOAc/hexane 5:95 to 50:50) to yield a solid (1.34 g, 94%).

Step 2

A stirring solution of the tosylate (100 mg, 0.167 mmol) and NaCN (25 mg, 0.501 mmol) in DMF (2 mls) was heated to 110-120° C. for 3 hrs. The reaction was diluted with an EtOAc (2 mls)/hexane(2 mls) mixture and was partitioned with H₂O (2×3 mls). The organic phase was dried over anhydrous Na₂SO₄ and was evaporated. The residue was purified by flash-chromatography on silica gel (eluted with EtOAc/hexane 5:95 to 100:0) to give a solid (62 mg, 82%).

TABLE 71

| Example No. | STRUCTURE | Mass Spec (M⁺ except as otherwise noted); retention time (min) |
|---|---|---|
| 336 | (see structure) | 454.2: 4.49 |

Example 337

10b-(4-Chloro-benzenesulfonyl)-7,10-difluoro-4-[2-(propane-2-sulfonyl)-ethyl]-1,4-a,5,10b-tetrahydro-2H,4H-pyrano[3,4-c]chromene

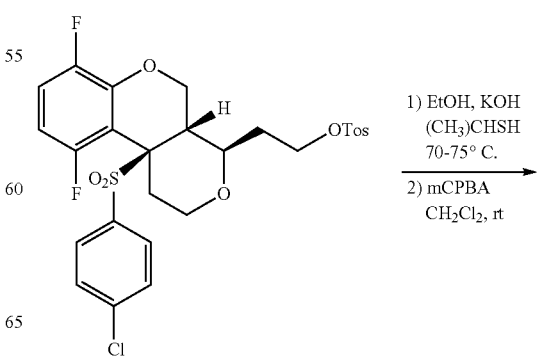

-continued

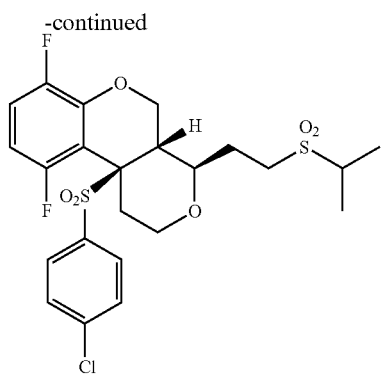

Step 1

A stirring mixture of the tosylate (96 mg, 0.160 mmol), isopropyl mercaptan (24 mg, 0.32 mmol) and 1M KOH in EtOH (13.5 mg, 24 mmol) in EtOH (3 mls) was heated to 70-75° C. for 30 min. The reaction mixture was evaporated. The residue was taken up with DCM (15 mls) and was washed with $H_2O$ (2×5 mls). The DCM was dried over anhydrous $Na_2SO_4$ and was evaporated to a solid (79 mg). This product was used as is in the subsequent reaction.

Step 2

A stirring solution of the sulfide (73 mg, 0.145 mmol) in DCM (3 mls) at room temperature was treated with mCPBA (75 mg, 0.435 mmol). After 1 hr, the reaction was diluted with DCM (10 mls) and was extracted with saturated $NaHCO_3$ (2×5 mls) and $H_2O$ (5 mls). The DCM was dried over anhydrous $Na_2SO_4$ and was concentrated. The residue was purified by flash-chromatography on silica gel (eluted with EtOAc/hexane 5:95 to 80:20) to yield a the expected product as a solid (57 mg, 73%).

TABLE 72

| Example No. | STRUCTURE | Mass Spec ($M^+$ except as otherwise noted); retention time (min) |
|---|---|---|
| 337 | 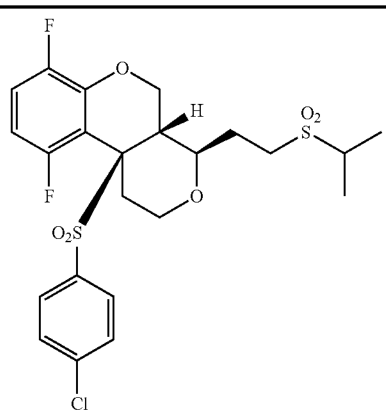 | 535.3: 4.59 |

Example 338

Using the general procedure of Example 337, the compound in Table 73 was prepared.

TABLE 73

| Example No. | STRUCTURE | Mass Spec ($M^+$ except as otherwise noted); retention time (min) |
|---|---|---|
| 338 | 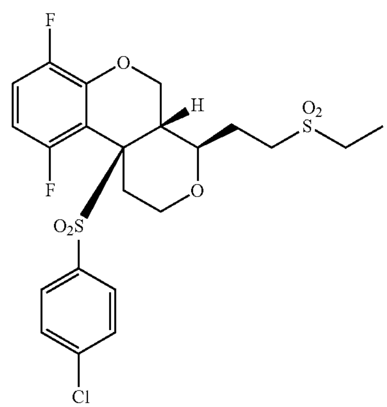 [SMILES: CCS(=O)(=O)CC[C@H]1OCC[C@]2(S(=O)(=O)c3ccc(Cl)cc3)c3c(F)ccc(F)c3OC[C@H]12] | 521.3: 4.30 |

Examples 339 and 340

The compounds in Table 74 were prepared according to Example 24.

TABLE 74

| Example No. | STRUCTURE | Mass Spec ($M^+$ except as otherwise noted); retention time (min) |
|---|---|---|
| 339 | 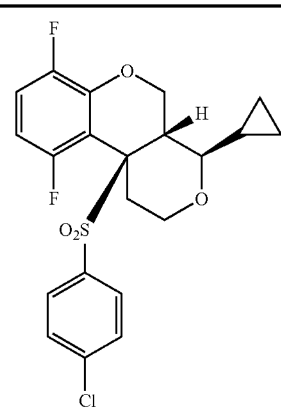 | 441.2: 4.90 |

TABLE 74-continued

| Example No. | STRUCTURE | Mass Spec (M+ except as otherwise noted); retention time (min) |
|---|---|---|
| 340 | 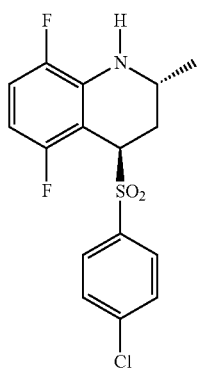 [SMILES: C[C@@H]1C[C@@H](S(=O)(=O)c2ccc(Cl)cc2)c2c(F)ccc(F)c2N1] | 457.3: 5.58 |

Example 341

4-(4-Chloro-benzenesulfonyl)-5,8-difluoro-2-methyl-1,2,3,4-tetrahydro-quinoline

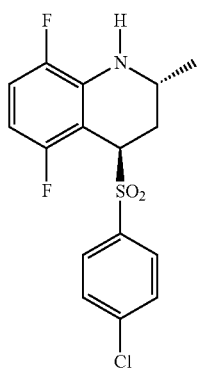 [SMILES: C[C@@H]1C[C@@H](S(=O)(=O)c2ccc(Cl)cc2)c2c(F)ccc(F)c2N1]

A solution of 2,5-difluoroaniline (5.0 g, 38.7 mmol) in ether (50 mL) was treated with a solution of HCl (1 M in Et₂O, 39 mL) and concentrated in vacuo. The resulting powder was dissolved in EtOH (30 mL) and cooled to 0° C. Acetaldehyde (2.2 mL, 39 mmol) was added dropwise and the solution warmed to ambient temperature. After 30 min, the reaction mixture was diluted with H₂O (6 mL) and 4-chlorophenyl sodium sulfinate (3.5 g, 17.7 mmol) was added quickly. After 4 h, the reaction mixture was concentrated in vacuo. The residue was diluted with saturated aqueous NaHCO₃ and extracted with CH₂Cl₂ (2×). The combined organic extracts were dried over MgSO₄ and concentrated. Flash chromatography (5→0.10% EtOAc/Hex) afforded Example 341 (1.23 g, 19%): ¹H NMR (CDCl₃ 400 MHz) δ 7.70 (dd, J=8.8, 2.2 Hz, 2H), 7.49 (dd, J=8.8, 2.2 Hz, 2H), 6.84 (m, 1H), 6.00 (m, 1H), 4.53 (dd, J=5.1, 2.2 Hz, 1H), 4.35 (br s, 1H), 4.18 (m, 1H), 2.76 (m, 1H), 1.68 (ddd, J=14.6, 12.4, 5.1 Hz, 1H), 1.33 (d, J=6.6 Hz, 3H).

Example 342

4-(4-Chloro-benzenesulfonyl)-5,8-difluoro-1,2,3,4-tetrahydro-quinoline

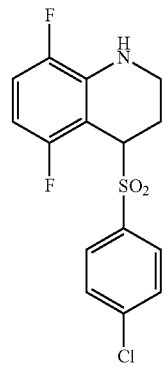 [SMILES: O=S(=O)(c1ccc(Cl)cc1)C1CCNc2c(F)ccc(F)c21]

Step 1

2N-[3-(4-Chloro-benzenesulfonyl)-3-(2,3,6-trifluoro-phenyl)-propyl]-4-methyl-benzenesulfonamide

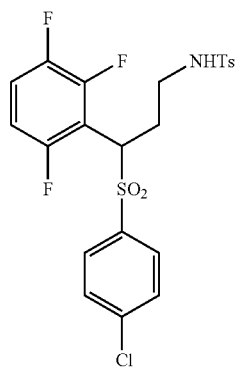

A solution of 2-(4-chloro-benzenesulfonylmethyl)-1,3,4-trifluoro-benzene (5.6 g, 17.5 mmol) in THF/TMEDA (5:1, 180 mL) at −78° C. was treated with n-BuLi (12 mL, 17.5 mmol, 1.5 M in hexanes). After 15 min, a solution of N-p-toluenesulfonyl aziridine (3.5 g, 17.5 mmol, prepared as described in Eur. J. Org. Chem. 2002, 3004) in THF (10 mL) was added, and the reaction mixture warmed slowly to ambient temperature. After 4 h, the reaction mixture was quenched with 1N HCl and extracted with EtOAc (2×). The combined organic extracts were washed with saturated aqueous NaHCO₃, brine, dried over MgSO₄ and concentrated in vacuo. Flash chromatography (25→50% EtOAc/Hex) provided the title compound (4.9 g, 54%): ¹H NMR (CDCl₃ 400 MHz) δ 7.64 (d, J=8.1 Hz, 2H), 7.57 (d, J=8.1 Hz, 2H), 7.43 (d, J=8.1 Hz, 2H), 7.28 (d, J=8.1 Hz, 2H), 7.14 (m, 1H), 6.75

(m, 1H), 4.81 (m, 1H), 3.17 (ddd, J=7.1, 7.1, 5.6 Hz, 1H), 2.96 (m, 1H), 2.64 (m, 1H), 2.47 (m, 1H), 2.41 (s, 3H).

Step 2

3-(4-Chloro-benzenesulfonyl)-3-(2,3,6-trifluoro-phenyl)-propylamine

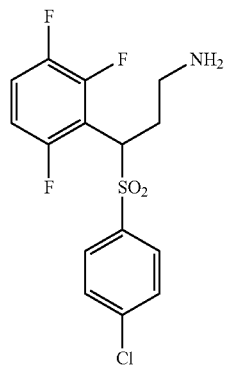 [SMILES: NCCC(c1c(F)ccc(F)c1F)S(=O)(=O)c1ccc(Cl)cc1]

A solution of 2N-[3-(4-chloro-benzenesulfonyl)-3-(2,3,6-trifluoro-phenyl)-propyl]-4-methyl-benzenesulfonamide (500 mg, 0.97 mmol) was in 48% HBr/H$_2$O (4 mL) was treated with phenol (282 mg, 3.0 mmol) was heated to reflux. After 7 h, another portion of 48% HBr/H$_2$O (3 mL) was added. After an additional 36 h, the reaction mixture was cooled to ambient temperature and quenched dropwise with 1N NaOH. The reaction mixture was extracted with CH$_2$Cl$_2$ (4×) and the combined organic layers were dried over MgSO$_4$, filtered and concentrated in vacuo. Flash chromatography [1% MeOH/CH$_2$Cl$_2$→5% NH$_4$OH/MeOH (1:9)/CH$_2$Cl$_2$) provided the title compound (240 mg, 68%): $^1$H NMR (CDCl$_3$ 400 MHz) δ 7.64 (d, J=8.1 Hz, 2H), 7.43 (d, J=8.1 Hz, 2H), 7.14 (m, 1H), 6.78 (m, 1H), 4.89 (dd, J=9.5, 5.1 Hz, 1H), 2.87 (m, 1H), 2.56-2.40 (m, 3H), 1.22 (s, 2H).

Step 3

4-(4-Chloro-benzenesulfonyl)-5,8-difluoro-1,2,3,4-tetrahydro-quinoline

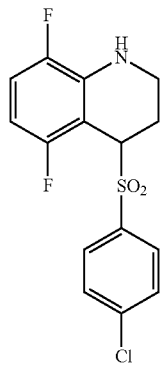

A solution of 3-(4-chloro-benzenesulfonyl)-3-(2,3,6-trifluoro-phenyl)-propylamine (100 mg, 0.27 mmol) in DMF (3 mL) was heated to 80° C. After 4 h, the reaction mixture was cooled to ambient temperature, diluted with saturated aqueous NaHCO$_3$, and extracted with EtOAc (2×). The combined organic layers were washed with water (2×), brine, dried over MgSO$_4$ and concentrated in vacuo. Flash chromatography (20% EtOAc/Hex) provided Example 342 (78 mg, 84%): $^1$H NMR (CDCl$_3$ 400 MHz) δ 7.69 (dd, J=8.1, 2.2 Hz, 2H), 7.49 (dd, J=8.1, 2.2 Hz, 2H), 6.84 (m, 1H), 6.03 (m, 1H), 4.52 (d, J=5.1 Hz, 1H), 4.50 (br s, 1H), 3.95 (ddd, J=12.4, 12.4, 4.4 Hz, 1H), 3.48 (m, 1H), 2.81 (m, 1H), 2.00 (m, 1H).

Example 343

4-(4-Chloro-benzenesulfonyl)-5,8-difluoro-1-methyl-1,2,3,4-tetrahydro-quinoline

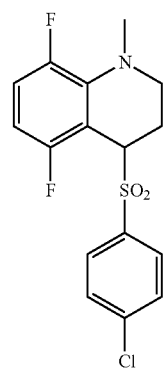 [SMILES: CN1CCC(S(=O)(=O)c2ccc(Cl)cc2)c2c(F)ccc(F)c21]

A solution of 4-(4-chloro-benzenesulfonyl)-5,8-difluoro-1,2,3,4-tetrahydro-quinoline (50 mg, 0.145 mmol) in CH$_3$CN (1 mL) was treated with K$_2$CO$_3$ (4 mg, 0.16 mmol), MeI (10 μL, 0.16 mmol) and heated to 50° C. After 6 h, the reaction mixture was treated with MeI (10 μL, 0.16 mmol) and heated to 80° C. After 12 h, the reaction mixture was transferred to a sealed tube and diluted with propionitrile (2 mL). Potassium carbonate (20 mg) and MeI (50 μL) were added and the reaction mixture was heated to 80° C. After 48 h, the reaction mixture was cooled to ambient temperature, diluted with saturated aqueous NH$_4$Cl and extracted with EtOAc (2×). The combined organic layers were with saturated aqueous NaHCO$_3$, brine, dried over MgSO$_4$ and concentrated in vacuo. Preparative thin layer chromatography (20% EtOAc/Hex) provided Example 343 (25.6 mg, 49%): $^1$H NMR (CDCl$_3$ 400 MHz) δ 7.67 (dd, J=8.8, 2.2 Hz, 2H), 7.48 (dd, J=8.8, 2.2 Hz, 2H), 6.87 (m, 1H), 6.12 (m, 1H), 4.53 (d, J=5.1

Hz, 1H), 3.69 (ddd, J=13.9, 11.7, 4.4 Hz, 1H), 3.32 (m, 1H), 3.13 (d, J=4.4 Hz, 3H), 2.82 (m, 1H), 2.07 (m, 1H).

Example 344

Trans-11a-(4-chloro-benzenesulfonyl-1,4-difluoro-6,6a,7,8,9,10,11,11a-octahydro-cyclohepta[c]chromen-cis-8-ol and trans-11a-(4-chloro-benzenesulfonyl)-1,4-difluoro-6,6a,7,8,9,10,11,11a-octahydro-cyclohepta[c]chromen-trans-8-ol

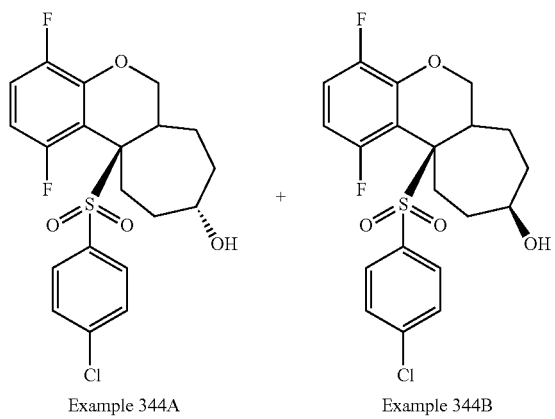 [SMILES: O=S(=O)(c1ccc(Cl)cc1)[C@]12CC[C@@H](O)CCC1COc1c(F)ccc(F)c12 ; O=S(=O)(c1ccc(Cl)cc1)[C@]12CC[C@H](O)CCC1COc1c(F)ccc(F)c12]

Example 344A          Example 344B

Step 1

4-(4-Chloro-benzenesulfonyl)-5,8-difluoro-3-(2-iodo-ethyl)-chroman

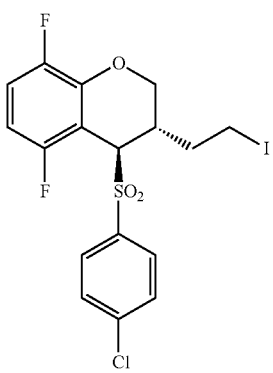 [SMILES: O=S(=O)(c1ccc(Cl)cc1)[C@H]1c2c(F)ccc(F)c2OC[C@@H]1CCI]

A solution of the product from Example 27 Step 5 (2.7 g, 6.94 mmol) in CH$_3$CN/tol (1:2, 70 mL) at 0° C. was treated with Ph$_3$P (2.2 g, 8.3 mmol), imidazole (0.61 g, 9.0 mmol), iodine (2.1 g, 8.3 mmol) and warmed to ambient temperature. After 1 h, the reaction mixture was diluted with saturated aqueous NaHCO$_3$/Na$_2$S$_2$O$_3$ (1:1) and extracted with Et$_2$O (2×). The combined organic extracts were washed with 1N HCl, saturated aqueous NaHCO$_3$, brine, dried over MgSO$_4$ and concentrated in vacuo. Flash chromatography (2→10% EtOAc/Hex) provided the title compound (3.47 g, 99%): $^1$H NMR (CDCl$_3$ 400 MHz) δ 7.77 (dd, J=8.1, 1.5 Hz, 2H), 7.55 (dd, J=8.1, 1.5 Hz, 2H), 7.04 (m, 1H), 6.46 (m, 1H), 4.92 (dd, J=11.7, 2.9 Hz, 1H), 4.31 (dd, J=11.7, 1.5 Hz, 1H), 4.28 (s, 1H), 3.17-3.10 (m, 2H), 2.97 (t, J=6.6 Hz, 1H), 1.89 (m, 1H), 1.74 (m, 1H).

Step 2

3-[4-(4-Chloro-benzenesulfonyl)-5,8-difluoro-chroman-3-yl]-propionitrile

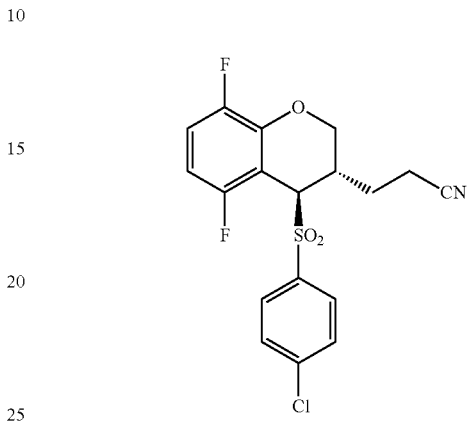

A solution of 4-(4-chloro-benzenesulfonyl)-5,8-difluoro-3-(2-iodo-ethyl)-chroman (3.47 g, 6.94 mmol) in CH$_3$CN (70 mL) was treated with n-Bu$_4$NCN (2.2 g, 8.0 mmol). After 12 h, the reaction mixture was diluted with 1N HCl and extracted with Et$_2$O (3×). The combined organic extracts were washed with 1N HCl (2×), saturated aqueous NaHCO$_3$, brine, dried over MgSO$_4$ and concentrated in vacuo to afford the title compound (2.6 g, 94%): $^1$H NMR (CDCl$_3$ 400 MHz) δ 7.74 (dd, J=8.8, 2.2 Hz, 2H), 7.55 (dd, J=8.8, 2.2 Hz, 2H), 7.07 (m, 1H), 6.46 (m, 1H), 4.99 (dd, J=12.4, 2.9 Hz, 1H), 4.34 (dd, J=12.4, 2.2 Hz, 1H), 4.32 (s, 1H), 2.99 (t, J=6.6 Hz, 1H), 2.47 (t, J=7.3 Hz, 2H), 1.76 (m, 1H), 1.65 (m, 1H).

Step 3

3-[4-(4-Chloro-benzenesulfonyl)-5,8-difluoro-chroman-3-yl]-propionaldehyde

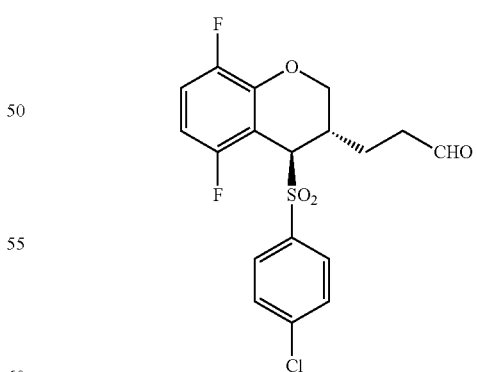

A solution of 3-[4-(4-chloro-benzenesulfonyl)-5,8-difluoro-chroman-3-yl]-propionitrile (500 mg, 1.26 mmol) in CH$_2$Cl$_2$ (15 mL) at −78° C. was treated with DIABAL (1 M in hexanes, 1.5 mL, 1.5 mmol) and warmed to 0° C. over 1 h. After 1 h further, the reaction mixture was quenched with 1N HCl, stirred vigorously for 30 min, and extracted with CH₂Cl₂ (3×). The combined organic extracts were washed with H₂O, dried over MgSO₄ and concentrated in vacuo. Flash chromatography (8→60% EtOAc/Hex) afforded the title compound (455 mg, 90%): ¹H NMR (CDCl₃ 400 MHz) δ 9.75 (s, 1H), 7.73 (dd, J=8.8, 2.2 Hz, 2H), 7.51 (dd, J=8.8, 2.2 Hz, 2H), 7.04 (m, 1H), 6.43 (m, 1H), 4.90 (dd, J=12.4, 2.2 Hz, 1H), 4.32 (dd, J=12.4, 2.2 Hz, 1H), 4.31 (s, 1H), 2.83 (t, J=6.6 Hz, 1H), 2.56 (m, 1H), 1.76-1.54 (m, 3H).

Step 4

1-[4-(4-Chloro-benzenesulfonyl-5,8-difluoro-chroman-3-yl]-hex-5-en-3-ol

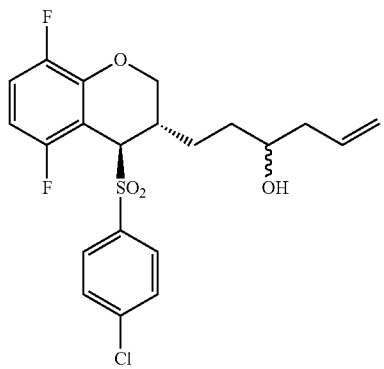 [SMILES: C=CCC(O)CC[C@H]1COc2c(F)ccc(F)c2[C@@H]1S(=O)(=O)c1ccc(Cl)cc1]

A solution of 3-[4-(4-chloro-benzenesulfonyl)-5,8-difluoro-chroman-3-yl]-propionaldehyde (1.79 g, 4.47 mmol) in THF (45 mL) at −78° C. was treated with allylmagnesium bromide (1 M in Et₂O, 5.8 mL, 5.8 mmol) and warmed to 0° C. over 1 h. The reaction mixture was quenched with saturated aqueous NH₄Cl, and extracted with EtOAc (2×). The combined organic extracts were washed saturated aqueous NaHCO₃, brine, dried over MgSO₄ and concentrated in vacuo. Flash chromatography (2→10% EtOAc/CH₂Cl₂) afforded the title compound (1.3 g, 66%): ¹H NMR (CDCl₃ 400 MHz) δ 7.71 (dd, J=8.1, 1.5 Hz, 2H), 7.53 (dd, J=8.1, 1.5 Hz, 2H), 7.03 (m, 1H), 6.41 (m, 1H), 5.76 (m, 1H), 5.16-5.08 (m, 2H), 4.93 (ddd, J=11.7, 2.9, 2.9 Hz, 1H), 4.32 (dd, J=12.4, 2.2 Hz, 1H), 4.31 (s, 1H), 3.59 (m, 1H), 2.85 (m, 1H), 2.29-2.10 (m, 2H), 1.68-1.43 (m, 4H).

Step 5

Tert-Butyl-(1-{2-[4-(4-chloro-benzenesulfonyl)-5,8-difluoro-chroman-3-yl]-ethyl}-but-3-enyloxy)-dimethyl-silane

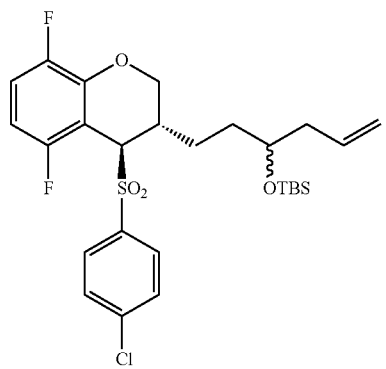 [SMILES: C=CCC(CC[C@H]1COc2c(F)ccc(F)c2[C@@H]1S(=O)(=O)c1ccc(Cl)cc1)O[Si](C)(C)C(C)(C)C]

A solution of 1-[4-(4-chloro-benzenesulfonyl)-5,8-difluoro-chroman-3-yl]-hex-5-en-3-ol (1.30 g, 2.93 mmol) in DMF (29 mL) 0° C. was treated with imidazole (0.41 g, 6.0 mmol), TBSCl (0.66 g, 4.4 mmol) and warmed to ambient temperature. After 36 h, the reaction mixture was quenched with saturated aqueous NH₄Cl and extracted with EtOAc (2×). The combined organic extracts were washed H₂O (3×), saturated aqueous NaHCO₃, brine, dried over MgSO₄ and concentrated in vacuo. Flash chromatography (1-+10% EtOAc/Hex) afforded the title compound (1.45 g, 89%): ¹H NMR (CDCl₃ 400 MHz) δ 7.71 (dd, J=8.1, 1.5 Hz, 2H), 7.52 (dd, J=8.1, 1.5 Hz, 2H), 7.03 (m, 1H), 6.42 (m, 1H), 5.72 (m, 1H), 5.01-4.89 (m, 3H), 4.33 (dd, J=11.0, 2.2 Hz, 1H), 4.27 (s, 1H), 3.62 (m, 1H), 2.74 (m, 1H), 2.12-2.10 (m, 2H), 1.55-1.24 (m, 4H), 0/8 (s, 4.5H), 0.76 (s, 4.5H), −0.01 (s, 3H), −0.08 (s, 3H).

Step 6

3-(tert-Butyl-dimethyl-silanyloxy)-5-[4-(4-chloro-benzenesulfonyl)-5,8-difluoro-chroman-3-yl]-pentan-1-ol

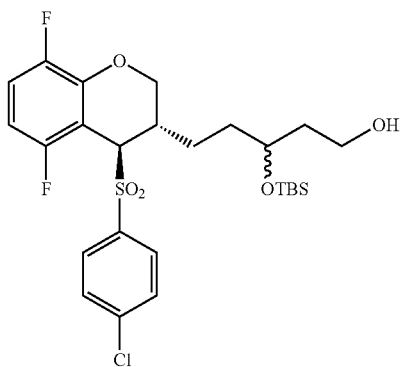 [SMILES: CC(C)(C)[Si](C)(C)OC(CCO)CC[C@H]1COc2c(F)ccc(F)c2[C@@H]1S(=O)(=O)c1ccc(Cl)cc1]

A solution of tert-butyl-(1-{2-[4-(4-chloro-benzenesulfonyl)-5,8-difluoro-chroman-3-yl]-ethyl}-but-3-enyloxy)-dimethyl-silane (1.45 g, 2.60 mmol) in 1:1 MeOH/CH$_2$Cl$_2$ (25 mL) at −78° C. was purged with ozone until the blue color persisted. The reaction mixture was then purged with N$_2$ for 5 min, treated with NaBH$_4$ (300 mg, 7.8 mmol) portionwise and slowly warmed to ambient temperature. Over the next 4.5 h, 2 additional portions of NaBH$_4$ (500 mg each) were added, and the reaction mixture was quenched with saturated aqueous NH$_4$Cl and concentrated in vacuo. The residue was extracted with CH$_2$Cl$_2$ (3×). The combined organic extracts were washed saturated aqueous NaHCO$_3$, dried over MgSO$_4$ and concentrated in vacuo. Flash chromatography (5→40% EtOAc/Hex) afforded the title compound (730 mg, 50%): $^1$H NMR (CDCl$_3$ 400 MHz) δ 7.72 (dd, J=8.8, 1.5 Hz, 2H), 7.52 (dd, J=8.8, 1.5 Hz, 2H), 7.02 (m, 1H), 6.38 (m, 1H), 4.90 (dd, J=11.7, 2.2 Hz, 1H), 4.33 (d, J=12.4 Hz, 1H), 4.28 (s, 1H), 3.85 (m, 1H), 3.73-3.64 (m, 2H), 2.76 (m, 1H), 1.91 (br s, 1H), 1.71-1.22 (m, 6H), 0.80 (s, 4.5H), 0.79 (s, 4.5H), 0.03 (s, 3H), −0.04 (s, 3H).

Step 7

Tert-Butyl-[11a-(4-chloro-benzenesulfonyl-1,4-difluoro-6,6a,7,8,9,10,11,11a-octahydro-cyclohepta[c]chromen-9-yloxy]-dimethyl-silane

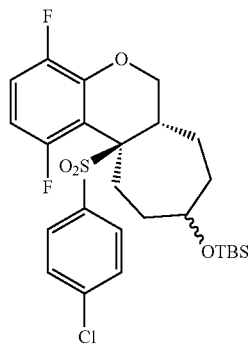

A solution of 3-(tert-butyl-dimethyl-silanyloxy)-5-[4-(4-chloro-benzenesulfonyl)-5,8-difluoro-chroman-3-yl]-pentan-1-ol (730 mg, 1.30 mmol) in CH$_2$Cl$_2$ (10 mL) at 0° C. was treated with Et$_3$N (360 μL, 2.6 mmol) followed by MsCl (150 μL, 1.95 mmol). After 30 min, the reaction mixture was quenched with saturated aqueous NH$_4$Cl and extracted with CH$_2$Cl$_2$ (2×). The combined organic extracts were washed with saturated aqueous NaHCO$_3$, dried over MgSO$_4$ and concentrated in vacuo to provide the crude product. The residue was dissolved in THF (13 mL), cooled to 0° C. and treated with KOt-Bu (1 M in THF, 3.0 mL, 3.0 mmol). After 1 h, the reaction mixture was quenched with saturated aqueous NH$_4$Cl and extracted with EtOAc (2×). The combined organic extracts were washed with saturated aqueous NaHCO$_3$, brine, dried over MgSO$_4$ and concentrated in vacuo to give the title compound (700 mg, 99% over 2 steps): $^1$H NMR (CDCl$_3$ 400 MHz) δ 7.63 (dd, J=8.8, 1.5 Hz, 2H), 7.49 (dd, J=8.8, 1.5 Hz, 2H), 7.04 (m, 1H), 6.43 (m, 1H), 5.07 (dd, J=10.9, 2.2 Hz, 1H), 4.23 (m, 1H), 4.04 (m, 0.5H), 3.58 (m, 0.5H), 2.97 (m, 1H), 2.71-2.26 (m, 2H), 2.10 (m, 1H), 1.83-1.43 (m, 5H), 0.90 (s, 4.5H), 0.77 (s, 4.5H), 0.03 (s, 3H), −0.01 (s, 3H).

Step 8

11a-(4-Chloro-benzenesulfonyl)-1,4-difluoro-6,6a,7,8,9,10,11,11a-octahydro-cyclohepta[c]chromen-9-ol

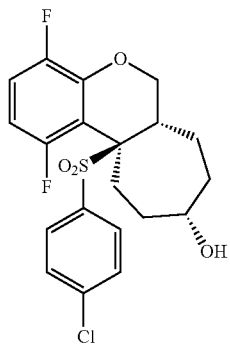

Example 344A1

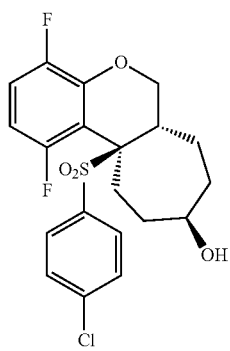

Example 344B1

A solution of tert-butyl-[11a-(4-chloro-benzenesulfonyl)-1,4-difluoro-6,6a,7,8,9,10,11,11a-octahydro-cyclohepta[c]chromen-9-yloxy]-dimethyl-silane (700 mg, 1.30 mmol) in THF (10 mL) at 0° C. was treated with TBAF (1 M in THF, 2.6 mL, 2.6 mmol) and warmed to ambient temperature. After 12 h, the reaction mixture was quenched with saturated aqueous NH$_4$Cl and extracted with EtOAc (2×). The combined organic extracts were washed with saturated aqueous NaHCO$_3$, brine, dried over MgSO$_4$ and concentrated in vacuo. Flash chromatography (2→20% EtOAc/CH$_2$Cl$_2$) afforded Example 344A1 (200 mg, Rf=0.49, 10% EtOAc/CH$_2$Cl$_2$): $^1$H NMR (CDCl$_3$ 400 MHz) δ 7.61 (d, J=8.7 Hz, 2H), 7.49 (d, J=8.7 Hz, 2H), 7.04 (m, 1H), 6.40 (m, 1H), 5.13 (dd, J=11.7, 2.2 Hz, 1H), 4.26 (dd, J=11.0, 2.2 Hz, 1H), 4.14 (m, 1H), 2.85 (d, J=6.6 Hz, 1H), 2.52 (ddd, J=14.6, 10.3, 2.2 Hz, 1H), 2.34 (m, 1H), 2.22 (m, 1H), 1.87-1.62 (m, 5H); followed by Example 344B1 (130 mg, Rf=0.33, 10% EtOAc/CH$_2$Cl$_2$): $^1$H NMR (CDCl$_3$ 400 MHz) δ 7.64 (d, J=8.8 Hz, 2H), 7.50 (d, J=8.8 Hz, 2H), 7.04 (m, 1H), 6.40 (m, 1H), 5.13

(dd, J=11.0, 2.2 Hz, 1H), 4.26 (dd, J=11.7, 2.2 Hz, 1H), 3.67 (m, 1H), 2.96 (m, 1H), 2.75 (m, 1H), 2.19 (m, 1H), 2.02 (m, 1H), 1.81-1.49 (m, 5H).

Example 345

N-[11a-(4-Chloro-benzenesulfonyl-1,4-difluoro-6,6a,7,8,9,10,11,11a-octahydro-cyclohepta[c]chromen-9-yl]-C,C,C-trifluoro-methanesulfonamide

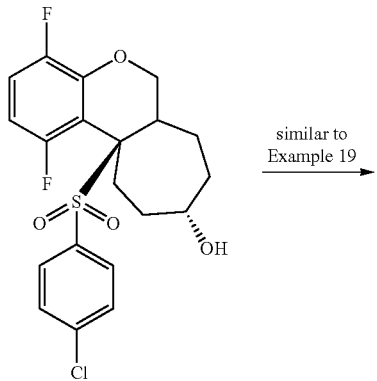

Example 344A

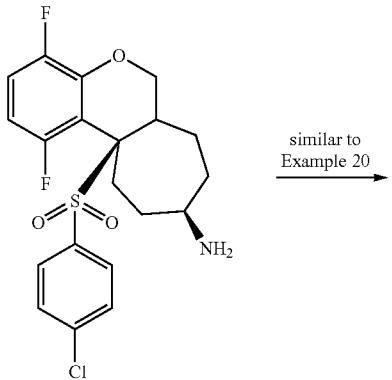

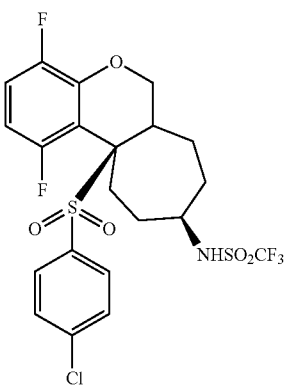

Example 345A

Step 1

A solution of Example 344A was subjected to conditions similar to the ones described in Example 20 to provide Example 345A: $^1$H NMR (CDCl$_3$, 400 MHz) δ 7.60 (d, J=8.8 Hz, 2H), 7.52 (d, J=8.8 Hz, 2H), 7.04 (m, 1H), 6.41 (m, 1H), 5.15 (dt, J=11.7, 9.5, 2.2 Hz, 1H), 4.28 (dd, J=11.7, 1.5 Hz, 1H), 3.46 (m, 1H), 2.97 (d, J=10.2 Hz, 1H), 2.34-2.28 (m, 2H), 2.09-1.91 (m, 2H), 1.81 (m, 1H), 1.66-1.52 (m, 2H).

Using methods similar to those in Example 345 and substituting an appropriate isocyanate, acyl or sulfonyl halide, the compounds in Table 75 were prepared.

TABLE 75

| Ex. No. | Structure | LCMS (M + 1, retention time) |
|---|---|---|
| 346 | ![structure with NH2] | 428.2, 2.99 min |
| 347 | ![structure with NHSO2Me] | 506.3, 4.42 min |
| 348 | ![structure with NHAc] | 470.3, 4.19 min |

TABLE 75-continued
| Ex. No. | Structure | LCMS (M + 1, retention time) |
|---|---|---|
| 349 | 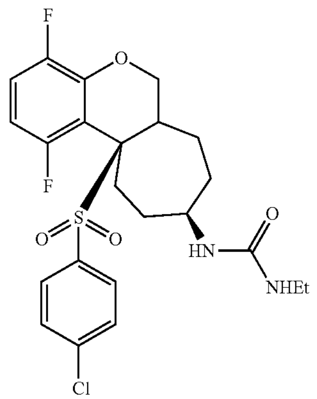 | 499.3, 4.35 min |
| 350 | 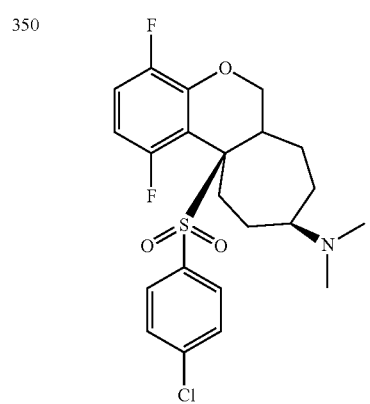 | 456.3, 3.05 min |
| 351 | 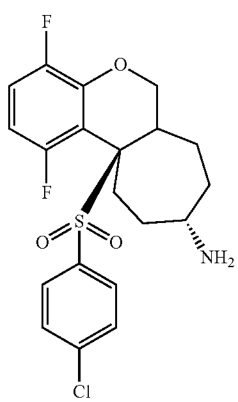 [SMILES: N[C@H]1CCC2COc3c(F)ccc(F)c3[C@@]2(S(=O)(=O)c2ccc(Cl)cc2)CC1] | 428.2, 2.95 min |
| 352 | 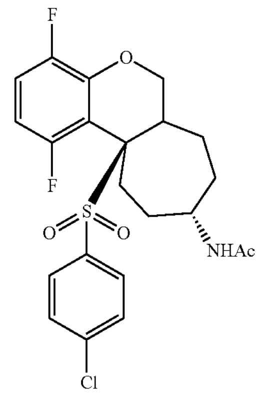 [SMILES: CC(=O)N[C@H]1CCC2COc3c(F)ccc(F)c3[C@@]2(S(=O)(=O)c2ccc(Cl)cc2)CC1] | 470.3, 4.15 min |
| 353 | 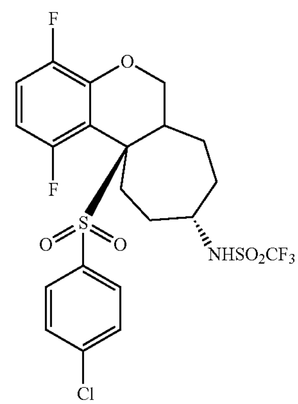 | 560.3, 5.07 min |
Example 354
11a-(4-Chloro-benzenesulfonyl-1,4-difluoro-6a,7,8,10,11,11a-hexahydro-6H-5,9-dioxa-cyclohepta[a]naphthalene
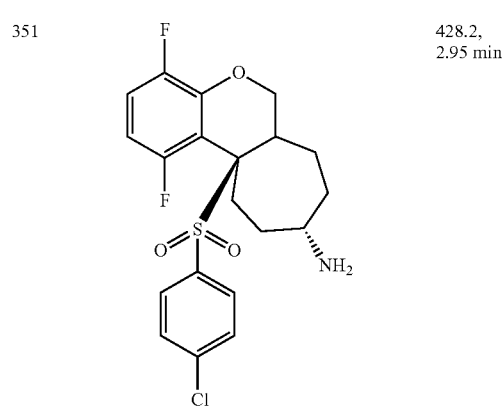

Step 1

3-(2-Allyloxy-ethyl)-4-(4-chloro-benzenesulfonyl)-5,8-difluoro-chroman

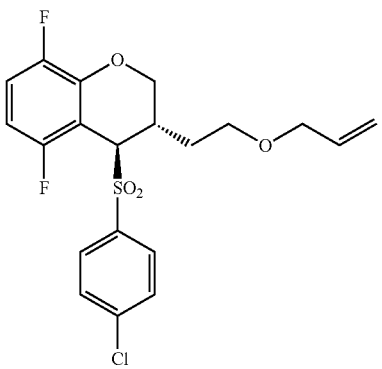 [SMILES: C=CCOCC[C@H]1COc2c(F)ccc(F)c2[C@@H]1S(=O)(=O)c1ccc(Cl)cc1]

A solution of the product from Example 27 Step 5 (268 mg, 0.692 mmol) in THF (7 mL) at 0° C. was treated with 60% NaH (30 mg, 0.76 mmol) and allyl iodide (76 μL, 0.83 mmol) and warmed to ambient temperature. After 12 h, the reaction mixture was heated to 60° C. After an additional 6 h, the reaction mixture was cooled to ambient temperature, quenched with saturated aqueous NH$_4$Cl and extracted with EtOAc (2×). The combined organic extracts were washed with saturated aqueous NaHCO$_3$, brine, dried over MgSO$_4$ and concentrated in vacuo. Flash chromatography (5→30% EtOAc/Hex) provided the title compound (200 mg, 67%): $^1$H NMR (CDCl$_3$ 400 MHz) δ 7.74 (d, J=8.8 Hz, 2H), 7.50 (d, J=8.8 Hz, 2H), 7.02 (m, 1H), 6.44 (m, 1H), 5.80 (m, 1H), 5.23-5.18 (m, 2H), 4.94 (dd, J=11.7, 2.9 Hz, 1H), 4.57 (s, 1H), 4.33 (d, J=11.7 Hz, 1H), 4.88-4.83 (m, 2H), 3.50-3.35 (m, 2H), 2.96 (t, J=6.6 Hz, 1H), 1.68 (m, 1H), 1.50 (m, 1H).

Step 2

A solution of 3-(2-allyloxy-ethyl)-4-(4-chloro-benzenesulfonyl)-5,8-difluoro-chroman was subjected to conditions similar to the ones described in Example 345 steps 6 and 7 to provide Example 354: $^1$H NMR (CDCl$_3$ 400 MHz) 7.57 (d, J=8.8 Hz, 2H), 7.49 (d, J=8.8 Hz, 2H), 7.06 (m, 1H), 6.44 (m, 1H), 5.15 (dd, J=11.7, 2.9 Hz, 1H), 4.25 (dd, J=11.7, 2.2 Hz, 1H), 3.99-3.90 (m, 2H), 3.82 (dd, J=13.1, 8.1 Hz, 1H), 3.66 (m, 1H), 3.21 (m, 1H), 2.96 (m, 1H), 2.40 (m, 1H), 1.95-1.85 (m, 2H).

Example 355

(+)-Isomer

Acetic acid 10a-(4-chloro-benzenesulfonyl)-1,4-difluoro-6a,7,8,9,10,10a-hexahydro-6H-benzo[c]chromen-8-yl ester

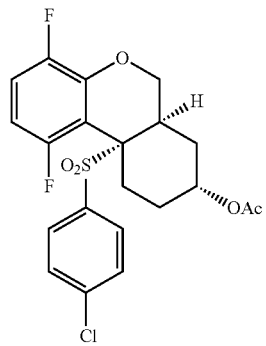 [SMILES: CC(=O)O[C@@H]1CC[C@@]2(S(=O)(=O)c3ccc(Cl)cc3)c3c(F)ccc(F)c3OC[C@H]2C1]

A solution of cis-10a-(4-chloro-benzenesulfonyl)-1,4-difluoro-6a,7,8,9,10,10a-hexahydro-6H-benzo[c]chromen-8-ol (Example 18B) (50 mg, 0.121 mmol) in pyridine (1 mL) was treated with acetyl chloride (40 μL, 0.54 mmol), DMAP (10 mg) and heated to 80° C. After 12 h, the reaction mixture was cooled to ambient temperature and diluted with EtOAc. The organic layer was washed with 1N HCl, saturated aqueous NaHSO$_3$, brine, dried over MgSO$_4$ and concentrated in vacuo. Preparative thin layer chromatography (25% EtOAc/Hex) afforded the title compound (Example 355) (24.9 mg, 45%): $^1$H NMR (CDCl$_3$ 400 MHz) δ 7.61 (d, J=8.1 Hz, 2H), 7.50 (d, J=8.1 Hz, 2H), 7.05 (m, 1H), 6.41 (m, 1H), 5.28 (dd, J=11.7, 2.9 Hz, 1H), 4.96 (m, 1H), 4.12 (m, 1H), 3.02 (m, 1H), 2.41-2.37 (m, 2H), 2.11 (s, 3H), 1.97-1.85 (m, 2H), 1.67 (m, 1H), 1.31 (m, 1H).

Using methods similar to those in Example 355 and substituting an appropriate acyl halide, the compounds in Table 76 were prepared.

TABLE 76

| Ex. No. | Structure | LCMS (M + 1, retention time) |
|---|---|---|
| (+)-isomer 356 | 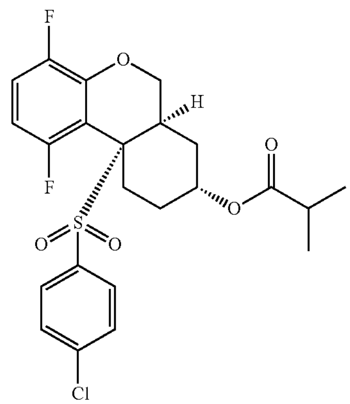 [SMILES: CC(C)C(=O)O[C@@H]1CC[C@@]2(S(=O)(=O)c3ccc(Cl)cc3)c3c(F)ccc(F)c3OC[C@H]2C1] | 485.3, 4.89 min |
| (−)-isomer 357 | 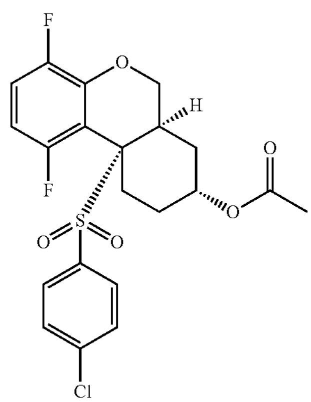 [SMILES: CC(=O)O[C@@H]1CC[C@@]2(S(=O)(=O)c3ccc(Cl)cc3)c3c(F)ccc(F)c3OC[C@H]2C1] | 457.3, 4.52 min |
| (−)-isomer 358 | 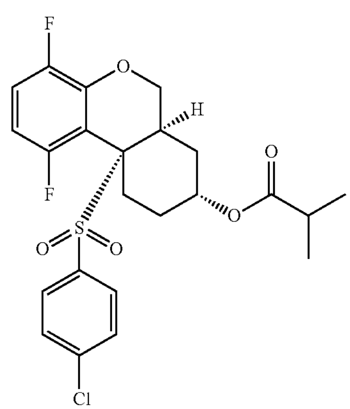 [SMILES: CC(C)C(=O)O[C@@H]1CC[C@@]2(S(=O)(=O)c3ccc(Cl)cc3)c3c(F)ccc(F)c3OC[C@H]2C1] | 485.3, 4.89 min |

Example 358A 10a-(4-Chloro-benzenesulfonyl)-1,4-difluoro-8-methoxy-6a,7,8,9,10,10a-hexahydro-6H-benzo[c]chromene

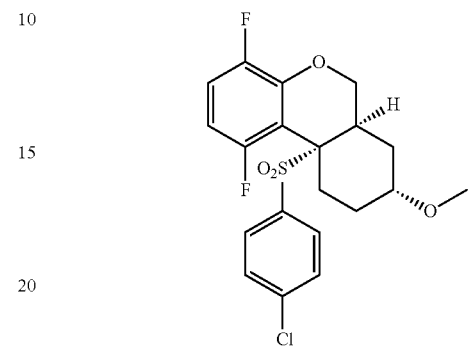

A solution of cis-10a-(4-chloro-benzenesulfonyl)-1,4-difluoro-6a,7,8,9,10,10a-hexahydro-6H-benzo[c]chromen-8-ol (Example 18B) (75 mg, 0.180 mmol) in THF (1 mL) at 0° C. was treated with 15-crown-5 (60 μL, 0.30 mmol) and NaH (60% in oil, 12 mg, 0.27 mmol). After 30 min, MeI (20 μL, 0.32 mmol) was added and the reaction mixture was warmed to ambient temperature. After 1.5 h, the reaction mixture was directly purified via preparative thin layer chromatography (25% EtOAc/Hex) to provide the title compound (Example (−)-358A) (56.5 mg, 73%): $^1$H NMR (CDCl$_3$ 400 MHz) δ δ7.60 (d, J=8.8 Hz, 2H), 7.49 (d, J=8.1 Hz, 2H), 7.05 (m, 1H), 6.41 (m, 1H), 5.21 (dd, J=11.7, 2.9 Hz, 1H), 4.09 (d, J=11.7 Hz, 1H), 3.40 (m, 1H), 3.31 (s, 3H), 3.00 (d, J=13.2 Hz, 1H), 2.41-2.26 (m, 2H), 1.99-1.87 (m, 2H), 1.45 (m, 1H), 1.15 (m, 1H).

Using methods similar to those in Example (−)-358 and substituting an appropriate alkyl halide, the compounds in Table 77 were prepared.

TABLE 77

| Ex. No. | Structure | LCMS (M + 1, retention time) |
|---|---|---|
| (−)-isomer 359 | 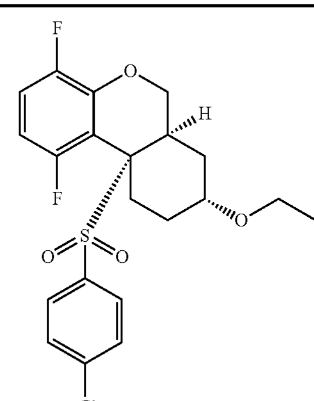 | 443.2, 5.13 min |

TABLE 77-continued

| Ex. No. | Structure | LCMS (M + 1, retention time) |
|---|---|---|
| (−)-isomer 360 | 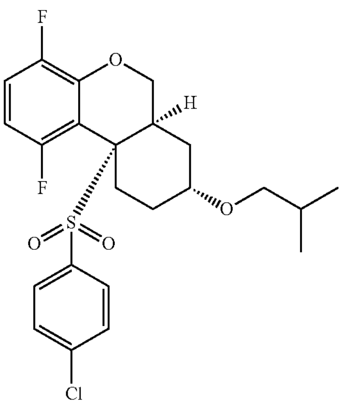 [SMILES: CC(C)CO[C@@H]1CC[C@@]2(S(=O)(=O)c3ccc(Cl)cc3)c3c(F)ccc(F)c3OC[C@H]2C1] | 471.3, 5.65 min |
| (−)-isomer 361 | 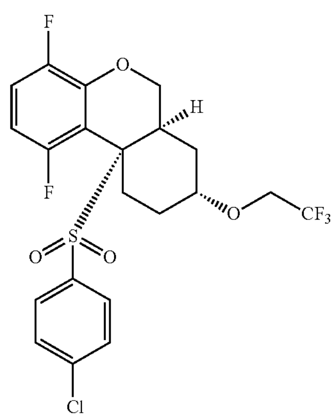 [SMILES: O=S(=O)(c1ccc(Cl)cc1)[C@@]12CC[C@@H](OCC(F)(F)F)C[C@@H]1COc1c(F)ccc(F)c12] | No M + 1, 4.97 min |

Example 362

N-{2-[10a-(4-Chloro-benzenesulfonyl)-1,4-difluoro-6a,7,8,9,10,10a-hexahydro-6H-benzo[c]chromen-8-yloxy]-ethyl}-C,C,C-trifluoro-methanesulfonamide

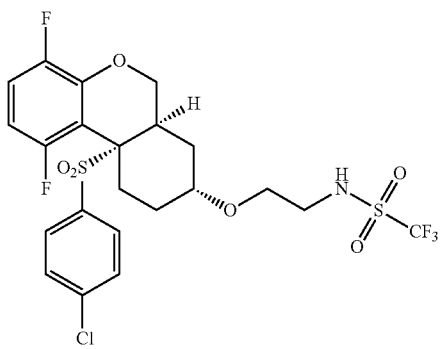 [SMILES: O=S(=O)(NCCO[C@@H]1CC[C@@]2(S(=O)(=O)c3ccc(Cl)cc3)c3c(F)ccc(F)c3OC[C@H]2C1)C(F)(F)F]

Step 1

8-Allyloxy-10a-(4-chloro-benzenesulfonyl)-1,4-difluoro-6a,7,8,9,10,10a-hexahydro-6H-benzo[c]chromene

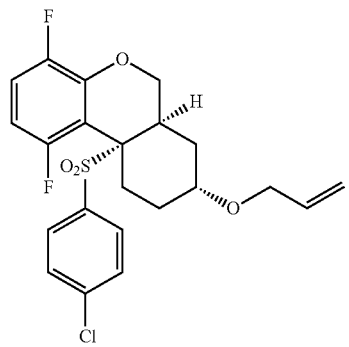 [SMILES: C=CCO[C@@H]1CC[C@@]2(S(=O)(=O)c3ccc(Cl)cc3)c3c(F)ccc(F)c3OC[C@H]2C1]

A solution of cis-10a-(4-chloro-benzenesulfonyl)-1,4-difluoro-6a,7,8,9,10,10a-hexahydro-6H-benzo[c]chromen-8-ol (Example 18B) (1.00 g, 2.41 mmol) in THF (20 mL) was treated with 15-crown-5 (0.80 mL, 4.00 mmol) and 60% NaH (150 mg, 3.80 mmol). After 20 min, allyl iodide (460 μL, 5.00 mmol) was added and the reaction mixture was heated to reflux. After 18 h, the reaction mixture was cooled to ambient temperature, quenched with 1N HCl and extracted with EtOAc (2×). The combined organic extracts were washed with saturated aqueous $NaHCO_3$, brine, dried over $MgSO_4$ and concentrated in vacuo. Flash chromatography (2→20% EtOAc/Hex) provided the title compound (990 mg, 90%): $^1$H NMR ($CDCl_3$ 400 MHz) δ 7.61 (d, J=8.8 Hz, 2H), 7.49 (d, J=8.8 Hz, 2H), 7.06 (m, 1H), 6.40 (m, 1H), 5.90 (m, 1H), 5.27-5.22 (m, 2H), 5.15 (d, J=10.2 Hz, 1H), 4.12 (d, J=11.0 Hz, 1H), 3.99-3.92 (m, 2H), 3.55 (m, 1H), 3.01 (m, 1H), 2.41-2.34 (m, 2H), 1.96-1.86 (m, 2H), 1.50 (m, 1H), 1.13 (m, 1H).

Step 2

2-[10a-(4-Chloro-benzenesulfonyl)-1,4-difluoro-6a,7,8,9,10,10a-hexahydro-6H-benzo[c]chromen-8-yloxy]-ethanol

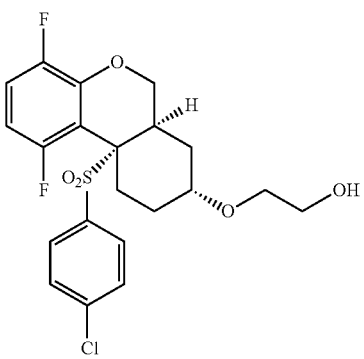 [SMILES: O=S(=O)(c1ccc(Cl)cc1)[C@@]12CC[C@@H](OCCO)C[C@@H]1COc1c(F)ccc(F)c12]

A solution of 8-allyloxy-10a-(4-chloro-benzenesulfonyl)-1,4-difluoro-6a,7,8,9,10,10a-hexahydro-6H-benzo[c]chromene (1.55 g, 3.41 mmol) in 1:1 MeOH/$CH_2Cl_2$ (30 mL)

at −78° C. was purged with O₃ until a blue color persisted. The reaction mixture was then purged with nitrogen until the blue color dissipated, NaBH₄ (0.39 g, 10.2 mmol) was added and the reaction mixture was warmed slowly to ambient temperature, After 18 h, the reaction mixture was quenched with saturated aqueous NH₄Cl and concentrated in vacuo. The residue was diluted with water and extracted with CH₂Cl₂ (3×). The combined organic extracts were washed with saturated aqueous NaHCO₃, dried over MgSO₄ and concentrated in vacuo to afford the title compound (1.46 g, 93%): ¹H NMR (CDCl₃ 400 MHz) δ 7.60 (d, J=8.8 Hz, 2H), 7.50 (d, J=8.8 Hz, 2H), 7.06 (m, 1H), 6.41 (m, 1H), 5.23 (dd, J=11.7, 3.7 Hz, 1H), 4.13 (d, J=11.7 Hz, 1H), 3.76 (t, J=5.1 Hz, 2H), 3.56-3.50 (m, 3H), 2.99 (m, 1H), 2.40-2.30 (m, 2H), 1.96-1.84 (m, 2H), 1.60 (br s, 1H), 1.54 (m, 1H), 1.16 (m, 1H).

Step 3

Methanesulfonic acid 2-[10a-(4-Chloro-benzene sulfonyl)-1,4-difluoro-6a,7,8,9,10,10a-hexahydro-6H-benzo[c]chromen-8-yloxy]-ethyl ester

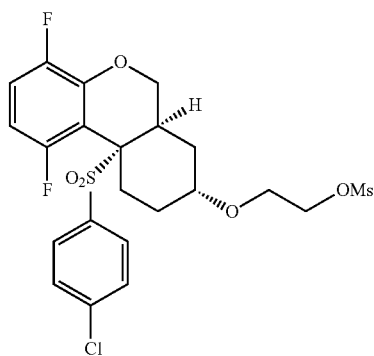 [SMILES: CS(=O)(=O)OCCO[C@@H]1CC[C@@]2(S(=O)(=O)c3ccc(Cl)cc3)c3c(F)ccc(F)c3OC[C@H]2C1]

A solution of 2-[10a-(4-chloro-benzenesulfonyl)-1,4-difluoro-6a,7,8,9,10,10a-hexahydro-6H-benzo[c]chromen-8-yloxy]-ethanol (1.09 g, 2.54 mmol) in CH₂Cl₂ (25 mL) at 0° C. was treated with Et₃N (0.37 mL) and MsCl (0.65 mL), the reaction mixture was slowly warmed to room temperature. After 14 h, the reaction mixture was quenched with saturated aqueous NH₄Cl and extracted with EtOAc (2×). The combined organic extracts were washed with saturated aqueous NaHCO₃, dried over MgSO₄ and concentrated in vacuo to afford the title compound (1.24 g, 97%): ¹H NMR (CDCl₃ 400 MHz) δ 7.58 (d, J=8.1 Hz, 2H), 7.47 (d, J=8.1 Hz, 2H), 7.07 (m, 1H), 6.40 (m, 1H), 5.23 (dd, J=2.9, 11.7 Hz, 1H), 4.37 (dd, J=3.7, 4.4 Hz, 2H), 4.11 (d, J=11.7 Hz, 1H), 3.72 (m, 2H), 3.58 (m, 1H), 3.13 (s, 1H), 3.01 (m, 1H), 2.40 (m, 2H), 1.87 (m, 2H), 1.56 (ddd, J=1.6, 14.7, 14.7 Hz, 1H), 1.14 (m, 1H).

Step 4

8-(2-Azido-ethoxy)-10a-(4-Chloro-benzenesulfonyl)-1,4-difluoro-6a,7,8,9,10,10a-hexahydro-6H-benzo[c]chromene

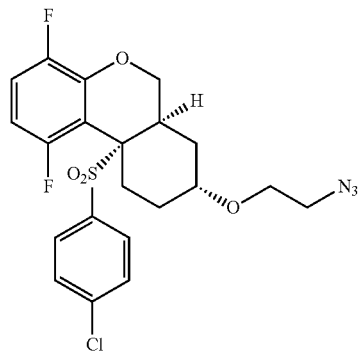 [SMILES: [N-]=[N+]=NCCO[C@@H]1CC[C@@]2(S(=O)(=O)c3ccc(Cl)cc3)c3c(F)ccc(F)c3OC[C@H]2C1]

A solution of methanesulfonic acid 2-[10a-(4-chloro-benzene sulfonyl)-1,4-difluoro-6a,7,8,9,10,10a-hexahydro-6H-benzo[c]chromen-8-yloxy]-ethyl ester (180 mg, 0.355 mmol) in DMF (5 mL) was treated with NaN₃ (46 mg, 0.707 mmol) and the reaction mixture was heated to 80° C. After 16 h, the reaction mixture was cooled to ambient temperature and diluted with saturated aqueous NH₄Cl and extracted with EtOAc (2×). The combined organic extracts were washed with H₂O, saturated aqueous NaHCO₃, brine, dried over MgSO₄, and concentrated in vacuo to afford the title compound (153 mg, 95%): ¹H NMR (CDCl₃ 400 MHz) δ 7.63 (d, J=8.1 Hz, 2H), 7.49 (d, J=7.3 Hz, 2H), 7.07 (m, 1H), 6.42 (m, 1H), 5.25 (dd, J=2.9, 11.7 Hz, 1H), 4.12 (d, J=11.7 Hz), 3.60 (m, 2H), 3.36 (m, 2H), 3.02 (m, 1H), 2.37 (m, 2H), 1.94 (m, 2H), 1.56 (m, 2H), 1.16 (m, 2H).

Step 5

2-[10a-(4-Chloro-benzene sulfonyl)-1,4-difluoro-6a,7,8,9,10,10a-hexahydro-6H-benzo[c]chromen-8-yloxy]-ethylamine

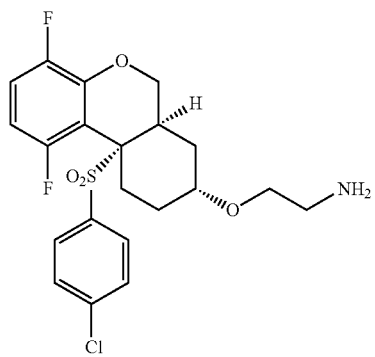

A solution of 8-(2-azido-ethoxy)-10a-(4-chloro-benzenesulfonyl)-1,4-difluoro-6a,7,8,9,10,10a-hexahydro-6H- benzo[c]chromene (110 mg, 0.242 mmol) in 4:1 THF/H₂O (5 mL) was treated with Ph₃P (127 mg, 0.484 mmol) and the reaction was heated to 60° C. After 16 h, the reaction mixture was cooled to ambient temperature and concentrated in vacuo to remove the THF. The reaction mixture was diluted with saturated aqueous NH₄Cl and extracted with CH₂Cl₂ (3×). The combined organic extracts were dried over MgSO₄ and concentrated in vacuo. Flash chromatography (10% MeOH/CH₂Cl₂) provided the title compound (52 mg, 52%): ¹H NMR (CDCl₃ 400 MHz) δ 7.62 (d, J=8.8 Hz, 2H), 7.49 (d, J=8.8 Hz, 2H), 7.06 (m, 1H), 6.43 (m, 1H), 5.22 (dd, J=10.9, 2.9 Hz, 1H), 4.11 (d, J=11.7 Hz, 1H), 3.51 (m, 1H), 3.41 (m, 2H), 2.98 (m, 1H), 2.88 (br s, 2H,), 2.39 (m, 2H), 1.94 (m, 2H), 1.49 (m, 3H), 1.13 (m, 1H).

Step 6

N-{2-[10a-(4-Chloro-benzenesulfonyl-1,4-difluoro-6a,7,8,9,10,10a-hexahydro-6H-benzo[c]chromen-8-yloxy]-ethyl}-C,C,C-trifluoro-methanesulfonamide

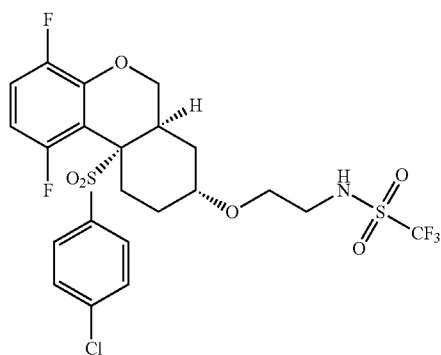 [SMILES: O=S(=O)(NCCO[C@@H]1CC[C@@]2(S(=O)(=O)c3ccc(Cl)cc3)c3c(F)ccc(F)c3OC[C@H]2C1)C(F)(F)F]

A solution of 2-[10a-(4-chloro-benzene sulfonyl)-1,4-difluoro-6a,7,8,9,10,10a-hexahydro-6H-benzo[c]chromen-8-yloxy]-ethylamine (71 mg, 0.168 mmol) in CH₂Cl₂ (5 mL) at −78° C. was treated with 2,6-lutidine (33 μL, 0.284 mmol), Tf₂O (45 μL, 0.948 mmol) and warmed slowly to ambient temperature. After 17 h, the reaction mixture was diluted with saturated aqueous NH₄Cl and extracted with CH₂Cl₂ (2×). The combined organic extracts were washed with saturated aqueous NaHCO₃, dried over MgSO₄, and concentrated in vacuo. The residue was purified by preparative-chromatography over silica gel (eluted in hexanes/EtOAc 1:1) to afford the title compound (29 mg, 30%): ¹H NMR (CDCl₃ 400 MHz) δ 7.61 (d, J=8.8 Hz, 2H), 7.48 (d, J=8.8 Hz, 2H), 7.08 (m, 1H), 6.44 (m, 1H), 5.22 (dd, J=11.7, 2.9 Hz, 1H), 4.12 (d, J=11.7 Hz, 1H), 3.57 (m, 3H), 3.01 (m, 1H), 2.56 (m, 1H), 2.33 (m, 1H), 1.91 (m, 2H), 1.56 (m, 1H), 1.15 (m, 2H).

Using methods similar to those in Example 362 and substituting an appropriate acyl halide, isocyanate or sulfonyl halide, the compounds in Table 78 were prepared.

TABLE 78

| Ex. No. | Structure | LCMS (M + 1, retention time) |
|---|---|---|
| 363 | 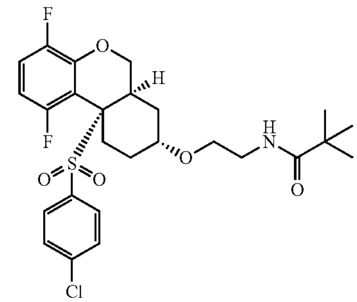 [SMILES: CC(C)(C)C(=O)NCCO[C@@H]1CC[C@@]2(S(=O)(=O)c3ccc(Cl)cc3)c3c(F)ccc(F)c3OC[C@H]2C1] | 542.3, 4.64 min |
| 364 | 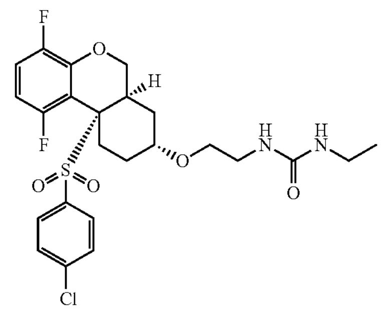 [SMILES: CCNC(=O)NCCO[C@@H]1CC[C@@]2(S(=O)(=O)c3ccc(Cl)cc3)c3c(F)ccc(F)c3OC[C@H]2C1] | 529.3, 4.10 min |
| 365 | 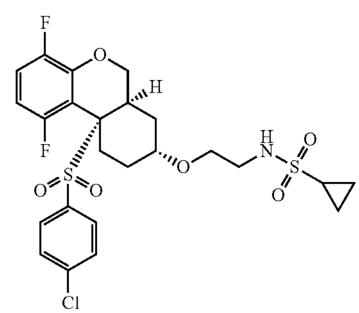 [SMILES: O=S(=O)(NCCO[C@@H]1CC[C@@]2(S(=O)(=O)c3ccc(Cl)cc3)c3c(F)ccc(F)c3OC[C@H]2C1)C1CC1] | 562.3, 4.51 min |
| 366 | 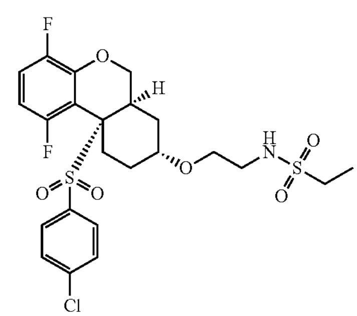 [SMILES: CCS(=O)(=O)NCCO[C@@H]1CC[C@@]2(S(=O)(=O)c3ccc(Cl)cc3)c3c(F)ccc(F)c3OC[C@H]2C1] | 550.3, 4.42 min |

TABLE 78-continued

| Ex. No. | Structure | LCMS (M + 1, retention time) |
|---|---|---|
| 367 | 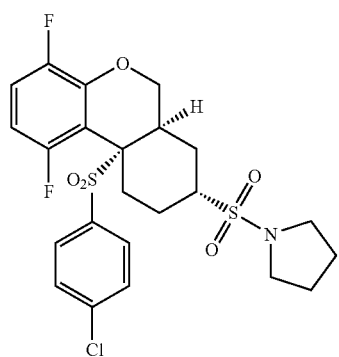 | 536.3, 4.29 min |

Example 368

A and B

Cis and trans-1-[10a-(4-Chloro-benzenesulfonyl)-1,4-difluoro-6a,7,8,9,10,10a-hexahydro-6H-benzo[c]chromene-8-sulfonyl]-pyrrolidine

A

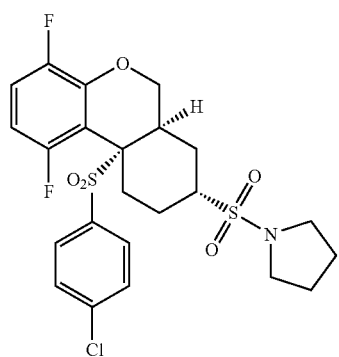

B

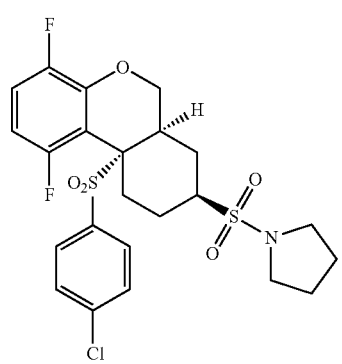

Step 1

Thioacetic acid S-[10a-(4-chloro-benzenesulfonyl)-1,4-difluoro-6a,7,8,9,10,10a-hexahydro-6H-benzo[c]chromen-8-yl]ester

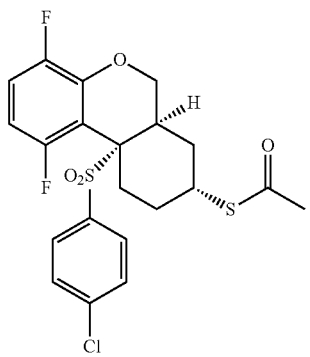 [SMILES: CC(=O)S[C@@H]1CC[C@@]2(S(=O)(=O)c3ccc(Cl)cc3)c3c(F)ccc(F)c3OC[C@H]2C1]

A solution of trans-10a-(4-chloro-benzenesulfonyl)-1,4-difluoro-6a,7,8,9,10,10a-hexahydro-6H-benzo[c]chromen-8-ol (Example 18A) (750 mg, 1.81 mmol) at 0° C. was treated with Et$_3$N (750 µL, 5.40 mmol), MsCl (560 µL, 7.20 mmol) and warmed to ambient temperature. After 1.5 h, the reaction mixture was quenched with saturated aqueous NH$_4$Cl and extracted with EtOAc (2×). The combined organic extracts were washed with saturated aqueous NaHCO$_3$, dried over MgSO$_4$ and concentrated in vacuo to provide the crude product. The residue was dissolved in DMF (15 mL), treated with KSAc (270 mg, 2.30 mmol) and heated to 120° C. After 3 h, the reaction mixture was cooled to ambient temperature, quenched with saturated aqueous NH$_4$Cl and extracted with EtOAc (2×). The combined organic extracts were washed with H$_2$O (3×), saturated aqueous NaHCO$_3$, brine, dried over MgSO$_4$ and concentrated in vacuo. Flash chromatography (2→20% EtOAc/Hex) gave the title compound (420 mg, 61% over 2 steps): $^1$H NMR (CDCl$_3$ 400 MHz) δ 7.58 (d, J=8.1 Hz, 2H), 7.49 (d, J=8.1 Hz, 2H), 7.07 (m, 1H), 6.41 (m, 1H), 5.21 (dd, J=11.7, 2.9 Hz, 1H), 4.10 (d, J=10.3 Hz, 1H), 3.88 (m, 1H), 2.83 (m, 1H), 2.50 (d, J=14.6 Hz, 1H), 2.35 (s, 3H), 2.18 (m, 1H), 1.92-1.77 (m, 3H), 1.53 (m, 1H).

Step 2

10a-(4-Chloro-benzenesulfonyl-1,4-difluoro-6a,7,8,9,10,10a-hexahydro-6H-benzo[c]chromene-8-thiol)

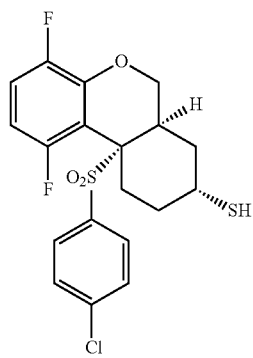 [SMILES: O=S(=O)(c1ccc(Cl)cc1)[C@@]12CC[C@@H](S)C[C@@H]1COc1c(F)ccc(F)c12]

A solution of thioacetic acid S-[10a-(4-chloro-benzenesulfonyl)-1,4-difluoro-6a,7,8,9,10,10a-hexahydro-6H-benzo[c]chromen-8-yl]ester (420 mg, 0.888 mmol) in MeOH (8 mL) was treated with 1N NaOH (2 mL) followed by THF (3 mL). After 4 h, the reaction mixture was concentrated in vacuo, diluted with 1N HCl and extracted with EtOAc (2×). The combined organic extracts were washed with saturated aqueous NaHCO$_3$, brine, dried over MgSO$_4$ and concentrated in vacuo. Flash chromatography (2→20% EtOAc/Hex) gave the disulfide of the title compound (133 mg, 17%): $^1$H NMR (CDCl$_3$ 400 MHz) δ 7.62 (d, J=8.8 Hz, 4H), 7.51 (d, J=8.8 Hz, 4H), 7.07 (m, 2H), 6.41 (m, 2H), 5.24 (dd, J=11.0, 2.9 Hz, 2H), 4.11 (d, J=11.0 Hz, 2H), 3.48 (m, 2H), 3.14 (d, J=13.2 Hz, 2H), 2.55 (m, 2H), 2.42 (m, 2H), 1.92-1.52 (m, 8H); followed by the title compound (169 mg, 44%): $^1$H NMR (CDCl$_3$ 400 MHz) δ 7.60 (dd, J=8.8, 1.5 Hz, 2H), 7.48 (dd, J=8.8, 1.5 Hz, 2H), 7.08 (m, 1H), 6.42 (m, 1H), 5.25 (dd, J=11.7, 2.2 Hz, 1H), 4.11 (d, J=11.0 Hz, 1H), 3.11 (m, 1H), 2.95 (d, J=12.5 Hz, 1H), 2.40-2.38 (m, 2H), 2.04-1.82 (m, 3H), 1.49 (m, 1H).

The disulfide of the title compound was converted to the title compound by the following method:

A solution of the disulfide of the title compound (380 mg, 0.44 mmol) in THF (3 mL) was treated with NaBH$_4$ (50 mg, 1.30 mmol) and heated to 60° C. After 4 h, the reaction mixture was cooled to ambient temperature, quenched with 1N HCl and extracted with Et$_2$O (2×). The combined organic extracts were dried over MgSO$_4$ and concentrated in vacuo. Flash chromatography (2→20% EtOAc/Hex) gave the title compound (370 mg, 98%).

Step 3

10a-(4-Chloro-benzenesulfonyl)-1,4-difluoro-6a,7,8,9,10,10a-hexahydro-6H-benzo[c]chromene-8-sulfonyl chloride

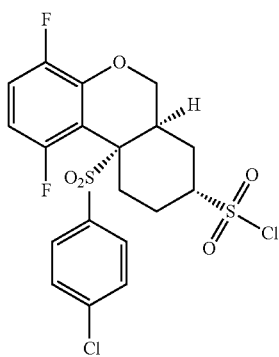 [SMILES: O=S(=O)(Cl)[C@@H]1CC[C@@]2(S(=O)(=O)c3ccc(Cl)cc3)c3c(F)ccc(F)c3OC[C@H]2C1]

A solution of 10a-(4-chloro-benzenesulfonyl)-1,4-difluoro-6a,7,8,9,10,10a-hexahydro-6H-benzo[c]chromene-8-thiol (370 mg, 0.860 mmol) in CH$_3$CN (30 mL) at −10° C. was treated with KNO$_3$ (191 mg, 1.89 mmol) followed by SO$_2$Cl$_2$ (152 μL, 1.89 mmol) dropwise. After 3 h, the reaction mixture was quenched with saturated aqueous NaHCO$_3$ and extracted with EtOAc (2×). The combined organic extracts were washed with saturated aqueous NaHCO$_3$, brine, dried over MgSO$_4$ and concentrated in vacuo to provide the title compound (380 mg, 89%): $^1$H NMR (CDCl$_3$ 400 MHz) δ 7.62 (d, J=8.8 Hz, 2H), 7.52 (d, J=8.8 Hz, 2H), 7.11 (m, 1H), 6.48 (m, 1H), 5.24 (dd, J=11.7, 2.9 Hz, 1H), 4.22 (d, J=11.7 Hz, 1H), 3.80 (m, 1H), 3.17 (d, J=12.4 Hz, 1H), 2.64-2.48 (m, 5H), 1.67 (m, 1H).

Step 4

Cis and trans-1-[10a-(4-Chloro-benzenesulfonyl)-1,4-difluoro-6a,7,8,9,10,10a-hexahydro-6H-benzo[c]chromene-8-sulfonyl]-pyrrolidine

A

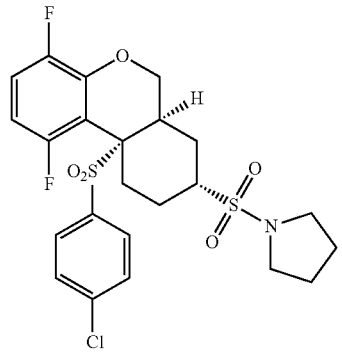

B

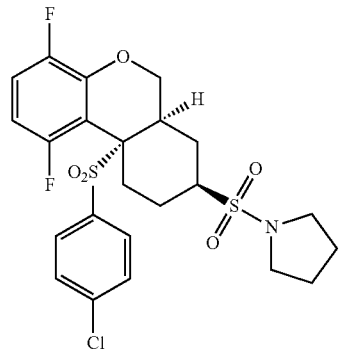

A solution of 10a-(4-chloro-benzenesulfonyl)-1,4-difluoro-6a,7,8,9,10,10a-hexahydro-6H-benzo[c]chromene-8-sulfonyl chloride (50 mg, 0.10 mmol) in CH$_2$Cl$_2$ (1.0 mL) was treated with Et$_3$N (30 μL, 0.20 mmol) followed by pyrrolidine (20 μL, 0.24 mmol). After 12 h, the reaction mixture was quenched with saturated aqueous NH$_4$Cl and extracted with CH$_2$Cl$_2$ (2×). The combined organic extracts were dried over MgSO$_4$ and concentrated in vacuo. Preparative thin layer chromatography (33% EtOAc/Hex) afforded Example 368A (7.1 mg, 13%): $^1$H NMR (CDCl$_3$ 400 MHz) δ 7.63 (dd, J=8.8, 2.2 Hz, 2H), 7.50 (dd, J=8.8, 2.2 Hz, 2H), 7.10 (m, 1H), 6.46 (m, 1H), 5.22 (dd, J=11.7, 2.9 Hz, 1H), 4.17 (d, J=11.7 Hz, 1H), 3.39-3.35 (m, 4H), 3.27 (d, J=12.4 Hz, 1H), 3.12 (m, 1H), 2.71 (m, 1H), 2.46 (m, 1H), 2.31-2.27 (m, 2H), 1.96-1.93 (m, 4H), 1.82 (m, 1H), 1.50 (m, 1H); followed by Example 368B (12.0 mg, 22%): $^1$H NMR (CDCl$_3$ 400 MHz) δ 7.56 (dd, J=8.8, 2.2 Hz, 2H), 7.50 (dd, J=8.8, 2.2 Hz, 2H), 7.10 (m, 1H), 6.42 (m, 1H), 5.24 (dd, J=11.7, 2.9 Hz, 1H), 4.20 (d, J=11.7 Hz, 1H), 3.34-3.30 (m, 4H), 3.13 (m, 1H), 2.78-2.74 (m, 2H), 2.13-2.02 (m, 3H), 1.90-1.87 (m, 4H), 1.78 (m, 1H), 1.38 (m, 1H).

Using methods similar to those in Example 368 and substituting an appropriate amine, the compounds in Table 79 were prepared.

TABLE 79

| Ex. No. | Structure | LCMS (M + 1, retention time) |
|---|---|---|
| 369 | 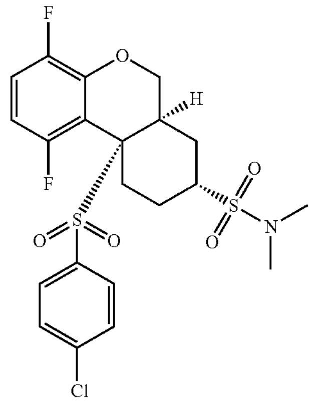 [SMILES: CN(C)S(=O)(=O)[C@@H]1CC[C@@]2(S(=O)(=O)c3ccc(Cl)cc3)c3c(F)ccc(F)c3OC[C@H]2C1] | 508.3, 4.45 min |
| 370 | 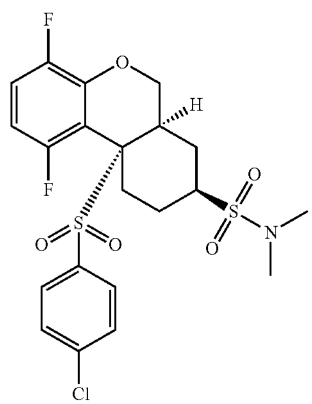 [SMILES: CN(C)S(=O)(=O)[C@H]1CC[C@@]2(S(=O)(=O)c3ccc(Cl)cc3)c3c(F)ccc(F)c3OC[C@H]2C1] | 506.3, 4.39 min |
| 371 | 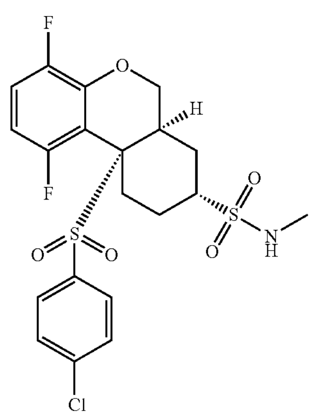 [SMILES: CNS(=O)(=O)[C@@H]1CC[C@@]2(S(=O)(=O)c3ccc(Cl)cc3)c3c(F)ccc(F)c3OC[C@H]2C1] | 492.3, 4.17 min |
| 372 | | 492.3, 4.11 min |
| 373 | | — |

Example 374

8-Aminomethyl-10a-(4-chloro-benzenesulfonyl-1,4-difluoro-6a,7,8,9,10,10a-hexahydro-6H-benzo[c]chromen-8-ylamine A solution of trans-10a-(4-chloro-benzenesulfonyl)-1,4-difluoro-6a,7,8,9,10,10a-tetrahydro-6H,7H-benzo[c] chromen-8-one (as described in Example 17, step 7)(2.50 g, 6.06 mmol) in conc NH$_4$OH/MeOH (1:1, 40 mL) was treated with KCN (0.51 g, 7.9 mmol) and NH$_4$Cl (0.42 g, 7.9 mmol).

After 12 h, the reaction mixture was concentrated in vacuo, diluted with H₂O and extracted with CH₂Cl₂ (4×). The combined organic extracts were dried over MgSO₄ and concentrated in vacuo. The crude reaction mixture was dissolved with THF (20 mL) and added dropwise to a suspension of LAH (0.41 g, 10.9 mmol) in THF (40 mL) at 0° C. After 1 h, the reaction mixture was quenched via sequential addition of H₂O (400 µL), 1N NaOH (800 µL), H₂O (800 µL), and stirred for 15 min. The suspension was filtered, rinsed with CH₂Cl₂, and the filtrate was concentrated in vacuo. Flash chromatography (1%→15% NH₄OH/MeOH (1:9), CH₂Cl₂) afforded Example 374 (950 mg, 35% over 2 steps): ¹H NMR (CDCl₃ 400 MHz) δ 7.54 (d, J=8.8 Hz, 2H), 7.44 (d, J=8.5 Hz, 2H), 7.05 (m, 1H), 6.38 (m, 1H), 5.17 (dd, J=11.7, 2.9 Hz, 1H), 4.10 (d, J=11.0 Hz, 1H), 2.80 (d, J=12.4 Hz, 1H), 2.70 (m, 1H), 2.69 (d, J=12.4 Hz, 1H), 2.40 (m, 1H), 2.04 (m, 1H), 1.77-1.68 (m, 2H), 1.34 (dd, J=13.9, 13.2 Hz, 1H), 1.13 (br s, 4H), 0.95 (ddd, J=13.9, 13.9, 2.9 Hz, 1H).

Example 375

A solution of 8-aminomethyl-10a-(4-chloro-benzenesulfonyl)-1,4-difluoro-6a,7,8,9,10,10a-hexahydro-6H-benzo[c]chromen-8-ylamine (Example 374) (50 mg, 0.113 mmol) in CH₂Cl₂ (1 mL) at 0° C. was treated with Et₃N (31 µL, 0.22 mmol), cyclopropyl sulfonyl chloride (20 µL, 0.14 mmol), and warmed to ambient temperature. After 12 h, the reaction mixture was diluted with saturated aqueous NaHCO₃, and extracted with CH₂Cl₂ (2×). The combined organic extracts were dried over MgSO₄ and concentrated in vacuo. Preparative thin layer chromatography (5% NH₄OH/MeOH (1:9), 95% CH₂Cl₂) afforded Example 375 (8.4 mg, 14%): ¹H NMR (CDCl₃ 400 MHz) δ 7.59 (d, J=8.1 Hz, 2H), 7.48 (d, J=8.1 Hz, 2H), 7.09 (m, 1H), 6.43 (m, 1H), 5.21 (dd, J=11.7, 2.2 Hz, 1H), 5.01 (br s, 1H), 4.12 (d, J=11.7 Hz, 1H), 3.19 (d, J=13.2 Hz, 1H), 3.15 (d, J=12.4 Hz, 1H), 2.78 (d, J=12.4 Hz, 1H), 2.55 (m, 1H), 2.42 (m, 1H), 2.10 (m, 1H), 1.86-1.79 (m, 2H), 1.45-1.18 (m, 6H), 1.04-1.00 (m, 2H).

Example 376 (−)-376 and (+)-376

10a-(4-chloro-benzenesulfonyl-1,4-difluoro-6a,7,8,9,10,10a-hexahydro-6H-benzo[c]chromen-8-ol

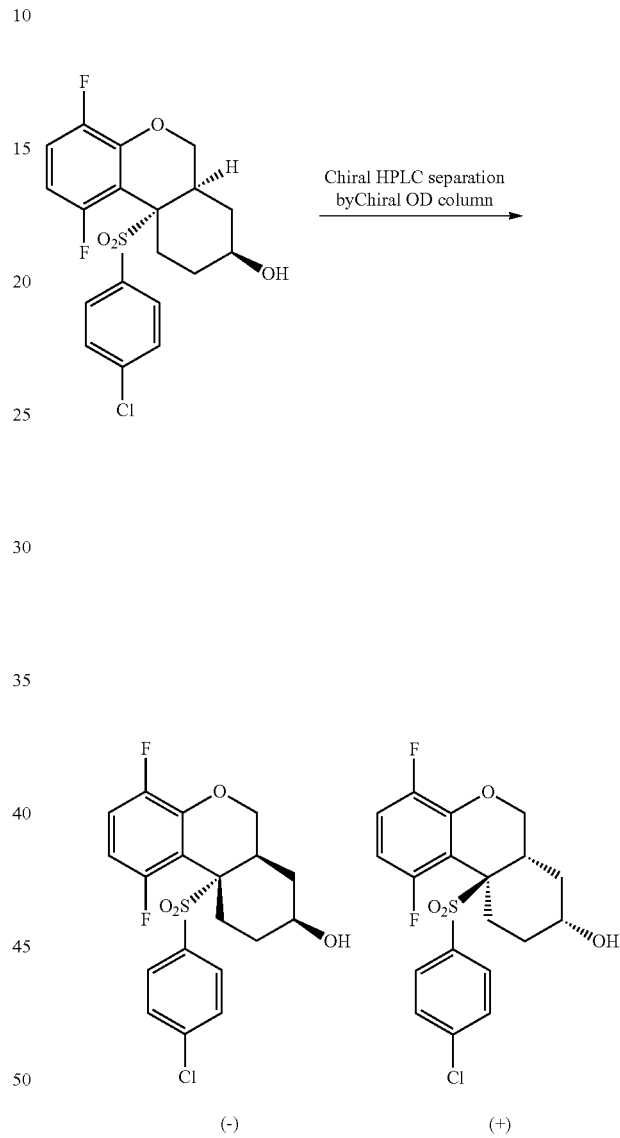

The racemic mixture, prepared according to the procedure in Example 20 can be separated into two pure enantiomers using Chiral OD column with hexane/isopropanol (75/25) as solvent.

First fraction ((−)-isomer): [α]=−162.3 deg. (c=1.095 in DCM).

Second fraction ((+)-isomer): [α]=137. deg. (c=0.95 in DCM).

Starting with the (−)-isomer of Example 376, and using methods similar to those in Example 20 and substituting an appropriate acyl or sulfonyl halide, the compounds in Table 80 were prepared.

TABLE 80

| Ex. No. | Structure | LCMS (M + 1, retention time) |
|---|---|---|
| 377 | (-) structure with F, F, O, S(O)₂-C₆H₄-Cl, NHS(O)₂CF₃ | 546.3, 4.96 min. |
| 378 | (-) structure with F, F, O, S(O)₂-C₆H₄-Cl, NHS(O)₂-2-pyridyl | 555.3, 4.56 min. |
| 379 | (-) structure with F, F, O, S(O)₂-C₆H₄-Cl, NHS(O)₂-cyclopropyl | 340.2 (M-phenylsulfone), 4.24 min. |

Example 380

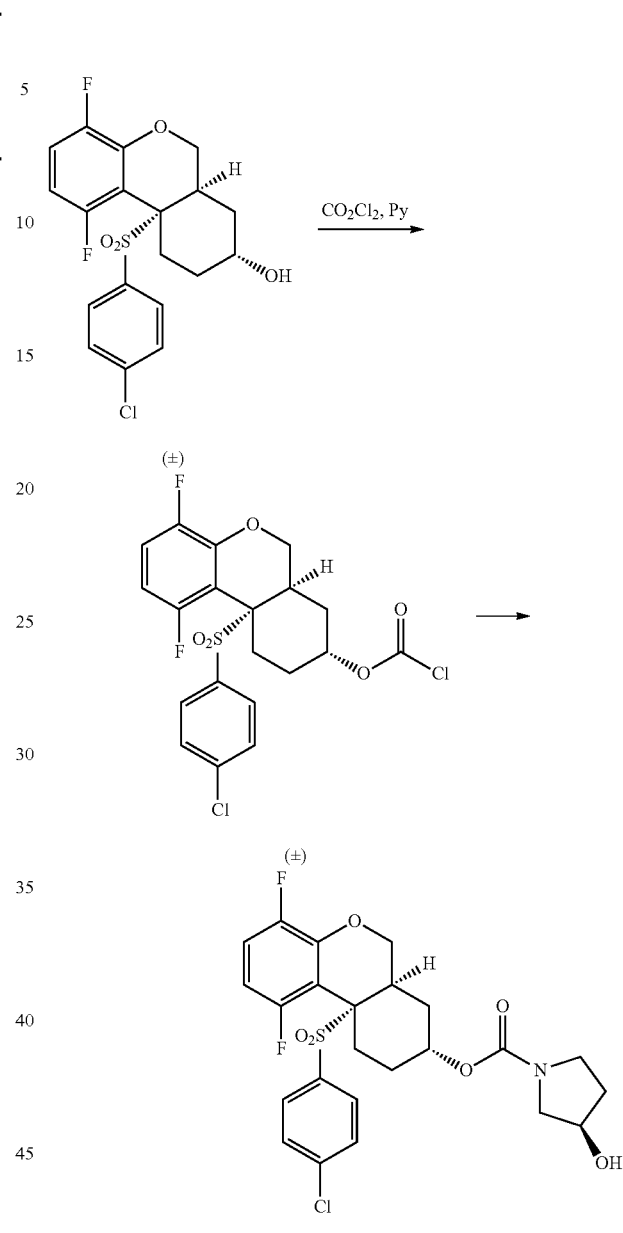

Step 1

10a-(4-chloro-benzenesulfonyl)-1,4-difluoro-6a,7,8,9,10,10a-hexahydro-6H-benzo[c]chromen-8-yl chloroformate 10a-(4-chloro-benzenesulfonyl)-1,4-difluoro-6a,7,8,9,10,10a-hexahydro-6H-benzo[c]chromen-8-ol (0.46 g, 1.11 mmole) was dissolved in 30 ml DCM. Phosgene (20% in toluene, 4 ml) and pyridine (1 ml) were added and the reaction was stirred at room temperature for 10 minutes. 20 ml DCM was added and the reaction was quenched by slowly adding 10 ml water. The organic layer was washed with 50 ml 1N HCl solution, dried over sodium sulfate. After the solvent was removed, the residue was purified by column using EtOAc/

Hex. as the solvent (gradient from 0/100 to 25/75 in 25 minutes). Yield: 0.37 g, 70%. $^1$H NMR (CDCl$_3$ 400 MHz) δ 7.62 (d, 2H, J=8.8 Hz), 7.50 (d, 2H, J=8.8 Hz), 7.06-7.13 (m, 1H), 6.40-6.47 (m, 1H), 5.28 (dd, 1H, J=11.7 and 2.9 Hz), 5.05 (s, 1H,), 4.14 (d, 1H, J=11.7 Hz), 3.02 (dt, J=13.2 and 2.9 Hz, 1H), 2.31-2.49 (m, 2H), 2.01-2.16 (m, 2H), 1.66-1.75 (m, 1H), 1.30-1.40 (m, 1H).

Step 2

(6aR)-10aS-[(4-chlorophenyl)sulfonyl]-1,4-difluoro-6a,7,8,9,10,10a-hexahydro-6h-dibenzo[b,d]pyran-8(R)-hydroxy-1-pyrrolinecarboxylate (racemic)

10a-(4-chloro-benzenesulfonyl)-1,4-difluoro-6a,7,8,9,10,10a-hexahydro-6H-benzo[c]chromen-8-yl chloroformate (40 mg) was dissolved in 5 ml DCM. 2(R)-hydroxypyrroline (40 ul) and diisopropylethylamine (50 ul) were added and the reaction was stirred at room temperature for 1 hour. 20 ml DCM was added and the reaction was washed with 50 ml saturated sodium carbonate solution, dried over sodium sulfate and concentrated. The residue was purified by column using EtOAc/Hex. as the solvent (gradient from 25/75 to 100/0 in 25 minutes). Yield: 42 mg, 95%. $^1$H NMR (CDCl$_3$ 400 MHz) δ 7.60 (m, 2H), 7.49 (m, 2H), 7.03-7.11 (m, 1H), 6.37-6.46 (m, 1H), 5.21-5-28 (m, 1H), 4.87 (s, 1H,), 4.49 (d, J=15.3 Hz, 1H), 4.10 (m, 1H), 3.33-3.55 (m, 4H), 2.89 (d J=12.4 Hz, 1H), 2.48 (m, 2H), 2.32 (m, 1H), 1.95 (m, 3H), 1.61 (m, 1H), 1.26 (m, 1H).

Using methods similar to those in Example 380 and substituting appropriate amines, the compounds in Table 81 were prepared.

TABLE 81

| Ex. No. | Structure | LCMS (M + 1, retention time) |
|---|---|---|
| 381 | 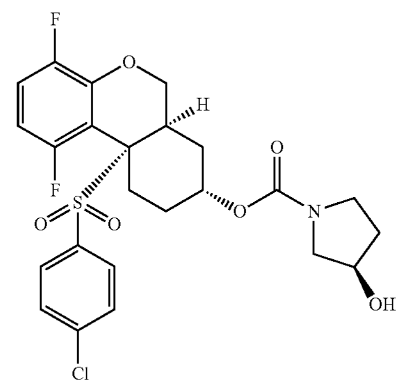 [SMILES: O=C(O[C@@H]1CC[C@@]2(S(=O)(=O)c3ccc(Cl)cc3)c3c(F)ccc(F)c3OC[C@H]2C1)N1CC[C@@H](O)C1] | 528.3, 3.78 min. |
| 382 | 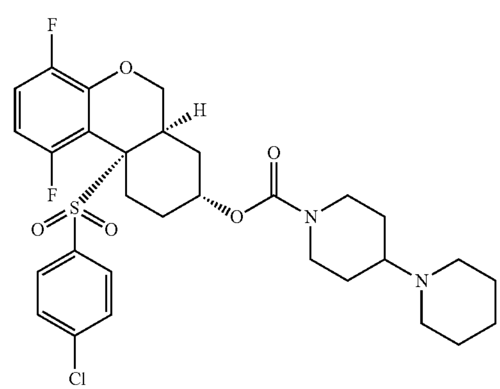 [SMILES: O=C(O[C@@H]1CC[C@@]2(S(=O)(=O)c3ccc(Cl)cc3)c3c(F)ccc(F)c3OC[C@H]2C1)N1CCC(N2CCCCC2)CC1] | 609.3, 3.51 min. |
| 383 | 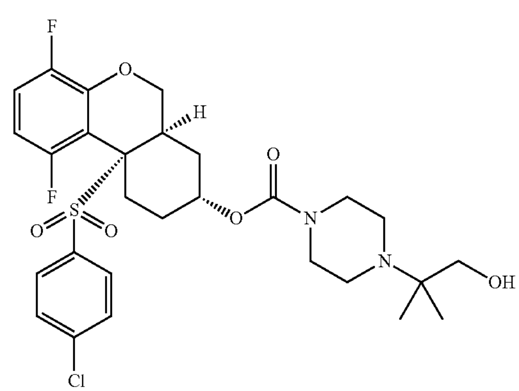 [SMILES: CC(C)(CO)N1CCN(C(=O)O[C@@H]2CC[C@@]3(S(=O)(=O)c4ccc(Cl)cc4)c4c(F)ccc(F)c4OC[C@H]3C2)CC1] | 599.3, 3.28 min. |

TABLE 81-continued

| Ex. No. | Structure | LCMS (M + 1, retention time) |
|---|---|---|
| 384 | 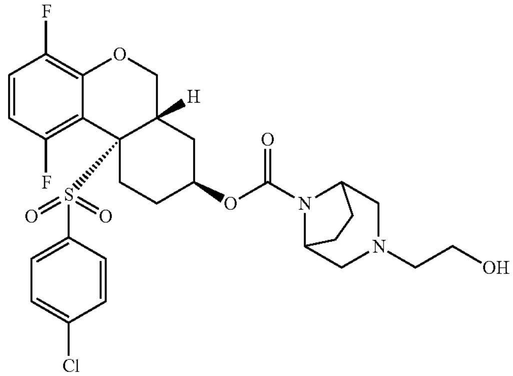 [SMILES: O=C(O[C@H]1CC[C@@]2(S(=O)(=O)c3ccc(Cl)cc3)c3c(F)ccc(F)c3OC[C@@H]2C1)N1C2CCC1CN(CCO)C2] | 597.3, 3.27 min. |
| 385 | 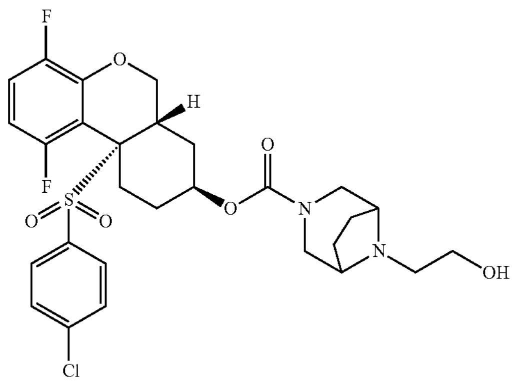 [SMILES: O=C(O[C@H]1CC[C@@]2(S(=O)(=O)c3ccc(Cl)cc3)c3c(F)ccc(F)c3OC[C@@H]2C1)N1CC2CCC(C1)N2CCO] | 597.3, 3.24 min. |
| 386 | 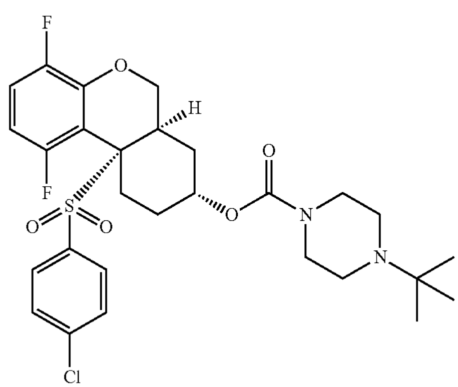 [SMILES: CC(C)(C)N1CCN(C(=O)O[C@@H]2CC[C@@]3(S(=O)(=O)c4ccc(Cl)cc4)c4c(F)ccc(F)c4OC[C@H]3C2)CC1] | 583.3, 3.48 min. |

Example 387

N-[[(6aR)-10aS-[(4-chlorophenyl)sulfonyl]-1,4-difluoro-6a,7,8,9,10,10a-hexahydro-6h-dibenzo[b,d]pyran-8(R)-yl]methanesulfonamide (racemic)

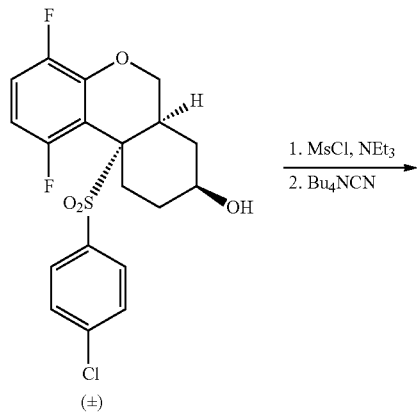
(±)

1. MsCl, NEt₃
2. Bu₄NCN

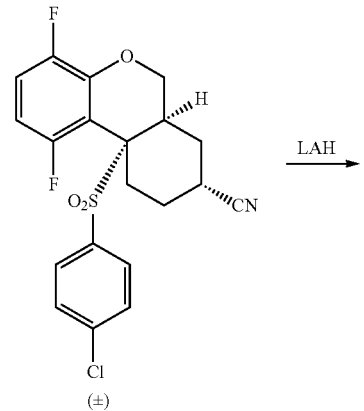
(±)

LAH

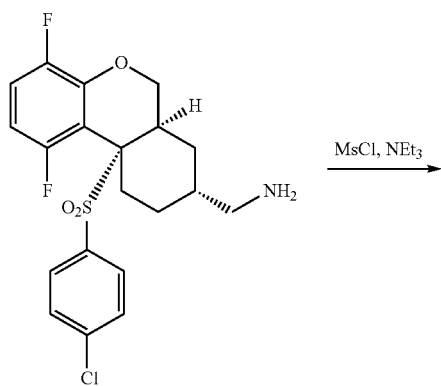

MsCl, NEt₃

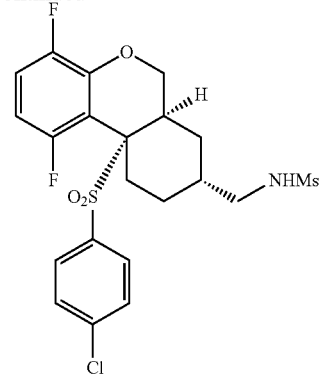

Step 1

(6aR)-10aS-[(4-chlorophenyl)sulfonyl]-1,4-difluoro-6a,7,8,9,10,10a-hexahydro-6h-dibenzo[b,d]pyran-8(R)-carbonitrile (racemic)

Trans-10a-(4-chloro-benzenesulfonyl)-1,4-difluoro-6a,7,8,9,10,10a-hexahydro-6H-benzo[c]chromen-8-ol (1.3 g, 3.1 mmole) was dissolved in 10 ml DCM. Mesyl chloride (0.53 g, 4.7 mmole) and triethylamine (1 ml) were added. The reaction was stirred at room temperature for 10 minutes. 100 ml brine and 50 ml DCM were added. The organic layer was washed with 1N HCl solution (50 ml), water (50 ml), brine (50 ml), dried over $Na_2SO_4$ and concentrated. The residue was dissolved in 50 ml toluene. Tetrabutylammonium cyanide (1.6 g, 6.1 mmole) was added. The reaction was heated to 80° C. overnight. The reaction was cooled to room temperature and 100 ml EtOAc was added. The organic layer was washed with brine (2×100 ml), dried over $Na_2SO_4$ and concentrated. The residue was purified by column (EtOAc/hexane from 0/100 to 50/50 in 35 minutes). Yield: 0.70 g, 53%. $^1$H NMR ($CDCl_3$ 400 MHz δ 7.64 (d, J=8.8 Hz, 2H), 7.52 (d, J=8.8 Hz, 2H), 7.06-7.13 (m, 1H), 6.42-6.49 (m, 1H), 5.29 (dd, J=11.7 and 2.9 Hz, 1H), 4.17 (d, J=11.7 Hz, 1H), 2.94-3.02 (m, 2H), 2.62 (d, J=13.9 Hz, 1H), 2.34 (tt, J=13.8 and 2.9 Hz, 1H), 1.94-2.09 (m, 2H), 1.66-1.75 (m, 1H), 1.30-1.40 (m, 1H).

Step 2

(6aR)-10aS-[(4-chlorophenyl)sulfonyl]-1,4-difluoro-6a,7,8,9,10,10a-hexahydro-6h-dibenzo[b,d]pyran-8(R)-yl-aminomethane (racemic)

(6aR)-10aS-[(4-chlorophenyl)sulfonyl]-1,4-difluoro-6a,7,8,9,10,10a-hexahydro-6h-dibenzo[b,d]pyran-8(R)-carbonitrile (0.34 g, 0.80 mmole) was dissolved in 50 ml THF and the reaction was cooled to 0° C. LAH (1M in ether, 1.6 ml) was added and the reaction was stirred at room temperature for 1 hour. 100 ml N NaOH solution and 100 ml EtOAc were added. The organic layer was washed with brine (2×100 ml), dried over sodium sulfate and concentrated. The residue was purified by column (EtOAc/2.5N NH3 in MeOH from 100/0 to 80/20 in 35 minutes). Yield: 0.24 g, 70%. $^1$H NMR ($CDCl_3$ 400 MHz δ 7.57 (d, J=8.8 Hz, 2H), 7.47 (d, J=8.8 Hz, 2H), 7.02-7.09 (m, 1H), 6.35-6.43 (m, 1H), 5.19 (dd, J=11.7 and 2.9 Hz, 1H), 4.10 (d, J=11.7 Hz, 1H), 2.70-2.85 (m, 3H), 2.33 (tt, J=13.2 and 2.9 Hz, 1H), 2.08 (m, 1H), 1.58-1.80 (m, 4H), 1.20-1.30 (m, 1H).

Step 3

N-[[(6aR)-10aS-[4(4-chlorophenyl)sulfonyl]-1,4-difluoro-6a,7,8,9,10,10a-hexahydro-6h-dibenzo[b,d]pyran-8(R)-yl]methanesulfonamide (racemic)

(6aR)-10aS-[(4-chlorophenyl)sulfonyl]-1,4-difluoro-6a,7,8,9,10,10a-hexahydro-6h-dibenzo[b,d]pyran-8(R)-yl-aminomethane (50 mg, 0.12 mmole) was dissolved in 5 ml DCM, Mesyl chloride (50 ul) and triethylamine (30 ul) were added. The reaction was stirred at room temperature for two hours. 50 ml saturated sodium carbonate solution and 50 ml EtOAc were added. The organic layer was washed with water (50 ml), brine (50 ml), dried over Na2SO4 and concentrated. The residue was purified by column (EtOAc/hexane from 0/100 to 100/0 in 35 minutes). Yield: 38 mg, 64%. $^1$H NMR (CDCl$_3$ 400 MHz δ 7.57 (d, J=8.8 Hz, 2H), 7.47 (d, J=8.8 Hz, 2H), 7.03-7.09 (m, 1H), 6.36-6.43 (m, 1H), 5.17 (dd, J=11.0 and 2.9 Hz, 1H), 4.81 (t, J=6.6 Hz, 1H) 4.09 (m, 1H), 3.22 (t, J=7.3, 2H), 2.98 (s, 3H), 2.75 (d, J=12.5 Hz, 1H), 2.36 (d, J=13.9 Hz, 1H), 2.08 (t, J=13.9 Hz, 1H), 1.59-1.90 (m, 4H), 1.20-1.30 (m, 1H).

Using methods similar to those in Example 387 and substituting an appropriate acyl or sulfonyl halide, the compounds in Table 82 were prepared.

TABLE 82

| Ex. No. | Structure | LCMS (M + 1, retention time) |
|---|---|---|
| 388 | | 470.3, 3.90 min. |
| 389 | | 356.2(M-phenyl-sulfone), 4.30 min. |
| 390 | 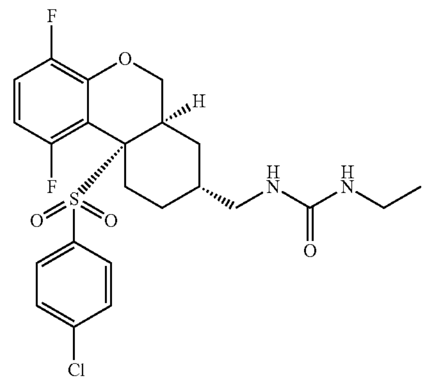 [SMILES: CCNC(=O)NC[C@@H]1CC[C@@]2(S(=O)(=O)c3ccc(Cl)cc3)c3c(F)ccc(F)c3OC[C@H]2C1] | 323.2(M-phenyl-sulfone), 4.02 min. |
| 391 | 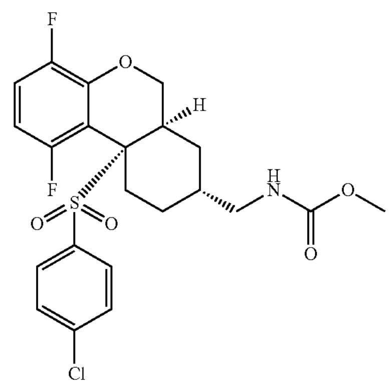 [SMILES: COC(=O)NC[C@@H]1CC[C@@]2(S(=O)(=O)c3ccc(Cl)cc3)c3c(F)ccc(F)c3OC[C@H]2C1] | 486.3, 4.31 min. |
| 387 | 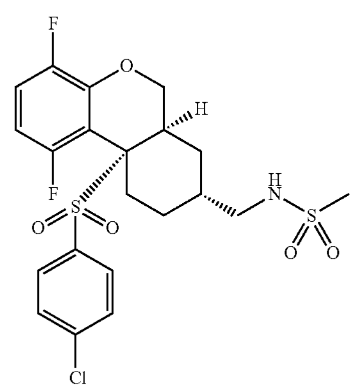 [SMILES: CS(=O)(=O)NC[C@@H]1CC[C@@]2(S(=O)(=O)c3ccc(Cl)cc3)c3c(F)ccc(F)c3OC[C@H]2C1] | 330.2(M-phenyl-sulfone), 4.12 min. |
| 392 | 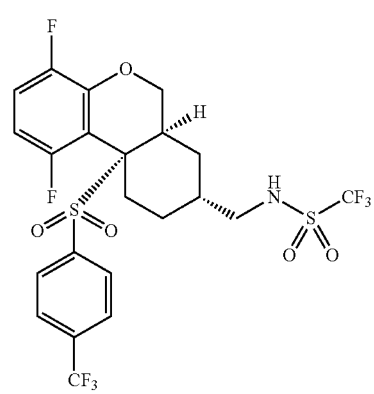 [SMILES: O=S(=O)(NC[C@@H]1CC[C@@]2(S(=O)(=O)c3ccc(C(F)(F)F)cc3)c3c(F)ccc(F)c3OC[C@H]2C1)C(F)(F)F] | 594.3, 4.99 min. |

TABLE 82-continued
| Ex. No. | Structure | LCMS (M + 1, retention time) |
|---|---|---|
| 393 | 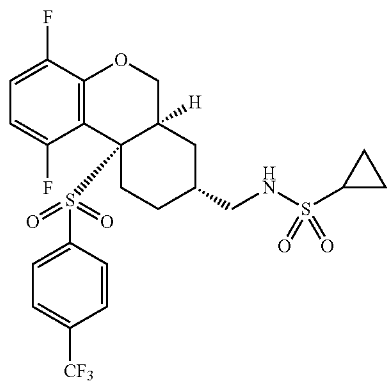 [SMILES: O=S(=O)(NC[C@@H]1CC[C@@]2(S(=O)(=O)c3ccc(C(F)(F)F)cc3)c3c(F)ccc(F)c3OC[C@H]2C1)C1CC1] | 566.3, 4.64 min. |
| 394 | 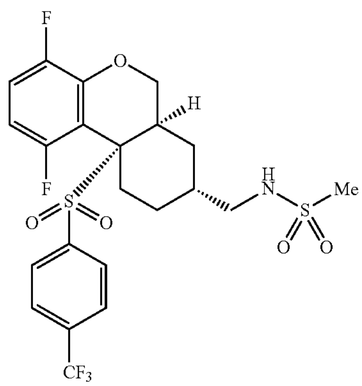 [SMILES: CS(=O)(=O)NC[C@@H]1CC[C@@]2(S(=O)(=O)c3ccc(C(F)(F)F)cc3)c3c(F)ccc(F)c3OC[C@H]2C1] | 540.3, 4.21 min. |
Example 395
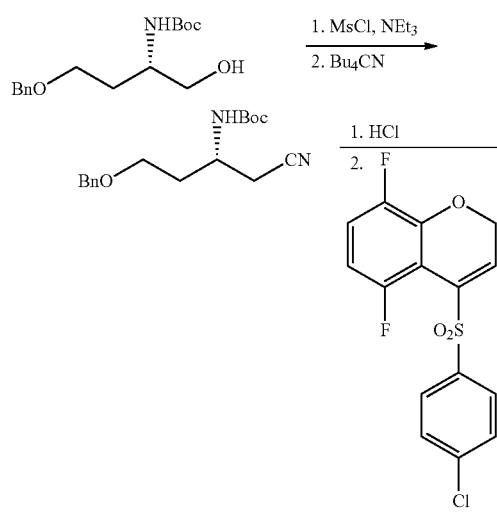
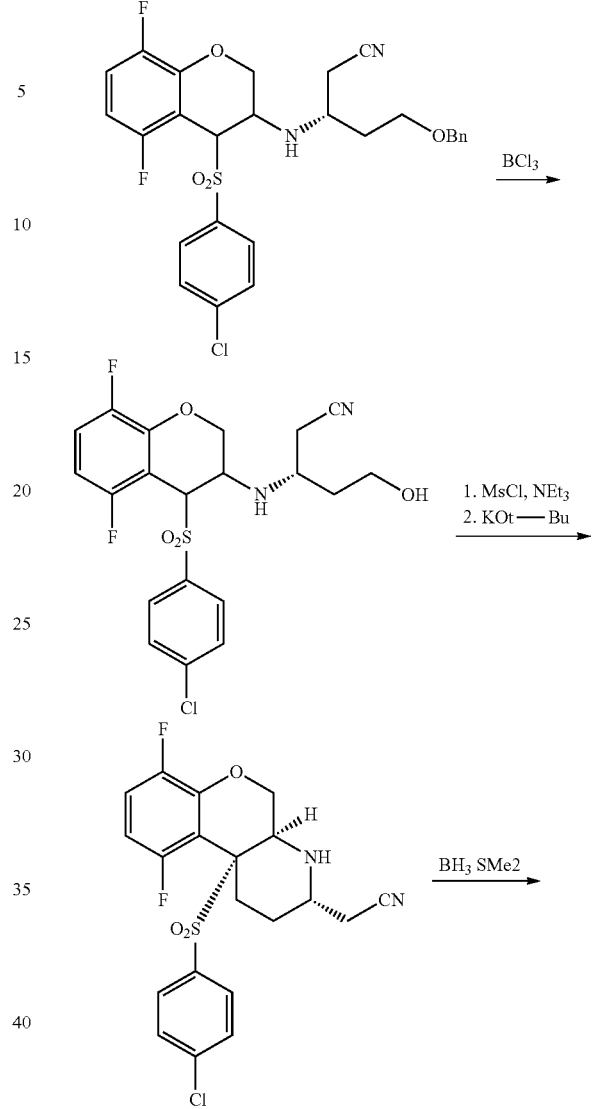
Step 1
[3-Benzyloxy-1(R)-cyanomethyl-propyl]-carbamic acid tert-butyl ester
(3-Benzyloxy-1-hydroxymethyl-propyl)-carbamic acid tert-butyl ester (7.4 g, 25 mmole) was dissolved in 100 ml DCM. Mesyl chloride (4.3 g, 37.5 mmole) and triethylamine (5.0 g, 50 mmole) were added. The reaction was stirred at room temperature for 20 minutes. 100 ml DCM and 100 ml water were added. The organic layer was washed with brine (100 ml), dried over sodium sulfate and concentrated. The residue was dissolved in 200 ml toluene. Tetraammonium cyanide (10 g, 37.5 mmole) was added and the reaction was stirred at room temperature overnight. The organic layer was washed with water (2×100 ml), brine (100 ml), dried over sodium sulfate and concentrated. The residue was purified by column (EtOAc/hexane from 100/0 to 30/70 in 45 minutes). Yield, 6.4 g, 84%. $^1$H NMR (CDCl$_3$ 400 MHz δ 7.29-7.38 (m, 5H), 5.20 (d, J=5.9 Hz, 1H), 4.50 (m, 2H), 3.91 (m, 1H), 3.54-3.66 (m, 2H), 2.60-2.77 (m, 2H), 1.89-1.99 (m, 2H), 1.44 (s, 9H).

Step 2

5-Benzyloxy-3(R)-[4-(4-chloro-benzenesulfonyl)-5,8-difluoro-chroman-3-ylamino]-pentanenitrile

[3-Benzyloxy-1(R)-cyanomethyl-propyl]-carbamic acid tert-butyl ester (6.4 g, 21 mmole) was dissolved in 20 ml DCM. 4N HCl in dioxane (20 ml) was added and the reaction was stirred at room temperature for 1 hour. The solvent was removed and the residue was dissolved in 200 ml THF and 4-(4-Chloro-benzenesulfonyl)-5,8-difluoro-2H-chromene was added. Diisopropylethylamine (10 ml) was added and the reaction was stirred at room temperature overnight then refluxed for 5 hours. The reaction was cooled to room temperature and 100 ml EtOAc was added. The organic layer was washed with brine (100 ml), dried over Na2SO4 and concentrated. The residue was purified by column (EtOAc/hexane from 100/0 to 30/70 in 45 minutes). 6.0 g, 58%, it is a mixture of two diastereomers.

Step 3

3-[4-(4-Chloro-benzenesulfonyl)-5,8-difluoro-chroman-3-yl-(R)-amino]-5-hydroxy-pentanenitrile 5-Benzyloxy-3(R)-[4-(4-chloro-benzenesulfonyl)-5,8-difluoro-chroman-3-ylamino]-pentanenitrile (0.9 g, 1.64 mmole) was dissolved in 20 ml DCM and the reaction was cooled to −78° C. Boron trichloride (1 M in Hexane, 8.2 ml) was then added and the reaction was stirred 30 minutes. The reaction was quenched by adding 50 ml Saturated NaHCO$_3$ solution and 100 ml DCM was added. The organic layer was washed with brine (100 ml), dried over sodium sulfate and concentrated. The residue was purified by column (EtOAc/hexane from 0/100 to 75/25 in 40 minutes). Yield: 0.64 g, 88%. It is a mixture of diastereomers.

Step 4

(4aR)-10bR-[(4-Chlorophenylsulfonyl)-7,10-difluoro-1,3,4,4a,5,10b-hexahydro-2H-[1]benzopyrano[3,4-b]pyridine-3(S)-acetonitrile 3-[4-(4-Chloro-benzenesulfonyl)-5,8-difluoro-chroman-3-yl-(R)-amino]-5-hydroxy-pentanenitrile (1.7 g, 3.7 mmole) was dissolved in 50 ml DCM. Mesyl chloride (1 ml) and triethylamine (2 ml) were added. The reaction was stirred at room temperature for 5 minutes. 500 ml DCM and 50 ml water were added. The organic layer was washed with 1N HCl solution (2×100 ml), brine (100 ml), dried over sodium sulfate and concentrated. The residue was dissolved in 100 ml dry THF and KOt-Bu (1M in t-BuOH, 4.5 ml) was added. The reaction was stirred at room temperature for 10 minutes. 100 ml EtOAc was added. The organic layer was washed with brine (2×100 ml), dried over Na2SO4 and concentrated. The residue was purified by column (EtOAc/hexane from 100/0 to 40/60 in 45 minutes). Yield: 0.72 g, 44% (0.51 g trans compound was also isolated from the reaction). $^1$H NMR (CDCl$_3$ 400 MHz δ 7.59 (d, J=8.8 Hz, 2H), 7.50 (d, J=8.8 Hz, 2H), 7.06-7.13 (m, 1H), 6.40-6.47 (m, 1H), 5.18 (dd, J=11.7 and 2.9 Hz, 1H), 4.29 (dd, J=11.7 and 1.5 Hz, 1H), 3.82 (d, J=7.3 Hz, 1H), 3.36 (bs, 1H), 2.62-2.82 (m, 2H), 2.32-2.52 (m, 2H), 2.70-2.86 (m, 2H), 1.52 (m, 1H).

Step 5

(4aR)-10bR-[(4-Chlorophenyl)sulfonyl]-7,10-difluoro-1,3,4,4a,5,10b-hexahydro-2H-[1]benzopyran[3,4-b]pyridine-3(S)-ethylamine (pure enantiomer) (4aR)-10bR-[(4-Chlorophenylsulfonyl)-7,10-difluoro-1,3,4,4a,5,10b-hexahydro-2H-[1]benzopyrano[3,4-b]pyridine-3(S)-acetonitrile (0.47 g, 1.1 mmole) was dissolved in 100 ml THF and boron trichloride (2M in THF, 5.4 ml) was added. The reaction was heated to 60° C. for three hours. The reaction was cooled to room temperature and 100 ml water was added dropwise to quench the reaction. 100 ml 2N NaOH solution and 200 ml EtOAc were added. The organic layer was washed with brine (100 ml), dried over sodium sulfate and concentrated. The residue was dissolved in 100 ml methanol. 10 ml 1N HCl in ether was added and the reaction was stirred at room temperature for one hour. Solvent was removed and the residue was partitioned between 100 ml 1N NaOH solution and 100 ml EtOAc. The organic layer was washed with brine (100 ml), dried over sodium sulfate and concentrated. The product was purified by column (DCM/0.7N NH3 in MeOH from 0/100 to 50/50 in 45 minutes). Yield: 0.40 g, 84%. $^1$H NMR (CDCl$_3$ 400 MHz δ 7.59 (d, J=8.8 Hz, 2H), 7.47 (d, J=8.8 Hz, 2H), 7.02-7.10 (m, 1H), 6.37-6.45 (m, 1H), 5.15 (dd, J=11.7 and 2.2 Hz, 1H), 4.25 (dd, J=11.7 and 1.5 Hz, 1H), 3.86 (s, 1H), 2.95-3.03 (m, 1H), 2.82 (t, J=5.8 Hz, 2H), 2.38-2.45 (m, 2H), 1.94-2.05 (m, 1H), 1.45-2.55 (m, 2H), 1.32-1.44 (m, 1H).

Following procedures similar to those of Example 395, the compounds in Table 83 were obtained.

TABLE 83

| Ex. No. | Structure | LCMS (M + 1, retention time) |
|---|---|---|
| 396 | 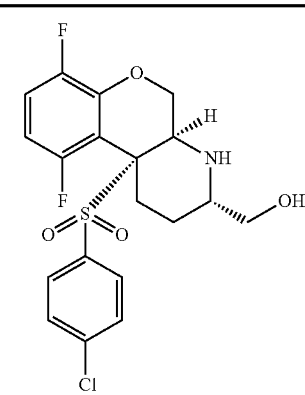 | 430.2, 2.89 min. |

TABLE 83-continued
| Ex. No. | Structure | LCMS (M + 1, retention time) |
|---|---|---|
| 397 | 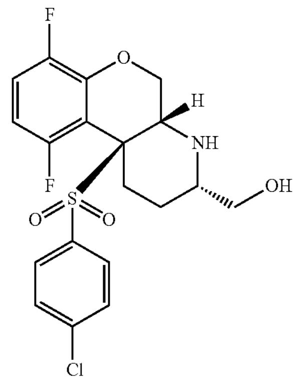 [SMILES: O=S(=O)(c1ccc(Cl)cc1)[C@]12CC[C@@H](CO)N[C@H]1COc1c(F)ccc(F)c12] | 430.2, 2.92 min. |
| 398 | 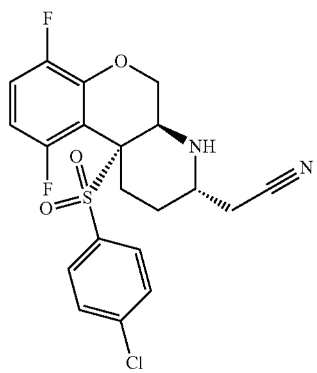 [SMILES: N#CC[C@@H]1CC[C@@]2(S(=O)(=O)c3ccc(Cl)cc3)c3c(F)ccc(F)c3OC[C@H]2N1] | 439.2, 4.21 min. |
| 399 | 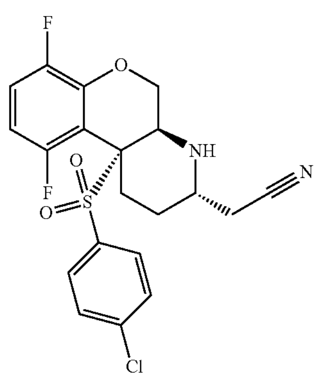 [SMILES: N#CC[C@@H]1CC[C@@]2(S(=O)(=O)c3ccc(Cl)cc3)c3c(F)ccc(F)c3OC[C@H]2N1] | 439.2, 4.22 min. |
| 400 | 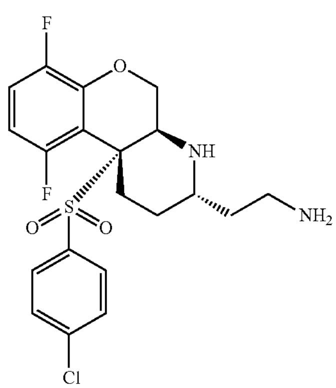 [SMILES: NCC[C@@H]1CC[C@@]2(S(=O)(=O)c3ccc(Cl)cc3)c3c(F)ccc(F)c3OC[C@H]2N1] | 443.2, 2.61 min. |
Examples 403 to 410
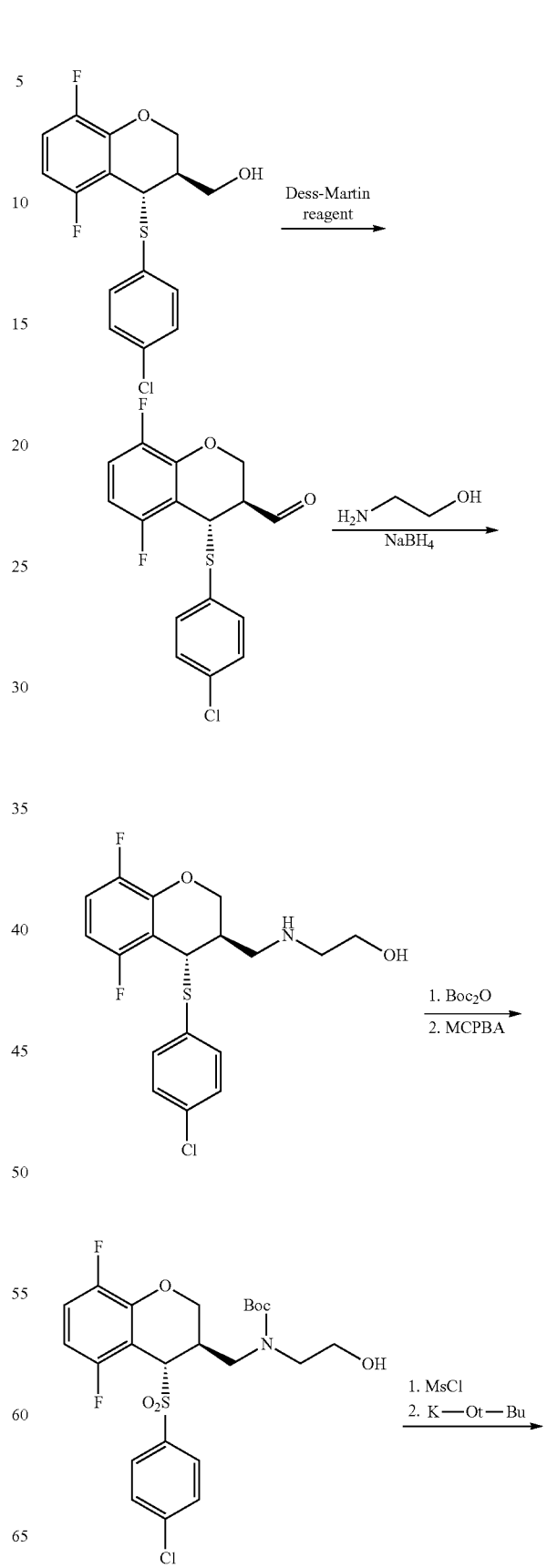

-continued

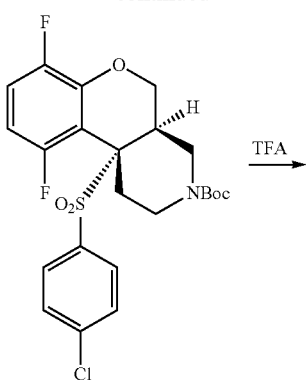

TFA →

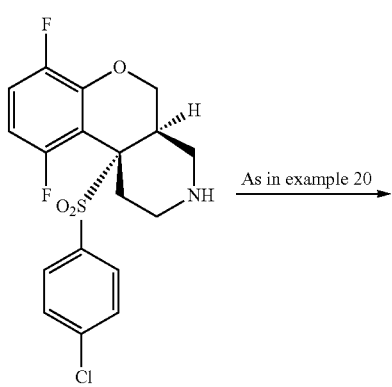

As in example 20 →

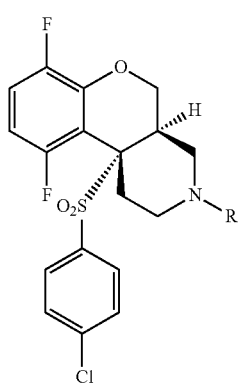

(wherein R is identified in Table 84)

Step 1

Trans-4-(4-chloro-phenylsulfanyl-5,8-difluoro-chroman-3-carbaldehyde

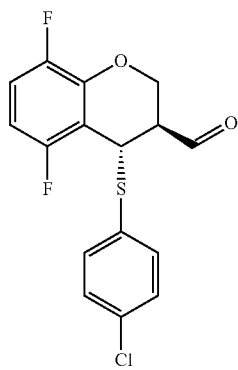 [SMILES: O=C[C@@H]1COc2c(F)ccc(F)c2[C@H]1Sc1ccc(Cl)cc1]

Trans-[4-(4-chloro-phenylsulfanyl)-5,8-difluoro-chroman-3-yl]-methanol (Example 16 Step 2) (2.8 g, 8.8 mmole) was dissolved in 15 ml DCM and Dess-Martin reagent (4.1 g, 9.7 mmole) was then added. The reaction was stirred at room temperature for three hours. 40 ml EtOAc and 30 ml saturated sodium thiosulfate solution were added and the organic layer was washed with saturated sodium bicarbonate solution, dried over sodium sulfate and concentrated. The residue was used in next step without further purification.). Yield: 2.8 g, 100%. $^1$H NMR (CDCl$_3$ 400 MHz) δ 9.70 (s, 1H), 7.45 (d, J=8.8 Hz, 2H), 7.34 (d, J=8.8 Hz, 2H), 6.93-7.00 (m, 1H), 6.59-6.65 (m, 1H), 4.92 (dt, J=11.7 and 2.2 Hz, 1H), 4.89 (br, 1H), 4.74 (dd, J=11.7 and 2.9 Hz, 1H), 2.83 (m, 1H).

Step 2

2-[{(4-Chloro-phenylsulfanyl)-5,8-difluoro-chroman-3-ylmethyl]-amino}-ethanol

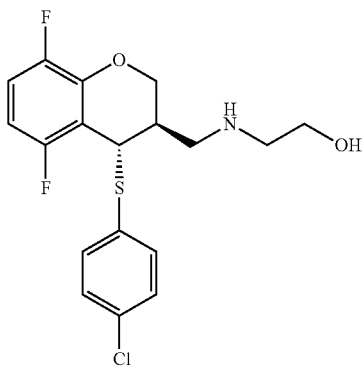 [SMILES: OCCNC[C@@H]1COc2c(F)ccc(F)c2[C@H]1Sc1ccc(Cl)cc1]

Trans-4-(4-chloro-phenylsulfanyl)-5,8-difluoro-chroman-3-carbaldehyde (2.2 g, 5.9 mmole) and ethanolamine (1.1 g, 18 mmole) were dissolved in 20 ml THF. The reaction was stirred at room temperature overnight. 2 g Sodium borohydride and 10 ml MeOH were added and the reaction was stirred for three hours. 100 ml water and 100 ml EtOAc were added. The organic layer was washed with water, dried over sodium sulfate and concentrated. The product was purified by column chromatography (EtOAc/hexane from 25/75 to 100/0 in 45 minutes). Yield, 0.40 g, 17.5%. $^1$H NMR (CDCl$_3$ 400 MHz) δ 7.45 (d, J=8.1 Hz, 2H), 7.31 (d, J=8.1 Hz, 2H), 6.92-7.00 (m, 1H), 6.54-6.60 (m, 1H), 4.62 (dd, J=8.8 and 2.2 Hz, 1H), 4.48 (br, 1H), 4.38 (dt, J=11.7 and 2.2 Hz, 1H), 3.55 (t, J=5.1 Hz, 2H), 2.67 (dd, J=12.4 and 7.3 Hz, 1H), 2.62 (t, J=5.1 Hz, 2H), 2.48 (dd, J=12.4 and 8.1 Hz, 1H), 2.09 (m, 1H).

Step 3

[4-(4-Chloro-benzenesulfonyl)-5,8-difluoro-chroman-3-ylmethyl]-(2-hydroxy-ethyl)-carbamic acid tert-butyl ester

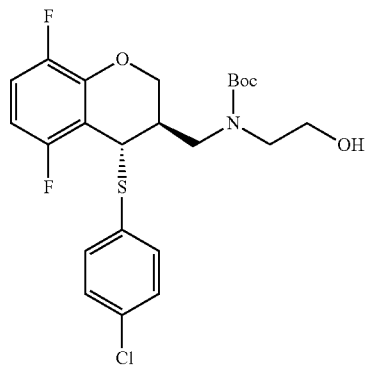 [SMILES: CC(C)(C)OC(=O)N(CCO)C[C@@H]1COc2c(F)ccc(F)c2[C@H]1Sc1ccc(Cl)cc1]

2-{[4-(4-Chloro-phenylsulfanyl)-5,8-difluoro-chroman-3-ylmethyl]-amino}-ethanol (0.4 g, 1.0 mmole) was dissolved in 20 ml DCM and Boc$_2$O (0.24 g, 1.2 mmole) was added. The reaction was stirred at room temperature for 3 hours. MCPBA (77%, 0.8 g, 3.6 mmole) was then added and the reaction was stirred at room temperature for two hours. 2 g sodium thiosulfate in 50 ml water was added to quench the reaction and 100 ml EtOAc was added to extract the product. The organic layer was washed with 1N NaOH solution (50 ml), brine (50 ml), dried over sodium sulfate and concentrated. The product was purified by column chromatography (EtOAc/Hexane from 0/100 to 50/50 in 45 minutes). Yield: 0.44 g, 85%. $^1$H NMR (CDCl$_3$ 400 MHz) δ 7.71 (d, J=8.1 Hz, 2H), 7.49 (d, J=8.1 Hz, 2H), 6.98-7.05 (m, 1H), 6.36-6.44 (m, 1H), 4.90 (d, J=11.7 Hz, 1H), 4.40 (br, 1H), 4.28 (d, J=11.7 Hz, 1H), 3.70 (br, 2H), 3.15-3.40 (m, 5H), 1.26 (s, 9H).

Step 4

1,1-dimethylethyl (4aR)-10bS-[(4-Chlorophenyl)sulfonyl]-7,10-difluoro-1,4-a,5,10b-tetrahydro-2H-[1]benzopyrano[3,4-c]pyridine-3(4H)-carboxylate (racemic)

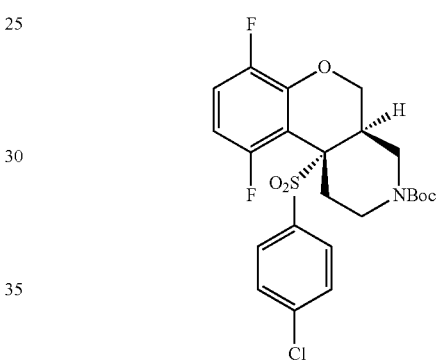

[4-(4-Chloro-benzenesulfonyl)-5,8-difluoro-chroman-3-ylmethyl]-(2-hydroxy-ethyl)-carbamic acid tert-butyl ester (0.44 g, 0.85 mmole) was dissolved in 5 ml DCM. Mesyl chloride (0.11 g, 1.0 mmole) and triethylamine (0.86 g, 8.5 mmole) were added. The mixture was stirred at room temperature for two hours. 50 ml water and 50 ml EtOAc were added. The organic layer was washed with water (50 ml), brine (50 ml), dried over sodium sulfate and concentrated. The residue was dissolved in 5 ml THF and KOt-Bu (1M in THF, 2 ml) was added. The mixture was stirred at room temperature for two hours. 50 ml water and 50 ml EtOAc were added. The organic layer was washed with brine (50 ml), dried over sodium sulfate and concentrated. The product was purified by column (EtOAc/hexane from 0/100 to 25/75 in 45 minutes). Yield: 0.23 g, 54%. $^1$H NMR (CDCl$_3$ 400 MHz) δ 7.60 (d, J=8.8 Hz, 2H), 7.50 (d, J=8.8 Hz, 2H), 7.06-7.13 (m, 1H), 6.40-6.47 (m, 1H), 5.20 (dd, J=11.7 and 2.2 Hz, 1H), 4.23 (d, J=11.7 Hz, 1H), 4.10 (br, 2H), 2.76 (br, 2H), 2.57 (d, J=12.7 Hz, 1H), 2.43 (br, 1H), 2.11 (m, 1H), 1.44 (s, 9H).

Step 5

(4aR)-10bS-[(4-Chlorophenyl)sulfonyl]-7,10-difluoro-1,3,4,4a,5,10b-hexahydro-2H-[1]benzopyrano[3,4-c]pyridine (racemic)

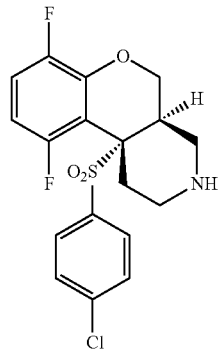 [SMILES: O=S(=O)(c1ccc(Cl)cc1)[C@@]12CCNC[C@@H]1COc1c(F)ccc(F)c12]

1,1-dimethylethyl (4aR)-10bS-[(4-Chlorophenyl)sulfonyl]-7,10-difluoro-1,4-a , 5,10b-tetrahydro-2H-[1]benzopyrano[3,4-c]pyridine-3(4H)-carboxylate (0.21 g, 0.42 mmole) was dissolved in 20 ml DCM and II 5 ml TFA. The mixture was stirred at room temperature for one hour. 100 ml saturated sodium carbonate solution and 100 ml EtOAc were added. The organic layer was washed with saturated sodium carbonate solution (50 ml), dried over sodium sulfate and concentrated. The residue was recrystallized from EtOAc/hexane. Yield: 0.16 g, 100%. $^1$H NMR (CDCl$_3$ 400 MHz) δ 7.61 (d, J=8.8 Hz, 2H), 7.49 (d, J=8.8 Hz, 2H), 7.05-7.12 (m, 1H), 6.39-6.46 (m, 1H), 5.18 (dd, J=11.7 and 2.2 Hz, 1H), 4.26 (d, J=11.7 Hz, 1H), 3.08 (d, J=9.5 Hz, 1H), 301 (dt, J=13.2 and 2.9 Hz, 1H), 2.58-2.73 (m, 3H), 2.35 (td, J=12.4 and 1.5 Hz, 1H), 2.09 (dt, J=12.4 and 2.9 Hz, 1H).

The product of Step 5 is converted to the compounds in Table 84 using the method described in Example 20.

TABLE 84

| Ex. No. | Structure | LCMS (M + 1, retention time) |
|---|---|---|
| 403 | | 500.3, 5.15 Min. |
| 404 | 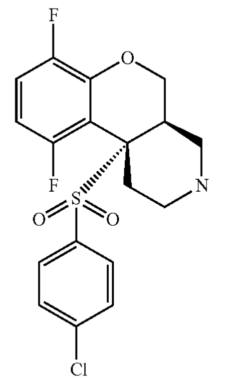 [SMILES: O=S(=O)(c1ccc(Cl)cc1)[C@@]12CCNC[C@@H]1COc1c(F)ccc(F)c12] | 400.2, 3.04 Min. |
| 405 | 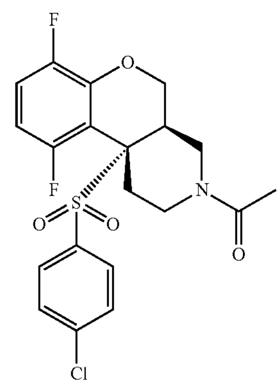 [SMILES: CC(=O)N1CC[C@@]2(S(=O)(=O)c3ccc(Cl)cc3)c3c(F)ccc(F)c3OC[C@H]2C1] | 442.2, 3.90 Min. |
| 406 | 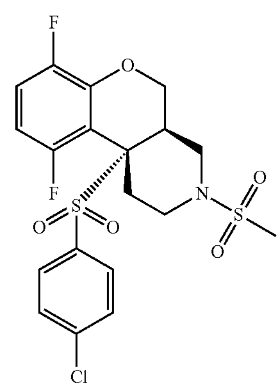 [SMILES: CS(=O)(=O)N1CC[C@@]2(S(=O)(=O)c3ccc(Cl)cc3)c3c(F)ccc(F)c3OC[C@H]2C1] | 478.3, 4.28 Min. |
| 407 | 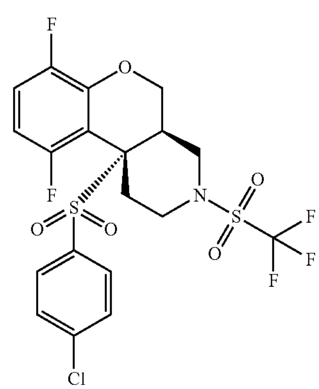 [SMILES: O=S(=O)(N1CC[C@@]2(S(=O)(=O)c3ccc(Cl)cc3)c3c(F)ccc(F)c3OC[C@H]2C1)C(F)(F)F] | 554.3 (M + Na), 4.94 Min. |

TABLE 84-continued
| Ex. No. | Structure | LCMS (M + 1, retention time) |
|---|---|---|
| 408 | 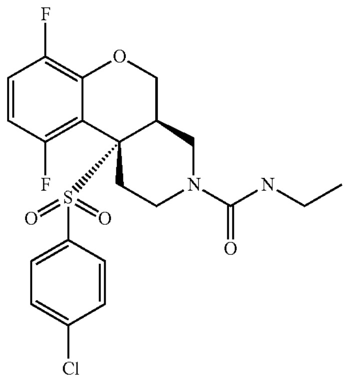 [SMILES: CCNC(=O)N1CC[C@@]2(S(=O)(=O)c3ccc(Cl)cc3)c3c(F)ccc(F)c3OC[C@H]2C1] | 471.3, 3.96 Min. |
| 409 | 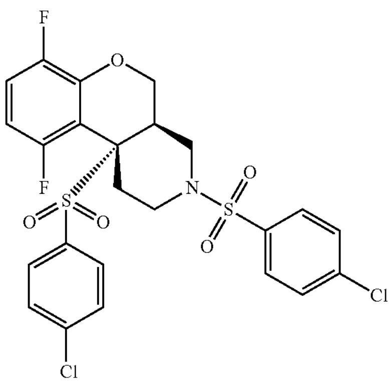 [SMILES: O=S(=O)(c1ccc(Cl)cc1)N1CC[C@@]2(S(=O)(=O)c3ccc(Cl)cc3)c3c(F)ccc(F)c3OC[C@H]2C1] | No M + 1 peak, 4.97 Min. |
| 410 | 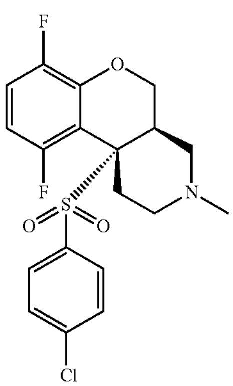 [SMILES: CN1CC[C@@]2(S(=O)(=O)c3ccc(Cl)cc3)c3c(F)ccc(F)c3OC[C@H]2C1] | 414.2, 3.11 Min. |
Example 411
Alternate Synthesis of the Compound 18B in Example 18
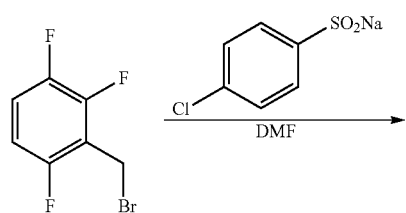
-continued
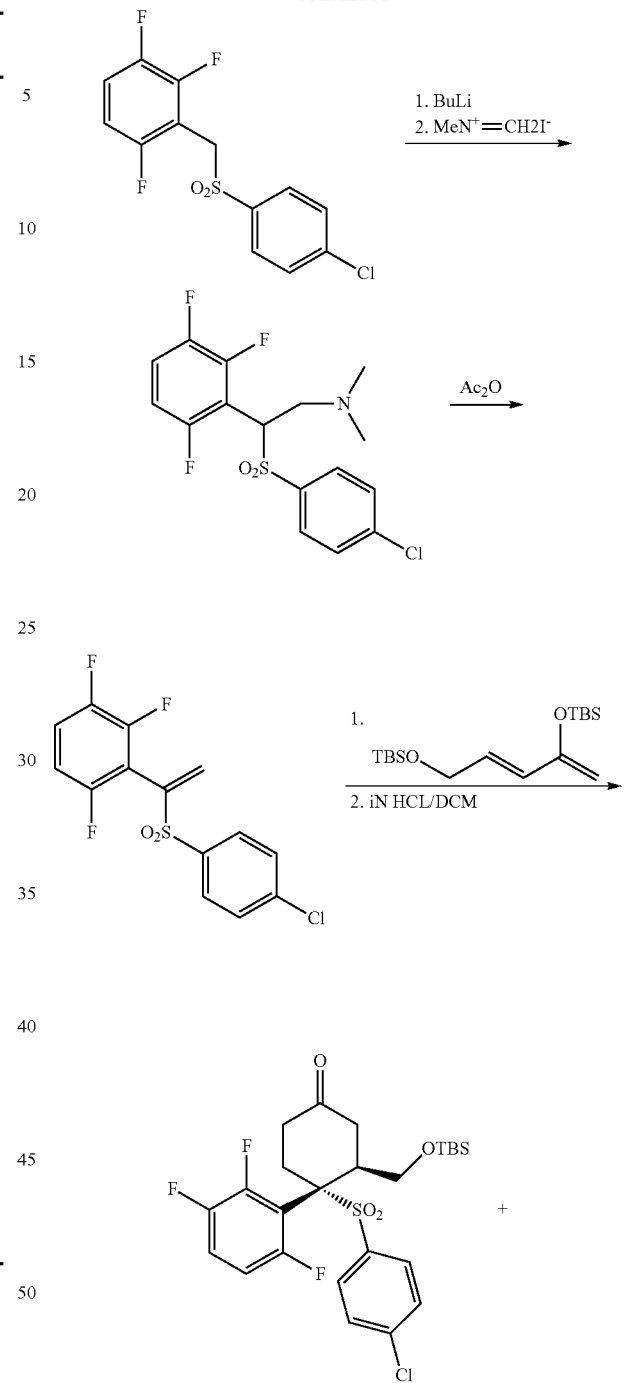
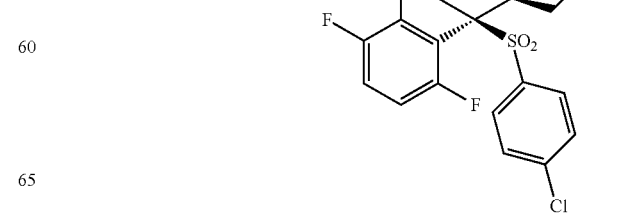

393

-continued

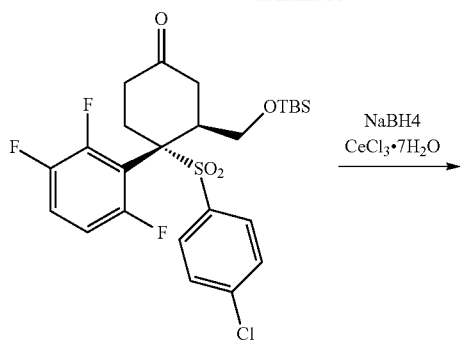

Step 1

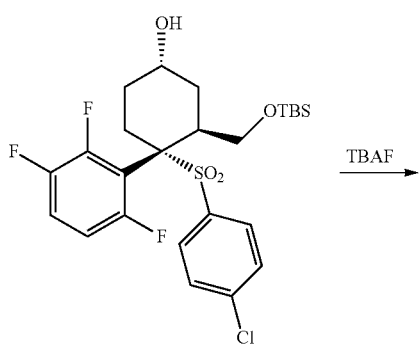

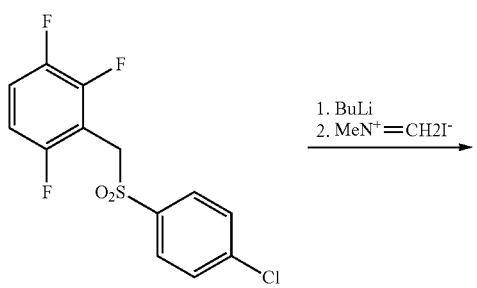

394

-continued

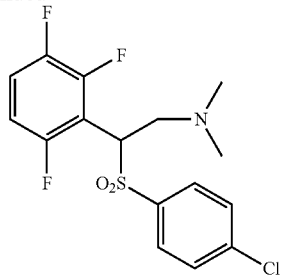

To a solution of I (2.0 g, 6.2 mmol) in THF (30 mL) was slowly added nBuLi (2.8 mL, 6.9 mmol, 2.5M Hexanes) at −78° C. After stirring for 15 min, Eschenmoser salt (1.3 g, 7.0 mmol) was added at once and the reaction mixture was allowed to warm gradually to room temperature over 16 h period. The reaction mixture was quenched into saturated $NH_4Cl$ solution and extracted with EtOAc. The organic phase was washed with brine, dried over $Na_2SO_4$, filtered and concentrated. The residue was purified by flash-chromatography over silica gel (eluting with hexanes/EtOAc 75:25) to provide 1.11 g of the title compound. $^1H$ NMR ($CDCl_3$ 400 MHz) δ 7.68-7.65 (m, 2H), 7.48-7.44 (m, 2H) 7.21-7.09 (m, 1H), 5.29 (s, 1H), 4.79 (d, J=4.2, 4.2 Hz, 1H), 3.44-3.33 m, 1H), 3.14-3.10, m, 1H), 2.19 (s, 6H).

Step 2

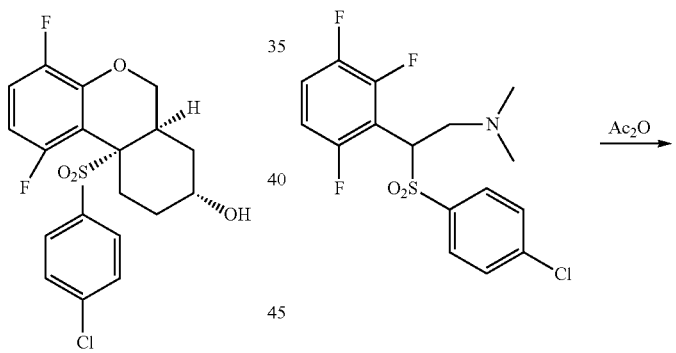

A solution of the amine product from step 1 (4.57 g, 12.1 mmol), acetic anhydride (3.6 mL, 38.0 mmol) and toluene (40 mL) was heated at reflux for 2 h. After cooling to room temperature, the reaction mixture was concentrated and the residue purified by flash-chromatography over silica gel (eluting with hexanes/EtOAc 75:25) to provide 2.57 g of the title compound as white solid. $^1H$ NMR ($CDCl_3$ 400 MHz) δ

7.62 (d, J=6.6 Hz, 2H), 7.49 (d, J=6.3 Hz, 2H) 7.10-7.04 (m, 1H), 6.93 (s, 1H), 6.83-6.72 (m, 1H), 6.10 (s, 1H).

Step 3

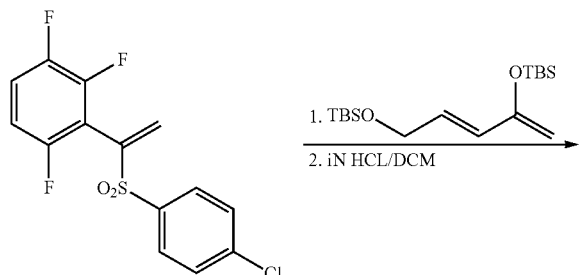

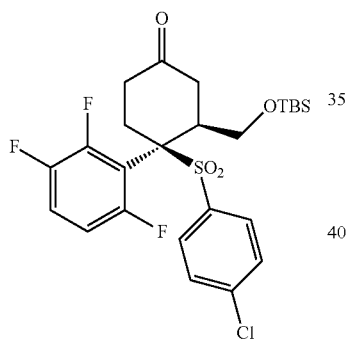

Isomer A

Isomer B

A solution of the alkene product from step 2: (7.8 g, 23.8 mmol), (E)-1,4-Bis(tert-butyldimethylsiloxy)-2,4-pentadiene [Frey, B.; Schnaubelt, J.; Hans-Ulrich, R .; *Eur. J. Org. Chem.* 1999, (6), 1377-1384] (3.95 g, 11.9 mmol) and o-xylene (10 mL) was heated at reflux in a sealed tube for 16 h. After cooling to room temperature, the solvent was concentrated and the residue was dissolved in ice-cold solution of 1N HCl in DCM (140 mL). The reaction mixture was kept at 0° C. for 1 h, then carefully neutralized to PH 8 with saturated NaHCO3. Separated layers, extracted aqueous ohase with DCM, washed combined organic phase with brine, dried over Na2SO4 and concentrated. The residue purified by flash-chromatography over silica gel (eluting with hexanes/EtOAc 75:25) to provide 1.26 g of Isomer A and 1.08 g of Isomer B.

Isomer A: $^1$H NMR (CDCl$_3$ 400 MHz) δ 7.71-7.35 (m, 4H), 7.26-7.17 (m, 1H), 7.90-6.53 (m, 1H), 3.94 (s, br, 1H), 3.77-3.75 (m, 1H), 3.62-3.55 (m, 2H), 3.27-3.20 (m, 2H), 3.00-2.80 (m, 1H), 2.53-2.45 (m, 2H), 0.72 (s, 9H), −1.00 (s, 3H), −1.10 (s, 3H).

Isomer B: $^1$H NMR (CDCl$_3$ 400 MHz) 7.41 (d, J=7.2 Hz, 2H), 7.33 (d, J=8.4 Hz, 2H), 7.22-7.14 (m, 1H), 7.00-6.45 (m, 1H), 4.71 (dd J=2.4, 11.2 Hz, 1H), 4.10 (dd, J=4.4, 11.0 Hz, 1H), 3.97 (s, br, 1H), 3.30-3.26 (m, 1H), 2.98-2.95 (m, 1H), 2.68-2.59 (m, 2H), 2.25-2.09 (m, 2H), 0.92 (s, 9H), 0.15 (s, 3H), 0.1. (s, 3H).

Step 4

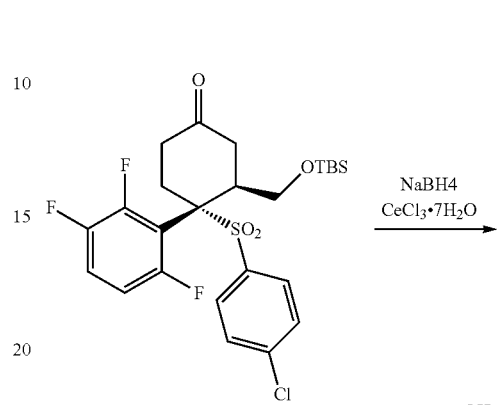

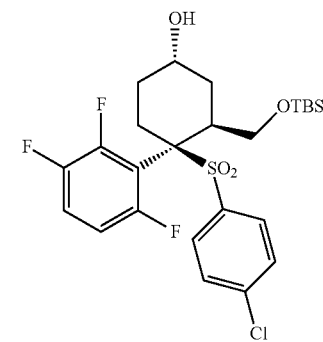

To a solution of Isomer A from step 3 (1.26 g, 2.3 mmol) in THF (60 mL) at 0° C. was added CeCl$_3$.7H$_2$O (2.0 g, 5.3 mmol) followed by BaBH4 (0.575 g, 15.2 mmol). After stirring at room temperature for 16 h, the reaction mixture was cooled to 0° C. and quenched with water. It was then extracted with EtOAc, the organic phase washed with brine, dried over Na$_2$SO$_4$ and concentrated. The residue purified by flash-chromatography over silica gel (eluting with hexanes/EtOAc 1:1) to provide 1.19 g of the title product. $^1$H NMR (CDCl$_3$ 400 MHz) δ 7.40-7.30 (m, 4H), 7.20-7.06 (m, 1H), 6.85-6.50 (m, 1H), 4.23-4.10 (m, 1H), 3.70-3.50 (m, 2H), 3.05-2.10 (m, 4H), 2.90-2.30 (m, 3H), 0.95-0.85 (m, 1H), 0.80 (s, 9H), −1.00 (s, 3H), −2.05 (s, 3H).

Step 5

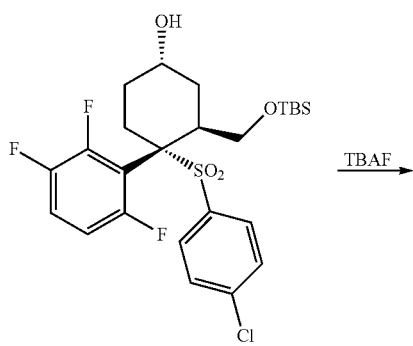

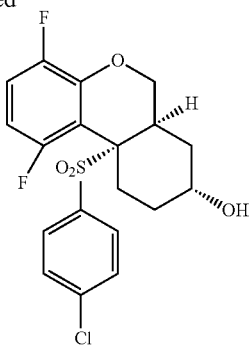

To a solution of the alcohol product from step 4 (1.19 g, 2.17 mmol) in THF (40 mL) was added TBAF at 0° C. The cooling bath was removed and the reaction mixture was stirred at room temperature for 2 h. The solvent was concentrated and the residue purified by flash-chromatography over silica gel (eluting with hexanes/EtOAc 1:1) to provide 403 mg of the title product. $^1$H NMR (CDCl$_3$ 400 MHz) δ 7.63 (d, J=6.0 Hz, 2H), 7.49 (d, J=6.0 Hz, 2H), 7.10-7.94 (m, 1H), 6.45-6.39 (m, 1H), 5.26 (d, J=12.9 Hz, 1H), 4.10 (d, J=8.7 Hz, 1H), 4.05 (s, br, 1H), 3.07 (d, J=9.9 Hz, 1H), 2.51-2.48 (m, 1H), 2.37-2.34 (m, 1H), 1.85-1.26 (m, 5H).

Example 412

(3aR)-9bS-[(4-Chlorophenyl)sulfonyl]-6,9-difluoro-1,2,3,3a,4,9b-hexahydro-2-(phenylmethyl)[1]benzopyrano[3,4-c]pyrrole (racemic)

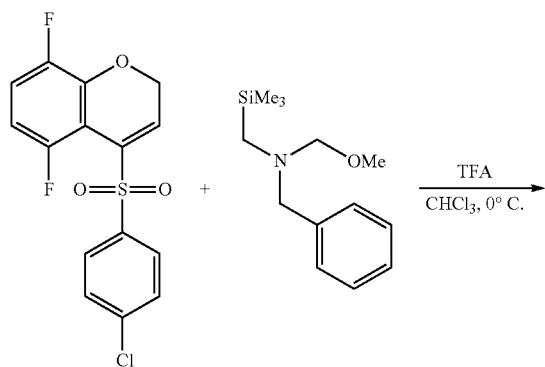

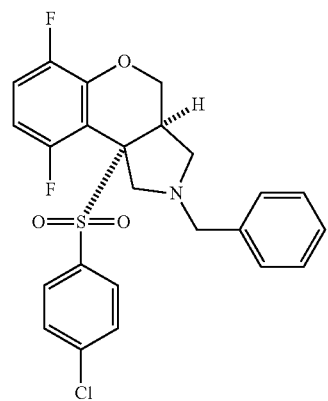

Example 412

To a solution of vinyl sulfone (50 mg, 0.145 mmol) and dipole precursor (100 mg, 0.42 mmol) in CHCl3 (2 mL) was added TFA (10 mg) at 0° C. and stirred at that temperature for 2 h and then worked-up in water and EtOAc. The mixture was subjected to preparative TLC over silica gel (eluted with Hexanes/EtOAc 80:20) to yield 50 mg of Example 412: $^1$H-NMR (CDCl$_3$ 400 MHz) δ 7.47 (d, 2H), 7.38 (d, 2H), 7.21 (m, 5H), 7.03 (m, 1H), 6.60 (m, 1H), 4.40 (m, 1H), 3.67 (m, 4H), 3.41 (m, 2H), 2.95 (m, 1H), 2.43 (m, 1H) LCMS (MH$^+$)= 476.3; retention time=3.29 min.

Example 413

(3aR)-9bS-[(4-Chlorophenyl)sulfonyl]-6,9-difluoro-1,2,3,3a,4,9b-hexahydro-2-methylenebenzo[b]cyclopenta[d]pyran (racemic)

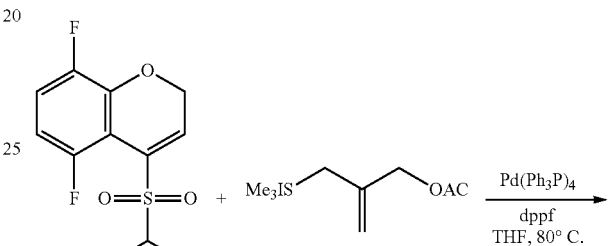

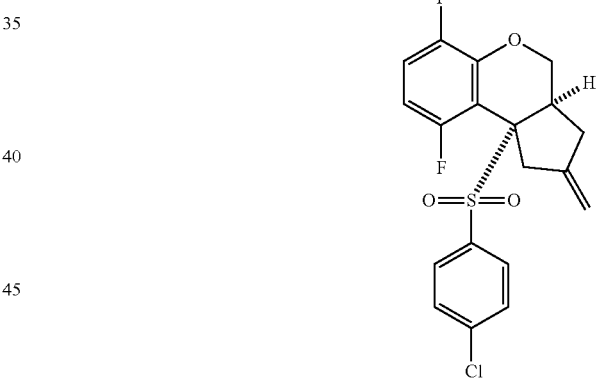

Example 413

To a solution of vinyl sulfone (100 mg, 0.29 mmol) and dipole precursor (70 mg, 0.37 mmol) in THF (4 mL) was added dppf (10 mg) followed by Pd(PPh3)4 (20 mg, 0.017 mmol) at room temperature and the reaction mixture was heated at 80° C. for 12 h. The reaction mixture was passed through a short pad of celite. The mixture was subjected to preparative TLC over silica gel (eluted with Hexanes/EtOAc 80:20) to yield 20 mg of Example 413: $^1$H-NMR (CDCl$_3$ 400 MHz) δ 7.59 (d, 2H), 7.48 (d, 2H), 7.0 (m, 1H), 6.41 (m, 1H), 4.90 (s, 1H), 4.85 (s, 1H), 4.74 (d, 1H), 4.14 (d, 1H), 3.41 (m, 2H), 3.15 (d, 2H), 2.76 (m, 1H), 2.33 (m, 1H)

Examples 414 to 416

The compounds in Table 85 were prepared following the procedure described in Example 61.

TABLE 85

| Example No. | STRUCTURE | Mass Spec (M+ except as otherwise noted); retention time (min) |
|---|---|---|
| 414 | 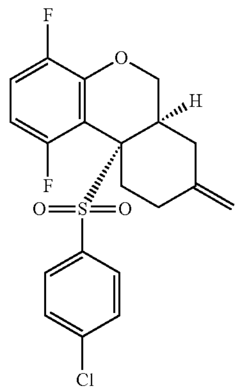 [SMILES: C=C1CC[C@@]2(S(=O)(=O)c3ccc(Cl)cc3)c3c(F)ccc(F)c3OC[C@H]2C1] | 4.96 |
| 415 | 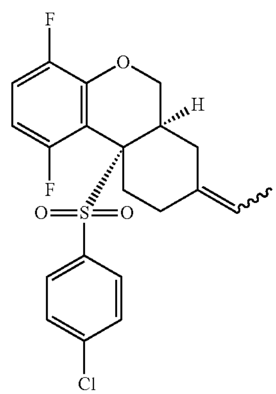 | 4.80 |
| 416 | 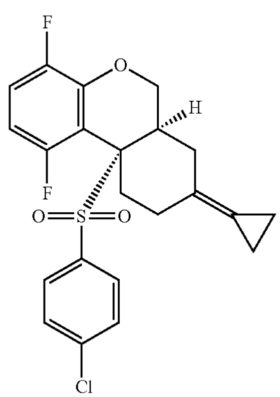 [SMILES: O=S(=O)(c1ccc(Cl)cc1)[C@@]12CCC(=C3CC3)C[C@@H]1COc1c(F)ccc(F)c12] | 5.62 |

Examples 417 and 418

(6aR)-10aS-[(4-Chlorophenyl)sulfonyl]-1,4-difluoro-6a,7,8,9,10,10a-hexahydro-8(r)-hydroxy-6h-dibenzo[b,d]pyran-8-methanol (racemic)

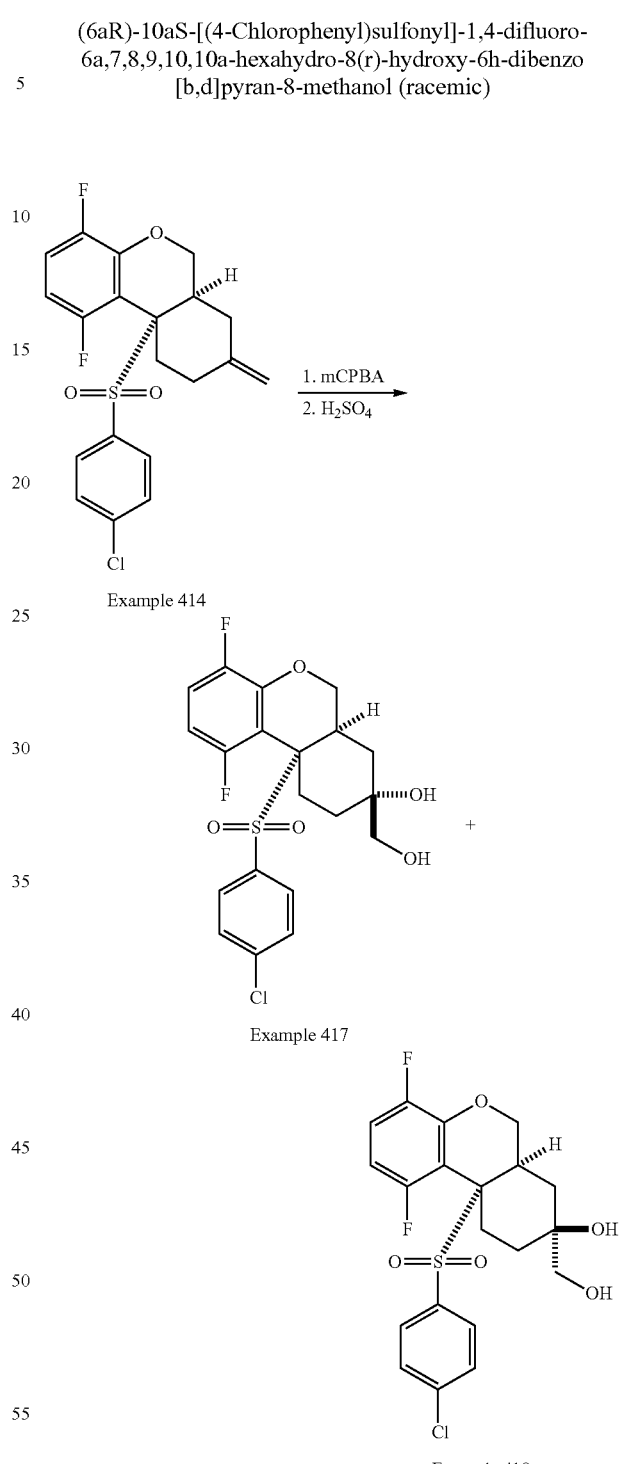

Example 414

Example 417

Example 418

To a solution of olefin (10 mg, 0.024 mmol) in DCM (2 mL) was added mCPBA (10 mg, 2 eq) at room temperature and stirred for 2 h. Sodium thiosulfate (200 mg in 0.5 mL water) was added and extracted with DCM. The solvent was removed in vacuo and redissolved in THF (2 mL) and treated with 2 drops of con. H2SO4 and stirred at room temperature for 30 minutes. Saturated aq. NaHCO3 solution (2 mL) was added and extracted with DCM. The mixture was subjected to preparative TLC over silica gel (eluted with DCM/MeOH 95:5) to yield 4 mg of Example 417 and 4 mg of 418.

Example 417

$^1$H-NMR (CDCl$_3$ 400 MHz) δ 7.62 (d, 2H), 7.49 (d, 2H), 7.0 (m, 1H), 6.41 (m, 1H), 5.30 (d, 1H), 4.12 (d, 1H), 3.61 (s, 1H), 3.44 (m, 3H), 3.05 (m, 2H), 2.48 (m, 2H), 1.78 (m, 1H), 1.25 (m, 2H).

TABLE 86

| Example No. | STRUCTURE | Mass Spec (M$^+$ except as otherwise noted); retention time (min) |
|---|---|---|
| 418 | 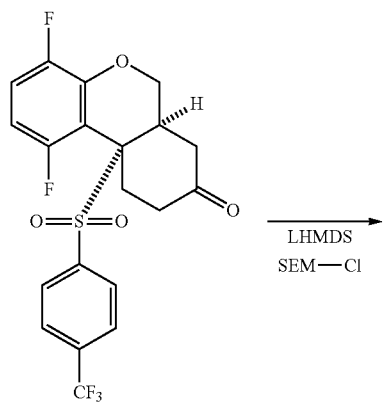 | 444.2 (MH+) |

Examples 419 and 420

(6aR)-1,4-difluoro-6a,7,8,9,10,10a-hexahydro-8(S)-hydroxy-10aS-[[4-(trifluoromethyl)phenyl]sulfonyl]-6h-dibenzo[b,d]pyran-7(R)-methanol (racemic)

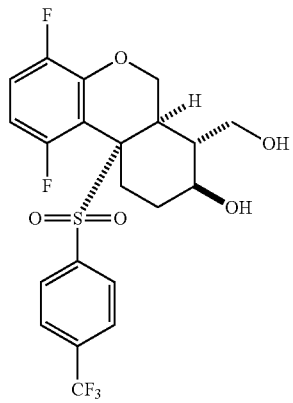

LHMDS
SEM—Cl

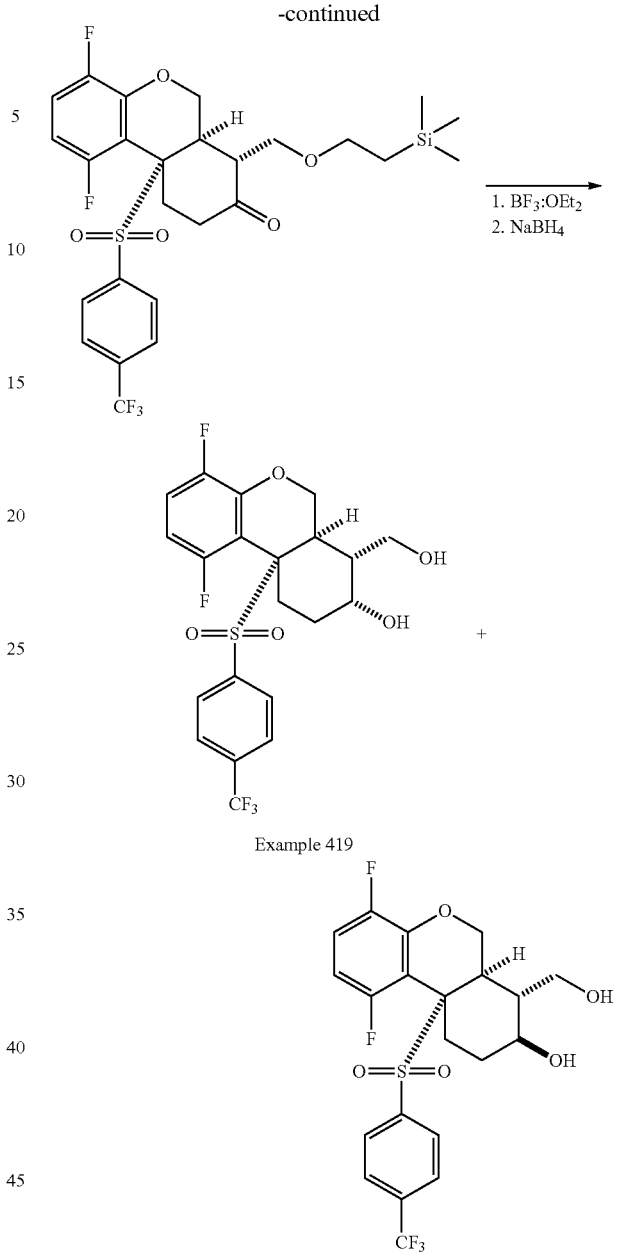

1. BF$_3$:OEt$_2$
2. NaBH$_4$

Example 419

Example 420

To a solution of tricyclic ketone (5 g, 0.0112 mol) in THF (50 mL) was added LHMDS (1 M in THF, 13.44 mL, 1.2 eq) at −78° C. and stirred for 30 minutes. In a separate flask, SEM-Cl (2.24 g, 0.0134 mol) and NaI (2 g, 0.0133 mol) were taken in THF (50 mL) and cooled to −78° C. The ketone enolated generated was transferred to the SEM-Cl/NaI mixture via cannula and stirred at −78° C. for 6 h. The reaction mixture was slowly warmed to room temperature and stirred overnight and then poured into saturated NH$_4$Cl and extracted with EtOAc The residue was purified by flash-chromatography over silica gel (eluted with hexanes/EtOAc 0-20% EtOAc) to afford 1.7 g (26%) of product.

The above product (1.6 g, 0.0027 mol) was dissolved in DCM (50 mL) and treated with BF3:OEt2 (0.3 mL) at 0° C. and stirred for 3 h. Aqueous sodium hydroxide (5 mL, 2.5 M) solution was added and extracted with EtOAc. The solvent was removed in vacuo and redissolved in THF (10 mL) and treated with NaBH4 (500 mg) at 0° C. The reaction mixture was stirred at 0° C. for 2 h and warmed to room temperature and stirred for another 2 h. Aqueous work up followed by EtOAc extraction and silica gel column chromatography afforded the compounds of Examples 419 and 420.

| Example No. | STRUCTURE | Mass Spec (M+ except as otherwise noted); retention time (min) |
|---|---|---|
| 419 | 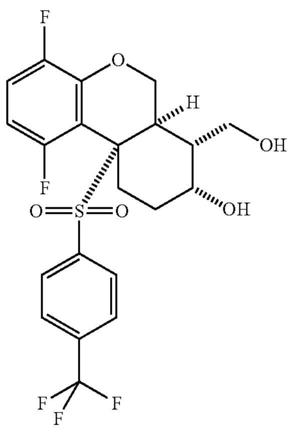 [SMILES: O=S(=O)(c1ccc(C(F)(F)F)cc1)[C@@]12CC[C@@H](O)[C@@H](CO)[C@@H]1COc1c(F)ccc(F)c12] | 478.3 (MH+), 4.32 |
| 420 | 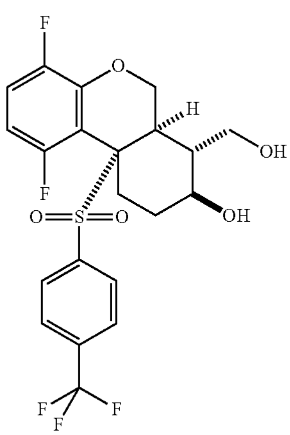 [SMILES: O=S(=O)(c1ccc(C(F)(F)F)cc1)[C@@]12CC[C@H](O)[C@@H](CO)[C@@H]1COc1c(F)ccc(F)c12] | 478.3 (MH+), 4.11 |

Example 420

$^1$H-NMR (CDCl$_3$ 400 MHz) δ 7.77 (s, 4H), 7.06 (m, 1H), 6.39 (m, 1H), 5.16 (d, 1H), 4.12 (d, 1H), 3.74 (m, 1H), 2.74 (d, 1H), 2.56 (d, 1H), 2.01 (m, 6H), 1.36 (m, 1H), 0.98 (m, 1H).

Examples 421 to 426

Examples 421 and 422

(6aR)-10aS-[(4-chlorophenyl)sulfonyl]-1,4-difluoro-6a,7,8,9,10,10a-hexahydro-7(R)-[[2-(trimethylsilyl)ethoxy]methyl]-6h-dibenzo[b,d]pyran-8(s)-ol (racemic)

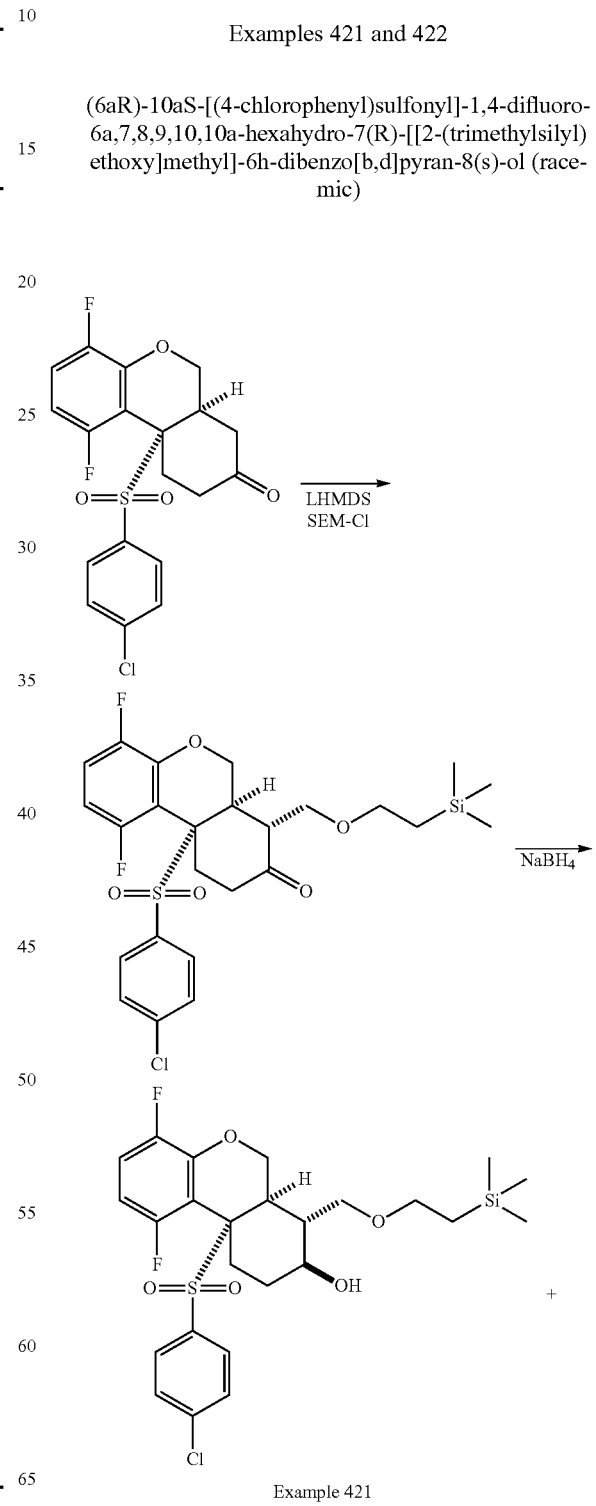

Example 421

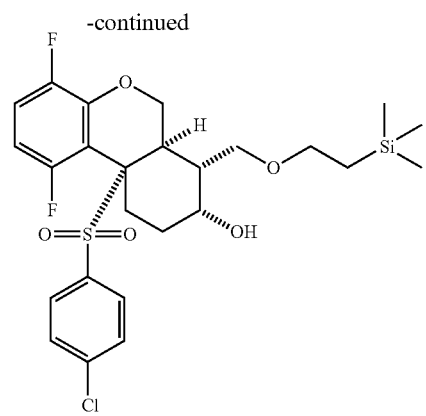

Example 422

To a solution of tricyclic ketone (100 mg, 0.24 mmol) in THF (3 mL) was added LHMDS (1 M in THF, 0.29 mL, 1.2 eq) at −78° C. and stirred for 30 minutes. In a separate flask, SEM-Cl (200 mg, 1.1 mol) and NaI (50 mg) were taken in THF (2 mL) and cooled to −78° C. The ketone enolated generated was transferred to the SEM-Cl/NaI mixture via cannula and stirred at −78° C. for 2 h. The reaction mixture was slowly warmed to room temperature and stirred for 4 h and then poured into saturated NH$_4$Cl and extracted with EtOAc The mixture was subjected to preparative TLC over silica gel (eluted with Hexanes/EtOAc 80:20) to yield 18 mg of product. This product was dissolved in isopropanol (1 mL) and treated with NaBH4 (5 mg, 5 eq) at −40° C. and stirred for 1 h. The reaction mixture was warmed to room temperature and stirred overnight. Citric acid solution (8% aqueous, 1 mL) was added and extracted with EtOAc. The mixture was subjected to preparative TLC over silica gel (eluted with Hexanes/EtOAc 80:20) to yield 2 mg of product of Example 421. $^1$H-NMR (CDCl$_3$ 400 MHz) δ 7.60 (d, 2H), 7.50 (d, 2H), 7.06 (m, 1H), 6.43 (m, 1H), 5.17 (d, 1H), 4.48 (d, 1H), 3.89 (d, 1H), 3.60 (m, 3H), 3.17 (s, 1H), 2.68 (d, 1H), 2.51 (d, 1H), 1.97 (m, 2H), 1.15 (m, 1H), 1.12 (m, 1H), 0.94 (m, 3H), 0.02 s, 9H). Compound TKS-11 was also isolated.

The compounds of Examples 423 to 426 in Table 88 were prepared according to the procedure of Examples 421 and 422.

TABLE 88

| Example No. | STRUCTURE | Mass Spec (M$^+$ except as otherwise noted); retention time (min) |
|---|---|---|
| 422 | 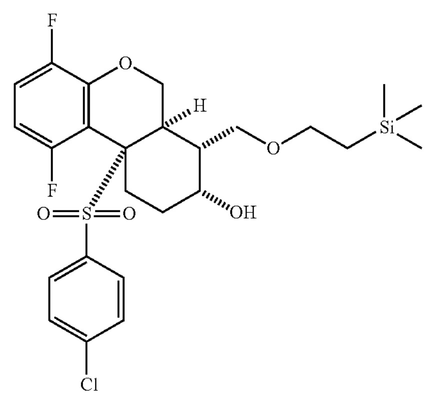 [SMILES: C[Si](C)(C)CCOC[C@@H]1[C@H](O)CC[C@@]2(S(=O)(=O)c3ccc(Cl)cc3)c3c(F)ccc(F)c3OC[C@@H]12] | 4.51 |
| 423 | 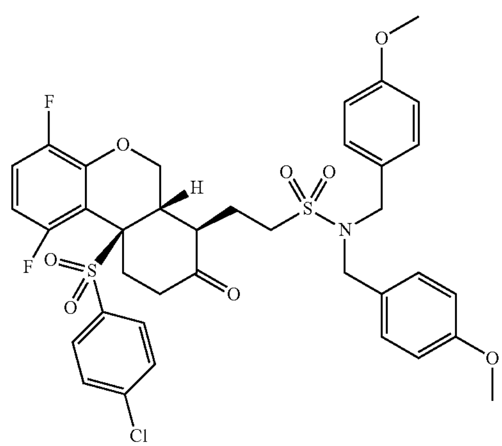 [SMILES: COc1ccc(CN(Cc2ccc(OC)cc2)S(=O)(=O)CC[C@H]2C(=O)CC[C@]3(S(=O)(=O)c4ccc(Cl)cc4)c4c(F)ccc(F)c4OC[C@H]23)cc1] | 760.4, 5.38 |

TABLE 88-continued

| Example No. | STRUCTURE | Mass Spec (M+ except as otherwise noted); retention time (min) |
|---|---|---|
| 424 | 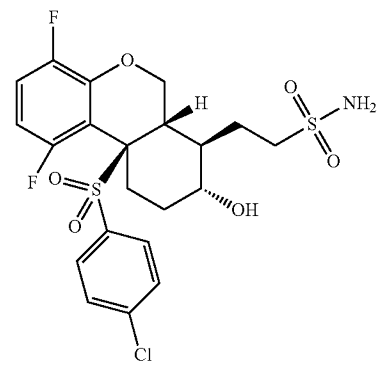 [SMILES: NS(=O)(=O)CC[C@H]1[C@H](O)CC[C@]2(S(=O)(=O)c3ccc(Cl)cc3)c3c(F)ccc(F)c3OC[C@H]12] | 548.3, 4.46 |
| 425 | 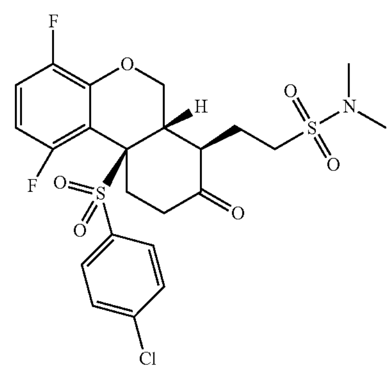 [SMILES: CN(C)S(=O)(=O)CC[C@H]1C(=O)CC[C@]2(S(=O)(=O)c3ccc(Cl)cc3)c3c(F)ccc(F)c3OC[C@H]12] | 550.3, 4.31 |
| 426 | 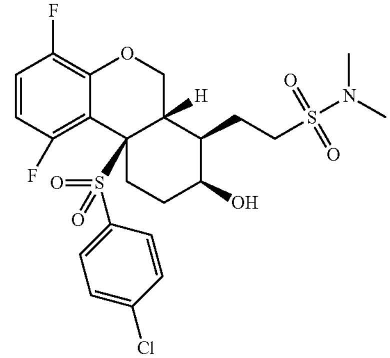 [SMILES: CN(C)S(=O)(=O)CC[C@@H]1[C@H]2COc3c(F)ccc(F)c3[C@@]2(S(=O)(=O)c2ccc(Cl)cc2)CC[C@@H]1O] | 522.3, 3.81 |

Example 427

(6aR)-10aS-[(4-chlorophenyl)sulfonyl]-1,4-difluoro-6A,7,8,9,10,10A-hexahydro-6h-dibenzo[B,D]pyran-8(R)-acetonitrile (racemic)

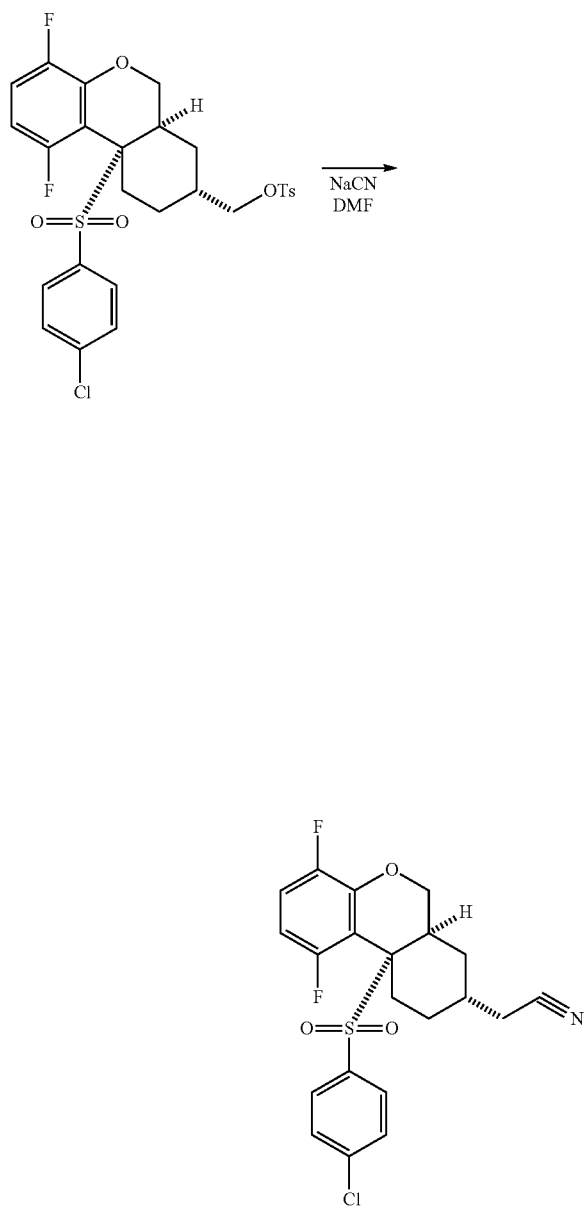

Example 427

To a solution of tosylate (20 mg, 0.034 mmol) in DMF (2 mL) was added NaCN (5 mg, 0.102 mmol) and the reaction mixture was heated at 120° C. for 2 h and then worked-up in water and EtOAc. The mixture was subjected to preparative TLC over silica gel (eluted with Hexanes/EtOAc 50:50) to yield 11 mg of Example 427. $^1$H-NMR (CDCl$_3$ 400 MHz) δ 7.58 (d, 2H), 7.48 (d, 2H), 7.08 (m, 1H), 6.43 (m, 1H), 5.24 (d, 1H), 4.12 (d, 1H), 2.76 (m, 1H), 2.55 (d, 2H), 2.44 (d, 1H), 2.22 (m, 1H), 2.07 (m, 1H), 1.76 (m, 3H), 1.56 (s, 1H), 1.41 (m, 1H) LCMS (MH$^+$)=83.2; retention time=4.43 min.

Examples 428 and 429

Example 428

(6aR)-1,4-difluoro-6a,9,10,10a-tetrahydro-7(S)-[2-(phenylsulfonyl)ethyl]-10aS-[[4-(trifluoromethyl)phenyl]sulfonyl]-6h-dibenzo[b,d]pyran-8(7h)-one (racemic)

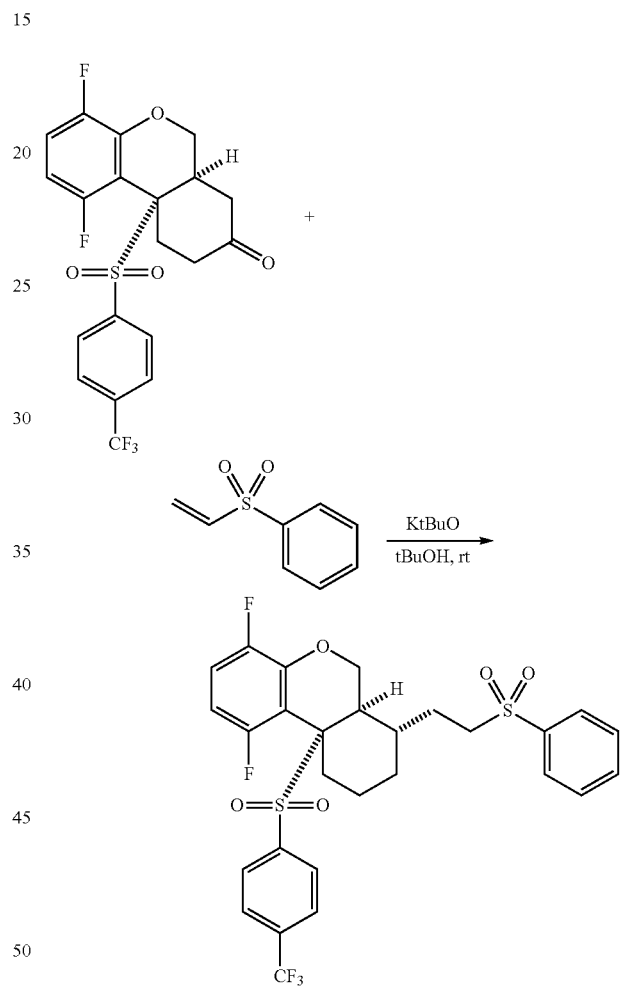

Example 428

To a solution of tricyclic ketone (115 mg, 0.25 mmol) and phenyl vinyl sulfone (50 mg, 0.29 mmol) in tBuOH/THF (3+1 mL) was added KtBuO solution (1 M in THF, 0.025 mL, 10 mol %) at room temperature and stirred for 4 h and then worked-up in water and EtOAc. The mixture was subjected to preparative TLC over silica gel (eluted with Hexanes/EtOAc 80:20) to yield 25 mg of Example 428: $^1$H-NMR (CDCl$_3$ 400 MHz) δ 7.91 (d, 2H), 7.82-7.59 (m, 7H), 7.19 (m, 1H), 6.52 (m, 1H), 5.21 (d, 1H), 4.40 (d, 1H), 3.25 (m, 2H), 2.86 (d, 1H), 2.72 (m, 1H), 2.44 (m, 3H), 2.11 (m, 3H).

Using a similar procedure, the compound in Table 89 was prepared.

TABLE 89

| Example No. | STRUCTURE | Mass Spec (M+ except as otherwise noted); retention time (min) |
|---|---|---|
| 429 | 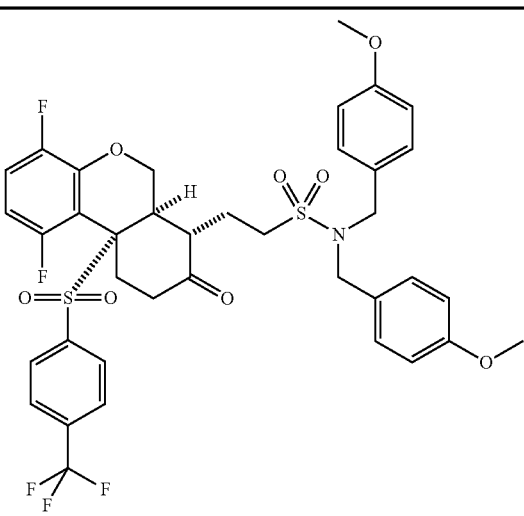 | 794.4 (MH+), 5.12 |

Example 430

The compound in Table 90 was made according to the method described for Example 19.

TABLE 90

| Example No. | STRUCTURE | Mass Spec (M+ except as otherwise noted); retention time (min) |
|---|---|---|
| 430 | 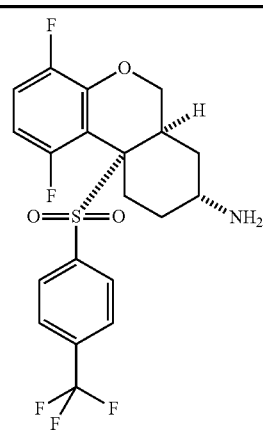 | 448.2 (MH+); 2.90 |

Examples 431 to 436

The compounds in Table 91 were made according to the method described for Example 20.

TABLE 91

| Example No. | STRUCTURE | Mass Spec (M+ except as otherwise noted); retention time (min) |
|---|---|---|
| 431 | ![structure] | 580.3 (MH+); 4.96 |

TABLE 91-continued

| Example No. | STRUCTURE | Mass Spec (M+ except as otherwise noted); retention time (min) |
|---|---|---|
| 432 | 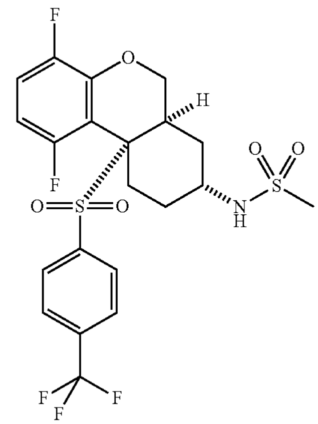 [SMILES: CS(=O)(=O)N[C@@H]1CC[C@@]2(S(=O)(=O)c3ccc(C(F)(F)F)cc3)c3c(F)ccc(F)c3OC[C@H]2C1] | 526.3 (MH+), 4.14 |
| 433 | 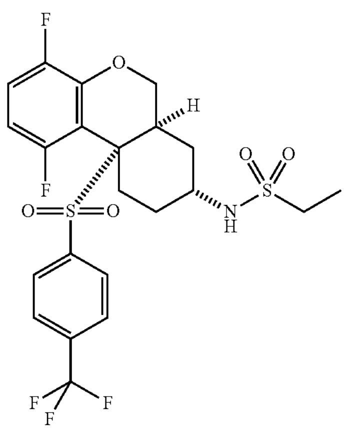 [SMILES: CCS(=O)(=O)N[C@@H]1CC[C@@]2(S(=O)(=O)c3ccc(C(F)(F)F)cc3)c3c(F)ccc(F)c3OC[C@H]2C1] | 540.3 (MH+), 4.26 |
| 434 | 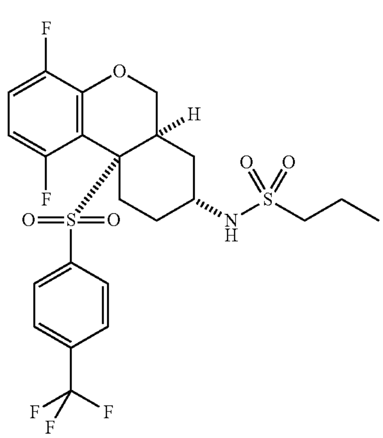 [SMILES: CCCS(=O)(=O)N[C@@H]1CC[C@@]2(S(=O)(=O)c3ccc(C(F)(F)F)cc3)c3c(F)ccc(F)c3OC[C@H]2C1] | 554.3 (MH+), 4.43 |
| 435 | | (MH+) 552.3; 4.36 |
| 436 | | (MH+) 594.3; 4.82 |

Examples 437 to 439

415
-continued

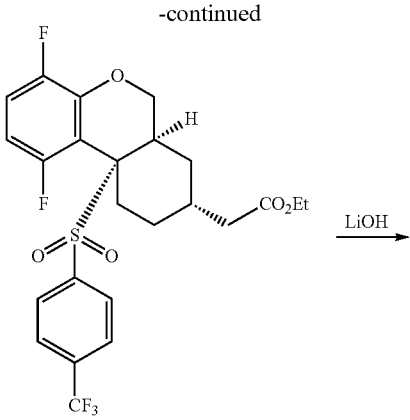

Example 437

→ LiOH →

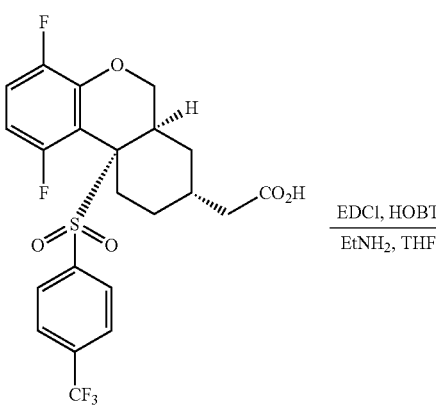

Example 438

EDCl, HOBT
―――――――→
EtNH₂, THF

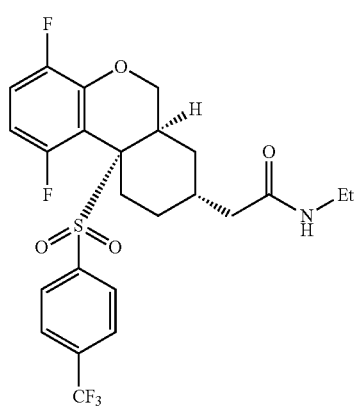

Example 439

416

Step 1

Ethyl 2-((6a,8,10a)-1,4-difluoro-10a-(4-(trifluoromethyl)phenylsulfonyl)-6a,7,8,9,10,10a-hexahydro-6H-benzo[c]chromen-8-yl)acetate

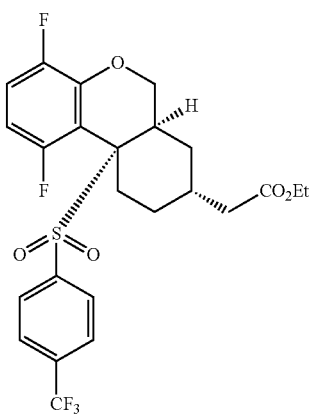

Example 437

To a 0° C. mixture of 60% NaH oil dispersion (0.12 g) in tetrahydrofuran (22 mL) was added triethyl phosphonoacetate (0.58 mL). After being stirred for 0.5 h at 0° C., 1,4-difluoro-10a-(4-trifluoromethyl-benzenesulfonyl)-6a,9,10,10a-tetrahydro-6H,7H-benzo[c]chromen-8-one (1.0 g, 2.24 mmol) was added to the resulting clear and colorless solution. After 0.5 h, saturated aqueous NH₄Cl was added to the reaction solution. This mixture was then extracted with ethyl acetate (3×). The combined organic layers were dried over Na₂SO₄, filtered. and absorbed onto silica gel (5 g). This absorbed crude material was purified by silica gel chromatography with ethyl acetate/hexanes (0/100 to 30/70 over 30 min) to afford 0.89 g of a white foam.

A portion of this white foam (0.62 g) was dissolved in tetrahydrofuran (22 mL). This solution was cooled to −78° C., and then 1.0 M L-Selectride in tetrahydrofuran (1.8 mL) was added. The cooling bath was then kept between −55° C. and -25° C. for 4.5 h. After this 4.5 h period, brine (1.8 mL), aqueous 1 M NaOH (1.8 mL), and then aqueous 30% H₂O₂ (0.7 mL) were added to the reaction. After being stirred another 0.5 h, aqueous 25% Na₂SO₃ (6 mL) was added. This mixture was extracted with ethyl acetate (3×). The combined organic layers were dried over Na₂SO₄, filtered. and absorbed onto silica gel (5 g). This absorbed crude material was purified by silica gel chromatography with ethyl acetate/hexanes (0/100 to 40/60 over 40 min) to afford Example 437 (0.236 g) as a white foam.

Example 437

LCMS: (M+1)=519.3, retention time=5.11 min.

Step 2

2-((6a,8,10a)-1,4-Difluoro-10a-(4-(trifluoromethyl)phenylsulfonyl)-6a,7,8,9,10,10a-hexahydro-6H-benzo[c]chromen-8-yl)acetic acid

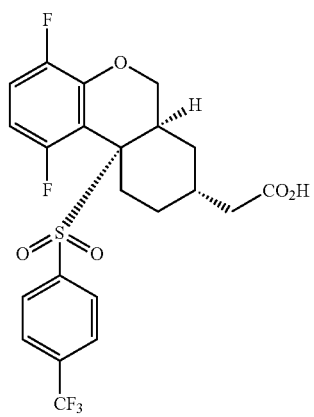

Example 438

A mixture of ethyl 2-((6a,8,10a)-1,4-difluoro-10a-(4-(trifluoromethyl)phenylsulfonyl)-6a,7,8,9,10,10a-hexahydro-6H-benzo[c]chromen-8-yl)acetate (Example 437, 0.23 g), lithium hydroxide (93 mg), water (3 mL), and tetrahydrofuran (9 mL) was placed in a 65° C. oil bath. After being stirred for 2.5 h at 65° C., the reaction mixture was diluted with water and acidified to pH 1-2. This mixture was then extracted with ethyl acetate (3x). The combined organic layers were dried over $Na_2SO_4$, filtered. and concentrated to afford Example 438 (0.202 g, 94%) as a white solid.

Example 438

LCMS: (M+1)=4913, retention time=4.30 min.

Step 3

2-((6a,8,10a)-1,4-Difluoro-10a-(4-(trifluoromethyl)phenylsulfonyl)-6a,7,8,9,10,10a-hexahydro-6H-benzo[c]chromen-8-yl)-N-ethylacetamide

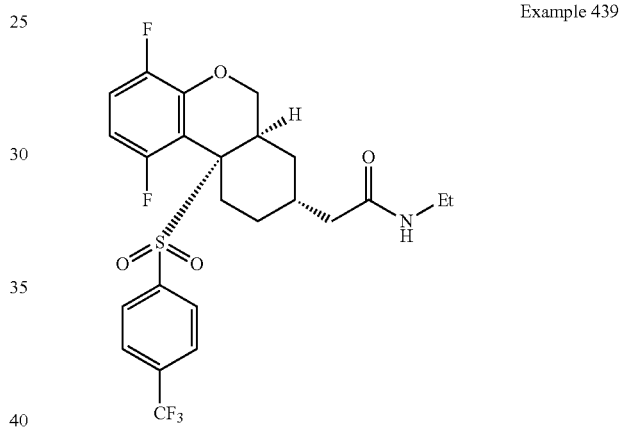

Example 439

To a room temperature mixture of EDCI (39 mg) in THF was added a 2 M solution of ethylamine in tetrahydrofuran (0.1 mL), followed by HOBT (28 mg). To this resulting mixture was added a solution of 2-((6a,8,10a)-1,4-Difluoro-10a-(4-(trifluoromethyl)phenylsulfonyl)-6a,7,8,9,10,10a-hexahydro-6H-benzo[c]chromen-8-yl)acetic acid (Example 438, 67 mg) in THF (3 mL). After being stirred for 16 h at room temperature, the reaction mixture was absorbed onto silica gel and purified by silica gel chromatography with ethyl acetate/hexanes (45/65 to 100/0 over 20 min) to afford Example 439 (66.5 mg, 94%) as a clear and colorless oil.

Example 439

LCMS: (M+1)=518.3, retention time=4.29 min.

Following procedures similar to those described for Example 439, the compounds in Table 92 were prepared.

TABLE 92

| Ex. No. | Structure | LCMS (M + 1, retention time) |
|---|---|---|
| 440 | 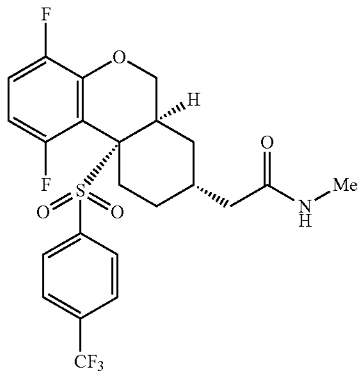 [SMILES: CNC(=O)C[C@@H]1CC[C@@]2(S(=O)(=O)c3ccc(C(F)(F)F)cc3)c3c(F)ccc(F)c3OC[C@H]2C1] | 504.3, 4.10 min. |
| 441 | 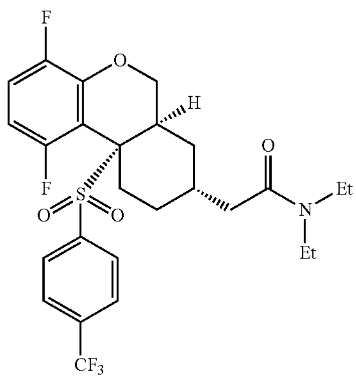 [SMILES: CCN(CC)C(=O)C[C@@H]1CC[C@@]2(S(=O)(=O)c3ccc(C(F)(F)F)cc3)c3c(F)ccc(F)c3OC[C@H]2C1] | 546.3, 4.85 min. |
| 442 | 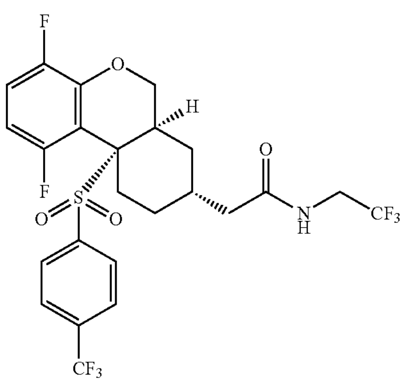 [SMILES: O=C(C[C@@H]1CC[C@@]2(S(=O)(=O)c3ccc(C(F)(F)F)cc3)c3c(F)ccc(F)c3OC[C@H]2C1)NCC(F)(F)F] | 572.3, 4.74 min. |
| 443 | 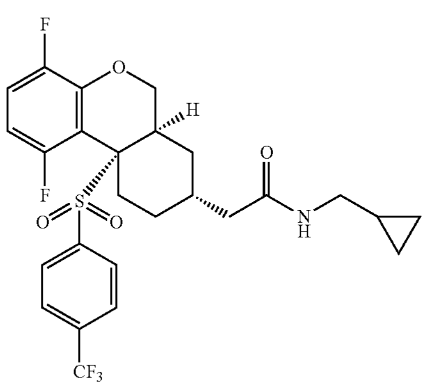 [SMILES: O=C(C[C@@H]1CC[C@@]2(S(=O)(=O)c3ccc(C(F)(F)F)cc3)c3c(F)ccc(F)c3OC[C@H]2C1)NCC1CC1] | 544.3, 4.71 min. |

TABLE 92-continued

| Ex. No. | Structure | LCMS (M + 1, retention time) |
|---|---|---|
| 444 | 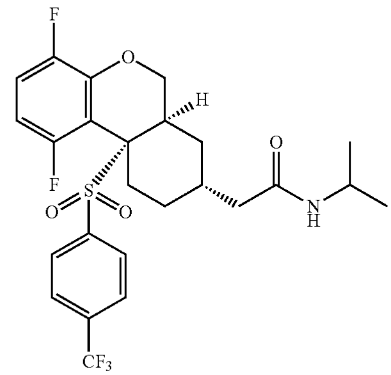 [SMILES: CC(C)NC(=O)C[C@@H]1CC[C@@]2(S(=O)(=O)c3ccc(C(F)(F)F)cc3)c3c(F)ccc(F)c3OC[C@H]2C1] | 532.3, 4.65 min. |
| 445 | 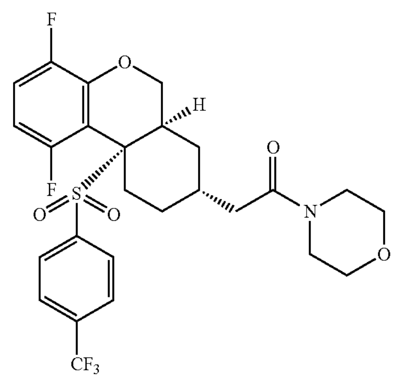 [SMILES: O=C(C[C@@H]1CC[C@@]2(S(=O)(=O)c3ccc(C(F)(F)F)cc3)c3c(F)ccc(F)c3OC[C@H]2C1)N1CCOCC1] | 560.3, 4.45 min. |
| 446 | 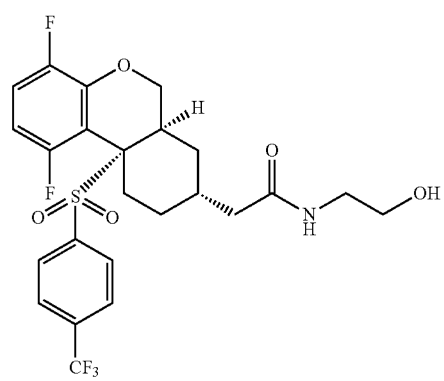 [SMILES: O=C(C[C@@H]1CC[C@@]2(S(=O)(=O)c3ccc(C(F)(F)F)cc3)c3c(F)ccc(F)c3OC[C@H]2C1)NCCO] | 534.3, 3.96 min. |
| 447 | 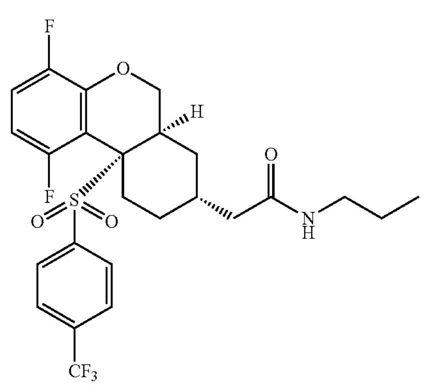 [SMILES: CCCNC(=O)C[C@@H]1CC[C@@]2(S(=O)(=O)c3ccc(C(F)(F)F)cc3)c3c(F)ccc(F)c3OC[C@H]2C1] | 532.3, 4.67 min. |

ASSAY

The pharmacological properties of the compounds of this invention may be evaluated by a number of pharmacological assays. The exemplified pharmacological assays, which are described later, have been carried out with the compounds according to the present invention, as well as with salts thereof.

Gamma-secretase activity was determined as described by Zhang et al. (Biochemistry, 40 (16), 5049-5055, 2001), which is herein incorporated by reference. Activity is expressed either as a percent inhibition or as the concentration of compound producing 50% inhibition of enzyme activity.

Reagents.

Antibodies W02, G2-10, and G2-11 were obtained from Dr. Konrad Beyreuther (University of Heidelberg, Heidelberg, Germany). W02 recognizes residues 5-8 of Aβ peptide, while G2-10 and G2-11 recognize the specific C-terminal structure of Aβ 40 and Aβ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction.

The construct SPC99-Ion, which contains the first 18 residues and the C-terminal 99 amino acids of APP carrying the London mutation, has been described (Zhang, L., Song, L, and Parker, E. (1999) J. Biol. Chem. 274, 8966-8972). Upon insertion into the membrane, the 17 amino acid signal peptide is processed, leaving an additional leucine at the N-terminus of Aβ. SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation.

C99 expression in cells was induced with 0.1 g/mL tetracycline for 20 h. The cells were pretreated with 1 M phorbol 12-myristate 13-acetate (PMA) and 1 M brefeldin A (BFA) for 5-6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70° C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis.

To measure γ-secretase activity, membranes were incubated at 37° C. for 1 h in 50 μL of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

The compounds of Examples 1-A, 1-B, 1-C, 1-D, 1-E, 1-I, 1-P, 1-Q, 1-U, 3G, 5-B, 7-A, 7-B, 8-A, 8-I, 8-L, 8-M, 8-P, 8-U, 8-Y, 8-Z, 9-B, and 11-C had an $IC_{50}$ higher than about 10 μM.

All other compounds from the other Examples had an $IC_{50}$ within the range of about 10 nM to about 10 μM.

The compounds of Examples 1, 2, 1-J, 1-K, 1-O, 1-R, 1-S, 1-T, 3, 4, 3-A, 3-B, 3-C, 3-E, 3-F, 3-H, 5, 6, 6-A, 7, 7-C, 7-E, 8, 8-B, 8-D, 8-J, 8-K, 8-O, 8-T, 8-V, 8-W, 10, 10-A, 10-B, 10-C, 10-D, 11, 11-B, 12, 13, 13A, 15, 15A, 16, 17, 18A, 18B, 19A, 20A-20L, 21-23, 24A-C, 25A, 25B, 26, 27A, 27B, and 28 had an $IC_{50}$ within the range of about 10 nM to about 3000 nM.

The compounds in Table 93 had a membrane $IC_{50}$ in the range of 1 nM to 100 nM.

TABLE 93

| Structure | Structure |
|---|---|
| (chemical structure) | (chemical structure) |

TABLE 93-continued

| Structure | Structure |
| --- | --- |

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
| --- | --- |

TABLE 93-continued

| Structure | Structure |
|---|---|

TABLE 93-continued

| Structure | Structure |
| --- | --- |

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
|---|---|

TABLE 93-continued

| Structure | Structure |
| --- | --- |

TABLE 93-continued

| Structure | Structure |
|---|---|

TABLE 93-continued
| Structure | Structure |
|---|---|
| 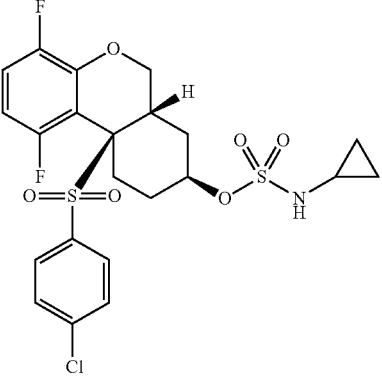 [SMILES: O=S(=O)(NC1CC1)O[C@H]1CC[C@]2(S(=O)(=O)c3ccc(Cl)cc3)c3c(F)ccc(F)c3OC[C@@H]2C1] | 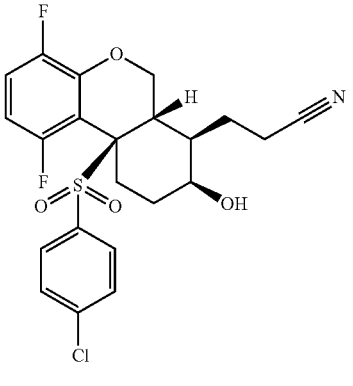 [SMILES: N#CCC[C@@H]1[C@H]2COc3c(F)ccc(F)c3[C@@]2(S(=O)(=O)c2ccc(Cl)cc2)CC[C@@H]1O] |
| 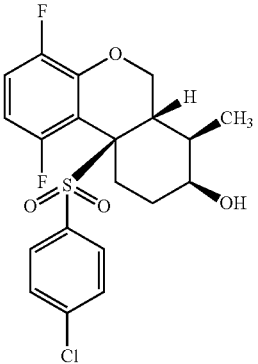 [SMILES: C[C@@H]1[C@H]2COc3c(F)ccc(F)c3[C@@]2(S(=O)(=O)c2ccc(Cl)cc2)CC[C@@H]1O] | 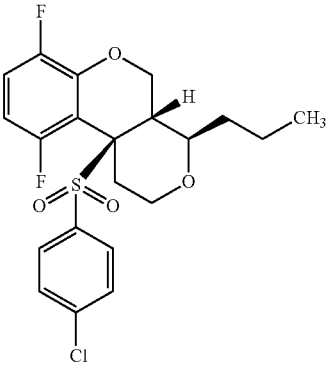 [SMILES: CCC[C@H]1OCC[C@]2(S(=O)(=O)c3ccc(Cl)cc3)c3c(F)ccc(F)c3OC[C@H]12] |
| 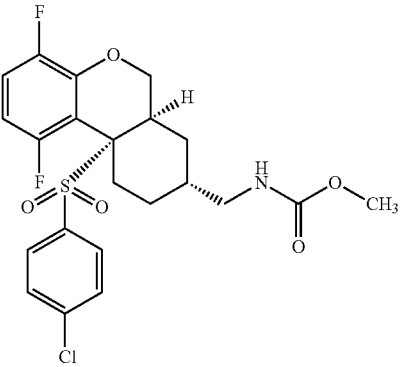 [SMILES: COC(=O)NC[C@@H]1CC[C@@]2(S(=O)(=O)c3ccc(Cl)cc3)c3c(F)ccc(F)c3OC[C@H]2C1] | 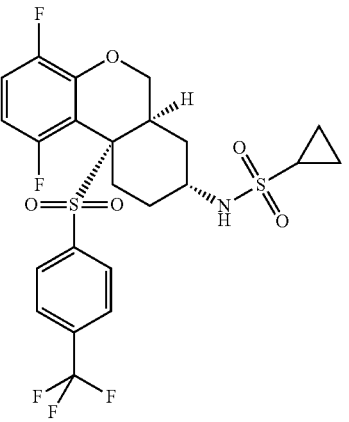 [SMILES: O=S(=O)(N[C@@H]1CC[C@@]2(S(=O)(=O)c3ccc(C(F)(F)F)cc3)c3c(F)ccc(F)c3OC[C@H]2C1)C1CC1] |
| 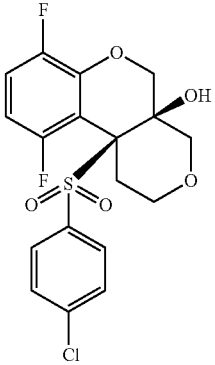 [SMILES: O=S(=O)(c1ccc(Cl)cc1)[C@]12CCOC[C@@]1(O)COc1c(F)ccc(F)c12] | 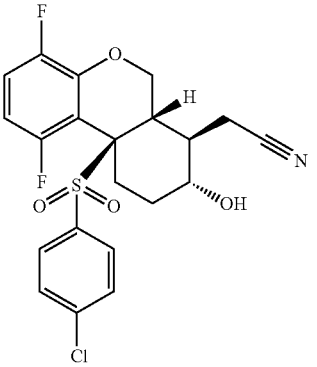 [SMILES: N#CC[C@H]1[C@H](O)CC[C@]2(S(=O)(=O)c3ccc(Cl)cc3)c3c(F)ccc(F)c3OC[C@H]12] |

TABLE 93-continued

| Structure | Structure |
|---|---|

TABLE 93-continued
| Structure | Structure |
|---|---|
| 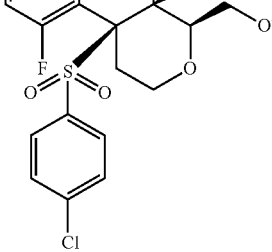 | 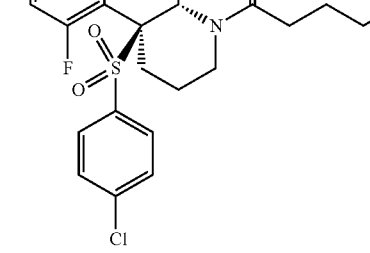 |
| 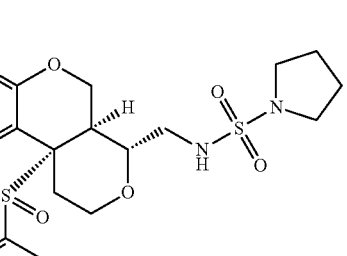 | 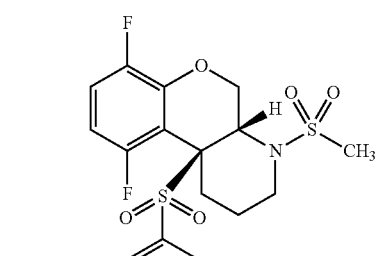 |
| 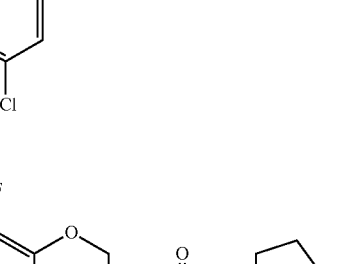 | 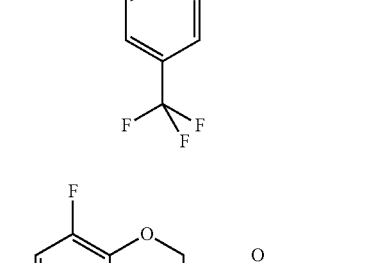 |
| 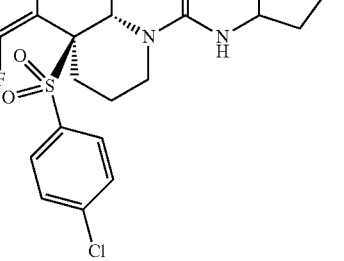 | 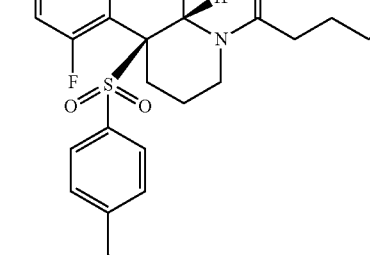 |

TABLE 93-continued

| Structure | Structure |
|---|---|

The IC$_{50}$ data for the compounds of Examples 20A, 141, 144, 180, 202, 208, 292, 379, 338, and 442, are given in Table 94.

TABLE 94

| Example | Structure | IC50 (nM) |
|---|---|---|
| 144 | 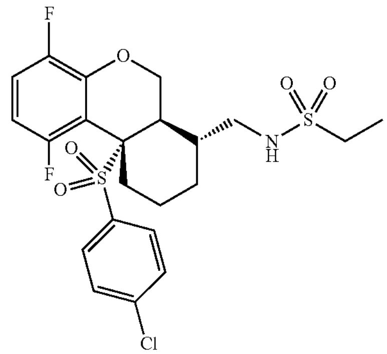 [SMILES: CCS(=O)(=O)NC[C@@H]1CCC[C@@]2(S(=O)(=O)c3ccc(Cl)cc3)c3c(F)ccc(F)c3OC[C@@H]12] | 1 |
| 202 | 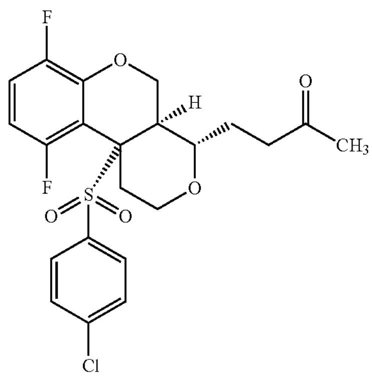 | 7 |
| 379 | 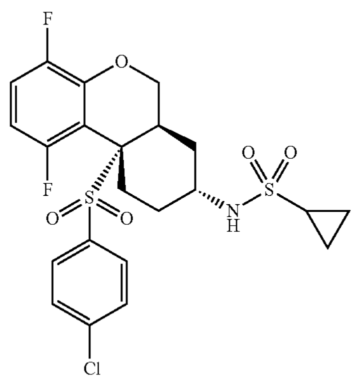 [SMILES: O=S(=O)(N[C@@H]1CC[C@@]2(S(=O)(=O)c3ccc(Cl)cc3)c3c(F)ccc(F)c3OC[C@H]2C1)C1CC1] | 8 |
| 338 | 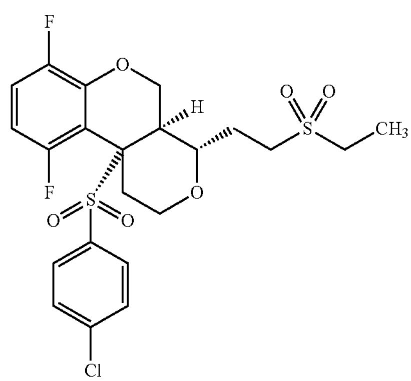 | 10 |

TABLE 94-continued

| Example | Structure | IC50 (nM) |
|---|---|---|
| 141 | 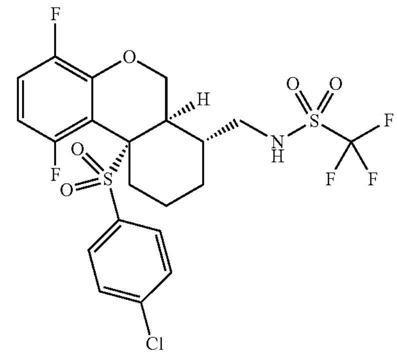 [SMILES: O=S(=O)(NC[C@@H]1CCC[C@@]2(S(=O)(=O)c3ccc(Cl)cc3)c3c(F)ccc(F)c3OC[C@@H]12)C(F)(F)F] | 14 |
| 208 | 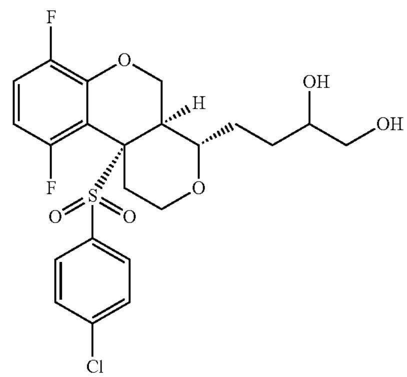 [SMILES: O=S(=O)(c1ccc(Cl)cc1)[C@@]12CCO[C@@H](CCC(O)CO)[C@@H]1COc1c(F)ccc(F)c12] | 15 |
| 442 | 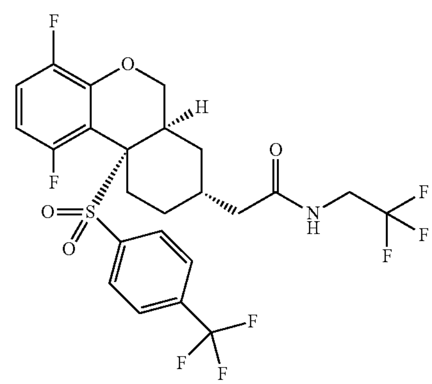 [SMILES: O=C(C[C@@H]1CC[C@@]2(S(=O)(=O)c3ccc(C(F)(F)F)cc3)c3c(F)ccc(F)c3OC[C@H]2C1)NCC(F)(F)F] | 25 |
| 20A (377) | 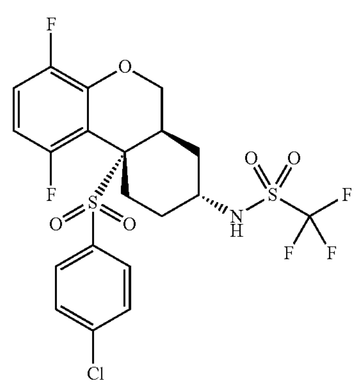 [SMILES: O=S(=O)(N[C@@H]1CC[C@@]2(S(=O)(=O)c3ccc(Cl)cc3)c3c(F)ccc(F)c3OC[C@H]2C1)C(F)(F)F] | 27 |

TABLE 94-continued

| Example | Structure | IC50 (nM) |
|---|---|---|
| 292 | 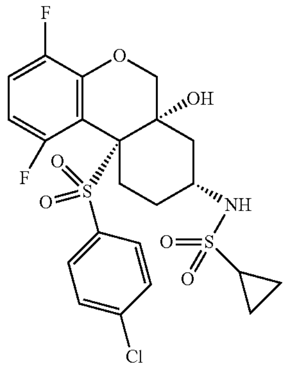 [SMILES: O=S(=O)(N[C@@H]1CC[C@@]2(S(=O)(=O)c3ccc(Cl)cc3)c3c(F)ccc(F)c3OC[C@@]2(O)C1)C1CC1] | 29 |
| 180 | 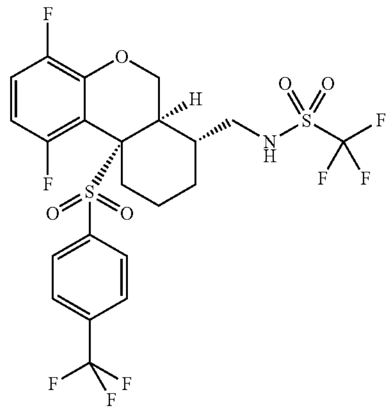 [SMILES: O=S(=O)(NC[C@@H]1CCC[C@@]2(S(=O)(=O)c3ccc(C(F)(F)F)cc3)c3c(F)ccc(F)c3OC[C@@H]12)C(F)(F)F] | 54 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound having the formula (IF):

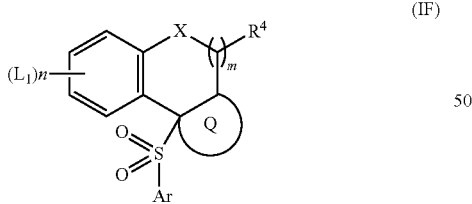

(IF)

or a pharmaceutically acceptable salt thereof,
wherein Q is a cyclohexyl ring unsubstituted or substituted with one or more independently selected $L^3$ groups;
X is —O—;
each $L^3$ is independently selected from the group consisting of: —CN, =O, $R^5$, —$OR^5$; =N—$R^5$ and —N($R^5$)$_2$;
$R^4$ is H or alkyl;
each $R^5$ is independently selected from the group consisting of: (1) H, (2) ($C_1$-$C_6$)alkyl, (3) hydroxyl substituted alkyl, (4) $R^6$, (5) $R^7$, (6) —C(O)—($C_1$-$C_6$)alkyl, (7) —C(O)—($C_1$-$C_6$)haloalkyl, (8) —C(O)—$R^6$, (9) —C(O)—$R^7$, (10) —C(O)NH—($C_1$-$C_6$)alkyl, (11) —C(O)N(($C_1$-$C_6$)alkyl)$_2$ wherein each alkyl group is independently selected, (12) —S(O)$_2$—($C_1$-$C_6$)alkyl, (13) —S(O)$_2$—($C_1$-$C_6$)haloalkyl, (14) —S(O)$_2$—$R^6$, (15) —S(O)$_2$—$R^7$, (16) —S(O)$_2$—$R^8$, (17) -alkylene-C(O)—($C_1$-$C_6$)alkyl, (18) -alkylene-C(O)—($C_1$-$C_6$)haloalkyl, (19) -alkylene-C(O)—$R^6$, (20) -alkylene-C(O)—$R^7$, (21) -alkylene-S(O)$_2$—($C_1$-$C_6$)alkyl, (22) -alkylene-S(O)$_2$—($C_1$-$C_6$)haloalkyl, (23) -alkylene-S(O)$_2$—$R^6$, (24) -alkylene-S(O)$_2$—$R^7$, (25) -alkylene-S(O)$_2$—$R^8$, (26) -alkylene-NHC(O)—($C_1$-$C_6$)alkyl, (27) -alkylene-NHC(O)—($C_1$-$C_6$)haloalkyl, (28) -alkylene-NHC(O)—$R^6$, (29) -alkylene-NHC(O)—$R^7$, (30) -alkylene-NHS(O)$_2$—($C_1$-$C_6$)alkyl, (31) -alkylene-NHS(O)$_2$—($C_1$-$C_6$)haloalkyl, (32) -alkylene-NHS(O)$_2$—$R^6$, (33) -alkylene-NHS(O)$_2$—$R^7$, (34) -alkylene-N(alkyl)C(O)—($C_1$-$C_6$)alkyl, (35) -alkylene-N(alkyl)C(O)—($C_1$-$C_6$)haloalkyl, (36) -alkylene-N(alkyl)C(O)—$R^6$, (37) -alkylene-N(alkyl)C(O)—$R^7$, (38) -alkylene-N(alkyl)S(O)$_2$—($C_1$-$C_6$)alkyl, (39) -alkylene-N(alkyl)S(O)$_2$—($C_1$-$C_6$)haloalkyl, (40) -alkylene-N(alkyl)S(O)$_2$—$R^6$, (41) -alkylene-N(alkyl)S(O)$_2$—$R^7$, (42) -alkylene-C(O)—NH—($C_1$-$C_6$)alkyl, (43) -alkylene-C(O)—NHR$^6$, (44) -alkylene-C(O)—NHR$^7$, (45) -alkylene-S(O)$_2$NH—($C_1$-$C_6$)alkyl, (46) -alkylene-S(O)$_2$NH—$R^6$, (47) -alkylene-S(O)$_2$NH—$R^7$, (48) -alkylene-C(O)—N(($C_1$-$C_6$)alkyl)$_2$ wherein each alkyl group is independently selected, (49) -alkylene-C(O)—N(alkyl)$R^6$, (50) -alkylene-C(O)—N(alkyl)$R^7$, (51) -alkylene-S(O)$_2$N(($C_1$-$C_6$)alkyl)$_2$ wherein each alkyl group is independently selected, (52) -alkylene-S(O)$_2$N(alkyl)-$R^6$, (53) -alkylene-S(O)$_2$N(alkyl)-$R^7$, (54) -alkylene-OH, (55) -alkylene-OC(O)—NH-alkyl, (56) -alkylene-OC(O)NH—$R^8$, (57) -alkylene-CN, (58) —$R^8$, (59) -alkylene-SH, (60) -alkylene-S(O)$_2$—NH—$R^8$, (61) -alkylene-S(O)$_2$-alkylene-$R^6$, (62) halo substituted alkylene, (63) —C(O)OR$^8$, (64) —C(O)O($C_1$-$C_6$)alkyl, (65) —C(O)R$^8$, (66) —C(O)-alkylene-β-($C_1$-$C_6$)alkyl, (67) —C(O)NH$_2$, (68) -alkylene-O—($C_1$-$C_6$)alkyl, (69) -alkylene-$R^8$, (70) —S(O)$_2$-halo($C_1$-$C_6$)alkyl, (71) hydroxy substituted halo($C_1$-$C_6$)alkyl, (72) -alkylene-NH$_2$, (73) -alkylene-NH—S(O)$_2$—$R^8$, (74) -alkylene-NH—C(O)—$R^8$, (75) -alkylene-NH—C(O)O—($C_1$-$C_6$)alkyl, (76) -alkylene-O—C(O)—($C_1$-$C_6$)alkyl, (77) -alkylene-O—S(O)$_2$—($C_1$-$C_6$)alkyl, (78) -alkylene-$R^6$, (79) -alkylene-$R^7$, (80) -alkylene-NH—C(O)—NH—($C_1$-$C_6$)alkyl, (81) -alkylene-N(S(O)$_2$halo($C_1$-$C_6$)alkyl)$_2$ wherein each —S(O)$_2$halo($C_1$-$C_6$)alkyl moiety is independently selected, (82) -alkylene-N(($C_1$-$C_6$)alkyl)S(O)$_2$R$^8$, (83) -alkylene-OC(O)—N(alkyl)$_2$ wherein each alkyl is independently selected, (84) -alkylene-NH—($C_1$-$C_6$)alkyl, (85) —C(O)-alkylene-C(O)O—($C_1$-$C_6$)alkyl, (86) —C(O)—C(O)—O—($C_1$-$C_6$)alkyl, (87) —C(O)-alkylene-$R^6$, (88) —C(O)—NH—$R^8$, (89) —C(O)—NH—$R^6$, (90) —C(O)—NH-alkylene-$R^6$, (91) —C(O)-alkylene-NH—S(O)$_2$-halo($C_1$-$C_6$)alkyl, (92) —C(O)-alkylene-NH—C(O)—O—($C_1$-$C_6$)alkyl, (93) —C(O)-alkylene-NH$_2$, (94) —C(O)-alkylene-NH—S(O)$_2$—$R^8$, (95) —C(O)-alkylene-NH—S(O)$_2$—($C_1$-$C_6$)alkyl, (96) —C(O)-alkylene-NH—C(O)—($C_1$-$C_6$)alkyl, (97) —C(O)-alkylene-N(S(O)$_2$($C_1$-$C_6$)alkyl)$_2$ wherein each —S(O)$_2$($C_1$-$C_6$)alkyl moiety is independently selected, (98) —C(O)-alkylene-NH—C(O)—NH—($C_1$-$C_6$)alkyl, (99)

-alkylene-O—$R^6$, (100) -alkylene-$R^7$, (101) —C(O)OH, (102) -alkylene-N(S(O)$_2$(C$_1$-C$_6$)alkyl)$_2$, (103) -alkylene-C(O)—O—(C$_1$-C$_6$)alkyl, (104) haloalkyl, (105) halo, (106) -alkylene —C(O)—NH$_2$, (107) =N—O—(C$_1$-C$_6$)alkyl, (108) =N—O-alkylene-$R^6$, (109) =N—O-alkenyl, (110) =N—O—$R^6$, (111) =N—NH—S(O)$_2$—$R^6$, (112) alkenyl, (113) =$R^8$, (114) -alkylene-O-alkylene-SK(C$_1$-C$_6$)alkyl)$_3$ wherein each alkyl is independently selected, (115) -alkylene-S(O)$_2$—N(alkylene-$R^6$)$_2$ wherein each alkylene-$R^6$ moiety is independently selected, (116) -alkylene-S(O)$_2$—NH$_2$, (117) —O—C(O)—$R^9$, (118) —O—C(O)—(C$_1$-C$_6$)alkyl, (119) —S(O)$_2$NH((C$_1$-C$_6$)alkyl), (120) —S(O)$_2$N((C$_1$-C$_6$)alkyl)$_2$ wherein each alkyl is independently selected, (121) —S(O)$_2$NH$R^8$, (122) -alkylene-C(O)OH, (123) -alkylene-C(O)NH(halo(C$_1$-C$_6$)alkyl), (124) -alkylene-C(O)—NH-alkylene-$R^8$, (125) -alkylene-C(O)—NH-alkylene-OH, (126) —C(O)O(haloC$_1$-C$_6$alkyl), (127) —C(O)O$R^6$, (128) —C(O)O$R^7$, (129) -alkylene-NHSO$_2$N(alkyl)$_2$ wherein each alkyl is independently selected, (130) -alkylene-NHSO$_2$NHalkyl, (131) -alkylene-N(alkyl)-SO$_2$N(alkyl)$_2$ wherein each alkyl is independently selected, (132) -alkylene-N(alkyl)-SO$_2$NHalkyl wherein each alkyl is independently selected, (133) -alkylene-O—SO$_2$-alkyl, (134) -alkylene-NH—C(O)—N(alkyl)$_2$ wherein each alkyl is independently selected, (135) -alkylene-NH—C(O)—NHalkyl, (136) -alkylene-N(alkyl)-C(O)—N-(alkyl)$_2$ wherein each alkyl is independently selected, (137) -alkylene-N(alkyl)-C(O)—NHalkyl, (138) —CN, (139) -alkylene-P(O)(Oalkyl)$_2$ wherein each alkyl is independently selected, (140) -alkylene-CH(OH)—P(O)(Oalkyl)$_2$ wherein each alkyl is independently selected, (141) -alkylene-OC(O)N(C$_1$-C$_6$ alkyl)-$R^8$, (142) -alkylene-S(O)$_2$—N(C$_1$-C$_6$ alkyl)-$R^8$, (143) -alkylene-N(C$_1$-C$_6$ alkyl)-S(O)$_2$—$R^8$, (144) -alkylene-N(C$_1$-C$_6$ alkyl)-C(O)—$R^8$, (145) -alkylene-N(C$_1$-C$_6$ alkyl)-C(O)O—(C$_1$-C$_6$) alkyl wherein each alkyl is independently selected, (146) -alkylene-N(C$_1$-C$_6$ alkyl)-C(O)—NH—(C$_1$-C$_6$)alkyl wherein each alkyl is independently selected, (147) -alkylene-NH—C(O)—N(C$_1$-C$_6$ alkyl)$_2$ wherein each alkyl is independently selected, (148) -alkylene-N(C$_1$-C$_6$ alkyl)-C(O)—N(C$_1$-C$_6$ alkyl)$_2$ wherein each alkyl is independently selected, (149) —C(O)—N(C$_1$-C$_6$ alkyl)-$R^8$, (150) —C(O)—N(C$_1$-C$_6$ alkyl)-$R^6$, (151) —C(O)—N(C$_1$-C$_6$ alkyl)-alkylene-$R^6$, (152) —C(O)-alkylene-N(C$_1$-C$_6$ alkyl)-S(O)$_2$-halo(C$_1$-C$_6$)alkyl wherein each alkyl is independently selected, (153) —C(O)-alkylene-N(C$_1$-C$_6$ alkyl)-C(O)—O—(C$_1$-C$_6$)alkyl wherein each alkyl is independently selected, (154) —C(O)-alkylene-NH(C$_1$-C$_6$ alkyl), (155) —C(O)-alkylene-N(C$_1$-C$_6$ alkyl)$_2$ wherein each alkyl is independently selected, (156) —C(O)-alkylene-N(C$_1$-C$_6$ alkyl)-S(O)$_2$—$R^8$, (157) —C(O)-alkylene-N(C$_1$-C$_6$ alkyl)-S(O)$_2$—(C$_1$-C$_6$)alkyl, (158) —C(O)-alkylene-N(C$_1$-C$_6$ alkyl)-C(O)—(C$_1$-C$_6$)alkyl, (159) —C(O)-alkylene-N(C$_1$-C$_6$ alkyl)-C(O)—NH—(C$_1$-C$_6$)alkyl wherein each alkyl is independently selected, (160) —C(O)-alkylene-NH—C(O)—N((C$_1$-C$_6$)alkyl)$_2$ wherein each alkyl is independently selected, (161) —C(O)-alkylene-N(C$_1$-C$_6$ alkyl)-C(O)—N((C$_1$-C$_6$) alkyl)$_2$ wherein each alkyl is independently selected, (162) -alkylene-C(O)—N(C$_1$-C$_6$ alkyl)$_2$ wherein each alkyl is independently selected, (163) =N—N(C$_1$-C$_6$ alkyl)-S(O)$_2$—$R^6$, (164) —S(O)$_2$N(C$_1$-C$_6$ alkyl)$R^8$, (165) -alkylene-C(O)N(C$_1$-C$_6$ alkyl)(halo(C$_1$-C$_6$)alkyl) wherein each alkyl group is independently selected, (166) -alkylene-C(O)N(halo(C$_1$-C$_6$)alkyl)$_2$ wherein each alkyl group is independently selected, (167) -alkylene-C(O)—N(C$_1$-C$_6$ alkyl)-alkylene-$R^8$, (168) -alkylene-C(O)—N(C$_1$-C$_6$ alkyl)-alkylene-OH, and (169) —O—C(O)—$R^7$;

$R^6$ is selected from the group consisting of: unsubstituted (C$_6$-C$_{14}$)aryl, (C$_6$-C$_{14}$)aryl substituted with one or more $L^1$ groups, unsubstituted (C$_5$-C$_{14}$)heteroaryl, and (C$_5$-C$_{14}$)heteroaryl substituted with one or more $L^1$ groups;

$R^7$ is selected from the group consisting of unsubstituted heterocycloalkyl and heterocycloalkyl substituted with one or more $L^2$ groups;

$R^8$ is selected from the group consisting of unsubstituted cycloalkyl and cycloalkyl substituted with one or more $L^3$ groups;

Ar is unsubstituted phenyl or phenyl substituted with one or more $L^1$ groups;

$R^9$ is a bridged multicyclic heterocycloalkyl ring wherein said $R^9$ moiety is unsubstituted or said $R^9$ moiety is substituted with one or more $L^2$ groups;

each $L^1$ is independently selected from the group consisting of: halogen, alkyl, —CN, —CF$_3$, —O—(C$_1$-C$_6$) alkyl, —O-(halo(C$_1$-C$_6$)alkyl), —C(O)—O—(C$_1$-C$_6$) alkyl, -alkylene-OH, halo(C$_1$-C$_6$)alkyl, hydroxyalkoxy-, and alkoxyalkoxy-;

each $L^2$ is independently selected from the group consisting of: (a) —OH, (b) alkyl, (c) alkyl substituted with one or more —OH groups, (d) halo, (e) haloalkyl, and (f) heterocycloalkyl;

n is 0, 1, 2 or 3; and m is 1; and provided that for the substituent —O$R^5$, the $R^5$ moiety and the oxygen atom to which it is bound to does not form a —O—O— group; and provided that for the substituents —O$R^5$, =N—$R^5$ and —NH$R^5$, $R^5$ is not —CH$_2$OH, —CH$_2$NH$_2$, —CH$_2$NHalkyl, —CH$_2$NHaryl or —C(O)OH.

2. The compound of claim 1 or a pharmaceutically acceptable salt thereof, wherein each $L^3$ is the same or different —NH$R^5$ group, and each $R^5$ is independently selected from the group consisting of: —S(O)$_2$—(C$_1$-C$_6$)alkyl, —S(O)$_2$—(C$_1$-C$_6$)haloalkyl, —S(O)$_2$$R^6$, —S(O)$_2$$R^7$ and —S(O)$_2$$R^8$.

3. The compound of claim 1 or a pharmaceutically acceptable salt thereof, wherein each $L^3$ is the same or different O$R^5$ group, and each $R^5$ is independently selected from the group consisting of: H, (C$_1$-C$_6$)alkyl, $R^6$, $R^7$, —C(O)—(C$_1$-C$_6$) alkyl, —C(O)—C$_1$-C$_6$)haloalkyl, —C(O)—$R^6$, and —C(O)—$R^7$.

4. The compound of claim 1 or a pharmaceutically acceptable salt thereof, wherein each $L^3$ is the same or different $R^5$ group, and each $R^5$ is independently selected from the group consisting of: H, (C$_1$-C$_6$)alkyl, $R^6$, $R^7$, S(O)$_2$—(C$_1$-C$_6$)alkyl, —S(O)$_2$—(C$_1$-C$_6$)haloalkyl, —S(O)$_2$$R^6$, —S(O)$_2$$R^7$, —S(O)$_2$$R^8$, —C(O)—(C$_1$-C$_6$)alkyl, —C(O)—(C$_1$-C$_6$)haloalkyl, —C(O)—$R^6$, and —C(O)—$R^7$.

5. The compound of claim 1 or a pharmaceutically acceptable salt thereof, wherein $R^4$ is H.

6. The compound of claim 1 or a pharmaceutically acceptable salt thereof, wherein $L^1$ is halogen.

7. The compound of claim 1 or a pharmaceutically acceptable salt thereof, wherein $L^1$ is halogen wherein each halogen is individually selected from the group consisting of: Cl and F.

8. The compound of claim 1 or a pharmaceutically acceptable salt thereof, wherein substituent Ar is phenyl substituted with one or more $L^1$ groups.

9. The compound of claim 1 or a pharmaceutically acceptable salt thereof, wherein substituent Ar is phenyl substituted with an $L^1$ group wherein said $L^1$ group is halogen or halo $(C_1\text{-}C_6)$alkyl.

10. The compound of claim 1 or a pharmaceutically acceptable salt thereof, wherein substituent Ar is phenyl substituted with an $L^1$ group wherein said $L^1$ group is Cl or —$CF_3$.

11. The compound of claim 1 or a pharmaceutically acceptable salt thereof, wherein n is 1 or 2.

12. The compound of claim 1 or a pharmaceutically acceptable salt thereof, wherein n is 1.

13. The compound of claim 1 or a pharmaceutically acceptable salt thereof, wherein n is 2.

14. The compound of claim 1 or a pharmaceutically acceptable salt thereof, wherein $L^1$ is halogen wherein each halogen is independently selected from the group consisting of Cl and Br, and n is 2.

15. The compound of claim 1 or a pharmaceutically acceptable salt thereof, wherein $L^1$ is F and n is 2.

16. The compound of claim 1 or a pharmaceutically acceptable salt thereof, wherein n is 2, and $L^1$ is selected from the group consisting of Cl and F.

17. The compound of claim 1 or a pharmaceutically acceptable salt thereof, wherein n is 2, $L^1$ is selected from the group consisting of Cl and F, and Ar is phenyl substituted with Cl.

18. The compound of claim 1 or a pharmaceutically acceptable salt thereof, wherein n is 2, and $L^1$ is F.

19. The compound of claim 1 or a pharmaceutically acceptable salt thereof, wherein n is 2, $L^1$ is F, and Ar is phenyl substituted with Cl.

20. The compound of claim 1 or a pharmaceutically acceptable salt thereof, wherein the compound of formula (IF) is a compound of formula (IF.1):

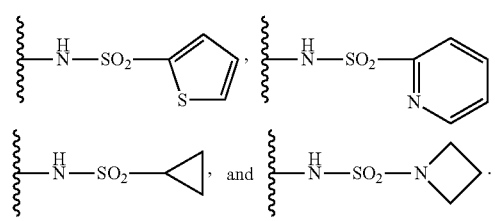

(IF.1)

21. The compound of claim 20 or a pharmaceutically acceptable salt thereof, wherein $R^4$ is H, $L^1$ is F, and Ar is phenyl substituted with Cl.

22. The compound of claim 1 or a pharmaceutically acceptable salt thereof, wherein Q is

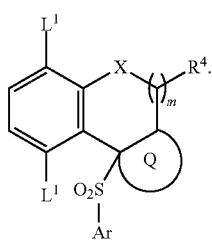

23. The compound of claim 1 or a pharmaceutically acceptable salt thereof, wherein Q is:

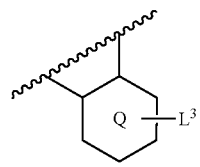

wherein $L^3$ is selected from the group consisting of: =O, —$OR^5$, —$NHR^5$, —$SO_2R^6$, —$SO_2R^7$, and —$SO_2R^8$, wherein $R^5$ is selected from the group consisting of: —$SO_2$—$(C_1\text{-}C_6)$haloalkyl, —$C(O)$—$(C_1\text{-}C_6)$alkyl, —$C(O)NH(C_1\text{-}C_6)$alkyl, —$SO_2$—$(C_1\text{-}C_6)$alkyl, and —$(C_1\text{-}C_6)$alkyl, and wherein $R^6$ is unsubstituted $(C_5\text{-}C_{14})$ heteroaryl, and wherein $R^7$ is an unsubstituted heterocycloalkyl ring, and wherein $R^8$ is an unsubstituted cycloalkyl ring.

24. The compound of claim 23 or a pharmaceutically acceptable salt thereof, wherein $L^3$ is selected from the group consisting of: =O, —OH, —$NH_2$, —$NHSO_2CF_3$, —$NHC(O)CH_3$, —$NHC(O)NHCH_2CH_3$, —$NHSO_2CH_3$, —$NHSO_2CH_2CH_3$, —$NHSO_2CH_2CH_2CH_3$, —$OCH_3$,

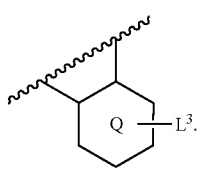

25. The compound of claim 20 or a pharmaceutically acceptable salt thereof, wherein Q is

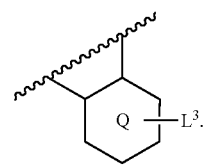

26. The compound of claim 20 or a pharmaceutically acceptable salt thereof, wherein Q is:

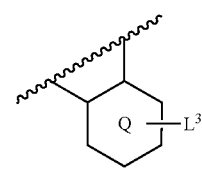

wherein $L^3$ is selected from the group consisting of: =O, —$OR^5$, —$NHR^5$, —$SO_2R^6$, —$SO_2R^7$, and —$SO_2R^8$, wherein $R^5$ is selected from the group consisting of: —$SO_2$—$(C_1\text{-}C_6)$haloalkyl, —$C(O)$—$(C_1\text{-}C_6)$alkyl, —$C(O)NH(C_1\text{-}C_6)$alkyl, —$SO_2$—$(C_1\text{-}C_6)$alkyl, and —$(C_1\text{-}C_6)$alkyl, and wherein $R^6$ is unsubstituted $(C_5\text{-}C_{14})$heteroaryl, and wherein $R^7$ is an unsubstituted heterocycloalkyl ring, and wherein $R^8$ is an unsubstituted cycloalkyl ring.

27. The compound of claim 26 or a pharmaceutically acceptable salt thereof, wherein $L^3$ is selected from the group consisting of: =O, —OH, —NH$_2$, —NHSO$_2$CF$_3$, —NHC(O)CH$_3$, —NHC(O)NHCH$_2$CH$_3$, —NHSO$_2$CH$_3$, —NHSO$_2$CH$_2$CH$_3$, —NHSO$_2$CH$_2$CH$_2$CH$_3$, —OCH$_3$,

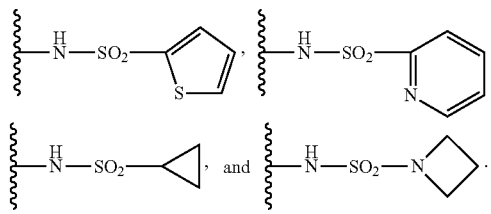

28. The compound of claim 21 or a pharmaceutically acceptable salt thereof, wherein Q is:

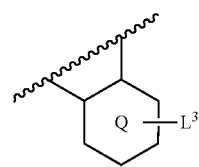

wherein L$^3$ is selected from the group consisting of: =O, —OR$^5$, —NHR$^5$, —SO$_2$R$^6$, —SO$_2$R$^7$, and —SO$_2$R$^8$, wherein R$^5$ is selected from the group consisting of: —SO$_2$—(C$_1$-C$_6$)haloalkyl, —C(O)—(C$_1$-C$_6$)alkyl, —C(O)NH(C$_1$-C$_6$)alkyl, —SO$_2$—(C$_1$-C$_6$)alkyl, and —(C$_1$-C$_6$)alkyl, and wherein R$^6$ is unsubstituted (C$_5$-C$_{14}$) heteroaryl, and wherein R$^7$ is an unsubstituted heterocycloalkyl ring, and wherein R$^8$ is an unsubstituted cycloalkyl ring.

29. The compound of claim 28 or a pharmaceutically acceptable salt thereof, wherein L$^3$ is selected from the group consisting of: =O, —OH, —NH$_2$, —NHSO$_2$CF$_3$, —NHC(O)CH$_3$, —NHC(O)NHCH$_2$CH$_3$, —NHSO$_2$CH$_3$, —NHSO$_2$CH$_2$CH$_3$, —NHSO$_2$CH$_2$CH$_2$CH$_3$, —OCH$_3$,

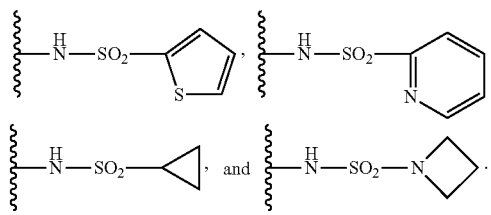

30. The compound of claim 1 or a pharmaceutically acceptable salt thereof, having formula (IF.1A):

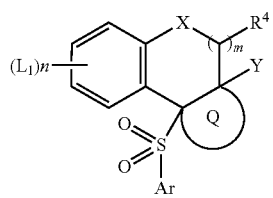

(IF.1A)

wherein Q is an unsubstituted cyclohexyl ring or, cyclohexyl substituted with one or more independently selected L$^3$ groups, unsubstituted heterocycloalkyl, and heterocycloalkyl substituted with one or more independently selected L$^3$ groups, and wherein Y is bound to the carbon atom common to the two fused rings and Y is selected from the group consisting of: —NHR$^5$, —OH, and —OR$^5$.

31. The compound of claim 1 or a pharmaceutically acceptable salt thereof, wherein ring Q is:

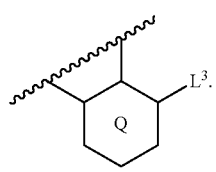

32. The compound of claim 1 or a pharmaceutically acceptable salt thereof, wherein ring Q is:

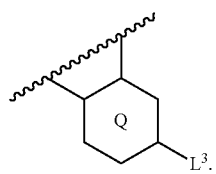

33. The compound of claim 20 or a pharmaceutically acceptable salt thereof, wherein ring Q is:

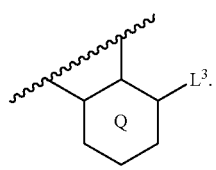

34. The compound of claim 20 or a pharmaceutically acceptable salt thereof, wherein ring Q is:

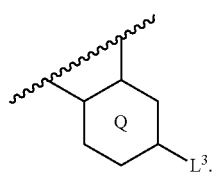

35. The compound of claim 1 or a pharmaceutically acceptable salt thereof, wherein ring Q is a substituted cyclohexyl ring:

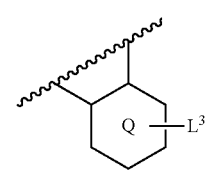

wherein L$^3$ is selected from the group consisting of: -alkylene-C(O)NH(C$_1$ to C$_6$)alkyl, alkylene-C(O)N((C$_1$ to C₆)alkyl)₂ wherein each alkyl is independently selected, -alkylene-C(O)NH(C₁ to C₆)haloalkyl, and -alkylene-C(O)N((C₁ to C₆)haloalkyl)₂ wherein each alkyl is independently selected.

36. The compound of claim 35 or a pharmaceutically acceptable salt thereof, wherein $L^3$ is selected from the group consisting of: —CH₂C(O)NHC₂H₅, —CH₂C(O)NHCH₃, and —CH₂C(O)NHCH₂CF₃.

37. The compound of claim 1 or a pharmaceutically acceptable salt thereof, wherein Q is a substituted cyclohexyl ring:

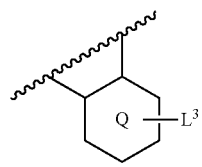

wherein $L^3$ is selected from the group consisting of: -alkylene-NHS(O)₂—(C₁-C₆)alkyl, and -alkylene-NHS(O)₂—(C₁-C₆)haloalkyl.

38. The compound of claim 37 or a pharmaceutically acceptable salt thereof, wherein $L^3$ is selected from the group consisting of: —CH₂NHS(O)₂CH₂CH₃ and —CH₂NHS(O)₂CF₃.

39. The compound of claim 1 or a pharmaceutically acceptable salt thereof, wherein Q is a substituted cyclohexyl ring:

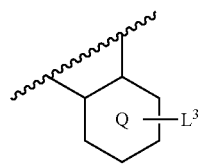

wherein $L^3$ is hydroxyl substituted alkyls.

40. The compound of claim 39 or a pharmaceutically acceptable salt thereof, wherein $L^3$ is selected from the group consisting of: —CH₂CH(OH)CH₂CH₃ and —CH₂CH₂CH(OH)CH₂OH).

41. The compound of claim 1 or a pharmaceutically acceptable salt thereof, wherein Q is a substituted cyclohexyl ring:

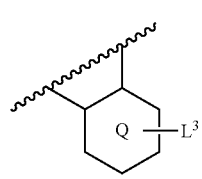

wherein $L^3$ is -alkylene-S(O)₂—(C₁-C₆)alkyl.

42. The compound of claim 41 or a pharmaceutically acceptable salt thereof, wherein $L^3$ is —CH₂CH₂SO₂CH₂CH₃ or —CH₂CH₂SO₂CH₃.

43. The compound of claim 1 or a pharmaceutically acceptable salt thereof, wherein Q is a substituted cyclohexyl ring:

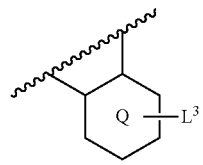

wherein $L^3$ is -alkylene-C(O)—(C₁-C₆)alkyl.

44. The compound of claim 43 or a pharmaceutically acceptable salt thereof, wherein $L^3$ is —CH₂CH₂—C(O)—CH₃.

45. The compound of claim 20 or a pharmaceutically acceptable salt thereof, wherein ring Q is a substituted cyclohexyl ring:

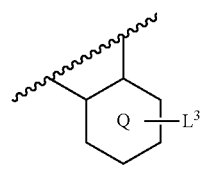

wherein $L^3$ is selected from the group consisting of: -alkylene-C(O)NH(C₁ to C₆)alkyl, alkylene-C(O)N((C₁ to C₆)alkyl)₂ wherein each alkyl is independently selected, -alkylene-C(O)NH(C₁ to C₆)haloalkyl, and -alkylene-C(O)N((C₁ to C₆)haloalkyl)₂ wherein each alkyl is independently selected.

46. The compound of claim 45 or a pharmaceutically acceptable salt thereof, wherein $L^3$ is selected from the group consisting of: —CH₂C(O)NHC₂H₆, —CH₂C(O)NHCH₃, and —CH₂C(O)NHCH₂CF₃.

47. The compound of claim 20 or a pharmaceutically acceptable salt thereof, wherein Q is a substituted cyclohexyl ring:

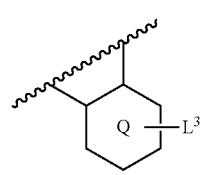

wherein $L^3$ is selected from the group consisting of: -alkylene-NHS(O)₂—(C₁-C₆)alkyl, and -alkylene-NHS(O)₂—(C₁-C₆)haloalkyl.

48. The compound of claim 47 or a pharmaceutically acceptable salt thereof, wherein $L^3$ is selected from the group consisting of: —CH₂NHS(O)₂CH₂CH₃ and —CH₂NHS(O)₂CF₃.

49. The compound of claim 20 or a pharmaceutically acceptable salt thereof, wherein Q is a substituted cyclohexyl ring:

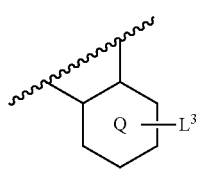

wherein L³ is hydroxyl substituted alkyls.

50. The compound of claim 49 or a pharmaceutically acceptable salt thereof, wherein L³ is selected from the group consisting of: —CH₂CH(OH)CH₂CH₃ and —CH₂CH₂CH(OH)CH₂OH).

51. The compound of claim 20 or a pharmaceutically acceptable salt thereof, wherein Q is a substituted cyclohexyl ring:

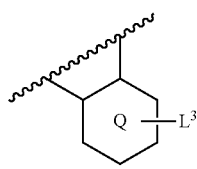

wherein L³ is selected from the group consisting of: -alkylene-S(O)₂—(C₁-C₆)alkyl.

52. The compound of claim 51 or a pharmaceutically acceptable salt thereof, wherein L³ is —CH₂CH₂SO₂CH₂CH₃ or —CH₂CH₂SO₂CH₃.

53. The compound of claim 20 or a pharmaceutically acceptable salt thereof, wherein Q is a substituted cyclohexyl ring:

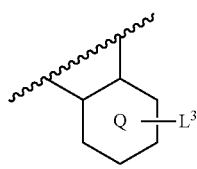

wherein L³ is -alkylene-C(O)—(C₁-C₆)alkyl.

54. The compound of claim 53 or a pharmaceutically acceptable salt thereof, wherein L³ is —CH₂CH₂—C(O)—CH₃.

55. The compound of claim 45 or a pharmaceutically acceptable salt thereof, wherein R⁴ is H, L¹ is F, and Ar is phenyl substituted with Cl.

56. The compound of claim 47 or a pharmaceutically acceptable salt thereof, wherein R⁴ is H, L¹ is F, and Ar is phenyl substituted with Cl.

57. The compound of claim 49 or a pharmaceutically acceptable salt thereof, wherein R⁴ is H, L¹ is F, and Ar is phenyl substituted with Cl.

58. The compound of claim 51 or a pharmaceutically acceptable salt thereof, R⁴ is H, L¹ is F, and Ar is phenyl substituted with Cl.

59. The compound of claim 53 or a pharmaceutically acceptable salt thereof, wherein R⁴ is H, L¹ is F, and Ar is phenyl substituted with Cl.

60. The compound of claim 58 or a pharmaceutically acceptable salt thereof, wherein L³ is selected from the group consisting of: —CH₂C(O)NHC₂H₅, —CH₂C(O)NHCH₃ and —CH₂C(O)NHCH₂CF₃.

61. The compound of claim 1 or a pharmaceutically acceptable salt thereof, selected from the group consisting of the compounds

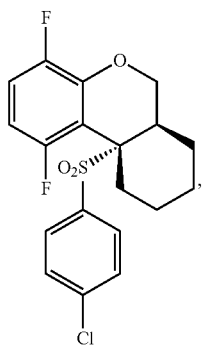 , 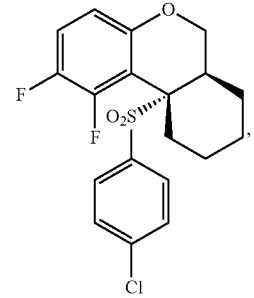 ,

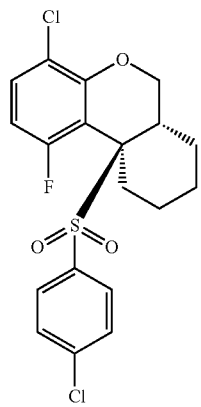 , 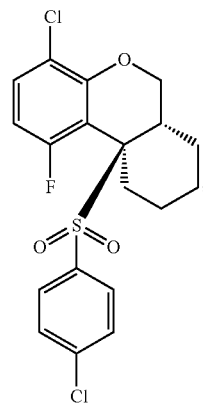 ,

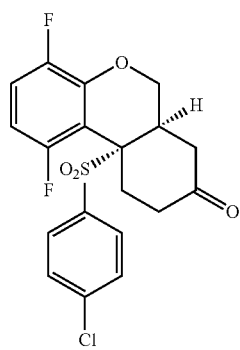 , 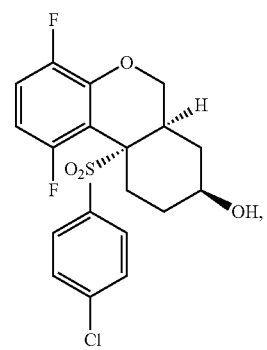 ,

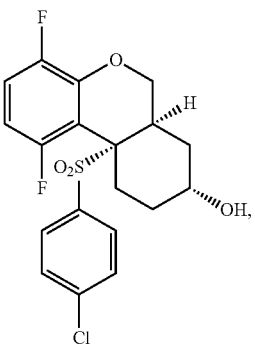 , 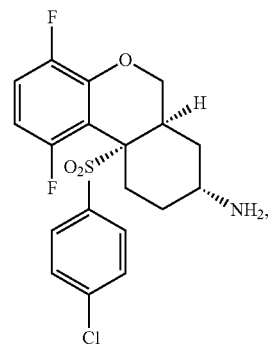 ,

487
-continued
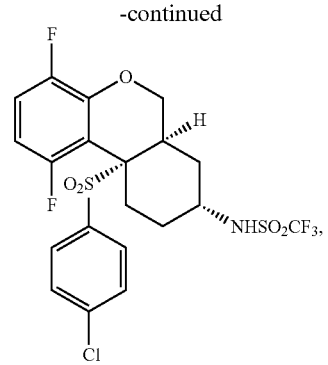
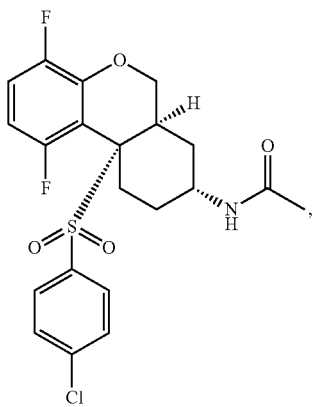
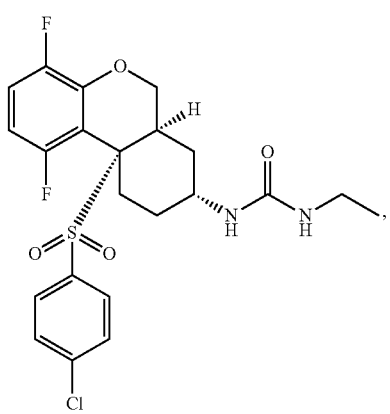
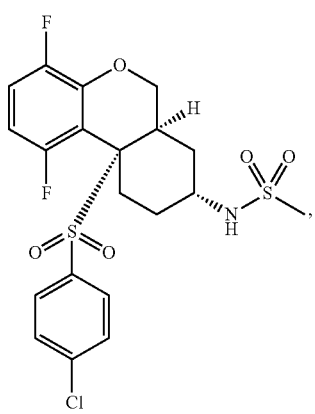
488
-continued
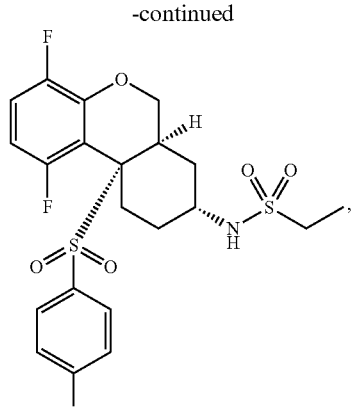
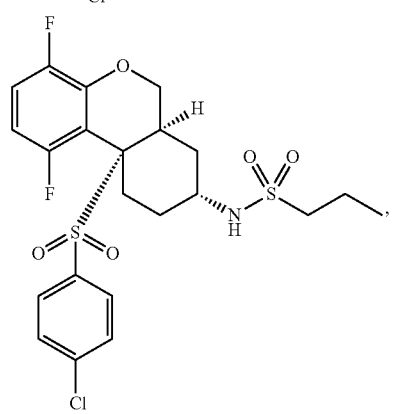
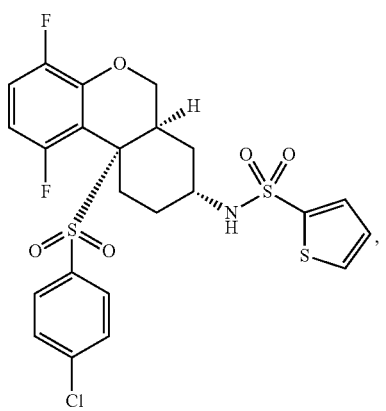
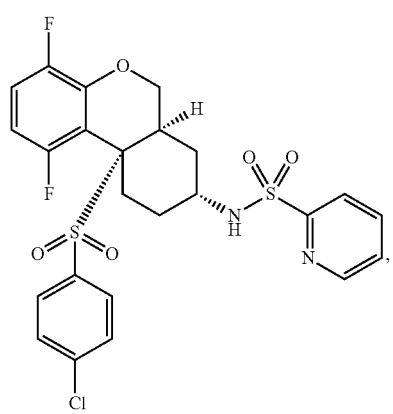

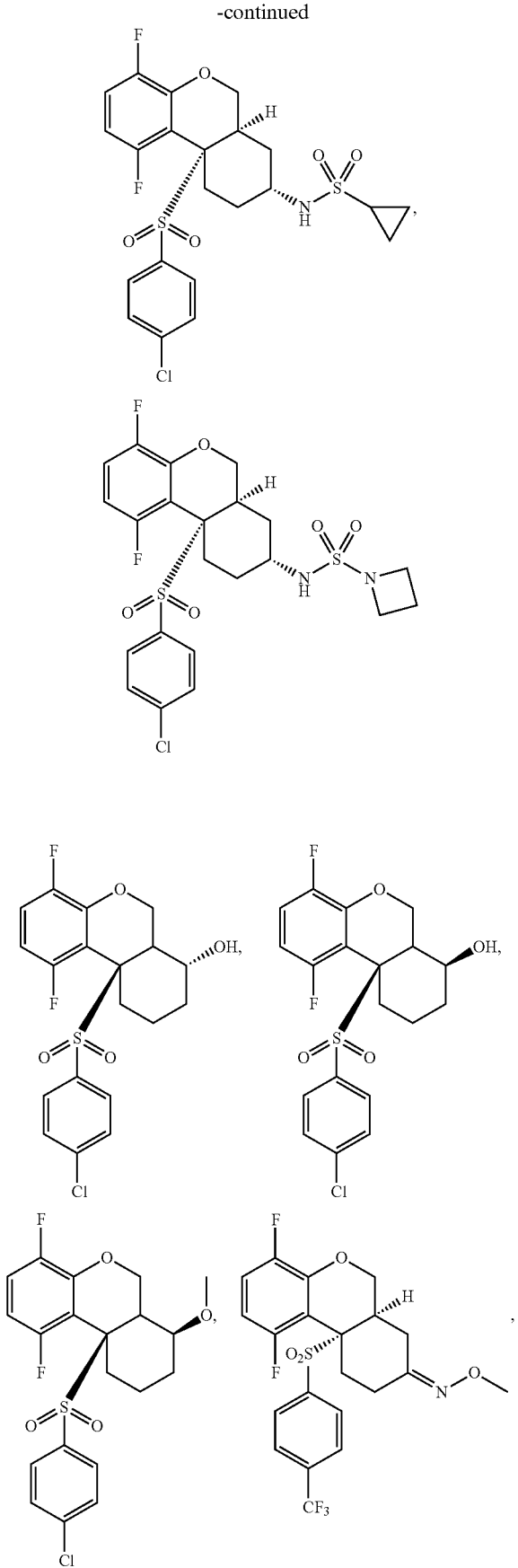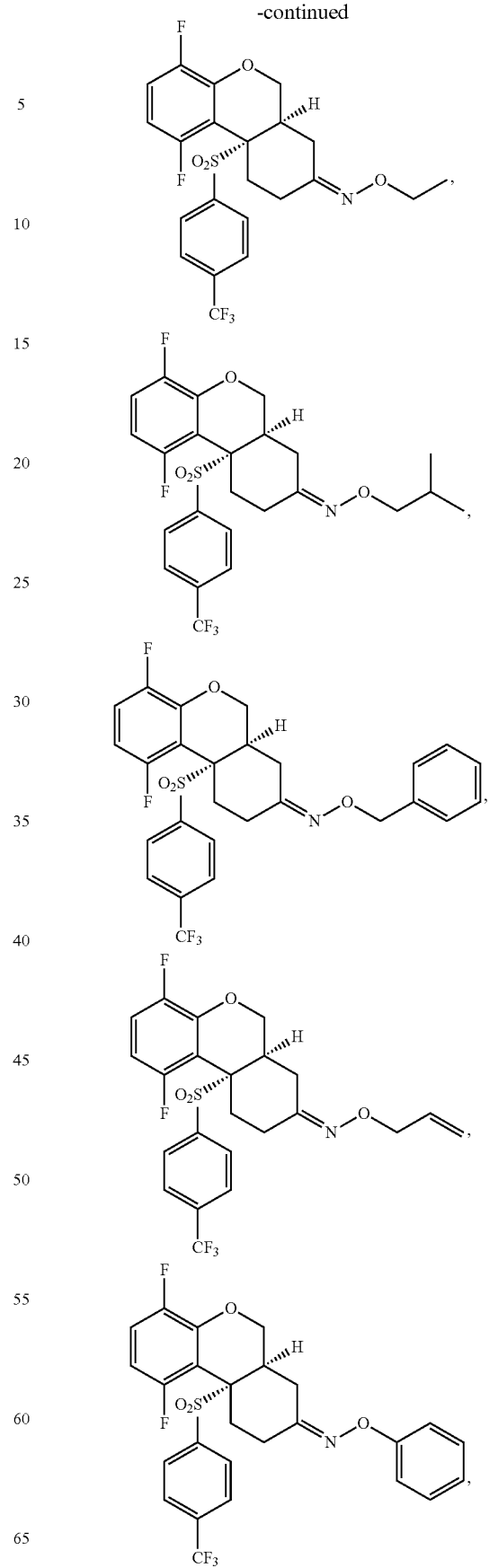

491
-continued
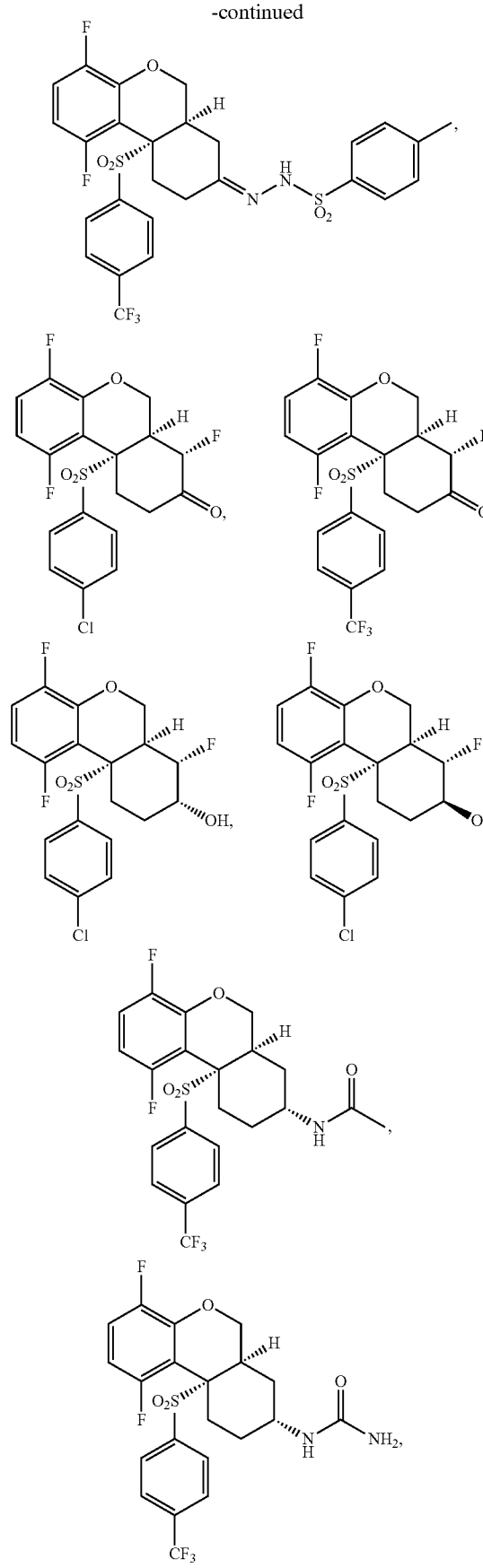
492
-continued
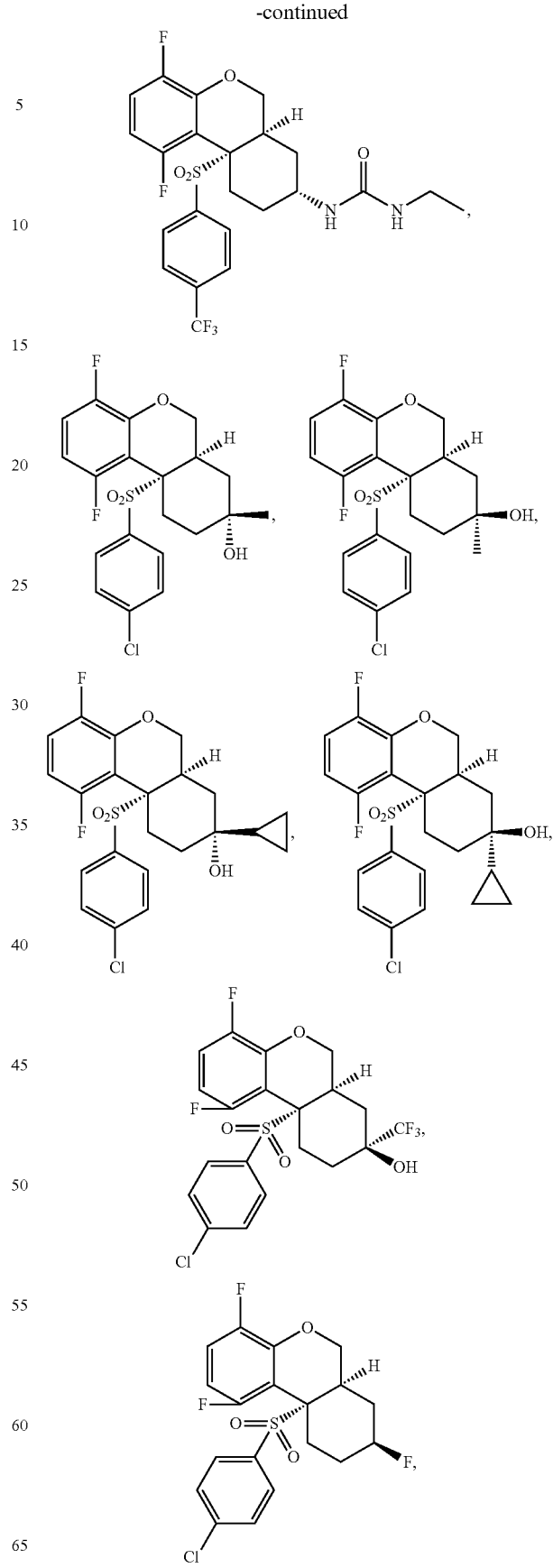

493
-continued
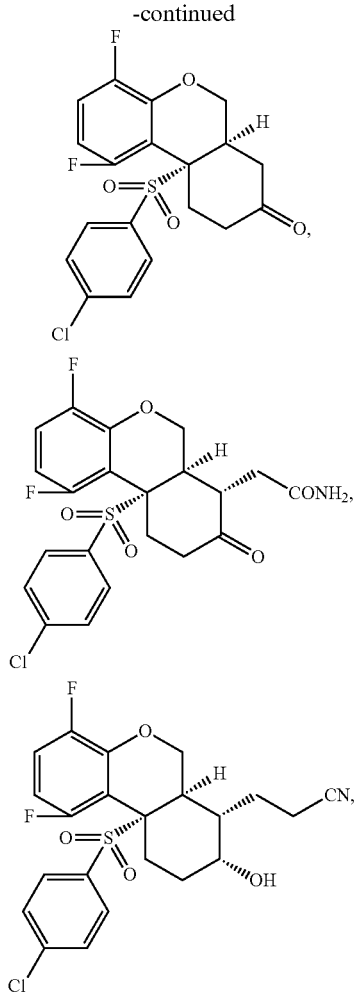
494
-continued
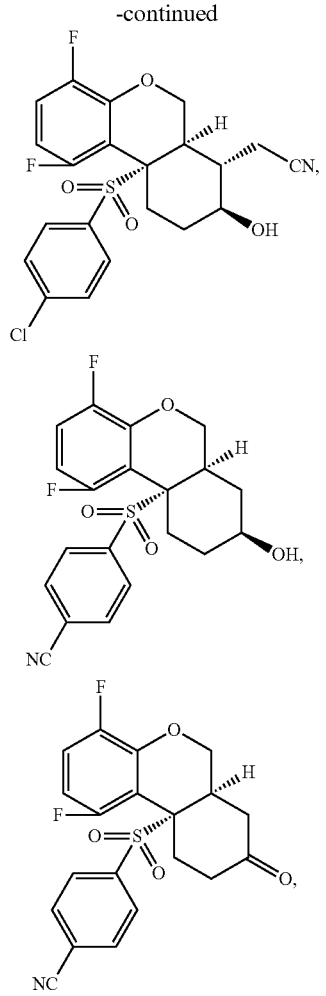
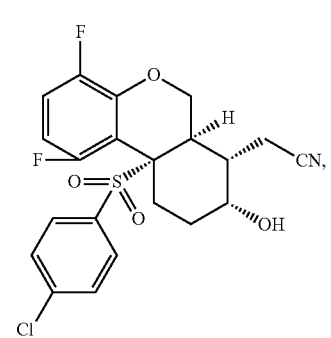
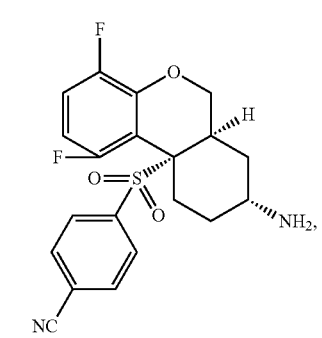
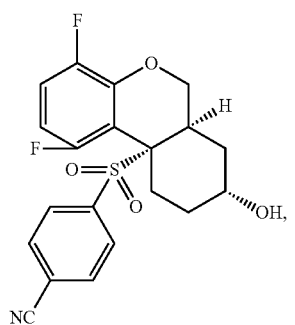
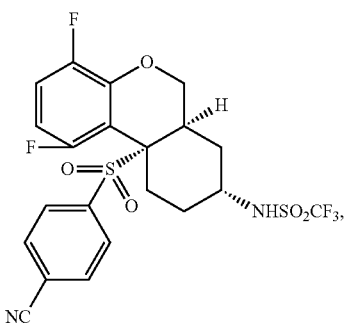

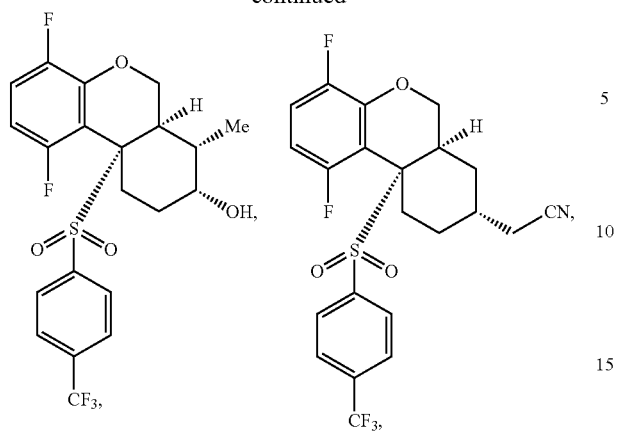
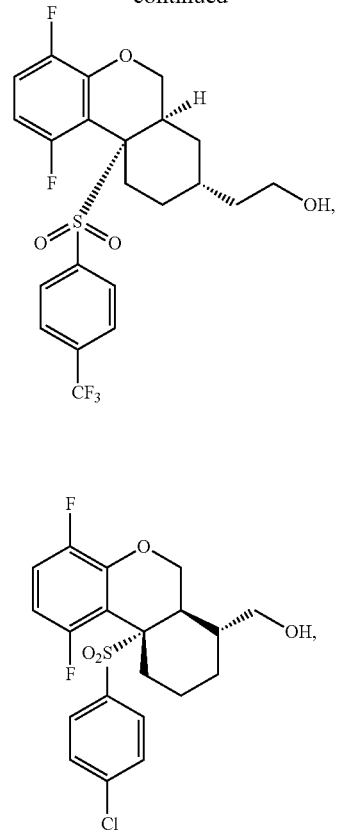
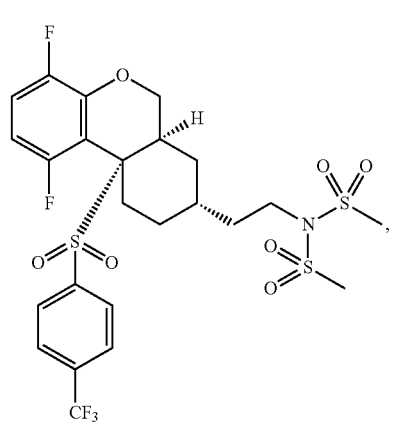
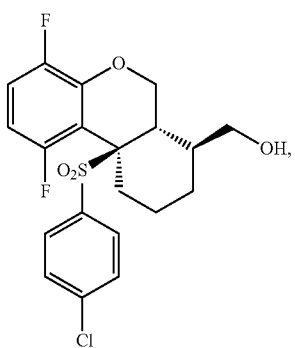
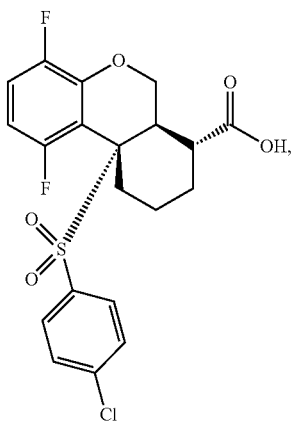

497
-continued
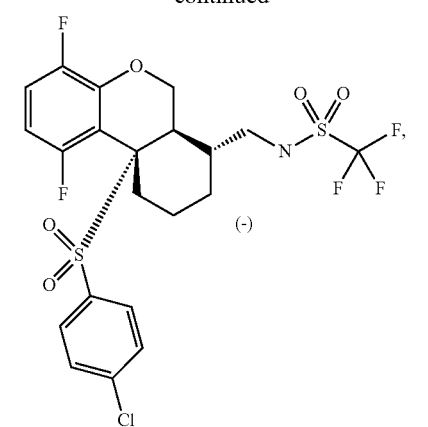
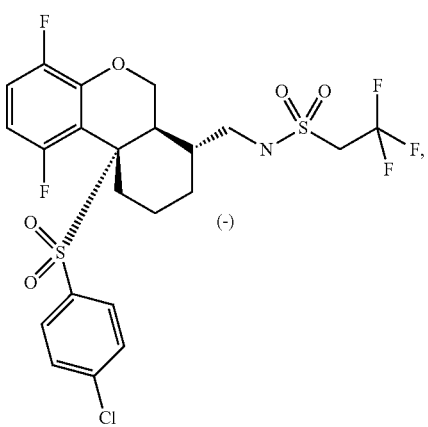
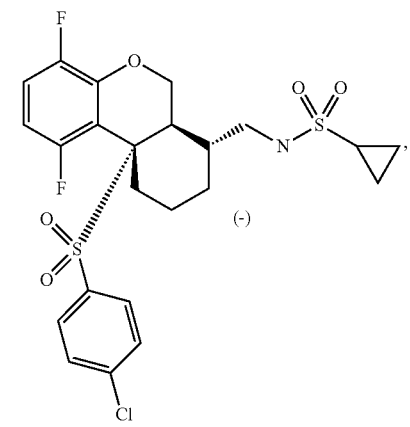
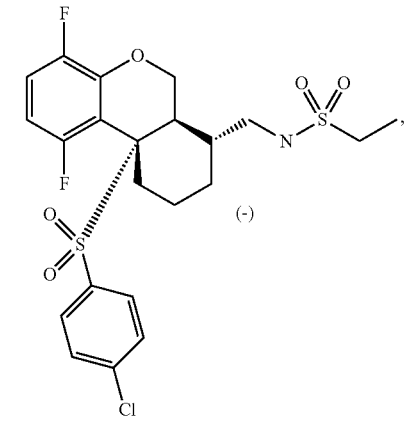
498
-continued
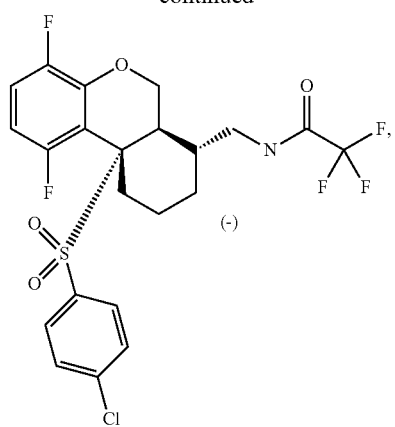
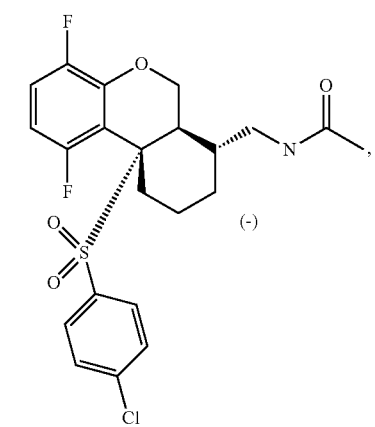
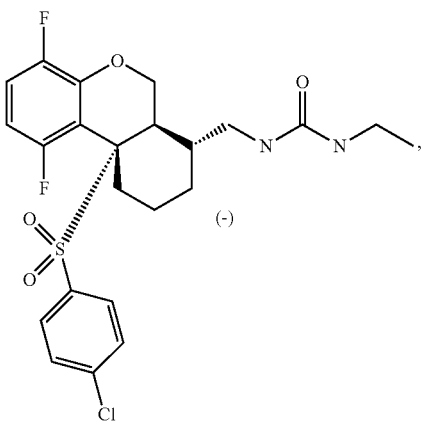
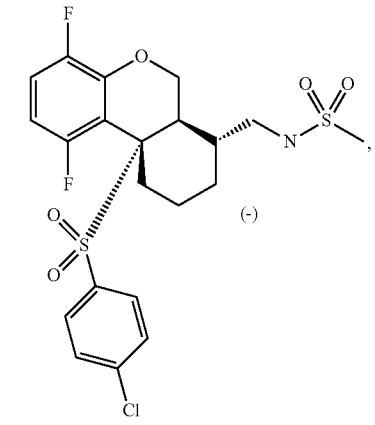

499
-continued
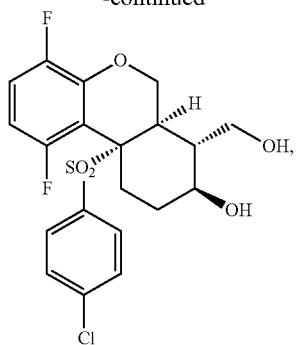
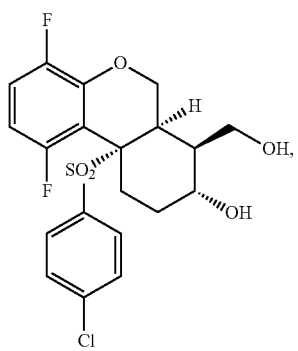
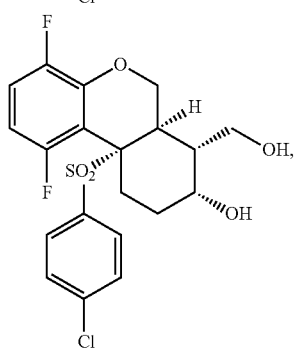
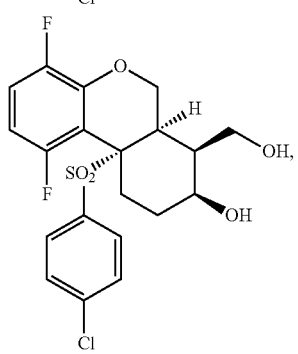
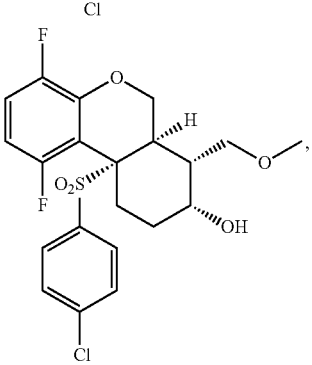
500
-continued
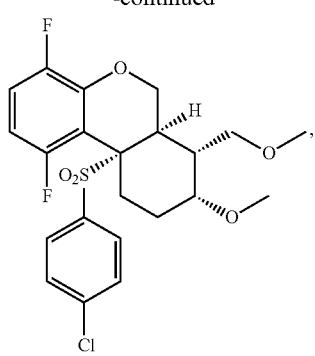
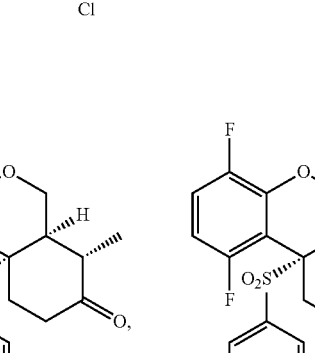
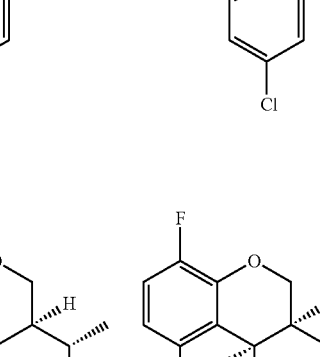
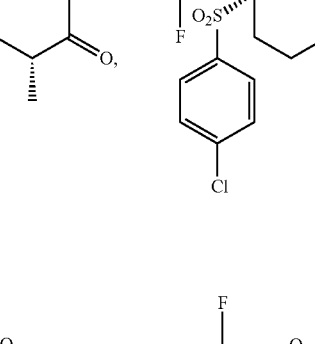
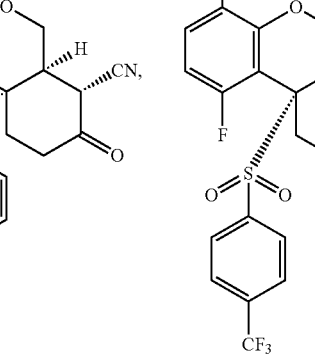

501
-continued
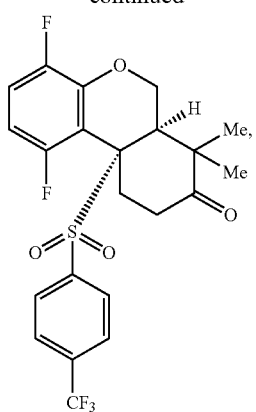
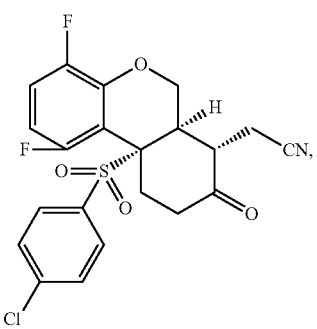
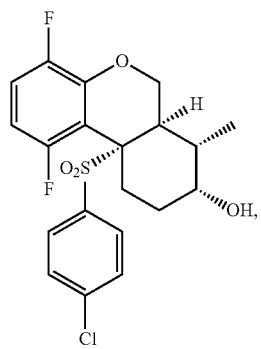 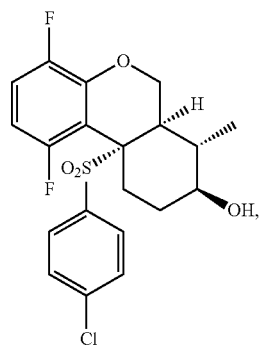
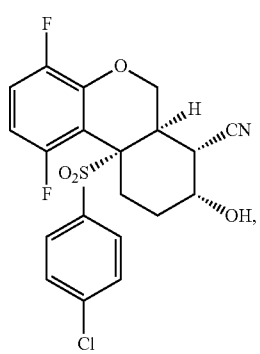 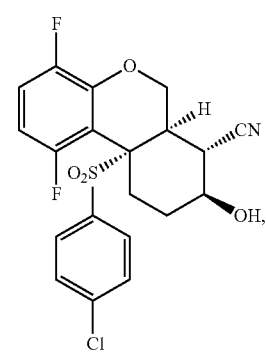
502
-continued
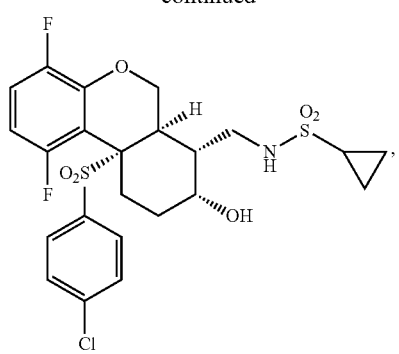
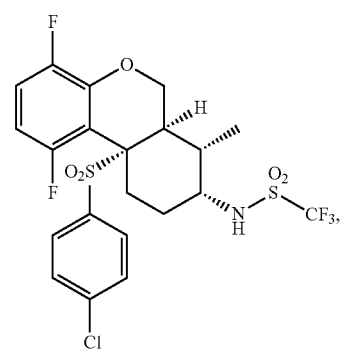
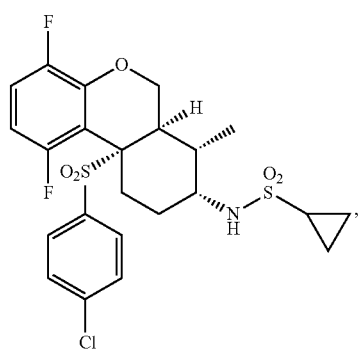
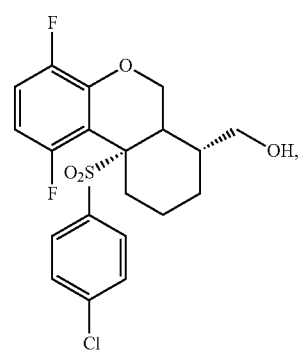

503
-continued
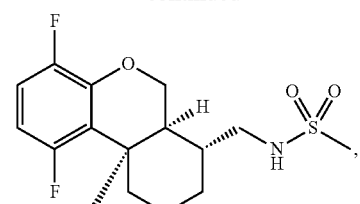
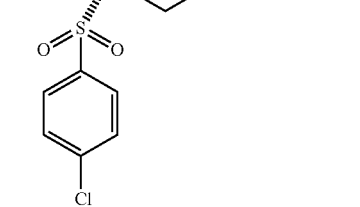
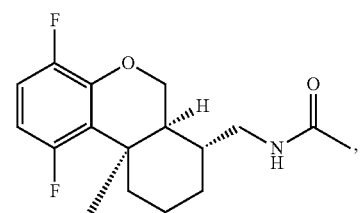
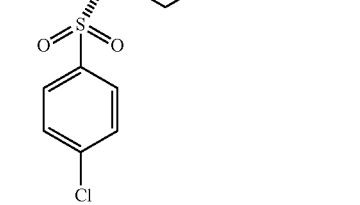
504
-continued
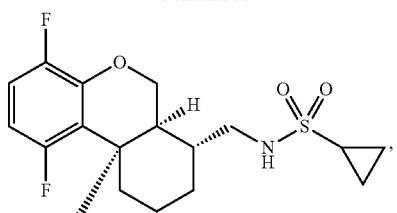
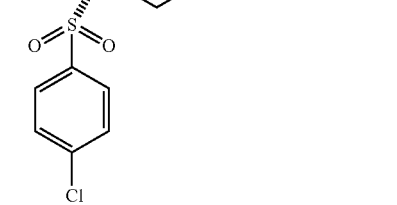
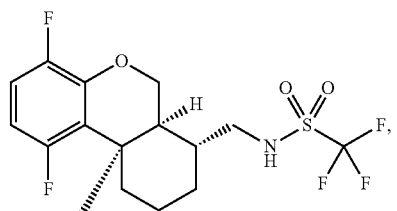
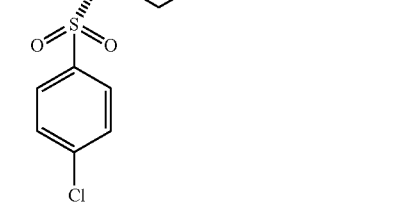
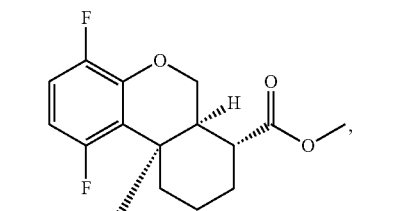
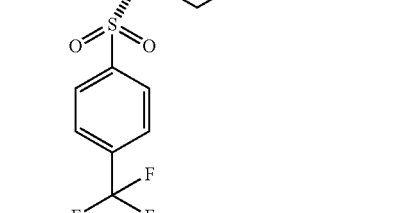
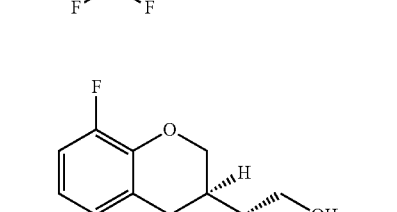
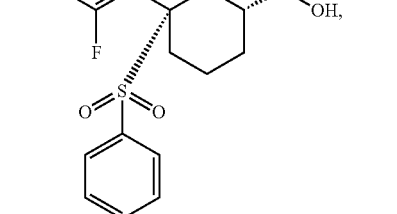

505
-continued
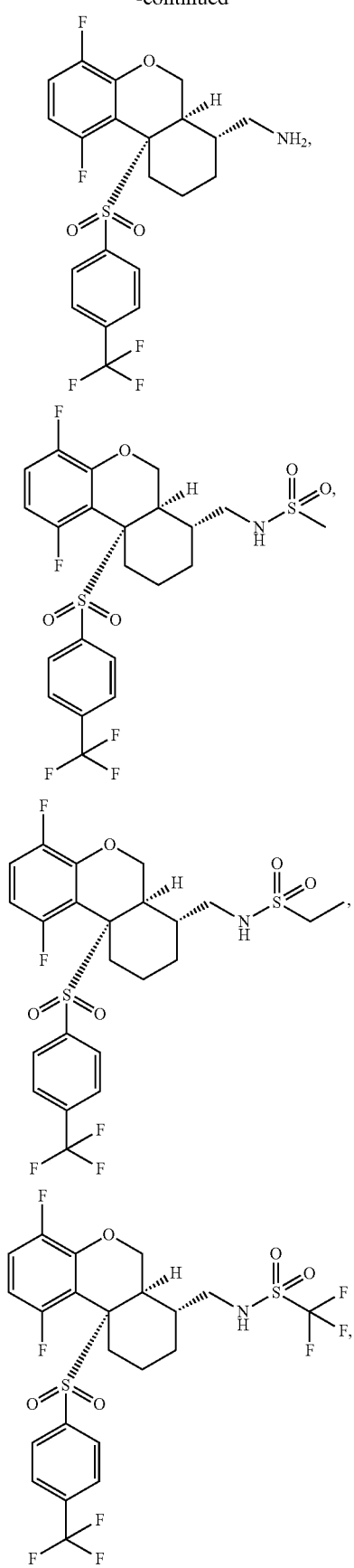
506
-continued
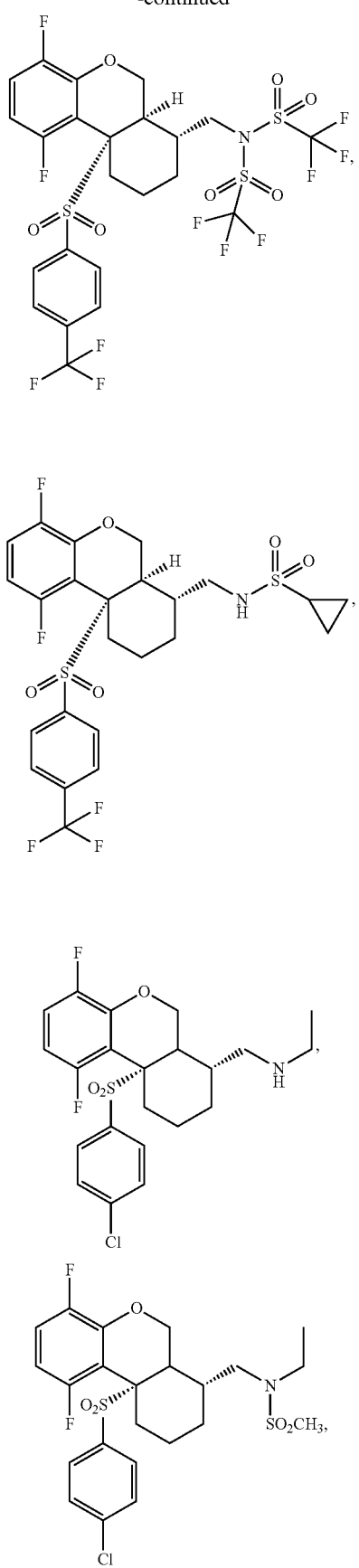

507
-continued
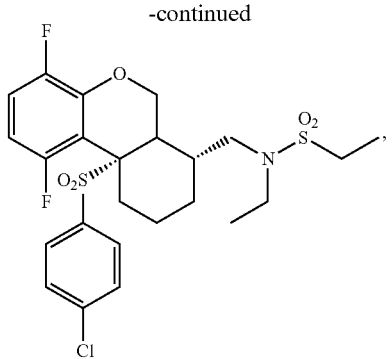
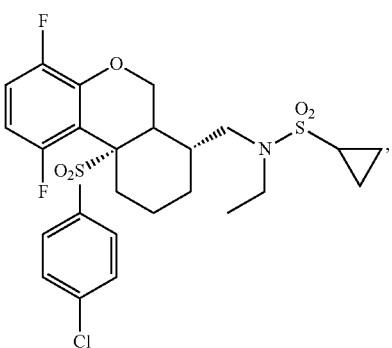
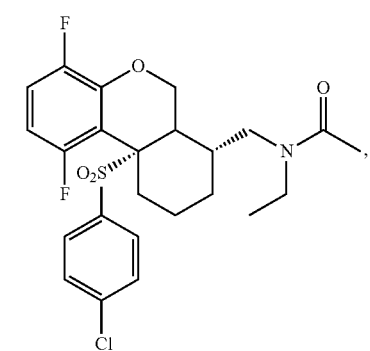
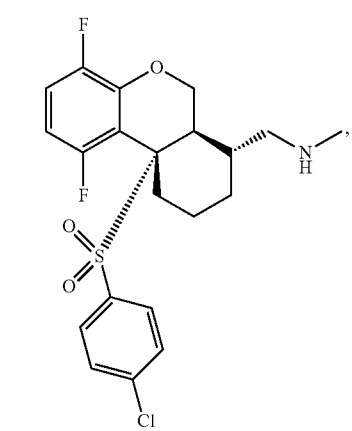
508
-continued
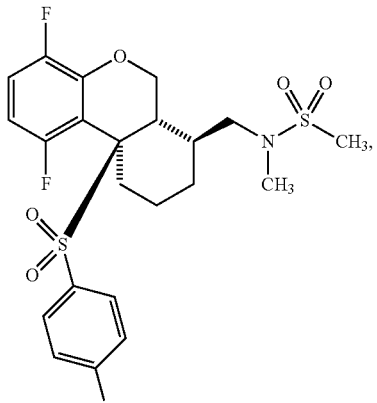
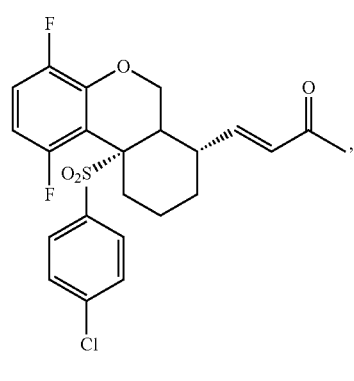
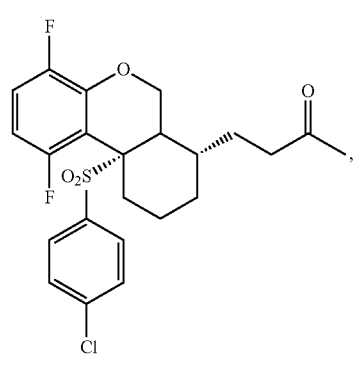
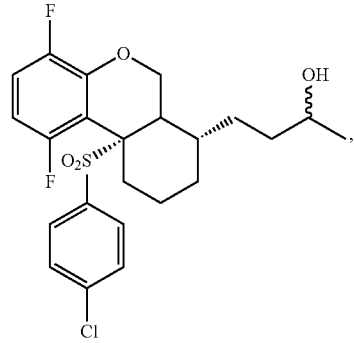

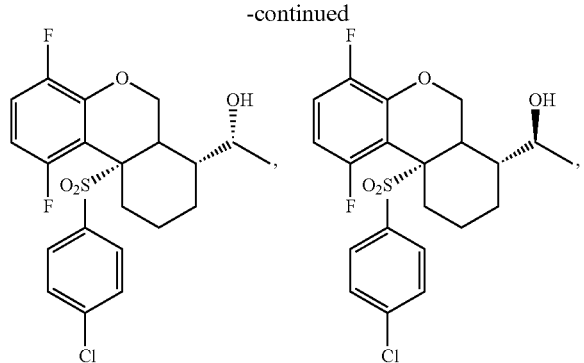
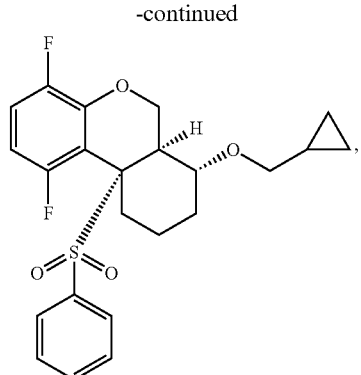
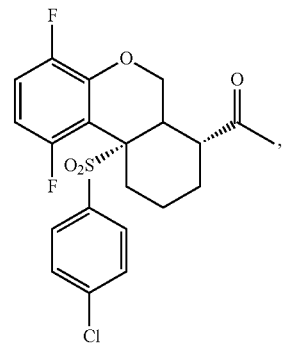
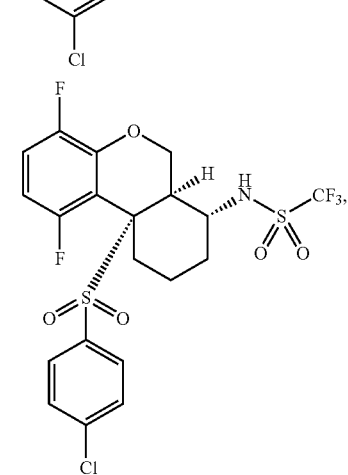
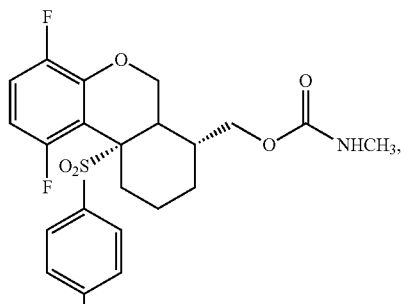
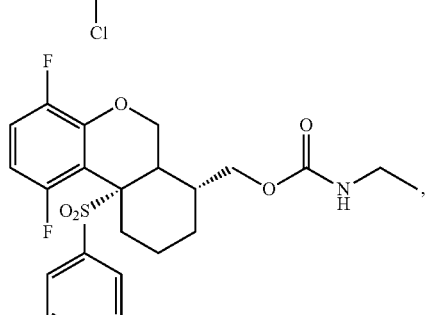
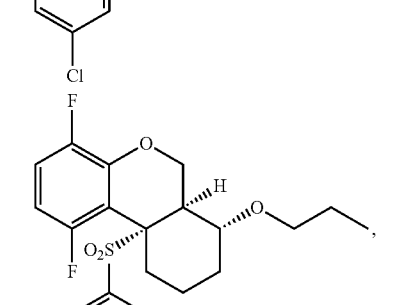

511
-continued
512
-continued
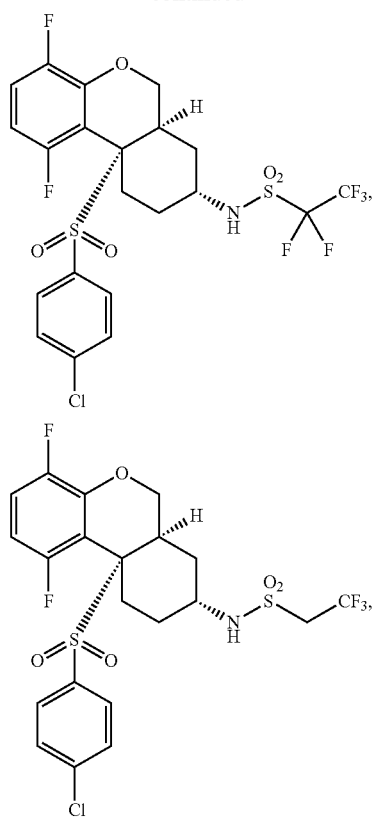
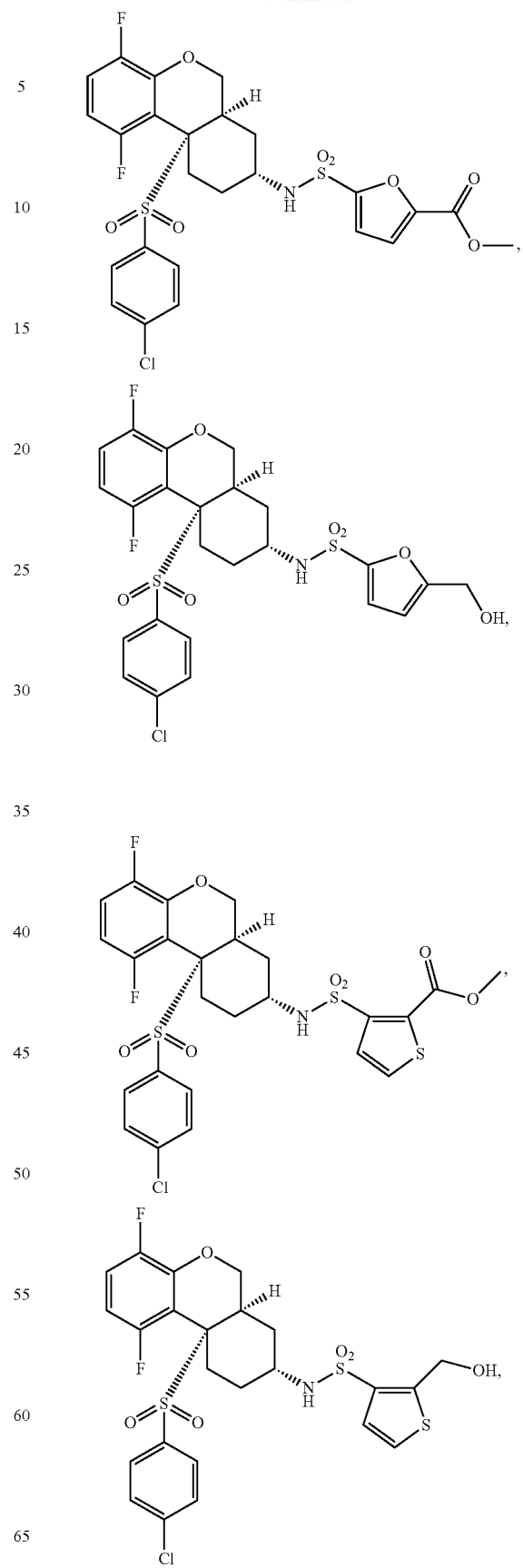

513
-continued
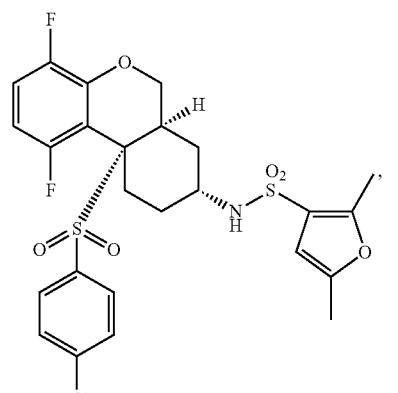
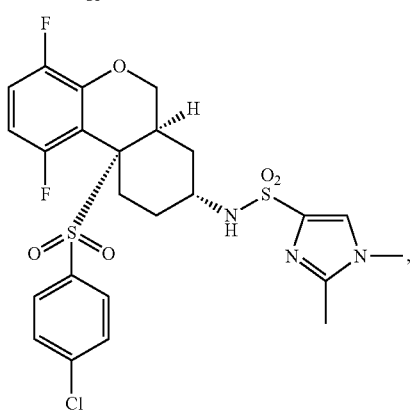
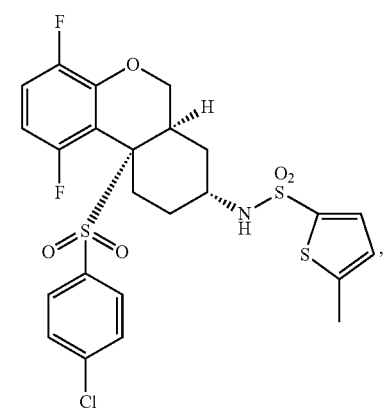
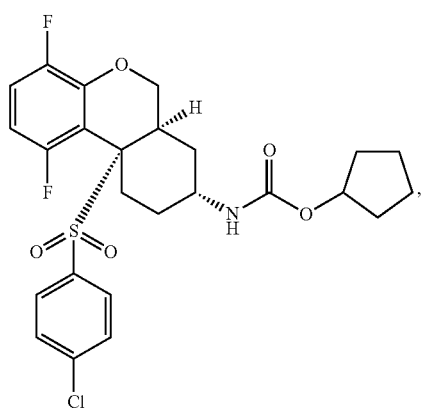
514
-continued
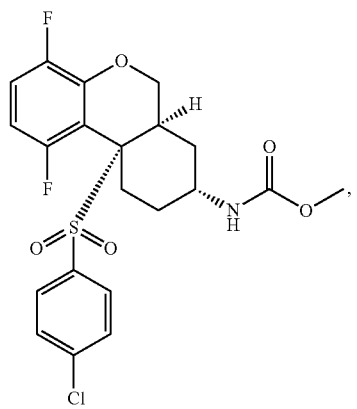
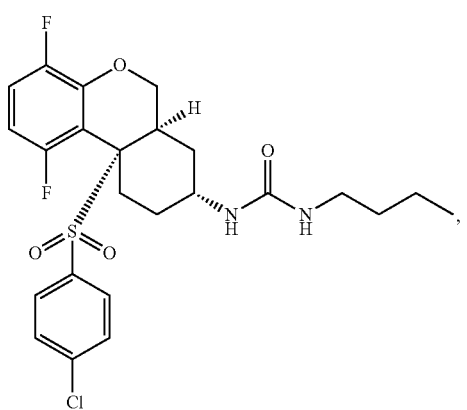
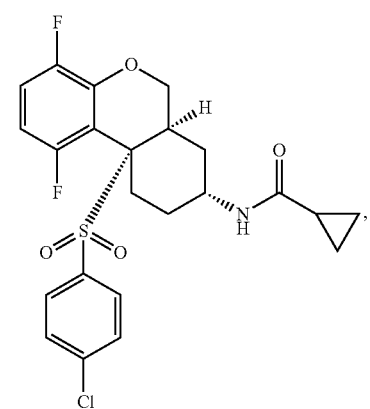
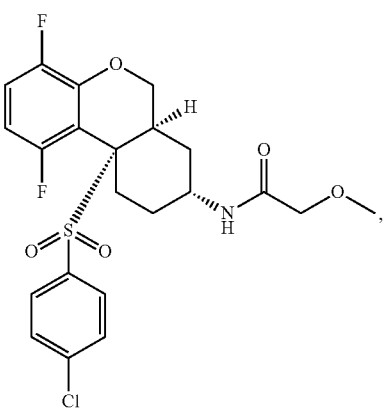

515
-continued
516
-continued
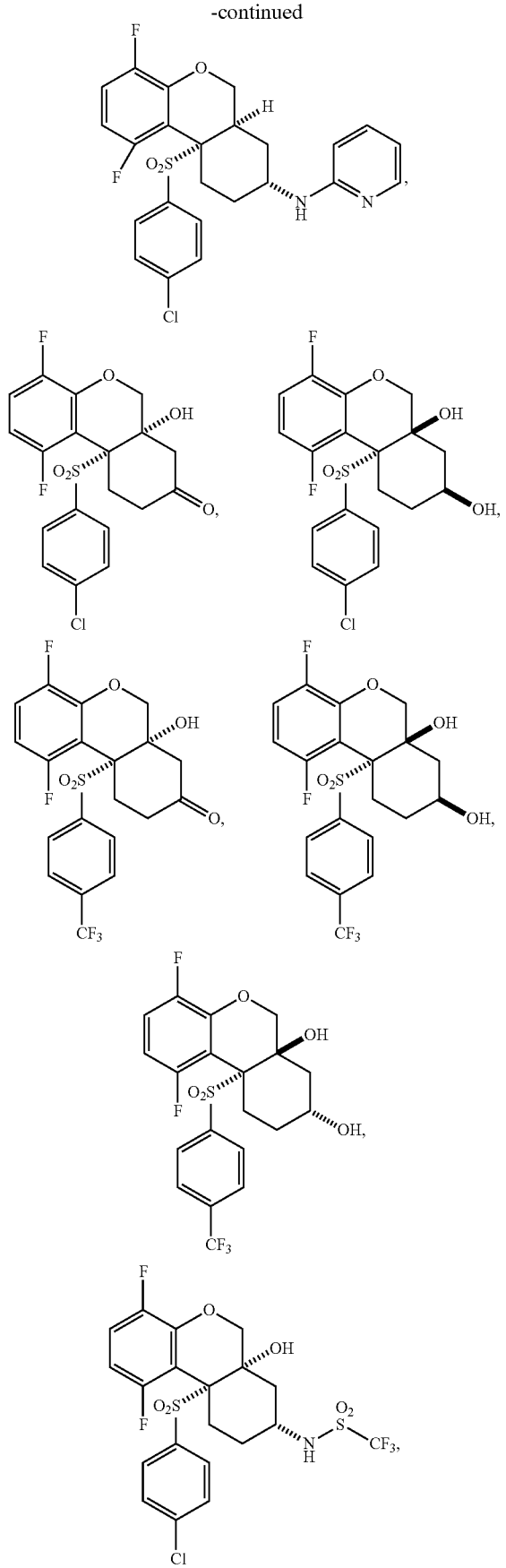
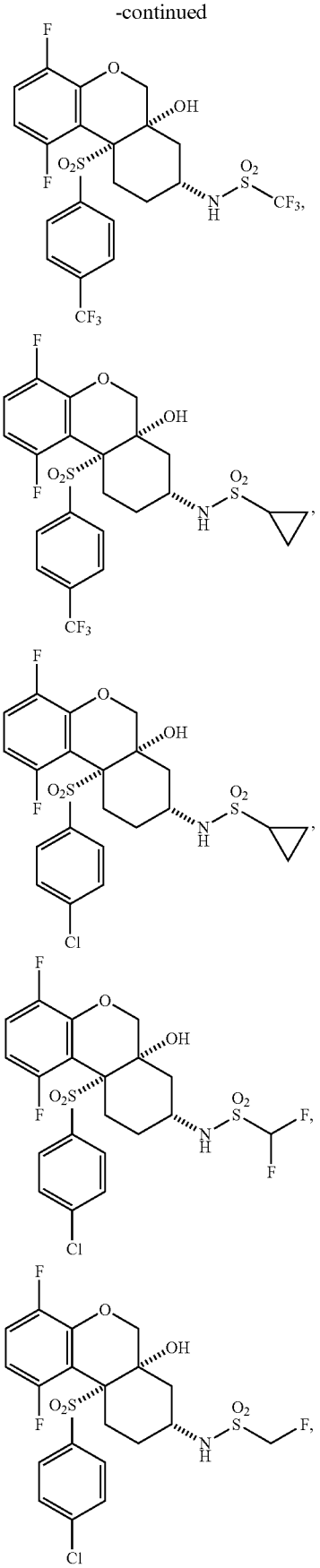

517
-continued
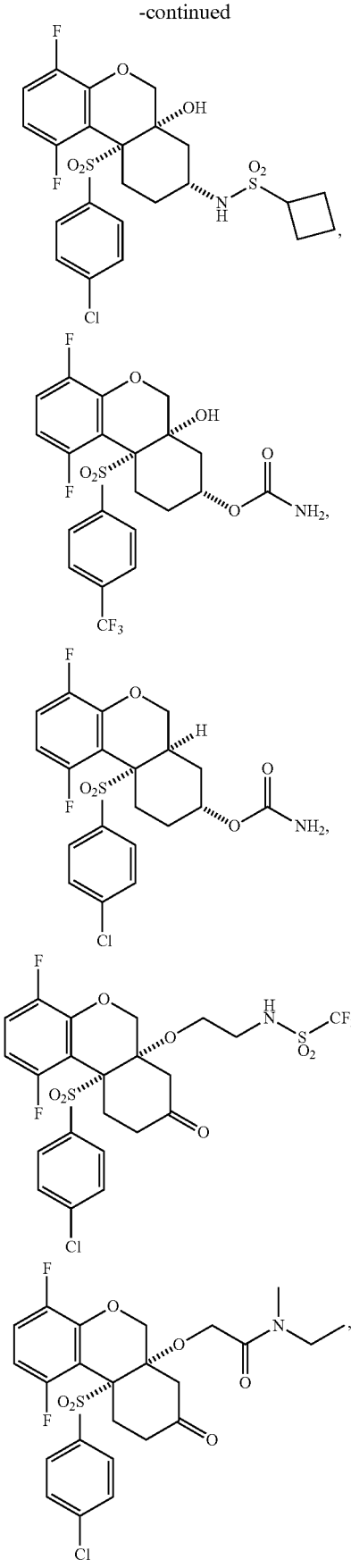
518
-continued
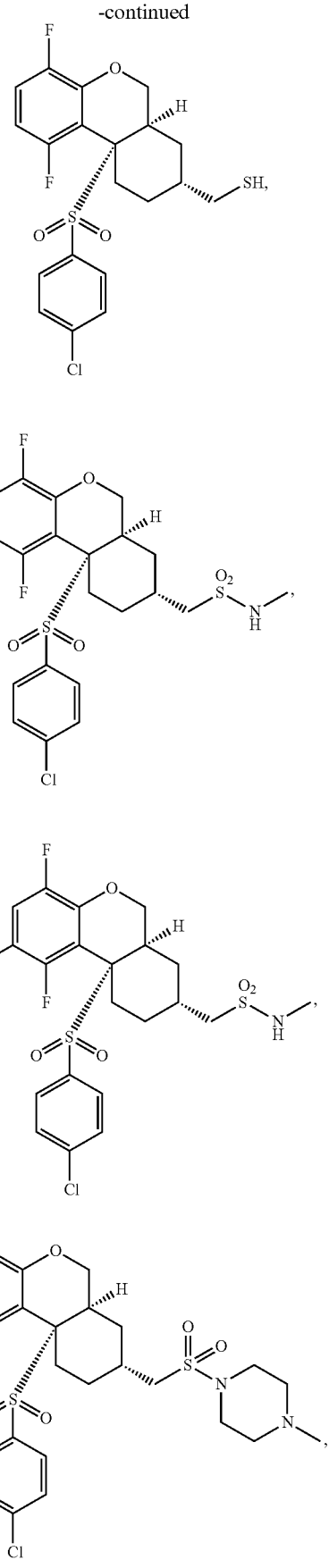

519
-continued
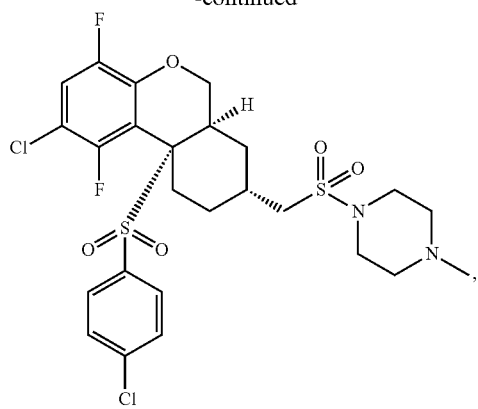
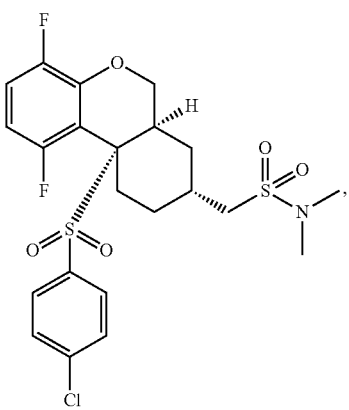
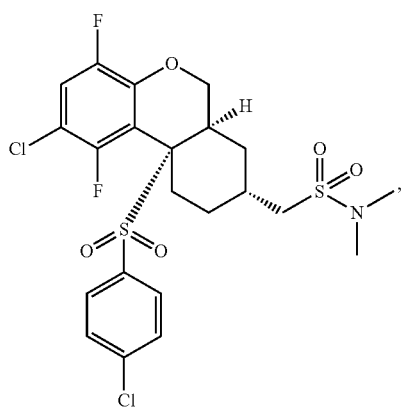
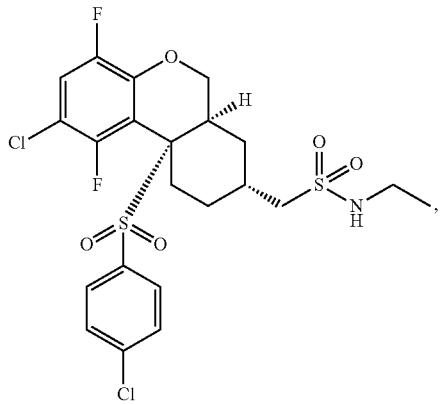
520
-continued
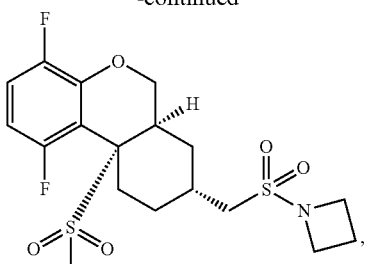
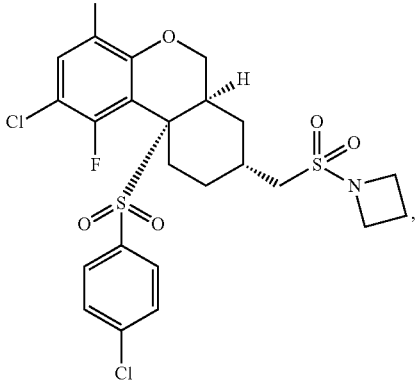
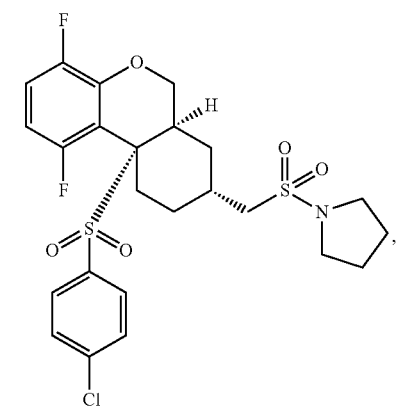
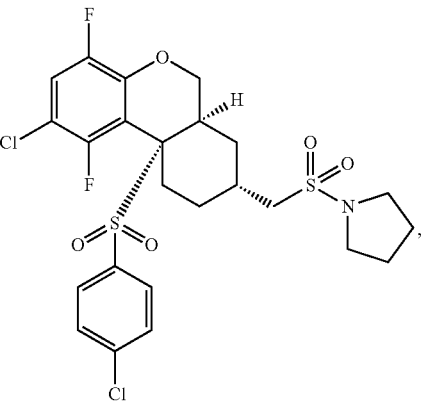

521
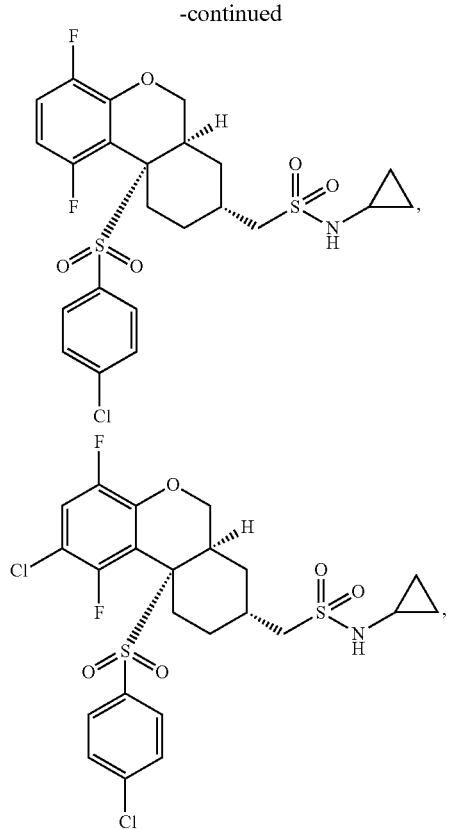
522
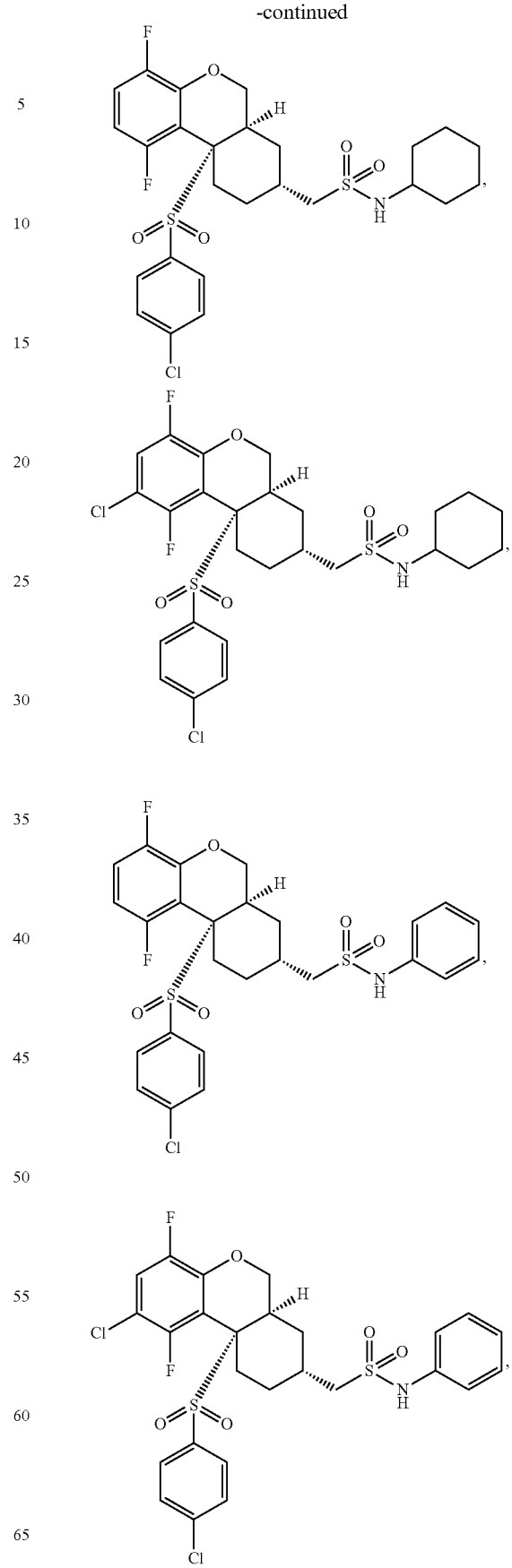

523
-continued
524
-continued
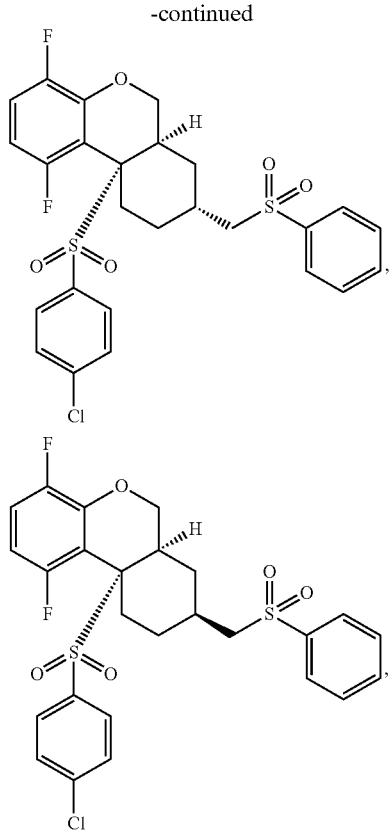
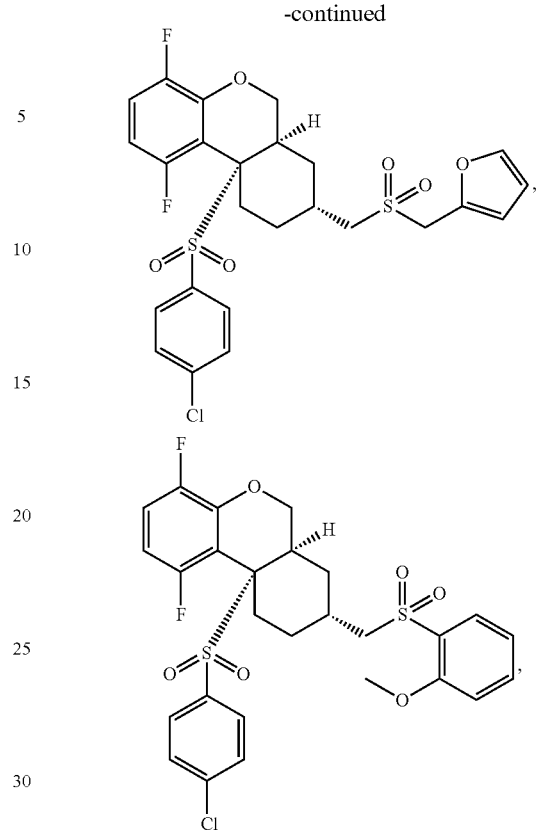
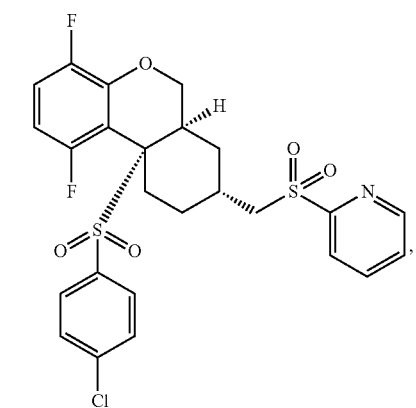
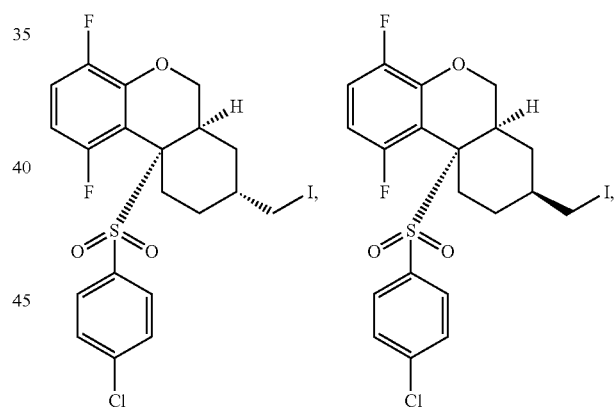
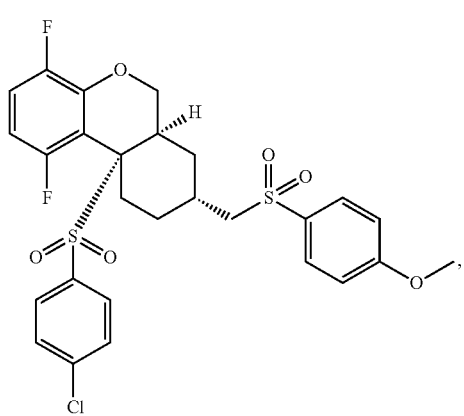

525
-continued
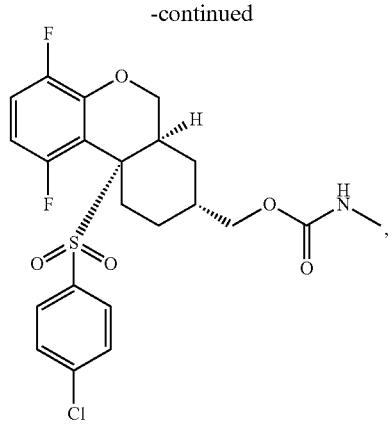
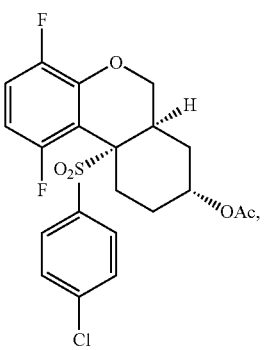
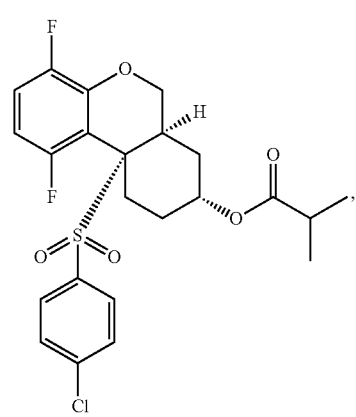
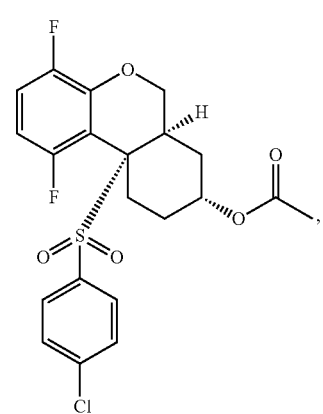
526
-continued
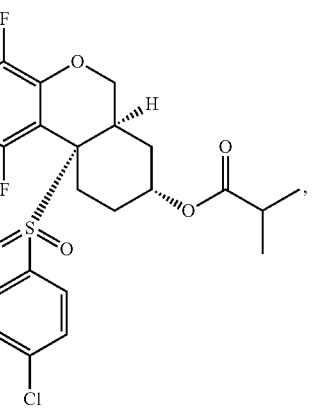
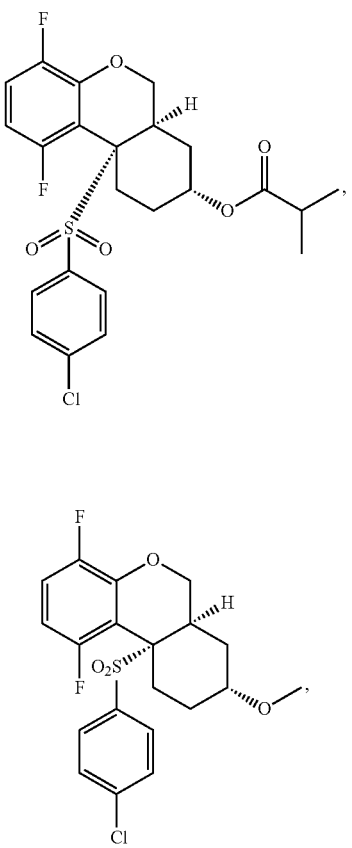
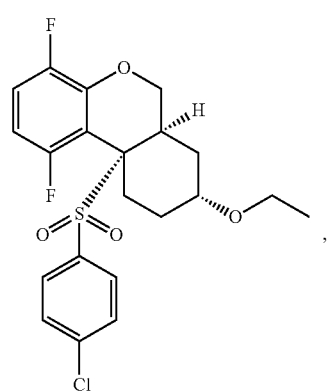
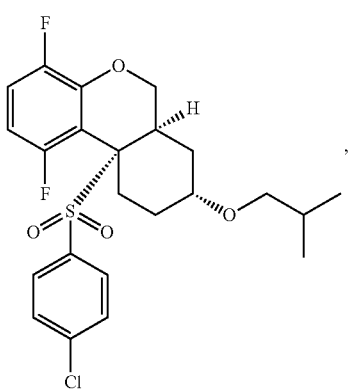

527
-continued
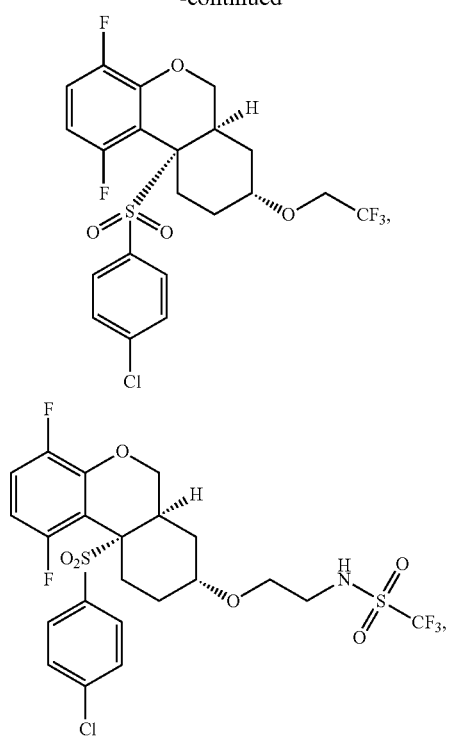
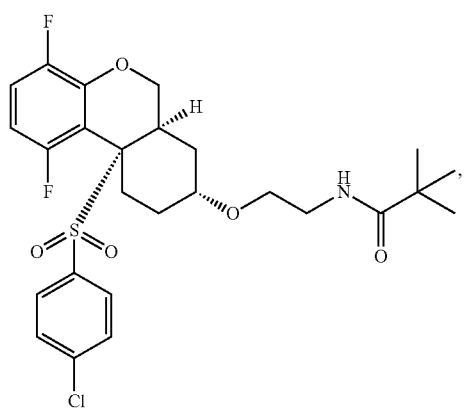
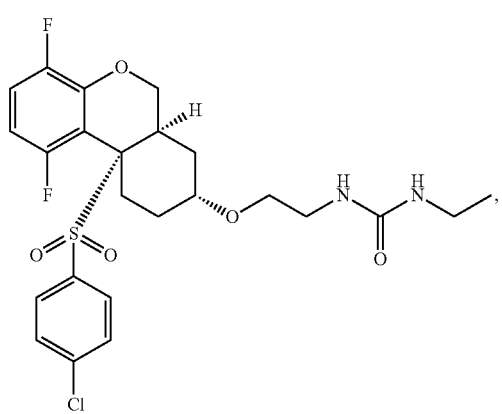
528
-continued
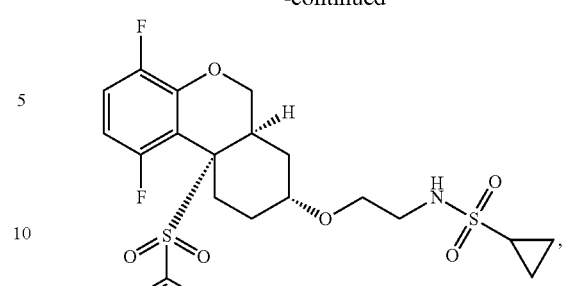
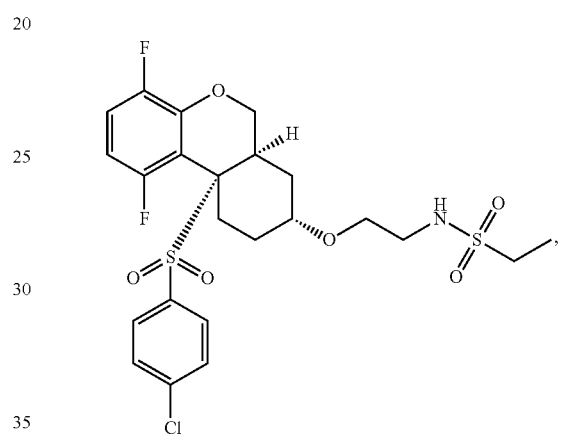
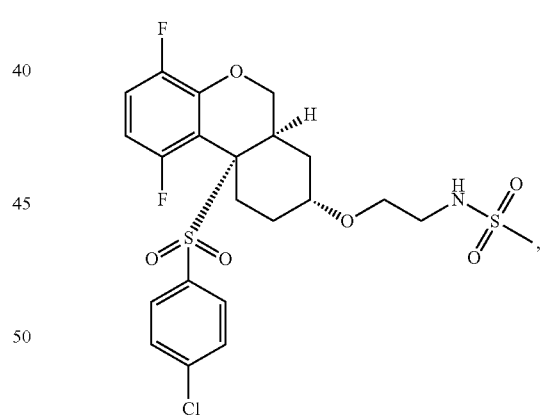
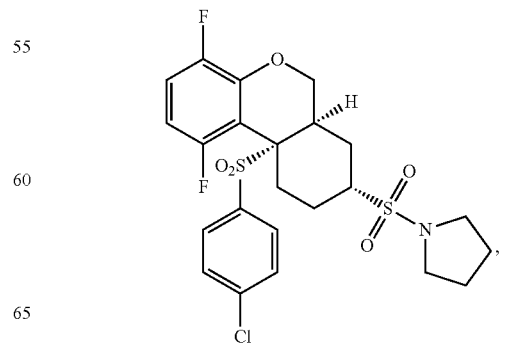

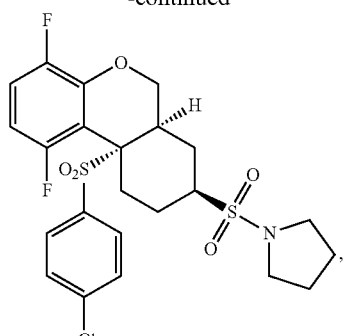
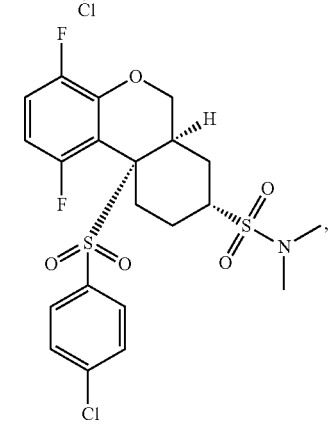
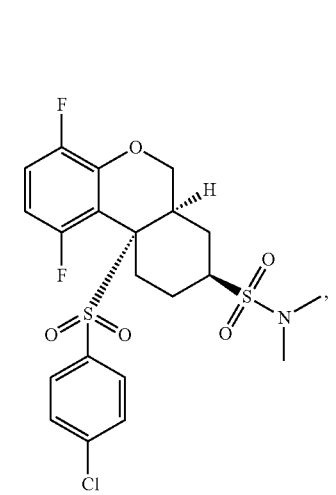
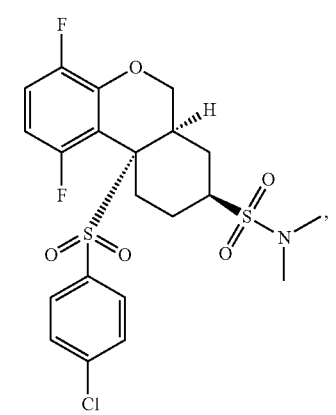
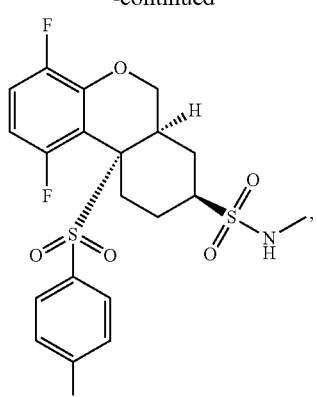
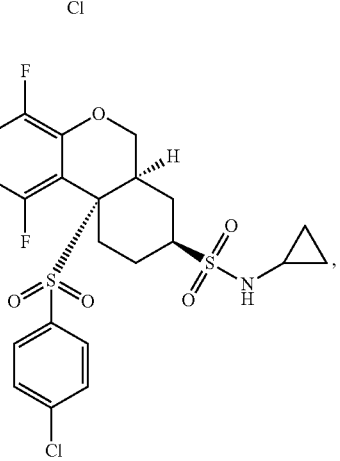
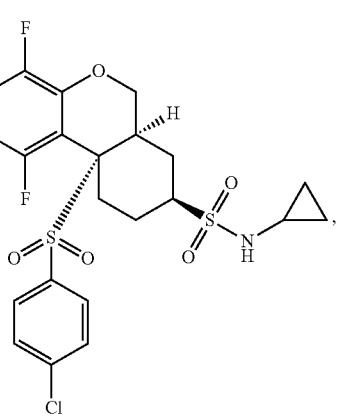
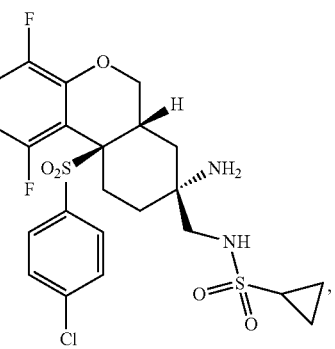

531
-continued
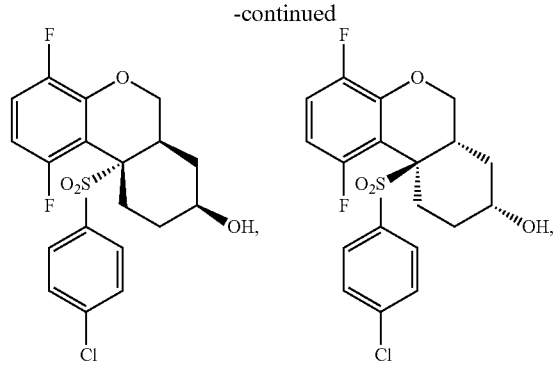
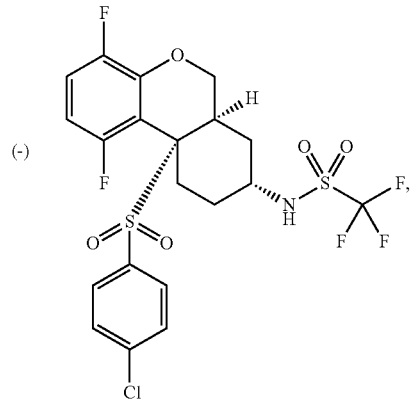
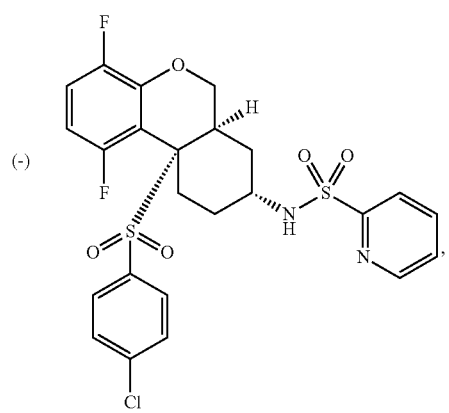
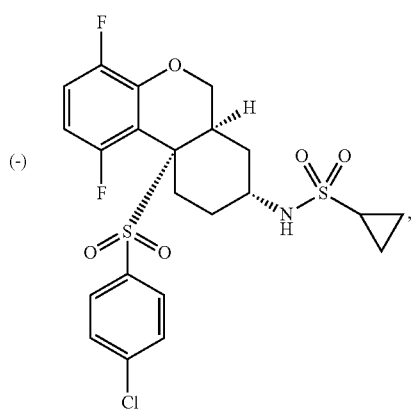
532
-continued
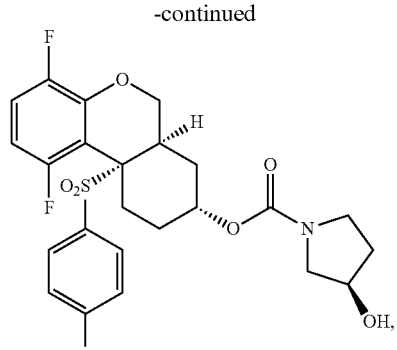
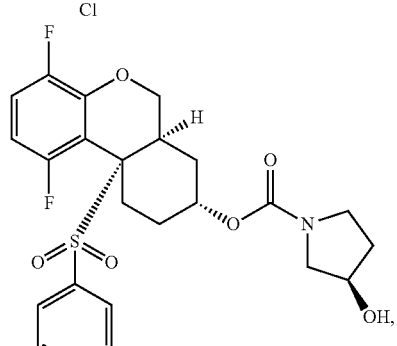
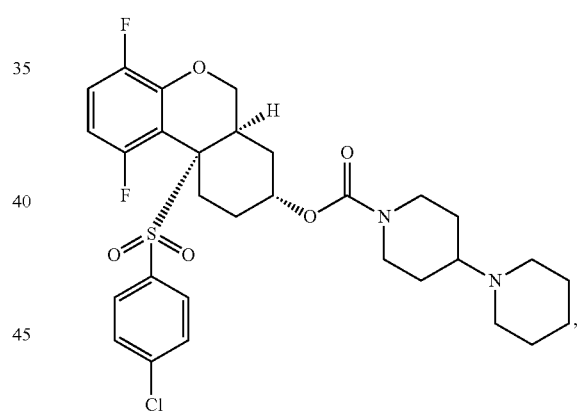
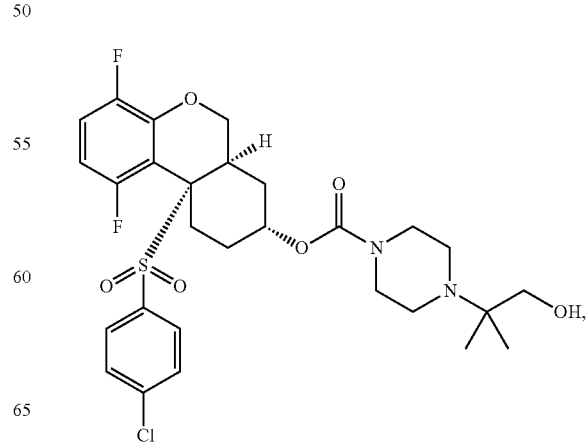

533
-continued
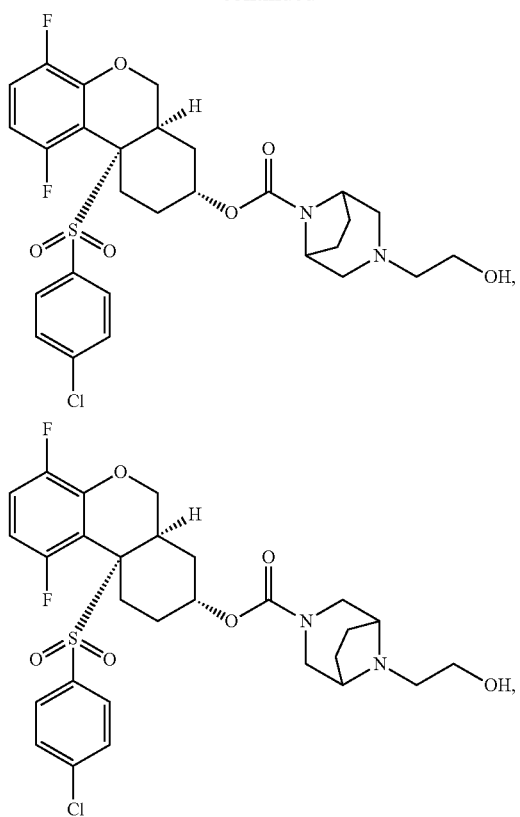
534
-continued
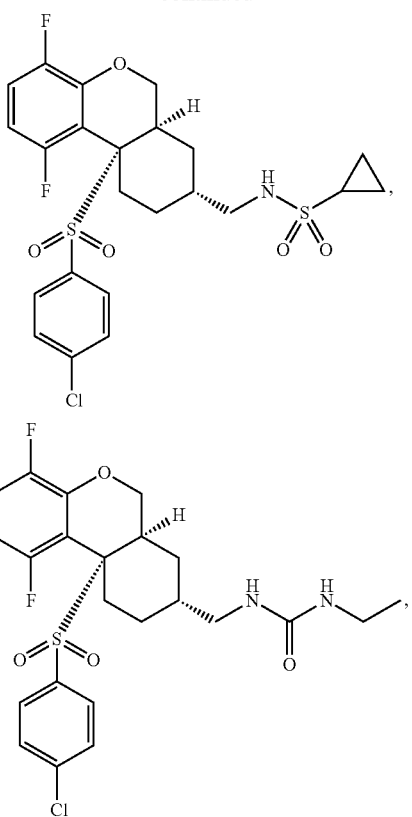

535
-continued
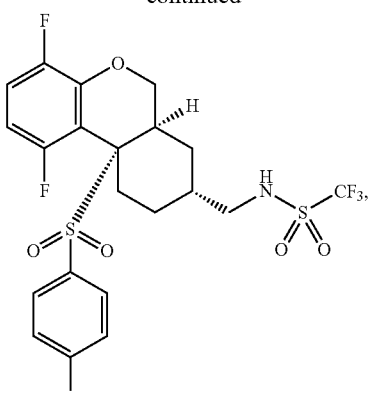
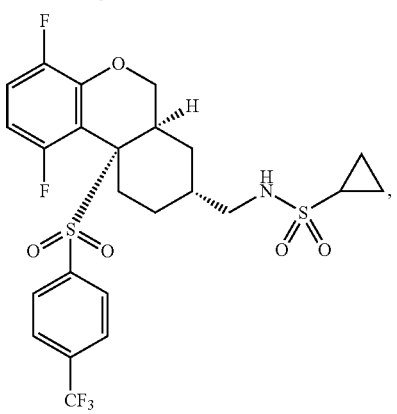
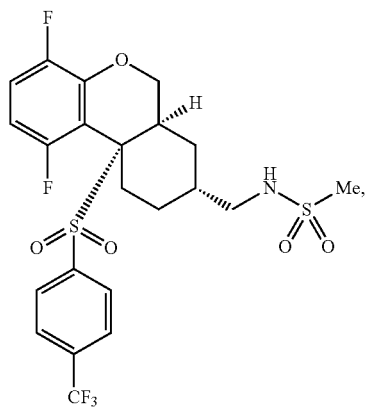
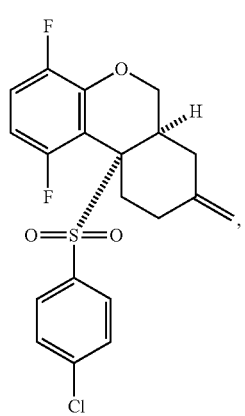 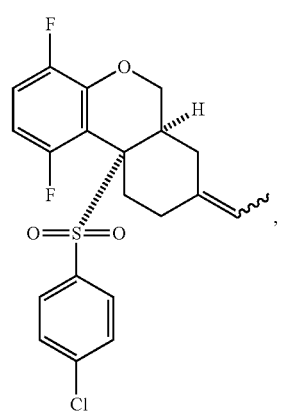
536
-continued
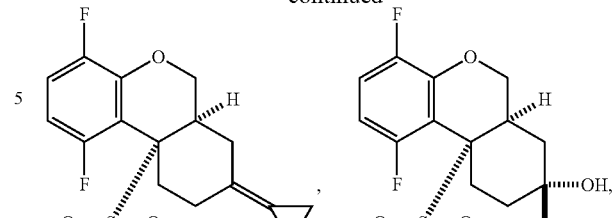
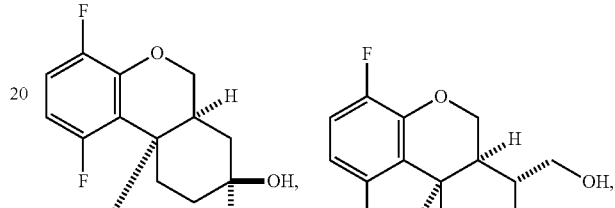
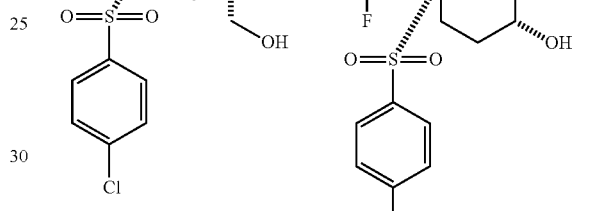
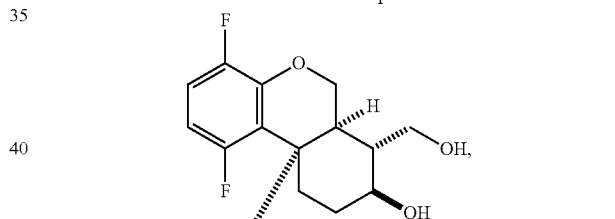
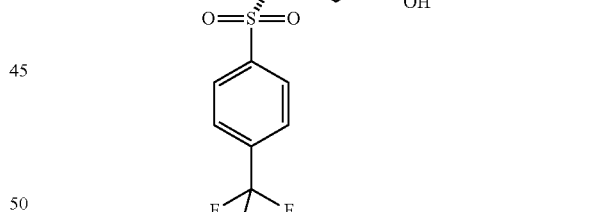
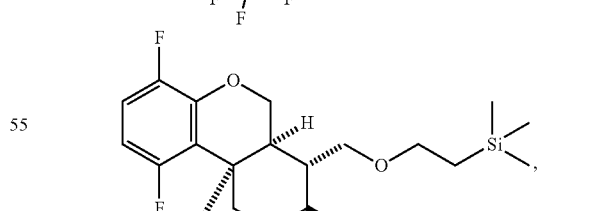
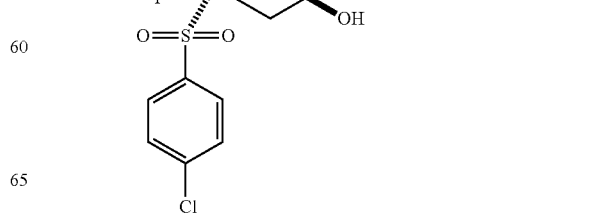

537
-continued
538
-continued
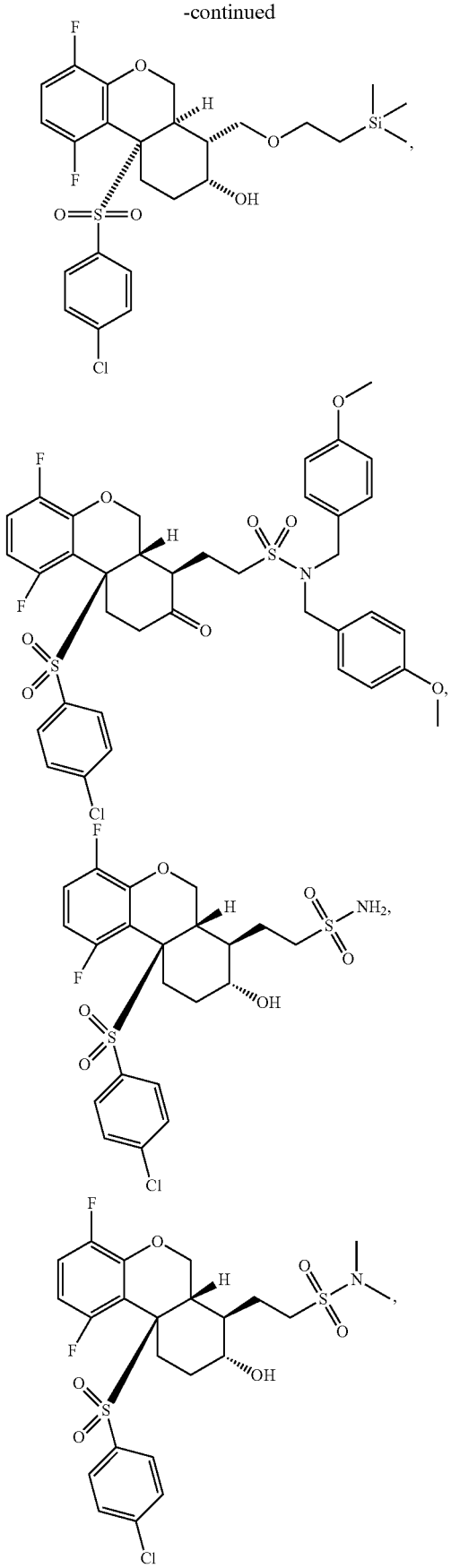
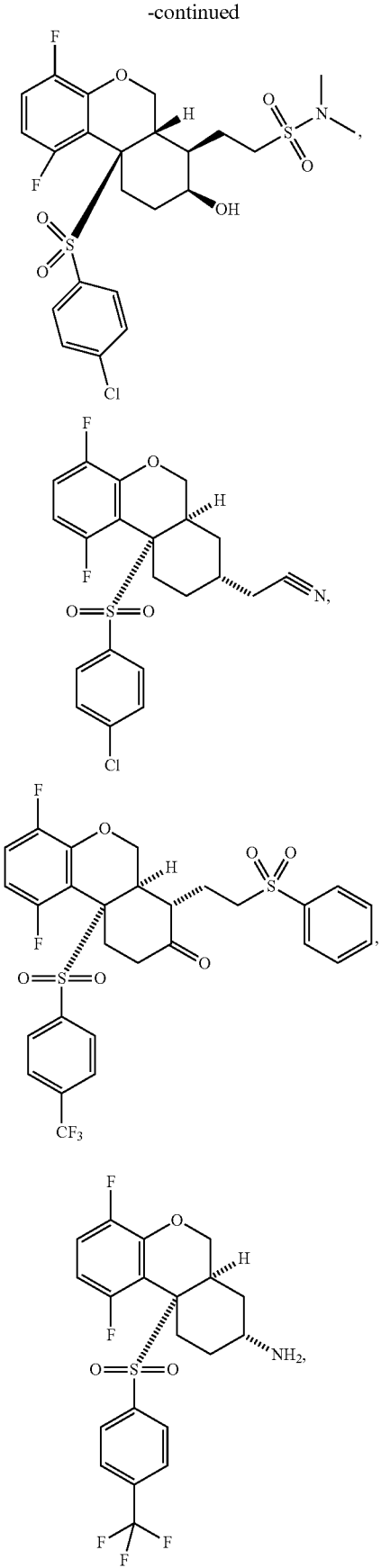

539
-continued
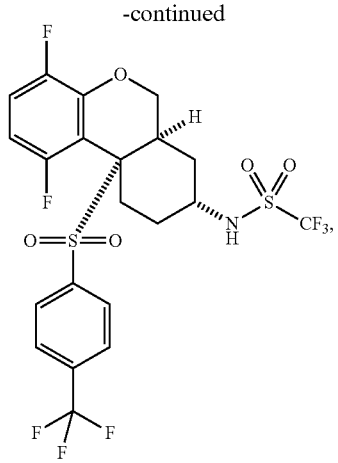
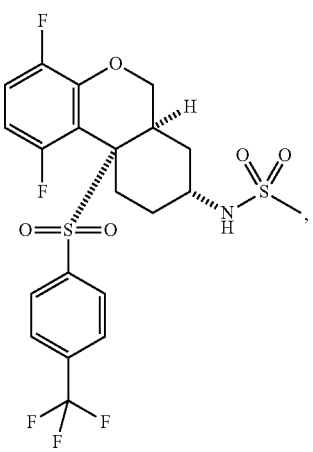
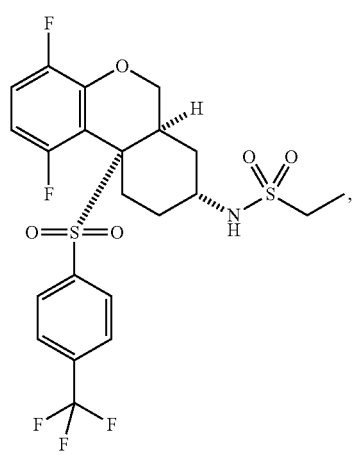
540
-continued
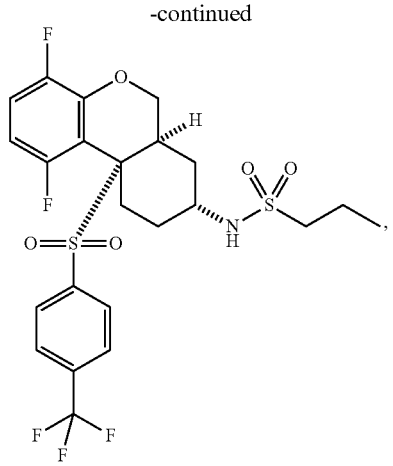
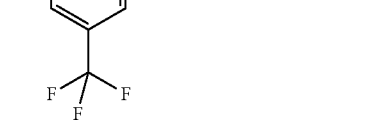
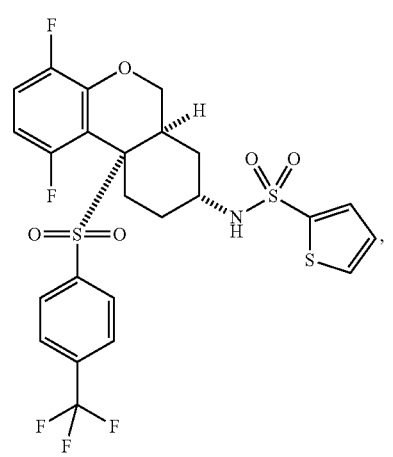

-continued
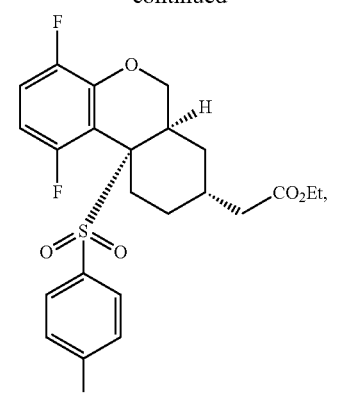
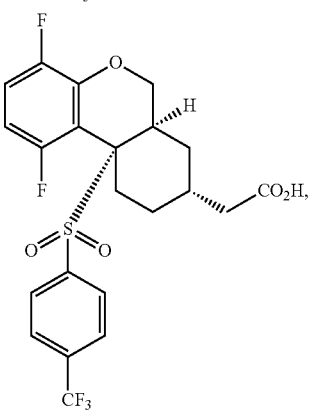
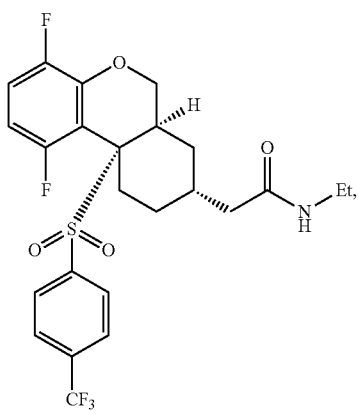
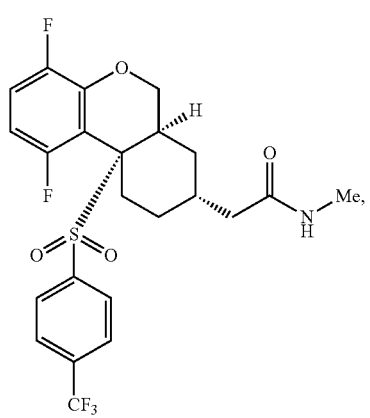
-continued
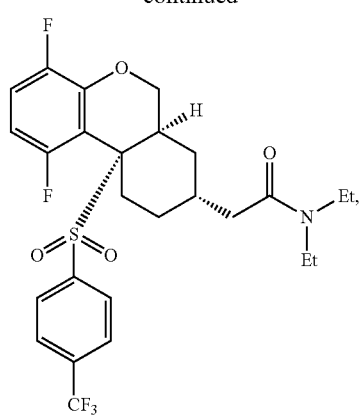
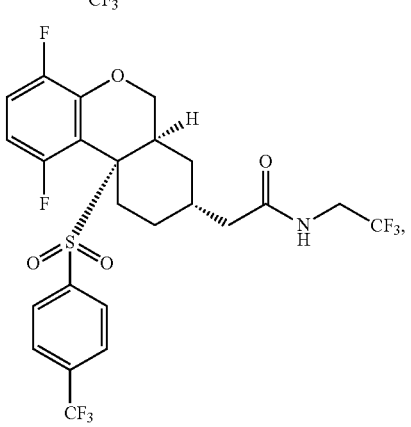
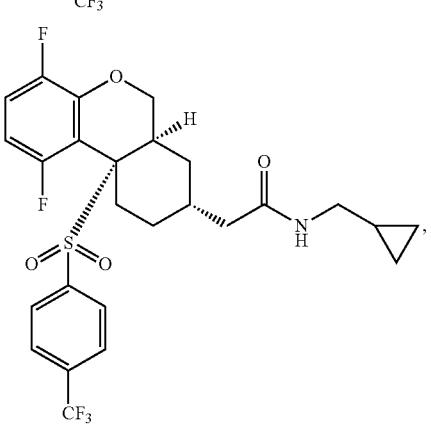
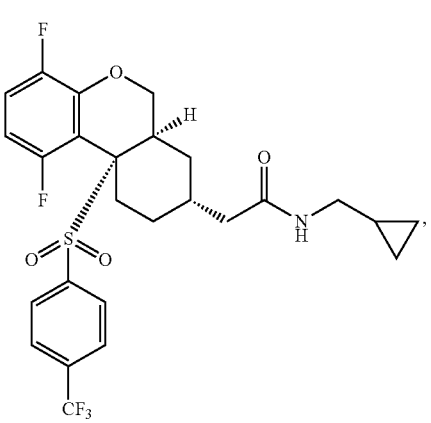

543
-continued
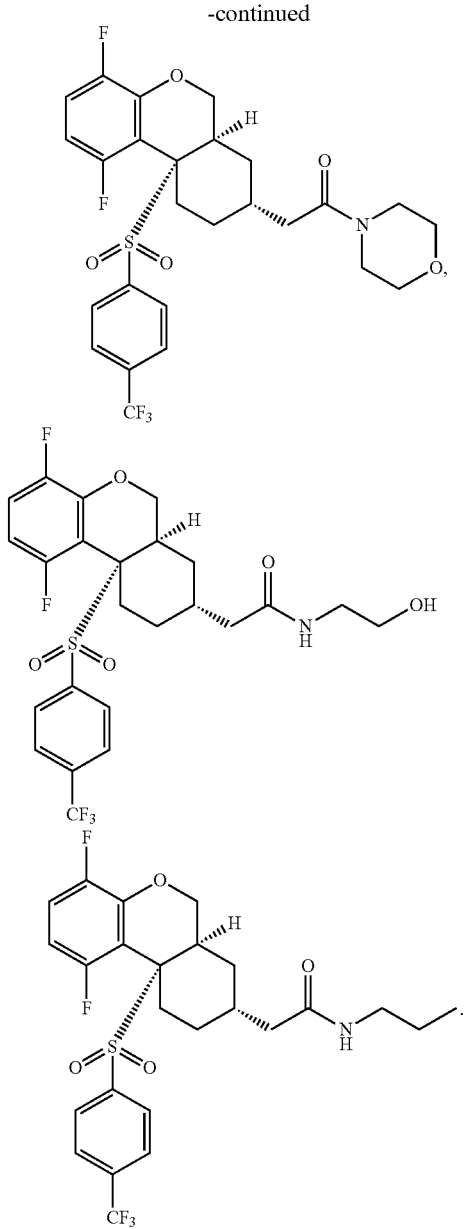
544
-continued
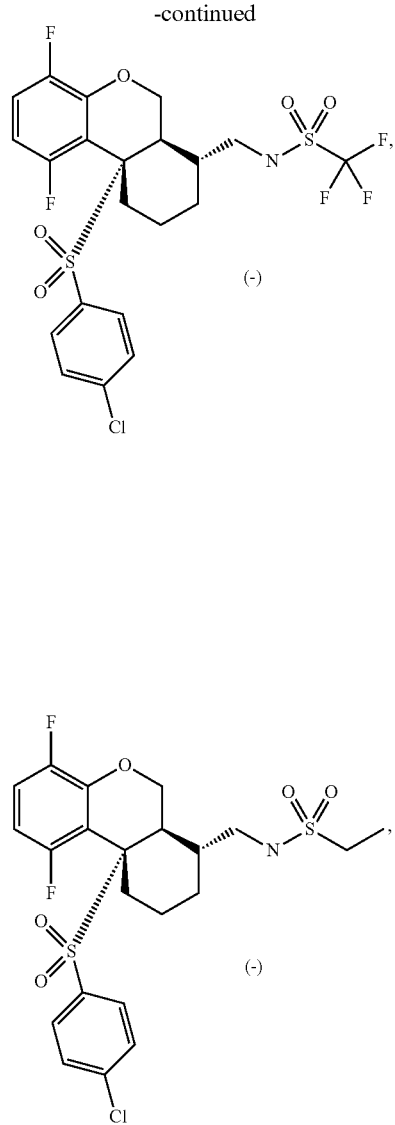
62. The compound of claim 1 or a pharmaceutically acceptable salt thereof, wherein said compound is selected from the group consisting of
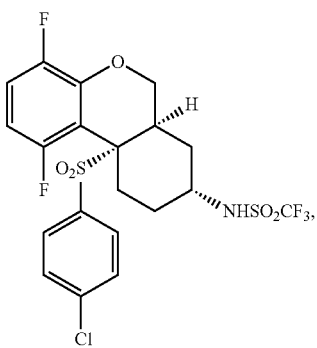
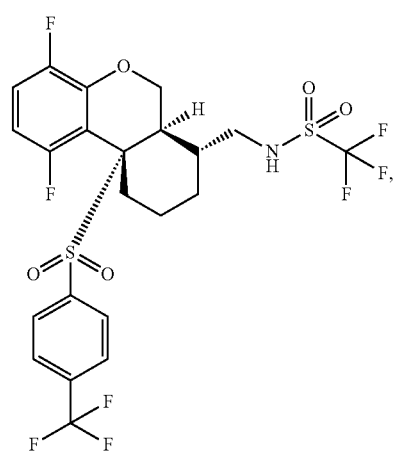

545
-continued
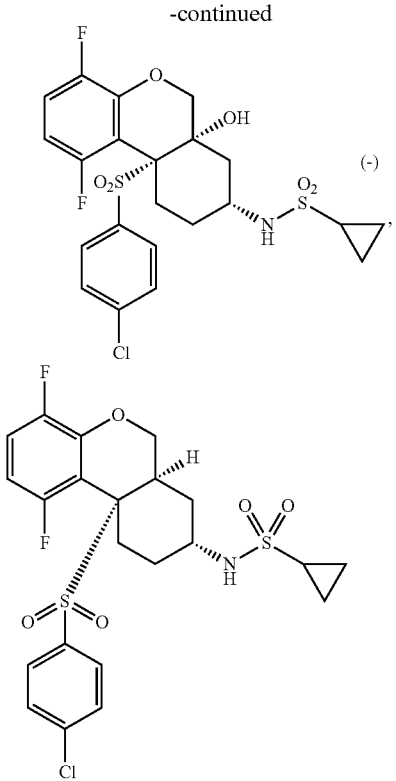
546
-continued
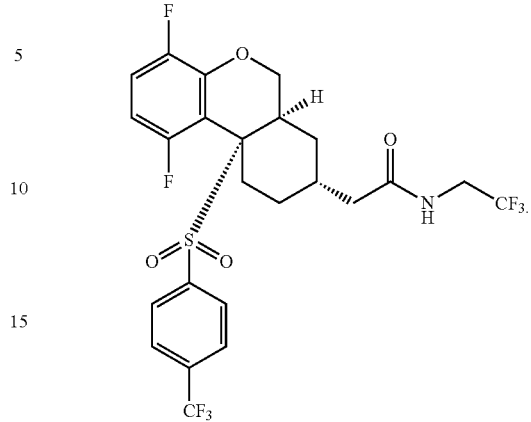
63. The compound of claim 1 or a pharmaceutically acceptable salt thereof in purified form.
64. A pharmaceutical composition comprising a compound of claim 1 or a pharmaceutically acceptable salt thereof and a pharmaceutically acceptable carrier.
* * * * *